US012440208B2

(12) United States Patent
Shelton, IV et al.

(10) Patent No.: US 12,440,208 B2
(45) **Date of Patent: *Oct. 14, 2025**

(54) POWERED SURGICAL INSTRUMENT

(71) Applicant: Cilag GmbH International, Zug (CH)

(72) Inventors: Frederick E. Shelton, IV, Hillsboro, OH (US); David C. Yates, Morrow, OH (US); Jason L. Harris, Lebanon, OH (US); Jerome R. Morgan, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/237,243

(22) Filed: Aug. 23, 2023

(65) Prior Publication Data

US 2024/0081818 A1 Mar. 14, 2024

Related U.S. Application Data

(63) Continuation of application No. 17/217,636, filed on Mar. 30, 2021, now abandoned, which is a (Continued)

(51) Int. Cl.
*A61B 17/00* (2006.01)
*A61B 17/068* (2006.01)
(Continued)

(52) U.S. Cl.
CPC .......... *A61B 17/068* (2013.01); *A61B 17/072* (2013.01); *A61B 17/07207* (2013.01); (Continued)

(58) Field of Classification Search
CPC ................ A61B 17/068; A61B 17/072; A61B 17/07207; A61B 17/295; A61B 18/1445; (Continued)

(56) References Cited

U.S. PATENT DOCUMENTS 66,052 A 6/1867 Smith
662,587 A 11/1900 Blake
(Continued)

FOREIGN PATENT DOCUMENTS

AU 2012200594 A1 2/2012
AU 2012203035 A1 6/2012
(Continued)

OTHER PUBLICATIONS

"ATM-MPLS Network Interworking Version 2.0, af-aic-0178.001" ATM Standard, The ATM Forum Technical Committee, published Aug. 2003.

(Continued)

*Primary Examiner* — Robert F Long

(57) ABSTRACT

A method of operating a surgical instrument is disclosed. The surgical instrument includes an electronic system comprising an electric motor coupled to the end effector; a motor controller coupled to the motor; a parameter threshold detection module configured to monitor multiple parameter thresholds; a sensing module configured to sense tissue compression; a processor coupled to the parameter threshold detection module and the motor controller; and a memory coupled to the processor. The memory stores executable instructions that when executed by the processor cause the processor to monitor multiple levels of action thresholds and monitor speed of the motor and increment a drive unit of the motor, sense tissue compression, and provide rate and control feedback to the user of the surgical instrument.

15 Claims, 127 Drawing Sheets

Related U.S. Application Data continuation of application No. 15/730,188, filed on Oct. 11, 2017, now abandoned, which is a continuation of application No. 14/640,746, filed on Mar. 6, 2015, now Pat. No. 9,808,246.

(51) Int. Cl.

| | |
|---|---|
| ***A61B 17/072*** | (2006.01) |
| ***A61B 17/295*** | (2006.01) |
| ***A61B 18/14*** | (2006.01) |
| *A61B 17/29* | (2006.01) |
| *A61B 18/00* | (2006.01) |
| *A61B 90/00* | (2016.01) |
| *A61B 90/98* | (2016.01) |

(52) U.S. Cl.

CPC ........ *A61B 17/295* (2013.01); *A61B 18/1445* (2013.01); *A61B 2017/00017* (2013.01); *A61B 2017/00022* (2013.01); *A61B 2017/00026* (2013.01); *A61B 2017/00119* (2013.01); *A61B 2017/0019* (2013.01); *A61B 2017/00367* (2013.01); *A61B 2017/00398* (2013.01); *A61B 2017/00411* (2013.01); *A61B 2017/0046* (2013.01); *A61B 2017/00734* (2013.01); *A61B 2017/07257* (2013.01); *A61B 2017/07271* (2013.01); *A61B 2017/07278* (2013.01); *A61B 2017/07285* (2013.01); *A61B 2017/2927* (2013.01); *A61B 2018/00607* (2013.01); *A61B 2018/1455* (2013.01); *A61B 2090/034* (2016.02); *A61B 2090/065* (2016.02); *A61B 2090/066* (2016.02); *A61B 2090/0803* (2016.02); *A61B 2090/0807* (2016.02); *A61B 2090/0808* (2016.02); *A61B 2090/0814* (2016.02); *A61B 2090/0818* (2016.02); *A61B 90/98* (2016.02); *A61B 2560/0475* (2013.01)

(58) Field of Classification Search

CPC .......... A61B 90/98; A61B 2017/00017; A61B 2017/00022; A61B 2017/00026; A61B 2017/00119; A61B 2017/0019; A61B 2017/00367; A61B 2017/00398; A61B 2017/00411; A61B 2017/0046; A61B 2017/00734; A61B 2017/07257; A61B 2017/07271; A61B 2017/07278; A61B 2017/07285; A61B 2017/2927; A61B 2018/00607; A61B 2018/1455; A61B 2090/034; A61B 2090/065; A61B 2090/066; A61B 2090/0803; A61B 2090/0807; A61B 2090/0808; A61B 2090/0814; A61B 2090/0818; A61B 2560/0475

USPC ................................ 227/175.1–182.1, 8, 19

See application file for complete search history.

(56) References Cited

U.S. PATENT DOCUMENTS 670,748 A 3/1901 Weddeler
719,487 A 2/1903 Minor
804,229 A 11/1905 Hutchinson
903,739 A 11/1908 Lesemann
951,393 A 3/1910 Hahn
1,075,556 A 10/1913 Fenoughty
1,082,105 A 12/1913 Anderson
1,188,721 A 6/1916 Bittner
1,306,107 A 6/1919 Elliott
1,314,601 A 9/1919 McCaskey
1,466,128 A 8/1923 Hallenbeck
1,677,337 A 7/1928 Grove
1,794,907 A 3/1931 Kelly
1,849,427 A 3/1932 Hook
1,912,783 A 6/1933 Meyer
1,944,116 A 1/1934 Stratman
1,954,048 A 4/1934 Jeffrey et al.
2,028,635 A 1/1936 Wappler
2,037,727 A 4/1936 La Chapelle
2,120,951 A 6/1938 Hodgman
2,132,295 A 10/1938 Hawkins
2,161,632 A 6/1939 Nattenheimer
D120,434 S 5/1940 Gold
2,211,117 A 8/1940 Hess
2,214,870 A 9/1940 West
2,224,108 A 12/1940 Ridgway
2,224,882 A 12/1940 Peck
2,256,295 A 9/1941 Schmid
2,318,379 A 5/1943 Davis et al.
2,329,440 A 9/1943 La Place
2,377,581 A 6/1945 Shaffrey
2,406,389 A 8/1946 Lee
2,420,552 A 5/1947 Morrill
2,441,096 A 5/1948 Happe
2,448,741 A 9/1948 Scott et al.
2,450,527 A 10/1948 Smith
2,491,872 A 12/1949 Neuman
2,507,872 A 5/1950 Unsinger
2,526,902 A 10/1950 Rublee
2,527,256 A 10/1950 Jackson
2,578,686 A 12/1951 Fish
2,638,901 A 5/1953 Sugarbaker
2,674,149 A 4/1954 Benson
2,701,489 A 2/1955 Osborn
2,711,461 A 6/1955 Happe
2,724,289 A 11/1955 Wight
2,742,955 A 4/1956 Dominguez
2,804,848 A 9/1957 O'Farrell et al.
2,808,482 A 10/1957 Zanichkowsky et al.
2,825,178 A 3/1958 Hawkins
2,853,074 A 9/1958 Olson
2,856,192 A 10/1958 Schuster
2,887,004 A 5/1959 Stewart
2,957,353 A 10/1960 Lewis
2,959,974 A 11/1960 Emrick
3,026,744 A 3/1962 Rouse
3,032,769 A 5/1962 Palmer
3,035,256 A 5/1962 Egbert
3,060,972 A 10/1962 Sheldon
3,075,062 A 1/1963 Iaccarino
3,078,465 A 2/1963 Bobrov
3,079,606 A 3/1963 Bobrov et al.
3,080,564 A 3/1963 Strekopitov et al.
3,166,072 A 1/1965 Sullivan, Jr.
3,180,236 A 4/1965 Beckett
3,196,869 A 7/1965 Scholl
3,204,731 A 9/1965 Bent et al.
3,252,643 A 5/1966 Strekopytov et al.
3,266,494 A 8/1966 Brownrigg et al.
3,269,630 A 8/1966 Fleischer
3,269,631 A 8/1966 Takaro
3,275,211 A 9/1966 Hirsch et al.
3,315,863 A 4/1967 O'Dea
3,317,103 A 5/1967 Cullen et al.
3,317,105 A 5/1967 Astafjev et al.
3,357,296 A 12/1967 Lefever
3,359,978 A 12/1967 Smith, Jr.
3,377,893 A 4/1968 Shorb
3,480,193 A 11/1969 Ralston
3,490,675 A 1/1970 Green et al.
3,494,533 A 2/1970 Green et al.
3,499,591 A 3/1970 Green
3,503,396 A 3/1970 Pierie et al.
3,509,629 A 5/1970 Kidokoro
3,551,987 A 1/1971 Wilkinson
3,568,675 A 3/1971 Harvey
3,572,159 A 3/1971 Tschanz
3,583,393 A 6/1971 Takahashi
3,589,589 A 6/1971 Akopov
3,598,943 A 8/1971 Barrett

(56) References Cited

U.S. PATENT DOCUMENTS 3,604,561 A 9/1971 Mallina et al.
3,608,549 A 9/1971 Merrill
3,616,278 A 10/1971 Jansen
3,618,842 A 11/1971 Bryan
3,635,394 A 1/1972 Natelson
3,638,652 A 2/1972 Kelley
3,640,317 A 2/1972 Panfili
3,643,851 A 2/1972 Green et al.
3,650,453 A 3/1972 Smith, Jr.
3,661,339 A 5/1972 Shimizu
3,661,666 A 5/1972 Foster et al.
3,662,939 A 5/1972 Bryan
3,685,250 A 8/1972 Henry et al.
3,688,966 A 9/1972 Perkins et al.
3,692,224 A 9/1972 Astafiev et al.
3,695,646 A 10/1972 Mommsen
3,709,221 A 1/1973 Riely
3,717,294 A 2/1973 Green
3,724,237 A 4/1973 Wood
3,726,755 A 4/1973 Shannon
3,727,904 A 4/1973 Gabbey
3,734,207 A 5/1973 Fishbein
3,740,994 A 6/1973 De Carlo, Jr.
3,744,495 A 7/1973 Johnson
3,746,002 A 7/1973 Haller
3,747,603 A 7/1973 Adler
3,747,692 A 7/1973 Davidson
3,751,902 A 8/1973 Kingsbury et al.
3,752,161 A 8/1973 Bent
3,797,494 A 3/1974 Zaffaroni
3,799,151 A 3/1974 Fukaumi et al.
3,808,452 A 4/1974 Hutchinson
3,815,476 A 6/1974 Green et al.
3,819,100 A 6/1974 Noiles et al.
3,821,919 A 7/1974 Knohl
3,822,818 A 7/1974 Strekopytov et al.
3,825,007 A 7/1974 Rand
3,826,978 A 7/1974 Kelly
3,836,171 A 9/1974 Hayashi et al.
3,837,555 A 9/1974 Green
3,841,474 A 10/1974 Maier
3,851,196 A 11/1974 Hinds
3,863,639 A 2/1975 Kleaveland
3,863,940 A 2/1975 Cummings
3,883,624 A 5/1975 McKenzie et al.
3,885,491 A 5/1975 Curtis
3,887,393 A 6/1975 La Rue, Jr.
3,892,228 A 7/1975 Mitsui
3,894,174 A 7/1975 Cartun
3,899,829 A 8/1975 Storm et al.
3,902,247 A 9/1975 Fleer et al.
3,940,844 A 3/1976 Colby et al.
3,944,163 A 3/1976 Hayashi et al.
3,950,686 A 4/1976 Randall
3,952,747 A 4/1976 Kimmell, Jr.
3,955,581 A 5/1976 Spasiano et al.
3,959,879 A 6/1976 Sellers
RE28,932 E 8/1976 Noiles et al.
3,972,734 A 8/1976 King
3,973,179 A 8/1976 Weber et al.
3,981,051 A 9/1976 Brumlik
3,993,072 A 11/1976 Zaffaroni
3,999,110 A 12/1976 Ramstrom et al.
4,000,782 A * 1/1977 Finkelston .............. B25B 23/14
73/862.24
4,025,216 A 5/1977 Hives
4,027,746 A 6/1977 Kine
4,034,143 A 7/1977 Sweet
4,038,987 A 8/1977 Komiya
4,047,654 A 9/1977 Alvarado
4,054,108 A 10/1977 Gill
4,060,089 A 11/1977 Noiles
4,066,133 A 1/1978 Voss
4,085,337 A 4/1978 Moeller
4,100,820 A 7/1978 Evett
4,106,446 A 8/1978 Yamada et al.
4,106,620 A 8/1978 Brimmer et al.
4,108,211 A 8/1978 Tanaka
4,111,206 A 9/1978 Vishnevsky et al.
4,127,227 A 11/1978 Green
4,129,059 A 12/1978 Van Eck
4,132,146 A 1/1979 Uhlig
4,135,517 A 1/1979 Reale
4,149,461 A 4/1979 Simeth
4,154,122 A 5/1979 Severin
4,160,857 A 7/1979 Nardella et al.
4,169,476 A 10/1979 Hiltebrandt
4,169,990 A 10/1979 Lerdman
4,180,285 A 12/1979 Reneau
4,185,701 A 1/1980 Boys
4,190,042 A 2/1980 Sinnreich
4,191,377 A 3/1980 Burnside
4,198,734 A 4/1980 Brumlik
4,198,982 A 4/1980 Fortner et al.
4,203,444 A 5/1980 Bonnell et al.
4,207,898 A 6/1980 Becht
4,213,562 A 7/1980 Garrett et al.
4,226,242 A 10/1980 Jarvik
4,239,431 A 12/1980 Davini
4,241,861 A 12/1980 Fleischer
4,244,372 A 1/1981 Kapitanov et al.
4,250,436 A 2/1981 Weissman
4,250,817 A 2/1981 Michel
4,261,244 A 4/1981 Becht et al.
4,272,002 A 6/1981 Moshofsky
4,272,662 A 6/1981 Simpson
4,274,304 A 6/1981 Curtiss
4,274,398 A 6/1981 Scott, Jr.
4,275,813 A 6/1981 Noiles
4,278,091 A 7/1981 Borzone
4,282,573 A 8/1981 Imai et al.
4,289,131 A 9/1981 Mueller
4,289,133 A 9/1981 Rothfuss
4,290,542 A 9/1981 Fedotov et al.
D261,356 S 10/1981 Robinson
4,293,604 A 10/1981 Campbell
4,296,654 A 10/1981 Mercer
4,296,881 A 10/1981 Lee
4,304,236 A 12/1981 Conta et al.
4,305,539 A 12/1981 Korolkov et al.
4,312,363 A 1/1982 Rothfuss et al.
4,312,685 A 1/1982 Riedl
4,317,451 A 3/1982 Cerwin et al.
4,319,576 A 3/1982 Rothfuss
4,321,002 A 3/1982 Froehlich
4,321,746 A 3/1982 Grinage
4,328,839 A 5/1982 Lyons et al.
4,331,277 A 5/1982 Green
4,340,331 A 7/1982 Savino
4,347,450 A 8/1982 Colligan
4,348,603 A 9/1982 Huber
4,349,028 A 9/1982 Green
4,350,151 A 9/1982 Scott
4,353,371 A 10/1982 Cosman
4,357,940 A 11/1982 Muller
4,361,057 A 11/1982 Kochera
4,366,544 A 12/1982 Shima et al.
4,369,013 A 1/1983 Abildgaard et al.
4,373,147 A 2/1983 Carlson, Jr.
4,376,380 A 3/1983 Burgess
4,379,457 A 4/1983 Gravener et al.
4,380,312 A 4/1983 Landrus
4,382,326 A 5/1983 Rabuse
4,383,634 A 5/1983 Green
4,389,963 A 6/1983 Pearson
4,393,728 A 7/1983 Larson et al.
4,394,613 A 7/1983 Cole
4,396,139 A 8/1983 Hall et al.
4,397,311 A 8/1983 Kanshin et al.
4,402,445 A 9/1983 Green
4,406,621 A 9/1983 Bailey
4,408,692 A 10/1983 Sigel et al.
4,409,057 A 10/1983 Molenda et al.
4,415,112 A 11/1983 Green

(56) References Cited

U.S. PATENT DOCUMENTS 4,416,276 A 11/1983 Newton et al.
4,417,890 A 11/1983 Dennehey et al.
4,421,264 A 12/1983 Arter et al.
4,423,456 A 12/1983 Zaidenweber
4,425,915 A 1/1984 Ivanov
4,428,376 A 1/1984 Mericle
4,429,695 A 2/1984 Green
4,430,997 A 2/1984 DiGiovanni et al.
4,434,796 A 3/1984 Karapetian et al.
4,438,659 A 3/1984 Desplats
4,442,964 A 4/1984 Becht
4,448,194 A 5/1984 DiGiovanni et al.
4,451,743 A 5/1984 Suzuki et al.
4,452,376 A 6/1984 Klieman et al.
4,454,887 A 6/1984 Kruger
4,459,519 A 7/1984 Erdman
4,461,305 A 7/1984 Cibley
4,467,805 A 8/1984 Fukuda
4,468,597 A 8/1984 Baumard et al.
4,469,481 A 9/1984 Kobayashi
4,470,414 A 9/1984 Imagawa et al.
4,471,780 A 9/1984 Menges et al.
4,471,781 A 9/1984 Di Giovanni et al.
4,473,077 A 9/1984 Noiles et al.
4,475,679 A 10/1984 Fleury, Jr.
4,476,864 A 10/1984 Tezel
4,478,220 A 10/1984 Di Giovanni et al.
4,480,641 A 11/1984 Failla et al.
4,481,458 A 11/1984 Lane
4,483,562 A 11/1984 Schoolman
4,485,816 A 12/1984 Krumme
4,485,817 A 12/1984 Swiggett
4,486,928 A 12/1984 Tucker et al.
4,488,523 A 12/1984 Shichman
4,489,875 A 12/1984 Crawford et al.
4,493,983 A 1/1985 Taggert
4,494,057 A 1/1985 Hotta
4,499,895 A 2/1985 Takayama
4,500,024 A 2/1985 DiGiovanni et al.
D278,081 S 3/1985 Green
4,503,842 A 3/1985 Takayama
4,505,272 A 3/1985 Utyamyshev et al.
4,505,273 A 3/1985 Braun et al.
4,505,414 A 3/1985 Filipi
4,506,671 A 3/1985 Green
4,512,038 A 4/1985 Alexander et al.
4,514,477 A 4/1985 Kobayashi
4,520,817 A 6/1985 Green
4,522,327 A 6/1985 Korthoff et al.
4,523,707 A 6/1985 Blake, III et al.
4,526,174 A 7/1985 Froehlich
4,527,724 A 7/1985 Chow et al.
4,530,357 A 7/1985 Pawloski et al.
4,530,453 A 7/1985 Green
4,531,522 A 7/1985 Bedi et al.
4,532,927 A 8/1985 Miksza, Jr.
4,540,202 A 9/1985 Amphoux et al.
4,548,202 A 10/1985 Duncan
4,556,058 A 12/1985 Green
4,560,915 A 12/1985 Soultanian
4,565,109 A 1/1986 Tsay
4,565,189 A 1/1986 Mabuchi
4,566,620 A 1/1986 Green et al.
4,569,346 A 2/1986 Poirier
4,569,469 A 2/1986 Mongeon et al.
4,571,213 A 2/1986 Ishimoto
4,573,468 A 3/1986 Conta et al.
4,573,469 A 3/1986 Golden et al.
4,573,622 A 3/1986 Green et al.
4,576,165 A 3/1986 Green et al.
4,576,167 A 3/1986 Noiles
4,580,712 A 4/1986 Green
4,585,153 A 4/1986 Failla et al.
4,586,501 A 5/1986 Claracq
4,586,502 A 5/1986 Bedi et al.
4,589,416 A 5/1986 Green
4,589,582 A 5/1986 Bilotti
4,589,870 A 5/1986 Citrin et al.
4,591,085 A 5/1986 Di Giovanni
RE32,214 E 7/1986 Schramm
4,597,753 A 7/1986 Turley
4,600,037 A 7/1986 Hatten
4,604,786 A 8/1986 Howie, Jr.
4,605,001 A 8/1986 Rothfuss et al.
4,605,004 A 8/1986 Di Giovanni et al.
4,606,343 A 8/1986 Conta et al.
4,607,636 A 8/1986 Kula et al.
4,607,638 A 8/1986 Crainich
4,608,980 A 9/1986 Aihara
4,608,981 A 9/1986 Rothfuss et al.
4,610,250 A 9/1986 Green
4,610,383 A 9/1986 Rothfuss et al.
4,612,933 A 9/1986 Brinkerhoff et al.
D286,180 S 10/1986 Korthoff
D286,442 S 10/1986 Korthoff et al.
4,617,893 A 10/1986 Donner et al.
4,617,914 A 10/1986 Ueda
4,617,935 A 10/1986 Cartmell et al.
4,619,262 A 10/1986 Taylor
4,619,391 A 10/1986 Sharkany et al.
4,624,401 A 11/1986 Gassner et al.
D287,278 S 12/1986 Spreckelmeier
4,628,459 A 12/1986 Shinohara et al.
4,628,636 A 12/1986 Folger
4,629,107 A 12/1986 Fedotov et al.
4,632,290 A 12/1986 Green et al.
4,633,861 A 1/1987 Chow et al.
4,633,874 A 1/1987 Chow et al.
4,634,419 A 1/1987 Kreizman et al.
4,635,638 A 1/1987 Weintraub et al.
4,641,076 A 2/1987 Linden
4,642,618 A 2/1987 Johnson et al.
4,642,738 A 2/1987 Meller
4,643,173 A 2/1987 Bell et al.
4,643,731 A 2/1987 Eckenhoff
4,646,722 A 3/1987 Silverstein et al.
4,646,745 A 3/1987 Noiles
4,651,734 A 3/1987 Doss et al.
4,652,820 A 3/1987 Maresca
4,654,028 A 3/1987 Suma
4,655,222 A 4/1987 Florez et al.
4,662,555 A 5/1987 Thornton
4,663,874 A 5/1987 Sano et al.
4,664,305 A 5/1987 Blake, III et al.
4,665,916 A 5/1987 Green
4,667,674 A 5/1987 Korthoff et al.
4,669,647 A 6/1987 Storace
4,671,278 A 6/1987 Chin
4,671,280 A 6/1987 Dorband et al.
4,671,445 A 6/1987 Barker et al.
4,672,964 A 6/1987 Dee et al.
4,675,944 A 6/1987 Wells
4,676,245 A 6/1987 Fukuda
4,679,460 A 7/1987 Yoshigai
4,679,719 A 7/1987 Kramer
4,684,051 A 8/1987 Akopov et al.
4,688,555 A 8/1987 Wardle
4,691,703 A 9/1987 Auth et al.
4,693,248 A 9/1987 Failla
4,698,579 A 10/1987 Richter et al.
4,700,703 A 10/1987 Resnick et al.
4,705,038 A 11/1987 Sjostrom et al.
4,708,141 A 11/1987 Inoue et al.
4,709,120 A 11/1987 Pearson
4,715,520 A 12/1987 Roehr, Jr. et al.
4,719,917 A 1/1988 Barrows et al.
4,721,099 A 1/1988 Chikama
4,722,340 A 2/1988 Takayama et al.
4,724,840 A 2/1988 McVay et al.
4,726,247 A 2/1988 Hormann
4,727,308 A 2/1988 Huljak et al.
4,728,020 A 3/1988 Green et al.
4,728,876 A 3/1988 Mongeon et al.
4,729,260 A 3/1988 Dudden

(56) References Cited

U.S. PATENT DOCUMENTS 4,730,726 A 3/1988 Holzwarth
4,741,336 A 5/1988 Failla et al.
4,743,214 A 5/1988 Tai-Cheng
4,744,363 A 5/1988 Hasson
4,747,820 A 5/1988 Hornlein et al.
4,750,902 A 6/1988 Wuchinich et al.
4,752,024 A 6/1988 Green et al.
4,754,909 A 7/1988 Barker et al.
4,755,070 A 7/1988 Cerutti
4,761,326 A 8/1988 Barnes et al.
4,763,669 A 8/1988 Jaeger
4,767,044 A 8/1988 Green
D297,764 S 9/1988 Hunt et al.
4,773,420 A 9/1988 Green
4,777,780 A 10/1988 Holzwarth
4,781,186 A 11/1988 Simpson et al.
4,784,137 A 11/1988 Kulik et al.
4,787,387 A 11/1988 Burbank, III et al.
4,788,485 A 11/1988 Kawagishi et al.
D298,967 S 12/1988 Hunt
4,788,978 A 12/1988 Strekopytov et al.
4,790,225 A 12/1988 Moody et al.
4,790,314 A 12/1988 Weaver
4,805,617 A 2/1989 Bedi et al.
4,805,823 A 2/1989 Rothfuss
4,807,628 A 2/1989 Peters et al.
4,809,695 A 3/1989 Gwathmey et al.
4,815,460 A 3/1989 Porat et al.
4,817,643 A 4/1989 Olson
4,817,847 A 4/1989 Redtenbacher et al.
4,819,495 A 4/1989 Hormann
4,819,853 A 4/1989 Green
4,821,939 A 4/1989 Green
4,827,552 A 5/1989 Bojar et al.
4,827,911 A 5/1989 Broadwin et al.
4,828,542 A 5/1989 Hermann
4,828,944 A 5/1989 Yabe et al.
4,830,855 A 5/1989 Stewart
4,832,158 A 5/1989 Farrar et al.
4,833,937 A 5/1989 Nagano
4,834,096 A 5/1989 Oh et al.
4,834,720 A 5/1989 Blinkhorn
4,838,859 A 6/1989 Strassmann
4,844,068 A 7/1989 Arata et al.
4,848,637 A 7/1989 Pruitt
4,856,078 A 8/1989 Konopka
4,860,644 A 8/1989 Kohl et al.
4,862,891 A 9/1989 Smith
4,863,423 A 9/1989 Wallace
4,865,030 A 9/1989 Polyak
4,868,530 A 9/1989 Ahs
4,868,958 A 9/1989 Suzuki et al.
4,869,414 A 9/1989 Green et al.
4,869,415 A 9/1989 Fox
4,870,966 A 10/1989 Dellon et al.
4,873,977 A 10/1989 Avant et al.
4,875,486 A 10/1989 Rapoport et al.
4,880,015 A 11/1989 Nierman
4,890,613 A 1/1990 Golden et al.
4,892,244 A 1/1990 Fox et al.
4,893,622 A 1/1990 Green et al.
4,894,051 A 1/1990 Shiber
4,896,584 A 1/1990 Stoll et al.
4,896,678 A 1/1990 Ogawa
4,900,303 A 2/1990 Lemelson
4,903,697 A 2/1990 Resnick et al.
4,909,789 A 3/1990 Taguchi et al.
4,915,100 A 4/1990 Green
4,919,039 A 4/1990 Nutter
4,919,679 A 4/1990 Averill et al.
4,921,479 A 5/1990 Grayzel
4,925,082 A 5/1990 Kim
4,928,699 A 5/1990 Sasai
4,930,503 A 6/1990 Pruitt
4,930,674 A 6/1990 Barak
4,931,047 A 6/1990 Broadwin et al.
4,931,737 A 6/1990 Hishiki
4,932,960 A 6/1990 Green et al.
4,933,800 A 6/1990 Yang
4,933,843 A 6/1990 Scheller et al.
D309,350 S 7/1990 Sutherland et al.
4,938,408 A 7/1990 Bedi et al.
4,941,623 A 7/1990 Pruitt
4,943,182 A 7/1990 Hoblingre
4,944,443 A 7/1990 Oddsen et al.
4,946,067 A 8/1990 Kelsall
4,948,327 A 8/1990 Crupi, Jr.
4,949,707 A 8/1990 LeVahn et al.
4,949,927 A 8/1990 Madocks et al.
4,950,268 A 8/1990 Rink
4,951,860 A 8/1990 Peters et al.
4,951,861 A 8/1990 Schulze et al.
4,954,960 A 9/1990 Lo et al.
4,955,959 A 9/1990 Tompkins et al.
4,957,212 A 9/1990 Duck et al.
4,962,681 A 10/1990 Yang
4,962,877 A 10/1990 Hervas
4,964,559 A 10/1990 Deniega et al.
4,964,863 A 10/1990 Kanshin et al.
4,965,709 A 10/1990 Ngo
4,970,656 A 11/1990 Lo et al.
4,973,274 A 11/1990 Hirukawa
4,973,302 A 11/1990 Armour et al.
4,976,173 A 12/1990 Yang
4,978,049 A 12/1990 Green
4,978,333 A 12/1990 Broadwin et al.
4,979,952 A 12/1990 Kubota et al.
4,984,564 A 1/1991 Yuen
4,986,808 A 1/1991 Broadwin et al.
4,987,049 A 1/1991 Komamura et al.
4,988,334 A 1/1991 Hornlein et al.
4,995,877 A 2/1991 Ams et al.
4,995,959 A 2/1991 Metzner
4,996,975 A 3/1991 Nakamura
5,001,649 A 3/1991 Lo et al.
5,002,543 A 3/1991 Bradshaw et al.
5,002,553 A 3/1991 Shiber
5,005,754 A 4/1991 Van Overloop
5,009,222 A 4/1991 Her
5,009,661 A 4/1991 Michelson
5,012,411 A 4/1991 Policastro et al.
D316,875 S 5/1991 Momot et al.
5,014,898 A 5/1991 Heidrich
5,014,899 A 5/1991 Presty et al.
5,015,227 A 5/1991 Broadwin et al.
5,018,515 A 5/1991 Gilman
5,018,657 A 5/1991 Pedlick et al.
5,019,077 A 5/1991 De Bastiani et al.
5,024,652 A 6/1991 Dumenek et al.
5,024,671 A 6/1991 Tu et al.
5,025,559 A 6/1991 McCullough
5,027,834 A 7/1991 Pruitt
5,030,226 A 7/1991 Green et al.
5,031,814 A 7/1991 Tompkins et al.
5,033,552 A 7/1991 Hu
5,035,040 A 7/1991 Kerrigan et al.
5,037,018 A 8/1991 Matsuda et al.
5,038,109 A 8/1991 Goble et al.
5,038,247 A 8/1991 Kelley et al.
5,040,715 A 8/1991 Green et al.
5,042,707 A 8/1991 Taheri
5,056,953 A 10/1991 Marot et al.
5,060,658 A 10/1991 Dejter, Jr. et al.
5,061,269 A 10/1991 Muller
5,062,491 A 11/1991 Takeshima et al.
5,062,563 A 11/1991 Green et al.
5,065,929 A 11/1991 Schulze et al.
5,071,052 A 12/1991 Rodak et al.
5,071,430 A 12/1991 de Salis et al.
5,074,454 A 12/1991 Peters
5,077,506 A 12/1991 Krause
5,079,006 A 1/1992 Urquhart
5,080,556 A 1/1992 Carreno
5,083,695 A 1/1992 Foslien et al.

(56) References Cited

U.S. PATENT DOCUMENTS

| | | | |
|---|---|---|---|
| 5,084,057 | A | 1/1992 | Green et al. |
| 5,088,979 | A | 2/1992 | Filipi et al. |
| 5,088,997 | A | 2/1992 | Delahuerga et al. |
| 5,089,606 | A | 2/1992 | Cole et al. |
| 5,094,247 | A | 3/1992 | Hernandez et al. |
| 5,098,004 | A | 3/1992 | Kerrigan |
| 5,098,360 | A | 3/1992 | Hirota |
| 5,100,042 | A | 3/1992 | Gravener et al. |
| 5,100,420 | A | 3/1992 | Green et al. |
| 5,100,422 | A | 3/1992 | Berguer et al. |
| 5,104,025 | A | 4/1992 | Main et al. |
| 5,104,397 | A | 4/1992 | Vasconcelos et al. |
| 5,104,400 | A | 4/1992 | Berguer et al. |
| 5,106,008 | A | 4/1992 | Tompkins et al. |
| 5,108,368 | A | 4/1992 | Hammerslag et al. |
| 5,109,722 | A | 5/1992 | Hufnagle et al. |
| 5,111,987 | A | 5/1992 | Moeinzadeh et al. |
| 5,116,349 | A | 5/1992 | Aranyi |
| D327,323 | S | 6/1992 | Hunt |
| 5,119,009 | A | 6/1992 | McCaleb et al. |
| 5,122,156 | A | 6/1992 | Granger et al. |
| 5,124,990 | A | 6/1992 | Williamson |
| 5,129,570 | A | 7/1992 | Schulze et al. |
| 5,135,483 | A | 8/1992 | Wagner et al. |
| 5,137,198 | A | 8/1992 | Nobis et al. |
| 5,139,513 | A | 8/1992 | Segato |
| 5,141,144 | A | 8/1992 | Foslien et al. |
| 5,142,932 | A | 9/1992 | Moya et al. |
| 5,151,102 | A | 9/1992 | Kamiyama et al. |
| 5,155,941 | A | 10/1992 | Takahashi et al. |
| 5,156,151 | A | 10/1992 | Imran |
| 5,156,315 | A | 10/1992 | Green et al. |
| 5,156,609 | A | 10/1992 | Nakao et al. |
| 5,156,614 | A | 10/1992 | Green et al. |
| 5,158,222 | A | 10/1992 | Green et al. |
| 5,158,567 | A | 10/1992 | Green |
| D330,699 | S | 11/1992 | Gill |
| 5,163,598 | A | 11/1992 | Peters et al. |
| 5,163,842 | A | 11/1992 | Nonomura |
| 5,164,652 | A | 11/1992 | Johnson et al. |
| 5,168,605 | A | 12/1992 | Bartlett |
| 5,170,925 | A | 12/1992 | Madden et al. |
| 5,171,247 | A | 12/1992 | Hughett et al. |
| 5,171,249 | A | 12/1992 | Stefanchik et al. |
| 5,171,253 | A | 12/1992 | Klieman |
| 5,173,053 | A | 12/1992 | Swanson et al. |
| 5,173,133 | A | 12/1992 | Morin et al. |
| 5,176,677 | A | 1/1993 | Wuchinich |
| 5,176,688 | A | 1/1993 | Narayan et al. |
| 5,180,375 | A | 1/1993 | Feibus |
| 5,181,514 | A | 1/1993 | Solomon et al. |
| 5,187,422 | A | 2/1993 | Izenbaard et al. |
| 5,188,102 | A | 2/1993 | Idemoto et al. |
| 5,188,111 | A | 2/1993 | Yates et al. |
| 5,188,126 | A | 2/1993 | Fabian et al. |
| 5,190,517 | A | 3/1993 | Zieve et al. |
| 5,190,544 | A | 3/1993 | Chapman et al. |
| 5,190,560 | A | 3/1993 | Woods et al. |
| 5,190,657 | A | 3/1993 | Heagle et al. |
| 5,192,288 | A | 3/1993 | Thompson et al. |
| 5,193,731 | A | 3/1993 | Aranyi |
| 5,195,505 | A | 3/1993 | Josefsen |
| 5,195,968 | A | 3/1993 | Lundquist et al. |
| 5,197,648 | A | 3/1993 | Gingold |
| 5,197,649 | A | 3/1993 | Bessler et al. |
| 5,197,966 | A | 3/1993 | Sommerkamp |
| 5,197,970 | A | 3/1993 | Green et al. |
| 5,200,280 | A | 4/1993 | Karasa |
| 5,201,750 | A | 4/1993 | Hocherl et al. |
| 5,205,459 | A | 4/1993 | Brinkerhoff et al. |
| 5,207,672 | A | 5/1993 | Roth et al. |
| 5,207,697 | A | 5/1993 | Carusillo et al. |
| 5,209,747 | A | 5/1993 | Knoepfler |
| 5,209,756 | A | 5/1993 | Seedhom et al. |
| 5,211,649 | A | 5/1993 | Kohler et al. |
| 5,211,655 | A | 5/1993 | Hasson |
| 5,217,457 | A | 6/1993 | Delahuerga et al. |
| 5,217,478 | A | 6/1993 | Rexroth |
| 5,219,111 | A | 6/1993 | Bilotti et al. |
| 5,220,269 | A | 6/1993 | Chen et al. |
| 5,221,036 | A | 6/1993 | Takase |
| 5,221,281 | A | 6/1993 | Klicek |
| 5,222,945 | A | 6/1993 | Basnight |
| 5,222,963 | A | 6/1993 | Brinkerhoff et al. |
| 5,222,975 | A | 6/1993 | Crainich |
| 5,222,976 | A | 6/1993 | Yoon |
| 5,223,675 | A | 6/1993 | Taft |
| D337,962 | S | 8/1993 | Avitan |
| D338,729 | S | 8/1993 | Sprecklemeier et al. |
| 5,234,447 | A | 8/1993 | Kaster et al. |
| 5,236,269 | A | 8/1993 | Handy |
| 5,236,424 | A | 8/1993 | Imran |
| 5,236,440 | A | 8/1993 | Hlavacek |
| 5,236,629 | A | 8/1993 | Mahabadi et al. |
| 5,239,981 | A | 8/1993 | Anapliotis |
| 5,240,163 | A | 8/1993 | Stein et al. |
| 5,242,456 | A | 9/1993 | Nash et al. |
| 5,242,457 | A | 9/1993 | Akopov et al. |
| 5,244,462 | A | 9/1993 | Delahuerga et al. |
| 5,246,156 | A | 9/1993 | Rothfuss et al. |
| 5,246,443 | A | 9/1993 | Mai |
| 5,251,801 | A | 10/1993 | Ruckdeschel et al. |
| 5,253,793 | A | 10/1993 | Green et al. |
| 5,258,007 | A | 11/1993 | Spetzler et al. |
| 5,258,008 | A | 11/1993 | Wilk |
| 5,258,009 | A | 11/1993 | Conners |
| 5,258,010 | A | 11/1993 | Green et al. |
| 5,258,012 | A | 11/1993 | Luscombe et al. |
| 5,259,366 | A | 11/1993 | Reydel et al. |
| 5,259,835 | A | 11/1993 | Clark et al. |
| 5,260,637 | A | 11/1993 | Pizzi |
| 5,261,135 | A | 11/1993 | Mitchell |
| 5,261,877 | A | 11/1993 | Fine et al. |
| 5,261,922 | A | 11/1993 | Hood |
| 5,263,629 | A | 11/1993 | Trumbull et al. |
| 5,263,937 | A | 11/1993 | Shipp |
| 5,263,973 | A | 11/1993 | Cook |
| 5,264,218 | A | 11/1993 | Rogozinski |
| 5,268,622 | A | 12/1993 | Philipp |
| 5,269,794 | A | 12/1993 | Rexroth |
| 5,271,543 | A | 12/1993 | Grant et al. |
| 5,271,544 | A | 12/1993 | Fox et al. |
| RE34,519 | E | 1/1994 | Fox et al. |
| 5,275,322 | A | 1/1994 | Brinkerhoff et al. |
| 5,275,323 | A | 1/1994 | Schulze et al. |
| 5,275,608 | A | 1/1994 | Forman et al. |
| 5,279,416 | A | 1/1994 | Malec et al. |
| 5,281,216 | A | 1/1994 | Klicek |
| 5,281,400 | A | 1/1994 | Berry, Jr. |
| 5,282,806 | A | 2/1994 | Haber et al. |
| 5,282,826 | A | 2/1994 | Quadri |
| 5,282,829 | A | 2/1994 | Hermes |
| 5,284,128 | A | 2/1994 | Hart |
| 5,285,381 | A | 2/1994 | Iskarous et al. |
| 5,285,945 | A | 2/1994 | Brinkerhoff et al. |
| 5,286,253 | A | 2/1994 | Fucci |
| 5,289,963 | A | 3/1994 | McGarry et al. |
| 5,290,271 | A | 3/1994 | Jernberg |
| 5,290,310 | A | 3/1994 | Makower et al. |
| 5,291,133 | A | 3/1994 | Gokhale et al. |
| 5,292,053 | A | 3/1994 | Bilotti et al. |
| 5,293,024 | A | 3/1994 | Sugahara et al. |
| 5,297,714 | A | 3/1994 | Kramer |
| 5,300,087 | A | 4/1994 | Knoepfler |
| 5,302,148 | A | 4/1994 | Heinz |
| 5,303,606 | A | 4/1994 | Kokinda |
| 5,304,204 | A | 4/1994 | Bregen |
| D347,474 | S | 5/1994 | Olson |
| 5,307,976 | A | 5/1994 | Olson et al. |
| 5,308,353 | A | 5/1994 | Beurrier |
| 5,308,358 | A | 5/1994 | Bond et al. |
| 5,308,576 | A | 5/1994 | Green et al. |
| 5,309,387 | A | 5/1994 | Mori et al. |
| 5,309,927 | A | 5/1994 | Welch |

(56) References Cited

U.S. PATENT DOCUMENTS

| | | | |
|---|---|---|---|
| 5,312,023 | A | 5/1994 | Green et al. |
| 5,312,024 | A | 5/1994 | Grant et al. |
| 5,312,329 | A | 5/1994 | Beaty et al. |
| 5,313,935 | A | 5/1994 | Kortenbach et al. |
| 5,313,967 | A | 5/1994 | Lieber et al. |
| 5,314,424 | A | 5/1994 | Nicholas |
| 5,314,445 | A | 5/1994 | Heidmueller et al. |
| 5,314,466 | A | 5/1994 | Stern et al. |
| 5,318,221 | A | 6/1994 | Green et al. |
| 5,318,589 | A | 6/1994 | Lichtman |
| 5,320,627 | A | 6/1994 | Sorensen et al. |
| D348,930 | S | 7/1994 | Olson |
| 5,326,013 | A | 7/1994 | Green et al. |
| 5,329,923 | A | 7/1994 | Lundquist |
| 5,330,486 | A | 7/1994 | Wilk |
| 5,330,487 | A | 7/1994 | Thornton et al. |
| 5,330,502 | A | 7/1994 | Hassler et al. |
| 5,331,971 | A | 7/1994 | Bales et al. |
| 5,332,142 | A | 7/1994 | Robinson et al. |
| 5,333,422 | A | 8/1994 | Warren et al. |
| 5,333,772 | A | 8/1994 | Rothfuss et al. |
| 5,333,773 | A | 8/1994 | Main et al. |
| 5,334,183 | A | 8/1994 | Wuchinich |
| 5,336,130 | A | 8/1994 | Ray |
| 5,336,229 | A | 8/1994 | Noda |
| 5,336,232 | A | 8/1994 | Green et al. |
| 5,338,317 | A | 8/1994 | Hasson et al. |
| 5,339,799 | A | 8/1994 | Kami et al. |
| 5,341,724 | A | 8/1994 | Vatel |
| 5,341,807 | A | 8/1994 | Nardella |
| 5,341,810 | A | 8/1994 | Dardel |
| 5,342,380 | A | 8/1994 | Hood |
| 5,342,381 | A | 8/1994 | Tidemand |
| 5,342,385 | A | 8/1994 | Norelli et al. |
| 5,342,395 | A | 8/1994 | Jarrett et al. |
| 5,342,396 | A | 8/1994 | Cook |
| 5,343,382 | A | 8/1994 | Hale et al. |
| 5,343,391 | A | 8/1994 | Mushabac |
| 5,344,059 | A | 9/1994 | Green et al. |
| 5,344,060 | A | 9/1994 | Gravener et al. |
| 5,344,454 | A | 9/1994 | Clarke et al. |
| 5,346,504 | A | 9/1994 | Ortiz et al. |
| 5,348,259 | A | 9/1994 | Blanco et al. |
| 5,350,104 | A | 9/1994 | Main et al. |
| 5,350,355 | A | 9/1994 | Sklar |
| 5,350,388 | A | 9/1994 | Epstein |
| 5,350,391 | A | 9/1994 | Iacovelli |
| 5,350,400 | A | 9/1994 | Esposito et al. |
| 5,352,229 | A | 10/1994 | Goble et al. |
| 5,352,235 | A | 10/1994 | Koros et al. |
| 5,352,238 | A | 10/1994 | Green et al. |
| 5,353,798 | A | 10/1994 | Sieben |
| 5,354,215 | A | 10/1994 | Viracola |
| 5,354,250 | A | 10/1994 | Christensen |
| 5,354,303 | A | 10/1994 | Spaeth et al. |
| 5,355,897 | A | 10/1994 | Pietrafitta et al. |
| 5,356,006 | A | 10/1994 | Alpern et al. |
| 5,356,064 | A | 10/1994 | Green et al. |
| 5,358,506 | A | 10/1994 | Green et al. |
| 5,358,510 | A | 10/1994 | Luscombe et al. |
| 5,359,231 | A | 10/1994 | Flowers et al. |
| D352,780 | S | 11/1994 | Glaeser et al. |
| 5,359,993 | A | 11/1994 | Slater et al. |
| 5,360,305 | A | 11/1994 | Kerrigan |
| 5,360,428 | A | 11/1994 | Hutchinson, Jr. |
| 5,361,902 | A | 11/1994 | Abidin et al. |
| 5,364,001 | A | 11/1994 | Bryan |
| 5,364,002 | A | 11/1994 | Green et al. |
| 5,364,003 | A | 11/1994 | Williamson, IV |
| 5,366,133 | A | 11/1994 | Geiste |
| 5,366,134 | A | 11/1994 | Green et al. |
| 5,366,479 | A | 11/1994 | McGarry et al. |
| 5,368,015 | A | 11/1994 | Wilk |
| 5,368,592 | A | 11/1994 | Stern et al. |
| 5,368,599 | A | 11/1994 | Hirsch et al. |
| 5,369,565 | A | 11/1994 | Chen et al. |
| 5,370,645 | A | 12/1994 | Klicek et al. |
| 5,372,124 | A | 12/1994 | Takayama et al. |
| 5,372,596 | A | 12/1994 | Klicek et al. |
| 5,372,602 | A | 12/1994 | Burke |
| 5,374,277 | A | 12/1994 | Hassler |
| 5,375,588 | A | 12/1994 | Yoon |
| 5,376,095 | A | 12/1994 | Ortiz |
| 5,379,933 | A | 1/1995 | Green et al. |
| 5,381,649 | A | 1/1995 | Webb |
| 5,381,782 | A | 1/1995 | DeLaRama et al. |
| 5,381,943 | A | 1/1995 | Allen et al. |
| 5,382,247 | A | 1/1995 | Cimino et al. |
| 5,383,460 | A | 1/1995 | Jang et al. |
| 5,383,738 | A | 1/1995 | Herbermann |
| 5,383,874 | A | 1/1995 | Jackson et al. |
| 5,383,880 | A | 1/1995 | Hooven |
| 5,383,881 | A | 1/1995 | Green et al. |
| 5,383,882 | A | 1/1995 | Buess et al. |
| 5,383,888 | A | 1/1995 | Zvenyatsky et al. |
| 5,383,895 | A | 1/1995 | Holmes et al. |
| 5,388,568 | A | 2/1995 | van der Heide |
| 5,388,748 | A | 2/1995 | Davignon et al. |
| 5,389,072 | A | 2/1995 | Imran |
| 5,389,098 | A | 2/1995 | Tsuruta et al. |
| 5,389,102 | A | 2/1995 | Green et al. |
| 5,389,104 | A | 2/1995 | Hahnen et al. |
| 5,391,180 | A | 2/1995 | Tovey et al. |
| 5,392,979 | A | 2/1995 | Green et al. |
| 5,395,030 | A | 3/1995 | Kuramoto et al. |
| 5,395,033 | A | 3/1995 | Byrne et al. |
| 5,395,034 | A | 3/1995 | Allen et al. |
| 5,395,312 | A | 3/1995 | Desai |
| 5,395,384 | A | 3/1995 | Duthoit et al. |
| 5,397,046 | A | 3/1995 | Savage et al. |
| 5,397,324 | A | 3/1995 | Carroll et al. |
| 5,400,267 | A | 3/1995 | Denen et al. |
| 5,403,276 | A | 4/1995 | Schechter et al. |
| 5,403,312 | A | 4/1995 | Yates et al. |
| 5,404,106 | A | 4/1995 | Matsuda |
| 5,404,870 | A | 4/1995 | Brinkerhoff et al. |
| 5,404,960 | A | 4/1995 | Wada et al. |
| 5,405,072 | A | 4/1995 | Zlock et al. |
| 5,405,073 | A | 4/1995 | Porter |
| 5,405,344 | A | 4/1995 | Williamson et al. |
| 5,405,360 | A | 4/1995 | Tovey |
| 5,407,293 | A | 4/1995 | Crainich |
| 5,408,409 | A | 4/1995 | Glassman et al. |
| 5,409,498 | A | 4/1995 | Braddock et al. |
| 5,409,703 | A | 4/1995 | McAnalley et al. |
| D357,981 | S | 5/1995 | Green et al. |
| 5,411,481 | A | 5/1995 | Allen et al. |
| 5,411,508 | A | 5/1995 | Bessler et al. |
| 5,413,107 | A | 5/1995 | Oakley et al. |
| 5,413,267 | A | 5/1995 | Solyntjes et al. |
| 5,413,268 | A | 5/1995 | Green et al. |
| 5,413,272 | A | 5/1995 | Green et al. |
| 5,413,573 | A | 5/1995 | Koivukangas |
| 5,415,334 | A | 5/1995 | Williamson et al. |
| 5,415,335 | A | 5/1995 | Knodell, Jr. |
| 5,417,203 | A | 5/1995 | Tovey et al. |
| 5,417,361 | A | 5/1995 | Williamson, IV |
| 5,419,766 | A | 5/1995 | Chang et al. |
| 5,421,829 | A | 6/1995 | Olichney et al. |
| 5,422,567 | A | 6/1995 | Matsunaga |
| 5,423,471 | A | 6/1995 | Mastri et al. |
| 5,423,809 | A | 6/1995 | Klicek |
| 5,423,835 | A | 6/1995 | Green et al. |
| 5,425,355 | A | 6/1995 | Kulick |
| 5,425,745 | A | 6/1995 | Green et al. |
| 5,427,298 | A | 6/1995 | Tegtmeier |
| 5,431,322 | A | 7/1995 | Green et al. |
| 5,431,323 | A | 7/1995 | Smith et al. |
| 5,431,645 | A | 7/1995 | Smith et al. |
| 5,431,654 | A | 7/1995 | Nic |
| 5,431,666 | A | 7/1995 | Sauer et al. |
| 5,431,668 | A | 7/1995 | Burbank, III et al. |
| 5,433,721 | A | 7/1995 | Hooven et al. |
| 5,437,681 | A | 8/1995 | Meade et al. |

(56) References Cited

U.S. PATENT DOCUMENTS

| | | | |
|---|---|---|---|
| 5,438,302 | A | 8/1995 | Goble |
| 5,438,997 | A | 8/1995 | Sieben et al. |
| 5,439,155 | A | 8/1995 | Viola |
| 5,439,156 | A | 8/1995 | Grant et al. |
| 5,439,479 | A | 8/1995 | Shichman et al. |
| 5,441,191 | A | 8/1995 | Linden |
| 5,441,193 | A | 8/1995 | Gravener |
| 5,441,483 | A | 8/1995 | Avitall |
| 5,441,494 | A | 8/1995 | Ortiz |
| 5,441,499 | A | 8/1995 | Fritzsch |
| 5,443,197 | A | 8/1995 | Malis et al. |
| 5,443,198 | A | 8/1995 | Viola et al. |
| 5,443,463 | A | 8/1995 | Stern et al. |
| 5,444,113 | A | 8/1995 | Sinclair et al. |
| 5,445,155 | A | 8/1995 | Sieben |
| 5,445,304 | A | 8/1995 | Plyley et al. |
| 5,445,604 | A | 8/1995 | Lang |
| 5,445,644 | A | 8/1995 | Pietrafitta et al. |
| 5,446,646 | A | 8/1995 | Miyazaki |
| 5,447,265 | A | 9/1995 | Vidal et al. |
| 5,447,417 | A | 9/1995 | Kuhl et al. |
| 5,447,513 | A | 9/1995 | Davison et al. |
| 5,449,355 | A | 9/1995 | Rhum et al. |
| 5,449,365 | A | 9/1995 | Green et al. |
| 5,449,370 | A | 9/1995 | Vaitekunas |
| 5,452,836 | A | 9/1995 | Huitema et al. |
| 5,452,837 | A | 9/1995 | Williamson, IV et al. |
| 5,454,378 | A | 10/1995 | Palmer et al. |
| 5,454,822 | A | 10/1995 | Schob et al. |
| 5,454,824 | A | 10/1995 | Fontayne et al. |
| 5,454,827 | A | 10/1995 | Aust et al. |
| 5,456,401 | A | 10/1995 | Green et al. |
| 5,456,917 | A | 10/1995 | Wise et al. |
| 5,458,279 | A | 10/1995 | Plyley |
| 5,458,579 | A | 10/1995 | Chodorow et al. |
| 5,462,215 | A | 10/1995 | Viola et al. |
| 5,464,013 | A | 11/1995 | Lemelson |
| 5,464,144 | A | 11/1995 | Guy et al. |
| 5,464,300 | A | 11/1995 | Crainich |
| 5,465,819 | A | 11/1995 | Weilant et al. |
| 5,465,894 | A | 11/1995 | Clark et al. |
| 5,465,895 | A | 11/1995 | Knodel et al. |
| 5,465,896 | A | 11/1995 | Allen et al. |
| 5,466,020 | A | 11/1995 | Page et al. |
| 5,467,911 | A | 11/1995 | Tsuruta et al. |
| 5,468,253 | A | 11/1995 | Bezwada et al. |
| 5,470,006 | A | 11/1995 | Rodak |
| 5,470,007 | A | 11/1995 | Plyley et al. |
| 5,470,008 | A | 11/1995 | Rodak |
| 5,470,009 | A | 11/1995 | Rodak |
| 5,470,010 | A | 11/1995 | Rothfuss et al. |
| 5,471,129 | A | 11/1995 | Mann |
| 5,472,132 | A | 12/1995 | Savage et al. |
| 5,472,442 | A | 12/1995 | Klicek |
| 5,473,204 | A | 12/1995 | Temple |
| 5,474,057 | A | 12/1995 | Makower et al. |
| 5,474,223 | A | 12/1995 | Viola et al. |
| 5,474,566 | A | 12/1995 | Alesi et al. |
| 5,474,570 | A | 12/1995 | Kockerling et al. |
| 5,474,738 | A | 12/1995 | Nichols et al. |
| 5,476,206 | A | 12/1995 | Green et al. |
| 5,476,479 | A | 12/1995 | Green et al. |
| 5,476,481 | A | 12/1995 | Schondorf |
| 5,478,003 | A | 12/1995 | Green et al. |
| 5,478,308 | A | 12/1995 | Cartmell et al. |
| 5,478,354 | A | 12/1995 | Tovey et al. |
| 5,480,089 | A | 1/1996 | Blewett |
| 5,480,409 | A | 1/1996 | Riza |
| 5,482,197 | A | 1/1996 | Green et al. |
| 5,483,630 | A | 1/1996 | Unuma et al. |
| 5,483,952 | A | 1/1996 | Aranyi |
| 5,484,095 | A | 1/1996 | Green et al. |
| 5,484,398 | A | 1/1996 | Stoddard |
| 5,484,451 | A | 1/1996 | Akopov et al. |
| 5,485,947 | A | 1/1996 | Olson et al. |
| 5,485,952 | A | 1/1996 | Fontayne |
| 5,487,377 | A | 1/1996 | Smith et al. |
| 5,487,499 | A | 1/1996 | Sorrentino et al. |
| 5,487,500 | A | 1/1996 | Knodel et al. |
| 5,489,058 | A | 2/1996 | Plyley et al. |
| 5,489,256 | A | 2/1996 | Adair |
| 5,489,290 | A | 2/1996 | Furnish |
| 5,490,819 | A | 2/1996 | Nicholas et al. |
| 5,492,671 | A | 2/1996 | Krafft |
| 5,496,312 | A | 3/1996 | Klicek |
| 5,496,317 | A | 3/1996 | Goble et al. |
| 5,497,933 | A | 3/1996 | DeFonzo et al. |
| 5,498,164 | A | 3/1996 | Ward et al. |
| 5,498,838 | A | 3/1996 | Furman |
| 5,501,654 | A | 3/1996 | Failla et al. |
| 5,503,320 | A | 4/1996 | Webster et al. |
| 5,503,635 | A | 4/1996 | Sauer et al. |
| 5,503,638 | A | 4/1996 | Cooper et al. |
| 5,505,363 | A | 4/1996 | Green et al. |
| 5,507,425 | A | 4/1996 | Ziglioli |
| 5,507,426 | A | 4/1996 | Young et al. |
| 5,507,773 | A | 4/1996 | Huitema et al. |
| 5,508,080 | A | 4/1996 | Sorimachi et al. |
| 5,509,596 | A | 4/1996 | Green et al. |
| 5,509,916 | A | 4/1996 | Taylor |
| 5,509,918 | A | 4/1996 | Romano |
| 5,510,138 | A | 4/1996 | Sanftleben et al. |
| 5,511,564 | A | 4/1996 | Wilk |
| 5,514,129 | A | 5/1996 | Smith |
| 5,514,149 | A | 5/1996 | Green et al. |
| 5,514,157 | A | 5/1996 | Nicholas et al. |
| 5,518,163 | A | 5/1996 | Hooven |
| 5,518,164 | A | 5/1996 | Hooven |
| 5,520,609 | A | 5/1996 | Moll et al. |
| 5,520,634 | A | 5/1996 | Fox et al. |
| 5,520,678 | A | 5/1996 | Heckele et al. |
| 5,520,700 | A | 5/1996 | Beyar et al. |
| 5,522,817 | A | 6/1996 | Sander et al. |
| 5,522,831 | A | 6/1996 | Sleister et al. |
| 5,527,264 | A | 6/1996 | Moll et al. |
| 5,527,320 | A | 6/1996 | Carruthers et al. |
| 5,529,235 | A | 6/1996 | Boiarski et al. |
| D372,086 | S | 7/1996 | Grasso et al. |
| 5,531,305 | A | 7/1996 | Roberts et al. |
| 5,531,744 | A | 7/1996 | Nardella et al. |
| 5,531,856 | A | 7/1996 | Moll et al. |
| 5,533,521 | A | 7/1996 | Granger |
| 5,533,581 | A | 7/1996 | Barth et al. |
| 5,533,661 | A | 7/1996 | Main et al. |
| 5,535,934 | A | 7/1996 | Boiarski et al. |
| 5,535,935 | A | 7/1996 | Vidal et al. |
| 5,535,937 | A | 7/1996 | Boiarski et al. |
| 5,540,375 | A | 7/1996 | Bolanos et al. |
| 5,540,705 | A | 7/1996 | Meade et al. |
| 5,541,376 | A | 7/1996 | Ladtkow et al. |
| 5,541,489 | A | 7/1996 | Dunstan |
| 5,542,594 | A | 8/1996 | McKean et al. |
| 5,542,945 | A | 8/1996 | Fritzsch |
| 5,542,949 | A | 8/1996 | Yoon |
| 5,543,119 | A | 8/1996 | Sutter et al. |
| 5,543,695 | A | 8/1996 | Culp et al. |
| 5,544,802 | A | 8/1996 | Crainich |
| 5,547,117 | A | 8/1996 | Hamblin et al. |
| 5,549,583 | A | 8/1996 | Sanford et al. |
| 5,549,621 | A | 8/1996 | Bessler et al. |
| 5,549,627 | A | 8/1996 | Kieturakis |
| 5,549,628 | A | 8/1996 | Cooper et al. |
| 5,549,637 | A | 8/1996 | Crainich |
| 5,551,622 | A | 9/1996 | Yoon |
| 5,553,624 | A | 9/1996 | Francese et al. |
| 5,553,675 | A | 9/1996 | Pitzen et al. |
| 5,553,765 | A | 9/1996 | Knodel et al. |
| 5,554,148 | A | 9/1996 | Aebischer et al. |
| 5,554,169 | A | 9/1996 | Green et al. |
| 5,556,020 | A | 9/1996 | Hou |
| 5,556,416 | A | 9/1996 | Clark et al. |
| 5,558,533 | A | 9/1996 | Hashizawa et al. |
| 5,558,665 | A | 9/1996 | Kieturakis |

(56) References Cited

U.S. PATENT DOCUMENTS 5,558,671 A * 9/1996 Yates ................ A61B 18/1206 606/50
5,560,530 A 10/1996 Bolanos et al.
5,560,532 A 10/1996 DeFonzo et al.
5,561,881 A 10/1996 Klinger et al.
5,562,239 A 10/1996 Boiarski et al.
5,562,241 A 10/1996 Knodel et al.
5,562,682 A 10/1996 Oberlin et al.
5,562,690 A 10/1996 Green et al.
5,562,694 A 10/1996 Sauer et al.
5,562,701 A 10/1996 Huitema et al.
5,562,702 A 10/1996 Huitema et al.
5,563,481 A 10/1996 Krause
5,564,615 A 10/1996 Bishop et al.
5,569,161 A 10/1996 Ebling et al.
5,569,270 A 10/1996 Weng
5,569,284 A 10/1996 Young et al.
5,571,090 A 11/1996 Sherts
5,571,100 A 11/1996 Goble et al.
5,571,116 A 11/1996 Bolanos et al.
5,571,285 A 11/1996 Chow et al.
5,571,488 A 11/1996 Beerstecher et al.
5,573,169 A 11/1996 Green et al.
5,573,543 A 11/1996 Akopov et al.
5,574,431 A 11/1996 McKeown et al.
5,575,054 A 11/1996 Klinzing et al.
5,575,789 A 11/1996 Bell et al.
5,575,799 A 11/1996 Bolanos et al.
5,575,803 A 11/1996 Cooper et al.
5,575,805 A 11/1996 Li
5,577,654 A 11/1996 Bishop
5,578,052 A 11/1996 Koros et al.
5,579,978 A 12/1996 Green et al.
5,580,067 A 12/1996 Hamblin et al.
5,582,611 A 12/1996 Tsuruta et al.
5,582,617 A 12/1996 Klieman et al.
5,582,907 A 12/1996 Pall
5,583,114 A 12/1996 Barrows et al.
5,584,425 A 12/1996 Savage et al.
5,586,711 A 12/1996 Plyley et al.
5,588,579 A 12/1996 Schnut et al.
5,588,580 A 12/1996 Paul et al.
5,588,581 A 12/1996 Conlon et al.
5,591,170 A 1/1997 Spievack et al.
5,591,187 A 1/1997 Dekel
5,597,107 A 1/1997 Knodel et al.
5,599,151 A 2/1997 Daum et al.
5,599,279 A 2/1997 Slotman et al.
5,599,344 A 2/1997 Paterson
5,599,350 A 2/1997 Schulze et al.
5,599,852 A 2/1997 Scopelianos et al.
5,601,224 A 2/1997 Bishop et al.
5,601,573 A 2/1997 Fogelberg et al.
5,601,604 A 2/1997 Vincent
5,602,449 A 2/1997 Krause et al.
5,603,443 A 2/1997 Clark et al.
5,605,272 A 2/1997 Witt et al.
5,605,273 A 2/1997 Hamblin et al.
D378,500 S 3/1997 Nakai et al.
5,607,094 A 3/1997 Clark et al.
5,607,095 A 3/1997 Smith et al.
5,607,303 A 3/1997 Nakamura
5,607,433 A 3/1997 Polla et al.
5,607,436 A 3/1997 Pratt et al.
5,607,450 A 3/1997 Zvenyatsky et al.
5,607,474 A 3/1997 Athanasiou et al.
5,609,285 A 3/1997 Grant et al.
5,609,601 A 3/1997 Kolesa et al.
5,611,709 A 3/1997 McAnulty
5,611,813 A 3/1997 Lichtman
5,613,499 A 3/1997 Palmer et al.
5,613,937 A 3/1997 Garrison et al.
5,613,966 A 3/1997 Makower et al.
5,614,887 A 3/1997 Buchbinder
5,615,820 A 4/1997 Viola
5,618,294 A 4/1997 Aust et al.
5,618,303 A 4/1997 Marlow et al.
5,618,307 A 4/1997 Donlon et al.
5,619,992 A 4/1997 Guthrie et al.
5,620,289 A 4/1997 Curry
5,620,326 A 4/1997 Younker
5,620,415 A 4/1997 Lucey et al.
5,620,452 A 4/1997 Yoon
5,624,398 A 4/1997 Smith et al.
5,624,452 A 4/1997 Yates
5,626,587 A 5/1997 Bishop et al.
5,626,595 A 5/1997 Sklar et al.
5,626,979 A 5/1997 Mitsui et al.
5,628,446 A 5/1997 Geiste et al.
5,628,743 A 5/1997 Cimino
5,628,745 A 5/1997 Bek
5,630,539 A 5/1997 Plyley et al.
5,630,540 A 5/1997 Blewett
5,630,541 A 5/1997 Williamson, IV et al.
5,630,782 A 5/1997 Adair
5,631,973 A 5/1997 Green
5,632,432 A 5/1997 Schulze et al.
5,632,433 A 5/1997 Grant et al.
5,633,374 A 5/1997 Humphrey et al.
5,634,584 A 6/1997 Okorocha et al.
5,636,779 A 6/1997 Palmer
5,636,780 A 6/1997 Green et al.
5,637,110 A 6/1997 Pennybacker et al.
5,638,582 A 6/1997 Klatt et al.
5,639,008 A 6/1997 Gallagher et al.
D381,077 S 7/1997 Hunt
5,643,291 A 7/1997 Pier et al.
5,643,293 A 7/1997 Kogasaka et al.
5,643,294 A 7/1997 Tovey et al.
5,643,319 A 7/1997 Green et al.
5,645,209 A 7/1997 Green et al.
5,647,526 A 7/1997 Green et al.
5,647,869 A 7/1997 Goble et al.
5,649,937 A 7/1997 Bito et al.
5,649,956 A 7/1997 Jensen et al.
5,651,491 A 7/1997 Heaton et al.
5,651,762 A 7/1997 Bridges
5,651,821 A 7/1997 Uchida
5,653,373 A 8/1997 Green et al.
5,653,374 A 8/1997 Young et al.
5,653,677 A 8/1997 Okada et al.
5,653,721 A 8/1997 Knodel et al.
5,653,748 A 8/1997 Strecker
5,655,698 A 8/1997 Yoon
5,656,917 A 8/1997 Theobald
5,657,417 A 8/1997 Di Troia
5,657,429 A 8/1997 Wang et al.
5,657,921 A 8/1997 Young et al.
5,658,238 A 8/1997 Suzuki et al.
5,658,281 A 8/1997 Heard
5,658,298 A 8/1997 Vincent et al.
5,658,300 A 8/1997 Bito et al.
5,658,307 A 8/1997 Exconde
5,662,258 A 9/1997 Knodel et al.
5,662,260 A 9/1997 Yoon
5,662,662 A 9/1997 Bishop et al.
5,662,667 A 9/1997 Knodel
5,664,404 A 9/1997 Ivanov et al.
5,665,085 A 9/1997 Nardella
5,667,517 A 9/1997 Hooven
5,667,526 A 9/1997 Levin
5,667,527 A 9/1997 Cook
5,667,864 A 9/1997 Landoll
5,669,544 A 9/1997 Schulze et al.
5,669,904 A 9/1997 Platt, Jr. et al.
5,669,907 A 9/1997 Platt, Jr. et al.
5,669,918 A 9/1997 Balazs et al.
5,672,945 A 9/1997 Krause
5,673,840 A 10/1997 Schulze et al.
5,673,841 A 10/1997 Schulze et al.
5,673,842 A 10/1997 Bittner et al.
5,674,184 A 10/1997 Hassler, Jr.
5,674,286 A 10/1997 D'Alessio et al.
5,678,748 A 10/1997 Plyley et al.

(56) References Cited

U.S. PATENT DOCUMENTS

| | | | |
|---|---|---|---|
| 5,680,981 | A | 10/1997 | Mililli et al. |
| 5,680,982 | A | 10/1997 | Schulze et al. |
| 5,680,983 | A | 10/1997 | Plyley et al. |
| 5,681,330 | A | 10/1997 | Hughett et al. |
| 5,681,341 | A | 10/1997 | Lunsford et al. |
| 5,683,349 | A | 11/1997 | Makower et al. |
| 5,683,432 | A | 11/1997 | Goedeke et al. |
| 5,685,474 | A | 11/1997 | Seeber |
| 5,686,090 | A | 11/1997 | Schilder et al. |
| 5,688,270 | A | 11/1997 | Yates et al. |
| 5,690,269 | A | 11/1997 | Bolanos et al. |
| 5,690,675 | A | 11/1997 | Sawyer et al. |
| 5,692,668 | A | 12/1997 | Schulze et al. |
| 5,693,020 | A | 12/1997 | Rauh |
| 5,693,042 | A | 12/1997 | Boiarski et al. |
| 5,693,051 | A | 12/1997 | Schulze et al. |
| 5,695,494 | A | 12/1997 | Becker |
| 5,695,502 | A | 12/1997 | Pier et al. |
| 5,695,504 | A | 12/1997 | Gifford, III et al. |
| 5,695,524 | A | 12/1997 | Kelley et al. |
| 5,697,542 | A | 12/1997 | Knodel et al. |
| 5,697,543 | A | 12/1997 | Burdorff |
| 5,697,909 | A | 12/1997 | Eggers et al. |
| 5,697,943 | A | 12/1997 | Sauer et al. |
| 5,700,265 | A | 12/1997 | Romano |
| 5,700,270 | A | 12/1997 | Peyser et al. |
| 5,700,276 | A | 12/1997 | Benecke |
| 5,702,387 | A | 12/1997 | Arts et al. |
| 5,702,408 | A | 12/1997 | Wales et al. |
| 5,702,409 | A | 12/1997 | Rayburn et al. |
| 5,704,087 | A | 1/1998 | Strub |
| 5,704,534 | A | 1/1998 | Huitema et al. |
| 5,704,792 | A | 1/1998 | Sobhani |
| 5,706,997 | A | 1/1998 | Green et al. |
| 5,706,998 | A | 1/1998 | Plyley et al. |
| 5,707,392 | A | 1/1998 | Kortenbach |
| 5,709,334 | A | 1/1998 | Sorrentino et al. |
| 5,709,335 | A | 1/1998 | Heck |
| 5,709,680 | A | 1/1998 | Yates et al. |
| 5,709,706 | A | 1/1998 | Kienzle et al. |
| 5,711,472 | A | 1/1998 | Bryan |
| 5,711,960 | A | 1/1998 | Shikinami |
| 5,712,460 | A | 1/1998 | Carr et al. |
| 5,713,128 | A | 2/1998 | Schrenk et al. |
| 5,713,505 | A | 2/1998 | Huitema |
| 5,713,895 | A | 2/1998 | Lontine et al. |
| 5,713,896 | A | 2/1998 | Nardella |
| 5,713,920 | A | 2/1998 | Bezwada et al. |
| 5,715,604 | A | 2/1998 | Lanzoni |
| 5,715,836 | A | 2/1998 | Kliegis et al. |
| 5,715,987 | A | 2/1998 | Kelley et al. |
| 5,715,988 | A | 2/1998 | Palmer |
| 5,716,352 | A | 2/1998 | Viola et al. |
| 5,716,366 | A | 2/1998 | Yates |
| 5,718,359 | A | 2/1998 | Palmer et al. |
| 5,718,360 | A | 2/1998 | Green et al. |
| 5,718,548 | A | 2/1998 | Cotellessa |
| 5,718,714 | A | 2/1998 | Livneh |
| 5,720,744 | A | 2/1998 | Eggleston et al. |
| D393,067 | S | 3/1998 | Geary et al. |
| 5,724,025 | A | 3/1998 | Tavori |
| 5,725,536 | A | 3/1998 | Oberlin et al. |
| 5,725,554 | A | 3/1998 | Simon et al. |
| 5,728,110 | A | 3/1998 | Vidal et al. |
| 5,728,113 | A | 3/1998 | Sherts |
| 5,728,121 | A | 3/1998 | Bimbo et al. |
| 5,730,758 | A | 3/1998 | Allgeyer |
| 5,732,712 | A | 3/1998 | Adair |
| 5,732,821 | A | 3/1998 | Stone et al. |
| 5,732,871 | A | 3/1998 | Clark et al. |
| 5,732,872 | A | 3/1998 | Bolduc et al. |
| 5,733,308 | A | 3/1998 | Daugherty et al. |
| 5,735,445 | A | 4/1998 | Vidal et al. |
| 5,735,848 | A | 4/1998 | Yates et al. |
| 5,735,874 | A | 4/1998 | Measamer et al. |
| 5,736,271 | A | 4/1998 | Cisar et al. |
| 5,738,474 | A | 4/1998 | Blewett |
| 5,738,629 | A | 4/1998 | Moll et al. |
| 5,738,648 | A | 4/1998 | Lands et al. |
| 5,741,271 | A | 4/1998 | Nakao et al. |
| 5,743,456 | A | 4/1998 | Jones et al. |
| 5,746,770 | A | 5/1998 | Zeitels et al. |
| 5,747,953 | A | 5/1998 | Philipp |
| 5,749,889 | A | 5/1998 | Bacich et al. |
| 5,749,893 | A | 5/1998 | Vidal et al. |
| 5,749,896 | A | 5/1998 | Cook |
| 5,749,968 | A | 5/1998 | Melanson et al. |
| 5,752,644 | A | 5/1998 | Bolanos et al. |
| 5,752,965 | A | 5/1998 | Francis et al. |
| 5,752,970 | A | 5/1998 | Yoon |
| 5,752,973 | A | 5/1998 | Kieturakis |
| 5,755,717 | A | 5/1998 | Yates et al. |
| 5,755,726 | A | 5/1998 | Pratt et al. |
| D395,645 | S | 6/1998 | Cappa et al. |
| 5,758,814 | A | 6/1998 | Gallagher et al. |
| 5,762,255 | A | 6/1998 | Chrisman et al. |
| 5,762,256 | A | 6/1998 | Mastri et al. |
| 5,762,458 | A | 6/1998 | Wang et al. |
| 5,765,565 | A | 6/1998 | Adair |
| 5,766,186 | A | 6/1998 | Faraz et al. |
| 5,766,188 | A | 6/1998 | Igaki |
| 5,766,205 | A | 6/1998 | Zvenyatsky et al. |
| 5,769,303 | A | 6/1998 | Knodel et al. |
| 5,769,640 | A | 6/1998 | Jacobus et al. |
| 5,769,748 | A | 6/1998 | Eyerly et al. |
| 5,769,791 | A | 6/1998 | Benaron et al. |
| 5,769,892 | A | 6/1998 | Kingwell |
| 5,772,099 | A | 6/1998 | Gravener |
| 5,772,379 | A | 6/1998 | Evensen |
| 5,772,578 | A | 6/1998 | Heimberger et al. |
| 5,772,659 | A | 6/1998 | Becker et al. |
| 5,773,991 | A | 6/1998 | Chen |
| 5,776,130 | A | 7/1998 | Buysse et al. |
| 5,778,939 | A | 7/1998 | Hok-Yin |
| 5,779,130 | A | 7/1998 | Alesi et al. |
| 5,779,131 | A | 7/1998 | Knodel et al. |
| 5,779,132 | A | 7/1998 | Knodel et al. |
| 5,782,396 | A | 7/1998 | Mastri et al. |
| 5,782,397 | A | 7/1998 | Koukline |
| 5,782,748 | A | 7/1998 | Palmer et al. |
| 5,782,749 | A | 7/1998 | Riza |
| 5,782,859 | A | 7/1998 | Nicholas et al. |
| 5,784,934 | A | 7/1998 | Izumisawa |
| 5,785,232 | A | 7/1998 | Vidal et al. |
| 5,785,647 | A | 7/1998 | Tompkins et al. |
| 5,787,897 | A | 8/1998 | Kieturakis |
| 5,791,231 | A | 8/1998 | Cohn et al. |
| 5,792,135 | A | 8/1998 | Madhani et al. |
| 5,792,162 | A | 8/1998 | Jolly et al. |
| 5,792,165 | A | 8/1998 | Klieman et al. |
| 5,792,573 | A | 8/1998 | Pitzen et al. |
| 5,794,834 | A | 8/1998 | Hamblin et al. |
| 5,796,188 | A | 8/1998 | Bays |
| 5,797,536 | A | 8/1998 | Smith et al. |
| 5,797,537 | A | 8/1998 | Oberlin et al. |
| 5,797,538 | A | 8/1998 | Heaton et al. |
| 5,797,637 | A | 8/1998 | Ervin |
| 5,797,900 | A | 8/1998 | Madhani et al. |
| 5,797,906 | A | 8/1998 | Rhum et al. |
| 5,797,927 | A | 8/1998 | Yoon |
| 5,797,941 | A | 8/1998 | Schulze et al. |
| 5,797,959 | A | 8/1998 | Castro et al. |
| 5,798,752 | A | 8/1998 | Buxton et al. |
| 5,799,857 | A | 9/1998 | Robertson et al. |
| 5,800,379 | A | 9/1998 | Edwards |
| 5,800,423 | A | 9/1998 | Jensen |
| 5,804,726 | A | 9/1998 | Geib et al. |
| 5,804,936 | A | 9/1998 | Brodsky et al. |
| 5,806,676 | A | 9/1998 | Wasgien |
| 5,807,241 | A | 9/1998 | Heimberger |
| 5,807,376 | A | 9/1998 | Viola et al. |
| 5,807,378 | A | 9/1998 | Jensen et al. |
| 5,807,393 | A | 9/1998 | Williamson, IV et al. |
| 5,809,441 | A | 9/1998 | McKee |

(56) References Cited

U.S. PATENT DOCUMENTS 5,810,240 A 9/1998 Robertson
5,810,721 A 9/1998 Mueller et al.
5,810,811 A 9/1998 Yates et al.
5,810,846 A 9/1998 Virnich et al.
5,810,855 A 9/1998 Rayburn et al.
5,812,188 A 9/1998 Adair
5,813,813 A 9/1998 Daum et al.
5,814,055 A 9/1998 Knodel et al.
5,814,057 A 9/1998 Oi et al.
5,816,471 A 10/1998 Plyley et al.
5,817,084 A 10/1998 Jensen
5,817,091 A 10/1998 Nardella et al.
5,817,093 A 10/1998 Williamson, IV et al.
5,817,109 A 10/1998 McGarry et al.
5,817,119 A 10/1998 Klieman et al.
5,820,009 A 10/1998 Melling et al.
5,823,066 A 10/1998 Huitema et al.
5,824,333 A 10/1998 Scopelianos et al.
5,826,776 A 10/1998 Schulze et al.
5,827,271 A 10/1998 Buysse et al.
5,827,298 A 10/1998 Hart et al.
5,827,323 A 10/1998 Klieman et al.
5,829,662 A 11/1998 Allen et al.
5,830,598 A 11/1998 Patterson
5,833,690 A 11/1998 Yates et al.
5,833,695 A 11/1998 Yoon
5,833,696 A 11/1998 Whitfield et al.
5,836,503 A 11/1998 Ehrenfels et al.
5,836,960 A 11/1998 Kolesa et al.
5,839,369 A 11/1998 Chatterjee et al.
5,839,639 A 11/1998 Sauer et al.
5,841,284 A 11/1998 Takahashi
5,843,021 A 12/1998 Edwards et al.
5,843,096 A 12/1998 Igaki et al.
5,843,097 A 12/1998 Mayenberger et al.
5,843,122 A 12/1998 Riza
5,843,132 A 12/1998 Ilvento
5,843,169 A 12/1998 Taheri
5,846,254 A 12/1998 Schulze et al.
5,847,566 A 12/1998 Marritt et al.
5,849,011 A 12/1998 Jones et al.
5,849,020 A 12/1998 Long et al.
5,849,023 A 12/1998 Mericle
5,851,179 A 12/1998 Ritson et al.
5,851,212 A 12/1998 Zirps et al.
5,853,366 A 12/1998 Dowlatshahi
5,855,311 A 1/1999 Hamblin et al.
5,855,583 A 1/1999 Wang et al.
5,860,581 A 1/1999 Robertson et al.
5,860,975 A 1/1999 Goble et al.
5,865,361 A 2/1999 Milliman et al.
5,865,638 A 2/1999 Trafton
5,868,361 A 2/1999 Rinderer
5,868,664 A 2/1999 Speier et al.
5,868,760 A 2/1999 McGuckin, Jr.
5,868,790 A 2/1999 Vincent et al.
5,871,135 A 2/1999 Williamson IV et al.
5,873,885 A 2/1999 Weidenbenner
5,876,401 A 3/1999 Schulze et al.
5,878,193 A 3/1999 Wang et al.
5,878,607 A 3/1999 Nunes et al.
5,878,937 A 3/1999 Green et al.
5,878,938 A 3/1999 Bittner et al.
5,881,777 A 3/1999 Bassi et al.
5,881,943 A 3/1999 Heck et al.
5,891,094 A 4/1999 Masterson et al.
5,891,160 A 4/1999 Williamson, IV et al.
5,891,558 A 4/1999 Bell et al.
5,893,506 A 4/1999 Powell
5,893,835 A 4/1999 Witt et al.
5,893,855 A 4/1999 Jacobs
5,893,863 A 4/1999 Yoon
5,893,878 A 4/1999 Pierce
5,894,979 A 4/1999 Powell
5,897,552 A 4/1999 Edwards et al.
5,897,562 A 4/1999 Bolanos et al.
5,899,824 A 5/1999 Kurtz et al.
5,899,914 A 5/1999 Zirps et al.
5,901,895 A 5/1999 Heaton et al.
5,902,312 A 5/1999 Frater et al.
5,903,117 A 5/1999 Gregory
5,904,647 A 5/1999 Ouchi
5,904,693 A 5/1999 Dicesare et al.
5,904,702 A 5/1999 Ek et al.
5,906,577 A 5/1999 Beane et al.
5,906,625 A 5/1999 Bito et al.
5,907,211 A 5/1999 Hall et al.
5,907,664 A 5/1999 Wang et al.
5,908,149 A 6/1999 Welch et al.
5,908,402 A 6/1999 Blythe
5,908,427 A 6/1999 McKean et al.
5,909,062 A 6/1999 Krietzman
5,911,353 A 6/1999 Bolanos et al.
5,915,616 A 6/1999 Viola et al.
5,916,225 A 6/1999 Kugel
5,918,791 A 7/1999 Sorrentino et al.
5,919,198 A 7/1999 Graves, Jr. et al.
5,921,956 A 7/1999 Grinberg et al.
5,922,001 A 7/1999 Yoon
5,922,003 A 7/1999 Anctil et al.
5,924,864 A 7/1999 Loge et al.
5,928,137 A 7/1999 Green
5,928,256 A 7/1999 Riza
5,931,847 A 8/1999 Bittner et al.
5,931,853 A 8/1999 McEwen et al.
5,937,951 A 8/1999 Izuchukwu et al.
5,938,667 A 8/1999 Peyser et al.
5,941,442 A 8/1999 Geiste et al.
5,941,890 A 8/1999 Voegele et al.
5,944,172 A 8/1999 Hannula
5,944,715 A 8/1999 Goble et al.
5,946,978 A 9/1999 Yamashita
5,947,984 A 9/1999 Whipple
5,947,996 A 9/1999 Logeman
5,948,030 A 9/1999 Miller et al.
5,948,429 A 9/1999 Bell et al.
5,951,301 A 9/1999 Younker
5,951,516 A 9/1999 Bunyan
5,951,552 A 9/1999 Long et al.
5,951,574 A 9/1999 Stefanchik et al.
5,951,575 A 9/1999 Bolduc et al.
5,951,581 A 9/1999 Saadat et al.
5,954,259 A 9/1999 Viola et al.
5,954,536 A 9/1999 Fuerst et al.
5,957,831 A 9/1999 Adair
5,964,394 A 10/1999 Robertson
5,964,774 A 10/1999 McKean et al.
5,966,126 A 10/1999 Szabo
5,971,916 A 10/1999 Koren
5,973,221 A 10/1999 Collyer et al.
D416,089 S 11/1999 Barton et al.
5,976,122 A 11/1999 Madhani et al.
5,977,746 A 11/1999 Hershberger et al.
5,980,248 A 11/1999 Kusakabe et al.
5,980,569 A 11/1999 Scirica
5,984,949 A 11/1999 Levin
5,988,479 A 11/1999 Palmer
5,990,379 A 11/1999 Gregory
5,993,464 A 11/1999 Knodel
5,993,466 A 11/1999 Yoon
5,997,528 A 12/1999 Bisch et al.
5,997,552 A 12/1999 Person et al.
6,001,108 A 12/1999 Wang et al.
6,003,517 A 12/1999 Sheffield et al.
6,004,319 A 12/1999 Goble et al.
6,004,335 A 12/1999 Vaitekunas et al.
6,007,521 A 12/1999 Bidwell et al.
6,010,054 A 1/2000 Johnson et al.
6,010,513 A 1/2000 Tormala et al.
6,010,520 A 1/2000 Pattison
6,012,494 A 1/2000 Balazs
6,013,076 A 1/2000 Goble et al.
6,013,991 A 1/2000 Philipp
6,015,406 A 1/2000 Goble et al.

(56) References Cited

U.S. PATENT DOCUMENTS

| | | | |
|---|---|---|---|
| 6,015,417 | A | 1/2000 | Reynolds, Jr. |
| 6,017,322 | A | 1/2000 | Snoke et al. |
| 6,017,354 | A | 1/2000 | Culp et al. |
| 6,017,356 | A | 1/2000 | Frederick et al. |
| 6,018,227 | A | 1/2000 | Kumar et al. |
| 6,019,745 | A | 2/2000 | Gray |
| 6,019,780 | A | 2/2000 | Lombardo et al. |
| 6,022,352 | A | 2/2000 | Vandewalle |
| 6,023,275 | A | 2/2000 | Horvitz et al. |
| 6,023,641 | A | 2/2000 | Thompson |
| 6,024,708 | A | 2/2000 | Bales et al. |
| 6,024,741 | A | 2/2000 | Williamson, IV et al. |
| 6,024,748 | A | 2/2000 | Manzo et al. |
| 6,024,750 | A | 2/2000 | Mastri et al. |
| 6,024,764 | A | 2/2000 | Schroeppel |
| 6,027,501 | A | 2/2000 | Goble et al. |
| 6,030,384 | A | 2/2000 | Nezhat |
| 6,031,148 | A | 2/2000 | Hayes et al. |
| 6,032,849 | A | 3/2000 | Mastri et al. |
| 6,033,105 | A | 3/2000 | Barker et al. |
| 6,033,378 | A | 3/2000 | Lundquist et al. |
| 6,033,399 | A | 3/2000 | Gines |
| 6,033,427 | A | 3/2000 | Lee |
| 6,036,641 | A | 3/2000 | Taylor et al. |
| 6,036,667 | A | 3/2000 | Manna et al. |
| 6,037,724 | A | 3/2000 | Buss et al. |
| 6,037,927 | A | 3/2000 | Rosenberg |
| 6,039,126 | A | 3/2000 | Hsieh |
| 6,039,733 | A | 3/2000 | Buysse et al. |
| 6,039,734 | A | 3/2000 | Goble |
| 6,042,601 | A | 3/2000 | Smith |
| 6,042,607 | A | 3/2000 | Williamson, IV et al. |
| 6,043,626 | A | 3/2000 | Snyder et al. |
| D422,545 | S | 4/2000 | Palalau et al. |
| 6,045,560 | A | 4/2000 | McKean et al. |
| 6,047,861 | A | 4/2000 | Vidal et al. |
| 6,049,145 | A | 4/2000 | Austin et al. |
| 6,050,172 | A | 4/2000 | Corves et al. |
| 6,050,472 | A | 4/2000 | Shibata |
| 6,050,989 | A | 4/2000 | Fox et al. |
| 6,050,990 | A | 4/2000 | Tankovich et al. |
| 6,050,996 | A | 4/2000 | Schmaltz et al. |
| 6,053,390 | A | 4/2000 | Green et al. |
| 6,053,899 | A | 4/2000 | Slanda et al. |
| 6,053,922 | A | 4/2000 | Krause et al. |
| 6,054,142 | A | 4/2000 | Li et al. |
| 6,055,062 | A | 4/2000 | Dina et al. |
| RE36,720 | E | 5/2000 | Green et al. |
| 6,056,735 | A | 5/2000 | Okada et al. |
| 6,056,746 | A | 5/2000 | Goble et al. |
| 6,059,806 | A | 5/2000 | Hoegerle |
| 6,062,360 | A | 5/2000 | Shields |
| 6,063,020 | A | 5/2000 | Jones et al. |
| 6,063,025 | A | 5/2000 | Bridges et al. |
| 6,063,050 | A | 5/2000 | Manna et al. |
| 6,063,095 | A | 5/2000 | Wang et al. |
| 6,063,097 | A | 5/2000 | Oi et al. |
| 6,063,098 | A | 5/2000 | Houser et al. |
| 6,065,679 | A | 5/2000 | Levie et al. |
| 6,065,919 | A | 5/2000 | Peck |
| 6,066,132 | A | 5/2000 | Chen et al. |
| 6,066,144 | A | 5/2000 | Wolf et al. |
| 6,066,151 | A | 5/2000 | Miyawaki et al. |
| 6,068,627 | A | 5/2000 | Orszulak et al. |
| 6,071,233 | A | 6/2000 | Ishikawa et al. |
| 6,072,299 | A | 6/2000 | Kurle et al. |
| 6,074,386 | A | 6/2000 | Goble et al. |
| 6,074,401 | A | 6/2000 | Gardiner et al. |
| 6,075,441 | A | 6/2000 | Maloney |
| 6,077,280 | A | 6/2000 | Fossum |
| 6,077,286 | A | 6/2000 | Cuschieri et al. |
| 6,077,290 | A | 6/2000 | Marini |
| 6,079,606 | A | 6/2000 | Milliman et al. |
| 6,080,181 | A | 6/2000 | Jensen et al. |
| 6,082,577 | A | 7/2000 | Coates et al. |
| 6,083,191 | A | 7/2000 | Rose |
| 6,083,223 | A | 7/2000 | Baker |
| 6,083,234 | A | 7/2000 | Nicholas et al. |
| 6,083,242 | A | 7/2000 | Cook |
| 6,086,544 | A | 7/2000 | Hibner et al. |
| 6,086,600 | A | 7/2000 | Kortenbach |
| 6,090,106 | A | 7/2000 | Goble et al. |
| 6,090,123 | A | 7/2000 | Culp et al. |
| 6,093,186 | A | 7/2000 | Goble |
| 6,094,021 | A | 7/2000 | Noro et al. |
| D429,252 | S | 8/2000 | Haitani et al. |
| 6,099,537 | A | 8/2000 | Sugai et al. |
| 6,099,551 | A | 8/2000 | Gabbay |
| 6,102,271 | A | 8/2000 | Longo et al. |
| 6,102,926 | A | 8/2000 | Tartaglia et al. |
| 6,104,162 | A | 8/2000 | Sainsbury et al. |
| 6,104,304 | A | 8/2000 | Clark et al. |
| 6,106,511 | A | 8/2000 | Jensen |
| 6,109,500 | A | 8/2000 | Alli et al. |
| 6,110,187 | A | 8/2000 | Donlon |
| 6,113,618 | A | 9/2000 | Nic |
| 6,117,148 | A | 9/2000 | Ravo et al. |
| 6,117,158 | A | 9/2000 | Measamer et al. |
| 6,119,913 | A | 9/2000 | Adams et al. |
| 6,120,433 | A | 9/2000 | Mizuno et al. |
| 6,120,462 | A | 9/2000 | Hibner et al. |
| 6,123,241 | A | 9/2000 | Walter et al. |
| 6,123,701 | A | 9/2000 | Nezhat |
| H1904 | H | 10/2000 | Yates et al. |
| RE36,923 | E | 10/2000 | Hiroi et al. |
| 6,126,058 | A | 10/2000 | Adams et al. |
| 6,126,359 | A | 10/2000 | Dittrich et al. |
| 6,126,670 | A | 10/2000 | Walker et al. |
| 6,131,789 | A | 10/2000 | Schulze et al. |
| 6,131,790 | A | 10/2000 | Piraka |
| 6,132,368 | A | 10/2000 | Cooper |
| 6,134,962 | A | 10/2000 | Sugitani |
| 6,139,546 | A | 10/2000 | Koenig et al. |
| 6,142,149 | A | 11/2000 | Steen |
| 6,142,933 | A | 11/2000 | Longo et al. |
| 6,147,135 | A | 11/2000 | Yuan et al. |
| 6,148,979 | A | 11/2000 | Roach et al. |
| 6,149,660 | A | 11/2000 | Laufer et al. |
| 6,151,323 | A | 11/2000 | O'Connell et al. |
| 6,152,935 | A | 11/2000 | Kammerer et al. |
| 6,155,083 | A | 12/2000 | Goeser et al. |
| 6,155,473 | A | 12/2000 | Tompkins et al. |
| 6,156,056 | A | 12/2000 | Kearns et al. |
| 6,157,169 | A | 12/2000 | Lee |
| 6,157,303 | A | 12/2000 | Bodie et al. |
| 6,159,146 | A | 12/2000 | El Gazayerli |
| 6,159,200 | A | 12/2000 | Verdura et al. |
| 6,159,224 | A | 12/2000 | Yoon |
| 6,162,208 | A | 12/2000 | Hipps |
| 6,162,220 | A | 12/2000 | Nezhat |
| 6,162,537 | A | 12/2000 | Martin et al. |
| 6,165,175 | A | 12/2000 | Wampler et al. |
| 6,165,184 | A | 12/2000 | Verdura et al. |
| 6,165,188 | A | 12/2000 | Saadat et al. |
| 6,167,185 | A | 12/2000 | Smiley et al. |
| 6,168,605 | B1 | 1/2001 | Measamer et al. |
| 6,171,305 | B1 | 1/2001 | Sherman |
| 6,171,316 | B1 | 1/2001 | Kovac et al. |
| 6,171,330 | B1 | 1/2001 | Benchetrit |
| 6,173,074 | B1 | 1/2001 | Russo |
| 6,174,308 | B1 | 1/2001 | Goble et al. |
| 6,174,309 | B1 | 1/2001 | Wrublewski et al. |
| 6,174,318 | B1 | 1/2001 | Bates et al. |
| 6,175,290 | B1 | 1/2001 | Forsythe et al. |
| 6,179,195 | B1 | 1/2001 | Adams et al. |
| 6,179,776 | B1 | 1/2001 | Adams et al. |
| 6,181,105 | B1 | 1/2001 | Cutolo et al. |
| 6,182,673 | B1 | 2/2001 | Kindermann et al. |
| 6,185,356 | B1 | 2/2001 | Parker et al. |
| 6,186,142 | B1 | 2/2001 | Schmidt et al. |
| 6,186,957 | B1 | 2/2001 | Milam |
| 6,187,003 | B1 | 2/2001 | Buysse et al. |
| 6,190,386 | B1 | 2/2001 | Rydell |
| 6,193,129 | B1 | 2/2001 | Bittner et al. |

(56) References Cited

U.S. PATENT DOCUMENTS 6,197,042 B1 3/2001 Ginn et al.
6,200,311 B1 3/2001 Danek et al.
6,200,330 B1 3/2001 Benderev et al.
6,202,914 B1 3/2001 Geiste et al.
6,206,894 B1 3/2001 Thompson et al.
6,206,897 B1 3/2001 Jamiolkowski et al.
6,206,903 B1 3/2001 Ramans
6,206,904 B1 3/2001 Ouchi
6,209,414 B1 4/2001 Uneme
6,210,403 B1 4/2001 Klicek
6,211,626 B1 4/2001 Lys et al.
6,213,999 B1 4/2001 Platt, Jr. et al.
6,214,028 B1 4/2001 Yoon et al.
6,217,168 B1 4/2001 Elgee
6,220,368 B1 4/2001 Ark et al.
6,221,007 B1 4/2001 Green
6,221,023 B1 4/2001 Matsuba et al.
6,223,100 B1 4/2001 Green
6,223,835 B1 5/2001 Habedank et al.
6,224,617 B1 5/2001 Saadat et al.
6,228,080 B1 5/2001 Gines
6,228,081 B1 5/2001 Goble
6,228,083 B1 5/2001 Lands et al.
6,228,084 B1 5/2001 Kirwan, Jr.
6,228,089 B1 5/2001 Wahrburg
6,228,098 B1 5/2001 Kayan et al.
6,231,565 B1 5/2001 Tovey et al.
6,234,178 B1 5/2001 Goble et al.
6,235,036 B1 5/2001 Gardner et al.
6,237,604 B1 5/2001 Burnside et al.
6,238,384 B1 5/2001 Peer
6,241,139 B1 6/2001 Milliman et al.
6,241,140 B1 6/2001 Adams et al.
6,241,723 B1 6/2001 Heim et al.
6,245,084 B1 6/2001 Mark et al.
6,248,116 B1 6/2001 Chevillon et al.
6,248,117 B1 6/2001 Blatter
6,249,076 B1 6/2001 Madden et al.
6,249,105 B1 6/2001 Andrews et al.
6,250,532 B1 6/2001 Green et al.
6,251,485 B1 6/2001 Harris et al.
D445,745 S 7/2001 Norman
6,254,534 B1 7/2001 Butler et al.
6,254,619 B1 7/2001 Garabet et al.
6,254,642 B1 7/2001 Taylor
6,258,107 B1 7/2001 Balazs et al.
6,261,246 B1 7/2001 Pantages et al.
6,261,286 B1 7/2001 Goble et al.
6,261,679 B1 7/2001 Chen et al.
6,264,086 B1 7/2001 McGuckin, Jr.
6,264,087 B1 7/2001 Whitman
6,264,617 B1 7/2001 Bales et al.
6,269,997 B1 8/2001 Balazs et al.
6,270,508 B1 8/2001 Klieman et al.
6,270,916 B1 8/2001 Sink et al.
6,273,252 B1 8/2001 Mitchell
6,273,876 B1 8/2001 Klima et al.
6,273,897 B1 8/2001 Dalessandro et al.
6,277,114 B1 8/2001 Bullivant et al.
6,280,407 B1 8/2001 Manna et al.
6,283,981 B1 9/2001 Beaupre
6,293,927 B1 9/2001 McGuckin, Jr.
6,293,942 B1 9/2001 Goble et al.
6,296,607 B1 10/2001 Milbocker
6,296,640 B1 10/2001 Wampler et al.
6,302,311 B1 10/2001 Adams et al.
6,302,743 B1 10/2001 Chiu et al.
6,305,891 B1 10/2001 Burlingame
6,306,134 B1 10/2001 Goble et al.
6,306,149 B1 10/2001 Meade
6,306,424 B1 10/2001 Vyakarnam et al.
6,309,397 B1 10/2001 Julian et al.
6,309,400 B2 10/2001 Beaupre
6,309,403 B1 10/2001 Minor et al.
6,312,435 B1 11/2001 Wallace et al.
6,315,184 B1 11/2001 Whitman
6,317,616 B1 11/2001 Glossop
6,319,510 B1 11/2001 Yates
6,320,123 B1 11/2001 Reimers
6,322,494 B1 11/2001 Bullivant et al.
6,324,339 B1 11/2001 Hudson et al.
6,325,799 B1 12/2001 Goble
6,325,805 B1 12/2001 Ogilvie et al.
6,325,810 B1 12/2001 Hamilton et al.
6,328,498 B1 12/2001 Mersch
6,330,965 B1 12/2001 Milliman et al.
6,331,181 B1 12/2001 Tierney et al.
6,331,761 B1 12/2001 Kumar et al.
6,333,029 B1 12/2001 Vyakarnam et al.
6,334,860 B1 1/2002 Dorn
6,334,861 B1 1/2002 Chandler et al.
6,336,926 B1 1/2002 Goble
6,338,737 B1 1/2002 Toledano
6,338,738 B1 1/2002 Bellotti et al.
6,343,731 B1 2/2002 Adams et al.
6,346,077 B1 2/2002 Taylor et al.
6,348,061 B1 2/2002 Whitman
6,349,868 B1 2/2002 Mattingly et al.
D454,951 S 3/2002 Bon
6,352,503 B1 3/2002 Matsui et al.
6,352,532 B1 3/2002 Kramer et al.
6,355,699 B1 3/2002 Vyakarnam et al.
6,356,072 B1 3/2002 Chass
6,358,224 B1 3/2002 Tims et al.
6,358,263 B2 3/2002 Mark et al.
6,358,459 B1 3/2002 Ziegler et al.
6,361,542 B1 3/2002 Dimitriu et al.
6,364,828 B1 4/2002 Yeung et al.
6,364,877 B1 4/2002 Goble et al.
6,364,888 B1 4/2002 Niemeyer et al.
6,366,441 B1 4/2002 Ozawa et al.
6,370,981 B2 4/2002 Watarai
6,371,114 B1 4/2002 Schmidt et al.
6,373,152 B1 4/2002 Wang et al.
6,377,011 B1 4/2002 Ben-Ur
6,383,201 B1 5/2002 Dong
6,387,092 B1 5/2002 Burnside et al.
6,387,113 B1 5/2002 Hawkins et al.
6,387,114 B2 5/2002 Adams
6,391,038 B2 5/2002 Vargas et al.
6,392,854 B1 5/2002 O'Gorman
6,394,998 B1 5/2002 Wallace et al.
6,398,779 B1 6/2002 Buysse et al.
6,398,781 B1 6/2002 Goble et al.
6,398,797 B2 6/2002 Bombard et al.
6,402,766 B2 6/2002 Bowman et al.
6,402,780 B2 6/2002 Williamson, IV et al.
6,406,440 B1 6/2002 Stefanchik
6,406,472 B1 6/2002 Jensen
6,409,724 B1 6/2002 Penny et al.
H2037 H 7/2002 Yates et al.
6,412,639 B1 7/2002 Hickey
6,413,274 B1 7/2002 Pedros
6,415,542 B1 7/2002 Bates et al.
6,416,486 B1 7/2002 Wampler
6,416,509 B1 7/2002 Goble et al.
6,419,695 B1 7/2002 Gabbay
6,423,079 B1 7/2002 Blake, III
6,424,885 B1 7/2002 Niemeyer et al.
RE37,814 E 8/2002 Allgeyer
6,428,070 B1 8/2002 Takanashi et al.
6,428,487 B1 8/2002 Burdorff et al.
6,429,611 B1 8/2002 Li
6,430,298 B1 8/2002 Kettl et al.
6,432,065 B1 8/2002 Burdorff et al.
6,436,097 B1 8/2002 Nardella
6,436,107 B1 8/2002 Wang et al.
6,436,110 B2 8/2002 Bowman et al.
6,436,115 B1 8/2002 Beaupre
6,436,122 B1 8/2002 Frank et al.
6,439,439 B1 8/2002 Rickard et al.
6,439,446 B1 8/2002 Perry et al.
6,440,146 B2 8/2002 Nicholas et al.
6,441,577 B2 8/2002 Blumenkranz et al.

(56) References Cited

U.S. PATENT DOCUMENTS

| | | | |
|---|---|---|---|
| D462,758 | S | 9/2002 | Epstein et al. |
| 6,443,973 | B1 | 9/2002 | Whitman |
| 6,445,530 | B1 | 9/2002 | Baker |
| 6,447,518 | B1 | 9/2002 | Krause et al. |
| 6,447,523 | B1 | 9/2002 | Middleman et al. |
| 6,447,799 | B1 | 9/2002 | Ullman |
| 6,447,864 | B2 | 9/2002 | Johnson et al. |
| 6,450,391 | B1 | 9/2002 | Kayan et al. |
| 6,450,989 | B2 | 9/2002 | Dubrul et al. |
| 6,454,656 | B2 | 9/2002 | Brissette et al. |
| 6,454,781 | B1 | 9/2002 | Witt et al. |
| 6,457,338 | B1 | 10/2002 | Frenken |
| 6,457,625 | B1 | 10/2002 | Tormala et al. |
| 6,458,077 | B1 | 10/2002 | Boebel et al. |
| 6,458,142 | B1 | 10/2002 | Faller et al. |
| 6,458,147 | B1 | 10/2002 | Cruise et al. |
| 6,460,627 | B1 | 10/2002 | Below et al. |
| 6,463,824 | B1 | 10/2002 | Prell et al. |
| 6,468,275 | B1 | 10/2002 | Wampler et al. |
| 6,468,286 | B2 | 10/2002 | Mastri et al. |
| 6,471,106 | B1 | 10/2002 | Reining |
| 6,471,659 | B2 | 10/2002 | Eggers et al. |
| 6,478,210 | B2 | 11/2002 | Adams et al. |
| 6,482,063 | B1 | 11/2002 | Frigard |
| 6,482,200 | B2 | 11/2002 | Shippert |
| 6,482,217 | B1 | 11/2002 | Pintor et al. |
| 6,485,490 | B2 | 11/2002 | Wampler et al. |
| 6,485,503 | B2 | 11/2002 | Jacobs et al. |
| 6,485,667 | B1 | 11/2002 | Tan |
| 6,486,286 | B1 | 11/2002 | McGall et al. |
| 6,488,196 | B1 | 12/2002 | Fenton, Jr. |
| 6,488,197 | B1 | 12/2002 | Whitman |
| 6,488,659 | B1 | 12/2002 | Rosenman |
| 6,491,201 | B1 | 12/2002 | Whitman |
| 6,491,690 | B1 | 12/2002 | Goble et al. |
| 6,491,701 | B2 | 12/2002 | Tierney et al. |
| 6,491,702 | B2 | 12/2002 | Heilbrun et al. |
| 6,492,785 | B1 | 12/2002 | Kasten et al. |
| 6,494,882 | B1 | 12/2002 | Lebouitz et al. |
| 6,494,885 | B1 | 12/2002 | Dhindsa |
| 6,494,888 | B1 | 12/2002 | Laufer et al. |
| 6,494,896 | B1 | 12/2002 | D'Alessio et al. |
| 6,498,480 | B1 | 12/2002 | Manara |
| 6,500,176 | B1 | 12/2002 | Truckai et al. |
| 6,500,189 | B1 | 12/2002 | Lang et al. |
| 6,500,194 | B2 | 12/2002 | Benderev et al. |
| D468,749 | S | 1/2003 | Friedman |
| 6,503,139 | B2 | 1/2003 | Coral |
| 6,503,257 | B2 | 1/2003 | Grant et al. |
| 6,503,259 | B2 | 1/2003 | Huxel et al. |
| 6,505,768 | B2 | 1/2003 | Whitman |
| 6,506,197 | B1 | 1/2003 | Rollero et al. |
| 6,506,399 | B2 | 1/2003 | Donovan |
| 6,510,854 | B2 | 1/2003 | Goble |
| 6,511,468 | B1 | 1/2003 | Cragg et al. |
| 6,512,360 | B1 | 1/2003 | Goto et al. |
| 6,514,252 | B2 | 2/2003 | Nezhat et al. |
| 6,516,073 | B1 | 2/2003 | Schulz et al. |
| 6,517,528 | B1 | 2/2003 | Pantages et al. |
| 6,517,535 | B2 | 2/2003 | Edwards |
| 6,517,565 | B1 | 2/2003 | Whitman et al. |
| 6,517,566 | B1 | 2/2003 | Hovland et al. |
| 6,520,971 | B1 | 2/2003 | Perry et al. |
| 6,520,972 | B2 | 2/2003 | Peters |
| 6,522,101 | B2 | 2/2003 | Malackowski |
| 6,524,180 | B1 | 2/2003 | Simms et al. |
| 6,525,499 | B2 | 2/2003 | Naganuma |
| D471,206 | S | 3/2003 | Buzzard et al. |
| 6,527,782 | B2 | 3/2003 | Hogg et al. |
| 6,527,785 | B2 | 3/2003 | Sancoff et al. |
| 6,530,942 | B2 | 3/2003 | Fogarty et al. |
| 6,532,958 | B1 | 3/2003 | Buan et al. |
| 6,533,157 | B1 | 3/2003 | Whitman |
| 6,533,723 | B1 | 3/2003 | Lockery et al. |
| 6,533,784 | B2 | 3/2003 | Truckai et al. |
| 6,535,764 | B2 | 3/2003 | Imran et al. |
| 6,539,297 | B2 | 3/2003 | Weiberle et al. |
| D473,239 | S | 4/2003 | Cockerill |
| 6,539,816 | B2 | 4/2003 | Kogiso et al. |
| 6,540,737 | B2 | 4/2003 | Bacher et al. |
| 6,543,456 | B1 | 4/2003 | Freeman |
| 6,545,384 | B1 | 4/2003 | Pelrine et al. |
| 6,547,786 | B1 | 4/2003 | Goble |
| 6,550,546 | B2 | 4/2003 | Thurler et al. |
| 6,551,333 | B2 | 4/2003 | Kuhns et al. |
| 6,554,844 | B2 | 4/2003 | Lee et al. |
| 6,554,861 | B2 | 4/2003 | Knox et al. |
| 6,555,770 | B2 | 4/2003 | Kawase |
| 6,558,378 | B2 | 5/2003 | Sherman et al. |
| 6,558,379 | B1 | 5/2003 | Batchelor et al. |
| 6,558,429 | B2 | 5/2003 | Taylor |
| 6,561,187 | B2 | 5/2003 | Schmidt et al. |
| 6,565,560 | B1 | 5/2003 | Goble et al. |
| 6,566,619 | B2 | 5/2003 | Gillman et al. |
| 6,569,085 | B2 | 5/2003 | Kortenbach et al. |
| 6,569,171 | B2 | 5/2003 | DeGuillebon et al. |
| 6,569,173 | B1 | 5/2003 | Blatter et al. |
| 6,572,629 | B2 | 6/2003 | Kalloo et al. |
| 6,575,969 | B1 | 6/2003 | Rittman, III et al. |
| 6,578,751 | B2 | 6/2003 | Hartwick |
| 6,582,364 | B2 | 6/2003 | Butler et al. |
| 6,582,427 | B1 | 6/2003 | Goble et al. |
| 6,582,441 | B1 | 6/2003 | He et al. |
| 6,583,533 | B2 | 6/2003 | Pelrine et al. |
| 6,585,144 | B2 | 7/2003 | Adams et al. |
| 6,585,664 | B2 | 7/2003 | Burdorff et al. |
| 6,586,898 | B2 | 7/2003 | King et al. |
| 6,587,750 | B2 | 7/2003 | Gerbi et al. |
| 6,588,277 | B2 | 7/2003 | Giordano et al. |
| 6,588,643 | B2 | 7/2003 | Bolduc et al. |
| 6,588,931 | B2 | 7/2003 | Betzner et al. |
| 6,589,118 | B1 | 7/2003 | Soma et al. |
| 6,589,164 | B1 | 7/2003 | Flaherty |
| 6,592,538 | B1 | 7/2003 | Hotchkiss et al. |
| 6,592,572 | B1 | 7/2003 | Suzuta |
| 6,592,597 | B2 | 7/2003 | Grant et al. |
| 6,594,552 | B1 | 7/2003 | Nowlin et al. |
| 6,595,914 | B2 | 7/2003 | Kato |
| 6,596,296 | B1 | 7/2003 | Nelson et al. |
| 6,596,304 | B1 | 7/2003 | Bayon et al. |
| 6,596,432 | B2 | 7/2003 | Kawakami et al. |
| 6,599,295 | B1 | 7/2003 | Tornier et al. |
| 6,599,323 | B2 | 7/2003 | Melican et al. |
| D478,665 | S | 8/2003 | Isaacs et al. |
| D478,986 | S | 8/2003 | Johnston et al. |
| 6,601,749 | B2 | 8/2003 | Sullivan et al. |
| 6,602,252 | B2 | 8/2003 | Mollenauer |
| 6,602,262 | B2 | 8/2003 | Griego et al. |
| 6,603,050 | B2 | 8/2003 | Heaton |
| 6,605,078 | B2 | 8/2003 | Adams |
| 6,605,669 | B2 | 8/2003 | Awokola et al. |
| 6,605,911 | B1 | 8/2003 | Klesing |
| 6,607,475 | B2 | 8/2003 | Doyle et al. |
| 6,611,793 | B1 | 8/2003 | Burnside et al. |
| 6,613,069 | B2 | 9/2003 | Boyd et al. |
| 6,616,686 | B2 | 9/2003 | Coleman et al. |
| 6,619,529 | B2 | 9/2003 | Green et al. |
| 6,620,111 | B2 | 9/2003 | Stephens et al. |
| 6,620,161 | B2 | 9/2003 | Schulze et al. |
| 6,620,166 | B1 | 9/2003 | Wenstrom, Jr. et al. |
| 6,623,482 | B2 | 9/2003 | Pendekanti et al. |
| 6,625,517 | B1 | 9/2003 | Bogdanov et al. |
| 6,626,834 | B2 | 9/2003 | Dunne et al. |
| 6,626,901 | B1 | 9/2003 | Treat et al. |
| 6,626,938 | B1 | 9/2003 | Butaric et al. |
| H2086 | H | 10/2003 | Amsler |
| 6,629,630 | B2 | 10/2003 | Adams |
| 6,629,974 | B2 | 10/2003 | Penny et al. |
| 6,629,988 | B2 | 10/2003 | Weadock |
| 6,635,838 | B1 | 10/2003 | Kornelson |
| 6,636,412 | B2 | 10/2003 | Smith |
| 6,638,108 | B2 | 10/2003 | Tach |
| 6,638,285 | B2 | 10/2003 | Gabbay |
| 6,638,297 | B1 | 10/2003 | Huitema |

(56) References Cited

U.S. PATENT DOCUMENTS

| | | | |
|---|---|---|---|
| RE38,335 | E | 11/2003 | Aust et al. |
| 6,641,528 | B2 | 11/2003 | Torii |
| 6,644,532 | B2 | 11/2003 | Green et al. |
| 6,645,201 | B1 | 11/2003 | Utley et al. |
| 6,646,307 | B1 | 11/2003 | Yu et al. |
| 6,648,816 | B2 | 11/2003 | Irion et al. |
| 6,648,901 | B2 | 11/2003 | Fleischman et al. |
| 6,652,595 | B1 | 11/2003 | Nicolo |
| D484,243 | S | 12/2003 | Ryan et al. |
| D484,595 | S | 12/2003 | Ryan et al. |
| D484,596 | S | 12/2003 | Ryan et al. |
| 6,656,177 | B2 | 12/2003 | Truckai et al. |
| 6,656,193 | B2 | 12/2003 | Grant et al. |
| 6,659,940 | B2 | 12/2003 | Adler |
| 6,660,008 | B1 | 12/2003 | Foerster et al. |
| 6,663,623 | B1 | 12/2003 | Oyama et al. |
| 6,663,641 | B1 | 12/2003 | Kovac et al. |
| 6,666,854 | B1 | 12/2003 | Lange |
| 6,666,860 | B1 | 12/2003 | Takahashi |
| 6,666,875 | B1 | 12/2003 | Sakurai et al. |
| 6,667,825 | B2 | 12/2003 | Lu et al. |
| 6,669,073 | B2 | 12/2003 | Milliman et al. |
| 6,670,806 | B2 | 12/2003 | Wendt et al. |
| 6,671,185 | B2 | 12/2003 | Duval |
| D484,977 | S | 1/2004 | Ryan et al. |
| 6,676,660 | B2 | 1/2004 | Wampler et al. |
| 6,677,687 | B2 | 1/2004 | Ho et al. |
| 6,679,269 | B2 | 1/2004 | Swanson |
| 6,679,410 | B2 | 1/2004 | Wursch et al. |
| 6,681,978 | B2 | 1/2004 | Geiste et al. |
| 6,681,979 | B2 | 1/2004 | Whitman |
| 6,682,527 | B2 | 1/2004 | Strul |
| 6,682,528 | B2 | 1/2004 | Frazier et al. |
| 6,682,544 | B2 | 1/2004 | Mastri et al. |
| 6,685,698 | B2 | 2/2004 | Morley et al. |
| 6,685,727 | B2 | 2/2004 | Fisher et al. |
| 6,689,153 | B1 | 2/2004 | Skiba |
| 6,692,507 | B2 | 2/2004 | Pugsley et al. |
| 6,692,692 | B2 | 2/2004 | Stetzel |
| 6,695,198 | B2 | 2/2004 | Adams et al. |
| 6,695,199 | B2 | 2/2004 | Whitman |
| 6,695,774 | B2 | 2/2004 | Hale et al. |
| 6,695,849 | B2 | 2/2004 | Michelson |
| 6,696,814 | B2 | 2/2004 | Henderson et al. |
| 6,697,048 | B2 | 2/2004 | Rosenberg et al. |
| 6,698,643 | B2 | 3/2004 | Whitman |
| 6,699,177 | B1 | 3/2004 | Wang et al. |
| 6,699,214 | B2 | 3/2004 | Gellman |
| 6,699,235 | B2 | 3/2004 | Wallace et al. |
| 6,704,210 | B1 | 3/2004 | Myers |
| 6,705,503 | B1 | 3/2004 | Pedicini et al. |
| 6,709,445 | B2 | 3/2004 | Boebel et al. |
| 6,712,773 | B1 | 3/2004 | Viola |
| 6,716,215 | B1 | 4/2004 | David et al. |
| 6,716,223 | B2 | 4/2004 | Leopold et al. |
| 6,716,232 | B1 | 4/2004 | Vidal et al. |
| 6,716,233 | B1 | 4/2004 | Whitman |
| 6,720,734 | B2 | 4/2004 | Norris |
| 6,722,550 | B1 | 4/2004 | Ricordi et al. |
| 6,722,552 | B2 | 4/2004 | Fenton, Jr. |
| 6,723,087 | B2 | 4/2004 | O’Neill et al. |
| 6,723,091 | B2 | 4/2004 | Goble et al. |
| 6,723,106 | B1 | 4/2004 | Charles et al. |
| 6,723,109 | B2 | 4/2004 | Solingen |
| 6,726,651 | B1 | 4/2004 | Robinson et al. |
| 6,726,697 | B2 | 4/2004 | Nicholas et al. |
| 6,726,705 | B2 | 4/2004 | Peterson et al. |
| 6,726,706 | B2 | 4/2004 | Dominguez |
| 6,729,119 | B2 | 5/2004 | Schnipke et al. |
| 6,731,976 | B2 | 5/2004 | Penn et al. |
| 6,736,810 | B2 | 5/2004 | Hoey et al. |
| 6,736,825 | B2 | 5/2004 | Blatter et al. |
| 6,736,854 | B2 | 5/2004 | Vadurro et al. |
| 6,740,030 | B2 | 5/2004 | Martone et al. |
| 6,743,230 | B2 | 6/2004 | Lutze et al. |
| 6,744,385 | B2 | 6/2004 | Kazuya et al. |
| 6,747,121 | B2 | 6/2004 | Gogolewski |
| 6,747,300 | B2 | 6/2004 | Nadd et al. |
| 6,749,560 | B1 | 6/2004 | Konstorum et al. |
| 6,749,600 | B1 | 6/2004 | Levy |
| 6,750,622 | B2 | 6/2004 | Simizu et al. |
| 6,752,768 | B2 | 6/2004 | Burdorff et al. |
| 6,752,816 | B2 | 6/2004 | Culp et al. |
| 6,754,959 | B1 | 6/2004 | Guiette, III et al. |
| 6,755,195 | B1 | 6/2004 | Lemke et al. |
| 6,755,338 | B2 | 6/2004 | Hahnen et al. |
| 6,755,825 | B2 | 6/2004 | Shoenman et al. |
| 6,755,843 | B2 | 6/2004 | Chung et al. |
| 6,756,705 | B2 | 6/2004 | Pulford, Jr. |
| 6,758,846 | B2 | 7/2004 | Goble et al. |
| 6,761,685 | B2 | 7/2004 | Adams et al. |
| 6,762,339 | B1 | 7/2004 | Klun et al. |
| 6,763,307 | B2 | 7/2004 | Berg et al. |
| 6,764,445 | B2 | 7/2004 | Ramans et al. |
| 6,766,957 | B2 | 7/2004 | Matsuura et al. |
| 6,767,352 | B2 | 7/2004 | Field et al. |
| 6,767,356 | B2 | 7/2004 | Kanner et al. |
| 6,769,590 | B2 | 8/2004 | Vresh et al. |
| 6,769,594 | B2 | 8/2004 | Orban, III |
| 6,770,027 | B2 | 8/2004 | Banik et al. |
| 6,770,070 | B1 | 8/2004 | Balbierz |
| 6,770,072 | B1 | 8/2004 | Truckai et al. |
| 6,770,078 | B2 | 8/2004 | Bonutti |
| 6,773,409 | B2 | 8/2004 | Truckai et al. |
| 6,773,437 | B2 | 8/2004 | Ogilvie et al. |
| 6,773,438 | B1 | 8/2004 | Knodel et al. |
| 6,773,458 | B1 | 8/2004 | Brauker et al. |
| 6,775,575 | B2 | 8/2004 | Bommannan et al. |
| 6,777,838 | B2 | 8/2004 | Miekka et al. |
| 6,778,846 | B1 | 8/2004 | Martinez et al. |
| 6,780,151 | B2 | 8/2004 | Grabover et al. |
| 6,780,180 | B1 | 8/2004 | Goble et al. |
| 6,783,524 | B2 | 8/2004 | Anderson et al. |
| 6,784,775 | B2 | 8/2004 | Mandell et al. |
| 6,786,382 | B1 | 9/2004 | Hoffman |
| 6,786,864 | B2 | 9/2004 | Matsuura et al. |
| 6,786,896 | B1 | 9/2004 | Madhani et al. |
| 6,788,018 | B1 | 9/2004 | Blumenkranz |
| 6,790,173 | B2 | 9/2004 | Saadat et al. |
| 6,793,652 | B1 | 9/2004 | Whitman et al. |
| 6,793,661 | B2 | 9/2004 | Hamilton et al. |
| 6,793,663 | B2 | 9/2004 | Kneifel et al. |
| 6,793,669 | B2 | 9/2004 | Nakamura et al. |
| 6,796,921 | B1 | 9/2004 | Buck et al. |
| 6,799,669 | B2 | 10/2004 | Fukumura et al. |
| 6,801,009 | B2 | 10/2004 | Makaran et al. |
| 6,802,822 | B1 | 10/2004 | Dodge |
| 6,802,843 | B2 | 10/2004 | Truckai et al. |
| 6,802,844 | B2 | 10/2004 | Ferree |
| 6,805,273 | B2 | 10/2004 | Bilotti et al. |
| 6,806,808 | B1 | 10/2004 | Watters et al. |
| 6,806,867 | B1 | 10/2004 | Arruda et al. |
| 6,808,525 | B2 | 10/2004 | Latterell et al. |
| 6,810,359 | B2 | 10/2004 | Sakaguchi |
| 6,814,154 | B2 | 11/2004 | Chou |
| 6,814,741 | B2 | 11/2004 | Bowman et al. |
| 6,817,508 | B1 | 11/2004 | Racenet et al. |
| 6,817,509 | B2 | 11/2004 | Geiste et al. |
| 6,817,974 | B2 | 11/2004 | Cooper et al. |
| 6,818,018 | B1 | 11/2004 | Sawhney |
| 6,819,269 | B2 | 11/2004 | Flick |
| 6,820,791 | B2 | 11/2004 | Adams |
| 6,821,273 | B2 | 11/2004 | Mollenauer |
| 6,821,282 | B2 | 11/2004 | Perry et al. |
| 6,821,284 | B2 | 11/2004 | Sturtz et al. |
| 6,827,246 | B2 | 12/2004 | Sullivan et al. |
| 6,827,712 | B2 | 12/2004 | Tovey et al. |
| 6,827,725 | B2 | 12/2004 | Batchelor et al. |
| 6,828,902 | B2 | 12/2004 | Casden |
| 6,830,174 | B2 | 12/2004 | Hillstead et al. |
| 6,831,629 | B2 | 12/2004 | Nishino et al. |
| 6,832,998 | B2 | 12/2004 | Goble |
| 6,834,001 | B2 | 12/2004 | Myono |
| 6,835,173 | B2 | 12/2004 | Couvillon, Jr. |

(56) References Cited

U.S. PATENT DOCUMENTS

| | | | |
|---|---|---|---|
| 6,835,199 | B2 | 12/2004 | McGuckin, Jr. et al. |
| 6,835,336 | B2 | 12/2004 | Watt |
| 6,836,611 | B2 | 12/2004 | Popovic et al. |
| 6,837,846 | B2 | 1/2005 | Jaffe et al. |
| 6,837,883 | B2 | 1/2005 | Moll et al. |
| 6,838,493 | B2 | 1/2005 | Williams et al. |
| 6,840,423 | B2 | 1/2005 | Adams et al. |
| 6,840,938 | B1 | 1/2005 | Morley et al. |
| 6,841,967 | B2 | 1/2005 | Kim et al. |
| 6,843,403 | B2 | 1/2005 | Whitman |
| 6,843,789 | B2 | 1/2005 | Goble |
| 6,843,793 | B2 | 1/2005 | Brock et al. |
| 6,846,307 | B2 | 1/2005 | Whitman et al. |
| 6,846,308 | B2 | 1/2005 | Whitman et al. |
| 6,846,309 | B2 | 1/2005 | Whitman et al. |
| 6,847,190 | B2 | 1/2005 | Schaefer et al. |
| 6,849,071 | B2 | 2/2005 | Whitman et al. |
| 6,850,817 | B1 | 2/2005 | Green |
| 6,852,122 | B2 | 2/2005 | Rush |
| 6,852,330 | B2 | 2/2005 | Bowman et al. |
| 6,853,879 | B2 | 2/2005 | Sunaoshi |
| 6,858,005 | B2 | 2/2005 | Ohline et al. |
| 6,859,882 | B2 | 2/2005 | Fung |
| RE38,708 | E | 3/2005 | Bolanos et al. |
| D502,994 | S | 3/2005 | Blake, III |
| 6,860,169 | B2 | 3/2005 | Shinozaki |
| 6,861,142 | B1 | 3/2005 | Wilkie et al. |
| 6,861,954 | B2 | 3/2005 | Levin |
| 6,863,668 | B2 | 3/2005 | Gillespie et al. |
| 6,863,694 | B1 | 3/2005 | Boyce et al. |
| 6,863,924 | B2 | 3/2005 | Ranganathan et al. |
| 6,866,178 | B2 | 3/2005 | Adams et al. |
| 6,866,668 | B2 | 3/2005 | Giannetti et al. |
| 6,866,671 | B2 | 3/2005 | Tierney et al. |
| 6,867,248 | B1 | 3/2005 | Martin et al. |
| 6,869,430 | B2 | 3/2005 | Balbierz et al. |
| 6,869,435 | B2 | 3/2005 | Blake, III |
| 6,872,214 | B2 | 3/2005 | Sonnenschein et al. |
| 6,874,669 | B2 | 4/2005 | Adams et al. |
| 6,876,850 | B2 | 4/2005 | Maeshima et al. |
| 6,877,647 | B2 | 4/2005 | Green et al. |
| 6,878,106 | B1 | 4/2005 | Herrmann |
| 6,882,127 | B2 | 4/2005 | Konigbauer |
| 6,883,199 | B1 | 4/2005 | Lundell et al. |
| 6,884,392 | B2 | 4/2005 | Malkin et al. |
| 6,884,428 | B2 | 4/2005 | Binette et al. |
| 6,886,730 | B2 | 5/2005 | Fujisawa et al. |
| 6,887,244 | B1 | 5/2005 | Walker et al. |
| 6,887,710 | B2 | 5/2005 | Call et al. |
| 6,889,116 | B2 | 5/2005 | Jinno |
| 6,893,435 | B2 | 5/2005 | Goble |
| 6,894,140 | B2 | 5/2005 | Roby |
| 6,895,176 | B2 | 5/2005 | Archer et al. |
| 6,899,538 | B2 | 5/2005 | Matoba |
| 6,899,593 | B1 | 5/2005 | Moeller et al. |
| 6,899,705 | B2 | 5/2005 | Niemeyer |
| 6,899,915 | B2 | 5/2005 | Yelick et al. |
| 6,905,057 | B2 | 6/2005 | Swayze et al. |
| 6,905,497 | B2 | 6/2005 | Truckai et al. |
| 6,905,498 | B2 | 6/2005 | Hooven |
| 6,908,472 | B2 | 6/2005 | Wiener et al. |
| 6,911,033 | B2 | 6/2005 | de Guillebon et al. |
| 6,911,916 | B1 | 6/2005 | Wang et al. |
| 6,913,579 | B2 | 7/2005 | Truckai et al. |
| 6,913,608 | B2 | 7/2005 | Liddicoat et al. |
| 6,913,613 | B2 | 7/2005 | Schwarz et al. |
| 6,921,397 | B2 | 7/2005 | Corcoran et al. |
| 6,921,412 | B1 | 7/2005 | Black et al. |
| 6,923,093 | B2 | 8/2005 | Ullah |
| 6,923,803 | B2 | 8/2005 | Goble |
| 6,923,819 | B2 | 8/2005 | Meade et al. |
| 6,925,849 | B2 | 8/2005 | Jairam |
| 6,926,716 | B2 | 8/2005 | Baker et al. |
| 6,927,315 | B1 | 8/2005 | Heinecke et al. |
| 6,928,902 | B1 | 8/2005 | Eyssallenne |
| 6,929,641 | B2 | 8/2005 | Goble et al. |
| 6,929,644 | B2 | 8/2005 | Truckai et al. |
| 6,931,830 | B2 | 8/2005 | Liao |
| 6,932,218 | B2 | 8/2005 | Kosann et al. |
| 6,932,810 | B2 | 8/2005 | Ryan |
| 6,936,042 | B2 | 8/2005 | Wallace et al. |
| 6,936,948 | B2 | 8/2005 | Bell et al. |
| D509,297 | S | 9/2005 | Wells |
| D509,589 | S | 9/2005 | Wells |
| 6,938,706 | B2 | 9/2005 | Ng |
| 6,939,358 | B2 | 9/2005 | Palacios et al. |
| 6,942,662 | B2 | 9/2005 | Goble et al. |
| 6,942,674 | B2 | 9/2005 | Belef et al. |
| 6,945,444 | B2 | 9/2005 | Gresham et al. |
| 6,945,981 | B2 | 9/2005 | Donofrio et al. |
| 6,949,196 | B2 | 9/2005 | Schmitz et al. |
| 6,951,562 | B2 | 10/2005 | Zwirnmann |
| 6,953,138 | B1 | 10/2005 | Dworak et al. |
| 6,953,139 | B2 | 10/2005 | Milliman et al. |
| 6,953,461 | B2 | 10/2005 | McClurken et al. |
| 6,957,758 | B2 | 10/2005 | Aranyi |
| 6,958,035 | B2 | 10/2005 | Friedman et al. |
| 6,958,070 | B2 | 10/2005 | Witt et al. |
| D511,525 | S | 11/2005 | Hernandez et al. |
| 6,959,851 | B2 | 11/2005 | Heinrich |
| 6,959,852 | B2 | 11/2005 | Shelton, IV et al. |
| 6,960,107 | B1 | 11/2005 | Schaub et al. |
| 6,960,163 | B2 | 11/2005 | Ewers et al. |
| 6,960,220 | B2 | 11/2005 | Marino et al. |
| 6,960,894 | B2 | 11/2005 | Carusillo et al. |
| 6,962,587 | B2 | 11/2005 | Johnson et al. |
| 6,963,792 | B1 | 11/2005 | Green |
| 6,964,363 | B2 | 11/2005 | Wales et al. |
| 6,966,907 | B2 | 11/2005 | Goble |
| 6,966,909 | B2 | 11/2005 | Marshall et al. |
| 6,968,908 | B2 | 11/2005 | Tokunaga et al. |
| 6,969,385 | B2 | 11/2005 | Moreyra |
| 6,969,395 | B2 | 11/2005 | Eskuri |
| 6,971,988 | B2 | 12/2005 | Orban, III |
| 6,972,199 | B2 | 12/2005 | Lebouitz et al. |
| 6,974,435 | B2 | 12/2005 | Daw et al. |
| 6,974,462 | B2 | 12/2005 | Sater |
| 6,978,921 | B2 | 12/2005 | Shelton, IV et al. |
| 6,978,922 | B2 | 12/2005 | Bilotti et al. |
| 6,981,628 | B2 | 1/2006 | Wales |
| 6,981,941 | B2 | 1/2006 | Whitman et al. |
| 6,981,978 | B2 | 1/2006 | Gannoe |
| 6,984,203 | B2 | 1/2006 | Tartaglia et al. |
| 6,984,231 | B2 | 1/2006 | Goble et al. |
| 6,986,451 | B1 | 1/2006 | Mastri et al. |
| 6,988,649 | B2 | 1/2006 | Shelton, IV et al. |
| 6,988,650 | B2 | 1/2006 | Schwemberger et al. |
| 6,989,034 | B2 | 1/2006 | Hammer et al. |
| 6,990,731 | B2 | 1/2006 | Haytayan |
| 6,990,796 | B2 | 1/2006 | Schnipke et al. |
| 6,991,146 | B2 | 1/2006 | Sinisi et al. |
| 6,993,200 | B2 | 1/2006 | Tastl et al. |
| 6,993,413 | B2 | 1/2006 | Sunaoshi |
| 6,994,708 | B2 | 2/2006 | Manzo |
| 6,995,729 | B2 | 2/2006 | Govari et al. |
| 6,996,433 | B2 | 2/2006 | Burbank et al. |
| 6,997,931 | B2 | 2/2006 | Sauer et al. |
| 6,997,935 | B2 | 2/2006 | Anderson et al. |
| 6,998,736 | B2 | 2/2006 | Lee et al. |
| 6,998,816 | B2 | 2/2006 | Wieck et al. |
| 6,999,821 | B2 | 2/2006 | Jenney et al. |
| 7,000,818 | B2 | 2/2006 | Shelton, IV et al. |
| 7,000,819 | B2 | 2/2006 | Swayze et al. |
| 7,000,911 | B2 | 2/2006 | McCormick et al. |
| 7,001,380 | B2 | 2/2006 | Goble |
| 7,001,408 | B2 | 2/2006 | Knodel et al. |
| 7,004,174 | B2 | 2/2006 | Eggers et al. |
| 7,005,828 | B2 | 2/2006 | Karikomi |
| 7,007,176 | B2 | 2/2006 | Goodfellow et al. |
| 7,008,433 | B2 | 3/2006 | Voellmicke et al. |
| 7,008,435 | B2 | 3/2006 | Cummins |
| 7,009,039 | B2 | 3/2006 | Yayon et al. |
| 7,011,213 | B2 | 3/2006 | Clark et al. |
| 7,011,657 | B2 | 3/2006 | Truckai et al. |

(56) References Cited

U.S. PATENT DOCUMENTS 7,014,640 B2 3/2006 Kemppainen et al.
7,018,357 B2 3/2006 Emmons
7,018,390 B2 3/2006 Turovskiy et al.
7,021,399 B2 4/2006 Driessen
7,021,669 B1 4/2006 Lindermeir et al.
7,022,131 B1 4/2006 Derowe et al.
7,023,159 B2 4/2006 Gorti et al.
7,025,064 B2 4/2006 Wang et al.
7,025,732 B2 4/2006 Thompson et al.
7,025,743 B2 4/2006 Mann et al.
7,025,774 B2 4/2006 Freeman et al.
7,025,775 B2 4/2006 Gadberry et al.
7,028,570 B2 4/2006 Ohta et al.
7,029,435 B2 4/2006 Nakao
7,029,439 B2 4/2006 Roberts et al.
7,030,904 B2 4/2006 Adair et al.
7,032,798 B2 4/2006 Whitman et al.
7,032,799 B2 4/2006 Viola et al.
7,033,356 B2 4/2006 Latterell et al.
7,033,378 B2 4/2006 Smith et al.
7,035,716 B2 4/2006 Harris et al.
7,035,762 B2 4/2006 Menard et al.
7,036,680 B1 5/2006 Flannery
7,037,314 B2 5/2006 Armstrong
7,037,344 B2 5/2006 Kagan et al.
7,038,421 B2 5/2006 Trifilo
7,041,088 B2 5/2006 Nawrocki et al.
7,041,102 B2 5/2006 Truckai et al.
7,041,868 B2 5/2006 Greene et al.
7,043,852 B2 5/2006 Hayashida et al.
7,044,350 B2 5/2006 Kameyama et al.
7,044,352 B2 5/2006 Shelton, IV et al.
7,044,353 B2 5/2006 Mastri et al.
7,046,082 B2 5/2006 Komiya et al.
7,048,165 B2 5/2006 Haramiishi
7,048,687 B1 5/2006 Reuss et al.
7,048,716 B1 5/2006 Kucharczyk et al.
7,048,745 B2 5/2006 Tierney et al.
7,052,454 B2 5/2006 Taylor
7,052,494 B2 5/2006 Goble et al.
7,052,499 B2 5/2006 Steger et al.
7,055,730 B2 6/2006 Ehrenfels et al.
7,055,731 B2 6/2006 Shelton, IV et al.
7,056,123 B2 6/2006 Gregorio et al.
7,056,284 B2 6/2006 Martone et al.
7,056,330 B2 6/2006 Gayton
7,059,331 B2 6/2006 Adams et al.
7,059,508 B2 6/2006 Shelton, IV et al.
7,063,671 B2 6/2006 Couvillon, Jr.
7,063,712 B2 6/2006 Vargas et al.
7,064,509 B1 6/2006 Fu et al.
7,066,879 B2 6/2006 Fowler et al.
7,066,944 B2 6/2006 Laufer et al.
7,067,038 B2 6/2006 Trokhan et al.
7,070,083 B2 7/2006 Jankowski
7,070,559 B2 7/2006 Adams et al.
7,070,597 B2 7/2006 Truckai et al.
7,071,287 B2 7/2006 Rhine et al.
7,075,412 B1 7/2006 Reynolds et al.
7,075,770 B1 7/2006 Smith
7,077,856 B2 7/2006 Whitman
7,080,769 B2 7/2006 Vresh et al.
7,081,114 B2 7/2006 Rashidi
7,081,318 B2 7/2006 Lee et al.
7,083,073 B2 8/2006 Yoshie et al.
7,083,075 B2 8/2006 Swayze et al.
7,083,571 B2 8/2006 Wang et al.
7,083,615 B2 8/2006 Peterson et al.
7,083,619 B2 8/2006 Truckai et al.
7,083,620 B2 8/2006 Jahns et al.
7,083,626 B2 8/2006 Hart et al.
7,086,267 B2 8/2006 Dworak et al.
7,087,049 B2 8/2006 Nowlin et al.
7,087,054 B2 8/2006 Truckai et al.
7,087,071 B2 8/2006 Nicholas et al.
7,090,637 B2 8/2006 Danitz et al.
7,090,673 B2 8/2006 Dycus et al.
7,090,683 B2 8/2006 Brock et al.
7,090,684 B2 8/2006 McGuckin, Jr. et al.
7,091,191 B2 8/2006 Laredo et al.
7,091,412 B2 8/2006 Wang et al.
7,093,492 B2 8/2006 Treiber et al.
7,094,202 B2 8/2006 Nobis et al.
7,094,247 B2 8/2006 Monassevitch et al.
7,094,916 B2 8/2006 DeLuca et al.
7,096,972 B2 8/2006 Orozco, Jr.
7,097,089 B2 8/2006 Marczyk
7,097,644 B2 8/2006 Long
7,097,650 B2 8/2006 Weller et al.
7,098,794 B2 8/2006 Lindsay et al.
7,100,949 B2 9/2006 Williams et al.
7,101,187 B1 9/2006 Deconinck et al.
7,101,363 B2 9/2006 Nishizawa et al.
7,101,371 B2 9/2006 Dycus et al.
7,101,394 B2 9/2006 Hamm et al.
7,104,741 B2 9/2006 Krohn
7,108,695 B2 9/2006 Witt et al.
7,108,701 B2 9/2006 Evens et al.
7,108,709 B2 9/2006 Cummins
7,111,768 B2 9/2006 Cummins et al.
7,111,769 B2 9/2006 Wales et al.
7,112,201 B2 9/2006 Truckai et al.
7,112,214 B2 9/2006 Peterson et al.
RE39,358 E 10/2006 Goble
D530,339 S 10/2006 Hernandez et al.
7,114,642 B2 10/2006 Whitman
7,116,100 B1 10/2006 Mock et al.
7,118,020 B2 10/2006 Lee et al.
7,118,528 B1 10/2006 Piskun
7,118,563 B2 10/2006 Weckwerth et al.
7,118,582 B1 10/2006 Wang et al.
7,119,534 B2 10/2006 Butzmann
7,121,446 B2 10/2006 Arad et al.
7,121,773 B2 10/2006 Mikiya et al.
7,122,028 B2 10/2006 Looper et al.
7,125,403 B2 10/2006 Julian et al.
7,125,409 B2 10/2006 Truckai et al.
7,126,303 B2 10/2006 Farritor et al.
7,126,879 B2 10/2006 Snyder
7,128,253 B2 10/2006 Mastri et al.
7,128,254 B2 10/2006 Shelton, IV et al.
7,128,748 B2 10/2006 Mooradian et al.
7,131,445 B2 11/2006 Amoah
7,133,601 B2 11/2006 Phillips et al.
7,134,364 B2 11/2006 Kageler et al.
7,134,587 B2 11/2006 Schwemberger et al.
7,135,027 B2 11/2006 Delmotte
7,137,980 B2 11/2006 Buysse et al.
7,137,981 B2 11/2006 Long
7,139,016 B2 11/2006 Squilla et al.
7,140,527 B2 11/2006 Ehrenfels et al.
7,140,528 B2 11/2006 Shelton, IV
7,141,055 B2 11/2006 Abrams et al.
7,143,923 B2 12/2006 Shelton, IV et al.
7,143,924 B2 12/2006 Scirica et al.
7,143,925 B2 12/2006 Shelton, IV et al.
7,143,926 B2 12/2006 Shelton, IV et al.
7,146,191 B2 12/2006 Kerner et al.
7,147,138 B2 12/2006 Shelton, IV
7,147,139 B2 12/2006 Schwemberger et al.
7,147,140 B2 12/2006 Wukusick et al.
7,147,637 B2 12/2006 Goble
7,147,648 B2 12/2006 Lin
7,147,650 B2 12/2006 Lee
7,150,748 B2 12/2006 Ebbutt et al.
7,153,300 B2 12/2006 Goble
7,153,314 B2 12/2006 Laufer et al.
7,155,316 B2 12/2006 Sutherland et al.
7,156,846 B2 1/2007 Dycus et al.
7,156,863 B2 1/2007 Sonnenschein et al.
7,159,750 B2 1/2007 Racenet et al.
7,160,296 B2 1/2007 Pearson et al.
7,160,299 B2 1/2007 Baily
7,160,311 B2 1/2007 Blatter et al.

(56) References Cited

U.S. PATENT DOCUMENTS

| | | | |
|---|---|---|---|
| 7,161,036 | B2 | 1/2007 | Oikawa et al. |
| 7,161,580 | B2 | 1/2007 | Bailey et al. |
| 7,162,758 | B2 | 1/2007 | Skinner |
| 7,163,563 | B2 | 1/2007 | Schwartz et al. |
| 7,166,117 | B2 | 1/2007 | Hellenkamp |
| 7,166,133 | B2 | 1/2007 | Evans et al. |
| 7,168,604 | B2 | 1/2007 | Milliman et al. |
| 7,169,146 | B2 | 1/2007 | Truckai et al. |
| 7,170,910 | B2 | 1/2007 | Chen et al. |
| 7,171,279 | B2 | 1/2007 | Buckingham et al. |
| 7,172,104 | B2 | 2/2007 | Scirica et al. |
| 7,172,593 | B2 | 2/2007 | Trieu et al. |
| 7,172,615 | B2 | 2/2007 | Morriss et al. |
| 7,174,202 | B2 | 2/2007 | Bladen et al. |
| 7,174,636 | B2 | 2/2007 | Lowe |
| 7,177,533 | B2 | 2/2007 | McFarlin et al. |
| 7,179,223 | B2 | 2/2007 | Motoki et al. |
| 7,179,267 | B2 | 2/2007 | Nolan et al. |
| 7,182,239 | B1 | 2/2007 | Myers |
| 7,182,763 | B2 | 2/2007 | Nardella |
| 7,183,737 | B2 | 2/2007 | Kitagawa |
| 7,187,960 | B2 | 3/2007 | Abreu |
| 7,188,758 | B2 | 3/2007 | Viola et al. |
| 7,189,207 | B2 | 3/2007 | Viola |
| 7,190,147 | B2 | 3/2007 | Gileff et al. |
| 7,193,199 | B2 | 3/2007 | Jang |
| 7,195,627 | B2 | 3/2007 | Amoah et al. |
| 7,196,911 | B2 | 3/2007 | Takano et al. |
| D541,418 | S | 4/2007 | Schechter et al. |
| 7,197,965 | B1 | 4/2007 | Anderson |
| 7,199,537 | B2 | 4/2007 | Okamura et al. |
| 7,199,545 | B2 | 4/2007 | Oleynikov et al. |
| 7,202,576 | B1 | 4/2007 | Dechene et al. |
| 7,202,653 | B2 | 4/2007 | Pai |
| 7,204,404 | B2 | 4/2007 | Nguyen et al. |
| 7,204,835 | B2 | 4/2007 | Latterell et al. |
| 7,205,959 | B2 | 4/2007 | Henriksson |
| 7,206,626 | B2 | 4/2007 | Quaid, III |
| 7,207,233 | B2 | 4/2007 | Wadge |
| 7,207,471 | B2 | 4/2007 | Heinrich et al. |
| 7,207,472 | B2 | 4/2007 | Wukusick et al. |
| 7,207,556 | B2 | 4/2007 | Saitoh et al. |
| 7,208,005 | B2 | 4/2007 | Frecker et al. |
| 7,210,609 | B2 | 5/2007 | Leiboff et al. |
| 7,211,081 | B2 | 5/2007 | Goble |
| 7,211,084 | B2 | 5/2007 | Goble et al. |
| 7,211,092 | B2 | 5/2007 | Hughett |
| 7,211,979 | B2 | 5/2007 | Khatib et al. |
| 7,213,736 | B2 | 5/2007 | Wales et al. |
| 7,214,224 | B2 | 5/2007 | Goble |
| 7,215,517 | B2 | 5/2007 | Takamatsu |
| 7,217,285 | B2 | 5/2007 | Vargas et al. |
| 7,220,260 | B2 | 5/2007 | Fleming et al. |
| 7,220,272 | B2 | 5/2007 | Weadock |
| 7,225,959 | B2 | 6/2007 | Patton et al. |
| 7,225,963 | B2 | 6/2007 | Scirica |
| 7,225,964 | B2 | 6/2007 | Mastri et al. |
| 7,226,450 | B2 | 6/2007 | Athanasiou et al. |
| 7,226,467 | B2 | 6/2007 | Lucatero et al. |
| 7,228,505 | B2 | 6/2007 | Shimazu et al. |
| 7,229,408 | B2 | 6/2007 | Douglas et al. |
| 7,234,624 | B2 | 6/2007 | Gresham et al. |
| 7,235,072 | B2 | 6/2007 | Sartor et al. |
| 7,235,089 | B1 | 6/2007 | McGuckin, Jr. |
| 7,235,302 | B2 | 6/2007 | Jing et al. |
| 7,237,708 | B1 | 7/2007 | Guy et al. |
| 7,238,195 | B2 | 7/2007 | Viola |
| 7,238,901 | B2 | 7/2007 | Kim et al. |
| 7,239,657 | B1 | 7/2007 | Gunnarsson |
| 7,241,288 | B2 | 7/2007 | Braun |
| 7,241,289 | B2 | 7/2007 | Braun |
| 7,246,734 | B2 | 7/2007 | Shelton, IV |
| 7,247,161 | B2 | 7/2007 | Johnston et al. |
| 7,249,267 | B2 | 7/2007 | Chapuis |
| 7,252,641 | B2 | 8/2007 | Thompson et al. |
| 7,252,660 | B2 | 8/2007 | Kunz |
| 7,255,012 | B2 | 8/2007 | Hedtke |
| 7,255,696 | B2 | 8/2007 | Goble et al. |
| 7,256,695 | B2 | 8/2007 | Hamel et al. |
| 7,258,262 | B2 | 8/2007 | Mastri et al. |
| 7,258,546 | B2 | 8/2007 | Beier et al. |
| 7,260,431 | B2 | 8/2007 | Libbus et al. |
| 7,265,374 | B2 | 9/2007 | Lee et al. |
| 7,267,677 | B2 | 9/2007 | Johnson et al. |
| 7,267,679 | B2 | 9/2007 | McGuckin, Jr. et al. |
| 7,272,002 | B2 | 9/2007 | Drapeau |
| 7,273,483 | B2 | 9/2007 | Wiener et al. |
| 7,273,488 | B2 | 9/2007 | Nakamura et al. |
| D552,623 | S | 10/2007 | Vong et al. |
| 7,275,674 | B2 | 10/2007 | Racenet et al. |
| 7,276,044 | B2 | 10/2007 | Ferry et al. |
| 7,276,068 | B2 | 10/2007 | Johnson et al. |
| 7,278,562 | B2 | 10/2007 | Mastri et al. |
| 7,278,563 | B1 | 10/2007 | Green |
| 7,278,949 | B2 | 10/2007 | Bader |
| 7,278,994 | B2 | 10/2007 | Goble |
| 7,282,048 | B2 | 10/2007 | Goble et al. |
| 7,283,096 | B2 | 10/2007 | Geisheimer et al. |
| 7,286,850 | B2 | 10/2007 | Frielink et al. |
| 7,287,682 | B1 | 10/2007 | Ezzat et al. |
| 7,289,139 | B2 | 10/2007 | Amling et al. |
| 7,293,685 | B2 | 11/2007 | Ehrenfels et al. |
| 7,295,893 | B2 | 11/2007 | Sunaoshi |
| 7,295,907 | B2 | 11/2007 | Lu et al. |
| 7,296,722 | B2 | 11/2007 | Ivanko |
| 7,296,724 | B2 | 11/2007 | Green et al. |
| 7,297,149 | B2 | 11/2007 | Vitali et al. |
| 7,300,373 | B2 | 11/2007 | Jinno et al. |
| 7,300,431 | B2 | 11/2007 | Dubrovsky |
| 7,300,450 | B2 | 11/2007 | Vleugels et al. |
| 7,303,106 | B2 | 12/2007 | Milliman et al. |
| 7,303,107 | B2 | 12/2007 | Milliman et al. |
| 7,303,108 | B2 | 12/2007 | Shelton, IV |
| 7,303,502 | B2 | 12/2007 | Thompson |
| 7,303,556 | B2 | 12/2007 | Metzger |
| 7,306,597 | B2 | 12/2007 | Manzo |
| 7,308,998 | B2 | 12/2007 | Mastri et al. |
| 7,311,238 | B2 | 12/2007 | Liu |
| 7,311,709 | B2 | 12/2007 | Truckai et al. |
| 7,313,430 | B2 | 12/2007 | Urquhart et al. |
| 7,314,473 | B2 | 1/2008 | Jinno et al. |
| 7,317,955 | B2 | 1/2008 | McGreevy |
| 7,320,704 | B2 | 1/2008 | Lashinski et al. |
| 7,322,859 | B2 | 1/2008 | Evans |
| 7,322,975 | B2 | 1/2008 | Goble et al. |
| 7,322,994 | B2 | 1/2008 | Nicholas et al. |
| 7,324,572 | B2 | 1/2008 | Chang |
| 7,326,203 | B2 | 2/2008 | Papineau et al. |
| 7,326,213 | B2 | 2/2008 | Benderev et al. |
| 7,328,828 | B2 | 2/2008 | Ortiz et al. |
| 7,328,829 | B2 | 2/2008 | Arad et al. |
| 7,330,004 | B2 | 2/2008 | DeJonge et al. |
| 7,331,340 | B2 | 2/2008 | Barney |
| 7,331,343 | B2 | 2/2008 | Schmidt et al. |
| 7,331,403 | B2 | 2/2008 | Berry et al. |
| 7,331,406 | B2 | 2/2008 | Wottreng, Jr. et al. |
| 7,331,969 | B1 | 2/2008 | Inganas et al. |
| 7,334,717 | B2 | 2/2008 | Rethy et al. |
| 7,334,718 | B2 | 2/2008 | McAlister et al. |
| 7,335,199 | B2 | 2/2008 | Goble et al. |
| 7,335,401 | B2 | 2/2008 | Finke et al. |
| 7,336,045 | B2 | 2/2008 | Clermonts |
| 7,336,048 | B2 | 2/2008 | Lohr |
| 7,336,183 | B2 | 2/2008 | Reddy et al. |
| 7,336,184 | B2 | 2/2008 | Smith et al. |
| 7,337,774 | B2 | 3/2008 | Webb |
| 7,338,505 | B2 | 3/2008 | Belson |
| 7,338,513 | B2 | 3/2008 | Lee et al. |
| 7,341,554 | B2 | 3/2008 | Sekine et al. |
| 7,341,555 | B2 | 3/2008 | Ootawara et al. |
| 7,341,591 | B2 | 3/2008 | Grinberg |
| 7,343,920 | B2 | 3/2008 | Toby et al. |
| 7,344,532 | B2 | 3/2008 | Goble et al. |
| 7,344,533 | B2 | 3/2008 | Pearson et al. |

(56) References Cited

U.S. PATENT DOCUMENTS

| | | | |
|---|---|---|---|
| 7,346,344 | B2 | 3/2008 | Fontaine |
| 7,346,406 | B2 | 3/2008 | Brotto et al. |
| 7,348,763 | B1 | 3/2008 | Reinhart et al. |
| 7,348,875 | B2 | 3/2008 | Hughes et al. |
| RE40,237 | E | 4/2008 | Bilotti et al. |
| 7,351,258 | B2 | 4/2008 | Ricotta et al. |
| 7,354,398 | B2 | 4/2008 | Kanazawa |
| 7,354,440 | B2 | 4/2008 | Truckal et al. |
| 7,354,447 | B2 | 4/2008 | Shelton, IV et al. |
| 7,354,502 | B2 | 4/2008 | Polat et al. |
| 7,357,287 | B2 | 4/2008 | Shelton, IV et al. |
| 7,357,806 | B2 | 4/2008 | Rivera et al. |
| 7,361,168 | B2 | 4/2008 | Makower et al. |
| 7,361,195 | B2 | 4/2008 | Schwartz et al. |
| 7,362,062 | B2 | 4/2008 | Schneider et al. |
| 7,364,060 | B2 | 4/2008 | Milliman |
| 7,364,061 | B2 | 4/2008 | Swayze et al. |
| 7,367,485 | B2 | 5/2008 | Shelton, IV et al. |
| 7,367,973 | B2 | 5/2008 | Manzo et al. |
| 7,368,124 | B2 | 5/2008 | Chun et al. |
| 7,371,210 | B2 | 5/2008 | Brock et al. |
| 7,371,403 | B2 | 5/2008 | McCarthy et al. |
| 7,375,493 | B2 | 5/2008 | Calhoon et al. |
| 7,377,918 | B2 | 5/2008 | Amoah |
| 7,377,928 | B2 | 5/2008 | Zubik et al. |
| 7,378,817 | B2 | 5/2008 | Calhoon et al. |
| RE40,388 | E | 6/2008 | Gines |
| D570,868 | S | 6/2008 | Hosokawa et al. |
| 7,380,695 | B2 | 6/2008 | Doll et al. |
| 7,380,696 | B2 | 6/2008 | Shelton, IV et al. |
| 7,384,403 | B2 | 6/2008 | Sherman |
| 7,384,417 | B2 | 6/2008 | Cucin |
| 7,386,365 | B2 | 6/2008 | Nixon |
| 7,386,730 | B2 | 6/2008 | Uchikubo |
| 7,388,217 | B2 | 6/2008 | Buschbeck et al. |
| 7,388,484 | B2 | 6/2008 | Hsu |
| 7,391,173 | B2 | 6/2008 | Schena |
| 7,394,190 | B2 | 7/2008 | Huang |
| 7,396,356 | B2 | 7/2008 | Mollenauer |
| 7,397,364 | B2 | 7/2008 | Govari |
| 7,398,707 | B2 | 7/2008 | Morley et al. |
| 7,398,907 | B2 | 7/2008 | Racenet et al. |
| 7,398,908 | B2 | 7/2008 | Holsten et al. |
| 7,400,107 | B2 | 7/2008 | Schneider et al. |
| 7,400,752 | B2 | 7/2008 | Zacharias |
| 7,401,000 | B2 | 7/2008 | Nakamura |
| 7,401,721 | B2 | 7/2008 | Holsten et al. |
| 7,404,449 | B2 | 7/2008 | Bermingham et al. |
| 7,404,508 | B2 | 7/2008 | Smith et al. |
| 7,404,509 | B2 | 7/2008 | Ortiz et al. |
| 7,404,822 | B2 | 7/2008 | Viart et al. |
| D575,793 | S | 8/2008 | Ording |
| 7,407,074 | B2 | 8/2008 | Ortiz et al. |
| 7,407,075 | B2 | 8/2008 | Holsten et al. |
| 7,407,076 | B2 | 8/2008 | Racenet et al. |
| 7,407,077 | B2 | 8/2008 | Ortiz et al. |
| 7,407,078 | B2 | 8/2008 | Shelton, IV et al. |
| 7,408,310 | B2 | 8/2008 | Hong et al. |
| 7,410,085 | B2 | 8/2008 | Wolf et al. |
| 7,410,086 | B2 | 8/2008 | Ortiz et al. |
| 7,410,483 | B2 | 8/2008 | Danitz et al. |
| 7,413,563 | B2 | 8/2008 | Corcoran et al. |
| 7,416,101 | B2 | 8/2008 | Shelton, IV et al. |
| 7,418,078 | B2 | 8/2008 | Blanz et al. |
| RE40,514 | E | 9/2008 | Mastri et al. |
| 7,419,080 | B2 | 9/2008 | Smith et al. |
| 7,419,081 | B2 | 9/2008 | Ehrenfels et al. |
| 7,419,321 | B2 | 9/2008 | Tereschouk |
| 7,419,495 | B2 | 9/2008 | Menn et al. |
| 7,422,136 | B1 | 9/2008 | Marczyk |
| 7,422,138 | B2 | 9/2008 | Bilotti et al. |
| 7,422,139 | B2 | 9/2008 | Shelton, IV et al. |
| 7,422,582 | B2 | 9/2008 | Malackowski et al. |
| 7,424,965 | B2 | 9/2008 | Racenet et al. |
| 7,427,607 | B2 | 9/2008 | Suzuki |
| D578,644 | S | 10/2008 | Shumer et al. |
| 7,430,772 | B2 | 10/2008 | Van Es |
| 7,430,849 | B1 | 10/2008 | Coutts et al. |
| 7,431,188 | B1 | 10/2008 | Marczyk |
| 7,431,189 | B2 | 10/2008 | Shelton, IV et al. |
| 7,431,230 | B2 | 10/2008 | McPherson et al. |
| 7,431,694 | B2 | 10/2008 | Stefanchik et al. |
| 7,431,730 | B2 | 10/2008 | Viola |
| 7,434,715 | B2 | 10/2008 | Shelton, IV et al. |
| 7,434,717 | B2 | 10/2008 | Shelton, IV et al. |
| 7,435,249 | B2 | 10/2008 | Buysse et al. |
| 7,438,209 | B1 | 10/2008 | Hess et al. |
| 7,438,718 | B2 | 10/2008 | Milliman et al. |
| 7,439,354 | B2 | 10/2008 | Lenges et al. |
| 7,441,684 | B2 | 10/2008 | Shelton, IV et al. |
| 7,441,685 | B1 | 10/2008 | Boudreaux |
| 7,442,201 | B2 | 10/2008 | Pugsley et al. |
| 7,443,547 | B2 | 10/2008 | Moreno et al. |
| D580,942 | S | 11/2008 | Oshiro et al. |
| 7,446,131 | B1 | 11/2008 | Liu et al. |
| 7,448,525 | B2 | 11/2008 | Shelton, IV et al. |
| 7,450,010 | B1 | 11/2008 | Gravelle et al. |
| 7,450,991 | B2 | 11/2008 | Smith et al. |
| 7,451,904 | B2 | 11/2008 | Shelton, IV |
| 7,455,208 | B2 | 11/2008 | Wales et al. |
| 7,455,676 | B2 | 11/2008 | Holsten et al. |
| 7,455,682 | B2 | 11/2008 | Viola |
| 7,455,687 | B2 | 11/2008 | Saunders et al. |
| D582,934 | S | 12/2008 | Byeon |
| 7,461,767 | B2 | 12/2008 | Viola et al. |
| 7,462,187 | B2 | 12/2008 | Johnston et al. |
| 7,464,845 | B2 | 12/2008 | Chou |
| 7,464,846 | B2 | 12/2008 | Shelton, IV et al. |
| 7,464,847 | B2 | 12/2008 | Viola et al. |
| 7,464,848 | B2 | 12/2008 | Green et al. |
| 7,464,849 | B2 | 12/2008 | Shelton, IV et al. |
| 7,467,740 | B2 | 12/2008 | Shelton, IV et al. |
| 7,467,849 | B2 | 12/2008 | Silverbrook et al. |
| 7,472,814 | B2 | 1/2009 | Mastri et al. |
| 7,472,815 | B2 | 1/2009 | Shelton, IV et al. |
| 7,472,816 | B2 | 1/2009 | Holsten et al. |
| 7,473,221 | B2 | 1/2009 | Ewers et al. |
| 7,473,253 | B2 | 1/2009 | Dycus et al. |
| 7,473,263 | B2 | 1/2009 | Johnston et al. |
| 7,476,237 | B2 | 1/2009 | Taniguchi et al. |
| 7,479,147 | B2 | 1/2009 | Honeycutt et al. |
| 7,479,608 | B2 | 1/2009 | Smith |
| 7,481,347 | B2 | 1/2009 | Roy |
| 7,481,348 | B2 | 1/2009 | Marczyk |
| 7,481,349 | B2 | 1/2009 | Holsten et al. |
| 7,481,824 | B2 | 1/2009 | Boudreaux et al. |
| 7,485,124 | B2 | 2/2009 | Kuhns et al. |
| 7,485,133 | B2 | 2/2009 | Cannon et al. |
| 7,485,142 | B2 | 2/2009 | Milo |
| 7,487,899 | B2 | 2/2009 | Shelton, IV et al. |
| 7,489,055 | B2 | 2/2009 | Jeong et al. |
| 7,490,749 | B2 | 2/2009 | Schall et al. |
| 7,491,232 | B2 | 2/2009 | Bolduc et al. |
| 7,492,261 | B2 | 2/2009 | Cambre et al. |
| 7,494,039 | B2 | 2/2009 | Racenet et al. |
| 7,494,460 | B2 | 2/2009 | Haarstad et al. |
| 7,494,499 | B2 | 2/2009 | Nagase et al. |
| 7,494,501 | B2 | 2/2009 | Ahlberg et al. |
| 7,497,137 | B2 | 3/2009 | Tellenbach et al. |
| 7,500,979 | B2 | 3/2009 | Hueil et al. |
| 7,501,198 | B2 | 3/2009 | Barlev et al. |
| 7,503,474 | B2 | 3/2009 | Hillstead et al. |
| 7,506,790 | B2 | 3/2009 | Shelton, IV |
| 7,506,791 | B2 | 3/2009 | Omaits et al. |
| 7,507,202 | B2 | 3/2009 | Schoellhorn |
| 7,510,107 | B2 | 3/2009 | Timm et al. |
| 7,510,534 | B2 | 3/2009 | Burdorff et al. |
| 7,510,566 | B2 | 3/2009 | Jacobs et al. |
| 7,513,407 | B1 | 4/2009 | Chang |
| 7,513,408 | B2 | 4/2009 | Shelton, IV et al. |
| 7,517,356 | B2 | 4/2009 | Heinrich |
| 7,524,320 | B2 | 4/2009 | Tierney et al. |
| 7,527,632 | B2 | 5/2009 | Houghton et al. |
| 7,530,984 | B2 | 5/2009 | Sonnenschein et al. |

(56) References Cited

U.S. PATENT DOCUMENTS

| | | | |
|---|---|---|---|
| 7,530,985 | B2 | 5/2009 | Takemoto et al. |
| 7,533,790 | B1 | 5/2009 | Knodel et al. |
| 7,533,906 | B2 | 5/2009 | Luettgen et al. |
| 7,534,259 | B2 | 5/2009 | Lashinski et al. |
| 7,540,867 | B2 | 6/2009 | Jinno et al. |
| 7,540,872 | B2 | 6/2009 | Schechter et al. |
| 7,542,807 | B2 | 6/2009 | Bertolero et al. |
| 7,543,730 | B1 | 6/2009 | Marczyk |
| 7,544,197 | B2 | 6/2009 | Kelsch et al. |
| 7,546,939 | B2 | 6/2009 | Adams et al. |
| 7,546,940 | B2 | 6/2009 | Milliman et al. |
| 7,547,287 | B2 | 6/2009 | Boecker et al. |
| 7,547,312 | B2 | 6/2009 | Bauman et al. |
| 7,549,563 | B2 | 6/2009 | Mather et al. |
| 7,549,564 | B2 | 6/2009 | Boudreaux |
| 7,549,998 | B2 | 6/2009 | Braun |
| 7,552,854 | B2 | 6/2009 | Wixey et al. |
| 7,553,173 | B2 | 6/2009 | Kowalick |
| 7,553,275 | B2 | 6/2009 | Padget et al. |
| 7,554,343 | B2 | 6/2009 | Bromfield |
| 7,556,185 | B2 | 7/2009 | Viola |
| 7,556,186 | B2 | 7/2009 | Milliman |
| 7,556,647 | B2 | 7/2009 | Drews et al. |
| 7,559,449 | B2 | 7/2009 | Viola |
| 7,559,450 | B2 | 7/2009 | Wales et al. |
| 7,559,452 | B2 | 7/2009 | Wales et al. |
| 7,559,937 | B2 | 7/2009 | de la Torre et al. |
| 7,561,637 | B2 | 7/2009 | Jonsson et al. |
| 7,562,910 | B2 | 7/2009 | Kertesz et al. |
| 7,563,269 | B2 | 7/2009 | Hashiguchi |
| 7,563,862 | B2 | 7/2009 | Sieg et al. |
| 7,565,993 | B2 | 7/2009 | Milliman et al. |
| 7,566,300 | B2 | 7/2009 | Devierre et al. |
| 7,567,045 | B2 | 7/2009 | Fristedt |
| 7,568,603 | B2 | 8/2009 | Shelton, IV et al. |
| 7,568,604 | B2 | 8/2009 | Ehrenfels et al. |
| 7,568,619 | B2 | 8/2009 | Todd et al. |
| 7,572,285 | B2 | 8/2009 | Frey et al. |
| 7,572,298 | B2 | 8/2009 | Roller et al. |
| 7,575,144 | B2 | 8/2009 | Ortiz et al. |
| 7,578,825 | B2 | 8/2009 | Huebner |
| D600,703 | S | 9/2009 | LaManna et al. |
| D600,712 | S | 9/2009 | LaManna et al. |
| 7,582,086 | B2 | 9/2009 | Privitera et al. |
| 7,583,063 | B2 | 9/2009 | Dooley |
| 7,584,880 | B2 | 9/2009 | Racenet et al. |
| 7,586,289 | B2 | 9/2009 | Andruk et al. |
| 7,588,174 | B2 | 9/2009 | Holsten et al. |
| 7,588,175 | B2 | 9/2009 | Timm et al. |
| 7,588,176 | B2 | 9/2009 | Timm et al. |
| 7,588,177 | B2 | 9/2009 | Racenet |
| 7,591,783 | B2 | 9/2009 | Boulais et al. |
| 7,591,818 | B2 | 9/2009 | Bertolero et al. |
| 7,593,766 | B2 | 9/2009 | Faber et al. |
| 7,595,642 | B2 | 9/2009 | Doyle |
| D601,578 | S | 10/2009 | Poulet et al. |
| 7,597,229 | B2 | 10/2009 | Boudreaux et al. |
| 7,597,230 | B2 | 10/2009 | Racenet et al. |
| 7,597,693 | B2 | 10/2009 | Garrison |
| 7,597,699 | B2 | 10/2009 | Rogers |
| 7,598,972 | B2 | 10/2009 | Tomita |
| 7,600,663 | B2 | 10/2009 | Green |
| 7,604,118 | B2 | 10/2009 | Iio et al. |
| 7,604,150 | B2 | 10/2009 | Boudreaux |
| 7,604,151 | B2 | 10/2009 | Hess et al. |
| 7,604,668 | B2 | 10/2009 | Farnsworth et al. |
| 7,605,826 | B2 | 10/2009 | Sauer |
| 7,607,557 | B2 | 10/2009 | Shelton, IV et al. |
| 7,608,091 | B2 | 10/2009 | Goldfarb et al. |
| D604,325 | S | 11/2009 | Ebeling et al. |
| 7,611,038 | B2 | 11/2009 | Racenet et al. |
| 7,611,474 | B2 | 11/2009 | Hibner et al. |
| 7,615,003 | B2 | 11/2009 | Stefanchik et al. |
| 7,615,006 | B2 | 11/2009 | Abe |
| 7,615,067 | B2 | 11/2009 | Lee et al. |
| 7,617,961 | B2 | 11/2009 | Viola |
| 7,618,427 | B2 | 11/2009 | Ortiz et al. |
| D605,201 | S | 12/2009 | Lorenz et al. |
| D606,992 | S | 12/2009 | Liu et al. |
| D607,010 | S | 12/2009 | Kocmick |
| 7,624,902 | B2 | 12/2009 | Marczyk et al. |
| 7,624,903 | B2 | 12/2009 | Green et al. |
| 7,625,370 | B2 | 12/2009 | Hart et al. |
| 7,625,388 | B2 | 12/2009 | Boukhny et al. |
| 7,625,662 | B2 | 12/2009 | Vaisnys et al. |
| 7,630,841 | B2 | 12/2009 | Comisky et al. |
| 7,631,793 | B2 | 12/2009 | Rethy et al. |
| 7,631,794 | B2 | 12/2009 | Rethy et al. |
| 7,635,074 | B2 | 12/2009 | Olson et al. |
| 7,635,922 | B2 | 12/2009 | Becker |
| 7,637,409 | B2 | 12/2009 | Marczyk |
| 7,637,410 | B2 | 12/2009 | Marczyk |
| 7,638,958 | B2 | 12/2009 | Philipp et al. |
| 7,639,598 | B2 | 12/2009 | Sovenyi |
| 7,641,091 | B2 | 1/2010 | Olson et al. |
| 7,641,092 | B2 | 1/2010 | Kruszynski et al. |
| 7,641,093 | B2 | 1/2010 | Doll et al. |
| 7,641,095 | B2 | 1/2010 | Viola |
| 7,641,671 | B2 | 1/2010 | Crainich |
| 7,644,016 | B2 | 1/2010 | Nycz et al. |
| 7,644,484 | B2 | 1/2010 | Vereschagin |
| 7,644,783 | B2 | 1/2010 | Roberts et al. |
| 7,644,848 | B2 | 1/2010 | Swayze et al. |
| 7,645,230 | B2 | 1/2010 | Mikkaichi et al. |
| 7,648,055 | B2 | 1/2010 | Marczyk |
| 7,648,457 | B2 | 1/2010 | Stefanchik et al. |
| 7,648,519 | B2 | 1/2010 | Lee et al. |
| 7,650,185 | B2 | 1/2010 | Maile et al. |
| 7,651,017 | B2 | 1/2010 | Ortiz et al. |
| 7,651,498 | B2 | 1/2010 | Shifrin et al. |
| 7,654,431 | B2 | 2/2010 | Hueil et al. |
| 7,655,003 | B2 | 2/2010 | Lorang et al. |
| 7,655,004 | B2 | 2/2010 | Long |
| 7,655,288 | B2 | 2/2010 | Bauman et al. |
| 7,655,584 | B2 | 2/2010 | Biran et al. |
| 7,656,131 | B2 | 2/2010 | Embrey et al. |
| 7,658,311 | B2 | 2/2010 | Boudreaux |
| 7,658,312 | B2 | 2/2010 | Vidal et al. |
| 7,658,705 | B2 | 2/2010 | Melvin et al. |
| 7,659,219 | B2 | 2/2010 | Biran et al. |
| 7,661,448 | B2 | 2/2010 | Kim et al. |
| 7,662,161 | B2 | 2/2010 | Briganti et al. |
| 7,665,646 | B2 | 2/2010 | Prommersberger |
| 7,665,647 | B2 | 2/2010 | Shelton, IV et al. |
| 7,666,195 | B2 | 2/2010 | Kelleher et al. |
| 7,669,746 | B2 | 3/2010 | Shelton, IV |
| 7,669,747 | B2 | 3/2010 | Weisenburgh, II et al. |
| 7,670,334 | B2 | 3/2010 | Hueil et al. |
| 7,670,337 | B2 | 3/2010 | Young |
| 7,673,780 | B2 | 3/2010 | Shelton, IV et al. |
| 7,673,781 | B2 | 3/2010 | Swayze et al. |
| 7,673,782 | B2 | 3/2010 | Hess et al. |
| 7,673,783 | B2 | 3/2010 | Morgan et al. |
| 7,674,253 | B2 | 3/2010 | Fisher et al. |
| 7,674,255 | B2 | 3/2010 | Braun |
| 7,674,263 | B2 | 3/2010 | Ryan |
| 7,674,270 | B2 | 3/2010 | Layer |
| 7,678,121 | B1 | 3/2010 | Knodel |
| 7,682,307 | B2 | 3/2010 | Danitz et al. |
| 7,682,367 | B2 | 3/2010 | Shah et al. |
| 7,682,686 | B2 | 3/2010 | Curro et al. |
| 7,686,201 | B2 | 3/2010 | Csiky |
| 7,686,804 | B2 | 3/2010 | Johnson et al. |
| 7,686,826 | B2 | 3/2010 | Lee et al. |
| 7,688,028 | B2 | 3/2010 | Phillips et al. |
| 7,690,547 | B2 | 4/2010 | Racenet et al. |
| 7,691,098 | B2 | 4/2010 | Wallace et al. |
| 7,691,103 | B2 | 4/2010 | Fernandez et al. |
| 7,691,106 | B2 | 4/2010 | Schenberger et al. |
| 7,694,864 | B2 | 4/2010 | Okada et al. |
| 7,694,865 | B2 | 4/2010 | Scirica |
| 7,695,485 | B2 | 4/2010 | Whitman et al. |
| 7,695,493 | B2 | 4/2010 | Saadat et al. |
| 7,699,204 | B2 | 4/2010 | Viola |

(56) References Cited

U.S. PATENT DOCUMENTS

| | | | |
|---|---|---|---|
| 7,699,835 | B2 | 4/2010 | Lee et al. |
| 7,699,844 | B2 | 4/2010 | Utley et al. |
| 7,699,846 | B2 | 4/2010 | Ryan |
| 7,699,856 | B2 | 4/2010 | Van Wyk et al. |
| 7,699,859 | B2 | 4/2010 | Bombard et al. |
| 7,699,860 | B2 | 4/2010 | Huitema et al. |
| 7,699,868 | B2 | 4/2010 | Frank et al. |
| 7,703,653 | B2 | 4/2010 | Shah et al. |
| 7,705,559 | B2 | 4/2010 | Powell et al. |
| 7,706,853 | B2 | 4/2010 | Hacker et al. |
| 7,708,180 | B2 | 5/2010 | Murray et al. |
| 7,708,181 | B2 | 5/2010 | Cole et al. |
| 7,708,182 | B2 | 5/2010 | Viola |
| 7,708,758 | B2 | 5/2010 | Lee et al. |
| 7,708,768 | B2 | 5/2010 | Danek et al. |
| 7,709,136 | B2 | 5/2010 | Touchton et al. |
| 7,712,182 | B2 | 5/2010 | Zeiler et al. |
| 7,713,190 | B2 | 5/2010 | Brock et al. |
| 7,713,542 | B2 | 5/2010 | Xu et al. |
| 7,714,239 | B2 | 5/2010 | Smith |
| 7,714,334 | B2 | 5/2010 | Lin |
| 7,717,312 | B2 | 5/2010 | Beetel |
| 7,717,313 | B2 | 5/2010 | Criscuolo et al. |
| 7,717,846 | B2 | 5/2010 | Zirps et al. |
| 7,717,873 | B2 | 5/2010 | Swick |
| 7,717,915 | B2 | 5/2010 | Miyazawa |
| 7,717,926 | B2 | 5/2010 | Whitfield et al. |
| 7,718,180 | B2 | 5/2010 | Karp |
| 7,718,556 | B2 | 5/2010 | Matsuda et al. |
| 7,721,930 | B2 | 5/2010 | McKenna et al. |
| 7,721,931 | B2 | 5/2010 | Shelton, IV et al. |
| 7,721,932 | B2 | 5/2010 | Cole et al. |
| 7,721,933 | B2 | 5/2010 | Ehrenfels et al. |
| 7,721,934 | B2 | 5/2010 | Shelton, IV et al. |
| 7,721,936 | B2 | 5/2010 | Shalton, IV et al. |
| 7,722,527 | B2 | 5/2010 | Bouchier et al. |
| 7,722,607 | B2 | 5/2010 | Dumbauld et al. |
| 7,722,610 | B2 | 5/2010 | Viola et al. |
| 7,725,214 | B2 | 5/2010 | Diolaiti |
| 7,726,171 | B2 | 6/2010 | Langlotz et al. |
| 7,726,537 | B2 | 6/2010 | Olson et al. |
| 7,726,538 | B2 | 6/2010 | Holsten et al. |
| 7,726,539 | B2 | 6/2010 | Holsten et al. |
| 7,727,954 | B2 | 6/2010 | McKay |
| 7,728,553 | B2 | 6/2010 | Carrier et al. |
| 7,729,742 | B2 | 6/2010 | Govari |
| 7,731,072 | B2 | 6/2010 | Timm et al. |
| 7,731,073 | B2 | 6/2010 | Wixey et al. |
| 7,731,724 | B2 | 6/2010 | Huitema et al. |
| 7,735,703 | B2 | 6/2010 | Morgan et al. |
| 7,735,704 | B2 | 6/2010 | Bilotti |
| 7,736,254 | B2 | 6/2010 | Schena |
| 7,736,306 | B2 | 6/2010 | Brustad et al. |
| 7,736,356 | B2 | 6/2010 | Cooper et al. |
| 7,736,374 | B2 | 6/2010 | Vaughan et al. |
| 7,738,971 | B2 | 6/2010 | Swayze et al. |
| 7,740,159 | B2 | 6/2010 | Shelton, IV et al. |
| 7,742,036 | B2 | 6/2010 | Grant et al. |
| 7,743,960 | B2 | 6/2010 | Whitman et al. |
| 7,744,624 | B2 | 6/2010 | Bettuchi |
| 7,744,627 | B2 | 6/2010 | Orban, III et al. |
| 7,744,628 | B2 | 6/2010 | Viola |
| 7,747,146 | B2 | 6/2010 | Milano et al. |
| 7,748,587 | B2 | 7/2010 | Haramiishi et al. |
| 7,748,632 | B2 | 7/2010 | Coleman et al. |
| 7,749,204 | B2 | 7/2010 | Dhanaraj et al. |
| 7,749,240 | B2 | 7/2010 | Takahashi et al. |
| 7,751,870 | B2 | 7/2010 | Whitman |
| 7,753,245 | B2 | 7/2010 | Boudreaux et al. |
| 7,753,246 | B2 | 7/2010 | Scirica |
| 7,753,904 | B2 | 7/2010 | Shelton, IV et al. |
| 7,757,924 | B2 | 7/2010 | Gerbi et al. |
| 7,758,594 | B2 | 7/2010 | Lamson et al. |
| 7,758,612 | B2 | 7/2010 | Shipp |
| 7,758,613 | B2 | 7/2010 | Whitman |
| 7,762,462 | B2 | 7/2010 | Gelbman |
| 7,762,998 | B2 | 7/2010 | Birk et al. |
| D622,286 | S | 8/2010 | Umezawa |
| 7,766,207 | B2 | 8/2010 | Mather et al. |
| 7,766,209 | B2 | 8/2010 | Baxter, III et al. |
| 7,766,210 | B2 | 8/2010 | Shelton, IV et al. |
| 7,766,821 | B2 | 8/2010 | Brunnen et al. |
| 7,766,894 | B2 | 8/2010 | Weitzner et al. |
| 7,766,910 | B2 | 8/2010 | Hixson et al. |
| 7,770,658 | B2 | 8/2010 | Ito et al. |
| 7,770,773 | B2 | 8/2010 | Whitman et al. |
| 7,770,774 | B2 | 8/2010 | Mastri et al. |
| 7,770,775 | B2 | 8/2010 | Shelton, IV et al. |
| 7,770,776 | B2 | 8/2010 | Chen et al. |
| 7,771,396 | B2 | 8/2010 | Stefanchik et al. |
| 7,772,720 | B2 | 8/2010 | McGee et al. |
| 7,772,725 | B2 | 8/2010 | Siman-Tov |
| 7,775,972 | B2 | 8/2010 | Brock et al. |
| 7,776,037 | B2 | 8/2010 | Odom |
| 7,776,060 | B2 | 8/2010 | Mooradian et al. |
| 7,776,065 | B2 | 8/2010 | Griffiths et al. |
| 7,778,004 | B2 | 8/2010 | Nerheim et al. |
| 7,779,614 | B1 | 8/2010 | McGonagle et al. |
| 7,779,737 | B2 | 8/2010 | Newman, Jr. et al. |
| 7,780,054 | B2 | 8/2010 | Wales |
| 7,780,055 | B2 | 8/2010 | Scirica et al. |
| 7,780,309 | B2 | 8/2010 | McMillan et al. |
| 7,780,651 | B2 | 8/2010 | Madhani et al. |
| 7,780,663 | B2 | 8/2010 | Yates et al. |
| 7,780,685 | B2 | 8/2010 | Hunt et al. |
| 7,782,382 | B2 | 8/2010 | Fujimura |
| 7,784,662 | B2 | 8/2010 | Wales et al. |
| 7,784,663 | B2 | 8/2010 | Shelton, IV |
| 7,787,256 | B2 | 8/2010 | Chan et al. |
| 7,789,283 | B2 | 9/2010 | Shah |
| 7,789,875 | B2 | 9/2010 | Brock et al. |
| 7,789,883 | B2 | 9/2010 | Takashino et al. |
| 7,789,889 | B2 | 9/2010 | Zubik et al. |
| 7,793,812 | B2 | 9/2010 | Moore et al. |
| 7,794,475 | B2 | 9/2010 | Hess et al. |
| 7,798,386 | B2 | 9/2010 | Schall et al. |
| 7,799,039 | B2 | 9/2010 | Shelton, IV et al. |
| 7,799,044 | B2 | 9/2010 | Johnston et al. |
| 7,799,965 | B2 | 9/2010 | Patel et al. |
| 7,803,151 | B2 | 9/2010 | Whitman |
| 7,806,871 | B2 | 10/2010 | Li et al. |
| 7,806,891 | B2 | 10/2010 | Nowlin et al. |
| 7,810,690 | B2 | 10/2010 | Bilotti et al. |
| 7,810,691 | B2 | 10/2010 | Boyden et al. |
| 7,810,692 | B2 | 10/2010 | Hall et al. |
| 7,810,693 | B2 | 10/2010 | Broehl et al. |
| 7,811,275 | B2 | 10/2010 | Birk et al. |
| 7,814,816 | B2 | 10/2010 | Alberti et al. |
| 7,815,092 | B2 | 10/2010 | Whitman et al. |
| 7,815,565 | B2 | 10/2010 | Stefanchik et al. |
| 7,815,662 | B2 | 10/2010 | Spivey et al. |
| 7,819,296 | B2 | 10/2010 | Hueil et al. |
| 7,819,297 | B2 | 10/2010 | Doll et al. |
| 7,819,298 | B2 | 10/2010 | Hall et al. |
| 7,819,299 | B2 | 10/2010 | Shelton, IV et al. |
| 7,819,799 | B2 | 10/2010 | Merril et al. |
| 7,819,884 | B2 | 10/2010 | Lee et al. |
| 7,819,885 | B2 | 10/2010 | Cooper |
| 7,819,886 | B2 | 10/2010 | Whitfield et al. |
| 7,819,894 | B2 | 10/2010 | Mitsuishi et al. |
| 7,823,076 | B2 | 10/2010 | Borovsky et al. |
| 7,823,592 | B2 | 11/2010 | Bettuchi et al. |
| 7,823,760 | B2 | 11/2010 | Zemlok et al. |
| 7,824,401 | B2 | 11/2010 | Manzo et al. |
| 7,824,422 | B2 | 11/2010 | Benchetrit |
| 7,824,426 | B2 | 11/2010 | Racenet et al. |
| 7,828,189 | B2 | 11/2010 | Holsten et al. |
| 7,828,794 | B2 | 11/2010 | Sartor |
| 7,828,808 | B2 | 11/2010 | Hinman et al. |
| 7,829,416 | B2 | 11/2010 | Kudou et al. |
| 7,831,292 | B2 | 11/2010 | Quaid et al. |
| 7,832,408 | B2 | 11/2010 | Shelton, IV et al. |
| 7,832,611 | B2 | 11/2010 | Boyden et al. |
| 7,832,612 | B2 | 11/2010 | Baxter, III et al. |

(56) References Cited

U.S. PATENT DOCUMENTS 7,833,234 B2 11/2010 Bailly et al.
7,835,823 B2 11/2010 Sillman et al.
7,836,400 B2 11/2010 May et al.
7,837,079 B2 11/2010 Holsten et al.
7,837,080 B2 11/2010 Schwemberger
7,837,081 B2 11/2010 Holsten et al.
7,837,425 B2 11/2010 Saeki et al.
7,837,685 B2 11/2010 Weinberg et al.
7,837,687 B2 11/2010 Harp
7,837,694 B2 11/2010 Tethrake et al.
7,838,789 B2 11/2010 Stoffers et al.
7,839,109 B2 11/2010 Carmen, Jr. et al.
7,840,253 B2 11/2010 Tremblay et al.
7,841,503 B2 11/2010 Sonnenschein et al.
7,842,025 B2 11/2010 Coleman et al.
7,842,028 B2 11/2010 Lee
7,843,158 B2 11/2010 Prisco
7,845,533 B2 12/2010 Marczyk et al.
7,845,534 B2 12/2010 Viola et al.
7,845,535 B2 12/2010 Scircia
7,845,536 B2 12/2010 Viola et al.
7,845,537 B2 12/2010 Shelton, IV et al.
7,845,538 B2 12/2010 Whitman
7,845,912 B2 12/2010 Sung et al.
7,846,085 B2 12/2010 Silverman et al.
7,846,149 B2 12/2010 Jankowski
7,846,161 B2 12/2010 Dumbauld et al.
7,848,066 B2 12/2010 Yanagishima
7,850,623 B2 12/2010 Griffin et al.
7,850,642 B2 12/2010 Moll et al.
7,850,982 B2 12/2010 Stopek et al.
7,853,813 B2 12/2010 Lee
7,854,735 B2 12/2010 Houser et al.
7,854,736 B2 12/2010 Ryan
7,857,183 B2 12/2010 Shelton, IV
7,857,184 B2 12/2010 Viola
7,857,185 B2 12/2010 Swayze et al.
7,857,186 B2 12/2010 Baxter, III et al.
7,857,813 B2 12/2010 Schmitz et al.
7,861,906 B2 1/2011 Doll et al.
7,862,502 B2 1/2011 Pool et al.
7,862,546 B2 1/2011 Conlon et al.
7,862,579 B2 1/2011 Ortiz et al.
7,866,525 B2 1/2011 Scirica
7,866,527 B2 1/2011 Hall et al.
7,866,528 B2 1/2011 Olson et al.
7,870,989 B2 1/2011 Viola et al.
7,871,418 B2 1/2011 Thompson et al.
7,871,440 B2 1/2011 Schwartz et al.
7,875,055 B2 1/2011 Cichocki, Jr.
7,877,869 B2 2/2011 Mehdizadeh et al.
7,879,063 B2 2/2011 Khosravi
7,879,070 B2 2/2011 Ortiz et al.
7,879,367 B2 2/2011 Heublein et al.
7,883,461 B2 2/2011 Albrecht et al.
7,883,465 B2 2/2011 Donofrio et al.
7,883,540 B2 2/2011 Niwa et al.
7,886,951 B2 2/2011 Hessler
7,886,952 B2 2/2011 Scirica et al.
7,887,530 B2 2/2011 Zemlok et al.
7,887,535 B2 2/2011 Lands et al.
7,887,536 B2 2/2011 Johnson et al.
7,887,563 B2 2/2011 Cummins
7,887,755 B2 2/2011 Mingerink et al.
7,891,531 B1 2/2011 Ward
7,891,532 B2 2/2011 Mastri et al.
7,892,200 B2 2/2011 Birk et al.
7,892,245 B2 2/2011 Liddicoat et al.
7,893,586 B2 2/2011 West et al.
7,896,214 B2 3/2011 Farascioni
7,896,215 B2 3/2011 Adams et al.
7,896,671 B2 3/2011 Kim et al.
7,896,869 B2 3/2011 DiSilvestro et al.
7,896,877 B2 3/2011 Hall et al.
7,896,895 B2 3/2011 Boudreaux et al.
7,896,897 B2 3/2011 Gresham et al.
7,896,900 B2 3/2011 Frank et al.
7,898,198 B2 3/2011 Murphree
7,900,805 B2 3/2011 Shelton, IV et al.
7,900,806 B2 3/2011 Chen et al.
7,901,381 B2 3/2011 Birk et al.
7,905,380 B2 3/2011 Shelton, IV et al.
7,905,381 B2 3/2011 Baxter, III et al.
7,905,881 B2 3/2011 Masuda et al.
7,905,889 B2 3/2011 Catanese, III et al.
7,905,890 B2 3/2011 Whitfield et al.
7,905,902 B2 3/2011 Huitema et al.
7,909,039 B2 3/2011 Hur
7,909,191 B2 3/2011 Baker et al.
7,909,220 B2 3/2011 Viola
7,909,221 B2 3/2011 Viola et al.
7,909,224 B2 3/2011 Prommersberger
7,913,891 B2 3/2011 Doll et al.
7,913,893 B2 3/2011 Mastri et al.
7,914,521 B2 3/2011 Wang et al.
7,914,543 B2 3/2011 Roth et al.
7,914,551 B2 3/2011 Ortiz et al.
7,918,230 B2 4/2011 Whitman et al.
7,918,376 B1 4/2011 Knodel et al.
7,918,377 B2 4/2011 Measamer et al.
7,918,845 B2 4/2011 Saadat et al.
7,918,848 B2 4/2011 Lau et al.
7,918,861 B2 4/2011 Brock et al.
7,918,867 B2 4/2011 Dana et al.
7,922,061 B2 4/2011 Shelton, IV et al.
7,922,063 B2 4/2011 Zemlok et al.
7,922,743 B2 4/2011 Heinrich et al.
7,923,144 B2 4/2011 Kohn et al.
7,926,691 B2 4/2011 Viola et al.
7,926,692 B2 4/2011 Racenet et al.
7,927,328 B2 4/2011 Orszulak et al.
7,928,281 B2 4/2011 Augustine
7,930,040 B1 4/2011 Kelsch et al.
7,930,065 B2 4/2011 Larkin et al.
7,931,660 B2 4/2011 Aranyi et al.
7,931,695 B2 4/2011 Ringeisen
7,931,877 B2 4/2011 Steffens et al.
D638,028 S 5/2011 Cook et al.
7,934,630 B2 5/2011 Shelton, IV et al.
7,934,631 B2 5/2011 Balbierz et al.
7,934,896 B2 5/2011 Schnier
7,935,130 B2 5/2011 Williams
7,935,773 B2 5/2011 Hadba et al.
7,936,142 B2 5/2011 Otsuka et al.
7,938,307 B2 5/2011 Bettuchi
7,939,152 B2 5/2011 Haskin et al.
7,941,865 B2 5/2011 Seman, Jr. et al.
7,942,300 B2 5/2011 Rethy et al.
7,942,303 B2 5/2011 Shah
7,942,890 B2 5/2011 D'Agostino et al.
7,944,175 B2 5/2011 Mori et al.
7,945,792 B2 5/2011 Cherpantier
7,945,798 B2 5/2011 Carlson et al.
7,946,453 B2 5/2011 Voegele et al.
7,947,011 B2 5/2011 Birk et al.
7,948,381 B2 5/2011 Lindsay et al.
7,950,560 B2 5/2011 Zemlok et al.
7,950,561 B2 5/2011 Aranyi
7,950,562 B2 5/2011 Beardsley et al.
7,951,071 B2 5/2011 Whitman et al.
7,951,166 B2 5/2011 Orban, III et al.
7,952,464 B2 5/2011 Nikitin et al.
7,954,682 B2 6/2011 Giordano et al.
7,954,684 B2 6/2011 Boudreaux
7,954,685 B2 6/2011 Viola
7,954,686 B2 6/2011 Baxter, III et al.
7,954,687 B2 6/2011 Zemlok et al.
7,954,688 B2 6/2011 Argentine et al.
7,955,253 B2 6/2011 Ewers et al.
7,955,257 B2 6/2011 Frasier et al.
7,955,322 B2 6/2011 Devengenzo et al.
7,955,327 B2 6/2011 Sartor et al.
7,955,380 B2 6/2011 Chu et al.
7,959,050 B2 6/2011 Smith et al.

(56) References Cited

U.S. PATENT DOCUMENTS

| | | | |
|---|---|---|---|
| 7,959,051 | B2 | 6/2011 | Smith et al. |
| 7,959,052 | B2 | 6/2011 | Sonnenschein et al. |
| 7,963,432 | B2 | 6/2011 | Knodel et al. |
| 7,963,433 | B2 | 6/2011 | Whitman et al. |
| 7,963,913 | B2 | 6/2011 | Devengenzo et al. |
| 7,963,963 | B2 | 6/2011 | Francischelli et al. |
| 7,963,964 | B2 | 6/2011 | Santilli et al. |
| 7,964,206 | B2 | 6/2011 | Suokas et al. |
| 7,966,236 | B2 | 6/2011 | Noriega et al. |
| 7,966,269 | B2 | 6/2011 | Bauer et al. |
| 7,966,799 | B2 | 6/2011 | Morgan et al. |
| 7,967,178 | B2 | 6/2011 | Scirica et al. |
| 7,967,179 | B2 | 6/2011 | Olson et al. |
| 7,967,180 | B2 | 6/2011 | Scirica |
| 7,967,181 | B2 | 6/2011 | Viola et al. |
| 7,967,791 | B2 | 6/2011 | Franer et al. |
| 7,967,839 | B2 | 6/2011 | Flock et al. |
| 7,972,298 | B2 | 7/2011 | Wallace et al. |
| 7,972,315 | B2 | 7/2011 | Birk et al. |
| 7,976,213 | B2 | 7/2011 | Bertolotti et al. |
| 7,976,508 | B2 | 7/2011 | Hoag |
| 7,976,563 | B2 | 7/2011 | Summerer |
| 7,979,137 | B2 | 7/2011 | Tracey et al. |
| 7,980,443 | B2 | 7/2011 | Scheib et al. |
| 7,981,025 | B2 | 7/2011 | Pool et al. |
| 7,981,102 | B2 | 7/2011 | Patel et al. |
| 7,981,132 | B2 | 7/2011 | Dubrul et al. |
| 7,987,405 | B2 | 7/2011 | Turner et al. |
| 7,988,015 | B2 | 8/2011 | Mason, II et al. |
| 7,988,026 | B2 | 8/2011 | Knodel et al. |
| 7,988,027 | B2 | 8/2011 | Olson et al. |
| 7,988,028 | B2 | 8/2011 | Farascioni et al. |
| 7,988,779 | B2 | 8/2011 | Disalvo et al. |
| 7,992,757 | B2 | 8/2011 | Wheeler et al. |
| 7,993,360 | B2 | 8/2011 | Hacker et al. |
| 7,994,670 | B2 | 8/2011 | Ji |
| 7,996,064 | B2 | 8/2011 | Simon et al. |
| 7,997,054 | B2 | 8/2011 | Bertsch et al. |
| 7,997,468 | B2 | 8/2011 | Farascioni |
| 7,997,469 | B2 | 8/2011 | Olson et al. |
| 8,002,696 | B2 | 8/2011 | Suzuki |
| 8,002,784 | B2 | 8/2011 | Jinno et al. |
| 8,002,785 | B2 | 8/2011 | Weiss et al. |
| 8,002,795 | B2 | 8/2011 | Beetel |
| 8,006,365 | B2 | 8/2011 | Levin et al. |
| 8,006,885 | B2 | 8/2011 | Marczyk |
| 8,006,889 | B2 | 8/2011 | Adams et al. |
| 8,007,370 | B2 | 8/2011 | Hirsch et al. |
| 8,007,465 | B2 | 8/2011 | Birk et al. |
| 8,007,479 | B2 | 8/2011 | Birk et al. |
| 8,007,511 | B2 | 8/2011 | Brock et al. |
| 8,007,513 | B2 | 8/2011 | Nalagatla et al. |
| 8,008,598 | B2 | 8/2011 | Whitman et al. |
| 8,010,180 | B2 | 8/2011 | Quaid et al. |
| 8,011,550 | B2 | 9/2011 | Aranyi et al. |
| 8,011,551 | B2 | 9/2011 | Marczyk et al. |
| 8,011,553 | B2 | 9/2011 | Mastri et al. |
| 8,011,555 | B2 | 9/2011 | Tarinelli et al. |
| 8,012,170 | B2 | 9/2011 | Whitman et al. |
| 8,016,176 | B2 | 9/2011 | Kasvikis et al. |
| 8,016,177 | B2 | 9/2011 | Bettuchi et al. |
| 8,016,178 | B2 | 9/2011 | Olson et al. |
| 8,016,849 | B2 | 9/2011 | Wenchell |
| 8,016,855 | B2 | 9/2011 | Whitman et al. |
| 8,016,858 | B2 | 9/2011 | Whitman |
| 8,016,881 | B2 | 9/2011 | Furst |
| 8,020,741 | B2 | 9/2011 | Cole et al. |
| 8,020,742 | B2 | 9/2011 | Marczyk |
| 8,020,743 | B2 | 9/2011 | Shelton, IV |
| 8,021,375 | B2 | 9/2011 | Aldrich et al. |
| 8,025,199 | B2 | 9/2011 | Whitman et al. |
| 8,025,896 | B2 | 9/2011 | Malaviya et al. |
| 8,028,835 | B2 | 10/2011 | Yasuda et al. |
| 8,028,882 | B2 | 10/2011 | Viola |
| 8,028,883 | B2 | 10/2011 | Stopek |
| 8,028,884 | B2 | 10/2011 | Sniffin et al. |
| 8,028,885 | B2 | 10/2011 | Smith et al. |
| 8,029,510 | B2 | 10/2011 | Hoegerle |
| 8,031,069 | B2 | 10/2011 | Cohn et al. |
| 8,033,438 | B2 | 10/2011 | Scirica |
| 8,033,439 | B2 | 10/2011 | Racenet et al. |
| 8,033,440 | B2 | 10/2011 | Wenchell et al. |
| 8,033,442 | B2 | 10/2011 | Racenet et al. |
| 8,034,077 | B2 | 10/2011 | Smith et al. |
| 8,034,337 | B2 | 10/2011 | Simard |
| 8,034,363 | B2 | 10/2011 | Li et al. |
| 8,035,487 | B2 | 10/2011 | Malackowski |
| 8,037,591 | B2 | 10/2011 | Spivey et al. |
| 8,038,044 | B2 | 10/2011 | Viola |
| 8,038,045 | B2 | 10/2011 | Bettuchi et al. |
| 8,038,046 | B2 | 10/2011 | Smith et al. |
| 8,038,686 | B2 | 10/2011 | Huitema et al. |
| 8,043,207 | B2 | 10/2011 | Adams |
| 8,043,328 | B2 | 10/2011 | Hahnen et al. |
| 8,044,536 | B2 | 10/2011 | Nguyen et al. |
| 8,044,604 | B2 | 10/2011 | Hagino et al. |
| 8,047,236 | B2 | 11/2011 | Perry |
| 8,048,503 | B2 | 11/2011 | Farnsworth et al. |
| 8,052,024 | B2 | 11/2011 | Viola et al. |
| 8,052,636 | B2 | 11/2011 | Moll et al. |
| 8,052,697 | B2 | 11/2011 | Phillips |
| 8,056,787 | B2 | 11/2011 | Boudreaux et al. |
| 8,056,788 | B2 | 11/2011 | Mastri et al. |
| 8,056,789 | B1 | 11/2011 | White et al. |
| 8,057,508 | B2 | 11/2011 | Shelton, IV |
| 8,058,771 | B2 | 11/2011 | Giordano et al. |
| 8,060,250 | B2 | 11/2011 | Reiland et al. |
| 8,061,014 | B2 | 11/2011 | Smith et al. |
| 8,061,576 | B2 | 11/2011 | Cappola |
| 8,062,236 | B2 | 11/2011 | Soltz |
| 8,062,306 | B2 | 11/2011 | Nobis et al. |
| 8,062,330 | B2 | 11/2011 | Prommersberger et al. |
| 8,063,619 | B2 | 11/2011 | Zhu et al. |
| 8,066,158 | B2 | 11/2011 | Vogel et al. |
| 8,066,166 | B2 | 11/2011 | Demmy et al. |
| 8,066,167 | B2 | 11/2011 | Measamer et al. |
| 8,066,168 | B2 | 11/2011 | Vidal et al. |
| 8,066,720 | B2 | 11/2011 | Knodel et al. |
| D650,074 | S | 12/2011 | Hunt et al. |
| D650,789 | S | 12/2011 | Arnold |
| 8,070,033 | B2 | 12/2011 | Milliman et al. |
| 8,070,034 | B1 | 12/2011 | Knodel |
| 8,070,035 | B2 | 12/2011 | Holsten et al. |
| 8,070,743 | B2 | 12/2011 | Kagan et al. |
| 8,074,858 | B2 | 12/2011 | Marczyk |
| 8,074,859 | B2 | 12/2011 | Kostrzewski |
| 8,074,861 | B2 | 12/2011 | Ehrenfels et al. |
| 8,075,476 | B2 | 12/2011 | Vargas |
| 8,075,571 | B2 | 12/2011 | Vitali et al. |
| 8,079,950 | B2 | 12/2011 | Stern et al. |
| 8,079,989 | B2 | 12/2011 | Birk et al. |
| 8,080,004 | B2 | 12/2011 | Downey et al. |
| 8,083,118 | B2 | 12/2011 | Milliman et al. |
| 8,083,119 | B2 | 12/2011 | Prommersberger |
| 8,083,120 | B2 | 12/2011 | Shelton, IV et al. |
| 8,084,001 | B2 | 12/2011 | Burns et al. |
| 8,084,969 | B2 | 12/2011 | David et al. |
| 8,085,013 | B2 | 12/2011 | Wei et al. |
| D652,048 | S | 1/2012 | Joseph |
| 8,087,562 | B1 | 1/2012 | Manoux et al. |
| 8,087,563 | B2 | 1/2012 | Milliman et al. |
| 8,089,509 | B2 | 1/2012 | Chatenever et al. |
| 8,091,753 | B2 | 1/2012 | Viola |
| 8,091,756 | B2 | 1/2012 | Viola |
| 8,092,443 | B2 | 1/2012 | Bischoff |
| 8,092,932 | B2 | 1/2012 | Phillips et al. |
| 8,093,572 | B2 | 1/2012 | Kuduvalli |
| 8,096,458 | B2 | 1/2012 | Hessler |
| 8,096,459 | B2 | 1/2012 | Ortiz et al. |
| 8,097,017 | B2 | 1/2012 | Viola |
| 8,100,310 | B2 | 1/2012 | Zemlok |
| 8,100,824 | B2 | 1/2012 | Hegeman et al. |
| 8,100,872 | B2 | 1/2012 | Patel |
| 8,102,138 | B2 | 1/2012 | Sekine et al. |

(56) References Cited

U.S. PATENT DOCUMENTS 8,102,278 B2 1/2012 Deck et al.
8,105,320 B2 1/2012 Manzo
8,105,350 B2 1/2012 Lee et al.
8,107,925 B2 1/2012 Natsuno et al.
8,108,033 B2 1/2012 Drew et al.
8,108,072 B2 1/2012 Zhao et al.
8,109,426 B2 2/2012 Milliman et al.
8,110,208 B1 2/2012 Hen
8,113,405 B2 2/2012 Milliman
8,113,407 B2 2/2012 Holsten et al.
8,113,408 B2 2/2012 Wenchell et al.
8,113,410 B2 2/2012 Hall et al.
8,114,017 B2 2/2012 Bacher
8,114,100 B2 2/2012 Smith et al.
8,114,345 B2 2/2012 Dlugos, Jr. et al.
8,118,206 B2 2/2012 Zand et al.
8,118,207 B2 2/2012 Racenet et al.
8,120,301 B2 2/2012 Goldberg et al.
8,122,128 B2 2/2012 Burke, II et al.
8,123,103 B2 2/2012 Milliman
8,123,523 B2 2/2012 Carron et al.
8,123,766 B2 2/2012 Bauman et al.
8,123,767 B2 2/2012 Bauman et al.
8,125,168 B2 2/2012 Johnson et al.
8,127,975 B2 3/2012 Olson et al.
8,127,976 B2 3/2012 Scirica et al.
8,128,624 B2 3/2012 Couture et al.
8,128,642 B2 3/2012 Heeps et al.
8,128,643 B2 3/2012 Aranyi et al.
8,128,645 B2 3/2012 Sonnenschein et al.
8,128,662 B2 3/2012 Altarac et al.
8,132,703 B2 3/2012 Milliman et al.
8,132,705 B2 3/2012 Viola et al.
8,132,706 B2 3/2012 Marczyk et al.
8,133,500 B2 3/2012 Ringeisen et al.
8,134,306 B2 3/2012 Drader et al.
8,136,711 B2 3/2012 Beardsley et al.
8,136,712 B2 3/2012 Zingman
8,136,713 B2 3/2012 Hathaway et al.
8,137,339 B2 3/2012 Jinno et al.
8,140,417 B2 3/2012 Shibata
8,141,762 B2 3/2012 Bedi et al.
8,141,763 B2 3/2012 Milliman
8,142,200 B2 3/2012 Crunkilton et al.
8,142,425 B2 3/2012 Eggers
8,142,461 B2 3/2012 Houser et al.
8,142,515 B2 3/2012 Therin et al.
8,143,520 B2 3/2012 Cutler
8,146,790 B2 4/2012 Milliman
8,147,421 B2 4/2012 Farquhar et al.
8,147,456 B2 4/2012 Fisher et al.
8,147,485 B2 4/2012 Wham et al.
8,152,041 B2 4/2012 Kostrzewski
8,152,756 B2 4/2012 Webster et al.
8,154,239 B2 4/2012 Katsuki et al.
8,157,145 B2 4/2012 Shelton, IV et al.
8,157,148 B2 4/2012 Scirica
8,157,150 B2 4/2012 Viola et al.
8,157,151 B2 4/2012 Ingmanson et al.
8,157,152 B2 4/2012 Holsten et al.
8,157,153 B2 4/2012 Shelton, IV et al.
8,157,793 B2 4/2012 Omori et al.
8,157,834 B2 4/2012 Conlon
8,161,977 B2 4/2012 Shelton, IV et al.
8,162,138 B2 4/2012 Bettenhausen et al.
8,162,197 B2 4/2012 Mastri et al.
8,162,668 B2 4/2012 Toly
8,162,933 B2 4/2012 Francischelli et al.
8,162,965 B2 4/2012 Reschke et al.
8,167,185 B2 5/2012 Shelton, IV et al.
8,167,622 B2 5/2012 Zhou
8,167,895 B2 5/2012 D'Agostino et al.
8,167,898 B1 5/2012 Schaller et al.
8,170,241 B2 5/2012 Roe et al.
8,172,004 B2 5/2012 Ho
8,172,120 B2 5/2012 Boyden et al.
8,172,122 B2 5/2012 Kasvikis et al.
8,172,124 B2 5/2012 Shelton, IV et al.
8,177,776 B2 5/2012 Humayun et al.
8,177,797 B2 5/2012 Shimoji et al.
8,179,705 B2 5/2012 Chapuis
8,180,458 B2 5/2012 Kane et al.
8,181,839 B2 5/2012 Beetel
8,181,840 B2 5/2012 Milliman
8,182,422 B2 5/2012 Bayer et al.
8,182,444 B2 5/2012 Uber, III et al.
8,183,807 B2 5/2012 Tsai et al.
8,186,555 B2 5/2012 Shelton, IV et al.
8,186,556 B2 5/2012 Viola
8,186,558 B2 5/2012 Sapienza
8,186,560 B2 5/2012 Hess et al.
8,190,238 B2 5/2012 Moll et al.
D661,314 S 6/2012 Marchetti
D661,315 S 6/2012 Marchetti et al.
8,191,752 B2 6/2012 Scirica
8,192,350 B2 6/2012 Ortiz et al.
8,192,460 B2 6/2012 Orban, III et al.
8,192,651 B2 6/2012 Young et al.
8,193,129 B2 6/2012 Tagawa et al.
8,196,795 B2 6/2012 Moore et al.
8,196,796 B2 6/2012 Shelton, IV et al.
8,197,501 B2 6/2012 Shadeck et al.
8,197,502 B2 6/2012 Smith et al.
8,197,837 B2 6/2012 Jamiolkowski et al.
8,201,720 B2 6/2012 Hessler
8,201,721 B2 6/2012 Zemlok et al.
8,202,549 B2 6/2012 Stucky et al.
8,205,779 B2 6/2012 Ma et al.
8,205,780 B2 6/2012 Sorrentino et al.
8,205,781 B2 6/2012 Baxter, III et al.
8,207,863 B2 6/2012 Neubauer et al.
8,210,411 B2 7/2012 Yates et al.
8,210,413 B2 7/2012 Whitman et al.
8,210,414 B2 7/2012 Bettuchi et al.
8,210,415 B2 7/2012 Ward
8,210,416 B2 7/2012 Milliman et al.
8,210,721 B2 7/2012 Chen et al.
8,211,125 B2 7/2012 Spivey
8,214,019 B2 7/2012 Govari et al.
8,215,531 B2 7/2012 Shelton, IV et al.
8,215,532 B2 7/2012 Marczyk
8,215,533 B2 7/2012 Viola et al.
8,220,468 B2 7/2012 Cooper et al.
8,220,688 B2 7/2012 Laurent et al.
8,220,690 B2 7/2012 Hess et al.
8,221,402 B2 7/2012 Francischelli et al.
8,221,424 B2 7/2012 Cha
8,221,433 B2 7/2012 Lozier et al.
8,225,799 B2 7/2012 Bettuchi
8,225,979 B2 7/2012 Farascioni et al.
8,226,553 B2 7/2012 Shelton, IV et al.
8,226,635 B2 7/2012 Petrie et al.
8,226,675 B2 7/2012 Houser et al.
8,226,715 B2 7/2012 Hwang et al.
8,227,946 B2 7/2012 Kim
8,228,020 B2 7/2012 Shin et al.
8,228,048 B2 7/2012 Spencer
8,229,549 B2 7/2012 Whitman et al.
8,230,235 B2 7/2012 Goodman et al.
8,231,040 B2 7/2012 Zemlok et al.
8,231,042 B2 7/2012 Hessler et al.
8,231,043 B2 7/2012 Tarinelli et al.
8,235,272 B2 8/2012 Nicholas et al.
8,235,274 B2 8/2012 Cappola
8,236,010 B2 8/2012 Ortiz et al.
8,236,011 B2 8/2012 Harris et al.
8,236,020 B2 8/2012 Smith et al.
8,237,388 B2 8/2012 Jinno et al.
8,240,536 B2 8/2012 Marczyk
8,240,537 B2 8/2012 Marczyk
8,241,271 B2 8/2012 Millman et al.
8,241,284 B2 8/2012 Dycus et al.
8,241,308 B2 8/2012 Kortenbach et al.
8,241,322 B2 8/2012 Whitman et al.

(56) References Cited

U.S. PATENT DOCUMENTS 8,245,594 B2 8/2012 Rogers et al.
8,245,898 B2 8/2012 Smith et al.
8,245,899 B2 8/2012 Swensgard et al.
8,245,900 B2 8/2012 Scirica
8,245,901 B2 8/2012 Stopek
8,246,608 B2 8/2012 Omori et al.
8,246,637 B2 8/2012 Viola et al.
8,251,921 B2 8/2012 Briggs et al.
8,252,009 B2 8/2012 Weller et al.
D667,450 S 9/2012 Eby et al.
8,256,654 B2 9/2012 Bettuchi et al.
8,256,655 B2 9/2012 Sniffin et al.
8,256,656 B2 9/2012 Milliman et al.
8,257,251 B2 9/2012 Shelton, IV et al.
8,257,356 B2 9/2012 Bleich et al.
8,257,386 B2 9/2012 Lee et al.
8,257,391 B2 9/2012 Orban, III et al.
8,257,634 B2 9/2012 Scirica
8,258,745 B2 9/2012 Smith et al.
8,261,958 B1 9/2012 Knodel
8,262,560 B2 9/2012 Whitman
8,262,655 B2 9/2012 Ghabrial et al.
8,266,232 B2 9/2012 Piper et al.
8,267,300 B2 9/2012 Boudreaux
8,267,849 B2 9/2012 Wazer et al.
8,267,924 B2 9/2012 Zemlok et al.
8,267,946 B2 9/2012 Whitfield et al.
8,267,951 B2 9/2012 Whayne et al.
8,268,344 B2 9/2012 Ma et al.
8,269,121 B2 9/2012 Smith
8,272,553 B2 9/2012 Mastri et al.
8,272,554 B2 9/2012 Whitman et al.
8,272,918 B2 9/2012 Lam
8,273,404 B2 9/2012 Dave et al.
8,276,594 B2 10/2012 Shah
8,276,801 B2 10/2012 Zemlok et al.
8,276,802 B2 10/2012 Kostrzewski
8,277,473 B2 10/2012 Sunaoshi et al.
8,281,446 B2 10/2012 Moskovich
8,281,973 B2 10/2012 Wenchell et al.
8,281,974 B2 10/2012 Hessler et al.
8,282,654 B2 10/2012 Ferrari et al.
8,285,367 B2 10/2012 Hyde et al.
8,286,723 B2 10/2012 Puzio et al.
8,286,845 B2 10/2012 Perry et al.
8,286,846 B2 10/2012 Smith et al.
8,286,847 B2 10/2012 Taylor
8,287,487 B2 10/2012 Estes
8,287,522 B2 10/2012 Moses et al.
8,287,561 B2 10/2012 Nunez et al.
8,288,984 B2 10/2012 Yang
8,289,403 B2 10/2012 Dobashi et al.
8,290,883 B2 10/2012 Takeuchi et al.
8,292,147 B2 10/2012 Viola
8,292,148 B2 10/2012 Viola
8,292,150 B2 10/2012 Bryant
8,292,151 B2 10/2012 Viola
8,292,152 B2 10/2012 Milliman et al.
8,292,155 B2 10/2012 Shelton, IV et al.
8,292,157 B2 10/2012 Smith et al.
8,292,158 B2 10/2012 Sapienza
8,292,801 B2 10/2012 Dejima et al.
8,292,888 B2 10/2012 Whitman
8,292,906 B2 10/2012 Taylor et al.
8,294,399 B2 10/2012 Suzuki et al.
8,298,161 B2 10/2012 Vargas
8,298,189 B2 10/2012 Fisher et al.
8,298,233 B2 10/2012 Mueller
8,298,677 B2 10/2012 Wiesner et al.
8,302,323 B2 11/2012 Fortier et al.
8,303,621 B2 11/2012 Miyamoto et al.
8,308,040 B2 11/2012 Huang et al.
8,308,041 B2 11/2012 Kostrzewski
8,308,042 B2 11/2012 Aranyi
8,308,043 B2 11/2012 Bindra et al.
8,308,046 B2 11/2012 Prommersberger
8,308,659 B2 11/2012 Scheibe et al.
8,308,725 B2 11/2012 Bell et al.
8,310,188 B2 11/2012 Nakai
8,313,444 B2 11/2012 Thompson et al.
8,313,496 B2 11/2012 Sauer et al.
8,313,499 B2 11/2012 Magnusson et al.
8,313,509 B2 11/2012 Kostrzewski
8,317,070 B2 11/2012 Hueil et al.
8,317,071 B1 11/2012 Knodel
8,317,074 B2 11/2012 Ortiz et al.
8,317,437 B2 11/2012 Merkley et al.
8,317,744 B2 11/2012 Kirschenman
8,317,790 B2 11/2012 Bell et al.
8,319,002 B2 11/2012 Daniels et al.
D672,784 S 12/2012 Clanton et al.
8,322,455 B2 12/2012 Shelton, IV et al.
8,322,589 B2 12/2012 Boudreaux
8,322,590 B2 12/2012 Patel et al.
8,322,901 B2 12/2012 Michelotti
8,323,271 B2 12/2012 Humayun et al.
8,323,789 B2 12/2012 Rozhin et al.
8,324,585 B2 12/2012 McBroom et al.
8,327,514 B2 12/2012 Kim
8,328,061 B2 12/2012 Kasvikis
8,328,062 B2 12/2012 Viola
8,328,063 B2 12/2012 Milliman et al.
8,328,064 B2 12/2012 Racenet et al.
8,328,065 B2 12/2012 Shah
8,328,802 B2 12/2012 Deville et al.
8,328,823 B2 12/2012 Aranyi et al.
8,333,313 B2 12/2012 Boudreaux et al.
8,333,691 B2 12/2012 Schaaf
8,333,764 B2 12/2012 Francischelli et al.
8,333,779 B2 12/2012 Smith et al.
8,334,468 B2 12/2012 Palmer et al.
8,336,753 B2 12/2012 Olson et al.
8,336,754 B2 12/2012 Cappola et al.
8,342,377 B2 1/2013 Milliman et al.
8,342,378 B2 1/2013 Marczyk et al.
8,342,379 B2 1/2013 Whitman et al.
8,342,380 B2 1/2013 Viola
8,343,150 B2 1/2013 Artale
8,347,978 B2 1/2013 Forster et al.
8,348,118 B2 1/2013 Segura
8,348,123 B2 1/2013 Scirica et al.
8,348,124 B2 1/2013 Scirica
8,348,125 B2 1/2013 Viola et al.
8,348,126 B2 1/2013 Olson et al.
8,348,127 B2 1/2013 Marczyk
8,348,129 B2 1/2013 Bedi et al.
8,348,130 B2 1/2013 Shah et al.
8,348,131 B2 1/2013 Omaits et al.
8,348,837 B2 1/2013 Wenchell
8,348,948 B2 1/2013 Bahney
8,348,959 B2 1/2013 Wolford et al.
8,348,972 B2 1/2013 Soltz et al.
8,349,987 B2 1/2013 Kapiamba et al.
8,352,004 B2 1/2013 Mannheimer et al.
8,353,437 B2 1/2013 Boudreaux
8,353,438 B2 1/2013 Baxter, III et al.
8,353,439 B2 1/2013 Baxter, III et al.
8,356,740 B1 1/2013 Knodel
8,357,144 B2 1/2013 Whitman et al.
8,357,158 B2 1/2013 McKenna et al.
8,357,161 B2 1/2013 Mueller
8,359,174 B2 1/2013 Nakashima et al.
8,360,296 B2 1/2013 Zingman
8,360,297 B2 1/2013 Shelton, IV et al.
8,360,298 B2 1/2013 Farascioni et al.
8,360,299 B2 1/2013 Zemlok et al.
8,361,501 B2 1/2013 DiTizio et al.
D676,866 S 2/2013 Chaudhri
8,365,972 B2 2/2013 Aranyi et al.
8,365,973 B1 2/2013 White et al.
8,365,975 B1 2/2013 Manoux et al.
8,365,976 B2 2/2013 Hess et al.
8,366,559 B2 2/2013 Papenfuss et al.
8,366,719 B2 2/2013 Markey et al.

(56) References Cited

U.S. PATENT DOCUMENTS

| | | | |
|---|---|---|---|
| 8,366,787 | B2 | 2/2013 | Brown et al. |
| 8,368,327 | B2 | 2/2013 | Benning et al. |
| 8,369,056 | B2 | 2/2013 | Senriuchi et al. |
| 8,371,393 | B2 | 2/2013 | Higuchi et al. |
| 8,371,491 | B2 | 2/2013 | Huitema et al. |
| 8,371,492 | B2 | 2/2013 | Aranyi et al. |
| 8,371,493 | B2 | 2/2013 | Aranyi et al. |
| 8,371,494 | B2 | 2/2013 | Racenet et al. |
| 8,372,094 | B2 | 2/2013 | Bettuchi et al. |
| 8,374,723 | B2 | 2/2013 | Zhao et al. |
| 8,376,865 | B2 | 2/2013 | Forster et al. |
| 8,377,029 | B2 | 2/2013 | Nagao et al. |
| 8,377,044 | B2 | 2/2013 | Coe et al. |
| 8,377,059 | B2 | 2/2013 | Deville et al. |
| 8,381,828 | B2 | 2/2013 | Whitman et al. |
| 8,381,834 | B2 | 2/2013 | Barhitte et al. |
| 8,382,773 | B2 | 2/2013 | Whitfield et al. |
| 8,382,790 | B2 | 2/2013 | Uenohara et al. |
| D677,273 | S | 3/2013 | Randall et al. |
| 8,387,848 | B2 | 3/2013 | Johnson et al. |
| 8,388,633 | B2 | 3/2013 | Rousseau et al. |
| 8,389,588 | B2 | 3/2013 | Ringeisen et al. |
| 8,393,513 | B2 | 3/2013 | Jankowski |
| 8,393,514 | B2 | 3/2013 | Shelton, IV et al. |
| 8,393,516 | B2 | 3/2013 | Kostrzewski |
| 8,395,342 | B2 | 3/2013 | Prisco |
| 8,397,832 | B2 | 3/2013 | Blickle et al. |
| 8,397,971 | B2 | 3/2013 | Yates et al. |
| 8,397,972 | B2 | 3/2013 | Kostrzewski |
| 8,397,973 | B1 | 3/2013 | Hausen |
| 8,398,633 | B2 | 3/2013 | Mueller |
| 8,398,669 | B2 | 3/2013 | Kim |
| 8,398,673 | B2 | 3/2013 | Hinchliffe et al. |
| 8,398,674 | B2 | 3/2013 | Prestel |
| 8,400,108 | B2 | 3/2013 | Powell et al. |
| 8,400,851 | B2 | 3/2013 | Byun |
| 8,403,138 | B2 | 3/2013 | Weisshaupt et al. |
| 8,403,195 | B2 | 3/2013 | Beardsley et al. |
| 8,403,196 | B2 | 3/2013 | Beardsley et al. |
| 8,403,198 | B2 | 3/2013 | Sorrentino et al. |
| 8,403,832 | B2 | 3/2013 | Cunningham et al. |
| 8,403,926 | B2 | 3/2013 | Nobis et al. |
| 8,403,945 | B2 | 3/2013 | Whitfield et al. |
| 8,403,946 | B2 | 3/2013 | Whitfield et al. |
| 8,403,950 | B2 | 3/2013 | Palmer et al. |
| D679,726 | S | 4/2013 | Kobayashi |
| D680,646 | S | 4/2013 | Hunt et al. |
| 8,408,439 | B2 | 4/2013 | Huang et al. |
| 8,408,442 | B2 | 4/2013 | Racenet et al. |
| 8,409,079 | B2 | 4/2013 | Okamoto et al. |
| 8,409,174 | B2 | 4/2013 | Omori |
| 8,409,175 | B2 | 4/2013 | Lee et al. |
| 8,409,211 | B2 | 4/2013 | Baroud |
| 8,409,222 | B2 | 4/2013 | Whitfield et al. |
| 8,409,223 | B2 | 4/2013 | Sorrentino et al. |
| 8,409,234 | B2 | 4/2013 | Stahler et al. |
| 8,411,500 | B2 | 4/2013 | Gapihan et al. |
| 8,413,661 | B2 | 4/2013 | Rousseau et al. |
| 8,413,870 | B2 | 4/2013 | Pastorelli et al. |
| 8,413,871 | B2 | 4/2013 | Racenet et al. |
| 8,413,872 | B2 | 4/2013 | Patel |
| 8,414,469 | B2 | 4/2013 | Diolaiti |
| 8,414,577 | B2 | 4/2013 | Boudreaux et al. |
| 8,414,598 | B2 | 4/2013 | Brock et al. |
| 8,418,073 | B2 | 4/2013 | Mohr et al. |
| 8,418,906 | B2 | 4/2013 | Farascioni et al. |
| 8,418,907 | B2 | 4/2013 | Johnson et al. |
| 8,418,908 | B1 | 4/2013 | Beardsley |
| 8,418,909 | B2 | 4/2013 | Kostrzewski |
| 8,419,635 | B2 | 4/2013 | Shelton, IV et al. |
| 8,419,717 | B2 | 4/2013 | Diolaiti et al. |
| 8,419,747 | B2 | 4/2013 | Hinman et al. |
| 8,419,754 | B2 | 4/2013 | Laby et al. |
| 8,419,755 | B2 | 4/2013 | Deem et al. |
| 8,423,182 | B2 | 4/2013 | Robinson et al. |
| 8,424,737 | B2 | 4/2013 | Scirica |
| 8,424,739 | B2 | 4/2013 | Racenet et al. |
| 8,424,740 | B2 | 4/2013 | Shelton, IV et al. |
| 8,424,741 | B2 | 4/2013 | McGuckin, Jr. et al. |
| 8,424,742 | B2 | 4/2013 | Bettuchi |
| 8,425,600 | B2 | 4/2013 | Maxwell |
| 8,427,430 | B2 | 4/2013 | Lee et al. |
| 8,430,292 | B2 | 4/2013 | Patel et al. |
| 8,430,892 | B2 | 4/2013 | Bindra et al. |
| 8,430,898 | B2 | 4/2013 | Wiener et al. |
| D681,674 | S | 5/2013 | Koehn et al. |
| 8,435,257 | B2 | 5/2013 | Smith et al. |
| 8,439,246 | B1 | 5/2013 | Knodel |
| 8,439,830 | B2 | 5/2013 | McKinley et al. |
| 8,444,036 | B2 | 5/2013 | Shelton, IV |
| 8,444,037 | B2 | 5/2013 | Nicholas et al. |
| 8,444,549 | B2 | 5/2013 | Viola et al. |
| 8,449,536 | B2 | 5/2013 | Selig |
| 8,449,560 | B2 | 5/2013 | Roth et al. |
| 8,453,904 | B2 | 6/2013 | Eskaros et al. |
| 8,453,906 | B2 | 6/2013 | Huang et al. |
| 8,453,907 | B2 | 6/2013 | Laurent et al. |
| 8,453,908 | B2 | 6/2013 | Bedi et al. |
| 8,453,912 | B2 | 6/2013 | Mastri et al. |
| 8,453,914 | B2 | 6/2013 | Laurent et al. |
| 8,454,495 | B2 | 6/2013 | Kawano et al. |
| 8,454,551 | B2 | 6/2013 | Allen et al. |
| 8,454,628 | B2 | 6/2013 | Smith et al. |
| 8,454,640 | B2 | 6/2013 | Johnston et al. |
| 8,457,757 | B2 | 6/2013 | Cauller et al. |
| 8,459,520 | B2 | 6/2013 | Giordano et al. |
| 8,459,521 | B2 | 6/2013 | Zemlok et al. |
| 8,459,524 | B2 | 6/2013 | Pribanic et al. |
| 8,459,525 | B2 | 6/2013 | Yates et al. |
| 8,460,207 | B2 | 6/2013 | Burdorff et al. |
| 8,464,921 | B2 * | 6/2013 | Shima ........................ B25C 1/06 227/8 |
| 8,464,922 | B2 | 6/2013 | Marczyk |
| 8,464,923 | B2 | 6/2013 | Shelton, IV |
| 8,464,924 | B2 | 6/2013 | Gresham et al. |
| 8,464,925 | B2 | 6/2013 | Hull et al. |
| 8,465,475 | B2 | 6/2013 | Isbell, Jr. |
| 8,465,502 | B2 | 6/2013 | Zergiebel |
| 8,465,515 | B2 | 6/2013 | Drew et al. |
| 8,469,254 | B2 | 6/2013 | Czernik et al. |
| 8,469,946 | B2 | 6/2013 | Sugita |
| 8,469,973 | B2 | 6/2013 | Meade et al. |
| 8,470,355 | B2 | 6/2013 | Skalla et al. |
| D686,240 | S | 7/2013 | Lin |
| D686,244 | S | 7/2013 | Moriya et al. |
| 8,474,677 | B2 | 7/2013 | Woodard, Jr. et al. |
| 8,475,453 | B2 | 7/2013 | Marczyk et al. |
| 8,475,454 | B1 | 7/2013 | Alshemari |
| 8,475,474 | B2 | 7/2013 | Bombard et al. |
| 8,479,968 | B2 | 7/2013 | Hodgkinson et al. |
| 8,479,969 | B2 | 7/2013 | Shelton, IV |
| 8,480,703 | B2 | 7/2013 | Nicholas et al. |
| 8,483,509 | B2 | 7/2013 | Matsuzaka |
| 8,485,412 | B2 | 7/2013 | Shelton, IV et al. |
| 8,485,413 | B2 | 7/2013 | Scheib et al. |
| 8,485,970 | B2 | 7/2013 | Widenhouse et al. |
| 8,486,047 | B2 | 7/2013 | Stopek |
| 8,487,199 | B2 | 7/2013 | Palmer et al. |
| 8,487,487 | B2 | 7/2013 | Dietz et al. |
| 8,490,851 | B2 | 7/2013 | Blier et al. |
| 8,490,852 | B2 | 7/2013 | Viola |
| 8,490,853 | B2 | 7/2013 | Criscuolo et al. |
| 8,491,581 | B2 | 7/2013 | Deville et al. |
| 8,491,603 | B2 | 7/2013 | Yeung et al. |
| 8,491,624 | B2 | 7/2013 | Kerr et al. |
| 8,496,153 | B2 | 7/2013 | Demmy et al. |
| 8,496,154 | B2 | 7/2013 | Marczyk et al. |
| 8,496,156 | B2 | 7/2013 | Sniffin et al. |
| 8,496,683 | B2 | 7/2013 | Prommersberger et al. |
| 8,498,691 | B2 | 7/2013 | Moll et al. |
| 8,499,673 | B2 | 8/2013 | Keller |
| 8,499,966 | B2 | 8/2013 | Palmer et al. |
| 8,499,992 | B2 | 8/2013 | Whitman et al. |
| 8,499,993 | B2 | 8/2013 | Shelton, IV et al. |

(56) References Cited

U.S. PATENT DOCUMENTS 8,499,994 B2 8/2013 D'Arcangelo
8,500,721 B2 8/2013 Jinno
8,500,762 B2 8/2013 Sholev et al.
8,502,091 B2 8/2013 Palmer et al.
8,505,649 B2 8/2013 Scrimshaw et al.
8,505,799 B2 8/2013 Viola et al.
8,505,801 B2 8/2013 Ehrenfels et al.
8,505,802 B2 8/2013 Viola et al.
8,506,555 B2 8/2013 Ruiz Morales
8,506,557 B2 8/2013 Zemlok et al.
8,506,580 B2 8/2013 Zergiebel et al.
8,506,581 B2 8/2013 Wingardner, III et al.
8,511,308 B2 8/2013 Hecox et al.
8,512,359 B2 8/2013 Whitman et al.
8,512,402 B2 8/2013 Marczyk et al.
8,517,239 B2 8/2013 Scheib et al.
8,517,241 B2 8/2013 Nicholas et al.
8,517,243 B2 8/2013 Giordano et al.
8,517,244 B2 8/2013 Shelton, IV et al.
8,517,938 B2 8/2013 Eisenhardt et al.
8,518,024 B2 8/2013 Williams et al.
8,521,273 B2 8/2013 Kliman
8,523,042 B2 9/2013 Masiakos et al.
8,523,043 B2 9/2013 Ullrich et al.
8,523,787 B2 9/2013 Ludwin et al.
8,523,881 B2 9/2013 Cabiri et al.
8,523,882 B2 9/2013 Huitema et al.
8,523,900 B2 9/2013 Jinno et al.
8,529,588 B2 9/2013 Ahlberg et al.
8,529,599 B2 9/2013 Holsten
8,529,600 B2 9/2013 Woodard, Jr. et al.
8,529,819 B2 9/2013 Ostapoff et al.
8,531,153 B2 9/2013 Baarman et al.
8,532,747 B2 9/2013 Nock et al.
8,534,527 B2 9/2013 Brendel et al.
8,534,528 B2 9/2013 Shelton, IV
8,535,304 B2 9/2013 Sklar et al.
8,535,340 B2 9/2013 Allen
8,539,866 B2 9/2013 Nayak et al.
8,540,128 B2 9/2013 Shelton, IV et al.
8,540,129 B2 9/2013 Baxter, III et al.
8,540,130 B2 9/2013 Moore et al.
8,540,131 B2 9/2013 Swayze
8,540,133 B2 9/2013 Bedi et al.
8,540,646 B2 9/2013 Mendez-Coll
8,540,733 B2 9/2013 Whitman et al.
8,540,735 B2 9/2013 Mitelberg et al.
D690,614 S 10/2013 Mascadri et al.
8,550,984 B2 10/2013 Takemoto
8,551,076 B2 10/2013 Duval et al.
8,555,660 B2 10/2013 Takenaka et al.
8,556,151 B2 10/2013 Viola
8,556,918 B2 10/2013 Bauman et al.
8,556,935 B1 10/2013 Knodel et al.
8,560,147 B2 10/2013 Taylor et al.
8,561,617 B2 10/2013 Lindh et al.
8,561,870 B2 10/2013 Baxter, III et al.
8,561,871 B2 10/2013 Rajappa et al.
8,561,873 B2 10/2013 Ingmanson et al.
8,562,592 B2 10/2013 Conlon et al.
8,562,598 B2 10/2013 Falkenstein et al.
8,567,656 B2 10/2013 Shelton, IV et al.
8,568,416 B2 10/2013 Schmitz et al.
8,568,425 B2 10/2013 Ross et al.
D692,916 S 11/2013 Granchi et al.
8,573,459 B2 11/2013 Smith et al.
8,573,461 B2 11/2013 Shelton, IV et al.
8,573,462 B2 11/2013 Smith et al.
8,573,465 B2 11/2013 Shelton, IV
8,574,199 B2 11/2013 von Bulow et al.
8,574,263 B2 11/2013 Mueller
8,575,880 B2 11/2013 Grantz
8,575,895 B2 11/2013 Garrastacho et al.
8,579,176 B2 11/2013 Smith et al.
8,579,178 B2 11/2013 Holsten et al.
8,579,897 B2 11/2013 Vakharia et al.
8,579,937 B2 11/2013 Gresham
8,584,919 B2 11/2013 Hueil et al.
8,584,920 B2 11/2013 Hodgkinson
8,584,921 B2 11/2013 Scirica
8,585,583 B2 11/2013 Sakaguchi et al.
8,585,598 B2 11/2013 Razzaque et al.
8,585,721 B2 11/2013 Kirsch
8,590,760 B2 11/2013 Cummins et al.
8,590,762 B2 11/2013 Hess et al.
8,590,764 B2 11/2013 Hartwick et al.
8,591,400 B2 11/2013 Sugiyama
D695,310 S 12/2013 Jang et al.
8,596,515 B2 12/2013 Okoniewski
8,597,745 B2 12/2013 Farnsworth et al.
8,599,450 B2 12/2013 Kubo et al.
8,602,125 B2 12/2013 King
8,602,287 B2 12/2013 Yates et al.
8,602,288 B2 12/2013 Shelton, IV et al.
8,603,077 B2 12/2013 Cooper et al.
8,603,089 B2 12/2013 Viola
8,603,110 B2 12/2013 Maruyama et al.
8,603,135 B2 12/2013 Mueller
8,608,043 B2 12/2013 Scirica
8,608,044 B2 12/2013 Hueil et al.
8,608,045 B2 12/2013 Smith et al.
8,608,046 B2 12/2013 Laurent et al.
8,608,745 B2 12/2013 Guzman et al.
8,613,383 B2 12/2013 Beckman et al.
8,613,384 B2 12/2013 Pastorelli et al.
8,616,427 B2 12/2013 Viola
8,616,431 B2 12/2013 Timm et al.
8,617,155 B2 12/2013 Johnson et al.
8,620,473 B2 12/2013 Diolaiti et al.
8,622,274 B2 1/2014 Yates et al.
8,622,275 B2 1/2014 Baxter, III et al.
8,627,993 B2 1/2014 Smith et al.
8,627,994 B2 1/2014 Zemlok et al.
8,627,995 B2 1/2014 Smith et al.
8,628,467 B2 1/2014 Whitman et al.
8,628,518 B2 1/2014 Blumenkranz et al.
8,628,544 B2 1/2014 Farascioni
8,628,545 B2 1/2014 Cabrera et al.
8,631,987 B2 1/2014 Shelton, IV et al.
8,631,992 B1 1/2014 Hausen et al.
8,631,993 B2 1/2014 Kostrzewski
8,632,462 B2 1/2014 Yoo et al.
8,632,525 B2 1/2014 Kerr et al.
8,632,535 B2 1/2014 Shelton, IV et al.
8,632,539 B2 1/2014 Twomey et al.
8,632,563 B2 1/2014 Nagase et al.
8,636,187 B2 1/2014 Hueil et al.
8,636,190 B2 1/2014 Zemlok et al.
8,636,191 B2 1/2014 Meagher
8,636,193 B2 1/2014 Whitman et al.
8,636,736 B2 1/2014 Yates et al.
8,636,766 B2 1/2014 Milliman et al.
8,639,936 B2 1/2014 Hu et al.
8,640,788 B2 2/2014 Dachs, II et al.
8,646,674 B2 2/2014 Schulte et al.
8,647,258 B2 2/2014 Aranyi et al.
8,652,120 B2 2/2014 Giordano et al.
8,652,151 B2 2/2014 Lehman et al.
8,652,155 B2 2/2014 Houser et al.
8,656,929 B2 2/2014 Miller et al.
8,657,174 B2 2/2014 Yates et al.
8,657,175 B2 2/2014 Sonnenschein et al.
8,657,176 B2 2/2014 Shelton, IV et al.
8,657,177 B2 2/2014 Scirica et al.
8,657,178 B2 2/2014 Hueil et al.
8,657,482 B2 2/2014 Malackowski et al.
8,657,808 B2 2/2014 McPherson et al.
8,657,814 B2 2/2014 Werneth et al.
8,657,821 B2 2/2014 Palermo
D701,238 S 3/2014 Lai et al.
8,662,370 B2 3/2014 Takei
8,663,106 B2 3/2014 Stivoric et al.
8,663,192 B2 3/2014 Hester et al.
8,663,245 B2 3/2014 Francischelli et al.

(56) References Cited

U.S. PATENT DOCUMENTS 8,663,262 B2 3/2014 Smith et al.
8,663,270 B2 3/2014 Donnigan et al.
8,664,792 B2 3/2014 Rebsdorf
8,668,129 B2 3/2014 Olson
8,668,130 B2 3/2014 Hess et al.
8,672,206 B2 3/2014 Aranyi et al.
8,672,207 B2 3/2014 Shelton, IV et al.
8,672,208 B2 3/2014 Hess et al.
8,672,209 B2 3/2014 Crainich
8,672,922 B2 3/2014 Loh et al.
8,672,935 B2 3/2014 Okada et al.
8,672,951 B2 3/2014 Smith et al.
8,673,210 B2 3/2014 Deshays
8,675,820 B2 3/2014 Baic et al.
8,678,263 B2 3/2014 Viola
8,678,994 B2 3/2014 Sonnenschein et al.
8,679,093 B2 3/2014 Farra
8,679,098 B2 3/2014 Hart
8,679,114 B2 3/2014 Chapman et al.
8,679,137 B2 3/2014 Bauman et al.
8,679,154 B2 3/2014 Smith et al.
8,679,156 B2 3/2014 Smith et al.
8,679,454 B2 3/2014 Guire et al.
8,684,248 B2 4/2014 Milliman
8,684,249 B2 4/2014 Racenet et al.
8,684,250 B2 4/2014 Bettuchi et al.
8,684,253 B2 4/2014 Giordano et al.
8,684,962 B2 4/2014 Kirschenman et al.
8,685,004 B2 4/2014 Zemlock et al.
8,685,020 B2 4/2014 Weizman et al.
8,690,893 B2 4/2014 Deitch et al.
8,695,866 B2 4/2014 Leimbach et al.
8,696,665 B2 4/2014 Hunt et al.
8,701,958 B2 4/2014 Shelton, IV et al.
8,701,959 B2 4/2014 Shah
8,706,316 B1 4/2014 Hoevenaar
8,708,210 B2 4/2014 Zemlok et al.
8,708,211 B2 4/2014 Zemlok et al.
8,708,212 B2 4/2014 Williams
8,708,213 B2 4/2014 Shelton, IV et al.
8,709,012 B2 4/2014 Muller
8,712,549 B2 4/2014 Zdeblick et al.
8,714,352 B2 5/2014 Farascioni et al.
8,714,429 B2 5/2014 Demmy
8,714,430 B2 5/2014 Natarajan et al.
8,715,256 B2 5/2014 Greener
8,715,302 B2 5/2014 Ibrahim et al.
8,720,766 B2 5/2014 Hess et al.
8,721,630 B2 5/2014 Ortiz et al.
8,721,666 B2 5/2014 Schroeder et al.
8,727,197 B2 5/2014 Hess et al.
8,727,199 B2 5/2014 Wenchell
8,727,200 B2 5/2014 Roy
8,727,961 B2 5/2014 Ziv
8,728,099 B2 5/2014 Cohn et al.
8,728,119 B2 5/2014 Cummins
8,733,470 B2 5/2014 Matthias et al.
8,733,611 B2 5/2014 Milliman
8,733,612 B2 5/2014 Ma
8,733,613 B2 5/2014 Huitema et al.
8,733,614 B2 5/2014 Ross et al.
8,734,336 B2 5/2014 Bonadio et al.
8,734,359 B2 5/2014 Ibanez et al.
8,734,431 B2 5/2014 Shimada et al.
8,734,478 B2 5/2014 Widenhouse et al.
8,734,831 B2 5/2014 Kim et al.
8,739,033 B2 5/2014 Rosenberg
8,739,417 B2 6/2014 Tokunaga et al.
8,740,034 B2 6/2014 Morgan et al.
8,740,037 B2 6/2014 Shelton, IV et al.
8,740,038 B2 6/2014 Shelton, IV et al.
8,740,987 B2 6/2014 Geremakis et al.
8,746,529 B2 6/2014 Shelton, IV et al.
8,746,530 B2 6/2014 Giordano et al.
8,746,533 B2 6/2014 Whitman et al.
8,746,535 B2 6/2014 Shelton, IV et al.
8,747,238 B2 6/2014 Shelton, IV et al.
8,747,441 B2 6/2014 Konieczynski et al.
8,752,264 B2 6/2014 Ackley et al.
8,752,699 B2 6/2014 Morgan et al.
8,752,747 B2 6/2014 Shelton, IV et al.
8,752,748 B2 6/2014 Whitman et al.
8,752,749 B2 6/2014 Moore et al.
8,753,664 B2 6/2014 Dao et al.
8,757,287 B2 6/2014 Mak et al.
8,757,465 B2 6/2014 Woodard, Jr. et al.
8,758,235 B2 6/2014 Jaworek
8,758,366 B2 6/2014 McLean et al.
8,758,391 B2 6/2014 Swayze et al.
8,758,438 B2 6/2014 Boyce et al.
8,763,875 B2 7/2014 Morgan et al.
8,763,876 B2 7/2014 Kostrzewski
8,763,877 B2 7/2014 Schall et al.
8,763,879 B2 7/2014 Shelton, IV et al.
8,764,732 B2 7/2014 Hartwell
8,765,942 B2 7/2014 Feraud et al.
8,770,458 B2 7/2014 Scirica
8,770,459 B2 7/2014 Racenet et al.
8,770,460 B2 7/2014 Belzer
8,771,169 B2 7/2014 Whitman et al.
8,771,260 B2 7/2014 Conlon et al.
8,777,004 B2 7/2014 Shelton, IV et al.
8,777,082 B2 7/2014 Scirica
8,777,083 B2 7/2014 Racenet et al.
8,777,898 B2 7/2014 Suon et al.
8,783,541 B2 7/2014 Shelton, IV et al.
8,783,542 B2 7/2014 Riestenberg et al.
8,783,543 B2 7/2014 Shelton, IV et al.
8,784,304 B2 7/2014 Mikkaichi et al.
8,784,404 B2 7/2014 Doyle et al.
8,784,415 B2 7/2014 Malackowski et al.
8,789,737 B2 7/2014 Hodgkinson et al.
8,789,739 B2 7/2014 Swensgard
8,789,740 B2 7/2014 Baxter, III et al.
8,789,741 B2 7/2014 Baxter, III et al.
8,790,658 B2 7/2014 Cigarini et al.
8,790,684 B2 7/2014 Dave et al.
D711,905 S 8/2014 Morrison et al.
8,794,098 B2 8/2014 Long
8,794,496 B2 8/2014 Scirica
8,794,497 B2 8/2014 Zingman
8,795,159 B2 8/2014 Moriyama
8,795,276 B2 8/2014 Dietz et al.
8,795,308 B2 8/2014 Valin
8,795,324 B2 8/2014 Kawai et al.
8,796,995 B2 8/2014 Cunanan et al.
8,800,681 B2 8/2014 Rousson et al.
8,800,837 B2 8/2014 Zemlok
8,800,838 B2 8/2014 Shelton, IV
8,800,839 B2 8/2014 Beetel
8,800,840 B2 8/2014 Jankowski
8,800,841 B2 8/2014 Ellerhorst et al.
8,801,710 B2 8/2014 Ullrich et al.
8,801,734 B2 8/2014 Shelton, IV et al.
8,801,735 B2 8/2014 Shelton, IV et al.
8,801,752 B2 8/2014 Fortier et al.
8,801,801 B2 8/2014 Datta et al.
8,806,973 B2 8/2014 Ross et al.
8,807,414 B2 8/2014 Ross et al.
8,808,161 B2 8/2014 Gregg et al.
8,808,164 B2 8/2014 Hoffman et al.
8,808,274 B2 8/2014 Hartwell
8,808,294 B2 8/2014 Fox et al.
8,808,308 B2 8/2014 Boukhny et al.
8,808,311 B2 8/2014 Heinrich et al.
8,808,325 B2 8/2014 Hess et al.
8,810,197 B2 8/2014 Juergens
8,811,017 B2 8/2014 Fujii et al.
8,813,866 B2 8/2014 Suzuki
8,814,024 B2 8/2014 Woodard, Jr. et al.
8,814,025 B2 8/2014 Miller et al.
8,814,836 B2 8/2014 Ignon et al.
8,815,594 B2 8/2014 Harris et al.
8,818,523 B2 8/2014 Olson et al.

(56) References Cited

U.S. PATENT DOCUMENTS 8,820,603 B2 9/2014 Shelton, IV et al.
8,820,605 B2 9/2014 Shelton, IV
8,820,606 B2 9/2014 Hodgkinson
8,820,607 B2 9/2014 Marczyk
8,820,608 B2 9/2014 Miyamoto
8,821,514 B2 9/2014 Aranyi
8,822,934 B2 9/2014 Sayeh et al.
8,825,164 B2 9/2014 Tweden et al.
8,827,133 B2 9/2014 Shelton, IV et al.
8,827,134 B2 9/2014 Viola et al.
8,827,903 B2 9/2014 Shelton, IV et al.
8,828,046 B2 9/2014 Stefanchik et al.
8,831,779 B2 9/2014 Ortmaier et al.
8,833,219 B2 9/2014 Pierce
8,833,630 B2 9/2014 Milliman
8,833,632 B2 9/2014 Swensgard
8,834,353 B2 9/2014 Dejima et al.
8,834,465 B2 9/2014 Ramstein et al.
8,834,498 B2 9/2014 Byrum et al.
8,834,518 B2 9/2014 Faller et al.
8,840,003 B2 9/2014 Morgan et al.
8,840,004 B2 9/2014 Holsten et al.
8,840,603 B2 9/2014 Shelton, IV et al.
8,840,609 B2 9/2014 Stuebe
8,840,876 B2 9/2014 Eemeta et al.
8,844,789 B2 9/2014 Shelton, IV et al.
8,844,790 B2 9/2014 Demmy et al.
8,845,622 B2 9/2014 Paik et al.
8,851,215 B2 10/2014 Goto
8,851,354 B2 10/2014 Swensgard et al.
8,851,355 B2 10/2014 Aranyi et al.
8,852,174 B2 10/2014 Burbank
8,852,185 B2 10/2014 Twomey
8,852,199 B2 10/2014 Deslauriers et al.
8,852,218 B2 10/2014 Hughett, Sr. et al.
8,852,473 B1 10/2014 Tan
8,855,822 B2 10/2014 Bartol et al.
8,857,692 B2 10/2014 Shima et al.
8,857,693 B2 10/2014 Schuckmann et al.
8,857,694 B2 10/2014 Shelton, IV et al.
8,858,538 B2 10/2014 Belson et al.
8,858,547 B2 10/2014 Brogna
8,858,571 B2 10/2014 Shelton, IV et al.
8,858,590 B2 10/2014 Shelton, IV et al.
8,864,007 B2 10/2014 Widenhouse et al.
8,864,009 B2 10/2014 Shelton, IV et al.
8,864,010 B2 10/2014 Williams
8,864,750 B2 10/2014 Ross et al.
8,869,912 B2 10/2014 Roßkamp et al.
8,869,913 B2 10/2014 Matthias et al.
8,870,049 B2 10/2014 Amid et al.
8,870,050 B2 10/2014 Hodgkinson
8,870,867 B2 10/2014 Walberg et al.
8,870,912 B2 10/2014 Brisson et al.
8,871,829 B2 10/2014 Gerold et al.
D716,820 S 11/2014 Wood
8,875,971 B2 11/2014 Hall et al.
8,875,972 B2 11/2014 Weisenburgh, II et al.
8,876,698 B2 11/2014 Sakamoto et al.
8,876,857 B2 11/2014 Burbank
8,876,858 B2 11/2014 Braun
8,882,660 B2 11/2014 Phee et al.
8,882,792 B2 11/2014 Dietz et al.
8,884,560 B2 11/2014 Ito
8,887,979 B2 11/2014 Mastri et al.
8,888,688 B2 11/2014 Julian et al.
8,888,695 B2 11/2014 Piskun et al.
8,888,792 B2 11/2014 Harris et al.
8,888,809 B2 11/2014 Davison et al.
8,893,946 B2 11/2014 Boudreaux et al.
8,893,949 B2 11/2014 Shelton, IV et al.
8,893,950 B2 11/2014 Marczyk
8,894,634 B2 11/2014 Devengenzo et al.
8,894,647 B2 11/2014 Beardsley et al.
8,894,654 B2 11/2014 Anderson
8,899,460 B2 12/2014 Wojcicki
8,899,461 B2 12/2014 Farascioni
8,899,462 B2 12/2014 Kostrzewski et al.
8,899,463 B2 12/2014 Schall et al.
8,899,464 B2 12/2014 Hueil et al.
8,899,465 B2 12/2014 Shelton, IV et al.
8,899,466 B2 12/2014 Baxter, III et al.
8,900,267 B2 12/2014 Woolfson et al.
8,905,287 B2 12/2014 Racenet et al.
8,905,977 B2 12/2014 Shelton et al.
8,910,846 B2 12/2014 Viola
8,910,847 B2 12/2014 Nalagatla et al.
8,911,426 B2 12/2014 Coppeta et al.
8,911,448 B2 12/2014 Stein
8,911,460 B2 12/2014 Neurohr et al.
8,911,471 B2 12/2014 Spivey et al.
8,912,746 B2 12/2014 Reid et al.
8,915,842 B2 12/2014 Weisenburgh, II et al.
8,920,368 B2 12/2014 Sandhu et al.
8,920,433 B2 12/2014 Barrier et al.
8,920,435 B2 12/2014 Smith et al.
8,920,438 B2 12/2014 Aranyi et al.
8,920,443 B2 12/2014 Hiles et al.
8,920,444 B2 12/2014 Hiles et al.
8,922,163 B2 12/2014 Macdonald
8,925,782 B2 1/2015 Shelton, IV
8,925,783 B2 1/2015 Zemlok et al.
8,925,788 B2 1/2015 Hess et al.
8,926,506 B2 1/2015 Widenhouse et al.
8,926,598 B2 1/2015 Mollere et al.
8,931,576 B2 1/2015 Iwata
8,931,679 B2 1/2015 Kostrzewski
8,931,680 B2 1/2015 Milliman
8,931,682 B2 1/2015 Timm et al.
8,931,692 B2 1/2015 Sancak
8,936,614 B2 1/2015 Allen, IV
8,937,408 B2 1/2015 Ganem et al.
8,939,343 B2 1/2015 Milliman et al.
8,939,344 B2 1/2015 Olson et al.
8,939,898 B2 1/2015 Omoto
8,944,069 B2 2/2015 Miller et al.
8,945,095 B2 2/2015 Blumenkranz et al.
8,945,098 B2 2/2015 Seibold et al.
8,945,163 B2 2/2015 Voegele et al.
8,955,732 B2 2/2015 Zemlok et al.
8,956,342 B1 2/2015 Russo et al.
8,956,390 B2 2/2015 Shah et al.
8,958,860 B2 2/2015 Banerjee et al.
8,960,519 B2 2/2015 Whitman et al.
8,960,520 B2 2/2015 McCuen
8,960,521 B2 2/2015 Kostrzewski
8,961,191 B2 2/2015 Hanshew
8,961,504 B2 2/2015 Hoarau et al.
8,961,542 B2 2/2015 Whitfield et al.
8,963,714 B2 2/2015 Medhal et al.
D725,674 S 3/2015 Jung et al.
8,967,443 B2 3/2015 McCuen
8,967,444 B2 3/2015 Beetel
8,967,446 B2 3/2015 Beardsley et al.
8,967,448 B2 3/2015 Carter et al.
8,968,276 B2 3/2015 Zemlok et al.
8,968,308 B2 3/2015 Horner et al.
8,968,312 B2 3/2015 Marczyk et al.
8,968,337 B2 3/2015 Whitfield et al.
8,968,340 B2 3/2015 Chowaniec et al.
8,968,355 B2 3/2015 Malkowski et al.
8,968,358 B2 3/2015 Reschke
8,970,507 B2 3/2015 Holbein et al.
8,973,803 B2 3/2015 Hall et al.
8,973,804 B2 3/2015 Hess et al.
8,973,805 B2 3/2015 Scirica et al.
8,974,440 B2 3/2015 Farritor et al.
8,974,542 B2 3/2015 Fujimoto et al.
8,974,932 B2 3/2015 McGahan et al.
8,978,954 B2 3/2015 Shelton, IV et al.
8,978,955 B2 3/2015 Aronhalt et al.
8,978,956 B2 3/2015 Schall et al.
8,979,843 B2 3/2015 Timm et al.
8,979,890 B2 3/2015 Boudreaux

(56) References Cited

U.S. PATENT DOCUMENTS 8,982,195 B2 3/2015 Claus et al.
8,984,711 B2 3/2015 Ota et al.
8,985,240 B2 3/2015 Winnard
8,985,429 B2 3/2015 Balek et al.
8,986,302 B2 3/2015 Aldridge et al.
8,989,903 B2 3/2015 Weir et al.
8,991,676 B2 3/2015 Hess et al.
8,991,677 B2 3/2015 Moore et al.
8,991,678 B2 3/2015 Wellman et al.
8,992,042 B2 3/2015 Eichenholz
8,992,422 B2 3/2015 Spivey et al.
8,992,565 B2 3/2015 Brisson et al.
8,996,165 B2 3/2015 Wang et al.
8,998,058 B2 4/2015 Moore et al.
8,998,059 B2 4/2015 Smith et al.
8,998,060 B2 4/2015 Bruewer et al.
8,998,061 B2 4/2015 Williams et al.
8,998,939 B2 4/2015 Price et al.
9,000,720 B2 4/2015 Stulen et al.
9,002,518 B2 4/2015 Manzo et al.
9,004,339 B1 4/2015 Park
9,004,799 B1 4/2015 Tibbits
9,005,230 B2 4/2015 Yates et al.
9,005,238 B2 4/2015 DeSantis et al.
9,005,243 B2 4/2015 Stopek et al.
9,010,606 B2 4/2015 Aranyi et al.
9,010,608 B2 4/2015 Casasanta, Jr. et al.
9,010,609 B2 4/2015 Carter et al.
9,010,611 B2 4/2015 Ross et al.
9,011,437 B2 4/2015 Woodruff et al.
9,011,439 B2 4/2015 Shalaby et al.
9,011,471 B2 4/2015 Timm et al.
9,014,856 B2 4/2015 Manzo et al.
9,016,539 B2 4/2015 Kostrzewski et al.
9,016,540 B2 4/2015 Whitman et al.
9,016,541 B2 4/2015 Viola et al.
9,016,542 B2 4/2015 Shelton, IV et al.
9,016,545 B2 4/2015 Aranyi et al.
9,017,331 B2 4/2015 Fox
9,017,355 B2 4/2015 Smith et al.
9,017,369 B2 4/2015 Renger et al.
9,017,371 B2 4/2015 Whitman et al.
9,017,849 B2 4/2015 Stulen et al.
9,017,851 B2 4/2015 Felder et al.
D729,274 S 5/2015 Clement et al.
D730,393 S 5/2015 Bray et al.
9,021,684 B2 5/2015 Lenker et al.
9,023,014 B2 5/2015 Chowaniec et al.
9,023,069 B2 5/2015 Kasvikis et al.
9,023,071 B2 5/2015 Miller et al.
9,026,347 B2 5/2015 Gadh et al.
9,027,817 B2 5/2015 Milliman et al.
9,028,468 B2 5/2015 Scarfogliero et al.
9,028,494 B2 5/2015 Shelton, IV et al.
9,028,495 B2 5/2015 Mueller et al.
9,028,510 B2 5/2015 Miyamoto et al.
9,028,511 B2 5/2015 Weller et al.
9,028,519 B2 5/2015 Yates et al.
9,028,529 B2 5/2015 Fox et al.
9,030,166 B2 5/2015 Kano
9,030,169 B2 5/2015 Christensen et al.
9,033,203 B2 5/2015 Woodard, Jr. et al.
9,033,204 B2 5/2015 Shelton, IV et al.
9,034,505 B2 5/2015 Detry et al.
9,038,881 B1 5/2015 Schaller et al.
9,039,690 B2 5/2015 Kersten et al.
9,039,694 B2 5/2015 Ross et al.
9,039,720 B2 5/2015 Madan
9,039,736 B2 5/2015 Scirica et al.
9,040,062 B2 5/2015 Maeda et al.
9,043,027 B2 5/2015 Durant et al.
9,044,227 B2 6/2015 Shelton, IV et al.
9,044,228 B2 6/2015 Woodard, Jr. et al.
9,044,229 B2 6/2015 Scheib et al.
9,044,230 B2 6/2015 Morgan et al.
9,044,238 B2 6/2015 Orszulak
9,044,241 B2 6/2015 Barner et al.
9,044,261 B2 6/2015 Houser
9,044,281 B2 6/2015 Pool et al.
9,050,083 B2 6/2015 Yates et al.
9,050,084 B2 6/2015 Schmid et al.
9,050,089 B2 6/2015 Orszulak
9,050,100 B2 6/2015 Yates et al.
9,050,120 B2 6/2015 Swarup et al.
9,050,123 B2 6/2015 Krause et al.
9,050,176 B2 6/2015 Datta et al.
9,050,192 B2 6/2015 Mansmann
9,055,941 B2 6/2015 Schmid et al.
9,055,942 B2 6/2015 Balbierz et al.
9,055,943 B2 6/2015 Zemlok et al.
9,055,944 B2 6/2015 Hodgkinson et al.
9,055,961 B2 6/2015 Manzo et al.
9,060,770 B2 6/2015 Shelton, IV et al.
9,060,776 B2 6/2015 Yates et al.
9,060,794 B2 6/2015 Kang et al.
9,060,894 B2 6/2015 Wubbeling
9,061,392 B2 6/2015 Forgues et al.
9,070,068 B2 6/2015 Coveley et al.
D733,727 S 7/2015 Cojuangco et al.
9,072,515 B2 7/2015 Hall et al.
9,072,523 B2 7/2015 Houser et al.
9,072,535 B2 7/2015 Shelton, IV et al.
9,072,536 B2 7/2015 Shelton, IV et al.
9,078,653 B2 7/2015 Leimbach et al.
9,078,654 B2 7/2015 Whitman et al.
9,084,586 B2 7/2015 Hafner et al.
9,084,601 B2 7/2015 Moore et al.
9,084,602 B2 7/2015 Gleiman
9,086,875 B2 7/2015 Harrat et al.
9,089,317 B2 7/2015 Burdorff et al.
9,089,326 B2 7/2015 Krumanaker et al.
9,089,330 B2 7/2015 Widenhouse et al.
9,089,338 B2 7/2015 Smith et al.
9,089,352 B2 7/2015 Jeong
9,089,360 B2 7/2015 Messerly et al.
9,091,588 B2 7/2015 Lefler
D736,792 S 8/2015 Brinda et al.
9,095,339 B2 8/2015 Moore et al.
9,095,346 B2 8/2015 Houser et al.
9,095,362 B2 8/2015 Dachs, II et al.
9,095,367 B2 8/2015 Olson et al.
9,095,642 B2 8/2015 Harder et al.
9,096,033 B2 8/2015 Holop et al.
9,098,153 B2 8/2015 Shen et al.
9,099,863 B2 8/2015 Smith et al.
9,099,877 B2 8/2015 Banos et al.
9,099,922 B2 8/2015 Toosky et al.
9,101,358 B2 8/2015 Kerr et al.
9,101,359 B2 8/2015 Smith et al.
9,101,385 B2 8/2015 Shelton, IV et al.
9,101,475 B2 8/2015 Wei et al.
9,101,621 B2 8/2015 Zeldis
9,107,663 B2 8/2015 Swensgard
9,107,667 B2 8/2015 Hodgkinson
9,107,690 B2 8/2015 Bales, Jr. et al.
9,110,587 B2 8/2015 Kim et al.
9,113,862 B2 8/2015 Morgan et al.
9,113,864 B2 8/2015 Morgan et al.
9,113,865 B2 8/2015 Shelton, IV et al.
9,113,866 B2 8/2015 Felder et al.
9,113,868 B2 8/2015 Felder et al.
9,113,873 B2 8/2015 Marczyk et al.
9,113,874 B2 8/2015 Shelton, IV et al.
9,113,875 B2 8/2015 Viola et al.
9,113,876 B2 8/2015 Zemlok et al.
9,113,877 B1 8/2015 Whitman et al.
9,113,879 B2 8/2015 Felder et al.
9,113,880 B2 8/2015 Zemlok et al.
9,113,881 B2 8/2015 Scirica
9,113,883 B2 8/2015 Aronhalt et al.
9,113,884 B2 8/2015 Shelton, IV et al.
9,113,887 B2 8/2015 Behnke, II et al.
9,119,615 B2 9/2015 Felder et al.
9,119,657 B2 9/2015 Shelton, IV et al.

(56) References Cited

U.S. PATENT DOCUMENTS 9,119,898 B2 9/2015 Bayon et al.
9,119,957 B2 9/2015 Gantz et al.
9,123,286 B2 9/2015 Park
9,124,097 B2 9/2015 Cruz
9,125,651 B2 9/2015 Mandakolathur Vasudevan et al.
9,125,654 B2 9/2015 Aronhalt et al.
9,125,662 B2 9/2015 Shelton, IV
9,126,317 B2 9/2015 Lawton et al.
9,131,835 B2 9/2015 Widenhouse et al.
9,131,940 B2 9/2015 Huitema et al.
9,131,950 B2 9/2015 Matthew
9,131,957 B2 9/2015 Skarbnik et al.
9,138,225 B2 9/2015 Huang et al.
9,138,226 B2 9/2015 Racenet et al.
9,144,455 B2 9/2015 Kennedy et al.
D740,414 S 10/2015 Katsura
D741,882 S 10/2015 Shmilov et al.
9,149,274 B2 10/2015 Spivey et al.
9,149,324 B2 10/2015 Huang et al.
9,149,325 B2 10/2015 Worrell et al.
9,153,994 B2 10/2015 Wood et al.
9,154,189 B2 10/2015 Von Novak et al.
9,161,753 B2 10/2015 Prior
9,161,769 B2 10/2015 Stoddard et al.
9,161,803 B2 10/2015 Yates et al.
9,161,807 B2 10/2015 Garrison
9,161,855 B2 10/2015 Rousseau et al.
9,164,271 B2 10/2015 Ebata et al.
9,167,960 B2 10/2015 Yamaguchi et al.
9,168,038 B2 10/2015 Shelton, IV et al.
9,168,039 B1 10/2015 Knodel
9,168,042 B2 10/2015 Milliman
9,168,054 B2 10/2015 Turner et al.
9,168,144 B2 10/2015 Rivin et al.
9,171,244 B2 10/2015 Endou et al.
9,179,832 B2 11/2015 Diolaiti
9,179,911 B2 11/2015 Morgan et al.
9,179,912 B2 11/2015 Yates et al.
9,180,223 B2 11/2015 Yu et al.
9,182,244 B2 11/2015 Luke et al.
9,186,046 B2 11/2015 Ramamurthy et al.
9,186,137 B2 11/2015 Farascioni et al.
9,186,140 B2 11/2015 Hiles et al.
9,186,142 B2 11/2015 Fanelli et al.
9,186,143 B2 11/2015 Timm et al.
9,186,148 B2 11/2015 Felder et al.
9,186,221 B2 11/2015 Burbank
9,192,376 B2 11/2015 Almodovar
9,192,380 B2 11/2015 (Tarinelli) Racenet et al.
9,192,384 B2 11/2015 Bettuchi
9,192,430 B2 11/2015 Rachlin et al.
9,192,434 B2 11/2015 Twomey et al.
9,193,045 B2 11/2015 Saur et al.
9,197,079 B2 11/2015 Yip et al.
D744,528 S 12/2015 Agrawal
D746,459 S 12/2015 Kaercher et al.
9,198,642 B2 12/2015 Storz
9,198,644 B2 12/2015 Balek et al.
9,198,661 B2 12/2015 Swensgard
9,198,662 B2 12/2015 Barton et al.
9,198,683 B2 12/2015 Friedman et al.
9,204,830 B2 12/2015 Zand et al.
9,204,877 B2 12/2015 Whitman et al.
9,204,878 B2 12/2015 Hall et al.
9,204,879 B2 12/2015 Shelton, IV
9,204,880 B2 12/2015 Baxter, III et al.
9,204,881 B2 12/2015 Penna
9,204,923 B2 12/2015 Manzo et al.
9,204,924 B2 12/2015 Marczyk et al.
9,211,120 B2 12/2015 Scheib et al.
9,211,121 B2 12/2015 Hall et al.
9,211,122 B2 12/2015 Hagerty et al.
9,216,013 B2 12/2015 Scirica et al.
9,216,019 B2 12/2015 Schmid et al.
9,216,020 B2 12/2015 Zhang et al.
9,216,030 B2 12/2015 Fan et al.
9,216,062 B2 12/2015 Duque et al.
9,220,500 B2 12/2015 Swayze et al.
9,220,501 B2 12/2015 Baxter, III et al.
9,220,502 B2 12/2015 Zemlok et al.
9,220,504 B2 12/2015 Viola et al.
9,220,508 B2 12/2015 Dannaher
9,220,559 B2 12/2015 Worrell et al.
9,220,570 B2 12/2015 Kim et al.
D746,854 S 1/2016 Shardlow et al.
9,226,686 B2 1/2016 Blair
9,226,750 B2 1/2016 Weir et al.
9,226,751 B2 1/2016 Shelton, IV et al.
9,226,754 B2 1/2016 D'Agostino et al.
9,226,760 B2 1/2016 Shelton, IV
9,226,761 B2 1/2016 Burbank
9,226,767 B2 1/2016 Stulen et al.
9,226,799 B2 1/2016 Lightcap et al.
9,232,941 B2 1/2016 Mandakolathur Vasudevan et al.
9,232,945 B2 1/2016 Zingman
9,232,979 B2 1/2016 Parihar et al.
9,233,610 B2 1/2016 Kim et al.
9,237,891 B2 1/2016 Shelton, IV
9,237,892 B2 1/2016 Hodgkinson
9,237,895 B2 1/2016 McCarthy et al.
9,237,900 B2 1/2016 Boudreaux et al.
9,237,921 B2 1/2016 Messerly et al.
9,239,064 B2 1/2016 Helbig et al.
9,240,740 B2 1/2016 Zeng et al.
9,241,711 B2 1/2016 Ivanko
9,241,712 B2 1/2016 Zemlok et al.
9,241,714 B2 1/2016 Timm et al.
9,241,716 B2 1/2016 Whitman
9,241,731 B2 1/2016 Boudreaux et al.
9,241,758 B2 1/2016 Franer et al.
9,244,524 B2 1/2016 Inoue et al.
D748,668 S 2/2016 Kim et al.
D749,128 S 2/2016 Perez et al.
D749,623 S 2/2016 Gray et al.
D750,122 S 2/2016 Shardlow et al.
D750,129 S 2/2016 Kwon
9,254,131 B2 2/2016 Soltz et al.
9,254,170 B2 2/2016 Parihar et al.
9,259,265 B2 2/2016 Harris et al.
9,259,268 B2 2/2016 Behnke, II et al.
9,259,274 B2 2/2016 Prisco
9,259,275 B2 2/2016 Burbank
9,261,172 B2 2/2016 Solomon et al.
9,265,500 B2 2/2016 Sorrentino et al.
9,265,510 B2 2/2016 Dietzel et al.
9,265,516 B2 2/2016 Casey et al.
9,265,585 B2 2/2016 Wingardner et al.
9,271,718 B2 3/2016 Milad et al.
9,271,727 B2 3/2016 McGuckin, Jr. et al.
9,271,753 B2 3/2016 Butler et al.
9,271,799 B2 3/2016 Shelton, IV et al.
9,272,406 B2 3/2016 Aronhalt et al.
9,274,095 B2 3/2016 Humayun et al.
9,277,919 B2 3/2016 Timmer et al.
9,277,922 B2 3/2016 Carter et al.
9,277,969 B2 3/2016 Brannan et al.
9,282,962 B2 3/2016 Schmid et al.
9,282,963 B2 3/2016 Bryant
9,282,966 B2 3/2016 Shelton, IV et al.
9,282,974 B2 3/2016 Shelton, IV
9,283,028 B2 3/2016 Johnson
9,283,045 B2 3/2016 Rhee et al.
9,283,054 B2 3/2016 Morgan et al.
9,283,334 B2 3/2016 Mantell et al.
9,289,206 B2 3/2016 Hess et al.
9,289,207 B2 3/2016 Shelton, IV
9,289,210 B2 3/2016 Baxter, III et al.
9,289,211 B2 3/2016 Williams et al.
9,289,212 B2 3/2016 Shelton, IV et al.
9,289,225 B2 3/2016 Shelton, IV et al.
9,289,256 B2 3/2016 Shelton, IV et al.
9,293,757 B2 3/2016 Toussaint et al.
9,295,464 B2 3/2016 Shelton, IV et al.
9,295,465 B2 3/2016 Farascioni

(56) References Cited

U.S. PATENT DOCUMENTS 9,295,466 B2 3/2016 Hodgkinson et al.
9,295,467 B2 3/2016 Scirica
9,295,468 B2 3/2016 Heinrich et al.
9,295,514 B2 3/2016 Shelton, IV et al.
9,295,522 B2 3/2016 Kostrzewski
9,295,565 B2 3/2016 McLean
9,295,784 B2 3/2016 Eggert et al.
D753,167 S 4/2016 Yu et al.
9,301,691 B2 4/2016 Hufnagel et al.
9,301,752 B2 4/2016 Mandakolathur Vasudevan et al.
9,301,753 B2 4/2016 Aldridge et al.
9,301,755 B2 4/2016 Shelton, IV et al.
9,301,759 B2 4/2016 Spivey et al.
9,301,811 B2 4/2016 Goldberg et al.
9,307,965 B2 4/2016 Ming et al.
9,307,986 B2 4/2016 Hall et al.
9,307,987 B2 4/2016 Swensgard et al.
9,307,988 B2 4/2016 Shelton, IV
9,307,989 B2 4/2016 Shelton, IV et al.
9,307,994 B2 4/2016 Gresham et al.
9,308,009 B2 4/2016 Madan et al.
9,308,011 B2 4/2016 Chao et al.
9,308,646 B2 4/2016 Lim et al.
9,313,915 B2 4/2016 Niu et al.
9,314,246 B2 4/2016 Shelton, IV et al.
9,314,247 B2 4/2016 Shelton, IV et al.
9,314,261 B2 4/2016 Bales, Jr. et al.
9,314,291 B2 4/2016 Schall et al.
9,314,339 B2 4/2016 Mansmann
9,314,908 B2 4/2016 Tanimoto et al.
9,320,518 B2 4/2016 Henderson et al.
9,320,520 B2 4/2016 Shelton, IV et al.
9,320,521 B2 4/2016 Shelton, IV et al.
9,320,523 B2 4/2016 Shelton, IV et al.
9,325,516 B2 4/2016 Pera et al.
D755,196 S 5/2016 Meyers et al.
D756,373 S 5/2016 Raskin et al.
D756,377 S 5/2016 Connolly et al.
D757,028 S 5/2016 Goldenberg et al.
9,326,767 B2 5/2016 Koch, Jr. et al.
9,326,768 B2 5/2016 Shelton, IV
9,326,769 B2 5/2016 Shelton, IV et al.
9,326,770 B2 5/2016 Shelton, IV et al.
9,326,771 B2 5/2016 Baxter, III et al.
9,326,773 B2 5/2016 Casasanta, Jr. et al.
9,326,788 B2 5/2016 Batross et al.
9,326,812 B2 5/2016 Waaler et al.
9,326,824 B2 5/2016 Inoue et al.
9,327,061 B2 5/2016 Govil et al.
9,331,721 B2 5/2016 Martinez Nuevo et al.
9,332,890 B2 5/2016 Ozawa
9,332,974 B2 5/2016 Henderson et al.
9,332,984 B2 5/2016 Weaner et al.
9,332,987 B2 5/2016 Leimbach et al.
9,333,040 B2 5/2016 Shellenberger et al.
9,333,082 B2 5/2016 Wei et al.
9,337,668 B2 5/2016 Yip
9,339,226 B2 5/2016 van der Walt et al.
9,339,342 B2 5/2016 Prisco et al.
9,345,477 B2 5/2016 Anim et al.
9,345,479 B2 5/2016 (Tarinelli) Racenet et al.
9,345,480 B2 5/2016 Hessler et al.
9,345,481 B2 5/2016 Hall et al.
9,345,503 B2 5/2016 Ishida et al.
9,351,726 B2 5/2016 Leimbach et al.
9,351,727 B2 5/2016 Leimbach et al.
9,351,728 B2 5/2016 Sniffin et al.
9,351,730 B2 5/2016 Schmid et al.
9,351,731 B2 5/2016 Carter et al.
9,351,732 B2 5/2016 Hodgkinson
9,352,071 B2 5/2016 Landgrebe et al.
D758,433 S 6/2016 Lee et al.
D759,063 S 6/2016 Chen
9,358,003 B2 6/2016 Hall et al.
9,358,004 B2 6/2016 Sniffin et al.
9,358,005 B2 6/2016 Shelton, IV et al.
9,358,015 B2 6/2016 Sorrentino et al.
9,358,031 B2 6/2016 Manzo
9,358,065 B2 6/2016 Ladtkow et al.
9,364,217 B2 6/2016 Kostrzewski et al.
9,364,219 B2 6/2016 Olson et al.
9,364,220 B2 6/2016 Williams
9,364,223 B2 6/2016 Scirica
9,364,226 B2 6/2016 Zemlok et al.
9,364,228 B2 6/2016 Straehnz et al.
9,364,229 B2 6/2016 D'Agostino et al.
9,364,230 B2 6/2016 Shelton, IV et al.
9,364,231 B2 6/2016 Wenchell
9,364,233 B2 6/2016 Alexander, III et al.
9,364,279 B2 6/2016 Houser et al.
9,368,991 B2 6/2016 Qahouq
9,370,341 B2 6/2016 Ceniccola et al.
9,370,358 B2 6/2016 Shelton, IV et al.
9,370,361 B2 6/2016 Viola et al.
9,370,362 B2 6/2016 Petty et al.
9,370,364 B2 6/2016 Smith et al.
9,370,400 B2 6/2016 Parihar
9,375,206 B2 6/2016 Vidal et al.
9,375,218 B2 6/2016 Wheeler et al.
9,375,230 B2 6/2016 Ross et al.
9,375,232 B2 6/2016 Hunt et al.
9,375,255 B2 6/2016 Houser et al.
D761,309 S 7/2016 Lee et al.
9,381,058 B2 7/2016 Houser et al.
9,383,881 B2 7/2016 Day et al.
9,385,640 B2 7/2016 Sun et al.
9,386,983 B2 7/2016 Swensgard et al.
9,386,984 B2 7/2016 Aronhalt et al.
9,386,985 B2 7/2016 Koch, Jr. et al.
9,386,988 B2 7/2016 Baxter, III et al.
9,387,003 B2 7/2016 Kaercher et al.
9,392,885 B2 7/2016 Vogler et al.
9,393,015 B2 7/2016 Laurent et al.
9,393,017 B2 7/2016 Flanagan et al.
9,393,018 B2 7/2016 Wang et al.
9,393,354 B2 7/2016 Freedman et al.
9,396,369 B1 7/2016 Whitehurst et al.
9,396,669 B2 7/2016 Karkanias et al.
9,398,905 B2 7/2016 Martin
9,398,911 B2 7/2016 Auld
D763,277 S 8/2016 Ahmed et al.
D764,498 S 8/2016 Capela et al.
9,402,604 B2 8/2016 Williams et al.
9,402,625 B2 8/2016 Coleman et al.
9,402,626 B2 8/2016 Ortiz et al.
9,402,627 B2 8/2016 Stevenson et al.
9,402,629 B2 8/2016 Ehrenfels et al.
9,402,679 B2 8/2016 Ginnebaugh et al.
9,402,682 B2 8/2016 Worrell et al.
9,402,688 B2 8/2016 Min et al.
9,408,604 B2 8/2016 Shelton, IV et al.
9,408,605 B1 8/2016 Knodel et al.
9,408,606 B2 8/2016 Shelton, IV
9,408,622 B2 8/2016 Stulen et al.
9,408,668 B2 8/2016 Durant et al.
9,411,370 B2 8/2016 Benni et al.
9,413,128 B2 8/2016 Tien et al.
9,414,838 B2 8/2016 Shelton, IV et al.
9,414,849 B2 8/2016 Nagashimada
9,414,880 B2 8/2016 Monson et al.
9,420,967 B2 8/2016 Zand et al.
9,421,003 B2 8/2016 Williams et al.
9,421,014 B2 8/2016 Ingmanson et al.
9,421,030 B2 8/2016 Cole et al.
9,421,060 B2 8/2016 Monson et al.
9,421,062 B2 8/2016 Houser et al.
9,421,682 B2 8/2016 McClaskey et al.
9,427,223 B2 8/2016 Park et al.
9,427,231 B2 8/2016 Racenet et al.
9,429,204 B2 8/2016 Stefan et al.
D767,624 S 9/2016 Lee et al.
9,433,411 B2 9/2016 Racenet et al.
9,433,414 B2 9/2016 Chen et al.
9,433,418 B2 9/2016 Whitman et al.

(56) References Cited

U.S. PATENT DOCUMENTS 9,433,419 B2 9/2016 Gonzalez et al.
9,433,420 B2 9/2016 Hodgkinson
9,439,649 B2 9/2016 Shelton, IV et al.
9,439,650 B2 9/2016 McGuckin, Jr. et al.
9,439,651 B2 9/2016 Smith et al.
9,439,668 B2 9/2016 Timm et al.
9,445,808 B2 9/2016 Woodard, Jr. et al.
9,445,813 B2 9/2016 Shelton, IV et al.
9,445,816 B2 9/2016 Swayze et al.
9,445,817 B2 9/2016 Bettuchi
9,446,226 B2 9/2016 Zilberman
9,451,938 B2 9/2016 Overes et al.
9,451,958 B2 9/2016 Shelton, IV et al.
9,452,020 B2 9/2016 Griffiths et al.
D768,152 S 10/2016 Gutierrez et al.
D768,156 S 10/2016 Frincke
D768,167 S 10/2016 Jones et al.
D769,315 S 10/2016 Scotti
D769,930 S 10/2016 Agrawal
9,461,340 B2 10/2016 Li et al.
9,463,012 B2 10/2016 Bonutti et al.
9,463,040 B2 10/2016 Jeong et al.
9,463,260 B2 10/2016 Stopek
9,468,438 B2 10/2016 Baber et al.
9,468,447 B2 10/2016 Aman et al.
9,470,297 B2 10/2016 Aranyi et al.
9,471,969 B2 10/2016 Zeng et al.
9,474,506 B2 10/2016 Magnin et al.
9,474,513 B2 10/2016 Ishida et al.
9,474,523 B2 10/2016 Meade et al.
9,474,528 B2 10/2016 Marczyk
9,474,540 B2 10/2016 Stokes et al.
9,474,581 B2 10/2016 Niemeyer
9,475,180 B2 10/2016 Eshleman et al.
9,477,649 B1 10/2016 Davidson et al.
D770,476 S 11/2016 Jitkoff et al.
D770,515 S 11/2016 Cho et al.
D771,116 S 11/2016 Dellinger et al.
D772,905 S 11/2016 Ingenlath
9,480,476 B2 11/2016 Aldridge et al.
9,480,492 B2 11/2016 Aranyi et al.
9,483,095 B2 11/2016 Tran et al.
9,486,186 B2 11/2016 Fiebig et al.
9,486,213 B2 11/2016 Altman et al.
9,486,214 B2 11/2016 Shelton, IV
9,486,215 B2 11/2016 Olson et al.
9,486,302 B2 11/2016 Boey et al.
9,488,197 B2 11/2016 Wi
9,492,146 B2 11/2016 Kostrzewski et al.
9,492,167 B2 11/2016 Shelton, IV et al.
9,492,170 B2 11/2016 Bear et al.
9,492,172 B2 11/2016 Weisshaupt et al.
9,492,189 B2 11/2016 Williams et al.
9,492,192 B2 11/2016 To et al.
9,492,237 B2 11/2016 Kang et al.
9,498,213 B2 11/2016 Marczyk et al.
9,498,219 B2 11/2016 Moore et al.
9,498,231 B2 11/2016 Haider et al.
9,504,455 B2 11/2016 Whitman et al.
9,504,483 B2 11/2016 Houser et al.
9,504,520 B2 11/2016 Worrell et al.
9,504,521 B2 11/2016 Deutmeyer et al.
9,504,528 B2 11/2016 Ivinson et al.
9,507,399 B2 11/2016 Chien
D774,547 S 12/2016 Capela et al.
D775,336 S 12/2016 Shelton, IV et al.
9,510,827 B2 12/2016 Kostrzewski
9,510,828 B2 12/2016 Yates et al.
9,510,830 B2 12/2016 Shelton, IV et al.
9,510,846 B2 12/2016 Sholev et al.
9,510,895 B2 12/2016 Houser et al.
9,510,925 B2 12/2016 Hotter et al.
9,515,366 B2 12/2016 Herbsommer et al.
9,517,063 B2 12/2016 Swayze et al.
9,517,065 B2 12/2016 Simms et al.
9,517,068 B2 12/2016 Shelton, IV et al.
9,517,326 B2 12/2016 Hinman et al.
9,519,341 B2 12/2016 Hasegawa et al.
9,521,996 B2 12/2016 Armstrong
9,522,003 B2 12/2016 Weir et al.
9,522,005 B2 12/2016 Williams et al.
9,522,014 B2 12/2016 Nishizawa et al.
9,522,029 B2 12/2016 Yates et al.
9,526,481 B2 12/2016 Storz et al.
9,526,499 B2 12/2016 Kostrzewski et al.
9,526,563 B2 12/2016 Twomey
9,526,564 B2 12/2016 Rusin
9,526,921 B2 12/2016 Kimball et al.
D776,683 S 1/2017 Gobinski et al.
D777,773 S 1/2017 Shi
9,532,783 B2 1/2017 Swayze et al.
9,539,060 B2 1/2017 Lightcap et al.
9,539,726 B2 1/2017 Simaan et al.
9,545,253 B2 1/2017 Worrell et al.
9,545,258 B2 1/2017 Smith et al.
9,549,732 B2 1/2017 Yates et al.
9,549,733 B2 1/2017 Knodel
9,549,735 B2 1/2017 Shelton, IV et al.
9,549,750 B2 1/2017 Shelton, IV et al.
9,554,794 B2 1/2017 Baber et al.
9,554,796 B2 1/2017 Kostrzewski
9,554,803 B2 1/2017 Smith et al.
9,554,812 B2 1/2017 Inkpen et al.
9,554,854 B2 1/2017 Yates et al.
9,559,624 B2 1/2017 Philipp
9,561,013 B2 2/2017 Tsuchiya
9,561,029 B2 2/2017 Scheib et al.
9,561,030 B2 2/2017 Zhang et al.
9,561,031 B2 2/2017 Heinrich et al.
9,561,032 B2 2/2017 Shelton, IV et al.
9,561,038 B2 2/2017 Shelton, IV et al.
9,561,045 B2 2/2017 Hinman et al.
9,561,072 B2 2/2017 Ko
9,561,082 B2 2/2017 Yen et al.
9,566,061 B2 2/2017 Aronhalt et al.
9,566,062 B2 2/2017 Boudreaux
9,566,064 B2 2/2017 Williams et al.
9,566,065 B2 2/2017 Knodel
9,566,067 B2 2/2017 Milliman et al.
9,566,124 B2 2/2017 Prisco et al.
9,572,552 B1 2/2017 Bodor et al.
9,572,574 B2 2/2017 Shelton, IV et al.
9,572,576 B2 2/2017 Hodgkinson et al.
9,572,577 B2 2/2017 Lloyd et al.
9,572,592 B2 2/2017 Price et al.
9,574,644 B2 2/2017 Parihar
9,579,039 B2 2/2017 Jansen et al.
9,579,088 B2 2/2017 Farritor et al.
9,579,143 B2 2/2017 Ullrich et al.
9,579,158 B2 2/2017 Brianza et al.
D780,803 S 3/2017 Gill et al.
D781,879 S 3/2017 Butcher et al.
D782,530 S 3/2017 Paek et al.
9,585,550 B2 3/2017 Abel et al.
9,585,657 B2 3/2017 Shelton, IV et al.
9,585,658 B2 3/2017 Shelton, IV
9,585,659 B2 3/2017 Viola et al.
9,585,660 B2 3/2017 Laurent et al.
9,585,662 B2 3/2017 Shelton, IV et al.
9,585,663 B2 3/2017 Shelton, IV et al.
9,585,672 B2 3/2017 Bastia
9,590,433 B2 3/2017 Li
9,592,050 B2 3/2017 Schmid et al.
9,592,052 B2 3/2017 Shelton, IV
9,592,053 B2 3/2017 Shelton, IV et al.
9,592,054 B2 3/2017 Schmid et al.
9,597,073 B2 3/2017 Sorrentino et al.
9,597,075 B2 3/2017 Shelton, IV et al.
9,597,078 B2 3/2017 Scirica et al.
9,597,080 B2 3/2017 Milliman et al.
9,597,104 B2 3/2017 Nicholas et al.
9,597,143 B2 3/2017 Madan et al.
9,603,595 B2 3/2017 Shelton, IV et al.
9,603,598 B2 3/2017 Shelton, IV et al.

(56) References Cited

U.S. PATENT DOCUMENTS

| | | | |
|---|---|---|---|
| 9,603,599 | B2 | 3/2017 | Miller et al. |
| 9,603,991 | B2 | 3/2017 | Shelton, IV et al. |
| D783,658 | S | 4/2017 | Hurst et al. |
| 9,610,068 | B2 | 4/2017 | Kappel et al. |
| 9,610,079 | B2 | 4/2017 | Kamei et al. |
| 9,610,080 | B2 | 4/2017 | Whitfield et al. |
| 9,610,412 | B2 | 4/2017 | Zemlok et al. |
| 9,614,258 | B2 | 4/2017 | Takahashi et al. |
| 9,615,826 | B2 | 4/2017 | Shelton, IV et al. |
| 9,622,745 | B2 | 4/2017 | Ingmanson et al. |
| 9,622,746 | B2 | 4/2017 | Simms et al. |
| 9,629,623 | B2 | 4/2017 | Lytle, IV et al. |
| 9,629,626 | B2 | 4/2017 | Soltz et al. |
| 9,629,627 | B2 | 4/2017 | Kostrzewski et al. |
| 9,629,628 | B2 | 4/2017 | Aranyi |
| 9,629,629 | B2 | 4/2017 | Leimbach et al. |
| 9,629,631 | B2 | 4/2017 | Nicholas et al. |
| 9,629,632 | B2 | 4/2017 | Linder et al. |
| 9,629,652 | B2 | 4/2017 | Mumaw et al. |
| 9,629,814 | B2 | 4/2017 | Widenhouse et al. |
| D785,794 | S | 5/2017 | Magno, Jr. |
| D786,280 | S | 5/2017 | Ma |
| D786,896 | S | 5/2017 | Kim et al. |
| D787,547 | S | 5/2017 | Basargin et al. |
| D788,123 | S | 5/2017 | Shan et al. |
| D788,140 | S | 5/2017 | Hemsley et al. |
| 9,636,091 | B2 | 5/2017 | Beardsley et al. |
| 9,636,111 | B2 | 5/2017 | Wenchell |
| 9,636,112 | B2 | 5/2017 | Penna et al. |
| 9,636,113 | B2 | 5/2017 | Wenchell |
| 9,636,850 | B2 | 5/2017 | Stopek et al. |
| 9,641,122 | B2 | 5/2017 | Romanowich et al. |
| 9,642,620 | B2 | 5/2017 | Baxter, III et al. |
| 9,642,642 | B2 | 5/2017 | Lim |
| 9,649,096 | B2 | 5/2017 | Sholev |
| 9,649,110 | B2 | 5/2017 | Parihar et al. |
| 9,649,111 | B2 | 5/2017 | Shelton, IV et al. |
| 9,649,190 | B2 | 5/2017 | Mathies |
| 9,651,032 | B2 | 5/2017 | Weaver et al. |
| 9,655,613 | B2 | 5/2017 | Schaller |
| 9,655,614 | B2 | 5/2017 | Swensgard et al. |
| 9,655,615 | B2 | 5/2017 | Knodel et al. |
| 9,655,616 | B2 | 5/2017 | Aranyi |
| 9,655,624 | B2 | 5/2017 | Shelton, IV et al. |
| 9,661,991 | B2 | 5/2017 | Glossop |
| 9,662,108 | B2 | 5/2017 | Williams |
| 9,662,110 | B2 | 5/2017 | Huang et al. |
| 9,662,111 | B2 | 5/2017 | Holsten et al. |
| 9,662,116 | B2 | 5/2017 | Smith et al. |
| 9,662,130 | B2 | 5/2017 | Bartels et al. |
| 9,662,131 | B2 | 5/2017 | Omori et al. |
| D788,792 | S | 6/2017 | Alessandri et al. |
| D789,384 | S | 6/2017 | Lin et al. |
| D790,570 | S | 6/2017 | Butcher et al. |
| 9,668,728 | B2 | 6/2017 | Williams et al. |
| 9,668,729 | B2 | 6/2017 | Williams et al. |
| 9,668,732 | B2 | 6/2017 | Patel et al. |
| 9,668,733 | B2 | 6/2017 | Williams |
| 9,668,734 | B2 | 6/2017 | Kostrzewski et al. |
| 9,668,735 | B2 | 6/2017 | Beetel |
| 9,675,344 | B2 | 6/2017 | Combrowski et al. |
| 9,675,348 | B2 | 6/2017 | Smith et al. |
| 9,675,351 | B2 | 6/2017 | Hodgkinson et al. |
| 9,675,354 | B2 | 6/2017 | Weir et al. |
| 9,675,355 | B2 | 6/2017 | Shelton, IV et al. |
| 9,675,368 | B2 | 6/2017 | Guo et al. |
| 9,675,372 | B2 | 6/2017 | Laurent et al. |
| 9,675,375 | B2 | 6/2017 | Houser et al. |
| 9,675,405 | B2 | 6/2017 | Trees et al. |
| 9,675,819 | B2 | 6/2017 | Dunbar et al. |
| 9,681,870 | B2 | 6/2017 | Baxter, III et al. |
| 9,681,873 | B2 | 6/2017 | Smith et al. |
| 9,681,884 | B2 | 6/2017 | Clem et al. |
| 9,687,230 | B2 | 6/2017 | Leimbach et al. |
| 9,687,231 | B2 | 6/2017 | Baxter, III et al. |
| 9,687,232 | B2 | 6/2017 | Shelton, IV et al. |
| 9,687,233 | B2 | 6/2017 | Fernandez et al. |
| 9,687,236 | B2 | 6/2017 | Leimbach et al. |
| 9,687,237 | B2 | 6/2017 | Schmid et al. |
| 9,687,253 | B2 | 6/2017 | Detry et al. |
| 9,689,466 | B2 | 6/2017 | Kanai et al. |
| 9,690,362 | B2 | 6/2017 | Leimbach et al. |
| 9,693,772 | B2 | 7/2017 | Ingmanson et al. |
| 9,693,774 | B2 | 7/2017 | Gettinger et al. |
| 9,693,775 | B2 | 7/2017 | Agarwal et al. |
| 9,693,777 | B2 | 7/2017 | Schellin et al. |
| 9,700,309 | B2 | 7/2017 | Jaworek et al. |
| 9,700,310 | B2 | 7/2017 | Morgan et al. |
| 9,700,312 | B2 | 7/2017 | Kostrzewski et al. |
| 9,700,314 | B2 | 7/2017 | Marczyk |
| 9,700,315 | B2 | 7/2017 | Chen et al. |
| 9,700,317 | B2 | 7/2017 | Aronhalt et al. |
| 9,700,318 | B2 | 7/2017 | Scirica et al. |
| 9,700,319 | B2 | 7/2017 | Motooka et al. |
| 9,700,320 | B2 | 7/2017 | Dinardo et al. |
| 9,700,321 | B2 | 7/2017 | Shelton, IV et al. |
| 9,700,334 | B2 | 7/2017 | Hinman et al. |
| 9,700,381 | B2 | 7/2017 | Amat Girbau |
| 9,702,823 | B2 | 7/2017 | Maher et al. |
| 9,706,674 | B2 | 7/2017 | Collins et al. |
| 9,706,981 | B2 | 7/2017 | Nicholas et al. |
| 9,706,991 | B2 | 7/2017 | Hess et al. |
| 9,706,993 | B2 | 7/2017 | Hessler et al. |
| 9,707,003 | B2 | 7/2017 | Hoell, Jr. et al. |
| 9,707,005 | B2 | 7/2017 | Strobl et al. |
| 9,707,026 | B2 | 7/2017 | Malackowski et al. |
| 9,707,033 | B2 | 7/2017 | Parihar et al. |
| 9,707,043 | B2 | 7/2017 | Bozung |
| 9,707,684 | B2 | 7/2017 | Ruiz Morales et al. |
| 9,713,466 | B2 | 7/2017 | Kostrzewski |
| 9,713,468 | B2 | 7/2017 | Harris et al. |
| 9,713,470 | B2 | 7/2017 | Scirica et al. |
| 9,713,474 | B2 | 7/2017 | Lorenz |
| D795,919 | S | 8/2017 | Bischoff et al. |
| 9,717,497 | B2 | 8/2017 | Zerkle et al. |
| 9,717,498 | B2 | 8/2017 | Aranyi et al. |
| 9,718,190 | B2 | 8/2017 | Larkin et al. |
| 9,722,236 | B2 | 8/2017 | Sathrum |
| 9,724,091 | B2 | 8/2017 | Shelton, IV et al. |
| 9,724,092 | B2 | 8/2017 | Baxter, III et al. |
| 9,724,094 | B2 | 8/2017 | Baber et al. |
| 9,724,095 | B2 | 8/2017 | Gupta et al. |
| 9,724,096 | B2 | 8/2017 | Thompson et al. |
| 9,724,098 | B2 | 8/2017 | Baxter, III et al. |
| 9,724,118 | B2 | 8/2017 | Schulte et al. |
| 9,724,163 | B2 | 8/2017 | Orban |
| 9,730,692 | B2 | 8/2017 | Shelton, IV et al. |
| 9,730,695 | B2 | 8/2017 | Leimbach et al. |
| 9,730,697 | B2 | 8/2017 | Morgan et al. |
| 9,730,717 | B2 | 8/2017 | Katsuki et al. |
| 9,730,757 | B2 | 8/2017 | Brudniok |
| 9,731,410 | B2 | 8/2017 | Hirabayashi et al. |
| 9,733,663 | B2 | 8/2017 | Leimbach et al. |
| 9,737,297 | B2 | 8/2017 | Racenet et al. |
| 9,737,298 | B2 | 8/2017 | Isbell, Jr. |
| 9,737,299 | B2 | 8/2017 | Yan |
| 9,737,301 | B2 | 8/2017 | Baber et al. |
| 9,737,302 | B2 | 8/2017 | Shelton, IV et al. |
| 9,737,303 | B2 | 8/2017 | Shelton, IV et al. |
| 9,737,323 | B2 | 8/2017 | Thapliyal et al. |
| 9,737,365 | B2 | 8/2017 | Hegeman et al. |
| 9,743,927 | B2 | 8/2017 | Whitman |
| 9,743,928 | B2 | 8/2017 | Shelton, IV et al. |
| 9,743,929 | B2 | 8/2017 | Leimbach et al. |
| D798,319 | S | 9/2017 | Bergstrand et al. |
| 9,750,498 | B2 | 9/2017 | Timm et al. |
| 9,750,499 | B2 | 9/2017 | Leimbach et al. |
| 9,750,501 | B2 | 9/2017 | Shelton, IV et al. |
| 9,750,502 | B2 | 9/2017 | Scirica et al. |
| 9,750,503 | B2 | 9/2017 | Milliman |
| 9,750,639 | B2 | 9/2017 | Barnes et al. |
| 9,751,176 | B2 | 9/2017 | McRoberts et al. |
| 9,757,123 | B2 | 9/2017 | Giordano et al. |
| 9,757,124 | B2 | 9/2017 | Schellin et al. |

(56) References Cited

U.S. PATENT DOCUMENTS 9,757,126 B2 9/2017 Cappola
9,757,128 B2 9/2017 Baber et al.
9,757,129 B2 9/2017 Williams
9,757,130 B2 9/2017 Shelton, IV
9,763,662 B2 9/2017 Shelton, IV et al.
9,763,668 B2 9/2017 Whitfield et al.
9,770,245 B2 9/2017 Swayze et al.
9,770,274 B2 9/2017 Pool et al.
D798,886 S 10/2017 Prophete et al.
D800,742 S 10/2017 Rhodes
D800,744 S 10/2017 Jitkoff et al.
D800,766 S 10/2017 Park et al.
D800,904 S 10/2017 Leimbach et al.
9,775,608 B2 10/2017 Aronhalt et al.
9,775,609 B2 10/2017 Shelton, IV et al.
9,775,610 B2 10/2017 Nicholas et al.
9,775,611 B2 10/2017 Kostrzewski
9,775,613 B2 10/2017 Shelton, IV et al.
9,775,614 B2 10/2017 Shelton, IV et al.
9,775,618 B2 10/2017 Bettuchi et al.
9,775,635 B2 10/2017 Takei
9,775,678 B2 10/2017 Lohmeier
9,782,169 B2 10/2017 Kimsey et al.
9,782,170 B2 10/2017 Zemlok et al.
9,782,180 B2 10/2017 Smith et al.
9,782,187 B2 10/2017 Zergiebel et al.
9,782,193 B2 10/2017 Thistle
9,782,214 B2 10/2017 Houser et al.
9,788,834 B2 10/2017 Schmid et al.
9,788,835 B2 10/2017 Morgan et al.
9,788,836 B2 10/2017 Overmyer et al.
9,788,847 B2 10/2017 Jinno
9,788,851 B2 10/2017 Dannaher et al.
9,788,902 B2 10/2017 Inoue et al.
9,795,379 B2 10/2017 Leimbach et al.
9,795,380 B2 10/2017 Shelton, IV et al.
9,795,381 B2 10/2017 Shelton, IV
9,795,382 B2 10/2017 Shelton, IV
9,795,383 B2 10/2017 Aldridge et al.
9,795,384 B2 10/2017 Weaner et al.
9,797,486 B2 10/2017 Zergiebel et al.
9,801,626 B2 10/2017 Parihar et al.
9,801,627 B2 10/2017 Harris et al.
9,801,628 B2 10/2017 Harris et al.
9,801,634 B2 10/2017 Shelton, IV et al.
9,801,679 B2 10/2017 Trees et al.
9,802,033 B2 10/2017 Hibner et al.
9,804,618 B2 10/2017 Leimbach et al.
D803,234 S 11/2017 Day et al.
D803,235 S 11/2017 Markson et al.
D803,850 S 11/2017 Chang et al.
9,808,244 B2 11/2017 Leimbach et al.
9,808,246 B2 11/2017 Shelton, IV et al.
9,808,247 B2 11/2017 Shelton, IV et al.
9,808,248 B2 11/2017 Hoffman
9,808,249 B2 11/2017 Shelton, IV
9,814,460 B2 11/2017 Kimsey et al.
9,814,462 B2 11/2017 Woodard, Jr. et al.
9,814,463 B2 11/2017 Williams et al.
9,814,530 B2 11/2017 Weir et al.
9,814,561 B2 11/2017 Forsell
9,815,118 B1 11/2017 Schmitt et al.
9,820,445 B2 11/2017 Simpson et al.
9,820,737 B2 11/2017 Beardsley et al.
9,820,738 B2 11/2017 Lytle, IV et al.
9,820,741 B2 11/2017 Kostrzewski
9,820,768 B2 11/2017 Gee et al.
9,825,455 B2 11/2017 Sandhu et al.
9,826,976 B2 11/2017 Parihar et al.
9,826,977 B2 11/2017 Leimbach et al.
9,826,978 B2 11/2017 Shelton, IV et al.
9,829,698 B2 11/2017 Haraguchi et al.
D806,108 S 12/2017 Day
9,833,235 B2 12/2017 Penna et al.
9,833,236 B2 12/2017 Shelton, IV et al.
9,833,238 B2 12/2017 Baxter, III et al.
9,833,239 B2 12/2017 Yates et al.
9,833,241 B2 12/2017 Huitema et al.
9,833,242 B2 12/2017 Baxter, III et al.
9,839,420 B2 12/2017 Shelton, IV et al.
9,839,421 B2 12/2017 Zerkle et al.
9,839,422 B2 12/2017 Schellin et al.
9,839,423 B2 12/2017 Vendely et al.
9,839,427 B2 12/2017 Swayze et al.
9,839,428 B2 12/2017 Baxter, III et al.
9,839,429 B2 12/2017 Weisenburgh, II et al.
9,839,480 B2 12/2017 Pribanic et al.
9,839,481 B2 12/2017 Blumenkranz et al.
9,844,313 B2 12/2017 DiCarlo et al.
9,844,368 B2 12/2017 Boudreaux et al.
9,844,369 B2 12/2017 Huitema et al.
9,844,371 B2 12/2017 Scirica et al.
9,844,372 B2 12/2017 Shelton, IV et al.
9,844,373 B2 12/2017 Swayze et al.
9,844,374 B2 12/2017 Lytle, IV et al.
9,844,375 B2 12/2017 Overmyer et al.
9,844,376 B2 12/2017 Baxter, III et al.
9,844,379 B2 12/2017 Shelton, IV et al.
9,848,871 B2 12/2017 Harris et al.
9,848,873 B2 12/2017 Shelton, IV
9,848,875 B2 12/2017 Aronhalt et al.
9,848,877 B2 12/2017 Shelton, IV et al.
9,850,499 B2 12/2017 Baylink et al.
9,850,994 B2 12/2017 Schena
D808,989 S 1/2018 Ayvazian et al.
9,855,039 B2 1/2018 Racenet et al.
9,855,040 B2 1/2018 Kostrzewski
9,855,662 B2 1/2018 Ruiz Morales et al.
9,861,261 B2 1/2018 Shahinian
9,861,359 B2 1/2018 Shelton, IV et al.
9,861,361 B2 1/2018 Aronhalt et al.
9,861,362 B2 1/2018 Whitman et al.
9,861,366 B2 1/2018 Aranyi
9,861,382 B2 1/2018 Smith et al.
9,861,446 B2 1/2018 Lang
9,867,612 B2 1/2018 Parihar et al.
9,867,613 B2 1/2018 Marczyk et al.
9,867,615 B2 1/2018 Fanelli et al.
9,867,617 B2 1/2018 Ma
9,867,618 B2 1/2018 Hall et al.
9,867,620 B2 1/2018 Fischvogt et al.
9,868,198 B2 1/2018 Nicholas et al.
9,872,682 B2 1/2018 Hess et al.
9,872,683 B2 1/2018 Hopkins et al.
9,872,684 B2 1/2018 Hall et al.
9,872,722 B2 1/2018 Lech
9,877,718 B2 1/2018 Weir et al.
9,877,721 B2 1/2018 Schellin et al.
9,877,722 B2 1/2018 Schellin et al.
9,877,723 B2 1/2018 Hall et al.
9,877,776 B2 1/2018 Boudreaux
D810,099 S 2/2018 Riedel
9,883,843 B2 2/2018 Garlow
9,883,860 B2 2/2018 Leimbach et al.
9,883,861 B2 2/2018 Shelton, IV et al.
9,884,456 B2 2/2018 Schellin et al.
9,888,914 B2 2/2018 Martin et al.
9,888,919 B2 2/2018 Leimbach et al.
9,888,921 B2 2/2018 Williams et al.
9,888,924 B2 2/2018 Ebersole et al.
9,889,230 B2 2/2018 Bennett et al.
9,895,147 B2 2/2018 Shelton, IV
9,895,148 B2 2/2018 Shelton, IV et al.
9,895,813 B2 2/2018 Blumenkranz et al.
9,901,339 B2 2/2018 Farascioni
9,901,341 B2 2/2018 Kostrzewski
9,901,342 B2 2/2018 Shelton, IV et al.
9,901,344 B2 2/2018 Moore et al.
9,901,345 B2 2/2018 Moore et al.
9,901,346 B2 2/2018 Moore et al.
9,901,358 B2 2/2018 Faller et al.
9,901,406 B2 2/2018 State et al.
9,901,412 B2 2/2018 Lathrop et al.
D813,899 S 3/2018 Erant et al.

(56) References Cited

U.S. PATENT DOCUMENTS

| | | | |
|---|---|---|---|
| 9,907,456 | B2 | 3/2018 | Miyoshi |
| 9,907,552 | B2 | 3/2018 | Measamer et al. |
| 9,907,553 | B2 | 3/2018 | Cole et al. |
| 9,907,600 | B2 | 3/2018 | Stulen et al. |
| 9,907,620 | B2 | 3/2018 | Shelton, IV et al. |
| 9,913,641 | B2 | 3/2018 | Takemoto et al. |
| 9,913,642 | B2 | 3/2018 | Leimbach et al. |
| 9,913,644 | B2 | 3/2018 | McCuen |
| 9,913,646 | B2 | 3/2018 | Shelton, IV |
| 9,913,647 | B2 | 3/2018 | Weisenburgh, II et al. |
| 9,913,648 | B2 | 3/2018 | Shelton, IV et al. |
| 9,913,694 | B2 | 3/2018 | Brisson |
| 9,913,733 | B2 | 3/2018 | Piron et al. |
| 9,918,704 | B2 | 3/2018 | Shelton, IV et al. |
| 9,918,714 | B2 | 3/2018 | Gibbons, Jr. |
| 9,918,715 | B2 | 3/2018 | Menn |
| 9,918,716 | B2 | 3/2018 | Baxter, III et al. |
| 9,918,717 | B2 | 3/2018 | Czernik |
| 9,918,730 | B2 | 3/2018 | Trees et al. |
| 9,924,941 | B2 | 3/2018 | Burbank |
| 9,924,942 | B2 | 3/2018 | Swayze et al. |
| 9,924,943 | B2 | 3/2018 | Mohan Pinjala et al. |
| 9,924,944 | B2 | 3/2018 | Shelton, IV et al. |
| 9,924,945 | B2 | 3/2018 | Zheng et al. |
| 9,924,946 | B2 | 3/2018 | Vendely et al. |
| 9,924,947 | B2 | 3/2018 | Shelton, IV et al. |
| 9,924,961 | B2 | 3/2018 | Shelton, IV et al. |
| 9,931,106 | B2 | 4/2018 | Au et al. |
| 9,931,116 | B2 | 4/2018 | Racenet et al. |
| 9,931,117 | B2 | 4/2018 | Hathaway et al. |
| 9,931,118 | B2 | 4/2018 | Shelton, IV et al. |
| 9,931,120 | B2 | 4/2018 | Chen et al. |
| 9,936,949 | B2 | 4/2018 | Measamer et al. |
| 9,936,950 | B2 | 4/2018 | Shelton, IV et al. |
| 9,936,951 | B2 | 4/2018 | Hufnagel et al. |
| 9,936,952 | B2 | 4/2018 | Demmy |
| 9,936,954 | B2 | 4/2018 | Shelton, IV et al. |
| 9,937,626 | B2 | 4/2018 | Rockrohr |
| 9,943,309 | B2 | 4/2018 | Shelton, IV et al. |
| 9,943,310 | B2 | 4/2018 | Harris et al. |
| 9,943,312 | B2 | 4/2018 | Posada et al. |
| 9,949,754 | B2 | 4/2018 | Newhauser et al. |
| 9,953,193 | B2 | 4/2018 | Butler et al. |
| D819,072 | S | 5/2018 | Clediere |
| 9,955,954 | B2 | 5/2018 | Destoumieux et al. |
| 9,955,965 | B2 | 5/2018 | Chen et al. |
| 9,955,966 | B2 | 5/2018 | Zergiebel |
| 9,956,677 | B2 | 5/2018 | Baskar et al. |
| 9,962,129 | B2 | 5/2018 | Jerebko et al. |
| 9,962,157 | B2 | 5/2018 | Sapre |
| 9,962,158 | B2 | 5/2018 | Hall et al. |
| 9,962,159 | B2 | 5/2018 | Heinrich et al. |
| 9,962,161 | B2 | 5/2018 | Scheib et al. |
| 9,968,354 | B2 | 5/2018 | Shelton, IV et al. |
| 9,968,355 | B2 | 5/2018 | Shelton, IV et al. |
| 9,968,356 | B2 | 5/2018 | Shelton, IV et al. |
| 9,968,397 | B2 | 5/2018 | Taylor et al. |
| 9,974,529 | B2 | 5/2018 | Shelton, IV et al. |
| 9,974,538 | B2 | 5/2018 | Baxter, III et al. |
| 9,974,539 | B2 | 5/2018 | Yates et al. |
| 9,974,541 | B2 | 5/2018 | Calderoni |
| 9,974,542 | B2 | 5/2018 | Hodgkinson |
| 9,980,713 | B2 | 5/2018 | Aronhalt et al. |
| 9,980,724 | B2 | 5/2018 | Farascioni et al. |
| 9,980,729 | B2 | 5/2018 | Moore et al. |
| 9,980,740 | B2 | 5/2018 | Krause et al. |
| 9,980,769 | B2 | 5/2018 | Trees et al. |
| D819,680 | S | 6/2018 | Nguyen |
| D819,682 | S | 6/2018 | Howard et al. |
| D819,684 | S | 6/2018 | Dart |
| D820,307 | S | 6/2018 | Jian et al. |
| D820,867 | S | 6/2018 | Dickens et al. |
| 9,987,000 | B2 | 6/2018 | Shelton, IV et al. |
| 9,987,003 | B2 | 6/2018 | Timm et al. |
| 9,987,005 | B2 | 6/2018 | Viola et al. |
| 9,987,006 | B2 | 6/2018 | Morgan et al. |
| 9,987,008 | B2 | 6/2018 | Scirica et al. |
| 9,987,095 | B2 | 6/2018 | Chowaniec et al. |
| 9,987,097 | B2 | 6/2018 | van der Weide et al. |
| 9,987,099 | B2 | 6/2018 | Chen et al. |
| 9,993,248 | B2 | 6/2018 | Shelton, IV et al. |
| 9,993,258 | B2 | 6/2018 | Shelton, IV et al. |
| 9,993,284 | B2 | 6/2018 | Boudreaux |
| 9,999,408 | B2 | 6/2018 | Boudreaux et al. |
| 9,999,423 | B2 | 6/2018 | Schuckmann et al. |
| 9,999,426 | B2 | 6/2018 | Moore et al. |
| 9,999,431 | B2 | 6/2018 | Shelton, IV et al. |
| 9,999,472 | B2 | 6/2018 | Weir et al. |
| 9,999,759 | B2 | 6/2018 | Matonick et al. |
| 10,004,497 | B2 | 6/2018 | Overmyer et al. |
| 10,004,498 | B2 | 6/2018 | Morgan et al. |
| 10,004,500 | B2 | 6/2018 | Shelton, IV et al. |
| 10,004,501 | B2 | 6/2018 | Shelton, IV et al. |
| 10,004,505 | B2 | 6/2018 | Moore et al. |
| 10,004,506 | B2 | 6/2018 | Shelton, IV et al. |
| 10,004,552 | B1 | 6/2018 | Kleyman et al. |
| D822,206 | S | 7/2018 | Shelton, IV et al. |
| D823,858 | S | 7/2018 | Li et al. |
| 10,010,322 | B2 | 7/2018 | Shelton, IV et al. |
| 10,010,324 | B2 | 7/2018 | Huitema et al. |
| 10,010,395 | B2 | 7/2018 | Puckett et al. |
| 10,013,049 | B2 | 7/2018 | Leimbach et al. |
| 10,016,199 | B2 | 7/2018 | Baber et al. |
| 10,016,656 | B2 | 7/2018 | Devor et al. |
| 10,022,120 | B2 | 7/2018 | Martin et al. |
| 10,022,123 | B2 | 7/2018 | Williams et al. |
| 10,022,125 | B2 | 7/2018 | (Prommersberger) Stopek et al. |
| 10,024,407 | B2 | 7/2018 | Aranyi et al. |
| 10,028,742 | B2 | 7/2018 | Shelton, IV et al. |
| 10,028,743 | B2 | 7/2018 | Shelton, IV et al. |
| 10,028,744 | B2 | 7/2018 | Shelton, IV et al. |
| 10,028,761 | B2 | 7/2018 | Leimbach et al. |
| 10,029,108 | B2 | 7/2018 | Powers et al. |
| 10,029,125 | B2 | 7/2018 | Shapiro et al. |
| 10,034,344 | B2 | 7/2018 | Yoshida |
| 10,034,668 | B2 | 7/2018 | Ebner |
| D826,405 | S | 8/2018 | Shelton, IV et al. |
| 10,039,440 | B2 | 8/2018 | Fenech et al. |
| 10,039,529 | B2 | 8/2018 | Kerr et al. |
| 10,039,532 | B2 | 8/2018 | Srinivas et al. |
| 10,039,545 | B2 | 8/2018 | Sadowski et al. |
| 10,041,822 | B2 | 8/2018 | Zemlok |
| 10,045,769 | B2 | 8/2018 | Aronhalt et al. |
| 10,045,776 | B2 | 8/2018 | Shelton, IV et al. |
| 10,045,778 | B2 | 8/2018 | Yates et al. |
| 10,045,779 | B2 | 8/2018 | Savage et al. |
| 10,045,781 | B2 | 8/2018 | Cropper et al. |
| 10,045,782 | B2 | 8/2018 | Murthy Aravalli |
| 10,045,869 | B2 | 8/2018 | Forsell |
| 10,046,904 | B2 | 8/2018 | Evans et al. |
| 10,052,044 | B2 | 8/2018 | Shelton, IV et al. |
| 10,052,099 | B2 | 8/2018 | Morgan et al. |
| 10,052,100 | B2 | 8/2018 | Morgan et al. |
| 10,052,102 | B2 | 8/2018 | Baxter, III et al. |
| 10,052,104 | B2 | 8/2018 | Shelton, IV et al. |
| 10,052,164 | B2 | 8/2018 | Overmyer |
| 10,058,317 | B2 | 8/2018 | Fan et al. |
| 10,058,327 | B2 | 8/2018 | Weisenburgh, II et al. |
| 10,058,373 | B2 | 8/2018 | Takashino et al. |
| 10,058,395 | B2 | 8/2018 | Devengenzo et al. |
| 10,058,963 | B2 | 8/2018 | Shelton, IV et al. |
| 10,064,620 | B2 | 9/2018 | Gettinger et al. |
| 10,064,621 | B2 | 9/2018 | Kerr et al. |
| 10,064,622 | B2 | 9/2018 | Murthy Aravalli |
| 10,064,624 | B2 | 9/2018 | Shelton, IV et al. |
| 10,064,639 | B2 | 9/2018 | Ishida et al. |
| 10,064,642 | B2 | 9/2018 | Marczyk et al. |
| 10,064,649 | B2 | 9/2018 | Golebieski et al. |
| 10,064,688 | B2 | 9/2018 | Shelton, IV et al. |
| 10,070,861 | B2 | 9/2018 | Spivey et al. |
| 10,070,863 | B2 | 9/2018 | Swayze et al. |
| 10,071,452 | B2 | 9/2018 | Shelton, IV et al. |
| 10,076,325 | B2 | 9/2018 | Huang et al. |
| 10,076,326 | B2 | 9/2018 | Yates et al. |

(56) References Cited

U.S. PATENT DOCUMENTS

| | | | |
|---|---|---|---|
| 10,076,340 | B2 | 9/2018 | Belagali et al. |
| 10,080,552 | B2 | 9/2018 | Nicholas et al. |
| D830,550 | S | 10/2018 | Miller et al. |
| D831,209 | S | 10/2018 | Huitema et al. |
| D831,676 | S | 10/2018 | Park et al. |
| D832,301 | S | 10/2018 | Smith |
| 10,085,624 | B2 | 10/2018 | Isoda et al. |
| 10,085,643 | B2 | 10/2018 | Bandic et al. |
| 10,085,728 | B2 | 10/2018 | Jogasaki et al. |
| 10,085,746 | B2 | 10/2018 | Fischvogt |
| 10,085,748 | B2 | 10/2018 | Morgan et al. |
| 10,085,749 | B2 | 10/2018 | Cappola et al. |
| 10,085,750 | B2 | 10/2018 | Zergiebel et al. |
| 10,085,751 | B2 | 10/2018 | Overmyer et al. |
| 10,085,754 | B2 | 10/2018 | Sniffin et al. |
| 10,085,806 | B2 | 10/2018 | Hagn et al. |
| 10,092,290 | B2 | 10/2018 | Yigit et al. |
| 10,092,292 | B2 | 10/2018 | Boudreaux et al. |
| 10,098,635 | B2 | 10/2018 | Burbank |
| 10,098,636 | B2 | 10/2018 | Shelton, IV et al. |
| 10,098,640 | B2 | 10/2018 | Bertolero et al. |
| 10,098,642 | B2 | 10/2018 | Baxter, III et al. |
| 10,099,303 | B2 | 10/2018 | Yoshida et al. |
| 10,101,861 | B2 | 10/2018 | Kiyoto |
| 10,105,126 | B2 | 10/2018 | Sauer |
| 10,105,128 | B2 | 10/2018 | Cooper et al. |
| 10,105,136 | B2 | 10/2018 | Yates et al. |
| 10,105,139 | B2 | 10/2018 | Yates et al. |
| 10,105,140 | B2 | 10/2018 | Malinouskas et al. |
| 10,105,142 | B2 | 10/2018 | Baxter, III et al. |
| 10,105,149 | B2 | 10/2018 | Haider et al. |
| 10,106,932 | B2 | 10/2018 | Anderson et al. |
| 10,111,657 | B2 | 10/2018 | McCuen |
| 10,111,658 | B2 | 10/2018 | Chowaniec et al. |
| 10,111,660 | B2 | 10/2018 | Hemmann |
| 10,111,665 | B2 | 10/2018 | Aranyi et al. |
| 10,111,679 | B2 | 10/2018 | Baber et al. |
| 10,111,698 | B2 | 10/2018 | Scheib et al. |
| 10,111,702 | B2 | 10/2018 | Kostrzewski |
| D833,608 | S | 11/2018 | Miller et al. |
| 10,117,649 | B2 | 11/2018 | Baxter, III et al. |
| 10,117,650 | B2 | 11/2018 | Nicholas et al. |
| 10,117,652 | B2 | 11/2018 | Schmid et al. |
| 10,117,653 | B2 | 11/2018 | Leimbach et al. |
| 10,117,654 | B2 | 11/2018 | Ingmanson et al. |
| 10,123,798 | B2 | 11/2018 | Baxter, III et al. |
| 10,123,845 | B2 | 11/2018 | Yeung |
| 10,124,493 | B2 | 11/2018 | Rothfuss et al. |
| 10,130,352 | B2 | 11/2018 | Widenhouse et al. |
| 10,130,359 | B2 | 11/2018 | Hess et al. |
| 10,130,360 | B2 | 11/2018 | Olson et al. |
| 10,130,361 | B2 | 11/2018 | Yates et al. |
| 10,130,363 | B2 | 11/2018 | Huitema et al. |
| 10,130,366 | B2 | 11/2018 | Shelton, IV et al. |
| 10,130,367 | B2 | 11/2018 | Cappola et al. |
| 10,130,382 | B2 | 11/2018 | Gladstone |
| 10,130,738 | B2 | 11/2018 | Shelton, IV et al. |
| 10,130,830 | B2 | 11/2018 | Miret Carceller et al. |
| 10,133,248 | B2 | 11/2018 | Fitzsimmons et al. |
| 10,135,242 | B2 | 11/2018 | Baber et al. |
| 10,136,879 | B2 | 11/2018 | Ross et al. |
| 10,136,887 | B2 | 11/2018 | Shelton, IV et al. |
| 10,136,889 | B2 | 11/2018 | Shelton, IV et al. |
| 10,136,890 | B2 | 11/2018 | Shelton, IV et al. |
| 10,136,891 | B2 | 11/2018 | Shelton, IV et al. |
| 10,136,949 | B2 | 11/2018 | Felder et al. |
| D835,659 | S | 12/2018 | Anzures et al. |
| D836,124 | S | 12/2018 | Fan |
| 10,143,474 | B2 | 12/2018 | Bucciaglia et al. |
| 10,146,423 | B1 | 12/2018 | Reed et al. |
| 10,149,679 | B2 | 12/2018 | Shelton, IV et al. |
| 10,149,680 | B2 | 12/2018 | Parihar et al. |
| 10,149,682 | B2 | 12/2018 | Shelton, IV et al. |
| 10,149,683 | B2 | 12/2018 | Smith et al. |
| 10,149,712 | B2 | 12/2018 | Manwaring et al. |
| 10,152,789 | B2 | 12/2018 | Carnes et al. |
| 10,154,841 | B2 | 12/2018 | Weaner et al. |
| 10,159,481 | B2 | 12/2018 | Whitman et al. |
| 10,159,482 | B2 | 12/2018 | Swayze et al. |
| 10,159,483 | B2 | 12/2018 | Beckman et al. |
| 10,159,506 | B2 | 12/2018 | Boudreaux et al. |
| 10,161,816 | B2 | 12/2018 | Jackson et al. |
| 10,163,065 | B1 | 12/2018 | Koski et al. |
| 10,163,589 | B2 | 12/2018 | Zergiebel et al. |
| 10,164,466 | B2 | 12/2018 | Calderoni |
| D837,244 | S | 1/2019 | Kuo et al. |
| D837,245 | S | 1/2019 | Kuo et al. |
| 10,166,023 | B2 | 1/2019 | Vendely et al. |
| 10,166,025 | B2 | 1/2019 | Leimbach et al. |
| 10,166,026 | B2 | 1/2019 | Shelton, IV et al. |
| 10,172,611 | B2 | 1/2019 | Shelton, IV et al. |
| 10,172,615 | B2 | 1/2019 | Marczyk et al. |
| 10,172,616 | B2 | 1/2019 | Murray et al. |
| 10,172,617 | B2 | 1/2019 | Shelton, IV et al. |
| 10,172,618 | B2 | 1/2019 | Shelton, IV et al. |
| 10,172,619 | B2 | 1/2019 | Harris et al. |
| 10,172,620 | B2 | 1/2019 | Harris et al. |
| 10,172,636 | B2 | 1/2019 | Stulen et al. |
| 10,172,669 | B2 | 1/2019 | Felder et al. |
| 10,175,127 | B2 | 1/2019 | Collins et al. |
| 10,178,992 | B2 | 1/2019 | Wise et al. |
| 10,180,463 | B2 | 1/2019 | Beckman et al. |
| 10,182,813 | B2 | 1/2019 | Leimbach et al. |
| 10,182,815 | B2 | 1/2019 | Williams et al. |
| 10,182,816 | B2 | 1/2019 | Shelton, IV et al. |
| 10,182,818 | B2 | 1/2019 | Hensel et al. |
| 10,182,819 | B2 | 1/2019 | Shelton, IV |
| 10,182,868 | B2 | 1/2019 | Meier et al. |
| 10,188,385 | B2 | 1/2019 | Kerr et al. |
| 10,188,389 | B2 | 1/2019 | Vendely et al. |
| 10,188,393 | B2 | 1/2019 | Smith et al. |
| 10,188,394 | B2 | 1/2019 | Shelton, IV et al. |
| 10,190,888 | B2 | 1/2019 | Hryb et al. |
| D839,900 | S | 2/2019 | Gan |
| D841,667 | S | 2/2019 | Coren |
| 10,194,801 | B2 | 2/2019 | Elhawary et al. |
| 10,194,904 | B2 | 2/2019 | Viola et al. |
| 10,194,907 | B2 | 2/2019 | Marczyk et al. |
| 10,194,908 | B2 | 2/2019 | Duque et al. |
| 10,194,910 | B2 | 2/2019 | Shelton, IV et al. |
| 10,194,911 | B2 | 2/2019 | Miller et al. |
| 10,194,912 | B2 | 2/2019 | Scheib et al. |
| 10,194,913 | B2 | 2/2019 | Nalagatla et al. |
| 10,194,976 | B2 | 2/2019 | Boudreaux |
| 10,194,981 | B2 | 2/2019 | Balbas et al. |
| 10,194,992 | B2 | 2/2019 | Robinson |
| 10,201,348 | B2 | 2/2019 | Scheib et al. |
| 10,201,349 | B2 | 2/2019 | Leimbach et al. |
| 10,201,363 | B2 | 2/2019 | Shelton, IV |
| 10,201,364 | B2 | 2/2019 | Leimbach et al. |
| 10,201,365 | B2 | 2/2019 | Boudreaux et al. |
| 10,201,381 | B2 | 2/2019 | Zergiebel et al. |
| 10,206,605 | B2 | 2/2019 | Shelton, IV et al. |
| 10,206,676 | B2 | 2/2019 | Shelton, IV |
| 10,206,677 | B2 | 2/2019 | Harris et al. |
| 10,206,678 | B2 | 2/2019 | Shelton, IV et al. |
| 10,206,748 | B2 | 2/2019 | Burbank |
| 10,210,244 | B1 | 2/2019 | Branavan et al. |
| 10,211,586 | B2 | 2/2019 | Adams et al. |
| 10,213,198 | B2 | 2/2019 | Aronhalt et al. |
| 10,213,201 | B2 | 2/2019 | Shelton, IV et al. |
| 10,213,202 | B2 | 2/2019 | Flanagan et al. |
| 10,213,203 | B2 | 2/2019 | Swayze et al. |
| 10,213,204 | B2 | 2/2019 | Aranyi et al. |
| 10,213,262 | B2 | 2/2019 | Shelton, IV et al. |
| D842,328 | S | 3/2019 | Jian et al. |
| 10,219,811 | B2 | 3/2019 | Haider et al. |
| 10,219,832 | B2 | 3/2019 | Bagwell et al. |
| 10,220,522 | B2 | 3/2019 | Rockrohr |
| 10,226,239 | B2 | 3/2019 | Nicholas et al. |
| 10,226,249 | B2 | 3/2019 | Jaworek et al. |
| 10,226,250 | B2 | 3/2019 | Beckman et al. |
| 10,226,251 | B2 | 3/2019 | Scheib et al. |
| 10,226,274 | B2 | 3/2019 | Worrell et al. |

(56) References Cited

U.S. PATENT DOCUMENTS

| | | | |
|---|---|---|---|
| 10,231,634 | B2 | 3/2019 | Zand et al. |
| 10,231,653 | B2 | 3/2019 | Bohm et al. |
| 10,231,734 | B2 | 3/2019 | Thompson et al. |
| 10,231,794 | B2 | 3/2019 | Shelton, IV et al. |
| 10,238,385 | B2 | 3/2019 | Yates et al. |
| 10,238,386 | B2 | 3/2019 | Overmyer et al. |
| 10,238,387 | B2 | 3/2019 | Yates et al. |
| 10,238,389 | B2 | 3/2019 | Yates et al. |
| 10,238,390 | B2 | 3/2019 | Harris et al. |
| 10,238,391 | B2 | 3/2019 | Leimbach et al. |
| D844,666 | S | 4/2019 | Espeleta et al. |
| D844,667 | S | 4/2019 | Espeleta et al. |
| D845,342 | S | 4/2019 | Espeleta et al. |
| D847,199 | S | 4/2019 | Whitmore |
| 10,244,991 | B2 | 4/2019 | Shademan et al. |
| 10,245,027 | B2 | 4/2019 | Shelton, IV et al. |
| 10,245,028 | B2 | 4/2019 | Shelton, IV et al. |
| 10,245,029 | B2 | 4/2019 | Hunter et al. |
| 10,245,030 | B2 | 4/2019 | Hunter et al. |
| 10,245,032 | B2 | 4/2019 | Shelton, IV |
| 10,245,033 | B2 | 4/2019 | Overmyer et al. |
| 10,245,034 | B2 | 4/2019 | Shelton, IV et al. |
| 10,245,035 | B2 | 4/2019 | Swayze et al. |
| 10,245,038 | B2 | 4/2019 | Hopkins et al. |
| 10,245,058 | B2 | 4/2019 | Omori et al. |
| 10,251,645 | B2 | 4/2019 | Kostrzewski |
| 10,251,648 | B2 | 4/2019 | Harris et al. |
| 10,251,649 | B2 | 4/2019 | Schellin et al. |
| 10,251,725 | B2 | 4/2019 | Valentine et al. |
| 10,258,322 | B2 | 4/2019 | Fanton et al. |
| 10,258,330 | B2 | 4/2019 | Shelton, IV et al. |
| 10,258,331 | B2 | 4/2019 | Shelton, IV et al. |
| 10,258,332 | B2 | 4/2019 | Schmid et al. |
| 10,258,333 | B2 | 4/2019 | Shelton, IV et al. |
| 10,258,336 | B2 | 4/2019 | Baxter, III et al. |
| 10,258,363 | B2 | 4/2019 | Worrell et al. |
| 10,258,418 | B2 | 4/2019 | Shelton, IV et al. |
| 10,264,797 | B2 | 4/2019 | Zhang et al. |
| 10,265,065 | B2 | 4/2019 | Shelton, IV et al. |
| 10,265,067 | B2 | 4/2019 | Yates et al. |
| 10,265,068 | B2 | 4/2019 | Harris et al. |
| 10,265,072 | B2 | 4/2019 | Shelton, IV et al. |
| 10,265,073 | B2 | 4/2019 | Scheib et al. |
| 10,265,074 | B2 | 4/2019 | Shelton, IV et al. |
| 10,265,090 | B2 | 4/2019 | Ingmanson et al. |
| 10,271,840 | B2 | 4/2019 | Sapre |
| 10,271,844 | B2 | 4/2019 | Valentine et al. |
| 10,271,845 | B2 | 4/2019 | Shelton, IV |
| 10,271,846 | B2 | 4/2019 | Shelton, IV et al. |
| 10,271,847 | B2 | 4/2019 | Racenet et al. |
| 10,271,849 | B2 | 4/2019 | Vendely et al. |
| 10,271,851 | B2 | 4/2019 | Shelton, IV et al. |
| D847,989 | S | 5/2019 | Shelton, IV et al. |
| D848,473 | S | 5/2019 | Zhu et al. |
| D849,046 | S | 5/2019 | Kuo et al. |
| 10,278,696 | B2 | 5/2019 | Gurumurthy et al. |
| 10,278,697 | B2 | 5/2019 | Shelton, IV et al. |
| 10,278,702 | B2 | 5/2019 | Shelton, IV et al. |
| 10,278,703 | B2 | 5/2019 | Nativ et al. |
| 10,278,707 | B2 | 5/2019 | Thompson et al. |
| 10,278,722 | B2 | 5/2019 | Shelton, IV et al. |
| 10,278,780 | B2 | 5/2019 | Shelton, IV |
| 10,285,694 | B2 | 5/2019 | Viola et al. |
| 10,285,695 | B2 | 5/2019 | Jaworek et al. |
| 10,285,696 | B2 | 5/2019 | Marczyk |
| 10,285,699 | B2 | 5/2019 | Vendely et al. |
| 10,285,700 | B2 | 5/2019 | Scheib |
| 10,285,705 | B2 | 5/2019 | Shelton, IV et al. |
| 10,285,724 | B2 | 5/2019 | Faller et al. |
| 10,285,750 | B2 | 5/2019 | Coulson et al. |
| 10,292,701 | B2 | 5/2019 | Scheib et al. |
| 10,292,704 | B2 | 5/2019 | Harris et al. |
| 10,292,707 | B2 | 5/2019 | Shelton, IV et al. |
| 10,293,100 | B2 | 5/2019 | Shelton, IV et al. |
| 10,293,553 | B2 | 5/2019 | Racenet et al. |
| 10,299,787 | B2 | 5/2019 | Shelton, IV |
| 10,299,788 | B2 | 5/2019 | Heinrich et al. |
| 10,299,789 | B2 | 5/2019 | Marczyk et al. |
| 10,299,790 | B2 | 5/2019 | Beardsley |
| 10,299,792 | B2 | 5/2019 | Huitema et al. |
| 10,299,817 | B2 | 5/2019 | Shelton, IV et al. |
| 10,299,818 | B2 | 5/2019 | Riva |
| 10,299,878 | B2 | 5/2019 | Shelton, IV et al. |
| 10,303,851 | B2 | 5/2019 | Nguyen et al. |
| D850,617 | S | 6/2019 | Shelton, IV et al. |
| D851,676 | S | 6/2019 | Foss et al. |
| D851,762 | S | 6/2019 | Shelton, IV et al. |
| 10,307,159 | B2 | 6/2019 | Harris et al. |
| 10,307,160 | B2 | 6/2019 | Vendely et al. |
| 10,307,161 | B2 | 6/2019 | Jankowski |
| 10,307,163 | B2 | 6/2019 | Moore et al. |
| 10,307,170 | B2 | 6/2019 | Parfett et al. |
| 10,307,202 | B2 | 6/2019 | Smith et al. |
| 10,314,559 | B2 | 6/2019 | Razzaque et al. |
| 10,314,577 | B2 | 6/2019 | Laurent et al. |
| 10,314,578 | B2 | 6/2019 | Leimbach et al. |
| 10,314,579 | B2 | 6/2019 | Chowaniec et al. |
| 10,314,580 | B2 | 6/2019 | Scheib et al. |
| 10,314,582 | B2 | 6/2019 | Shelton, IV et al. |
| 10,314,584 | B2 | 6/2019 | Scirica et al. |
| 10,314,587 | B2 | 6/2019 | Harris et al. |
| 10,314,588 | B2 | 6/2019 | Turner et al. |
| 10,314,589 | B2 | 6/2019 | Shelton, IV et al. |
| 10,314,590 | B2 | 6/2019 | Shelton, IV et al. |
| 10,315,566 | B2 | 6/2019 | Choi et al. |
| 10,321,907 | B2 | 6/2019 | Shelton, IV et al. |
| 10,321,909 | B2 | 6/2019 | Shelton, IV et al. |
| 10,321,927 | B2 | 6/2019 | Hinman |
| 10,327,743 | B2 | 6/2019 | St. Goar et al. |
| 10,327,764 | B2 | 6/2019 | Harris et al. |
| 10,327,765 | B2 | 6/2019 | Timm et al. |
| 10,327,767 | B2 | 6/2019 | Shelton, IV et al. |
| 10,327,769 | B2 | 6/2019 | Overmyer et al. |
| 10,327,776 | B2 | 6/2019 | Harris et al. |
| 10,327,777 | B2 | 6/2019 | Harris et al. |
| D854,032 | S | 7/2019 | Jones et al. |
| D854,151 | S | 7/2019 | Shelton, IV et al. |
| 10,335,144 | B2 | 7/2019 | Shelton, IV et al. |
| 10,335,145 | B2 | 7/2019 | Harris et al. |
| 10,335,147 | B2 | 7/2019 | Rector et al. |
| 10,335,148 | B2 | 7/2019 | Shelton, IV et al. |
| 10,335,149 | B2 | 7/2019 | Baxter, III et al. |
| 10,335,150 | B2 | 7/2019 | Shelton, IV |
| 10,335,151 | B2 | 7/2019 | Shelton, IV et al. |
| 10,337,148 | B2 | 7/2019 | Rouse et al. |
| 10,342,533 | B2 | 7/2019 | Shelton, IV et al. |
| 10,342,535 | B2 | 7/2019 | Scheib et al. |
| 10,342,541 | B2 | 7/2019 | Shelton, IV et al. |
| 10,342,543 | B2 | 7/2019 | Shelton, IV et al. |
| 10,342,623 | B2 | 7/2019 | Huelman et al. |
| 10,349,937 | B2 | 7/2019 | Williams |
| 10,349,939 | B2 | 7/2019 | Shelton, IV et al. |
| 10,349,941 | B2 | 7/2019 | Marczyk et al. |
| 10,349,963 | B2 | 7/2019 | Fiksen et al. |
| 10,350,016 | B2 | 7/2019 | Burbank et al. |
| 10,357,246 | B2 | 7/2019 | Shelton, IV et al. |
| 10,357,247 | B2 | 7/2019 | Shelton, IV et al. |
| 10,357,248 | B2 | 7/2019 | Dalessandro et al. |
| 10,357,252 | B2 | 7/2019 | Harris et al. |
| 10,363,031 | B2 | 7/2019 | Alexander, III et al. |
| 10,363,033 | B2 | 7/2019 | Timm et al. |
| 10,363,036 | B2 | 7/2019 | Yates et al. |
| 10,363,037 | B2 | 7/2019 | Aronhalt et al. |
| D855,634 | S | 8/2019 | Kim |
| D856,359 | S | 8/2019 | Huang et al. |
| 10,368,838 | B2 | 8/2019 | Williams et al. |
| 10,368,861 | B2 | 8/2019 | Baxter, III et al. |
| 10,368,863 | B2 | 8/2019 | Timm et al. |
| 10,368,864 | B2 | 8/2019 | Harris et al. |
| 10,368,865 | B2 | 8/2019 | Harris et al. |
| 10,368,866 | B2 | 8/2019 | Wang et al. |
| 10,368,867 | B2 | 8/2019 | Harris et al. |
| 10,368,892 | B2 | 8/2019 | Stulen et al. |
| 10,374,544 | B2 | 8/2019 | Yokoyama et al. |

(56) References Cited

U.S. PATENT DOCUMENTS

| | | | |
|---|---|---|---|
| 10,376,263 | B2 | 8/2019 | Morgan et al. |
| 10,383,626 | B2 | 8/2019 | Soltz |
| 10,383,628 | B2 | 8/2019 | Kang et al. |
| 10,383,629 | B2 | 8/2019 | Ross et al. |
| 10,383,630 | B2 | 8/2019 | Shelton, IV et al. |
| 10,383,631 | B2 | 8/2019 | Collings et al. |
| 10,383,633 | B2 | 8/2019 | Shelton, IV et al. |
| 10,383,634 | B2 | 8/2019 | Shelton, IV et al. |
| 10,390,823 | B2 | 8/2019 | Shelton, IV et al. |
| 10,390,825 | B2 | 8/2019 | Shelton, IV et al. |
| 10,390,828 | B2 | 8/2019 | Vendely et al. |
| 10,390,829 | B2 | 8/2019 | Eckert et al. |
| 10,390,830 | B2 | 8/2019 | Schulz |
| 10,390,841 | B2 | 8/2019 | Shelton, IV et al. |
| 10,390,897 | B2 | 8/2019 | Kostrzewski |
| D859,466 | S | 9/2019 | Okada et al. |
| D860,219 | S | 9/2019 | Rasmussen et al. |
| D861,035 | S | 9/2019 | Park et al. |
| 10,398,433 | B2 | 9/2019 | Boudreaux et al. |
| 10,398,434 | B2 | 9/2019 | Shelton, IV et al. |
| 10,398,436 | B2 | 9/2019 | Shelton, IV et al. |
| 10,398,460 | B2 | 9/2019 | Overmyer |
| 10,404,136 | B2 | 9/2019 | Oktavec et al. |
| 10,405,854 | B2 | 9/2019 | Schmid et al. |
| 10,405,857 | B2 | 9/2019 | Shelton, IV et al. |
| 10,405,859 | B2 | 9/2019 | Harris et al. |
| 10,405,863 | B2 | 9/2019 | Wise et al. |
| 10,405,914 | B2 | 9/2019 | Manwaring et al. |
| 10,405,932 | B2 | 9/2019 | Overmyer |
| 10,405,937 | B2 | 9/2019 | Black et al. |
| 10,413,155 | B2 | 9/2019 | Inoue |
| 10,413,291 | B2 | 9/2019 | Worthington et al. |
| 10,413,293 | B2 | 9/2019 | Shelton, IV et al. |
| 10,413,294 | B2 | 9/2019 | Shelton, IV et al. |
| 10,413,297 | B2 | 9/2019 | Harris et al. |
| 10,413,370 | B2 | 9/2019 | Yates et al. |
| 10,413,373 | B2 | 9/2019 | Yates et al. |
| 10,420,548 | B2 | 9/2019 | Whitman et al. |
| 10,420,549 | B2 | 9/2019 | Yates et al. |
| 10,420,550 | B2 | 9/2019 | Shelton, IV |
| 10,420,551 | B2 | 9/2019 | Calderoni |
| 10,420,552 | B2 | 9/2019 | Shelton, IV et al. |
| 10,420,553 | B2 | 9/2019 | Shelton, IV et al. |
| 10,420,554 | B2 | 9/2019 | Collings et al. |
| 10,420,555 | B2 | 9/2019 | Shelton, IV et al. |
| 10,420,558 | B2 | 9/2019 | Nalagatla et al. |
| 10,420,559 | B2 | 9/2019 | Marczyk et al. |
| 10,420,560 | B2 | 9/2019 | Shelton, IV et al. |
| 10,420,561 | B2 | 9/2019 | Shelton, IV et al. |
| 10,420,577 | B2 | 9/2019 | Chowaniec et al. |
| D861,707 | S | 10/2019 | Yang |
| D862,518 | S | 10/2019 | Niven et al. |
| D863,343 | S | 10/2019 | Mazlish et al. |
| D864,388 | S | 10/2019 | Barber |
| D865,174 | S | 10/2019 | Auld et al. |
| D865,175 | S | 10/2019 | Widenhouse et al. |
| 10,426,463 | B2 | 10/2019 | Shelton, IV et al. |
| 10,426,466 | B2 | 10/2019 | Contini et al. |
| 10,426,467 | B2 | 10/2019 | Miller et al. |
| 10,426,468 | B2 | 10/2019 | Contini et al. |
| 10,426,469 | B2 | 10/2019 | Shelton, IV et al. |
| 10,426,471 | B2 | 10/2019 | Shelton, IV et al. |
| 10,426,476 | B2 | 10/2019 | Harris et al. |
| 10,426,477 | B2 | 10/2019 | Harris et al. |
| 10,426,478 | B2 | 10/2019 | Shelton, IV et al. |
| 10,426,481 | B2 | 10/2019 | Aronhalt et al. |
| 10,426,555 | B2 | 10/2019 | Crowley et al. |
| 10,433,837 | B2 | 10/2019 | Worthington et al. |
| 10,433,839 | B2 | 10/2019 | Scheib et al. |
| 10,433,840 | B2 | 10/2019 | Shelton, IV et al. |
| 10,433,842 | B2 | 10/2019 | Amariglio et al. |
| 10,433,844 | B2 | 10/2019 | Shelton, IV et al. |
| 10,433,845 | B2 | 10/2019 | Baxter, III et al. |
| 10,433,846 | B2 | 10/2019 | Vendely et al. |
| 10,433,849 | B2 | 10/2019 | Shelton, IV et al. |
| 10,433,918 | B2 | 10/2019 | Shelton, IV et al. |
| 10,441,279 | B2 | 10/2019 | Shelton, IV et al. |
| 10,441,280 | B2 | 10/2019 | Timm et al. |
| 10,441,281 | B2 | 10/2019 | Shelton, IV et al. |
| 10,441,285 | B2 | 10/2019 | Shelton, IV et al. |
| 10,441,286 | B2 | 10/2019 | Shelton, IV et al. |
| 10,441,345 | B2 | 10/2019 | Aldridge et al. |
| 10,441,369 | B2 | 10/2019 | Shelton, IV et al. |
| 10,448,948 | B2 | 10/2019 | Shelton, IV et al. |
| 10,448,950 | B2 | 10/2019 | Shelton, IV et al. |
| 10,448,952 | B2 | 10/2019 | Shelton, IV et al. |
| 10,456,122 | B2 | 10/2019 | Koltz et al. |
| 10,456,132 | B2 | 10/2019 | Gettinger et al. |
| 10,456,133 | B2 | 10/2019 | Yates et al. |
| 10,456,137 | B2 | 10/2019 | Vendely et al. |
| 10,456,140 | B2 | 10/2019 | Shelton, IV et al. |
| D865,796 | S | 11/2019 | Xu et al. |
| 10,463,367 | B2 | 11/2019 | Kostrzewski et al. |
| 10,463,369 | B2 | 11/2019 | Shelton, IV et al. |
| 10,463,370 | B2 | 11/2019 | Yates et al. |
| 10,463,371 | B2 | 11/2019 | Kostrzewski |
| 10,463,372 | B2 | 11/2019 | Shelton, IV et al. |
| 10,463,373 | B2 | 11/2019 | Mozdzierz et al. |
| 10,463,382 | B2 | 11/2019 | Ingmanson et al. |
| 10,463,383 | B2 | 11/2019 | Shelton, IV et al. |
| 10,463,384 | B2 | 11/2019 | Shelton, IV et al. |
| 10,470,762 | B2 | 11/2019 | Leimbach et al. |
| 10,470,763 | B2 | 11/2019 | Yates et al. |
| 10,470,764 | B2 | 11/2019 | Baxter, III et al. |
| 10,470,767 | B2 | 11/2019 | Gleiman et al. |
| 10,470,768 | B2 | 11/2019 | Harris et al. |
| 10,470,769 | B2 | 11/2019 | Shelton, IV et al. |
| 10,471,282 | B2 | 11/2019 | Kirk et al. |
| 10,471,576 | B2 | 11/2019 | Totsu |
| 10,471,607 | B2 | 11/2019 | Butt et al. |
| 10,478,181 | B2 | 11/2019 | Shelton, IV et al. |
| 10,478,182 | B2 | 11/2019 | Taylor |
| 10,478,185 | B2 | 11/2019 | Nicholas |
| 10,478,187 | B2 | 11/2019 | Shelton, IV et al. |
| 10,478,188 | B2 | 11/2019 | Harris et al. |
| 10,478,189 | B2 | 11/2019 | Bear et al. |
| 10,478,190 | B2 | 11/2019 | Miller et al. |
| 10,478,207 | B2 | 11/2019 | Lathrop |
| 10,482,292 | B2 | 11/2019 | Clouser et al. |
| 10,485,536 | B2 | 11/2019 | Ming et al. |
| 10,485,537 | B2 | 11/2019 | Yates et al. |
| 10,485,539 | B2 | 11/2019 | Shelton, IV et al. |
| 10,485,541 | B2 | 11/2019 | Shelton, IV et al. |
| 10,485,542 | B2 | 11/2019 | Shelton, IV et al. |
| 10,485,543 | B2 | 11/2019 | Shelton, IV et al. |
| 10,485,546 | B2 | 11/2019 | Shelton, IV et al. |
| 10,485,547 | B2 | 11/2019 | Shelton, IV et al. |
| D869,655 | S | 12/2019 | Shelton, IV et al. |
| D870,742 | S | 12/2019 | Cornell |
| 10,492,783 | B2 | 12/2019 | Shelton, IV et al. |
| 10,492,785 | B2 | 12/2019 | Overmyer et al. |
| 10,492,787 | B2 | 12/2019 | Smith et al. |
| 10,492,814 | B2 | 12/2019 | Snow et al. |
| 10,492,847 | B2 | 12/2019 | Godara et al. |
| 10,492,851 | B2 | 12/2019 | Hughett, Sr. et al. |
| 10,498,269 | B2 | 12/2019 | Zemlok et al. |
| 10,499,890 | B2 | 12/2019 | Shelton, IV et al. |
| 10,499,914 | B2 | 12/2019 | Huang et al. |
| 10,499,917 | B2 | 12/2019 | Scheib et al. |
| 10,499,918 | B2 | 12/2019 | Schellin et al. |
| 10,500,000 | B2 | 12/2019 | Swayze et al. |
| 10,500,004 | B2 | 12/2019 | Hanuschik et al. |
| 10,500,309 | B2 | 12/2019 | Shah et al. |
| 10,507,034 | B2 | 12/2019 | Timm |
| 10,508,720 | B2 | 12/2019 | Nicholas |
| 10,512,461 | B2 | 12/2019 | Gupta et al. |
| 10,512,462 | B2 | 12/2019 | Felder et al. |
| 10,512,464 | B2 | 12/2019 | Park et al. |
| 10,517,590 | B2 | 12/2019 | Giordano et al. |
| 10,517,592 | B2 | 12/2019 | Shelton, IV et al. |
| 10,517,594 | B2 | 12/2019 | Shelton, IV et al. |
| 10,517,595 | B2 | 12/2019 | Hunter et al. |
| 10,517,596 | B2 | 12/2019 | Hunter et al. |
| 10,517,599 | B2 | 12/2019 | Baxter, III et al. |

(56) References Cited

U.S. PATENT DOCUMENTS 10,517,682 B2 12/2019 Giordano et al.
10,524,784 B2 1/2020 Kostrzewski
10,524,787 B2 1/2020 Shelton, IV et al.
10,524,788 B2 1/2020 Vendely et al.
10,524,789 B2 1/2020 Swayze et al.
10,524,790 B2 1/2020 Shelton, IV et al.
10,524,795 B2 1/2020 Nalagatla et al.
10,524,870 B2 1/2020 Saraliev et al.
10,531,874 B2 1/2020 Morgan et al.
10,531,887 B2 1/2020 Shelton, IV et al.
10,537,323 B2 1/2020 Racenet et al.
10,537,324 B2 1/2020 Shelton, IV et al.
10,537,325 B2 1/2020 Bakos et al.
10,537,351 B2 1/2020 Shelton, IV et al.
10,537,381 B2 1/2020 Joseph et al.
10,542,908 B2 1/2020 Mei et al.
10,542,974 B2 1/2020 Yates et al.
10,542,976 B2 1/2020 Calderoni et al.
10,542,978 B2 1/2020 Chowaniec et al.
10,542,979 B2 1/2020 Shelton, IV et al.
10,542,982 B2 1/2020 Beckman et al.
10,542,985 B2 1/2020 Zhan et al.
10,542,988 B2 1/2020 Schellin et al.
10,542,991 B2 1/2020 Shelton, IV et al.
D876,478 S 2/2020 Sakata et al.
10,548,504 B2 2/2020 Shelton, IV et al.
10,548,593 B2 2/2020 Shelton, IV et al.
10,548,600 B2 2/2020 Shelton, IV et al.
10,548,673 B2 2/2020 Harris et al.
10,561,412 B2 2/2020 Bookbinder et al.
10,561,418 B2 2/2020 Richard et al.
10,561,419 B2 2/2020 Beardsley
10,561,420 B2 2/2020 Harris et al.
10,561,422 B2 2/2020 Schellin et al.
10,561,432 B2 2/2020 Estrella et al.
10,561,474 B2 2/2020 Adams et al.
10,562,160 B2 2/2020 Iwata et al.
10,568,493 B2 2/2020 Blase et al.
10,568,621 B2 2/2020 Shelton, IV et al.
10,568,624 B2 2/2020 Shelton, IV et al.
10,568,625 B2 2/2020 Harris et al.
10,568,626 B2 2/2020 Shelton, IV et al.
10,568,629 B2 2/2020 Shelton, IV et al.
10,568,632 B2 2/2020 Miller et al.
10,568,652 B2 2/2020 Hess et al.
10,569,071 B2 2/2020 Harris et al.
D879,808 S 3/2020 Harris et al.
D879,809 S 3/2020 Harris et al.
10,575,868 B2 3/2020 Hall et al.
10,580,320 B2 3/2020 Kamiguchi et al.
10,582,928 B2 3/2020 Hunter et al.
10,588,231 B2 3/2020 Sgroi, Jr. et al.
10,588,623 B2 3/2020 Schmid et al.
10,588,625 B2 3/2020 Weaner et al.
10,588,626 B2 3/2020 Overmyer et al.
10,588,629 B2 3/2020 Malinouskas et al.
10,588,630 B2 3/2020 Shelton, IV et al.
10,588,631 B2 3/2020 Shelton, IV et al.
10,588,632 B2 3/2020 Shelton, IV et al.
10,588,633 B2 3/2020 Shelton, IV et al.
10,589,410 B2 3/2020 Aho
10,595,835 B2 3/2020 Kerr et al.
10,595,862 B2 3/2020 Shelton, IV et al.
10,595,882 B2 3/2020 Parfett et al.
10,595,887 B2 3/2020 Shelton, IV et al.
10,595,929 B2 3/2020 Boudreaux et al.
10,603,036 B2 3/2020 Hunter et al.
10,603,039 B2 3/2020 Vendely et al.
10,603,041 B2 3/2020 Miller et al.
10,603,117 B2 3/2020 Schings et al.
10,603,128 B2 3/2020 Zergiebel et al.
D882,783 S 4/2020 Shelton, IV et al.
10,610,224 B2 4/2020 Shelton, IV et al.
10,610,225 B2 4/2020 Reed et al.
10,610,236 B2 4/2020 Baril
10,610,313 B2 4/2020 Bailey et al.
10,610,346 B2 4/2020 Schwartz
10,614,184 B2 4/2020 Solki
10,617,411 B2 4/2020 Williams
10,617,412 B2 4/2020 Shelton, IV et al.
10,617,413 B2 4/2020 Shelton, IV et al.
10,617,414 B2 4/2020 Shelton, IV et al.
10,617,416 B2 4/2020 Leimbach et al.
10,617,417 B2 4/2020 Baxter, III et al.
10,617,418 B2 4/2020 Barton et al.
10,617,420 B2 4/2020 Shelton, IV et al.
10,617,438 B2 4/2020 O'Keefe et al.
10,624,616 B2 4/2020 Mukherjee et al.
10,624,630 B2 4/2020 Deville et al.
10,624,633 B2 4/2020 Shelton, IV et al.
10,624,634 B2 4/2020 Shelton, IV et al.
10,624,635 B2 4/2020 Harris et al.
10,624,709 B2 4/2020 Remm
10,624,861 B2 4/2020 Widenhouse et al.
10,625,062 B2 4/2020 Matlock et al.
10,631,857 B2 4/2020 Kostrzewski
10,631,858 B2 4/2020 Burbank
10,631,859 B2 4/2020 Shelton, IV et al.
10,631,860 B2 4/2020 Bakos et al.
10,636,104 B2 4/2020 Mazar et al.
10,639,018 B2 5/2020 Shelton, IV et al.
10,639,034 B2 5/2020 Harris et al.
10,639,035 B2 5/2020 Shelton, IV et al.
10,639,036 B2 5/2020 Yates et al.
10,639,037 B2 5/2020 Shelton, IV et al.
10,639,038 B2 5/2020 Scott et al.
10,639,089 B2 5/2020 Manwaring et al.
10,639,115 B2 5/2020 Shelton, IV et al.
10,642,633 B1 5/2020 Chopra et al.
10,645,905 B2 5/2020 Gandola et al.
10,646,220 B2 5/2020 Shelton, IV et al.
10,646,292 B2 5/2020 Solomon et al.
10,653,413 B2 5/2020 Worthington et al.
10,653,417 B2 5/2020 Shelton, IV et al.
10,653,435 B2 5/2020 Shelton, IV et al.
10,653,477 B2 5/2020 Nagtegaal
10,660,640 B2 5/2020 Yates et al.
10,667,408 B2 5/2020 Sgroi, Jr. et al.
D888,953 S 6/2020 Baxter, III et al.
10,667,808 B2 6/2020 Baxter, III et al.
10,667,809 B2 6/2020 Bakos et al.
10,667,810 B2 6/2020 Shelton, IV et al.
10,667,811 B2 6/2020 Harris et al.
10,667,818 B2 6/2020 McLain et al.
10,674,895 B2 6/2020 Yeung et al.
10,675,021 B2 6/2020 Harris et al.
10,675,024 B2 6/2020 Shelton, IV et al.
10,675,025 B2 6/2020 Swayze et al.
10,675,026 B2 6/2020 Harris et al.
10,675,028 B2 6/2020 Shelton, IV et al.
10,675,035 B2 6/2020 Zingman
10,675,080 B2 6/2020 Woloszko et al.
10,675,102 B2 6/2020 Forgione et al.
10,677,035 B2 6/2020 Balan et al.
10,682,134 B2 6/2020 Shelton, IV et al.
10,682,136 B2 6/2020 Harris et al.
10,682,137 B2 6/2020 Stokes et al.
10,682,138 B2 6/2020 Shelton, IV et al.
10,682,141 B2 6/2020 Moore et al.
10,682,142 B2 6/2020 Shelton, IV et al.
10,687,806 B2 6/2020 Shelton, IV et al.
10,687,809 B2 6/2020 Shelton, IV et al.
10,687,810 B2 6/2020 Shelton, IV et al.
10,687,812 B2 6/2020 Shelton, IV et al.
10,687,813 B2 6/2020 Shelton, IV et al.
10,687,817 B2 6/2020 Shelton, IV et al.
10,687,819 B2 6/2020 Stokes et al.
10,687,904 B2 6/2020 Harris et al.
10,695,053 B2 6/2020 Hess et al.
10,695,055 B2 6/2020 Shelton, IV et al.
10,695,057 B2 6/2020 Shelton, IV et al.
10,695,058 B2 6/2020 Lytle, IV et al.
10,695,062 B2 6/2020 Leimbach et al.
10,695,063 B2 6/2020 Morgan et al.

(56) References Cited

U.S. PATENT DOCUMENTS

| | | | |
|---|---|---|---|
| 10,695,074 | B2 | 6/2020 | Carusillo |
| 10,695,081 | B2 | 6/2020 | Shelton, IV et al. |
| 10,695,119 | B2 | 6/2020 | Smith |
| 10,695,123 | B2 | 6/2020 | Allen, IV |
| 10,695,187 | B2 | 6/2020 | Moskowitz et al. |
| D890,784 | S | 7/2020 | Shelton, IV et al. |
| D890,805 | S | 7/2020 | Echeverri et al. |
| 10,702,266 | B2 | 7/2020 | Parihar et al. |
| 10,702,267 | B2 | 7/2020 | Hess et al. |
| 10,702,270 | B2 | 7/2020 | Shelton, IV et al. |
| 10,702,271 | B2 | 7/2020 | Aranyi et al. |
| 10,705,660 | B2 | 7/2020 | Xiao |
| 10,709,446 | B2 | 7/2020 | Harris et al. |
| 10,709,468 | B2 | 7/2020 | Shelton, IV et al. |
| 10,709,469 | B2 | 7/2020 | Shelton, IV et al. |
| 10,709,495 | B2 | 7/2020 | Broderick et al. |
| 10,709,496 | B2 | 7/2020 | Moua et al. |
| 10,716,563 | B2 | 7/2020 | Shelton, IV et al. |
| 10,716,565 | B2 | 7/2020 | Shelton, IV et al. |
| 10,716,568 | B2 | 7/2020 | Hall et al. |
| 10,716,614 | B2 | 7/2020 | Yates et al. |
| 10,717,179 | B2 | 7/2020 | Koenig et al. |
| 10,722,232 | B2 | 7/2020 | Yates et al. |
| 10,722,233 | B2 | 7/2020 | Wellman |
| 10,722,292 | B2 | 7/2020 | Arya et al. |
| 10,722,293 | B2 | 7/2020 | Arya et al. |
| 10,722,317 | B2 | 7/2020 | Ward et al. |
| D893,717 | S | 8/2020 | Messerly et al. |
| 10,729,432 | B2 | 8/2020 | Shelton, IV et al. |
| 10,729,434 | B2 | 8/2020 | Harris et al. |
| 10,729,435 | B2 | 8/2020 | Richard |
| 10,729,436 | B2 | 8/2020 | Shelton, IV et al. |
| 10,729,443 | B2 | 8/2020 | Cabrera et al. |
| 10,729,458 | B2 | 8/2020 | Stoddard et al. |
| 10,729,501 | B2 | 8/2020 | Leimbach et al. |
| 10,729,509 | B2 | 8/2020 | Shelton, IV et al. |
| 10,736,616 | B2 | 8/2020 | Scheib et al. |
| 10,736,628 | B2 | 8/2020 | Yates et al. |
| 10,736,629 | B2 | 8/2020 | Shelton, IV et al. |
| 10,736,630 | B2 | 8/2020 | Huang et al. |
| 10,736,633 | B2 | 8/2020 | Vendely et al. |
| 10,736,634 | B2 | 8/2020 | Shelton, IV et al. |
| 10,736,636 | B2 | 8/2020 | Baxter, III et al. |
| 10,736,644 | B2 | 8/2020 | Windolf et al. |
| 10,736,702 | B2 | 8/2020 | Harris et al. |
| 10,737,398 | B2 | 8/2020 | Remirez et al. |
| 10,743,849 | B2 | 8/2020 | Shelton, IV et al. |
| 10,743,850 | B2 | 8/2020 | Hibner et al. |
| 10,743,851 | B2 | 8/2020 | Swayze et al. |
| 10,743,868 | B2 | 8/2020 | Shelton, IV et al. |
| 10,743,870 | B2 | 8/2020 | Hall et al. |
| 10,743,872 | B2 | 8/2020 | Leimbach et al. |
| 10,743,873 | B2 | 8/2020 | Overmyer et al. |
| 10,743,874 | B2 | 8/2020 | Shelton, IV et al. |
| 10,743,875 | B2 | 8/2020 | Shelton, IV et al. |
| 10,743,877 | B2 | 8/2020 | Shelton, IV et al. |
| 10,743,930 | B2 | 8/2020 | Nagtegaal |
| 10,751,048 | B2 | 8/2020 | Whitman et al. |
| 10,751,051 | B2 | 8/2020 | Weir et al. |
| 10,751,053 | B2 | 8/2020 | Harris et al. |
| 10,751,076 | B2 | 8/2020 | Laurent et al. |
| 10,751,104 | B2 | 8/2020 | Mistry et al. |
| 10,751,138 | B2 | 8/2020 | Giordano et al. |
| 10,758,226 | B2 | 9/2020 | Weir et al. |
| 10,758,229 | B2 | 9/2020 | Shelton, IV et al. |
| 10,758,230 | B2 | 9/2020 | Shelton, IV et al. |
| 10,758,232 | B2 | 9/2020 | Shelton, IV et al. |
| 10,758,233 | B2 | 9/2020 | Scheib et al. |
| 10,758,259 | B2 | 9/2020 | Demmy et al. |
| 10,765,425 | B2 | 9/2020 | Yates et al. |
| 10,765,427 | B2 | 9/2020 | Shelton, IV et al. |
| 10,765,429 | B2 | 9/2020 | Leimbach et al. |
| 10,765,430 | B2 | 9/2020 | Wixey |
| 10,765,432 | B2 | 9/2020 | Moore et al. |
| 10,765,442 | B2 | 9/2020 | Strobl |
| 10,772,625 | B2 | 9/2020 | Shelton, IV et al. |
| 10,772,628 | B2 | 9/2020 | Chen et al. |
| 10,772,629 | B2 | 9/2020 | Shelton, IV et al. |
| 10,772,630 | B2 | 9/2020 | Wixey |
| 10,772,631 | B2 | 9/2020 | Zergiebel et al. |
| 10,772,632 | B2 | 9/2020 | Kostrzewski |
| 10,772,651 | B2 | 9/2020 | Shelton, IV et al. |
| 10,779,818 | B2 | 9/2020 | Zemlok et al. |
| 10,779,820 | B2 | 9/2020 | Harris et al. |
| 10,779,821 | B2 | 9/2020 | Harris et al. |
| 10,779,822 | B2 | 9/2020 | Yates et al. |
| 10,779,823 | B2 | 9/2020 | Shelton, IV et al. |
| 10,779,824 | B2 | 9/2020 | Shelton, IV et al. |
| 10,779,825 | B2 | 9/2020 | Shelton, IV et al. |
| 10,779,826 | B2 | 9/2020 | Shelton, IV et al. |
| 10,779,903 | B2 | 9/2020 | Wise et al. |
| 10,780,539 | B2 | 9/2020 | Shelton, IV et al. |
| 10,786,248 | B2 | 9/2020 | Rousseau et al. |
| 10,786,253 | B2 | 9/2020 | Shelton, IV et al. |
| 10,786,255 | B2 | 9/2020 | Hodgkinson et al. |
| D898,767 | S | 10/2020 | Shah et al. |
| D899,455 | S | 10/2020 | Rondoni et al. |
| 10,792,038 | B2 | 10/2020 | Becerra et al. |
| 10,796,471 | B2 | 10/2020 | Leimbach et al. |
| 10,799,240 | B2 | 10/2020 | Shelton, IV et al. |
| 10,799,306 | B2 | 10/2020 | Robinson et al. |
| 10,806,448 | B2 | 10/2020 | Shelton, IV et al. |
| 10,806,449 | B2 | 10/2020 | Shelton, IV et al. |
| 10,806,450 | B2 | 10/2020 | Yates et al. |
| 10,806,451 | B2 | 10/2020 | Harris et al. |
| 10,806,453 | B2 | 10/2020 | Chen et al. |
| 10,806,479 | B2 | 10/2020 | Shelton, IV et al. |
| 10,813,638 | B2 | 10/2020 | Shelton, IV et al. |
| 10,813,639 | B2 | 10/2020 | Shelton, IV et al. |
| 10,813,640 | B2 | 10/2020 | Adams et al. |
| 10,813,641 | B2 | 10/2020 | Setser et al. |
| 10,813,683 | B2 | 10/2020 | Baxter, III et al. |
| 10,813,705 | B2 | 10/2020 | Hares et al. |
| 10,813,710 | B2 | 10/2020 | Grubbs |
| 10,820,939 | B2 | 11/2020 | Sartor |
| 10,828,028 | B2 | 11/2020 | Harris et al. |
| 10,828,030 | B2 | 11/2020 | Weir et al. |
| 10,828,032 | B2 | 11/2020 | Leimbach et al. |
| 10,828,033 | B2 | 11/2020 | Shelton, IV et al. |
| 10,828,089 | B2 | 11/2020 | Clark et al. |
| 10,835,216 | B2 | 11/2020 | Stevenson et al. |
| 10,835,245 | B2 | 11/2020 | Swayze et al. |
| 10,835,246 | B2 | 11/2020 | Shelton, IV et al. |
| 10,835,247 | B2 | 11/2020 | Shelton, IV et al. |
| 10,835,249 | B2 | 11/2020 | Schellin et al. |
| 10,835,251 | B2 | 11/2020 | Shelton, IV et al. |
| 10,835,330 | B2 | 11/2020 | Shelton, IV et al. |
| 10,842,357 | B2 | 11/2020 | Moskowitz et al. |
| 10,842,473 | B2 | 11/2020 | Scheib et al. |
| 10,842,488 | B2 | 11/2020 | Swayze et al. |
| 10,842,489 | B2 | 11/2020 | Shelton, IV |
| 10,842,490 | B2 | 11/2020 | DiNardo et al. |
| 10,842,491 | B2 | 11/2020 | Shelton, IV et al. |
| 10,842,492 | B2 | 11/2020 | Shelton, IV et al. |
| 10,842,523 | B2 | 11/2020 | Shelton, IV et al. |
| D904,612 | S | 12/2020 | Wynn et al. |
| D904,613 | S | 12/2020 | Wynn et al. |
| D906,355 | S | 12/2020 | Messerly et al. |
| 10,849,621 | B2 | 12/2020 | Whitfield et al. |
| 10,849,623 | B2 | 12/2020 | Dunki-Jacobs et al. |
| 10,849,697 | B2 | 12/2020 | Yates et al. |
| 10,856,866 | B2 | 12/2020 | Shelton, IV et al. |
| 10,856,867 | B2 | 12/2020 | Shelton, IV et al. |
| 10,856,868 | B2 | 12/2020 | Shelton, IV et al. |
| 10,856,869 | B2 | 12/2020 | Shelton, IV et al. |
| 10,856,870 | B2 | 12/2020 | Harris et al. |
| 10,863,981 | B2 | 12/2020 | Overmyer et al. |
| 10,863,984 | B2 | 12/2020 | Shelton, IV et al. |
| 10,863,986 | B2 | 12/2020 | Yates et al. |
| 10,869,663 | B2 | 12/2020 | Shelton, IV et al. |
| 10,869,664 | B2 | 12/2020 | Shelton, IV |
| 10,869,665 | B2 | 12/2020 | Shelton, IV et al. |
| 10,869,666 | B2 | 12/2020 | Shelton, IV et al. |
| 10,869,669 | B2 | 12/2020 | Shelton, IV et al. |

(56) References Cited

U.S. PATENT DOCUMENTS

| | | | |
|---|---|---|---|
| 10,874,290 | B2 | 12/2020 | Walen et al. |
| 10,874,391 | B2 | 12/2020 | Shelton, IV et al. |
| 10,874,392 | B2 | 12/2020 | Scirica et al. |
| 10,874,393 | B2 | 12/2020 | Satti, III et al. |
| 10,874,396 | B2 | 12/2020 | Moore et al. |
| 10,874,399 | B2 | 12/2020 | Zhang |
| 10,874,474 | B2 | 12/2020 | Wu et al. |
| 10,879,275 | B2 | 12/2020 | Li et al. |
| D907,647 | S | 1/2021 | Siebel et al. |
| D907,648 | S | 1/2021 | Siebel et al. |
| D908,216 | S | 1/2021 | Messerly et al. |
| 10,881,339 | B2 | 1/2021 | Peyser et al. |
| 10,881,395 | B2 | 1/2021 | Merchant et al. |
| 10,881,396 | B2 | 1/2021 | Shelton, IV et al. |
| 10,881,398 | B2 | 1/2021 | Whitman et al. |
| 10,881,399 | B2 | 1/2021 | Shelton, IV et al. |
| 10,881,401 | B2 | 1/2021 | Baber et al. |
| 10,881,446 | B2 | 1/2021 | Strobl |
| 10,888,318 | B2 | 1/2021 | Parihar et al. |
| 10,888,321 | B2 | 1/2021 | Shelton, IV et al. |
| 10,888,322 | B2 | 1/2021 | Morgan et al. |
| 10,888,323 | B2 | 1/2021 | Chen et al. |
| 10,888,325 | B2 | 1/2021 | Harris et al. |
| 10,888,328 | B2 | 1/2021 | Shelton, IV et al. |
| 10,888,329 | B2 | 1/2021 | Moore et al. |
| 10,888,330 | B2 | 1/2021 | Moore et al. |
| 10,888,369 | B2 | 1/2021 | Messerly et al. |
| 10,892,899 | B2 | 1/2021 | Shelton, IV et al. |
| 10,893,853 | B2 | 1/2021 | Shelton, IV et al. |
| 10,893,863 | B2 | 1/2021 | Shelton, IV et al. |
| 10,893,864 | B2 | 1/2021 | Harris et al. |
| 10,893,867 | B2 | 1/2021 | Leimbach et al. |
| 10,898,183 | B2 | 1/2021 | Shelton, IV et al. |
| 10,898,184 | B2 | 1/2021 | Yates et al. |
| 10,898,185 | B2 | 1/2021 | Overmyer et al. |
| 10,898,186 | B2 | 1/2021 | Bakos et al. |
| 10,898,190 | B2 | 1/2021 | Yates et al. |
| 10,898,193 | B2 | 1/2021 | Shelton, IV et al. |
| 10,898,194 | B2 | 1/2021 | Moore et al. |
| 10,898,195 | B2 | 1/2021 | Moore et al. |
| 10,903,685 | B2 | 1/2021 | Yates et al. |
| D910,847 | S | 2/2021 | Shelton, IV et al. |
| 10,905,415 | B2 | 2/2021 | DiNardo et al. |
| 10,905,418 | B2 | 2/2021 | Shelton, IV et al. |
| 10,905,420 | B2 | 2/2021 | Jasemian et al. |
| 10,905,422 | B2 | 2/2021 | Bakos et al. |
| 10,905,423 | B2 | 2/2021 | Baber et al. |
| 10,905,426 | B2 | 2/2021 | Moore et al. |
| 10,905,427 | B2 | 2/2021 | Moore et al. |
| 10,911,515 | B2 | 2/2021 | Biasi et al. |
| 10,912,559 | B2 | 2/2021 | Harris et al. |
| 10,912,562 | B2 | 2/2021 | Dunki-Jacobs et al. |
| 10,912,575 | B2 | 2/2021 | Shelton, IV et al. |
| 10,918,364 | B2 | 2/2021 | Applegate et al. |
| 10,918,380 | B2 | 2/2021 | Morgan et al. |
| 10,918,385 | B2 | 2/2021 | Overmyer et al. |
| 10,918,386 | B2 | 2/2021 | Shelton, IV et al. |
| 10,919,156 | B2 | 2/2021 | Roberts et al. |
| 10,925,600 | B2 | 2/2021 | McCuen |
| 10,925,605 | B2 | 2/2021 | Moore et al. |
| D914,878 | S | 3/2021 | Shelton, IV et al. |
| 10,932,772 | B2 | 3/2021 | Shelton, IV et al. |
| 10,932,774 | B2 | 3/2021 | Shelton, IV |
| 10,932,775 | B2 | 3/2021 | Shelton, IV et al. |
| 10,932,778 | B2 | 3/2021 | Smith et al. |
| 10,932,779 | B2 | 3/2021 | Vendely et al. |
| 10,932,784 | B2 | 3/2021 | Mozdzierz et al. |
| 10,932,804 | B2 | 3/2021 | Scheib et al. |
| 10,932,806 | B2 | 3/2021 | Shelton, IV et al. |
| 10,932,872 | B2 | 3/2021 | Shelton, IV et al. |
| 10,944,728 | B2 | 3/2021 | Wiener et al. |
| 10,945,727 | B2 | 3/2021 | Shelton, IV et al. |
| 10,945,728 | B2 | 3/2021 | Morgan et al. |
| 10,945,729 | B2 | 3/2021 | Shelton, IV et al. |
| 10,945,731 | B2 | 3/2021 | Baxter, III et al. |
| 10,952,708 | B2 | 3/2021 | Scheib et al. |
| 10,952,726 | B2 | 3/2021 | Chowaniec |
| 10,952,727 | B2 | 3/2021 | Giordano et al. |
| 10,952,728 | B2 | 3/2021 | Shelton, IV et al. |
| 10,952,759 | B2 | 3/2021 | Messerly et al. |
| 10,952,767 | B2 | 3/2021 | Kostrzewski et al. |
| 10,959,722 | B2 | 3/2021 | Morgan et al. |
| 10,959,725 | B2 | 3/2021 | Kerr et al. |
| 10,959,726 | B2 | 3/2021 | Williams et al. |
| 10,959,727 | B2 | 3/2021 | Hunter et al. |
| 10,959,731 | B2 | 3/2021 | Casasanta, Jr. et al. |
| 10,959,744 | B2 | 3/2021 | Shelton, IV et al. |
| 10,959,797 | B2 | 3/2021 | Licht et al. |
| D917,500 | S | 4/2021 | Siebel et al. |
| 10,966,627 | B2 | 4/2021 | Shelton, IV et al. |
| 10,966,717 | B2 | 4/2021 | Shah et al. |
| 10,966,718 | B2 | 4/2021 | Shelton, IV et al. |
| 10,966,791 | B2 | 4/2021 | Harris et al. |
| 10,973,515 | B2 | 4/2021 | Harris et al. |
| 10,973,516 | B2 | 4/2021 | Shelton, IV et al. |
| 10,973,517 | B2 | 4/2021 | Wixey |
| 10,973,519 | B2 | 4/2021 | Weir et al. |
| 10,973,520 | B2 | 4/2021 | Shelton, IV et al. |
| 10,980,534 | B2 | 4/2021 | Yates et al. |
| 10,980,535 | B2 | 4/2021 | Yates et al. |
| 10,980,536 | B2 | 4/2021 | Weaner et al. |
| 10,980,537 | B2 | 4/2021 | Shelton, IV et al. |
| 10,980,538 | B2 | 4/2021 | Nalagatla et al. |
| 10,980,539 | B2 | 4/2021 | Harris et al. |
| 10,980,560 | B2 | 4/2021 | Shelton, IV et al. |
| 10,983,646 | B2 | 4/2021 | Yoon et al. |
| 10,987,102 | B2 | 4/2021 | Gonzalez et al. |
| 10,987,178 | B2 | 4/2021 | Shelton, IV et al. |
| 10,993,713 | B2 | 5/2021 | Shelton, IV et al. |
| 10,993,715 | B2 | 5/2021 | Shelton, IV et al. |
| 10,993,716 | B2 | 5/2021 | Shelton, IV et al. |
| 10,993,717 | B2 | 5/2021 | Shelton, IV et al. |
| 11,000,274 | B2 | 5/2021 | Shelton, IV et al. |
| 11,000,275 | B2 | 5/2021 | Shelton, IV et al. |
| 11,000,277 | B2 | 5/2021 | Giordano et al. |
| 11,000,278 | B2 | 5/2021 | Shelton, IV et al. |
| 11,000,279 | B2 | 5/2021 | Shelton, IV et al. |
| 11,005,291 | B2 | 5/2021 | Calderoni |
| 11,006,951 | B2 | 5/2021 | Giordano et al. |
| 11,006,955 | B2 | 5/2021 | Shelton, IV et al. |
| 11,007,004 | B2 | 5/2021 | Shelton, IV et al. |
| 11,007,022 | B2 | 5/2021 | Shelton, IV et al. |
| 11,013,511 | B2 | 5/2021 | Huang et al. |
| 11,013,552 | B2 | 5/2021 | Widenhouse et al. |
| 11,013,563 | B2 | 5/2021 | Shelton, IV et al. |
| 11,020,016 | B2 | 6/2021 | Wallace et al. |
| 11,020,112 | B2 | 6/2021 | Shelton, IV et al. |
| 11,020,113 | B2 | 6/2021 | Shelton, IV et al. |
| 11,020,114 | B2 | 6/2021 | Shelton, IV et al. |
| 11,020,115 | B2 | 6/2021 | Scheib et al. |
| 11,020,172 | B2 | 6/2021 | Garrison |
| 11,026,678 | B2 | 6/2021 | Overmyer et al. |
| 11,026,680 | B2 | 6/2021 | Shelton, IV et al. |
| 11,026,684 | B2 | 6/2021 | Shelton, IV et al. |
| 11,026,686 | B2 | 6/2021 | Aranyi |
| 11,026,687 | B2 | 6/2021 | Shelton, IV et al. |
| 11,026,712 | B2 | 6/2021 | Shelton, IV et al. |
| 11,026,713 | B2 | 6/2021 | Stokes et al. |
| 11,026,751 | B2 | 6/2021 | Shelton, IV et al. |
| 11,033,267 | B2 | 6/2021 | Shelton, IV et al. |
| 11,039,834 | B2 | 6/2021 | Harris et al. |
| 11,039,836 | B2 | 6/2021 | Shelton, IV et al. |
| 11,039,837 | B2 | 6/2021 | Shelton, IV et al. |
| 11,039,849 | B2 | 6/2021 | Bucciaglia et al. |
| 11,045,189 | B2 | 6/2021 | Yates et al. |
| 11,045,191 | B2 | 6/2021 | Shelton, IV et al. |
| 11,045,192 | B2 | 6/2021 | Harris et al. |
| 11,045,196 | B2 | 6/2021 | Olson et al. |
| 11,045,197 | B2 | 6/2021 | Shelton, IV et al. |
| 11,045,199 | B2 | 6/2021 | Mozdzierz et al. |
| 11,045,270 | B2 | 6/2021 | Shelton, IV et al. |
| D925,563 | S | 7/2021 | Melvin et al. |
| 11,051,807 | B2 | 7/2021 | Shelton, IV et al. |
| 11,051,810 | B2 | 7/2021 | Harris et al. |

(56) References Cited

U.S. PATENT DOCUMENTS 11,051,811 B2 7/2021 Shelton, IV et al.
11,051,813 B2 7/2021 Shelton, IV et al.
11,051,836 B2 7/2021 Shelton, IV et al.
11,051,840 B2 7/2021 Shelton, IV et al.
11,051,873 B2 7/2021 Wiener et al.
11,058,418 B2 7/2021 Shelton, IV et al.
11,058,420 B2 7/2021 Shelton, IV et al.
11,058,422 B2 7/2021 Harris et al.
11,058,423 B2 7/2021 Shelton, IV et al.
11,058,424 B2 7/2021 Shelton, IV et al.
11,058,425 B2 7/2021 Widenhouse et al.
11,058,426 B2 7/2021 Nalagatla et al.
11,058,498 B2 7/2021 Shelton, IV et al.
11,064,997 B2 7/2021 Shelton, IV et al.
11,064,998 B2 7/2021 Shelton, IV
11,065,000 B2 7/2021 Shankarsetty et al.
11,065,048 B2 7/2021 Messerly et al.
11,069,012 B2 7/2021 Shelton, IV et al.
11,071,542 B2 7/2021 Chen et al.
11,071,543 B2 7/2021 Shelton, IV et al.
11,071,545 B2 7/2021 Baber et al.
11,071,554 B2 7/2021 Parfett et al.
11,071,560 B2 7/2021 Deck et al.
11,076,853 B2 8/2021 Parfett et al.
11,076,854 B2 8/2021 Baber et al.
11,076,921 B2 8/2021 Shelton, IV et al.
11,076,929 B2 8/2021 Shelton, IV et al.
11,083,452 B2 8/2021 Schmid et al.
11,083,453 B2 8/2021 Shelton, IV et al.
11,083,454 B2 8/2021 Harris et al.
11,083,455 B2 8/2021 Shelton, IV et al.
11,083,456 B2 8/2021 Shelton, IV et al.
11,083,457 B2 8/2021 Shelton, IV et al.
11,083,458 B2 8/2021 Harris et al.
11,090,045 B2 8/2021 Shelton, IV
11,090,046 B2 8/2021 Shelton, IV et al.
11,090,047 B2 8/2021 Shelton, IV et al.
11,090,048 B2 8/2021 Fanelli et al.
11,090,049 B2 8/2021 Bakos et al.
11,090,075 B2 8/2021 Hunter et al.
11,096,687 B2 8/2021 Flanagan et al.
11,096,688 B2 8/2021 Shelton, IV et al.
11,096,689 B2 8/2021 Overmyer et al.
11,100,631 B2 8/2021 Yates et al.
11,103,241 B2 8/2021 Yates et al.
11,103,248 B2 8/2021 Shelton, IV et al.
11,103,268 B2 8/2021 Shelton, IV et al.
11,103,269 B2 8/2021 Shelton, IV et al.
11,103,301 B2 8/2021 Messerly et al.
11,109,858 B2 9/2021 Shelton, IV et al.
11,109,859 B2 9/2021 Overmyer et al.
11,109,860 B2 9/2021 Shelton, IV et al.
11,109,866 B2 9/2021 Shelton, IV et al.
11,109,878 B2 9/2021 Shelton, IV et al.
11,109,925 B2 9/2021 Cooper et al.
11,116,485 B2 9/2021 Scheib et al.
11,116,502 B2 9/2021 Shelton, IV et al.
11,116,594 B2 9/2021 Beardsley
11,123,069 B2 9/2021 Baxter, III et al.
11,123,070 B2 9/2021 Shelton, IV et al.
11,129,611 B2 9/2021 Shelton, IV et al.
11,129,613 B2 9/2021 Harris et al.
11,129,615 B2 9/2021 Scheib et al.
11,129,616 B2 9/2021 Shelton, IV et al.
11,129,634 B2 9/2021 Scheib et al.
11,129,636 B2 9/2021 Shelton, IV et al.
11,129,666 B2 9/2021 Messerly et al.
11,129,680 B2 9/2021 Shelton, IV et al.
11,132,462 B2 9/2021 Shelton, IV et al.
11,133,106 B2 9/2021 Shelton, IV et al.
11,134,938 B2 10/2021 Timm et al.
11,134,940 B2 10/2021 Shelton, IV et al.
11,134,942 B2 10/2021 Harris et al.
11,134,943 B2 10/2021 Giordano et al.
11,134,944 B2 10/2021 Wise et al.
11,134,947 B2 10/2021 Shelton, IV et al.
11,135,352 B2 10/2021 Shelton, IV et al.
11,141,152 B2 10/2021 Ingmanson et al.
11,141,153 B2 10/2021 Shelton, IV et al.
11,141,154 B2 10/2021 Shelton, IV et al.
11,141,155 B2 10/2021 Shelton, IV
11,141,156 B2 10/2021 Shelton, IV
11,141,159 B2 10/2021 Scheib et al.
11,141,160 B2 10/2021 Shelton, IV et al.
11,147,547 B2 10/2021 Shelton, IV et al.
11,147,549 B2 10/2021 Timm et al.
11,147,551 B2 10/2021 Shelton, IV
11,147,553 B2 10/2021 Shelton, IV
11,147,554 B2 10/2021 Aronhalt et al.
11,154,296 B2 10/2021 Aronhalt et al.
11,154,297 B2 10/2021 Swayze et al.
11,154,298 B2 10/2021 Timm et al.
11,154,299 B2 10/2021 Shelton, IV et al.
11,154,300 B2 10/2021 Nalagatla et al.
11,154,301 B2 10/2021 Beckman et al.
D936,684 S 11/2021 Luo et al.
11,160,551 B2 11/2021 Shelton, IV et al.
11,160,553 B2 11/2021 Simms et al.
11,160,601 B2 11/2021 Worrell et al.
11,166,716 B2 11/2021 Shelton, IV et al.
11,166,717 B2 11/2021 Shelton, IV et al.
11,166,720 B2 11/2021 Giordano et al.
11,166,772 B2 11/2021 Shelton, IV et al.
11,166,773 B2 11/2021 Ragosta et al.
11,172,580 B2 11/2021 Gaertner, II
11,172,927 B2 11/2021 Shelton, IV
11,172,929 B2 11/2021 Shelton, IV
11,179,150 B2 11/2021 Yates et al.
11,179,151 B2 11/2021 Shelton, IV et al.
11,179,152 B2 11/2021 Morgan et al.
11,179,153 B2 11/2021 Shelton, IV
11,179,155 B2 11/2021 Shelton, IV et al.
11,179,208 B2 11/2021 Yates et al.
11,185,325 B2 11/2021 Shelton, IV et al.
11,185,330 B2 11/2021 Huitema et al.
11,191,539 B2 12/2021 Overmyer et al.
11,191,540 B2 12/2021 Aronhalt et al.
11,191,543 B2 12/2021 Overmyer et al.
11,191,545 B2 12/2021 Vendely et al.
11,197,668 B2 12/2021 Shelton, IV et al.
11,197,670 B2 12/2021 Shelton, IV et al.
11,197,671 B2 12/2021 Shelton, IV et al.
11,197,672 B2 12/2021 Dunki-Jacobs et al.
11,202,570 B2 12/2021 Shelton, IV et al.
11,202,631 B2 12/2021 Shelton, IV et al.
11,202,633 B2 12/2021 Harris et al.
11,207,064 B2 12/2021 Shelton, IV et al.
11,207,065 B2 12/2021 Harris et al.
11,207,067 B2 12/2021 Shelton, IV et al.
11,207,089 B2 12/2021 Kostrzewski et al.
11,207,090 B2 12/2021 Shelton, IV et al.
11,207,146 B2 12/2021 Shelton, IV et al.
11,213,293 B2 1/2022 Worthington et al.
11,213,294 B2 1/2022 Shelton, IV et al.
11,213,302 B2 1/2022 Parfett et al.
11,213,359 B2 1/2022 Shelton, IV et al.
11,219,453 B2 1/2022 Shelton, IV et al.
11,219,455 B2 1/2022 Shelton, IV et al.
11,224,423 B2 1/2022 Shelton, IV et al.
11,224,426 B2 1/2022 Shelton, IV et al.
11,224,427 B2 1/2022 Shelton, IV et al.
11,224,428 B2 1/2022 Scott et al.
11,224,454 B2 1/2022 Shelton, IV et al.
11,224,497 B2 1/2022 Shelton, IV et al.
11,229,436 B2 1/2022 Shelton, IV et al.
11,229,437 B2 1/2022 Shelton, IV et al.
11,234,698 B2 2/2022 Shelton, IV et al.
11,234,700 B2 2/2022 Ragosta et al.
11,241,229 B2 2/2022 Shelton, IV et al.
11,241,230 B2 2/2022 Shelton, IV et al.
11,241,235 B2 2/2022 Shelton, IV et al.
11,246,590 B2 2/2022 Swayze et al.
11,246,592 B2 2/2022 Shelton, IV et al.
11,246,616 B2 2/2022 Shelton, IV et al.

(56) References Cited

U.S. PATENT DOCUMENTS 11,246,618 B2 2/2022 Hall et al.
11,246,678 B2 2/2022 Shelton, IV et al.
11,253,254 B2 2/2022 Kimball et al.
11,253,256 B2 2/2022 Harris et al.
D946,025 S 3/2022 Vogler-Ivashchanka et al.
D946,617 S 3/2022 Ahmed
11,259,799 B2 3/2022 Overmyer et al.
11,259,803 B2 3/2022 Shelton, IV et al.
11,259,805 B2 3/2022 Shelton, IV et al.
11,259,806 B2 3/2022 Shelton, IV et al.
11,259,807 B2 3/2022 Shelton, IV et al.
11,266,405 B2 3/2022 Shelton, IV et al.
11,266,406 B2 3/2022 Leimbach et al.
11,266,409 B2 3/2022 Huitema et al.
11,266,410 B2 3/2022 Shelton, IV et al.
11,266,468 B2 3/2022 Shelton, IV et al.
11,272,927 B2 3/2022 Swayze et al.
11,272,928 B2 3/2022 Shelton, IV
11,272,931 B2 3/2022 Boudreaux et al.
11,272,938 B2 3/2022 Shelton, IV et al.
11,278,279 B2 3/2022 Morgan et al.
11,278,280 B2 3/2022 Shelton, IV et al.
11,278,284 B2 3/2022 Shelton, IV et al.
11,278,288 B2 3/2022 Rector et al.
11,284,890 B2 3/2022 Nalagatla et al.
11,284,891 B2 3/2022 Shelton, IV et al.
11,284,898 B2 3/2022 Baxter, III et al.
11,284,953 B2 3/2022 Shelton, IV et al.
11,291,440 B2 4/2022 Harris et al.
11,291,441 B2 4/2022 Giordano et al.
11,291,442 B2 4/2022 Wixey et al.
11,291,443 B2 4/2022 Viola et al.
11,291,444 B2 4/2022 Boudreaux et al.
11,291,445 B2 4/2022 Shelton, IV et al.
11,291,447 B2 4/2022 Shelton, IV et al.
11,291,449 B2 4/2022 Swensgard et al.
11,291,451 B2 4/2022 Shelton, IV
11,291,465 B2 4/2022 Parihar et al.
11,291,510 B2 4/2022 Shelton, IV et al.
11,298,125 B2 4/2022 Ming et al.
11,298,127 B2 4/2022 Shelton, IV
11,298,128 B2 4/2022 Messerly et al.
11,298,129 B2 4/2022 Bakos et al.
11,298,130 B2 4/2022 Bakos et al.
11,298,132 B2 4/2022 Shelton, IV et al.
11,298,134 B2 4/2022 Huitema et al.
11,304,695 B2 4/2022 Shelton, IV et al.
11,304,696 B2 4/2022 Shelton, IV et al.
11,304,697 B2 4/2022 Fanelli et al.
11,304,699 B2 4/2022 Shelton, IV et al.
11,304,704 B2 4/2022 Thomas et al.
11,311,290 B2 4/2022 Shelton, IV et al.
11,311,292 B2 4/2022 Shelton, IV et al.
11,311,294 B2 4/2022 Swayze et al.
11,311,295 B2 4/2022 Wingardner et al.
11,311,342 B2 4/2022 Parihar et al.
D950,728 S 5/2022 Bakos et al.
D952,144 S 5/2022 Boudreaux
11,317,910 B2 5/2022 Miller et al.
11,317,912 B2 5/2022 Jenkins et al.
11,317,913 B2 5/2022 Shelton, IV et al.
11,317,915 B2 5/2022 Boudreaux et al.
11,317,917 B2 5/2022 Shelton, IV et al.
11,317,919 B2 5/2022 Shelton, IV et al.
11,317,978 B2 5/2022 Cameron et al.
11,324,501 B2 5/2022 Shelton, IV et al.
11,324,503 B2 5/2022 Shelton, IV et al.
11,324,506 B2 5/2022 Beckman et al.
11,324,557 B2 5/2022 Shelton, IV et al.
11,331,100 B2 5/2022 Boudreaux et al.
11,331,101 B2 5/2022 Harris et al.
11,337,691 B2 5/2022 Widenhouse et al.
11,337,693 B2 5/2022 Hess et al.
11,337,698 B2 5/2022 Baxter, III et al.
11,344,299 B2 5/2022 Yates et al.
11,344,303 B2 5/2022 Shelton, IV et al.
D954,736 S 6/2022 Teague et al.
11,350,843 B2 6/2022 Shelton, IV et al.
11,350,916 B2 6/2022 Shelton, IV et al.
11,350,928 B2 6/2022 Shelton, IV et al.
11,350,929 B2 6/2022 Giordano et al.
11,350,932 B2 6/2022 Shelton, IV et al.
11,350,934 B2 6/2022 Bakos et al.
11,350,935 B2 6/2022 Shelton, IV et al.
11,350,938 B2 6/2022 Shelton, IV et al.
11,357,503 B2 6/2022 Bakos et al.
11,361,176 B2 6/2022 Shelton, IV et al.
11,364,027 B2 6/2022 Harris et al.
11,364,046 B2 6/2022 Shelton, IV et al.
11,369,366 B2 6/2022 Scheib et al.
11,369,368 B2 6/2022 Shelton, IV et al.
11,369,376 B2 6/2022 Simms et al.
11,369,377 B2 6/2022 Boudreaux et al.
11,373,755 B2 6/2022 Shelton, IV et al.
11,376,001 B2 7/2022 Shelton, IV et al.
11,376,002 B2 7/2022 Shelton, IV et al.
11,376,082 B2 7/2022 Shelton, IV et al.
11,376,098 B2 7/2022 Shelton, IV et al.
11,382,625 B2 7/2022 Huitema et al.
11,382,626 B2 7/2022 Shelton, IV et al.
11,382,627 B2 7/2022 Huitema et al.
11,382,628 B2 7/2022 Baxter, III et al.
11,382,638 B2 7/2022 Harris et al.
11,382,697 B2 7/2022 Shelton, IV et al.
11,382,704 B2 7/2022 Overmyer et al.
11,389,160 B2 7/2022 Shelton, IV et al.
11,389,161 B2 7/2022 Shelton, IV et al.
11,389,162 B2 7/2022 Baber et al.
11,389,164 B2 7/2022 Yates et al.
11,395,651 B2 7/2022 Shelton, IV et al.
11,395,652 B2 7/2022 Parihar et al.
11,399,828 B2 8/2022 Swayze et al.
11,399,829 B2 8/2022 Leimbach et al.
11,399,831 B2 8/2022 Overmyer et al.
11,399,837 B2 8/2022 Shelton, IV et al.
11,406,377 B2 8/2022 Schmid et al.
11,406,378 B2 8/2022 Baxter, III et al.
11,406,380 B2 8/2022 Yates et al.
11,406,381 B2 8/2022 Parihar et al.
11,406,382 B2 8/2022 Shelton, IV et al.
11,406,386 B2 8/2022 Baber et al.
11,406,390 B2 8/2022 Shelton, IV et al.
11,406,442 B2 8/2022 Davison et al.
11,410,259 B2 8/2022 Harris et al.
11,413,041 B2 8/2022 Viola et al.
11,413,042 B2 8/2022 Shelton, IV et al.
11,413,102 B2 8/2022 Shelton, IV et al.
11,419,606 B2 8/2022 Overmyer et al.
11,419,630 B2 8/2022 Yates et al.
11,424,027 B2 8/2022 Shelton, IV
11,426,160 B2 8/2022 Shelton, IV et al.
11,426,167 B2 8/2022 Shelton, IV et al.
11,426,251 B2 8/2022 Kimball et al.
D962,980 S 9/2022 Frenkler et al.
D964,564 S 9/2022 Boudreaux
11,432,816 B2 9/2022 Leimbach et al.
11,432,819 B2 9/2022 Rector et al.
11,432,885 B2 9/2022 Shelton, IV et al.
11,439,391 B2 9/2022 Bruns et al.
11,439,470 B2 9/2022 Spivey et al.
11,446,029 B2 9/2022 Shelton, IV et al.
11,446,034 B2 9/2022 Shelton, IV et al.
11,452,526 B2 9/2022 Ross et al.
11,452,528 B2 9/2022 Leimbach et al.
D966,512 S 10/2022 Shelton, IV et al.
D967,421 S 10/2022 Shelton, IV et al.
11,457,918 B2 10/2022 Shelton, IV et al.
11,464,511 B2 10/2022 Timm et al.
11,464,512 B2 10/2022 Shelton, IV et al.
11,464,513 B2 10/2022 Shelton, IV et al.
11,464,514 B2 10/2022 Yates et al.
11,464,601 B2 10/2022 Shelton, IV et al.
11,471,155 B2 10/2022 Shelton, IV et al.
11,471,156 B2 10/2022 Shelton, IV et al.

(56) References Cited

U.S. PATENT DOCUMENTS 11,471,157 B2 10/2022 Baxter, III et al.
11,478,241 B2 10/2022 Shelton, IV et al.
11,478,242 B2 10/2022 Shelton, IV et al.
11,478,244 B2 10/2022 DiNardo et al.
D969,849 S 11/2022 Stipech et al.
D971,232 S 11/2022 Siebel et al.
11,484,307 B2 11/2022 Hall et al.
11,484,309 B2 11/2022 Harris et al.
11,484,310 B2 11/2022 Shelton, IV et al.
11,484,311 B2 11/2022 Shelton, IV et al.
11,484,312 B2 11/2022 Shelton, IV et al.
11,490,889 B2 11/2022 Overmyer et al.
11,497,488 B2 11/2022 Leimbach et al.
11,497,489 B2 11/2022 Baxter, III et al.
11,497,492 B2 11/2022 Shelton, IV
11,497,499 B2 11/2022 Shelton, IV et al.
11,504,116 B2 11/2022 Schmid et al.
11,504,119 B2 11/2022 Shelton, IV et al.
11,504,122 B2 11/2022 Shelton, IV et al.
11,504,192 B2 11/2022 Shelton, IV et al.
11,510,671 B2 11/2022 Shelton, IV et al.
11,510,673 B1 11/2022 Chen et al.
11,510,741 B2 11/2022 Shelton, IV et al.
11,517,304 B2 12/2022 Yates et al.
11,517,306 B2 12/2022 Miller et al.
11,517,309 B2 12/2022 Bakos et al.
11,517,311 B2 12/2022 Lytle, IV et al.
11,517,315 B2 12/2022 Huitema et al.
11,517,325 B2 12/2022 Shelton, IV et al.
11,517,390 B2 12/2022 Baxter, III
11,523,821 B2 12/2022 Harris et al.
11,523,822 B2 12/2022 Shelton, IV et al.
11,523,823 B2 12/2022 Hunter et al.
11,523,824 B2 12/2022 Williams
11,523,859 B2 12/2022 Shelton, IV et al.
11,529,137 B2 12/2022 Shelton, IV et al.
11,529,138 B2 12/2022 Jaworek et al.
11,529,139 B2 12/2022 Shelton, IV et al.
11,529,140 B2 12/2022 Shelton, IV et al.
11,529,142 B2 12/2022 Leimbach et al.
11,534,162 B2 12/2022 Shelton, IV
11,534,259 B2 12/2022 Leimbach et al.
D974,560 S 1/2023 Shelton, IV et al.
D975,278 S 1/2023 Shelton, IV et al.
D975,850 S 1/2023 Shelton, IV et al.
D975,851 S 1/2023 Shelton, IV et al.
D976,401 S 1/2023 Shelton, IV et al.
11,540,824 B2 1/2023 Shelton, IV et al.
11,540,829 B2 1/2023 Shelton, IV et al.
11,547,403 B2 1/2023 Shelton, IV et al.
11,547,404 B2 1/2023 Shelton, IV et al.
11,553,911 B2 1/2023 Shelton, IV et al.
11,553,916 B2 1/2023 Vendely et al.
11,553,919 B2 1/2023 Shelton, IV et al.
11,553,971 B2 1/2023 Shelton, IV et al.
11,559,302 B2 1/2023 Timm et al.
11,559,303 B2 1/2023 Shelton, IV et al.
11,559,304 B2 1/2023 Boudreaux et al.
11,559,307 B2 1/2023 Shelton, IV et al.
11,559,308 B2 1/2023 Yates et al.
11,559,496 B2 1/2023 Widenhouse et al.
11,564,679 B2 1/2023 Parihar et al.
11,564,682 B2 1/2023 Timm et al.
11,564,686 B2 1/2023 Yates et al.
11,564,688 B2 1/2023 Swayze et al.
11,564,703 B2 1/2023 Shelton, IV et al.
11,564,756 B2 1/2023 Shelton, IV et al.
11,571,207 B2 2/2023 Shelton, IV et al.
11,571,210 B2 2/2023 Shelton, IV et al.
11,571,212 B2 2/2023 Yates et al.
11,571,215 B2 2/2023 Shelton, IV et al.
11,571,231 B2 2/2023 Hess et al.
11,576,668 B2 2/2023 Shelton, IV et al.
11,576,672 B2 2/2023 Shelton, IV et al.
11,576,673 B2 2/2023 Shelton, IV
11,576,677 B2 2/2023 Shelton, IV et al.
11,583,274 B2 2/2023 Widenhouse et al.
11,583,277 B2 2/2023 Shelton, IV et al.
11,583,278 B2 2/2023 Shelton, IV et al.
11,583,279 B2 2/2023 Smith et al.
11,589,863 B2 2/2023 Weir et al.
11,589,865 B2 2/2023 Shelton, IV et al.
11,589,888 B2 2/2023 Shelton, IV et al.
D980,425 S 3/2023 Baxter, III
11,596,406 B2 3/2023 Huitema et al.
11,602,340 B2 3/2023 Schmid et al.
11,602,346 B2 3/2023 Shelton, IV
11,602,366 B2 3/2023 Shelton, IV et al.
11,607,219 B2 3/2023 Shelton, IV et al.
11,607,239 B2 3/2023 Swensgard et al.
11,607,278 B2 3/2023 Shelton, IV et al.
11,612,393 B2 3/2023 Morgan et al.
11,612,394 B2 3/2023 Morgan et al.
11,612,395 B2 3/2023 Yates et al.
11,617,575 B2 4/2023 Yates et al.
11,617,576 B2 4/2023 Yates et al.
11,617,577 B2 4/2023 Huang
11,622,763 B2 4/2023 Parihar et al.
11,622,766 B2 4/2023 Shelton, IV
11,622,785 B2 4/2023 Hess et al.
11,627,959 B2 4/2023 Shelton, IV et al.
11,627,960 B2 4/2023 Shelton, IV et al.
11,628,006 B2 4/2023 Henderson et al.
11,633,183 B2 4/2023 Parihar et al.
11,633,185 B2 4/2023 Wilson et al.
D985,009 S 5/2023 Barrett et al.
D985,617 S 5/2023 Bahatyrevich et al.
11,638,581 B2 5/2023 Parihar et al.
11,638,582 B2 5/2023 Bakos et al.
11,638,583 B2 5/2023 Yates et al.
11,638,587 B2 5/2023 Shelton, IV et al.
11,642,125 B2 5/2023 Harris et al.
11,642,128 B2 5/2023 Shelton, IV et al.
11,648,005 B2 5/2023 Yates et al.
11,648,006 B2 5/2023 Timm et al.
11,648,008 B2 5/2023 Shelton, IV et al.
11,648,009 B2 5/2023 Jenkins
11,648,022 B2 5/2023 Shelton, IV
11,648,024 B2 5/2023 Shelton, IV et al.
11,653,914 B2 5/2023 Shelton, IV et al.
11,653,915 B2 5/2023 Shelton, IV et al.
11,653,917 B2 5/2023 Scott et al.
11,653,918 B2 5/2023 Swayze et al.
11,653,920 B2 5/2023 Shelton, IV et al.
11,659,023 B2 5/2023 Shelton, IV et al.
11,660,090 B2 5/2023 Bakos et al.
11,660,110 B2 5/2023 Shelton, IV et al.
11,660,163 B2 5/2023 Shelton, IV et al.
11,666,327 B2 6/2023 Whitman et al.
11,666,332 B2 6/2023 Giordano et al.
11,672,531 B2 6/2023 Timm et al.
11,672,532 B2 6/2023 Shelton, IV et al.
11,672,536 B2 6/2023 Shelton, IV et al.
11,672,605 B2 6/2023 Messerly et al.
11,678,877 B2 6/2023 Shelton, IV et al.
11,678,880 B2 6/2023 Shelton, IV et al.
11,678,881 B2 6/2023 Yates et al.
11,678,882 B2 6/2023 Shelton, IV et al.
11,684,360 B2 6/2023 Shelton, IV et al.
11,684,361 B2 6/2023 Yates et al.
11,684,365 B2 6/2023 Shelton, IV et al.
11,684,369 B2 6/2023 Shelton, IV et al.
11,684,434 B2 6/2023 Shelton, IV
11,690,615 B2 7/2023 Parihar et al.
11,690,623 B2 7/2023 Shelton, IV et al.
11,696,757 B2 7/2023 Shelton, IV et al.
11,696,759 B2 7/2023 Shelton, IV et al.
11,696,761 B2 7/2023 Shelton, IV
11,696,778 B2 7/2023 Shelton, IV et al.
11,701,110 B2 7/2023 Yates et al.
11,701,111 B2 7/2023 Shelton, IV et al.
11,701,113 B2 7/2023 Shelton, IV et al.
11,701,114 B2 7/2023 Shelton, IV et al.
11,701,115 B2 7/2023 Harris et al.

(56) References Cited

U.S. PATENT DOCUMENTS 11,701,118 B2 7/2023 Viola et al.
11,707,273 B2 7/2023 Kerr et al.
11,712,244 B2 8/2023 Vendely et al.
11,712,303 B2 8/2023 Shelton, IV et al.
11,717,285 B2 8/2023 Yates et al.
11,717,289 B2 8/2023 Leimbach
11,717,291 B2 8/2023 Morgan et al.
11,717,294 B2 8/2023 Huitema et al.
11,717,297 B2 8/2023 Baber et al.
11,723,657 B2 8/2023 Shelton, IV et al.
11,723,658 B2 8/2023 Bakos et al.
11,723,662 B2 8/2023 Leimbach et al.
11,730,471 B2 8/2023 Worthington et al.
11,730,473 B2 8/2023 Creamer et al.
11,730,474 B2 8/2023 Shelton, IV
11,730,477 B2 8/2023 Smith et al.
11,737,749 B2 8/2023 Shelton, IV et al.
11,737,751 B2 8/2023 Shelton, IV et al.
11,737,754 B2 8/2023 Shelton, IV et al.
11,744,581 B2 9/2023 Shelton, IV et al.
11,744,583 B2 9/2023 Shelton, IV et al.
11,744,588 B2 9/2023 Beckman et al.
11,744,593 B2 9/2023 Shelton, IV et al.
11,744,603 B2 9/2023 Shelton, IV et al.
11,744,604 B2 9/2023 Shelton, IV et al.
11,749,877 B2 9/2023 Shelton, IV et al.
11,751,867 B2 9/2023 Shelton, IV et al.
11,751,869 B2 9/2023 Shelton, IV et al.
11,751,872 B2 9/2023 Zeiner et al.
11,751,937 B2 9/2023 Harlev et al.
11,759,202 B2 9/2023 Morgan et al.
11,759,208 B2 9/2023 Harris et al.
11,759,224 B2 9/2023 Shelton, IV et al.
11,766,257 B2 9/2023 Shelton, IV et al.
11,766,258 B2 9/2023 Shelton, IV et al.
11,766,259 B2 9/2023 Shelton, IV et al.
11,766,260 B2 9/2023 Harris et al.
11,771,419 B2 10/2023 Shelton, IV et al.
11,771,425 B2 10/2023 Swayze et al.
11,771,426 B2 10/2023 Giordano et al.
11,771,454 B2 10/2023 Swensgard et al.
11,779,336 B2 10/2023 Shelton, IV et al.
11,779,420 B2 10/2023 Shelton, IV et al.
11,786,245 B2 10/2023 Shelton, IV
11,793,509 B2 10/2023 Baxter, III et al.
11,793,512 B2 10/2023 Shelton, IV
11,793,513 B2 10/2023 Harris et al.
11,793,518 B2 10/2023 Shelton, IV et al.
11,793,522 B2 10/2023 Vendely et al.
11,793,537 B2 10/2023 Shelton, IV et al.
11,801,047 B2 10/2023 Yates et al.
11,801,051 B2 10/2023 Shelton, IV et al.
11,801,098 B2 10/2023 Stokes et al.
11,806,011 B2 11/2023 Bakos et al.
11,806,013 B2 11/2023 Shelton, IV et al.
11,812,954 B2 11/2023 Yates et al.
11,812,960 B2 11/2023 Shelton, IV et al.
11,812,961 B2 11/2023 Giordano et al.
11,812,965 B2 11/2023 Baxter, III et al.
11,819,231 B2 11/2023 Shelton, IV et al.
11,826,012 B2 11/2023 Adams et al.
11,826,042 B2 11/2023 Adams et al.
11,826,047 B2 11/2023 Huang et al.
11,826,048 B2 11/2023 Shelton, IV et al.
11,826,132 B2 11/2023 Shelton, IV et al.
2001/0000531 A1 4/2001 Casscells et al.
2001/0025183 A1 9/2001 Shahidi
2001/0025184 A1 9/2001 Messerly
2001/0030219 A1 10/2001 Green et al.
2001/0034530 A1 10/2001 Malackowski et al.
2001/0045442 A1 11/2001 Whitman
2002/0014510 A1 2/2002 Richter et al.
2002/0022810 A1 2/2002 Urich
2002/0022836 A1 2/2002 Goble et al.
2002/0022861 A1 2/2002 Jacobs et al.
2002/0023126 A1 2/2002 Flavin
2002/0029032 A1 3/2002 Arkin
2002/0029036 A1 3/2002 Goble et al.
2002/0042620 A1 4/2002 Julian et al.
2002/0045905 A1 4/2002 Gerbi et al.
2002/0054158 A1 5/2002 Asami
2002/0065535 A1 5/2002 Kneifel et al.
2002/0066764 A1 6/2002 Perry et al.
2002/0077660 A1 6/2002 Kayan et al.
2002/0082612 A1 6/2002 Moll et al.
2002/0082625 A1* 6/2002 Huxel ................. A61B 17/115
606/153
2002/0087048 A1 7/2002 Brock et al.
2002/0087148 A1 7/2002 Brock et al.
2002/0091374 A1 7/2002 Cooper
2002/0095175 A1 7/2002 Brock et al.
2002/0099374 A1 7/2002 Pendekanti et al.
2002/0103494 A1 8/2002 Pacey
2002/0111621 A1 8/2002 Wallace et al.
2002/0111624 A1 8/2002 Witt et al.
2002/0116063 A1 8/2002 Giannetti et al.
2002/0117533 A1 8/2002 Milliman et al.
2002/0117534 A1 8/2002 Green et al.
2002/0120254 A1* 8/2002 Julian ..................... B66C 23/48
606/1
2002/0127265 A1 9/2002 Bowman et al.
2002/0128633 A1 9/2002 Brock et al.
2002/0133236 A1 9/2002 Rousseau
2002/0134811 A1 9/2002 Napier et al.
2002/0135474 A1 9/2002 Sylliassen
2002/0138086 A1 9/2002 Sixto et al.
2002/0143340 A1 10/2002 Kaneko
2002/0151770 A1 10/2002 Noll et al.
2002/0156497 A1 10/2002 Nagase et al.
2002/0158593 A1 10/2002 Henderson et al.
2002/0161277 A1 10/2002 Boone et al.
2002/0165559 A1 11/2002 Grant et al.
2002/0165562 A1 11/2002 Grant et al.
2002/0177848 A1 11/2002 Truckai et al.
2002/0185514 A1 12/2002 Adams et al.
2002/0188170 A1 12/2002 Santamore et al.
2002/0188287 A1 12/2002 Zvuloni et al.
2003/0004610 A1 1/2003 Niemeyer et al.
2003/0009193 A1 1/2003 Corsaro
2003/0011245 A1 1/2003 Fiebig
2003/0012805 A1 1/2003 Chen et al.
2003/0018323 A1 1/2003 Wallace et al.
2003/0028236 A1 2/2003 Gillick et al.
2003/0040670 A1 2/2003 Govari
2003/0045835 A1 3/2003 Anderson et al.
2003/0045900 A1 3/2003 Hahnen et al.
2003/0047230 A1 3/2003 Kim
2003/0047582 A1 3/2003 Sonnenschein et al.
2003/0050628 A1 3/2003 Whitman et al.
2003/0050654 A1 3/2003 Whitman et al.
2003/0066858 A1 4/2003 Holgersson
2003/0078647 A1 4/2003 Vallana et al.
2003/0083648 A1 5/2003 Wang et al.
2003/0084983 A1 5/2003 Rangachari et al.
2003/0093103 A1 5/2003 Malackowski et al.
2003/0093160 A1 5/2003 Maksimovic et al.
2003/0094356 A1 5/2003 Waldron
2003/0096158 A1 5/2003 Takano et al.
2003/0105475 A1 6/2003 Sancoff et al.
2003/0114851 A1 6/2003 Truckai et al.
2003/0121586 A1 7/2003 Mitra et al.
2003/0129382 A1 7/2003 Treat
2003/0135204 A1 7/2003 Lee et al.
2003/0135388 A1 7/2003 Martucci et al.
2003/0139741 A1 7/2003 Goble et al.
2003/0144660 A1 7/2003 Mollenauer
2003/0149406 A1 8/2003 Martineau et al.
2003/0153908 A1 8/2003 Goble et al.
2003/0153968 A1 8/2003 Geis et al.
2003/0158463 A1 8/2003 Julian et al.
2003/0163029 A1 8/2003 Sonnenschein et al.
2003/0163085 A1 8/2003 Tanner et al.
2003/0164172 A1 9/2003 Chumas et al.
2003/0181800 A1 9/2003 Bonutti

(56) References Cited

U.S. PATENT DOCUMENTS

2003/0181900 A1 9/2003 Long
2003/0190584 A1 10/2003 Heasley
2003/0195387 A1 10/2003 Kortenbach et al.
2003/0205029 A1 11/2003 Chapolini et al.
2003/0212005 A1 11/2003 Petito et al.
2003/0216619 A1 11/2003 Scirica et al.
2003/0216732 A1 11/2003 Truckai et al.
2003/0220541 A1 11/2003 Salisbury et al.
2003/0236505 A1 12/2003 Bonadio et al.
2004/0006335 A1 1/2004 Garrison
2004/0006340 A1 1/2004 Latterell et al.
2004/0007608 A1 1/2004 Ehrenfels et al.
2004/0024457 A1 2/2004 Boyce et al.
2004/0028502 A1 2/2004 Cummins
2004/0030333 A1 2/2004 Goble
2004/0034287 A1 2/2004 Hickle
2004/0034357 A1 2/2004 Beane et al.
2004/0044295 A1 3/2004 Reinert et al.
2004/0044364 A1 3/2004 DeVries et al.
2004/0049121 A1 3/2004 Yaron
2004/0049172 A1 3/2004 Root et al.
2004/0059362 A1 3/2004 Knodel et al.
2004/0068161 A1 4/2004 Couvillon
2004/0068224 A1 4/2004 Couvillon et al.
2004/0068307 A1 4/2004 Goble
2004/0070369 A1 4/2004 Sakakibara
2004/0073222 A1 4/2004 Koseki
2004/0078037 A1 4/2004 Batchelor et al.
2004/0082952 A1 4/2004 Dycus et al.
2004/0085180 A1 5/2004 Juang
2004/0092967 A1 5/2004 Sancoff et al.
2004/0092992 A1 5/2004 Adams et al.
2004/0093020 A1 5/2004 Sinton
2004/0093024 A1 5/2004 Lousararian et al.
2004/0093029 A1 5/2004 Zubik et al.
2004/0098040 A1 5/2004 Taniguchi et al.
2004/0101822 A1 5/2004 Wiesner et al.
2004/0102783 A1 5/2004 Sutterlin et al.
2004/0108357 A1 6/2004 Milliman et al.
2004/0110439 A1 6/2004 Chaikof et al.
2004/0115022 A1 6/2004 Albertson et al.
2004/0116952 A1 6/2004 Sakurai et al.
2004/0119185 A1 6/2004 Chen
2004/0122419 A1 6/2004 Neuberger
2004/0122423 A1 6/2004 Dycus et al.
2004/0133095 A1 7/2004 Dunki-Jacobs et al.
2004/0133189 A1 7/2004 Sakurai
2004/0143297 A1 7/2004 Ramsey
2004/0147909 A1 7/2004 Johnston et al.
2004/0153100 A1 8/2004 Ahlberg et al.
2004/0158261 A1 8/2004 Vu
2004/0164123 A1 8/2004 Racenet et al.
2004/0166169 A1 8/2004 Malaviya et al.
2004/0167572 A1 8/2004 Roth et al.
2004/0181219 A1 9/2004 Goble et al.
2004/0193189 A1 9/2004 Kortenbach et al.
2004/0197367 A1 10/2004 Rezania et al.
2004/0199181 A1 10/2004 Knodel et al.
2004/0204735 A1 10/2004 Shiroff et al.
2004/0218451 A1 11/2004 Said et al.
2004/0222268 A1 11/2004 Bilotti et al.
2004/0225186 A1 11/2004 Horne et al.
2004/0230230 A1 11/2004 Lindstrom et al.
2004/0231870 A1 11/2004 McCormick et al.
2004/0232194 A1 11/2004 Pedicini et al.
2004/0232197 A1 11/2004 Shelton, IV et al.
2004/0232201 A1 11/2004 Wenchell et al.
2004/0236352 A1 11/2004 Wang et al.
2004/0239582 A1 12/2004 Seymour
2004/0243147 A1 12/2004 Lipow
2004/0243151 A1 12/2004 Demmy et al.
2004/0243163 A1 12/2004 Casiano et al.
2004/0247415 A1 12/2004 Mangone
2004/0249366 A1 12/2004 Kunz
2004/0254455 A1 12/2004 Iddan
2004/0254566 A1 12/2004 Plicchi et al.
2004/0254590 A1 12/2004 Hoffman et al.
2004/0254680 A1 12/2004 Sunaoshi
2004/0260315 A1 12/2004 Dell et al.
2004/0267310 A1 12/2004 Racenet et al.
2004/0267362 A1 12/2004 Hwang et al.
2005/0010158 A1 1/2005 Brugger et al.
2005/0010213 A1 1/2005 Stad et al.
2005/0021078 A1 1/2005 Vleugels et al.
2005/0023325 A1 2/2005 Gresham et al.
2005/0032511 A1 2/2005 Malone et al.
2005/0033136 A1 2/2005 Govari et al.
2005/0033352 A1 2/2005 Zepf et al.
2005/0044489 A1 2/2005 Yamagami et al.
2005/0051163 A1 3/2005 Deem et al.
2005/0054946 A1 3/2005 Krzyzanowski
2005/0057225 A1 3/2005 Marquet
2005/0058890 A1 3/2005 Brazell et al.
2005/0059997 A1 3/2005 Bauman et al.
2005/0067548 A1 3/2005 Inoue
2005/0070925 A1 3/2005 Shelton et al.
2005/0070929 A1 3/2005 Dalessandro et al.
2005/0074593 A1 4/2005 Day et al.
2005/0075561 A1 4/2005 Golden
2005/0079088 A1 4/2005 Wirth et al.
2005/0080342 A1 4/2005 Gilreath et al.
2005/0085693 A1 4/2005 Belson et al.
2005/0085838 A1 4/2005 Thompson et al.
2005/0090709 A1 4/2005 Okada et al.
2005/0090817 A1 4/2005 Phan
2005/0096683 A1 5/2005 Ellins et al.
2005/0108643 A1 5/2005 Schybergson et al.
2005/0116673 A1 6/2005 Carl et al.
2005/0118048 A1 6/2005 Traxinger
2005/0119524 A1 6/2005 Sekine et al.
2005/0120836 A1 6/2005 Anderson
2005/0121390 A1 6/2005 Wallace et al.
2005/0124855 A1 6/2005 Jaffe et al.
2005/0125028 A1 6/2005 Looper et al.
2005/0125897 A1 6/2005 Wyslucha et al.
2005/0129730 A1 6/2005 Pang et al.
2005/0129735 A1 6/2005 Cook et al.
2005/0130682 A1 6/2005 Takara et al.
2005/0131173 A1 6/2005 McDaniel et al.
2005/0131211 A1 6/2005 Bayley et al.
2005/0131390 A1 6/2005 Heinrich et al.
2005/0131436 A1 6/2005 Johnston et al.
2005/0131457 A1 6/2005 Douglas et al.
2005/0137454 A1 6/2005 Saadat et al.
2005/0137455 A1 6/2005 Ewers et al.
2005/0139635 A1 6/2005 Wukusick et al.
2005/0139636 A1 6/2005 Schwemberger et al.
2005/0143759 A1 6/2005 Kelly
2005/0143769 A1 6/2005 White et al.
2005/0145671 A1 7/2005 Viola
2005/0145672 A1 7/2005 Schwemberger et al.
2005/0150928 A1 7/2005 Kameyama et al.
2005/0154258 A1 7/2005 Tartaglia et al.
2005/0154406 A1 7/2005 Bombard et al.
2005/0159778 A1 7/2005 Heinrich et al.
2005/0165419 A1 7/2005 Sauer et al.
2005/0169974 A1 8/2005 Tenerz et al.
2005/0171522 A1 8/2005 Christopherson
2005/0177176 A1 8/2005 Gerbi et al.
2005/0177181 A1 8/2005 Kagan et al.
2005/0177249 A1 8/2005 Kladakis et al.
2005/0178813 A1 8/2005 Swayze et al.
2005/0182298 A1 8/2005 Ikeda et al.
2005/0182443 A1 8/2005 Jonn et al.
2005/0184121 A1 8/2005 Heinrich
2005/0186240 A1 8/2005 Ringeisen et al.
2005/0187545 A1 8/2005 Hooven et al.
2005/0191936 A1 9/2005 Marine et al.
2005/0197859 A1 9/2005 Wilson et al.
2005/0203550 A1 9/2005 Laufer et al.
2005/0209614 A1 9/2005 Fenter et al.
2005/0216055 A1 9/2005 Scirica et al.
2005/0222587 A1 10/2005 Jinno et al.
2005/0222611 A1 10/2005 Weitkamp

(56) References Cited

U.S. PATENT DOCUMENTS

2005/0222616 A1 10/2005 Rethy et al.
2005/0222665 A1 10/2005 Aranyi
2005/0228224 A1 10/2005 Okada et al.
2005/0228446 A1 10/2005 Mooradian et al.
2005/0230453 A1 10/2005 Viola
2005/0240178 A1 10/2005 Morley et al.
2005/0242950 A1 11/2005 Lindsay et al.
2005/0245965 A1 11/2005 Orban, III et al.
2005/0246881 A1 11/2005 Kelly et al.
2005/0251063 A1 11/2005 Basude
2005/0251110 A1 11/2005 Nixon
2005/0256452 A1 11/2005 DeMarchi et al.
2005/0256546 A1 11/2005 Vaisnys et al.
2005/0258963 A1 11/2005 Rodriguez et al.
2005/0261676 A1 11/2005 Hall et al.
2005/0263563 A1 12/2005 Racenet et al.
2005/0267455 A1 12/2005 Eggers et al.
2005/0267464 A1 12/2005 Truckai et al.
2005/0267529 A1 12/2005 Crockett et al.
2005/0274034 A1 12/2005 Hayashida et al.
2005/0283188 A1 12/2005 Loshakove et al.
2005/0283226 A1 12/2005 Haverkost
2006/0000867 A1 1/2006 Shelton et al.
2006/0008504 A1 1/2006 Kerr et al.
2006/0008787 A1 1/2006 Hayman et al.
2006/0011698 A1 1/2006 Okada et al.
2006/0015009 A1 1/2006 Jaffe et al.
2006/0016853 A1 1/2006 Racenet
2006/0019056 A1 1/2006 Turner et al.
2006/0020167 A1 1/2006 Sitzmann
2006/0020258 A1 1/2006 Strauss et al.
2006/0020272 A1 1/2006 Gildenberg
2006/0020336 A1 1/2006 Liddicoat
2006/0025812 A1 2/2006 Shelton
2006/0041188 A1 2/2006 Dirusso et al.
2006/0047275 A1 3/2006 Goble
2006/0049229 A1 3/2006 Milliman et al.
2006/0052824 A1 3/2006 Ransick et al.
2006/0052825 A1 3/2006 Ransick et al.
2006/0053951 A1 3/2006 Revelis et al.
2006/0064086 A1 3/2006 Odom
2006/0079735 A1 4/2006 Martone et al.
2006/0079874 A1 4/2006 Faller et al.
2006/0079879 A1 4/2006 Faller et al.
2006/0086032 A1 4/2006 Valencic et al.
2006/0087746 A1 4/2006 Lipow
2006/0089535 A1 4/2006 Raz et al.
2006/0089628 A1 4/2006 Whitman
2006/0097026 A1 5/2006 Shelton
2006/0097699 A1 5/2006 Kamenoff
2006/0100643 A1 5/2006 Laufer et al.
2006/0100649 A1 5/2006 Hart
2006/0106369 A1 5/2006 Desai et al.
2006/0111711 A1 5/2006 Goble
2006/0111723 A1 5/2006 Chapolini et al.
2006/0111738 A1 5/2006 Wenchell
2006/0116634 A1 6/2006 Shachar
2006/0142656 A1 6/2006 Malackowski et al.
2006/0142772 A1 6/2006 Ralph et al.
2006/0144898 A1 7/2006 Bilotti et al.
2006/0154546 A1 7/2006 Murphy et al.
2006/0161050 A1 7/2006 Butler et al.
2006/0161185 A1 7/2006 Saadat et al.
2006/0167471 A1 7/2006 Phillips
2006/0173290 A1 8/2006 Lavallee et al.
2006/0173470 A1 8/2006 Oray et al.
2006/0176031 A1 8/2006 Forman et al.
2006/0176242 A1 8/2006 Jaramaz et al.
2006/0178556 A1 8/2006 Hasser et al.
2006/0180633 A1 8/2006 Emmons
2006/0180634 A1 8/2006 Shelton et al.
2006/0185682 A1 8/2006 Marczyk
2006/0189440 A1 8/2006 Gravagne
2006/0199999 A1 9/2006 Ikeda et al.
2006/0201989 A1 9/2006 Ojeda
2006/0206100 A1 9/2006 Eskridge et al.
2006/0217729 A1 9/2006 Eskridge et al.
2006/0226196 A1 10/2006 Hueil et al.
2006/0226957 A1 10/2006 Miller et al.
2006/0229493 A1 10/2006 Weiser et al.
2006/0235368 A1 10/2006 Oz
2006/0241666 A1 10/2006 Briggs et al.
2006/0241691 A1 10/2006 Wilk
2006/0243469 A1 11/2006 Webster
2006/0244460 A1 11/2006 Weaver
2006/0247584 A1 11/2006 Sheetz et al.
2006/0252981 A1 11/2006 Matsuda et al.
2006/0252990 A1 11/2006 Kubach
2006/0252993 A1 11/2006 Freed et al.
2006/0258904 A1 11/2006 Stefanchik et al.
2006/0259073 A1 11/2006 Miyamoto et al.
2006/0261763 A1 11/2006 Lott et al.
2006/0263444 A1 11/2006 Ming et al.
2006/0264831 A1 11/2006 Skwarek et al.
2006/0264929 A1 11/2006 Goble et al.
2006/0271042 A1 11/2006 Latterell et al.
2006/0271102 A1 11/2006 Bosshard et al.
2006/0282064 A1 12/2006 Shimizu et al.
2006/0284730 A1 12/2006 Schmid et al.
2006/0287576 A1 12/2006 Tsuji et al.
2006/0289600 A1 12/2006 Wales et al.
2006/0289602 A1 12/2006 Wales et al.
2006/0291981 A1 12/2006 Viola et al.
2007/0005045 A1 1/2007 Mintz et al.
2007/0009570 A1 1/2007 Kim et al.
2007/0010702 A1 1/2007 Wang et al.
2007/0010838 A1 1/2007 Shelton et al.
2007/0016235 A1 1/2007 Tanaka et al.
2007/0016272 A1 1/2007 Thompson et al.
2007/0018958 A1 1/2007 Tavakoli et al.
2007/0026039 A1 2/2007 Drumheller et al.
2007/0026040 A1 2/2007 Crawley et al.
2007/0027459 A1 2/2007 Horvath et al.
2007/0027468 A1 2/2007 Wales et al.
2007/0027551 A1 2/2007 Farnsworth et al.
2007/0034668 A1 2/2007 Holsten et al.
2007/0034669 A1 2/2007 de la Torre et al.
2007/0043338 A1 2/2007 Moll et al.
2007/0043384 A1 2/2007 Ortiz et al.
2007/0043387 A1 2/2007 Vargas et al.
2007/0049951 A1 3/2007 Menn
2007/0049966 A1 3/2007 Bonadio et al.
2007/0051375 A1 3/2007 Milliman
2007/0055228 A1 3/2007 Berg et al.
2007/0055305 A1 3/2007 Schnyder et al.
2007/0069851 A1 3/2007 Sung et al.
2007/0073341 A1 3/2007 Smith et al.
2007/0073389 A1 3/2007 Bolduc et al.
2007/0078328 A1 4/2007 Ozaki et al.
2007/0078484 A1 4/2007 Talarico et al.
2007/0084897 A1 4/2007 Shelton et al.
2007/0088376 A1 4/2007 Zacharias
2007/0090788 A1 4/2007 Hansford et al.
2007/0093869 A1 4/2007 Bloom et al.
2007/0102472 A1 5/2007 Shelton
2007/0102476 A1 5/2007 Shelton et al.
2007/0103437 A1 5/2007 Rosenberg
2007/0106113 A1 5/2007 Ravo
2007/0106317 A1 5/2007 Shelton et al.
2007/0118115 A1 5/2007 Artale et al.
2007/0134251 A1 6/2007 Ashkenazi et al.
2007/0135686 A1 6/2007 Pruitt et al.
2007/0135803 A1 6/2007 Belson
2007/0152612 A1 7/2007 Chen et al.
2007/0152829 A1 7/2007 Lindsay et al.
2007/0155010 A1 7/2007 Farnsworth et al.
2007/0162056 A1 7/2007 Gerbi et al.
2007/0170225 A1 7/2007 Shelton et al.
2007/0173687 A1 7/2007 Shima et al.
2007/0173813 A1 7/2007 Odom
2007/0173872 A1 7/2007 Neuenfeldt
2007/0175950 A1 8/2007 Shelton et al.
2007/0175951 A1 8/2007 Shelton et al.
2007/0175955 A1 8/2007 Shelton et al.

(56) References Cited

U.S. PATENT DOCUMENTS

2007/0179476 A1 8/2007 Shelton et al.
2007/0179477 A1 8/2007 Danger
2007/0185545 A1 8/2007 Duke
2007/0187857 A1 8/2007 Riley et al.
2007/0190110 A1 8/2007 Pameijer et al.
2007/0191868 A1 8/2007 Theroux et al.
2007/0191915 A1 8/2007 Strother et al.
2007/0194079 A1 8/2007 Hueil et al.
2007/0194081 A1 8/2007 Hueil et al.
2007/0194082 A1 8/2007 Morgan et al.
2007/0197954 A1 8/2007 Keenan
2007/0198039 A1 8/2007 Jones et al.
2007/0203510 A1 8/2007 Bettuchi
2007/0207010 A1 9/2007 Caspi
2007/0207186 A1 9/2007 Scanlon et al.
2007/0208359 A1 9/2007 Hoffman
2007/0208375 A1 9/2007 Nishizawa et al.
2007/0213750 A1 9/2007 Weadock
2007/0221701 A1 9/2007 Ortiz et al.
2007/0225562 A1 9/2007 Spivey et al.
2007/0233163 A1 10/2007 Bombard et al.
2007/0243227 A1 10/2007 Gertner
2007/0244471 A1 10/2007 Malackowski
2007/0244496 A1 10/2007 Hellenkamp
2007/0246505 A1 10/2007 Pace-Floridia et al.
2007/0250093 A1 10/2007 Makower et al.
2007/0260132 A1 11/2007 Sterling
2007/0260242 A1 11/2007 Dycus et al.
2007/0262592 A1 11/2007 Hwang et al.
2007/0270660 A1 11/2007 Caylor et al.
2007/0270790 A1 11/2007 Smith et al.
2007/0275035 A1 11/2007 Herman et al.
2007/0276409 A1 11/2007 Ortiz et al.
2007/0279011 A1 12/2007 Jones et al.
2007/0286892 A1 12/2007 Herzberg et al.
2007/0290027 A1 12/2007 Maatta et al.
2007/0296286 A1 12/2007 Avenell
2008/0000941 A1 1/2008 Sonnenschein et al.
2008/0003196 A1 1/2008 Jonn et al.
2008/0007237 A1 1/2008 Nagashima et al.
2008/0015598 A1 1/2008 Prommersberger
2008/0021486 A1 1/2008 Oyola et al.
2008/0029570 A1 2/2008 Shelton et al.
2008/0029573 A1 2/2008 Shelton et al.
2008/0029574 A1 2/2008 Shelton et al.
2008/0029575 A1 2/2008 Shelton et al.
2008/0029576 A1 2/2008 Shelton et al.
2008/0030170 A1 2/2008 Dacquay et al.
2008/0039746 A1 2/2008 Hissong et al.
2008/0042861 A1 2/2008 Dacquay et al.
2008/0044622 A1 2/2008 Noda et al.
2008/0046000 A1 2/2008 Lee et al.
2008/0051833 A1 2/2008 Gramuglia et al.
2008/0064920 A1 3/2008 Bakos et al.
2008/0064921 A1 3/2008 Larkin et al.
2008/0065153 A1 3/2008 Allard et al.
2008/0069736 A1 3/2008 Mingerink et al.
2008/0071328 A1 3/2008 Haubrich et al.
2008/0077158 A1 3/2008 Haider et al.
2008/0078802 A1 4/2008 Hess et al.
2008/0081948 A1 4/2008 Weisenburgh et al.
2008/0082114 A1 4/2008 McKenna et al.
2008/0082125 A1 4/2008 Murray et al.
2008/0082126 A1 4/2008 Murray et al.
2008/0083807 A1 4/2008 Beardsley et al.
2008/0083811 A1 4/2008 Marczyk
2008/0085296 A1 4/2008 Powell et al.
2008/0086078 A1 4/2008 Powell et al.
2008/0091072 A1 4/2008 Omori et al.
2008/0094228 A1 4/2008 Welch et al.
2008/0108443 A1 5/2008 Jinno et al.
2008/0114250 A1 5/2008 Urbano et al.
2008/0125634 A1 5/2008 Ryan et al.
2008/0125749 A1 5/2008 Olson
2008/0126984 A1 5/2008 Fleishman et al.
2008/0128469 A1 6/2008 Dalessandro et al.
2008/0129253 A1 6/2008 Shiue et al.
2008/0132894 A1 6/2008 Coilard-Lavirotte et al.
2008/0134841 A1* 6/2008 Wilson .................. B25B 13/481 81/57.33
2008/0135600 A1 6/2008 Hiranuma et al.
2008/0140088 A1 6/2008 Orban, III
2008/0140115 A1 6/2008 Stopek
2008/0140159 A1 6/2008 Bornhoft et al.
2008/0149682 A1 6/2008 Uhm
2008/0154299 A1 6/2008 Livneh
2008/0154335 A1 6/2008 Thrope et al.
2008/0169328 A1 7/2008 Shelton
2008/0169330 A1 7/2008 Shelton et al.
2008/0169332 A1 7/2008 Shelton et al.
2008/0169333 A1 7/2008 Shelton et al.
2008/0172087 A1 7/2008 Fuchs et al.
2008/0177392 A1 7/2008 Williams et al.
2008/0179371 A1* 7/2008 Gardner .................... B25C 5/15 227/1
2008/0185419 A1* 8/2008 Smith .................. A61B 17/115 227/179.1
2008/0190989 A1 8/2008 Crews et al.
2008/0196253 A1 8/2008 Ezra et al.
2008/0196419 A1 8/2008 Dube
2008/0197167 A1 8/2008 Viola et al.
2008/0200755 A1 8/2008 Bakos
2008/0200762 A1 8/2008 Stokes et al.
2008/0200835 A1 8/2008 Monson et al.
2008/0200911 A1 8/2008 Long
2008/0200933 A1 8/2008 Bakos et al.
2008/0200934 A1 8/2008 Fox
2008/0206186 A1 8/2008 Butler et al.
2008/0208058 A1 8/2008 Sabata et al.
2008/0214967 A1 9/2008 Aranyi et al.
2008/0216704 A1 9/2008 Eisenbeis et al.
2008/0217376 A1 9/2008 Clauson et al.
2008/0234709 A1 9/2008 Houser
2008/0234866 A1 9/2008 Kishi et al.
2008/0237296 A1 10/2008 Boudreaux et al.
2008/0242939 A1 10/2008 Johnston
2008/0243088 A1 10/2008 Evans
2008/0243143 A1 10/2008 Kuhns et al.
2008/0249536 A1 10/2008 Stahler et al.
2008/0249608 A1 10/2008 Dave
2008/0255413 A1 10/2008 Zemlok et al.
2008/0255420 A1 10/2008 Lee et al.
2008/0255421 A1 10/2008 Hegeman et al.
2008/0255663 A1 10/2008 Akpek et al.
2008/0262654 A1 10/2008 Omori et al.
2008/0269596 A1 10/2008 Revie et al.
2008/0281171 A1 11/2008 Fennell et al.
2008/0281332 A1 11/2008 Taylor
2008/0287944 A1 11/2008 Pearson et al.
2008/0293910 A1 11/2008 Kapiamba et al.
2008/0294179 A1 11/2008 Balbierz et al.
2008/0296343 A1 12/2008 Schall et al.
2008/0296346 A1 12/2008 Shelton, IV et al.
2008/0296347 A1 12/2008 Shelton, IV et al.
2008/0297287 A1 12/2008 Shachar et al.
2008/0298784 A1 12/2008 Kastner
2008/0300579 A1 12/2008 Broehl et al.
2008/0308504 A1 12/2008 Hallan et al.
2008/0308602 A1 12/2008 Timm et al.
2008/0308603 A1 12/2008 Shelton et al.
2008/0308607 A1 12/2008 Timm et al.
2008/0308608 A1 12/2008 Prommersberger
2008/0308807 A1 12/2008 Yamazaki et al.
2008/0312686 A1 12/2008 Ellingwood
2008/0312687 A1 12/2008 Blier
2008/0315829 A1 12/2008 Jones et al.
2009/0001121 A1 1/2009 Hess et al.
2009/0001130 A1 1/2009 Hess et al.
2009/0004455 A1 1/2009 Gravagna et al.
2009/0005809 A1 1/2009 Hess et al.
2009/0007014 A1 1/2009 Coomer et al.
2009/0012534 A1 1/2009 Madhani et al.
2009/0015195 A1 1/2009 Loth-Krausser
2009/0020958 A1 1/2009 Soul

(56) References Cited

U.S. PATENT DOCUMENTS

2009/0030437 A1 1/2009 Houser et al.
2009/0043253 A1 2/2009 Podaima
2009/0048583 A1 2/2009 Williams et al.
2009/0048589 A1 2/2009 Takashino et al.
2009/0053288 A1 2/2009 Eskridge, Jr. et al.
2009/0057369 A1 3/2009 Smith et al.
2009/0069806 A1 3/2009 De La Mora Levy et al.
2009/0076506 A1 3/2009 Baker
2009/0076510 A1 3/2009 Bell et al.
2009/0078736 A1 3/2009 Van Lue
2009/0078739 A1 3/2009 Viola
2009/0081313 A1 3/2009 Aghion et al.
2009/0088659 A1 4/2009 Graham et al.
2009/0090763 A1 4/2009 Zemlok et al.
2009/0090764 A1 4/2009 Viola
2009/0099579 A1 4/2009 Nentwick et al.
2009/0099876 A1 4/2009 Whitman
2009/0110533 A1 4/2009 Jinno
2009/0112234 A1 4/2009 Crainich et al.
2009/0114701 A1 5/2009 Zemlok et al.
2009/0118762 A1 5/2009 Crainch et al.
2009/0119011 A1 5/2009 Kondo et al.
2009/0120994 A1 5/2009 Murray et al.
2009/0131819 A1 5/2009 Ritchie et al.
2009/0132400 A1 5/2009 Conway
2009/0135280 A1 5/2009 Johnston et al.
2009/0138003 A1 5/2009 Deville et al.
2009/0143797 A1 6/2009 Smith et al.
2009/0143855 A1 6/2009 Weber et al.
2009/0149871 A9 6/2009 Kagan et al.
2009/0167548 A1 7/2009 Sugahara
2009/0171147 A1 7/2009 Lee et al.
2009/0177218 A1 7/2009 Young et al.
2009/0177226 A1 7/2009 Reinprecht et al.
2009/0181290 A1 7/2009 Baldwin et al.
2009/0188964 A1 7/2009 Orlov
2009/0192534 A1 7/2009 Ortiz et al.
2009/0196903 A1 8/2009 Kliman
2009/0198272 A1 8/2009 Kerver et al.
2009/0204108 A1 8/2009 Steffen
2009/0204109 A1 8/2009 Grove et al.
2009/0204126 A1 8/2009 Le
2009/0204925 A1 8/2009 Bhat et al.
2009/0206125 A1 8/2009 Huitema et al.
2009/0206126 A1 8/2009 Huitema et al.
2009/0206131 A1 8/2009 Weisenburgh, II et al.
2009/0206133 A1 8/2009 Morgan et al.
2009/0206137 A1 8/2009 Hall et al.
2009/0206139 A1 8/2009 Hall et al.
2009/0206141 A1 8/2009 Huitema et al.
2009/0206142 A1 8/2009 Huitema et al.
2009/0206143 A1 8/2009 Huitema et al.
2009/0218384 A1 9/2009 Aranyi
2009/0221993 A1 9/2009 Sohi et al.
2009/0227834 A1 9/2009 Nakamoto et al.
2009/0234273 A1 9/2009 Intoccia et al.
2009/0236401 A1 9/2009 Cole et al.
2009/0242610 A1 10/2009 Shelton, IV et al.
2009/0246873 A1 10/2009 Yamamoto et al.
2009/0247368 A1 10/2009 Chiang
2009/0247901 A1 10/2009 Zimmer
2009/0248100 A1 10/2009 Vaisnys et al.
2009/0253959 A1 10/2009 Yoshie et al.
2009/0255974 A1 10/2009 Viola
2009/0255977 A1 10/2009 Zemlok
2009/0261141 A1 10/2009 Stratton et al.
2009/0262078 A1 10/2009 Pizzi
2009/0264940 A1 10/2009 Beale et al.
2009/0270853 A1 10/2009 Yachi et al.
2009/0270895 A1 10/2009 Churchill et al.
2009/0273353 A1 11/2009 Kroh et al.
2009/0277288 A1 11/2009 Doepker et al.
2009/0278406 A1 11/2009 Hoffman
2009/0287300 A1 11/2009 Dave et al.
2009/0290016 A1 11/2009 Suda
2009/0292283 A1 11/2009 Odom
2009/0306639 A1 12/2009 Nevo et al.
2009/0308907 A1 12/2009 Nalagatla et al.
2009/0318557 A1 12/2009 Stockel
2009/0318936 A1 12/2009 Harris et al.
2009/0325859 A1 12/2009 Ameer et al.
2010/0002013 A1 1/2010 Kagaya
2010/0005035 A1 1/2010 Carpenter et al.
2010/0012703 A1 1/2010 Calabrese et al.
2010/0015104 A1 1/2010 Fraser et al.
2010/0016853 A1 1/2010 Burbank
2010/0016888 A1 1/2010 Calabrese et al.
2010/0017715 A1 1/2010 Balassanian
2010/0023024 A1 1/2010 Zeiner et al.
2010/0030233 A1 2/2010 Whitman et al.
2010/0030239 A1 2/2010 Viola et al.
2010/0032179 A1 2/2010 Hanspers et al.
2010/0032470 A1 2/2010 Hess et al.
2010/0036370 A1 2/2010 Mirel et al.
2010/0036441 A1 2/2010 Procter
2010/0051668 A1 3/2010 Milliman et al.
2010/0057118 A1 3/2010 Dietz et al.
2010/0065604 A1 3/2010 Weng
2010/0069833 A1 3/2010 Wenderow et al.
2010/0069942 A1 3/2010 Shelton, IV
2010/0076433 A1 3/2010 Taylor et al.
2010/0076483 A1 3/2010 Imuta
2010/0076489 A1 3/2010 Stopek et al.
2010/0081883 A1 4/2010 Murray et al.
2010/0094312 A1 4/2010 Ruiz Morales et al.
2010/0094340 A1 4/2010 Stopek et al.
2010/0094400 A1 4/2010 Bolduc et al.
2010/0100123 A1 4/2010 Bennett
2010/0100124 A1 4/2010 Calabrese et al.
2010/0106167 A1 4/2010 Boulnois et al.
2010/0116519 A1 5/2010 Gareis
2010/0122339 A1 5/2010 Boccacci
2010/0125786 A1 5/2010 Ozawa et al.
2010/0133317 A1 6/2010 Shelton, IV et al.
2010/0137990 A1 6/2010 Apatsidis et al.
2010/0138659 A1 6/2010 Carmichael et al.
2010/0145146 A1 6/2010 Melder
2010/0147921 A1 6/2010 Olson
2010/0147922 A1 6/2010 Olson
2010/0159435 A1 6/2010 Mueller et al.
2010/0168741 A1 7/2010 Sanai et al.
2010/0179022 A1 7/2010 Shirokoshi
2010/0180711 A1 7/2010 Kilibarda et al.
2010/0181364 A1 7/2010 Shelton, IV et al.
2010/0187285 A1 7/2010 Harris et al.
2010/0191255 A1 7/2010 Crainich et al.
2010/0191262 A1 7/2010 Harris et al.
2010/0191292 A1 7/2010 DeMeo et al.
2010/0193566 A1 8/2010 Scheib et al.
2010/0194541 A1 8/2010 Stevenson et al.
2010/0198159 A1 8/2010 Voss et al.
2010/0200257 A1 8/2010 Scrimshaw et al.
2010/0204717 A1 8/2010 Knodel
2010/0204721 A1 8/2010 Young et al.
2010/0217281 A1 8/2010 Matsuoka et al.
2010/0218019 A1 8/2010 Eckhard
2010/0222901 A1 9/2010 Swayze et al.
2010/0228250 A1 9/2010 Brogna
2010/0234687 A1 9/2010 Azarbarzin et al.
2010/0237124 A1* 9/2010 Shima ....................... B25C 1/06
227/129
2010/0241115 A1 9/2010 Benamou et al.
2010/0241137 A1 9/2010 Doyle et al.
2010/0243707 A1 9/2010 Olson et al.
2010/0245102 A1 9/2010 Yokoi
2010/0249497 A1 9/2010 Peine et al.
2010/0249947 A1 9/2010 Lesh et al.
2010/0256675 A1 10/2010 Romans
2010/0258327 A1 10/2010 Esenwein et al.
2010/0267525 A1 10/2010 Tanner
2010/0267662 A1 10/2010 Fielder et al.
2010/0274160 A1 10/2010 Yachi et al.
2010/0291184 A1 11/2010 Clark et al.
2010/0292540 A1 11/2010 Hess et al.

(56) References Cited

U.S. PATENT DOCUMENTS

2010/0298636 A1 11/2010 Castro et al.
2010/0298642 A1 11/2010 Trusty et al.
2010/0301097 A1 12/2010 Scirica et al.
2010/0310623 A1 12/2010 Laurencin et al.
2010/0312261 A1 12/2010 Suzuki et al.
2010/0318085 A1 12/2010 Austin et al.
2010/0325568 A1 12/2010 Pedersen et al.
2010/0327041 A1 12/2010 Milliman et al.
2010/0331856 A1 12/2010 Carlson et al.
2011/0006101 A1 1/2011 Hall et al.
2011/0009694 A1 1/2011 Schultz et al.
2011/0009863 A1 1/2011 Marczyk et al.
2011/0011916 A1 1/2011 Levine
2011/0016960 A1 1/2011 Debrailly
2011/0021871 A1 1/2011 Berkelaar
2011/0022032 A1 1/2011 Zemlok et al.
2011/0024477 A1 2/2011 Hall
2011/0024478 A1 2/2011 Shelton, IV
2011/0025311 A1 2/2011 Chauvin et al.
2011/0028991 A1 2/2011 Ikeda et al.
2011/0029003 A1 2/2011 Lavigne et al.
2011/0029270 A1 2/2011 Mueglitz
2011/0036891 A1 2/2011 Zemlok et al.
2011/0046667 A1 2/2011 Culligan et al.
2011/0049213 A1 3/2011 Schneider et al.
2011/0052660 A1 3/2011 Yang et al.
2011/0056717 A1 3/2011 Herisse
2011/0060363 A1 3/2011 Hess et al.
2011/0066156 A1 3/2011 McGahan et al.
2011/0066243 A1 3/2011 Rivin et al.
2011/0071473 A1 3/2011 Rogers et al.
2011/0082538 A1 4/2011 Dahlgren et al.
2011/0087276 A1 4/2011 Bedi et al.
2011/0088921 A1 4/2011 Forgues et al.
2011/0091515 A1 4/2011 Zilberman et al.
2011/0095064 A1 4/2011 Taylor et al.
2011/0095067 A1 4/2011 Ohdaira
2011/0101069 A1 5/2011 Bombard et al.
2011/0101794 A1 5/2011 Schroeder et al.
2011/0112513 A1 5/2011 Hester et al.
2011/0112517 A1 5/2011 Peine et al.
2011/0112530 A1 5/2011 Keller
2011/0114697 A1 5/2011 Baxter, III et al.
2011/0118708 A1 5/2011 Burbank et al.
2011/0118754 A1 5/2011 Dachs, II et al.
2011/0125149 A1 5/2011 El-Galley et al.
2011/0125176 A1 5/2011 Yates et al.
2011/0127945 A1 6/2011 Yoneda
2011/0129706 A1 6/2011 Takahashi et al.
2011/0144764 A1 6/2011 Bagga et al.
2011/0147433 A1 6/2011 Shelton, IV et al.
2011/0160725 A1 6/2011 Kabaya et al.
2011/0163146 A1 7/2011 Ortiz et al.
2011/0172495 A1 7/2011 Armstrong
2011/0174861 A1 7/2011 Shelton, IV et al.
2011/0189957 A1 8/2011 Hocke
2011/0192882 A1 8/2011 Hess et al.
2011/0198381 A1 8/2011 McCardle et al.
2011/0199225 A1 8/2011 Touchberry et al.
2011/0218400 A1 9/2011 Ma et al.
2011/0218550 A1 9/2011 Ma
2011/0220381 A1 9/2011 Friese et al.
2011/0224543 A1 9/2011 Johnson et al.
2011/0225105 A1 9/2011 Scholer et al.
2011/0230713 A1 9/2011 Kleemann et al.
2011/0235168 A1 9/2011 Sander
2011/0238044 A1 9/2011 Main et al.
2011/0241597 A1 10/2011 Zhu et al.
2011/0251606 A1 10/2011 Kerr
2011/0256266 A1 10/2011 Orme et al.
2011/0271186 A1 11/2011 Owens
2011/0275901 A1 11/2011 Shelton, IV
2011/0276083 A1 11/2011 Shelton, IV et al.
2011/0278035 A1 11/2011 Chen
2011/0278343 A1 11/2011 Knodel et al.
2011/0279268 A1 11/2011 Konishi et al.
2011/0285507 A1 11/2011 Nelson
2011/0290856 A1 12/2011 Shelton, IV et al.
2011/0290858 A1 12/2011 Whitman et al.
2011/0292258 A1 12/2011 Adler et al.
2011/0293690 A1 12/2011 Griffin et al.
2011/0295295 A1 12/2011 Shelton, IV et al.
2011/0295299 A1 12/2011 Braithwaite et al.
2011/0313894 A1 12/2011 Dye et al.
2011/0315413 A1 12/2011 Fisher et al.
2012/0004636 A1 1/2012 Lo
2012/0007442 A1 1/2012 Rhodes et al.
2012/0008880 A1 1/2012 Toth
2012/0010615 A1 1/2012 Cummings et al.
2012/0016239 A1 1/2012 Barthe et al.
2012/0016413 A1 1/2012 Timm et al.
2012/0016467 A1 1/2012 Chen et al.
2012/0018487 A1 1/2012 Bettuchi et al.
2012/0022583 A1 1/2012 Sugalski et al.
2012/0029272 A1 2/2012 Shelton, IV et al.
2012/0029550 A1 2/2012 Forsell
2012/0033360 A1 2/2012 Hsu
2012/0043100 A1 2/2012 Isobe et al.
2012/0059286 A1 3/2012 Hastings et al.
2012/0064483 A1 3/2012 Lint et al.
2012/0074200 A1 3/2012 Schmid et al.
2012/0078243 A1 3/2012 Worrell et al.
2012/0078244 A1 3/2012 Worrell et al.
2012/0080336 A1 4/2012 Shelton, IV et al.
2012/0080344 A1 4/2012 Shelton, IV
2012/0080477 A1* 4/2012 Leimbach ............. H01M 10/42
227/175.2
2012/0080478 A1 4/2012 Morgan et al.
2012/0080489 A1 4/2012 Shelton, IV et al.
2012/0080491 A1 4/2012 Shelton, IV et al.
2012/0080498 A1 4/2012 Shelton, IV et al.
2012/0083836 A1 4/2012 Shelton, IV et al.
2012/0086276 A1 4/2012 Sawyers
2012/0095458 A1 4/2012 Cybulski et al.
2012/0101488 A1 4/2012 Aldridge et al.
2012/0109186 A1 5/2012 Parrott et al.
2012/0116261 A1 5/2012 Mumaw et al.
2012/0116262 A1 5/2012 Houser et al.
2012/0116263 A1 5/2012 Houser et al.
2012/0116265 A1 5/2012 Houser et al.
2012/0116266 A1 5/2012 Houser et al.
2012/0116381 A1 5/2012 Houser et al.
2012/0118595 A1 5/2012 Pellenc
2012/0123463 A1 5/2012 Jacobs
2012/0125792 A1 5/2012 Cassivi
2012/0130217 A1 5/2012 Kauphusman et al.
2012/0132286 A1 5/2012 Lim et al.
2012/0132663 A1 5/2012 Kasvikis et al.
2012/0143173 A1 6/2012 Steege et al.
2012/0143175 A1 6/2012 Hermann et al.
2012/0171539 A1 7/2012 Rejman et al.
2012/0175142 A1 7/2012 Van Der Linde et al.
2012/0175398 A1 7/2012 Sandborn et al.
2012/0190964 A1 7/2012 Hyde et al.
2012/0197239 A1 8/2012 Smith et al.
2012/0197272 A1 8/2012 Oray et al.
2012/0203213 A1 8/2012 Kimball et al.
2012/0211542 A1 8/2012 Racenet
2012/0220990 A1 8/2012 Mckenzie et al.
2012/0223121 A1* 9/2012 Viola ............... A61B 17/07207
227/175.1
2012/0233298 A1 9/2012 Verbandt et al.
2012/0234895 A1 9/2012 O'Connor et al.
2012/0234897 A1 9/2012 Shelton, IV et al.
2012/0239068 A1 9/2012 Morris et al.
2012/0241494 A1 9/2012 Marczyk
2012/0241503 A1 9/2012 Baxter, III et al.
2012/0248169 A1 10/2012 Widenhouse et al.
2012/0251861 A1 10/2012 Liang et al.
2012/0253328 A1 10/2012 Cunningham et al.
2012/0256494 A1 10/2012 Kesler et al.
2012/0271327 A1 10/2012 West et al.
2012/0273547 A1 11/2012 Hodgkinson et al.
2012/0283707 A1 11/2012 Giordano et al.

(56) References Cited

U.S. PATENT DOCUMENTS

2012/0286019 A1 11/2012 Hueil et al.
2012/0289811 A1 11/2012 Viola et al.
2012/0289979 A1 11/2012 Eskaros et al.
2012/0292367 A1 11/2012 Morgan et al.
2012/0296316 A1 11/2012 Imuta
2012/0296342 A1 11/2012 Haglund Wendelschafer
2012/0298722 A1 11/2012 Hess et al.
2012/0301498 A1 11/2012 Altreuter et al.
2012/0310254 A1 12/2012 Manzo et al.
2012/0312861 A1 12/2012 Gurumurthy et al.
2012/0316424 A1 12/2012 Stopek
2012/0330285 A1 12/2012 Hartoumbekis et al.
2012/0330329 A1 12/2012 Harris et al.
2013/0006227 A1 1/2013 Takashino
2013/0008937 A1 1/2013 Viola
2013/0012983 A1 1/2013 Kleyman
2013/0018400 A1 1/2013 Milton et al.
2013/0020375 A1 1/2013 Shelton, IV et al.
2013/0020376 A1 1/2013 Shelton, IV et al.
2013/0023861 A1 1/2013 Shelton, IV et al.
2013/0023910 A1 1/2013 Solomon et al.
2013/0023915 A1 1/2013 Mueller
2013/0026208 A1 1/2013 Shelton, IV et al.
2013/0026210 A1 1/2013 Shelton, IV et al.
2013/0030462 A1 1/2013 Keating et al.
2013/0041292 A1 2/2013 Cunningham
2013/0056522 A1 3/2013 Swensgard
2013/0057162 A1 3/2013 Pollischansky
2013/0068816 A1 3/2013 Mandakolathur Vasudevan et al.
2013/0069088 A1 3/2013 Speck et al.
2013/0075447 A1 3/2013 Weisenburgh, II et al.
2013/0087597 A1 4/2013 Shelton, IV et al.
2013/0090534 A1 4/2013 Burns et al.
2013/0096568 A1 4/2013 Justis
2013/0098968 A1 4/2013 Aranyi et al.
2013/0098970 A1 4/2013 Racenet et al.
2013/0105548 A1 5/2013 Hodgkinson et al.
2013/0106352 A1 5/2013 Nagamine
2013/0112729 A1 5/2013 Beardsley et al.
2013/0116669 A1 5/2013 Shelton, IV et al.
2013/0123816 A1 5/2013 Hodgkinson et al.
2013/0126202 A1 5/2013 Oomori et al.
2013/0126581 A1* 5/2013 Yates ................. A61B 17/1155 227/175.1
2013/0131476 A1 5/2013 Siu et al.
2013/0131651 A1 5/2013 Strobl et al.
2013/0136969 A1 5/2013 Yasui et al.
2013/0153639 A1 6/2013 Hodgkinson et al.
2013/0153641 A1 6/2013 Shelton, IV et al.
2013/0158390 A1 6/2013 Tan et al.
2013/0162198 A1 6/2013 Yokota et al.
2013/0165908 A1 6/2013 Purdy et al.
2013/0169217 A1 7/2013 Watanabe et al.
2013/0172713 A1 7/2013 Kirschenman
2013/0172878 A1 7/2013 Smith
2013/0175315 A1 7/2013 Milliman
2013/0175317 A1 7/2013 Yates et al.
2013/0178868 A1* 7/2013 Roh ....................... A61B 34/30 606/130
2013/0183769 A1 7/2013 Tajima
2013/0186936 A1 7/2013 Shelton, IV
2013/0211244 A1 8/2013 Nathaniel
2013/0214025 A1 8/2013 Zemlok et al.
2013/0215449 A1 8/2013 Yamasaki
2013/0231681 A1 9/2013 Robinson et al.
2013/0233906 A1 9/2013 Hess et al.
2013/0238021 A1 9/2013 Gross et al.
2013/0248578 A1 9/2013 Arteaga Gonzalez
2013/0253480 A1 9/2013 Kimball et al.
2013/0253499 A1 9/2013 Kimball et al.
2013/0256368 A1 10/2013 Timm et al.
2013/0256373 A1 10/2013 Schmid et al.
2013/0256380 A1 10/2013 Schmid et al.
2013/0267950 A1 10/2013 Rosa et al.
2013/0267978 A1 10/2013 Trissel
2013/0270322 A1 10/2013 Scheib et al.
2013/0277410 A1 10/2013 Fernandez et al.
2013/0282003 A1* 10/2013 Messerly ........... A61B 18/1442 606/169
2013/0284792 A1 10/2013 Ma
2013/0289565 A1 10/2013 Hassler, Jr.
2013/0293353 A1 11/2013 McPherson et al.
2013/0303845 A1 11/2013 Skula et al.
2013/0304084 A1 11/2013 Beira et al.
2013/0306704 A1 11/2013 Balbierz et al.
2013/0310849 A1 11/2013 Malkowski
2013/0327552 A1 12/2013 Lovelass et al.
2013/0331826 A1 12/2013 Steege
2013/0333910 A1 12/2013 Tanimoto et al.
2013/0334280 A1 12/2013 Krehel et al.
2013/0334283 A1 12/2013 Swayze et al.
2013/0334285 A1 12/2013 Swayze et al.
2013/0341374 A1 12/2013 Shelton, IV et al.
2014/0001231 A1 1/2014 Shelton, IV et al.
2014/0001234 A1 1/2014 Shelton, IV et al.
2014/0002322 A1 1/2014 Kanome et al.
2014/0005550 A1 1/2014 Lu et al.
2014/0005640 A1 1/2014 Shelton, IV et al.
2014/0005667 A1* 1/2014 Stulen ................ A61B 18/1445 606/45
2014/0005678 A1 1/2014 Shelton, IV et al.
2014/0005702 A1 1/2014 Timm et al.
2014/0005718 A1 1/2014 Shelton, IV et al.
2014/0008289 A1 1/2014 Williams et al.
2014/0014704 A1 1/2014 Onukuri et al.
2014/0014705 A1 1/2014 Baxter, III
2014/0014707 A1 1/2014 Onukuri et al.
2014/0018832 A1 1/2014 Shelton, IV
2014/0022283 A1 1/2014 Chan et al.
2014/0039549 A1 2/2014 Belsky et al.
2014/0041191 A1 2/2014 Knodel
2014/0048580 A1 2/2014 Merchant et al.
2014/0069240 A1 3/2014 Dauvin et al.
2014/0078715 A1 3/2014 Pickard et al.
2014/0081176 A1 3/2014 Hassan
2014/0088614 A1 3/2014 Blumenkranz
2014/0088639 A1 3/2014 Bartels et al.
2014/0094681 A1 4/2014 Valentine et al.
2014/0100554 A1 4/2014 Williams
2014/0100558 A1 4/2014 Schmitz et al.
2014/0107697 A1 4/2014 Patani et al.
2014/0110453 A1 4/2014 Wingardner et al.
2014/0114327 A1* 4/2014 Boudreaux ............ A61B 34/25 606/130
2014/0115229 A1 4/2014 Kothamasu et al.
2014/0131418 A1 5/2014 Kostrzewski
2014/0131419 A1 5/2014 Bettuchi
2014/0135832 A1 5/2014 Park et al.
2014/0148803 A1 5/2014 Taylor
2014/0151433 A1 6/2014 Shelton, IV et al.
2014/0155916 A1 6/2014 Hodgkinson et al.
2014/0158747 A1 6/2014 Measamer et al.
2014/0166718 A1 6/2014 Swayze et al.
2014/0166723 A1 6/2014 Beardsley et al.
2014/0166724 A1 6/2014 Schellin et al.
2014/0166725 A1 6/2014 Schellin et al.
2014/0166726 A1 6/2014 Schellin et al.
2014/0175147 A1 6/2014 Manoux et al.
2014/0175150 A1 6/2014 Shelton, IV et al.
2014/0175152 A1 6/2014 Hess et al.
2014/0181710 A1 6/2014 Baalu et al.
2014/0183244 A1 7/2014 Duque et al.
2014/0188091 A1 7/2014 Vidal et al.
2014/0188101 A1 7/2014 Bales, Jr. et al.
2014/0188159 A1 7/2014 Steege
2014/0194874 A1 7/2014 Dietz et al.
2014/0195048 A1* 7/2014 Moll ...................... A61B 34/37 700/247
2014/0207124 A1 7/2014 Aldridge et al.
2014/0209658 A1 7/2014 Skalla et al.
2014/0215242 A1 7/2014 Jung
2014/0224857 A1 8/2014 Schmid
2014/0228632 A1 8/2014 Sholev et al.
2014/0228867 A1 8/2014 Thomas et al.

(56) References Cited

U.S. PATENT DOCUMENTS

| | | | |
|---|---|---|---|
| 2014/0239047 | A1 | 8/2014 | Hodgkinson et al. |
| 2014/0243865 | A1 | 8/2014 | Swayze et al. |
| 2014/0246475 | A1 | 9/2014 | Hall et al. |
| 2014/0248167 | A1 | 9/2014 | Sugimoto et al. |
| 2014/0249557 | A1 | 9/2014 | Koch, Jr. et al. |
| 2014/0249573 | A1 | 9/2014 | Arav |
| 2014/0262408 | A1 | 9/2014 | Woodard |
| 2014/0263535 | A1 | 9/2014 | Rajani et al. |
| 2014/0263541 | A1 | 9/2014 | Leimbach et al. |
| 2014/0263552 | A1 | 9/2014 | Hall et al. |
| 2014/0263558 | A1 | 9/2014 | Hausen et al. |
| 2014/0276720 | A1 | 9/2014 | Parihar et al. |
| 2014/0276730 | A1 | 9/2014 | Boudreaux et al. |
| 2014/0276776 | A1 | 9/2014 | Parihar et al. |
| 2014/0284371 | A1 | 9/2014 | Morgan et al. |
| 2014/0287703 | A1 | 9/2014 | Herbsommer et al. |
| 2014/0288460 | A1 | 9/2014 | Ouyang et al. |
| 2014/0291379 | A1 | 10/2014 | Schellin et al. |
| 2014/0291383 | A1 | 10/2014 | Spivey et al. |
| 2014/0299648 | A1 | 10/2014 | Shelton, IV et al. |
| 2014/0303645 | A1 | 10/2014 | Morgan et al. |
| 2014/0303660 | A1 | 10/2014 | Boyden et al. |
| 2014/0330161 | A1 | 11/2014 | Swayze et al. |
| 2014/0330298 | A1 | 11/2014 | Arshonsky et al. |
| 2014/0330579 | A1 | 11/2014 | Cashman et al. |
| 2014/0358163 | A1 | 12/2014 | Farin et al. |
| 2014/0367445 | A1 | 12/2014 | Ingmanson et al. |
| 2014/0371764 | A1 | 12/2014 | Oyola et al. |
| 2014/0373003 | A1 | 12/2014 | Grez et al. |
| 2014/0374130 | A1 | 12/2014 | Nakamura et al. |
| 2014/0378950 | A1 | 12/2014 | Chiu |
| 2014/0379000 | A1 | 12/2014 | Romo et al. |
| 2015/0001272 | A1 | 1/2015 | Sniffin et al. |
| 2015/0002089 | A1 | 1/2015 | Rejman et al. |
| 2015/0022012 | A1 | 1/2015 | Kim et al. |
| 2015/0025549 | A1 | 1/2015 | Kilroy et al. |
| 2015/0025571 | A1 | 1/2015 | Suzuki et al. |
| 2015/0034697 | A1 | 2/2015 | Mastri et al. |
| 2015/0039010 | A1 | 2/2015 | Beardsley et al. |
| 2015/0053737 | A1 | 2/2015 | Leimbach et al. |
| 2015/0053743 | A1 | 2/2015 | Yates et al. |
| 2015/0053746 | A1 | 2/2015 | Shelton, IV et al. |
| 2015/0053748 | A1 | 2/2015 | Yates et al. |
| 2015/0060516 | A1 | 3/2015 | Collings et al. |
| 2015/0060519 | A1 | 3/2015 | Shelton, IV et al. |
| 2015/0060520 | A1 | 3/2015 | Shelton, IV et al. |
| 2015/0060521 | A1 | 3/2015 | Weisenburgh, II et al. |
| 2015/0066000 | A1 | 3/2015 | An et al. |
| 2015/0067582 | A1 | 3/2015 | Donnelly et al. |
| 2015/0076208 | A1 | 3/2015 | Shelton, IV |
| 2015/0076209 | A1 | 3/2015 | Shelton, IV et al. |
| 2015/0076210 | A1 | 3/2015 | Shelton, IV et al. |
| 2015/0076211 | A1 | 3/2015 | Irka et al. |
| 2015/0080883 | A1 | 3/2015 | Haverkost et al. |
| 2015/0082624 | A1 | 3/2015 | Craig et al. |
| 2015/0083781 | A1 | 3/2015 | Giordano et al. |
| 2015/0087952 | A1 | 3/2015 | Albert et al. |
| 2015/0088127 | A1 | 3/2015 | Craig et al. |
| 2015/0088547 | A1 | 3/2015 | Balram et al. |
| 2015/0090760 | A1 | 4/2015 | Giordano et al. |
| 2015/0090762 | A1 | 4/2015 | Giordano et al. |
| 2015/0127021 | A1 | 5/2015 | Harris et al. |
| 2015/0133957 | A1 | 5/2015 | Kostrzewski |
| 2015/0134077 | A1 | 5/2015 | Shelton, IV et al. |
| 2015/0150620 | A1 | 6/2015 | Miyamoto et al. |
| 2015/0173749 | A1 | 6/2015 | Shelton, IV et al. |
| 2015/0173756 | A1 | 6/2015 | Baxter, III et al. |
| 2015/0173789 | A1 | 6/2015 | Baxter, III et al. |
| 2015/0196295 | A1 | 7/2015 | Shelton, IV et al. |
| 2015/0196299 | A1 | 7/2015 | Swayze et al. |
| 2015/0201918 | A1 | 7/2015 | Kumar et al. |
| 2015/0201932 | A1 | 7/2015 | Swayze et al. |
| 2015/0201936 | A1 | 7/2015 | Swayze et al. |
| 2015/0201937 | A1 | 7/2015 | Swayze et al. |
| 2015/0201938 | A1 | 7/2015 | Swayze et al. |
| 2015/0201939 | A1 | 7/2015 | Swayze et al. |
| 2015/0201940 | A1 | 7/2015 | Swayze et al. |
| 2015/0201941 | A1 | 7/2015 | Swayze et al. |
| 2015/0202013 | A1 | 7/2015 | Teichtmann et al. |
| 2015/0209045 | A1 | 7/2015 | Hodgkinson et al. |
| 2015/0216605 | A1 | 8/2015 | Baldwin |
| 2015/0222212 | A1 | 8/2015 | Iwata |
| 2015/0223868 | A1 | 8/2015 | Brandt et al. |
| 2015/0230697 | A1 | 8/2015 | Phee et al. |
| 2015/0230794 | A1 | 8/2015 | Wellman et al. |
| 2015/0230861 | A1 | 8/2015 | Woloszko et al. |
| 2015/0231409 | A1 | 8/2015 | Racenet et al. |
| 2015/0238118 | A1 | 8/2015 | Legassey et al. |
| 2015/0272557 | A1 | 10/2015 | Overmyer et al. |
| 2015/0272571 | A1 | 10/2015 | Leimbach et al. |
| 2015/0272580 | A1 | 10/2015 | Leimbach et al. |
| 2015/0272582 | A1 | 10/2015 | Leimbach et al. |
| 2015/0272606 | A1 | 10/2015 | Nobis |
| 2015/0280424 | A1 * | 10/2015 | Leimbach .............. H02H 3/087 361/18 |
| 2015/0297200 | A1 | 10/2015 | Fitzsimmons et al. |
| 2015/0297222 | A1 | 10/2015 | Huitema et al. |
| 2015/0297223 | A1 | 10/2015 | Huitema et al. |
| 2015/0297225 | A1 | 10/2015 | Huitema et al. |
| 2015/0297824 | A1 | 10/2015 | Cabiri et al. |
| 2015/0303417 | A1 | 10/2015 | Koeder et al. |
| 2015/0305743 | A1 | 10/2015 | Casasanta et al. |
| 2015/0313594 | A1 | 11/2015 | Shelton, IV et al. |
| 2015/0324317 | A1 | 11/2015 | Collins et al. |
| 2015/0352699 | A1 | 12/2015 | Sakai et al. |
| 2015/0366585 | A1 | 12/2015 | Lemay et al. |
| 2015/0367497 | A1 | 12/2015 | Ito et al. |
| 2015/0372265 | A1 | 12/2015 | Morisaku et al. |
| 2015/0374372 | A1 | 12/2015 | Zergiebel et al. |
| 2015/0374378 | A1 | 12/2015 | Giordano et al. |
| 2016/0000437 | A1 | 1/2016 | Giordano et al. |
| 2016/0000452 | A1 | 1/2016 | Yates et al. |
| 2016/0029998 | A1 | 2/2016 | Brister et al. |
| 2016/0030042 | A1 | 2/2016 | Heinrich et al. |
| 2016/0030043 | A1 | 2/2016 | Fanelli et al. |
| 2016/0030076 | A1 | 2/2016 | Faller et al. |
| 2016/0034167 | A1 | 2/2016 | Wilson et al. |
| 2016/0047423 | A1 | 2/2016 | Bodtker |
| 2016/0051316 | A1 | 2/2016 | Boudreaux |
| 2016/0066913 | A1 | 3/2016 | Swayze et al. |
| 2016/0069449 | A1 | 3/2016 | Kanai et al. |
| 2016/0074035 | A1 | 3/2016 | Whitman et al. |
| 2016/0074040 | A1 | 3/2016 | Widenhouse et al. |
| 2016/0081678 | A1 | 3/2016 | Kappel et al. |
| 2016/0082161 | A1 | 3/2016 | Zilberman et al. |
| 2016/0089175 | A1 | 3/2016 | Hibner et al. |
| 2016/0099601 | A1 | 4/2016 | Leabman et al. |
| 2016/0100838 | A1 | 4/2016 | Beaupréet al. |
| 2016/0118201 | A1 | 4/2016 | Nicholas et al. |
| 2016/0132026 | A1 | 5/2016 | Wingardner et al. |
| 2016/0135835 | A1 | 5/2016 | Onuma |
| 2016/0135895 | A1 | 5/2016 | Faasse et al. |
| 2016/0139666 | A1 | 5/2016 | Rubin et al. |
| 2016/0174969 | A1 | 6/2016 | Kerr et al. |
| 2016/0174983 | A1 | 6/2016 | Shelton, IV et al. |
| 2016/0175021 | A1 | 6/2016 | Hassler, Jr. |
| 2016/0183939 | A1 | 6/2016 | Shelton, IV et al. |
| 2016/0183944 | A1 | 6/2016 | Swensgard et al. |
| 2016/0192927 | A1 | 7/2016 | Kostrzewski |
| 2016/0192960 | A1 | 7/2016 | Bueno et al. |
| 2016/0199063 | A1 | 7/2016 | Mandakolathur Vasudevan et al. |
| 2016/0199956 | A1 | 7/2016 | Shelton, IV et al. |
| 2016/0220150 | A1 | 8/2016 | Sharonov |
| 2016/0235494 | A1 | 8/2016 | Shelton, IV et al. |
| 2016/0242783 | A1 | 8/2016 | Shelton, IV et al. |
| 2016/0242855 | A1 | 8/2016 | Fichtinger et al. |
| 2016/0249910 | A1 | 9/2016 | Shelton, IV et al. |
| 2016/0249922 | A1 | 9/2016 | Morgan et al. |
| 2016/0249929 | A1 | 9/2016 | Cappola et al. |
| 2016/0256159 | A1 | 9/2016 | Pinjala et al. |
| 2016/0256184 | A1 | 9/2016 | Shelton, IV et al. |
| 2016/0256185 | A1 * | 9/2016 | Shelton, IV ......... A61B 17/295 |
| 2016/0256221 | A1 | 9/2016 | Smith |
| 2016/0256229 | A1 | 9/2016 | Morgan et al. |

(56) References Cited

U.S. PATENT DOCUMENTS

| | | | |
|---|---|---|---|
| 2016/0262745 | A1 | 9/2016 | Morgan et al. |
| 2016/0262921 | A1 | 9/2016 | Balbierz et al. |
| 2016/0270781 | A1 | 9/2016 | Scirica |
| 2016/0287265 | A1 | 10/2016 | Macdonald et al. |
| 2016/0287279 | A1 | 10/2016 | Bovay et al. |
| 2016/0302820 | A1 | 10/2016 | Hibner et al. |
| 2016/0310143 | A1 | 10/2016 | Bettuchi |
| 2016/0314716 | A1 | 10/2016 | Grubbs |
| 2016/0314717 | A1 | 10/2016 | Grubbs |
| 2016/0345972 | A1 | 12/2016 | Beardsley et al. |
| 2016/0367122 | A1 | 12/2016 | Ichimura et al. |
| 2016/0374669 | A1 | 12/2016 | Overmyer et al. |
| 2016/0374716 | A1 | 12/2016 | Kessler |
| 2017/0000549 | A1 | 1/2017 | Gilbert et al. |
| 2017/0007234 | A1 | 1/2017 | Chin et al. |
| 2017/0007244 | A1 | 1/2017 | Shelton, IV et al. |
| 2017/0007245 | A1 | 1/2017 | Shelton, IV et al. |
| 2017/0007347 | A1 | 1/2017 | Jaworek et al. |
| 2017/0020616 | A1 | 1/2017 | Vale et al. |
| 2017/0035419 | A1 | 2/2017 | Decker et al. |
| 2017/0055819 | A1 | 3/2017 | Hansen et al. |
| 2017/0055980 | A1 | 3/2017 | Vendely et al. |
| 2017/0056008 | A1 | 3/2017 | Shelton, IV et al. |
| 2017/0056016 | A1 | 3/2017 | Barton et al. |
| 2017/0056018 | A1 | 3/2017 | Zeiner et al. |
| 2017/0066054 | A1 | 3/2017 | Birky |
| 2017/0066147 | A1 | 3/2017 | Ball et al. |
| 2017/0079642 | A1 | 3/2017 | Overmyer et al. |
| 2017/0086829 | A1 | 3/2017 | Vendely et al. |
| 2017/0086830 | A1 | 3/2017 | Yates et al. |
| 2017/0086930 | A1 | 3/2017 | Thompson et al. |
| 2017/0086932 | A1 | 3/2017 | Auld et al. |
| 2017/0095252 | A1 | 4/2017 | Smith et al. |
| 2017/0095922 | A1 | 4/2017 | Licht et al. |
| 2017/0105727 | A1 | 4/2017 | Scheib et al. |
| 2017/0105733 | A1 | 4/2017 | Scheib et al. |
| 2017/0105786 | A1 | 4/2017 | Scheib et al. |
| 2017/0106302 | A1 | 4/2017 | Cummings et al. |
| 2017/0135711 | A1 | 5/2017 | Overmyer et al. |
| 2017/0135717 | A1 | 5/2017 | Boudreaux et al. |
| 2017/0135747 | A1 | 5/2017 | Broderick et al. |
| 2017/0143336 | A1 | 5/2017 | Shah et al. |
| 2017/0151021 | A1* | 6/2017 | Quaid, III .............. A61B 34/70 |
| 2017/0168187 | A1 | 6/2017 | Calderoni et al. |
| 2017/0172382 | A1 | 6/2017 | Nir et al. |
| 2017/0172549 | A1 | 6/2017 | Smaby et al. |
| 2017/0172662 | A1 | 6/2017 | Panescu et al. |
| 2017/0181803 | A1 | 6/2017 | Mayer-Ullmann et al. |
| 2017/0182195 | A1 | 6/2017 | Wagner |
| 2017/0182211 | A1 | 6/2017 | Raxworthy et al. |
| 2017/0196558 | A1 | 7/2017 | Morgan et al. |
| 2017/0196649 | A1 | 7/2017 | Yates et al. |
| 2017/0202605 | A1 | 7/2017 | Shelton, IV et al. |
| 2017/0202607 | A1 | 7/2017 | Shelton, IV et al. |
| 2017/0202770 | A1 | 7/2017 | Friedrich et al. |
| 2017/0224332 | A1 | 8/2017 | Hunter et al. |
| 2017/0224428 | A1 | 8/2017 | Kopp |
| 2017/0231628 | A1 | 8/2017 | Shelton, IV et al. |
| 2017/0231629 | A1 | 8/2017 | Stopek et al. |
| 2017/0238962 | A1 | 8/2017 | Hansen et al. |
| 2017/0238991 | A1 | 8/2017 | Worrell et al. |
| 2017/0242455 | A1 | 8/2017 | Dickens |
| 2017/0245880 | A1 | 8/2017 | Honda et al. |
| 2017/0245882 | A1* | 8/2017 | Houser .................. A61B 34/30 |
| 2017/0245949 | A1 | 8/2017 | Randle |
| 2017/0249431 | A1 | 8/2017 | Shelton, IV et al. |
| 2017/0252060 | A1 | 9/2017 | Ellingson et al. |
| 2017/0255799 | A1 | 9/2017 | Zhao et al. |
| 2017/0258471 | A1 | 9/2017 | DiNardo et al. |
| 2017/0262110 | A1 | 9/2017 | Polishchuk et al. |
| 2017/0265774 | A1 | 9/2017 | Johnson et al. |
| 2017/0281186 | A1 | 10/2017 | Shelton, IV et al. |
| 2017/0296173 | A1 | 10/2017 | Shelton, IV et al. |
| 2017/0296179 | A1* | 10/2017 | Shelton, IV ........... G16H 20/40 |
| 2017/0296189 | A1* | 10/2017 | Vendely ............... A61B 17/105 |
| 2017/0303984 | A1 | 10/2017 | Malackowski |
| 2017/0308665 | A1 | 10/2017 | Heck et al. |
| 2017/0312042 | A1 | 11/2017 | Giordano et al. |
| 2017/0319047 | A1 | 11/2017 | Poulsen et al. |
| 2017/0319201 | A1 | 11/2017 | Morgan et al. |
| 2017/0333034 | A1 | 11/2017 | Morgan et al. |
| 2017/0333035 | A1 | 11/2017 | Morgan et al. |
| 2017/0340325 | A1 | 11/2017 | Baril et al. |
| 2017/0348010 | A1 | 12/2017 | Chiang |
| 2017/0348042 | A1 | 12/2017 | Drochner et al. |
| 2017/0348043 | A1 | 12/2017 | Wang et al. |
| 2017/0354413 | A1 | 12/2017 | Chen et al. |
| 2017/0358052 | A1 | 12/2017 | Yuan |
| 2017/0360441 | A1 | 12/2017 | Sgroi |
| 2018/0008265 | A1 | 1/2018 | Hatanaka et al. |
| 2018/0036024 | A1 | 2/2018 | Allen, IV |
| 2018/0036025 | A1 | 2/2018 | Drochner et al. |
| 2018/0042610 | A1 | 2/2018 | Sgroi, Jr. |
| 2018/0042689 | A1 | 2/2018 | Mozdzierz et al. |
| 2018/0049738 | A1 | 2/2018 | Meloul et al. |
| 2018/0049794 | A1 | 2/2018 | Swayze et al. |
| 2018/0051780 | A1 | 2/2018 | Shelton, IV et al. |
| 2018/0055501 | A1 | 3/2018 | Zemlok et al. |
| 2018/0067004 | A1 | 3/2018 | Sgroi, Jr. |
| 2018/0085117 | A1 | 3/2018 | Shelton, IV et al. |
| 2018/0085120 | A1 | 3/2018 | Viola |
| 2018/0092710 | A1 | 4/2018 | Bosisio et al. |
| 2018/0114591 | A1 | 4/2018 | Pribanic et al. |
| 2018/0116658 | A1 | 5/2018 | Aronhalt, IV et al. |
| 2018/0125481 | A1 | 5/2018 | Yates et al. |
| 2018/0125487 | A1 | 5/2018 | Beardsley |
| 2018/0125488 | A1 | 5/2018 | Morgan et al. |
| 2018/0125594 | A1 | 5/2018 | Beardsley |
| 2018/0132849 | A1 | 5/2018 | Miller et al. |
| 2018/0132850 | A1 | 5/2018 | Leimbach et al. |
| 2018/0132926 | A1 | 5/2018 | Asher et al. |
| 2018/0132952 | A1 | 5/2018 | Spivey et al. |
| 2018/0133521 | A1 | 5/2018 | Frushour et al. |
| 2018/0140299 | A1 | 5/2018 | Weaner et al. |
| 2018/0146960 | A1 | 5/2018 | Shelton, IV et al. |
| 2018/0153542 | A1 | 6/2018 | Shelton, IV et al. |
| 2018/0153634 | A1 | 6/2018 | Zemlok et al. |
| 2018/0161034 | A1 | 6/2018 | Scheib et al. |
| 2018/0168572 | A1 | 6/2018 | Burbank |
| 2018/0168574 | A1 | 6/2018 | Robinson et al. |
| 2018/0168575 | A1 | 6/2018 | Simms et al. |
| 2018/0168577 | A1 | 6/2018 | Aronhalt et al. |
| 2018/0168579 | A1 | 6/2018 | Aronhalt et al. |
| 2018/0168598 | A1 | 6/2018 | Shelton, IV et al. |
| 2018/0168608 | A1 | 6/2018 | Shelton, IV et al. |
| 2018/0168609 | A1 | 6/2018 | Fanelli et al. |
| 2018/0168615 | A1 | 6/2018 | Shelton, IV et al. |
| 2018/0168618 | A1 | 6/2018 | Scott et al. |
| 2018/0168619 | A1 | 6/2018 | Scott et al. |
| 2018/0168623 | A1 | 6/2018 | Simms et al. |
| 2018/0168624 | A1* | 6/2018 | Shelton, IV ..... A61B 17/07207 |
| 2018/0168625 | A1 | 6/2018 | Posada et al. |
| 2018/0168633 | A1 | 6/2018 | Shelton, IV et al. |
| 2018/0168647 | A1 | 6/2018 | Shelton, IV et al. |
| 2018/0168648 | A1 | 6/2018 | Shelton, IV et al. |
| 2018/0168650 | A1 | 6/2018 | Shelton, IV et al. |
| 2018/0168754 | A1 | 6/2018 | Overmyer |
| 2018/0168756 | A1 | 6/2018 | Liao et al. |
| 2018/0206904 | A1 | 7/2018 | Felder et al. |
| 2018/0228490 | A1 | 8/2018 | Richard et al. |
| 2018/0231111 | A1 | 8/2018 | Mika et al. |
| 2018/0231475 | A1 | 8/2018 | Brown et al. |
| 2018/0235609 | A1 | 8/2018 | Harris et al. |
| 2018/0235617 | A1 | 8/2018 | Shelton, IV et al. |
| 2018/0235618 | A1 | 8/2018 | Kostrzewski |
| 2018/0235626 | A1 | 8/2018 | Shelton, IV et al. |
| 2018/0236181 | A1 | 8/2018 | Marlin et al. |
| 2018/0242970 | A1 | 8/2018 | Mozdzierz |
| 2018/0247711 | A1 | 8/2018 | Terry |
| 2018/0250002 | A1 | 9/2018 | Eschbach |
| 2018/0271526 | A1 | 9/2018 | Zammataro |
| 2018/0271553 | A1 | 9/2018 | Worrell |
| 2018/0271604 | A1 | 9/2018 | Grout et al. |
| 2018/0273597 | A1 | 9/2018 | Stimson |

(56) References Cited

U.S. PATENT DOCUMENTS

2018/0279994 A1 10/2018 Schaer et al.
2018/0280026 A1 10/2018 Zhang et al.
2018/0280073 A1 10/2018 Sanai et al.
2018/0289371 A1 10/2018 Wang et al.
2018/0296216 A1 10/2018 Shelton, IV et al.
2018/0296290 A1 10/2018 Namiki et al.
2018/0310995 A1 11/2018 Gliner et al.
2018/0317905 A1 11/2018 Olson et al.
2018/0317915 A1 11/2018 McDonald, II
2018/0325514 A1 11/2018 Harris et al.
2018/0333169 A1 11/2018 Leimbach et al.
2018/0353186 A1* 12/2018 Mozdzierz ........... A61B 17/072
2018/0360456 A1 12/2018 Shelton, IV et al.
2018/0368066 A1 12/2018 Howell et al.
2018/0368844 A1 12/2018 Bakos et al.
2018/0372806 A1 12/2018 Laughery et al.
2018/0375165 A1 12/2018 Shelton, IV et al.
2019/0000446 A1* 1/2019 Shelton, IV ..... A61B 17/07292
2019/0000459 A1 1/2019 Shelton, IV et al.
2019/0000461 A1 1/2019 Shelton, IV et al.
2019/0000481 A1 1/2019 Harris et al.
2019/0000533 A1 1/2019 Messerly et al.
2019/0000535 A1 1/2019 Messerly et al.
2019/0000536 A1 1/2019 Yates et al.
2019/0006047 A1 1/2019 Gorek et al.
2019/0008515 A1 1/2019 Beardsley et al.
2019/0015102 A1 1/2019 Baber et al.
2019/0015165 A1 1/2019 Giordano et al.
2019/0017311 A1 1/2019 McGettrick et al.
2019/0021733 A1 1/2019 Burbank
2019/0029682 A1 1/2019 Huitema et al.
2019/0029701 A1 1/2019 Shelton, IV et al.
2019/0038281 A1 2/2019 Shelton, IV et al.
2019/0038283 A1 2/2019 Shelton, IV et al.
2019/0038285 A1 2/2019 Mozdzierz
2019/0059888 A1 2/2019 Shelton, IV et al.
2019/0059890 A1 2/2019 Shelton, IV et al.
2019/0059891 A1 2/2019 Shelton, IV et al.
2019/0059984 A1 2/2019 Otrembiak et al.
2019/0059986 A1 2/2019 Shelton, IV et al.
2019/0076143 A1 3/2019 Smith
2019/0090871 A1 3/2019 Shelton, IV et al.
2019/0091183 A1 3/2019 Tomat et al.
2019/0104919 A1 4/2019 Shelton, IV et al.
2019/0105035 A1 4/2019 Shelton, IV et al.
2019/0105036 A1 4/2019 Morgan et al.
2019/0105037 A1 4/2019 Morgan et al.
2019/0105039 A1 4/2019 Morgan et al.
2019/0105044 A1 4/2019 Shelton, IV et al.
2019/0110779 A1 4/2019 Gardner et al.
2019/0110791 A1 4/2019 Shelton, IV et al.
2019/0117220 A1 4/2019 Nativ et al.
2019/0117224 A1 4/2019 Setser et al.
2019/0117287 A1 4/2019 Nativ et al.
2019/0122840 A1 4/2019 Zergiebel et al.
2019/0125320 A1 5/2019 Shelton, IV et al.
2019/0125336 A1 5/2019 Deck et al.
2019/0125342 A1 5/2019 Beardsley et al.
2019/0125344 A1 5/2019 DiNardo et al.
2019/0125361 A1 5/2019 Shelton, IV et al.
2019/0125432 A1 5/2019 Shelton, IV et al.
2019/0125476 A1 5/2019 Shelton, IV et al.
2019/0133422 A1 5/2019 Nakamura
2019/0133577 A1 5/2019 Weadock et al.
2019/0137349 A1 5/2019 Collins et al.
2019/0138770 A1 5/2019 Compaijen et al.
2019/0142423 A1 5/2019 Satti, III et al.
2019/0150925 A1 5/2019 Marczyk et al.
2019/0151029 A1 5/2019 Robinson
2019/0175847 A1 6/2019 Pocreva, III et al.
2019/0183501 A1* 6/2019 Shelton, IV ..... A61B 17/07207
2019/0183502 A1 6/2019 Shelton, IV et al.
2019/0192147 A1 6/2019 Shelton, IV et al.
2019/0192148 A1 6/2019 Shelton, IV et al.
2019/0192151 A1 6/2019 Shelton, IV et al.
2019/0192155 A1 6/2019 Shelton, IV et al.
2019/0200844 A1 7/2019 Shelton, IV et al.
2019/0200905 A1 7/2019 Shelton, IV et al.
2019/0200906 A1 7/2019 Shelton, IV et al.
2019/0200977 A1 7/2019 Shelton, IV et al.
2019/0200981 A1 7/2019 Harris et al.
2019/0200986 A1 7/2019 Shelton, IV et al.
2019/0200987 A1 7/2019 Shelton, IV et al.
2019/0200989 A1 7/2019 Burbank et al.
2019/0200997 A1 7/2019 Shelton, IV et al.
2019/0200998 A1 7/2019 Shelton, IV et al.
2019/0201020 A1 7/2019 Shelton, IV et al.
2019/0201024 A1 7/2019 Shelton, IV et al.
2019/0201027 A1 7/2019 Shelton, IV et al.
2019/0201029 A1 7/2019 Shelton, IV et al.
2019/0201030 A1 7/2019 Shelton, IV et al.
2019/0201034 A1 7/2019 Shelton, IV et al.
2019/0201045 A1 7/2019 Yates et al.
2019/0201079 A1 7/2019 Shelton, IV et al.
2019/0201104 A1 7/2019 Shelton, IV et al.
2019/0201112 A1 7/2019 Wiener et al.
2019/0201113 A1 7/2019 Shelton, IV et al.
2019/0201115 A1 7/2019 Shelton, IV et al.
2019/0201118 A1 7/2019 Shelton, IV et al.
2019/0201139 A1 7/2019 Shelton, IV et al.
2019/0201140 A1 7/2019 Yates et al.
2019/0201142 A1 7/2019 Shelton, IV et al.
2019/0201146 A1 7/2019 Shelton, IV et al.
2019/0201158 A1 7/2019 Shelton, IV et al.
2019/0201594 A1 7/2019 Shelton, IV et al.
2019/0205567 A1 7/2019 Shelton, IV et al.
2019/0206555 A1 7/2019 Morgan et al.
2019/0206561 A1 7/2019 Shelton, IV et al.
2019/0206564 A1 7/2019 Shelton, IV et al.
2019/0206569 A1 7/2019 Shelton, IV et al.
2019/0209247 A1 7/2019 Giordano et al.
2019/0209248 A1 7/2019 Giordano et al.
2019/0209249 A1 7/2019 Giordano et al.
2019/0209250 A1 7/2019 Giordano et al.
2019/0239873 A1 8/2019 Laurent et al.
2019/0247048 A1 8/2019 Gasparovich et al.
2019/0261982 A1 8/2019 Holsten
2019/0261983 A1 8/2019 Granger et al.
2019/0261984 A1 8/2019 Nelson et al.
2019/0261987 A1 8/2019 Viola et al.
2019/0262153 A1 8/2019 Tassoni et al.
2019/0269400 A1 9/2019 Mandakolathur Vasudevan et al.
2019/0269402 A1 9/2019 Murray et al.
2019/0269428 A1 9/2019 Allen et al.
2019/0274685 A1 9/2019 Olson et al.
2019/0274716 A1 9/2019 Nott et al.
2019/0282233 A1 9/2019 Burbank et al.
2019/0290264 A1 9/2019 Morgan et al.
2019/0290266 A1 9/2019 Scheib et al.
2019/0290297 A1 9/2019 Haider et al.
2019/0298353 A1 10/2019 Shelton, IV et al.
2019/0298361 A1 10/2019 Shelton, IV et al.
2019/0298362 A1 10/2019 Shelton, IV et al.
2019/0298381 A1 10/2019 Kreidler et al.
2019/0307452 A1 10/2019 Shelton, IV et al.
2019/0307453 A1 10/2019 Shelton, IV et al.
2019/0307454 A1 10/2019 Shelton, IV et al.
2019/0307456 A1 10/2019 Shelton, IV et al.
2019/0314015 A1 10/2019 Shelton, IV et al.
2019/0321062 A1 10/2019 Williams
2019/0328387 A1 10/2019 Overmyer et al.
2019/0339224 A1 11/2019 Bhavaraju et al.
2019/0388091 A1 12/2019 Eschbach et al.
2020/0008802 A1 1/2020 Aronhalt et al.
2020/0008809 A1 1/2020 Shelton, IV et al.
2020/0008827 A1 1/2020 Dearden et al.
2020/0015817 A1 1/2020 Harris et al.
2020/0015836 A1 1/2020 Nicholas et al.
2020/0015915 A1 1/2020 Swayze et al.
2020/0030020 A1 1/2020 Wang et al.
2020/0037939 A1 2/2020 Castagna et al.
2020/0038016 A1 2/2020 Shelton, IV et al.
2020/0038018 A1 2/2020 Shelton, IV et al.
2020/0038021 A1 2/2020 Contini et al.

(56) References Cited

U.S. PATENT DOCUMENTS

2020/0046355 A1 2/2020 Harris et al.
2020/0046356 A1 2/2020 Baxter, III et al.
2020/0054320 A1 2/2020 Harris et al.
2020/0054321 A1 2/2020 Harris et al.
2020/0054329 A1 2/2020 Shelton, IV et al.
2020/0054332 A1 2/2020 Shelton, IV et al.
2020/0054334 A1 2/2020 Shelton, IV et al.
2020/0054355 A1 2/2020 Laurent et al.
2020/0060523 A1 2/2020 Matsuda et al.
2020/0060713 A1 2/2020 Leimbach et al.
2020/0061385 A1 2/2020 Schwarz et al.
2020/0085435 A1 3/2020 Shelton, IV et al.
2020/0093484 A1 3/2020 Shelton, IV et al.
2020/0093506 A1 3/2020 Leimbach et al.
2020/0093550 A1 3/2020 Spivey et al.
2020/0107829 A1 4/2020 Shelton, IV et al.
2020/0113563 A1 4/2020 Gupta et al.
2020/0114505 A1 4/2020 Kikuchi
2020/0138507 A1 5/2020 Davison et al.
2020/0138534 A1 5/2020 Garcia Kilroy et al.
2020/0146166 A1 5/2020 Sgroi, Jr.
2020/0146741 A1 5/2020 Long et al.
2020/0187943 A1 6/2020 Shelton, IV et al.
2020/0197027 A1 6/2020 Hershberger et al.
2020/0205810 A1 7/2020 Posey et al.
2020/0205811 A1 7/2020 Posey et al.
2020/0205823 A1 7/2020 Vendely et al.
2020/0214706 A1 7/2020 Vendely et al.
2020/0214731 A1 7/2020 Shelton, IV et al.
2020/0229814 A1 7/2020 Amariglio et al.
2020/0237371 A1 7/2020 Huitema et al.
2020/0268377 A1 8/2020 Schmid et al.
2020/0268381 A1 8/2020 Roberts et al.
2020/0275927 A1 9/2020 Shelton, IV et al.
2020/0280219 A1 9/2020 Laughery et al.
2020/0289112 A1 9/2020 Whitfield et al.
2020/0289119 A1 9/2020 Viola et al.
2020/0305863 A1 10/2020 Yates et al.
2020/0305864 A1 10/2020 Yates et al.
2020/0305872 A1 10/2020 Weidner et al.
2020/0315623 A1 10/2020 Eisinger et al.
2020/0323526 A1 10/2020 Huang et al.
2020/0330181 A1 10/2020 Junger et al.
2020/0337706 A1 10/2020 Truckai et al.
2020/0345346 A1 11/2020 Shelton, IV et al.
2020/0345349 A1 11/2020 Kimball et al.
2020/0345352 A1 11/2020 Shelton, IV et al.
2020/0345353 A1 11/2020 Leimbach et al.
2020/0345356 A1 11/2020 Leimbach et al.
2020/0345357 A1 11/2020 Leimbach et al.
2020/0345359 A1 11/2020 Baxter, III et al.
2020/0345363 A1 11/2020 Shelton, IV et al.
2020/0345435 A1 11/2020 Traina
2020/0352562 A1 11/2020 Timm et al.
2020/0352569 A1 11/2020 Viola et al.
2020/0367886 A1 11/2020 Shelton, IV et al.
2020/0375585 A1 12/2020 Swayze et al.
2020/0375597 A1 12/2020 Shelton, IV et al.
2020/0390444 A1 12/2020 Harris et al.
2020/0397430 A1 12/2020 Patel et al.
2020/0397439 A1 12/2020 Eisinger
2020/0405292 A1 12/2020 Shelton, IV et al.
2020/0405302 A1 12/2020 Shelton, IV et al.
2020/0405304 A1 12/2020 Mozdzierz et al.
2020/0405306 A1 12/2020 Shelton, IV et al.
2020/0405307 A1 12/2020 Shelton, IV et al.
2020/0405308 A1 12/2020 Shelton, IV
2020/0405375 A1 12/2020 Shelton, IV et al.
2020/0405403 A1 12/2020 Shelton, IV et al.
2020/0410177 A1 12/2020 Shelton, IV
2021/0000466 A1 1/2021 Leimbach et al.
2021/0000467 A1 1/2021 Shelton, IV et al.
2021/0007742 A1 1/2021 Rector et al.
2021/0007826 A1 1/2021 Shafer et al.
2021/0015480 A1 1/2021 Shelton, IV et al.
2021/0045742 A1 2/2021 Shelton, IV et al.
2021/0059661 A1 3/2021 Schmid et al.
2021/0059662 A1 3/2021 Shelton, IV
2021/0059664 A1 3/2021 Hensel et al.
2021/0059670 A1 3/2021 Overmyer et al.
2021/0059672 A1 3/2021 Giordano et al.
2021/0059673 A1 3/2021 Shelton, IV et al.
2021/0068829 A1 3/2021 Miller et al.
2021/0068835 A1 3/2021 Shelton, IV et al.
2021/0077099 A1 3/2021 Shelton, IV et al.
2021/0077109 A1 3/2021 Harris et al.
2021/0084700 A1 3/2021 Daniels
2021/0085313 A1 3/2021 Morgan et al.
2021/0085315 A1 3/2021 Aronhalt et al.
2021/0085316 A1 3/2021 Harris et al.
2021/0085320 A1 3/2021 Leimbach et al.
2021/0085321 A1 3/2021 Shelton, IV et al.
2021/0085325 A1 3/2021 Shelton, IV et al.
2021/0093321 A1 4/2021 Auld et al.
2021/0093323 A1 4/2021 Scirica et al.
2021/0100541 A1 4/2021 Shelton, IV et al.
2021/0100982 A1 4/2021 Laby et al.
2021/0107031 A1 4/2021 Bales, Jr. et al.
2021/0128153 A1 5/2021 Sgroi
2021/0137522 A1 5/2021 Shelton, IV et al.
2021/0145441 A1 5/2021 Weir et al.
2021/0153866 A1 5/2021 Knapp et al.
2021/0177401 A1 6/2021 Abramek et al.
2021/0177411 A1 6/2021 Williams
2021/0177528 A1 6/2021 Cappelleri et al.
2021/0186492 A1 6/2021 Shelton, IV et al.
2021/0186497 A1 6/2021 Shelton, IV et al.
2021/0186499 A1 6/2021 Shelton, IV et al.
2021/0186501 A1 6/2021 Shelton, IV et al.
2021/0196265 A1 7/2021 Shelton, IV et al.
2021/0196269 A1 7/2021 Shelton, IV et al.
2021/0196270 A1 7/2021 Shelton, IV et al.
2021/0196425 A1 7/2021 Shelton, IV et al.
2021/0204941 A1 7/2021 Dewaele et al.
2021/0204951 A1 7/2021 Sgroi et al.
2021/0212671 A1 7/2021 Ramadan et al.
2021/0212776 A1 7/2021 Schmitt et al.
2021/0225140 A1 7/2021 Adachi et al.
2021/0228209 A1 7/2021 Shelton, IV et al.
2021/0244407 A1 8/2021 Shelton, IV et al.
2021/0244411 A1 8/2021 Smith et al.
2021/0251720 A1 8/2021 Jhaveri et al.
2021/0259681 A1 8/2021 Shelton, IV et al.
2021/0259687 A1 8/2021 Gonzalez et al.
2021/0259790 A1 8/2021 Kaiser
2021/0259986 A1 8/2021 Widenhouse et al.
2021/0259987 A1 8/2021 Widenhouse et al.
2021/0267589 A1 9/2021 Swayze et al.
2021/0267594 A1 9/2021 Morgan et al.
2021/0267595 A1 9/2021 Posada et al.
2021/0267596 A1 9/2021 Fanelli et al.
2021/0275172 A1 9/2021 Harris et al.
2021/0275173 A1 9/2021 Shelton, IV et al.
2021/0275175 A1 9/2021 Vadali et al.
2021/0282767 A1 9/2021 Shelton, IV et al.
2021/0282776 A1 9/2021 Overmyer et al.
2021/0290226 A1 9/2021 Mandakolathur Vasudevan et al.
2021/0290231 A1 9/2021 Baxter, III et al.
2021/0290232 A1 9/2021 Harris et al.
2021/0290233 A1 9/2021 Shelton, IV et al.
2021/0290236 A1 9/2021 Moore et al.
2021/0290322 A1 9/2021 Traina
2021/0298745 A1 9/2021 Leimbach et al.
2021/0298746 A1 9/2021 Leimbach et al.
2021/0307657 A1 10/2021 Halac et al.
2021/0307695 A1 10/2021 Halac et al.
2021/0307744 A1 10/2021 Walcott et al.
2021/0307748 A1 10/2021 Harris et al.
2021/0313975 A1 10/2021 Shan et al.
2021/0315573 A1 10/2021 Shelton, IV et al.
2021/0315574 A1 10/2021 Shelton, IV et al.
2021/0315576 A1 10/2021 Shelton, IV et al.
2021/0315577 A1 10/2021 Shelton, IV et al.
2021/0322009 A1 10/2021 Huang et al.

(56) References Cited

U.S. PATENT DOCUMENTS

| | | | |
|---|---|---|---|
| 2021/0330321 A1 | 10/2021 | Leimbach et al. | |
| 2021/0338233 A1 | 11/2021 | Shelton, IV et al. | |
| 2021/0338234 A1 | 11/2021 | Shelton, IV et al. | |
| 2021/0338260 A1 | 11/2021 | Le Rolland et al. | |
| 2021/0346082 A1 | 11/2021 | Adams et al. | |
| 2021/0353284 A1 | 11/2021 | Yang et al. | |
| 2021/0369271 A1 | 12/2021 | Schings et al. | |
| 2021/0378669 A1 | 12/2021 | Shelton, IV et al. | |
| 2021/0393366 A1 | 12/2021 | Shelton, IV et al. | |
| 2021/0401487 A1 | 12/2021 | Apostolopoulos et al. | |
| 2021/0401513 A1 | 12/2021 | Apostolopoulos et al. | |
| 2022/0000479 A1 | 1/2022 | Shelton, IV et al. | |
| 2022/0015760 A1 | 1/2022 | Beardsley et al. | |
| 2022/0022878 A1* | 1/2022 | Strassner | A61B 17/1155 |
| 2022/0031315 A1 | 2/2022 | Bakos et al. | |
| 2022/0031319 A1 | 2/2022 | Witte et al. | |
| 2022/0031320 A1 | 2/2022 | Hall et al. | |
| 2022/0031322 A1 | 2/2022 | Parks | |
| 2022/0031323 A1 | 2/2022 | Witte | |
| 2022/0031324 A1 | 2/2022 | Hall et al. | |
| 2022/0031345 A1 | 2/2022 | Witte | |
| 2022/0031346 A1 | 2/2022 | Parks | |
| 2022/0031350 A1 | 2/2022 | Witte | |
| 2022/0031351 A1 | 2/2022 | Moubarak et al. | |
| 2022/0049593 A1 | 2/2022 | Groover et al. | |
| 2022/0054125 A1 | 2/2022 | Ji et al. | |
| 2022/0054130 A1 | 2/2022 | Overmyer et al. | |
| 2022/0061642 A1 | 3/2022 | Park et al. | |
| 2022/0061836 A1 | 3/2022 | Parihar et al. | |
| 2022/0061842 A1 | 3/2022 | Shelton, IV et al. | |
| 2022/0061843 A1 | 3/2022 | Vendely et al. | |
| 2022/0061845 A1 | 3/2022 | Shelton, IV et al. | |
| 2022/0061862 A1 | 3/2022 | Shelton, IV et al. | |
| 2022/0071630 A1 | 3/2022 | Swayze et al. | |
| 2022/0071631 A1 | 3/2022 | Harris et al. | |
| 2022/0071632 A1 | 3/2022 | Patel et al. | |
| 2022/0071635 A1 | 3/2022 | Shelton, IV et al. | |
| 2022/0079580 A1 | 3/2022 | Vendely et al. | |
| 2022/0079586 A1 | 3/2022 | Shelton, IV et al. | |
| 2022/0079588 A1 | 3/2022 | Harris et al. | |
| 2022/0079589 A1 | 3/2022 | Harris et al. | |
| 2022/0079595 A1 | 3/2022 | Huitema et al. | |
| 2022/0079596 A1 | 3/2022 | Huitema et al. | |
| 2022/0104695 A1 | 4/2022 | Russell | |
| 2022/0104814 A1 | 4/2022 | Shelton, IV et al. | |
| 2022/0104816 A1 | 4/2022 | Fernandes et al. | |
| 2022/0104820 A1 | 4/2022 | Shelton, IV et al. | |
| 2022/0110673 A1 | 4/2022 | Boronyak et al. | |
| 2022/0117602 A1 | 4/2022 | Wise et al. | |
| 2022/0125472 A1 | 4/2022 | Beckman et al. | |
| 2022/0133299 A1 | 5/2022 | Baxter, III | |
| 2022/0133300 A1 | 5/2022 | Leimbach et al. | |
| 2022/0133302 A1 | 5/2022 | Zerkle et al. | |
| 2022/0133303 A1 | 5/2022 | Huang | |
| 2022/0133304 A1 | 5/2022 | Leimbach et al. | |
| 2022/0133310 A1 | 5/2022 | Ross | |
| 2022/0133312 A1 | 5/2022 | Huang | |
| 2022/0133318 A1 | 5/2022 | Hudson et al. | |
| 2022/0142643 A1 | 5/2022 | Shelton, IV et al. | |
| 2022/0151611 A1 | 5/2022 | Shelton, IV et al. | |
| 2022/0151614 A1 | 5/2022 | Vendely et al. | |
| 2022/0151615 A1 | 5/2022 | Shelton, IV et al. | |
| 2022/0151616 A1 | 5/2022 | Shelton, IV et al. | |
| 2022/0160355 A1 | 5/2022 | Harris et al. | |
| 2022/0160358 A1 | 5/2022 | Wixey | |
| 2022/0167970 A1 | 6/2022 | Aronhalt et al. | |
| 2022/0167972 A1 | 6/2022 | Shelton, IV et al. | |
| 2022/0167973 A1 | 6/2022 | Shelton, IV et al. | |
| 2022/0167977 A1 | 6/2022 | Shelton, IV et al. | |
| 2022/0167979 A1 | 6/2022 | Yates et al. | |
| 2022/0167981 A1 | 6/2022 | Shelton, IV et al. | |
| 2022/0167982 A1 | 6/2022 | Shelton, IV et al. | |
| 2022/0167995 A1 | 6/2022 | Parfett et al. | |
| 2022/0168038 A1 | 6/2022 | Shelton, IV et al. | |
| 2022/0175370 A1 | 6/2022 | Shelton, IV et al. | |
| 2022/0175371 A1 | 6/2022 | Hess et al. | |
| 2022/0175372 A1 | 6/2022 | Shelton, IV et al. | |
| 2022/0175375 A1 | 6/2022 | Harris et al. | |
| 2022/0175378 A1 | 6/2022 | Leimbach et al. | |
| 2022/0175381 A1 | 6/2022 | Scheib et al. | |
| 2022/0183685 A1 | 6/2022 | Shelton, IV et al. | |
| 2022/0183687 A1 | 6/2022 | Wixey et al. | |
| 2022/0202487 A1 | 6/2022 | Shelton, IV et al. | |
| 2022/0211367 A1 | 7/2022 | Schmid et al. | |
| 2022/0218332 A1 | 7/2022 | Shelton, IV et al. | |
| 2022/0218336 A1 | 7/2022 | Timm et al. | |
| 2022/0218338 A1 | 7/2022 | Shelton, IV et al. | |
| 2022/0218344 A1 | 7/2022 | Leimbach et al. | |
| 2022/0218345 A1 | 7/2022 | Shelton, IV et al. | |
| 2022/0218346 A1 | 7/2022 | Shelton, IV et al. | |
| 2022/0218347 A1 | 7/2022 | Shelton, IV et al. | |
| 2022/0218348 A1 | 7/2022 | Swensgard et al. | |
| 2022/0218349 A1 | 7/2022 | Shelton, IV et al. | |
| 2022/0218350 A1 | 7/2022 | Shelton, IV et al. | |
| 2022/0218351 A1 | 7/2022 | Shelton, IV et al. | |
| 2022/0218376 A1 | 7/2022 | Shelton, IV et al. | |
| 2022/0218381 A1 | 7/2022 | Leimbach et al. | |
| 2022/0218382 A1 | 7/2022 | Leimbach et al. | |
| 2022/0225993 A1 | 7/2022 | Huitema et al. | |
| 2022/0225994 A1 | 7/2022 | Setser et al. | |
| 2022/0226013 A1 | 7/2022 | Hall et al. | |
| 2022/0233186 A1 | 7/2022 | Timm et al. | |
| 2022/0233188 A1 | 7/2022 | Timm et al. | |
| 2022/0233194 A1 | 7/2022 | Baxter, III et al. | |
| 2022/0233195 A1 | 7/2022 | Shelton, IV et al. | |
| 2022/0233251 A1* | 7/2022 | Bowling | A61B 34/35 |
| 2022/0233257 A1 | 7/2022 | Shelton, IV et al. | |
| 2022/0240928 A1 | 8/2022 | Timm et al. | |
| 2022/0240929 A1 | 8/2022 | Timm et al. | |
| 2022/0240930 A1 | 8/2022 | Yates et al. | |
| 2022/0240936 A1 | 8/2022 | Huitema et al. | |
| 2022/0240937 A1 | 8/2022 | Shelton, IV et al. | |
| 2022/0265272 A1 | 8/2022 | Li et al. | |
| 2022/0273293 A1 | 9/2022 | Shelton, IV et al. | |
| 2022/0273294 A1 | 9/2022 | Creamer et al. | |
| 2022/0273300 A1 | 9/2022 | Shelton, IV et al. | |
| 2022/0273303 A1 | 9/2022 | Creamer et al. | |
| 2022/0273304 A1 | 9/2022 | Shelton, IV et al. | |
| 2022/0273306 A1 | 9/2022 | Shelton, IV et al. | |
| 2022/0273307 A1 | 9/2022 | Shelton, IV et al. | |
| 2022/0273308 A1 | 9/2022 | Shelton, IV et al. | |
| 2022/0287711 A1 | 9/2022 | Ming et al. | |
| 2022/0296230 A1 | 9/2022 | Adams et al. | |
| 2022/0304679 A1 | 9/2022 | Bakos et al. | |
| 2022/0304680 A1 | 9/2022 | Shelton, IV et al. | |
| 2022/0304681 A1 | 9/2022 | Shelton, IV et al. | |
| 2022/0304682 A1 | 9/2022 | Shelton, IV et al. | |
| 2022/0304683 A1 | 9/2022 | Shelton, IV et al. | |
| 2022/0304684 A1 | 9/2022 | Bakos et al. | |
| 2022/0304685 A1 | 9/2022 | Bakos et al. | |
| 2022/0304686 A1 | 9/2022 | Shelton, IV et al. | |
| 2022/0304687 A1 | 9/2022 | Shelton, IV et al. | |
| 2022/0304688 A1 | 9/2022 | Shelton, IV et al. | |
| 2022/0304689 A1 | 9/2022 | Shelton, IV | |
| 2022/0304690 A1 | 9/2022 | Baxter, III et al. | |
| 2022/0304715 A1 | 9/2022 | Shelton, IV | |
| 2022/0313253 A1 | 10/2022 | Shelton, IV et al. | |
| 2022/0313263 A1 | 10/2022 | Huitema et al. | |
| 2022/0313619 A1 | 10/2022 | Schmid et al. | |
| 2022/0323067 A1 | 10/2022 | Overmyer et al. | |
| 2022/0323070 A1 | 10/2022 | Ross et al. | |
| 2022/0330940 A1 | 10/2022 | Shelton, IV et al. | |
| 2022/0338870 A1 | 10/2022 | Swayze et al. | |
| 2022/0346774 A1 | 11/2022 | Hess et al. | |
| 2022/0346775 A1 | 11/2022 | Hess et al. | |
| 2022/0346776 A1 | 11/2022 | Aronhalt et al. | |
| 2022/0346781 A1 | 11/2022 | Shelton, IV et al. | |
| 2022/0346783 A1 | 11/2022 | Shelton, IV et al. | |
| 2022/0346785 A1 | 11/2022 | Aronhalt et al. | |
| 2022/0354492 A1 | 11/2022 | Baril | |
| 2022/0354493 A1 | 11/2022 | Shelton, IV et al. | |
| 2022/0354495 A1 | 11/2022 | Baxter, III et al. | |
| 2022/0361879 A1 | 11/2022 | Baxter, III et al. | |
| 2022/0370069 A1 | 11/2022 | Simms et al. | |

(56) References Cited

U.S. PATENT DOCUMENTS

| | | | |
|---|---|---|---|
| 2022/0378418 | A1 | 12/2022 | Huang et al. |
| 2022/0378424 | A1 | 12/2022 | Huang et al. |
| 2022/0378425 | A1 | 12/2022 | Huang et al. |
| 2022/0378426 | A1 | 12/2022 | Huang et al. |
| 2022/0378428 | A1 | 12/2022 | Shelton, IV et al. |
| 2022/0378435 | A1 | 12/2022 | Dholakia et al. |
| 2022/0387031 | A1 | 12/2022 | Yates et al. |
| 2022/0387032 | A1 | 12/2022 | Huitema et al. |
| 2022/0387033 | A1 | 12/2022 | Huitema et al. |
| 2022/0387034 | A1 | 12/2022 | Huitema et al. |
| 2022/0387035 | A1 | 12/2022 | Huitema et al. |
| 2022/0387036 | A1 | 12/2022 | Huitema et al. |
| 2022/0387037 | A1 | 12/2022 | Huitema et al. |
| 2022/0387038 | A1 | 12/2022 | Huitema et al. |
| 2022/0387125 | A1 | 12/2022 | Leimbach et al. |
| 2023/0016171 | A1 | 1/2023 | Yates et al. |
| 2023/0018950 | A1 | 1/2023 | Shelton, IV et al. |
| 2023/0048444 | A1* | 2/2023 | Shelton, IV ........... A61B 34/76 |
| 2023/0055711 | A1 | 2/2023 | Chen et al. |
| 2023/0088531 | A1 | 3/2023 | Hall et al. |
| 2023/0094712 | A1 | 3/2023 | Shelton, IV et al. |
| 2023/0120983 | A1 | 4/2023 | Stokes et al. |
| 2023/0121131 | A1 | 4/2023 | Swayze et al. |
| 2023/0121658 | A1 | 4/2023 | Stokes et al. |
| 2023/0133811 | A1 | 5/2023 | Huang |
| 2023/0134883 | A1 | 5/2023 | Leimbach |
| 2023/0135070 | A1 | 5/2023 | Shelton, IV et al. |
| 2023/0135282 | A1 | 5/2023 | Schings et al. |
| 2023/0135811 | A1 | 5/2023 | Guest |
| 2023/0138314 | A1 | 5/2023 | Jenkins |
| 2023/0138743 | A1 | 5/2023 | Ross et al. |
| 2023/0165582 | A1 | 6/2023 | Harris et al. |
| 2023/0165584 | A1 | 6/2023 | Leimbach et al. |
| 2023/0172607 | A1 | 6/2023 | DiNardo et al. |
| 2023/0200831 | A1 | 6/2023 | Swensgard et al. |
| 2023/0210525 | A1 | 7/2023 | Shelton, IV et al. |
| 2023/0218296 | A1 | 7/2023 | Yates et al. |
| 2023/0240677 | A1 | 8/2023 | Ming et al. |
| 2023/0240678 | A1 | 8/2023 | Overmyer et al. |
| 2023/0255631 | A1 | 8/2023 | Vendely et al. |
| 2023/0270438 | A1 | 8/2023 | Jaworek et al. |
| 2023/0277175 | A1 | 9/2023 | Shelton, IV et al. |
| 2023/0285021 | A1 | 9/2023 | Shelton, IV |
| 2023/0301654 | A1 | 9/2023 | Shelton, IV et al. |
| 2023/0309992 | A1 | 10/2023 | Leimbach et al. |
| 2023/0320729 | A1 | 10/2023 | Yates et al. |
| 2023/0355238 | A1 | 11/2023 | Shelton, IV |
| 2023/0355345 | A1 | 11/2023 | Shelton, IV et al. |
| 2023/0371947 | A1 | 11/2023 | Shelton, IV et al. |
| 2023/0380833 | A1 | 11/2023 | Shelton, IV et al. |

FOREIGN PATENT DOCUMENTS

| | | | | |
|---|---|---|---|---|
| AU | 2012268848 | A1 | 1/2013 | |
| AU | 2011218702 | B2 | 6/2013 | |
| AU | 2012200178 | B2 | 7/2013 | |
| BR | 112013007744 | A2 | 6/2016 | |
| BR | 112013027777 | A2 | 1/2017 | |
| CA | 1015829 | A | 8/1977 | |
| CA | 1125615 | A | 6/1982 | |
| CA | 2520413 | A1 | 3/2007 | |
| CA | 2725181 | A1 | 11/2007 | |
| CA | 2851239 | A1 | 11/2007 | |
| CA | 2550059 | C | 8/2008 | |
| CA | 2935353 | A1 * | 4/2009 | ............. A61B 17/00 |
| CA | 2664874 | A1 | 11/2009 | |
| CA | 2813230 | A1 | 4/2012 | |
| CA | 2905715 | A1 * | 10/2014 | ....... A61B 17/07207 |
| CA | 2940510 | A1 | 8/2015 | |
| CA | 2698728 | C | 8/2016 | |
| CN | 1163558 | A | 10/1997 | |
| CN | 2488482 | Y | 5/2002 | |
| CN | 1634601 | A | 7/2005 | |
| CN | 2716900 | Y | 8/2005 | |
| CN | 2738962 | Y | 11/2005 | |
| CN | 1777406 | A | 5/2006 | |
| CN | 2785249 | Y | 5/2006 | |
| CN | 2796654 | Y | 7/2006 | |
| CN | 2868212 | Y | 2/2007 | |
| CN | 200942099 | Y | 9/2007 | |
| CN | 200984209 | Y | 12/2007 | |
| CN | 200991269 | Y | 12/2007 | |
| CN | 201001747 | Y | 1/2008 | |
| CN | 101143105 | A | 3/2008 | |
| CN | 201029899 | Y | 3/2008 | |
| CN | 101188900 | A | 5/2008 | |
| CN | 101203085 | A | 6/2008 | |
| CN | 101273908 | A | 10/2008 | |
| CN | 101378791 | A | 3/2009 | |
| CN | 101401736 | A | 4/2009 | |
| CN | 101507635 | A | 8/2009 | |
| CN | 101522120 | A | 9/2009 | |
| CN | 101669833 | A | 3/2010 | |
| CN | 101716090 | A | 6/2010 | |
| CN | 101721236 | A | 6/2010 | |
| CN | 101756727 | A | 6/2010 | |
| CN | 101828940 | A | 9/2010 | |
| CN | 101856250 | A | 10/2010 | |
| CN | 101873834 | A | 10/2010 | |
| CN | 201719298 | U | 1/2011 | |
| CN | 102038532 | A | 5/2011 | |
| CN | 201879759 | U | 6/2011 | |
| CN | 201949071 | U | 8/2011 | |
| CN | 102217961 | A | 10/2011 | |
| CN | 102217963 | A | 10/2011 | |
| CN | 102243850 | A | 11/2011 | |
| CN | 102247182 | A | 11/2011 | |
| CN | 102247183 | A | 11/2011 | |
| CN | 101779977 | B | 12/2011 | |
| CN | 102309352 | A | 1/2012 | |
| CN | 101912284 | B | 7/2012 | |
| CN | 102125450 | B | 7/2012 | |
| CN | 202313537 | U | 7/2012 | |
| CN | 202397539 | U | 8/2012 | |
| CN | 202426586 | U | 9/2012 | |
| CN | 102743201 | A | 10/2012 | |
| CN | 202489990 | U | 10/2012 | |
| CN | 102228387 | B | 11/2012 | |
| CN | 102835977 | A | 12/2012 | |
| CN | 202568350 | U | 12/2012 | |
| CN | 103037781 | A | 4/2013 | |
| CN | 103083053 | A | 5/2013 | |
| CN | 103391037 | A | 11/2013 | |
| CN | 203328751 | U | 12/2013 | |
| CN | 103505264 | A | 1/2014 | |
| CN | 103584893 | A | 2/2014 | |
| CN | 103635150 | A | 3/2014 | |
| CN | 103690212 | A | 4/2014 | |
| CN | 103764046 | A | 4/2014 | |
| CN | 203564285 | U | 4/2014 | |
| CN | 203564287 | U | 4/2014 | |
| CN | 203597997 | U | 5/2014 | |
| CN | 103829981 | A | 6/2014 | |
| CN | 103829983 | A | 6/2014 | |
| CN | 103860221 | A | 6/2014 | |
| CN | 103908313 | A | 7/2014 | |
| CN | 203693685 | U | 7/2014 | |
| CN | 203736251 | U | 7/2014 | |
| CN | 103981635 | A | 8/2014 | |
| CN | 104027145 | A | 9/2014 | |
| CN | 203815517 | U | 9/2014 | |
| CN | 102783741 | B | 10/2014 | |
| CN | 102973300 | B | 10/2014 | |
| CN | 104321021 | A | 1/2015 | |
| CN | 204092074 | U | 1/2015 | |
| CN | 104337556 | A | 2/2015 | |
| CN | 204158440 | U | 2/2015 | |
| CN | 204158441 | U | 2/2015 | |
| CN | 102469995 | B | 3/2015 | |
| CN | 104422849 | A | 3/2015 | |
| CN | 104586463 | A | 5/2015 | |
| CN | 204520822 | U | 8/2015 | |
| CN | 204636451 | U | 9/2015 | |
| CN | 103860225 | B | 3/2016 | |

(56) References Cited

FOREIGN PATENT DOCUMENTS

| | | | |
|---|---|---|---|
| CN | 103750872 | B | 5/2016 |
| CN | 105682566 | A | 6/2016 |
| CN | 105919642 | A | 9/2016 |
| CN | 103648410 | B | 10/2016 |
| CN | 105997173 | A | 10/2016 |
| CN | 106344091 | A | 1/2017 |
| CN | 104921730 | B | 9/2017 |
| CN | 104349800 | B | 11/2017 |
| CN | 107635483 | A | 1/2018 |
| CN | 208625784 | U | 3/2019 |
| DE | 273689 | C | 5/1914 |
| DE | 1775926 | A | 1/1972 |
| DE | 3036217 | A1 | 4/1982 |
| DE | 3210466 | A1 | 9/1983 |
| DE | 3709067 | A1 | 9/1988 |
| DE | 19534043 | A1 | 3/1997 |
| DE | 19851291 | A1 | 1/2000 |
| DE | 19924311 | A1 | 11/2000 |
| DE | 20016423 | U1 | 2/2001 |
| DE | 20112837 | U1 | 10/2001 |
| DE | 20121753 | U1 | 4/2003 |
| DE | 202004012389 | U1 | 9/2004 |
| DE | 10314072 | A1 | 10/2004 |
| DE | 102004014011 | A1 | 10/2005 |
| DE | 102004041871 | A1 | 3/2006 |
| DE | 102004063606 | A1 | 7/2006 |
| DE | 202007003114 | U1 | 6/2007 |
| DE | 102010013150 | A1 | 9/2011 |
| DE | 102012213322 | A1 | 1/2014 |
| DE | 102013101158 | A1 | 8/2014 |
| EM | 002220467-0008 | | 4/2013 |
| EP | 0000756 | A1 | 2/1979 |
| EP | 0122046 | A1 | 10/1984 |
| EP | 0129442 | B1 | 11/1987 |
| EP | 0251444 | A1 | 1/1988 |
| EP | 0255631 | A1 | 2/1988 |
| EP | 0169044 | B1 | 6/1991 |
| EP | 0541950 | A1 | 5/1993 |
| EP | 0548998 | A1 | 6/1993 |
| EP | 0594148 | A1 | 4/1994 |
| EP | 0646357 | A1 | 4/1995 |
| EP | 0505036 | B1 | 5/1995 |
| EP | 0669104 | A1 | 8/1995 |
| EP | 0516544 | B1 | 3/1996 |
| EP | 0705571 | A1 | 4/1996 |
| EP | 0528478 | B1 | 5/1996 |
| EP | 0770355 | A1 | 5/1997 |
| EP | 0625335 | B1 | 11/1997 |
| EP | 0879742 | A1 | 11/1998 |
| EP | 0650701 | B1 | 3/1999 |
| EP | 0923907 | A1 | 6/1999 |
| EP | 0484677 | B2 | 7/2000 |
| EP | 1034747 | A1 | 9/2000 |
| EP | 1034748 | A1 | 9/2000 |
| EP | 0726632 | B1 | 10/2000 |
| EP | 1053719 | A1 | 11/2000 |
| EP | 1055399 | A1 | 11/2000 |
| EP | 1055400 | A1 | 11/2000 |
| EP | 1064882 | A1 | 1/2001 |
| EP | 1080694 | A1 | 3/2001 |
| EP | 1090592 | A1 | 4/2001 |
| EP | 1095627 | A1 | 5/2001 |
| EP | 0806914 | B1 | 9/2001 |
| EP | 1157666 | A1 | 11/2001 |
| EP | 1234587 | A1 | 8/2002 |
| EP | 1284120 | A1 | 2/2003 |
| EP | 0717967 | B1 | 5/2003 |
| EP | 0869742 | B1 | 5/2003 |
| EP | 1374788 | A1 | 1/2004 |
| EP | 1407719 | A2 | 4/2004 |
| EP | 0996378 | B1 | 6/2004 |
| EP | 1558161 | A1 | 8/2005 |
| EP | 0880338 | B1 | 10/2005 |
| EP | 1158917 | B1 | 11/2005 |
| EP | 1344498 | B1 | 11/2005 |

| | | | |
|---|---|---|---|
| EP | 1330989 | B1 | 12/2005 |
| EP | 1632191 | A2 | 3/2006 |
| EP | 1082944 | B1 | 5/2006 |
| EP | 1253866 | B1 | 7/2006 |
| EP | 1723914 | A1 | 11/2006 |
| EP | 1285633 | B1 | 12/2006 |
| EP | 1011494 | B1 | 1/2007 |
| EP | 1767163 | A1 | 3/2007 |
| EP | 1837041 | A1 | 9/2007 |
| EP | 0922435 | B1 | 10/2007 |
| EP | 1599146 | B1 | 10/2007 |
| EP | 1330201 | B1 | 6/2008 |
| EP | 2039302 | A2 | 3/2009 |
| EP | 1719461 | B1 | 6/2009 |
| EP | 2116196 | A2 | 11/2009 |
| EP | 2153793 | A2 | 2/2010 |
| EP | 1769754 | B1 | 6/2010 |
| EP | 1627605 | B1 | 12/2010 |
| EP | 2316345 | A1 | 5/2011 |
| EP | 1962711 | B1 | 2/2012 |
| EP | 2486862 | A2 | 8/2012 |
| EP | 2486868 | A2 | 8/2012 |
| EP | 2510891 | A1 | 10/2012 |
| EP | 2517638 | A1 | 10/2012 |
| EP | 2529671 | A2 | 12/2012 |
| EP | 2606812 | A1 | 6/2013 |
| EP | 2649948 | A1 | 10/2013 |
| EP | 2649949 | A1 | 10/2013 |
| EP | 2668910 | A2 | 12/2013 |
| EP | 2687164 | A2 | 1/2014 |
| EP | 2713902 | A1 | 4/2014 |
| EP | 2743042 | A2 | 6/2014 |
| EP | 2764827 | A2 | 8/2014 |
| EP | 2777524 | A2 | 9/2014 |
| EP | 2789299 | A1 | 10/2014 |
| EP | 2842500 | A1 | 3/2015 |
| EP | 2853220 | A1 | 4/2015 |
| EP | 2878274 | A1 | 6/2015 |
| EP | 2298220 | B1 | 6/2016 |
| EP | 3031404 | A1 | 6/2016 |
| EP | 3047806 | A1 | 7/2016 |
| EP | 3078334 | A1 | 10/2016 |
| EP | 2364651 | B1 | 11/2016 |
| EP | 2747235 | B1 | 11/2016 |
| EP | 3095399 | A2 | 11/2016 |
| EP | 3120781 | A2 | 1/2017 |
| EP | 3135225 | A2 | 3/2017 |
| EP | 2789299 | B1 | 5/2017 |
| EP | 3225190 | A2 | 10/2017 |
| EP | 3235445 | A1 | 10/2017 |
| EP | 3326548 | A1 | 5/2018 |
| EP | 3363378 | A1 | 8/2018 |
| EP | 3409216 | A1 | 12/2018 |
| EP | 3476301 | A1 | 5/2019 |
| EP | 3476334 | A1 | 5/2019 |
| EP | 3275378 | B1 | 7/2019 |
| EP | 3505095 | A1 | 7/2019 |
| EP | 3791810 | A1 | 3/2021 |
| ES | 1070456 | U | 9/2009 |
| FR | 459743 | A | 11/1913 |
| FR | 999646 | A | 2/1952 |
| FR | 1112936 | A | 3/1956 |
| FR | 2598905 | A1 | 11/1987 |
| FR | 2689749 | B1 | 7/1994 |
| FR | 2765794 | A1 | 1/1999 |
| FR | 2815842 | A1 | 5/2002 |
| GB | 939929 | A | 10/1963 |
| GB | 1210522 | A | 10/1970 |
| GB | 1217159 | A | 12/1970 |
| GB | 1339394 | A | 12/1973 |
| GB | 2024012 | A | 1/1980 |
| GB | 2109241 | A | 6/1983 |
| GB | 2090534 | B | 6/1984 |
| GB | 2272159 | A | 5/1994 |
| GB | 2336214 | A | 10/1999 |
| GB | 2509523 | A | 7/2014 |
| GR | 930100110 | A | 11/1993 |
| JP | S4711908 | Y1 | 5/1972 |
| JP | S5033988 | U | 4/1975 |

(56) References Cited

FOREIGN PATENT DOCUMENTS

| | | | |
|---|---|---|---|
| JP | S5367286 | A | 6/1978 |
| JP | S56112235 | A | 9/1981 |
| JP | S60113007 | A | 6/1985 |
| JP | S62170011 | U | 10/1987 |
| JP | S6333137 | A | 2/1988 |
| JP | S63270040 | A | 11/1988 |
| JP | S63318824 | A | 12/1988 |
| JP | H0129503 | B2 | 6/1989 |
| JP | H02106189 | A | 4/1990 |
| JP | H0378514 | U | 8/1991 |
| JP | H0385009 | U | 8/1991 |
| JP | H0489041 | A | 3/1992 |
| JP | H04215747 | A | 8/1992 |
| JP | H04131860 | U | 12/1992 |
| JP | H0584252 | A | 4/1993 |
| JP | H05123325 | A | 5/1993 |
| JP | H05226945 | A | 9/1993 |
| JP | H0630945 | A | 2/1994 |
| JP | H0636757 | A | 2/1994 |
| JP | H06237937 | A | 8/1994 |
| JP | H06304176 | A | 11/1994 |
| JP | H06327684 | A | 11/1994 |
| JP | H079622 | U | 2/1995 |
| JP | H07124166 | A | 5/1995 |
| JP | H07163573 | A | 6/1995 |
| JP | H07255735 | A | 10/1995 |
| JP | H07285089 | A | 10/1995 |
| JP | H0833642 | A | 2/1996 |
| JP | H08164141 | A | 6/1996 |
| JP | H08182684 | A | 7/1996 |
| JP | H08507708 | A | 8/1996 |
| JP | H08229050 | A | 9/1996 |
| JP | H08289895 | A | 11/1996 |
| JP | H0950795 | A | 2/1997 |
| JP | H09-323068 | A | 12/1997 |
| JP | H10118090 | A | 5/1998 |
| JP | H10-200699 | A | 7/1998 |
| JP | H10296660 | A | 11/1998 |
| JP | 2000014632 | A | 1/2000 |
| JP | 2000033071 | A | 2/2000 |
| JP | 2000112002 | A | 4/2000 |
| JP | 2000166932 | A | 6/2000 |
| JP | 2000171730 | A | 6/2000 |
| JP | 2000210299 | A | 8/2000 |
| JP | 2000271141 | A | 10/2000 |
| JP | 2000287987 | A | 10/2000 |
| JP | 2000325303 | A | 11/2000 |
| JP | 2001-69758 | A | 3/2001 |
| JP | 2001087272 | A | 4/2001 |
| JP | 2001208655 | A | 8/2001 |
| JP | 2001514541 | A | 9/2001 |
| JP | 2001276091 | A | 10/2001 |
| JP | 2002051974 | A | 2/2002 |
| JP | 2002054903 | A | 2/2002 |
| JP | 2002085415 | A | 3/2002 |
| JP | 2002143078 | A | 5/2002 |
| JP | 2002153481 | A | 5/2002 |
| JP | 2002528161 | A | 9/2002 |
| JP | 2002314298 | A | 10/2002 |
| JP | 2003135473 | A | 5/2003 |
| JP | 2003521301 | A | 7/2003 |
| JP | 3442423 | B2 | 9/2003 |
| JP | 2003300416 | A | 10/2003 |
| JP | 2004147701 | A | 5/2004 |
| JP | 2004162035 | A | 6/2004 |
| JP | 2004229976 | A | 8/2004 |
| JP | 2005013573 | A | 1/2005 |
| JP | 2005080702 | A | 3/2005 |
| JP | 2005131163 | A | 5/2005 |
| JP | 2005131164 | A | 5/2005 |
| JP | 2005131173 | A | 5/2005 |
| JP | 2005131211 | A | 5/2005 |
| JP | 2005131212 | A | 5/2005 |
| JP | 2005137423 | A | 6/2005 |
| JP | 2005187954 | A | 7/2005 |
| JP | 2005211455 | A | 8/2005 |
| JP | 2005328882 | A | 12/2005 |
| JP | 2005335432 | A | 12/2005 |
| JP | 2005342267 | A | 12/2005 |
| JP | 3791856 | B2 | 6/2006 |
| JP | 2006187649 | A | 7/2006 |
| JP | 2006218228 | A | 8/2006 |
| JP | 2006281405 | A | 10/2006 |
| JP | 2006291180 | A | 10/2006 |
| JP | 2006346445 | A | 12/2006 |
| JP | 2007-97252 | A | 4/2007 |
| JP | 2007289715 | A | 11/2007 |
| JP | 2007304057 | A | 11/2007 |
| JP | 2007306710 | A | 11/2007 |
| JP | D1322057 | | 2/2008 |
| JP | 2008154804 | A | 7/2008 |
| JP | 2008220032 | A | 9/2008 |
| JP | 2009507526 | A | 2/2009 |
| JP | 2009189838 | A | 8/2009 |
| JP | 2009189846 | A | 8/2009 |
| JP | 2009207260 | A | 9/2009 |
| JP | 2009226028 | A | 10/2009 |
| JP | 2009538684 | A | 11/2009 |
| JP | 2009539420 | A | 11/2009 |
| JP | D1383743 | | 2/2010 |
| JP | 2010065594 | A | 3/2010 |
| JP | 2010069307 | A | 4/2010 |
| JP | 2010069310 | A | 4/2010 |
| JP | 2010098844 | A | 4/2010 |
| JP | 2010214128 | A | 9/2010 |
| JP | 2011072574 | A | 4/2011 |
| JP | 4722849 | B2 | 7/2011 |
| JP | 4728996 | B2 | 7/2011 |
| JP | 2011524199 | A | 9/2011 |
| JP | 2011200665 | A | 10/2011 |
| JP | D1432094 | | 12/2011 |
| JP | 1433631 | S | 2/2012 |
| JP | 2012115542 | A | 6/2012 |
| JP | 2012143283 | A | 8/2012 |
| JP | 5154710 | B1 | 2/2013 |
| JP | 2013042921 | A | 3/2013 |
| JP | 2013099551 | A | 5/2013 |
| JP | 2013126430 | A | 6/2013 |
| JP | D1481426 | | 9/2013 |
| JP | 2013541982 | A | 11/2013 |
| JP | 2013541983 | A | 11/2013 |
| JP | 2013541997 | A | 11/2013 |
| JP | 2014018667 | A | 2/2014 |
| JP | D1492363 | | 2/2014 |
| JP | 2014121599 | A | 7/2014 |
| JP | 2014171879 | A | 9/2014 |
| JP | 1517663 | S | 2/2015 |
| JP | 2015512725 | A | 4/2015 |
| JP | 2015513956 | A | 5/2015 |
| JP | 2015513958 | A | 5/2015 |
| JP | 2015514471 | A | 5/2015 |
| JP | 2015516838 | A | 6/2015 |
| JP | 2015521524 | A | 7/2015 |
| JP | 2015521525 | A | 7/2015 |
| JP | 2016007800 | A | 1/2016 |
| JP | 2016508792 | A | 3/2016 |
| JP | 2016512057 | A | 4/2016 |
| JP | 2016518914 | A | 6/2016 |
| JP | 2016530949 | A | 10/2016 |
| JP | 2017513563 | A | 6/2017 |
| JP | 1601498 | S | 4/2018 |
| JP | 2019513530 | A | 5/2019 |
| JP | 2020501797 | A | 1/2020 |
| JP | D1677030 | S | 1/2021 |
| JP | D1696539 | S | 10/2021 |
| KR | 20100110134 | A | 10/2010 |
| KR | 20110003229 | A | 1/2011 |
| KR | 300631507 | | 3/2012 |
| KR | 300747646 | | 6/2014 |
| KR | 20180053811 | A | 5/2018 |
| RU | 1814161 | C | 5/1993 |
| RU | 2008830 | C1 | 3/1994 |
| RU | 2052979 | C1 | 1/1996 |
| RU | 2066128 | C1 | 9/1996 |

(56) References Cited

FOREIGN PATENT DOCUMENTS

| | | | |
|---|---|---|---|
| RU | 2069981 | C1 | 12/1996 |
| RU | 2098025 | C1 | 12/1997 |
| RU | 2104671 | C1 | 2/1998 |
| RU | 2110965 | C1 | 5/1998 |
| RU | 2141279 | C1 | 11/1999 |
| RU | 2144791 | C1 | 1/2000 |
| RU | 2161450 | C1 | 1/2001 |
| RU | 2181566 | C2 | 4/2002 |
| RU | 2187249 | C2 | 8/2002 |
| RU | 32984 | U1 | 10/2003 |
| RU | 2225170 | C2 | 3/2004 |
| RU | 42750 | U1 | 12/2004 |
| RU | 61114 | U1 | 2/2007 |
| RU | 61122 | U1 | 2/2007 |
| RU | 2430692 | C2 | 10/2011 |
| SU | 189517 | A | 1/1967 |
| SU | 297156 | A | 5/1971 |
| SU | 328636 | A | 9/1972 |
| SU | 511939 | A1 | 4/1976 |
| SU | 674747 | A1 | 7/1979 |
| SU | 728848 | A1 | 4/1980 |
| SU | 1009439 | A | 4/1983 |
| SU | 1042742 | A1 | 9/1983 |
| SU | 1271497 | A1 | 11/1986 |
| SU | 1333319 | A2 | 8/1987 |
| SU | 1377052 | A1 | 2/1988 |
| SU | 1377053 | A1 | 2/1988 |
| SU | 1443874 | A1 | 12/1988 |
| SU | 1509051 | A1 | 9/1989 |
| SU | 1561964 | A1 | 5/1990 |
| SU | 1708312 | A1 | 1/1992 |
| SU | 1722476 | A1 | 3/1992 |
| SU | 1752361 | A1 | 8/1992 |
| SU | 1814161 | A1 | 5/1993 |
| WO | WO-9308754 | A1 | 5/1993 |
| WO | WO-9315648 | A1 | 8/1993 |
| WO | WO-9420030 | A1 | 9/1994 |
| WO | WO-9517855 | A1 | 7/1995 |
| WO | WO-9520360 | A1 | 8/1995 |
| WO | WO-9623448 | A1 | 8/1996 |
| WO | WO-9635464 | A1 | 11/1996 |
| WO | WO-9639086 | A1 | 12/1996 |
| WO | WO-9639088 | A1 | 12/1996 |
| WO | WO-9724073 | A1 | 7/1997 |
| WO | WO-9734533 | A1 | 9/1997 |
| WO | WO-9827870 | A1 | 7/1998 |
| WO | WO-9903407 | A1 | 1/1999 |
| WO | WO-9903409 | A1 | 1/1999 |
| WO | WO-9948430 | A1 | 9/1999 |
| WO | WO-0024322 | A1 | 5/2000 |
| WO | WO-0024330 | A1 | 5/2000 |
| WO | WO-0036690 | A2 | 6/2000 |
| WO | WO-0053112 | A2 | 9/2000 |
| WO | WO-0024448 | A2 | 10/2000 |
| WO | WO-0057796 | A1 | 10/2000 |
| WO | WO-0105702 | A1 | 1/2001 |
| WO | WO-0154594 | A1 | 8/2001 |
| WO | WO-0158371 | A1 | 8/2001 |
| WO | WO-0162164 | A2 | 8/2001 |
| WO | WO-0162169 | A2 | 8/2001 |
| WO | WO-0191646 | A1 | 12/2001 |
| WO | WO-0219932 | A1 | 3/2002 |
| WO | WO-0226143 | A1 | 4/2002 |
| WO | WO-0236028 | A1 | 5/2002 |
| WO | WO-02065933 | A2 | 8/2002 |
| WO | WO-03055402 | A1 | 7/2003 |
| WO | WO-03094747 | A1 | 11/2003 |
| WO | WO-03079909 | A3 | 3/2004 |
| WO | WO-2004019803 | A1 | 3/2004 |
| WO | WO-2004032783 | A1 | 4/2004 |
| WO | WO-2004047626 | A1 | 6/2004 |
| WO | WO-2004047653 | A2 | 6/2004 |
| WO | WO-2004056277 | A1 | 7/2004 |
| WO | WO-2004078050 | A2 | 9/2004 |
| WO | WO-2004078051 | A2 | 9/2004 |
| WO | WO-2004096015 | A2 | 11/2004 |
| WO | WO-2006044581 | A2 | 4/2006 |
| WO | WO-2006051252 | A1 | 5/2006 |
| WO | WO-2006059067 | A1 | 6/2006 |
| WO | WO-2006073581 | A2 | 7/2006 |
| WO | WO-2006085389 | A1 | 8/2006 |
| WO | WO-2007015971 | A2 | 2/2007 |
| WO | WO-2007074430 | A1 | 7/2007 |
| WO | WO-2007129121 | A1 | 11/2007 |
| WO | WO-2007137304 | A2 | 11/2007 |
| WO | WO-2007142625 | A2 | 12/2007 |
| WO | WO-2008021969 | A2 | 2/2008 |
| WO | WO-2008061566 | A1 | 5/2008 |
| WO | WO-2008089404 | A2 | 7/2008 |
| WO | WO-2009005969 | A2 | 1/2009 |
| WO | WO-2009046490 | A1 | 4/2009 |
| WO | WO-2009067649 | A2 | 5/2009 |
| WO | WO-2009091497 | A2 | 7/2009 |
| WO | WO-2010126129 | A1 | 11/2010 |
| WO | WO-2010134913 | A1 | 11/2010 |
| WO | WO-2011008672 | A2 | 1/2011 |
| WO | WO-2011044343 | A2 | 4/2011 |
| WO | WO-2012006306 | A2 | 1/2012 |
| WO | WO-2012013577 | A1 | 2/2012 |
| WO | WO-2012044606 | A2 | 4/2012 |
| WO | WO-2012061725 | A1 | 5/2012 |
| WO | WO-2012072133 | A1 | 6/2012 |
| WO | WO-2012166503 | A1 | 12/2012 |
| WO | WO-2013087092 | A1 | 6/2013 |
| WO | WO-2013151888 | A1 | 10/2013 |
| WO | WO-2014004209 | A2 | 1/2014 |
| WO | WO-2014113438 | A1 | 7/2014 |
| WO | WO-2014175894 | A1 | 10/2014 |
| WO | WO-2015032797 | A1 | 3/2015 |
| WO | WO-2015076780 | A1 | 5/2015 |
| WO | WO-2015137040 | A1 | 9/2015 |
| WO | WO-2015138760 | A1 | 9/2015 |
| WO | WO-2015187107 | A1 | 12/2015 |
| WO | WO-2016100682 | A1 | 6/2016 |
| WO | WO-2016107448 | A1 | 7/2016 |
| WO | WO-2017138905 | A1 | 8/2017 |
| WO | WO-2018011664 | A1 | 1/2018 |
| WO | WO-2019036490 | A1 | 2/2019 |
| WO | WO-2019130087 | A1 | 7/2019 |
| WO | WO-2019130089 | A1 | 7/2019 |
| WO | WO-2019208902 | A1 | 10/2019 |
| WO | WO-2021189234 | A1 | 9/2021 |
| WO | WO-2022249091 | A1 | 12/2022 |
| WO | WO-2022249094 | A1 | 12/2022 |

OTHER PUBLICATIONS

"Council Directive 93/42/EEC of Jun. 14, 1993 Concerning Medical Devices," Official Journal of the European Communities, L&C. Ligislation and Competition, S, No. L 169, Jun. 14, 1993, pp. 1-43.

"Understanding the Requirements of ISO/IEC 14443 for Type B Proximity Contactless Identification Cards," retrieved from https://www.digchip.com/application-notes/22/15746.php on Mar. 2, 2020, pp. 1-28 (Nov. 2005).

A.V. Kasture and S.G. Wadodkar, Pharmaceutical Chemistry—II: Second Year Diploma in Pharmacy, Nirali Prakashan, p. 339, 2007.

Adeeb, et al., "An Inductive Link-Based Wireless Power Transfer System for Biomedical Applications," Research Article, Nov. 14, 2011, pp. 1-12, vol. 2012, Article ID 879294, Hindawi Publishing Corporation.

Allegro MicroSystems, LLC, Automotive Full Bridge MOSFET Driver, A3941-DS, Rev. 5, 21 pages, http://www.allegromicro.com/~/media/Files/Datasheets/A3941-Datasheet.ashx?la=en.

Anonymous, Analog Devices Wiki, Chapter 11: The Current Mirror, Aug. 20, 2017, 22 pages. https://wiki.analog.com/university/courses/electronics/text/chapter-11?rev=1503222341.

Anonymous: "Sense & Control Application Note Current Sensing Using Linear Hall Sensors," Feb. 3, 2009, pp. 1-18. Retrieved from the Internet: URL: http://www.infineon.com/dgdl/Current_Sensing_Rev.1.1.pdf?fileId=db3a304332d040720132d939503e5f17 [retrieved on Oct. 18, 2016].

(56) References Cited

OTHER PUBLICATIONS

Arjo Loeve et al., Scopes Too Flexible . . . and Too Stiff, 2010, IEEE Pulse, Nov./Dec. 2010 (Year: 2010), 16 pages.
Arrow Sign Icon Next Button, by Blan-k, shutterstock.com [online], published on or before Aug. 6, 2014, [retrieved on Jun. 4, 2019], retrieved from the Internet [URL:https://www.shutterstock.com/de/image-vector/arrow-sign-icon-next-button-navigation-207700303?irgwc=1&utm . . . see PDF in file for full URL] (Year: 2014).
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
Biomedical Coatings, Fort Wayne Metals, Research Products Corporation, obtained online at www.fwmetals.com on Jun. 21, 2010 (1 page).
Brar et al., "Investigation of the mechanical and degradation properties of Mg—Sr and Mg—Zn—Sr alloys for use as potential biodegradable implant materials," J. Mech. Behavior of Biomed. Mater. 7 (2012) pp. 87-95.
Breedveld et al., "A New, Easily Miniaturized Sterrable Endoscope," IEEE Engineering in Medicine and Biology Magazine (Nov./Dec. 2005).
Byrne et al., "Molecular Imprinting Within Hydrogels," Advanced Drug Delivery Reviews, 54 (2002) pp. 149-161.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.
Chen et al., "Elastomeric Biomaterials for Tissue Engineering," Progress in Polymer Science 38 (2013), pp. 584-671.
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien Brochure "iDrive™ Ultra Powered Stapling System," (6 pages).
Covidien Brochure, "Endo GIA™ Curved Tip Reload with Tri-Staple™ Technology," (2012), 2 pages.
Covidien Brochure, "Endo GIA™ Reloads with Tri-Staple™ Technology and Endo GIA™ Ultra Universal Staplers," (2010), 2 pages.
Covidien Brochure, "Endo GIA™ Reloads with Tri-Staple™ Technology," (2010), 1 page.
Covidien Brochure, "Endo GIA™ Reloads with Tri-Staple™ Technology," (2010), 2 pages.
Covidien Brochure, "Endo GIA™ Black Reload with Tri-Staple™ Technology," (2012), 2 pages.
Covidien Brochure, "Endo GIA™ Ultra Universal Stapler," (2010), 2 pages.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Cuper et al., "The Use of Near-Infrared Light for Safe and Effective Visualization of Subsurface Blood Vessels to Facilitate Blood Withdrawal in Children," Medical Engineering & Physics, vol. 35, No. 4, pp. 433-440 (2013).
D. Tuite, Ed., "Get The Lowdown On Ultracapacitors," Nov. 15, 2007; [online] URL: http://electronicdesign.com/Articles/Print.cfm?ArticleID=17465, accessed Jan. 15, 2008 (5 pages).
Data Sheet of LM4F230H5QR, 2007.
Datasheet for Panasonic TK Relays Ultra Low Profile 2 A Polarized Relay, Copyright Matsushita Electric Works, Ltd. (Known of at least as early as Aug. 17, 2010), 5 pages.
Disclosed Anonymously, "Motor-Driven Surgical Stapler Improvements," Research Disclosure Database No. 526041, Published: Feb. 2008.
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
Elite Icons, by smart/icons, iconfinder.com [online], published on Aug. 18, 2016, [retrieved on Jun. 4, 2019], retrieved from the Internet [URL: https://www.iconfinder.com/iconsets/elite] (Year: 2016).
Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.
Fischer, Martin H, "Colloid-Chemical Studies on Soaps", The Chemical Engineer, pp. 184-193, Aug. 1919.
Foot and Ankle: Core Knowledge in Orthopaedics; by DiGiovanni MD, Elsevier; (p. 27, left column, heading "Materials for Soft Orthoses", 7th bullet point); (Year: 2007).
Forum discussion regarding "Speed is Faster", published on Oct. 1, 2014 and retrieved on Nov. 8, 2019 from URL https://english.stackexchange.com/questions/199018/how-is-that-correct-speed-is-faster-or-prices-are-cheaper (Year: 2014).
Gao et al., "Mechanical Signature Enhancement of Response Vibrations in the Time Lag Domain," Fifth International Congress on Sound and Vibration, Dec. 15-18, 1997, pp. 1-8.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Honda HS1332AT and ATD Model Info, powerequipment.honda.com [online], published on or before Mar. 22, 2016, [retrieved on May 31, 2019], retrieved from the Internet [URL: https://powerequipment.honda.com/snowblowers/models/hss1332at-hss1332atd] {Year: 2016).
http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.
IEEE Std 802.3-2012 (Revision of IEEE Std 802.3-2008, published Dec. 28, 2012.
Indian Standard: Automotive Vehicles—Brakes and Braking Systems (IS 11852-1:2001), Mar. 1, 2001.
Jauchem, J.R., "Effects of low-level radio-frequency (3 kHz to 300 GHZ) enery on human cardiovascular, reproductive, immune, and other systems: A review of the recent literatured," Int. J. Hyg. Environ. Health 211 (2008) 1-29.
Jeong et al., "Thermosensitive Sol-Gel Reversible Hydrogels," Advanced Drug Delivery Reviews, 54 (2002) pp. 37-51.
Kawamura, Atsuo, et al. "Wireless Transmission of Power and Information Through One High-Frequency Resonant AC Link Inverter for Robot Manipulator Applications," Journal, May/Jun. 1996, pp. 503-508, vol. 32, No. 3, IEEE Transactions on Industry Applications.
Lee, Youbok, "Antenna Circuit Design for RFID Applications," 2003, pp. 1-50, DS00710C, Microchip Technology Inc., Available: http://ww1.microchip.com/downloads/en/AppNotes/00710c.pdf.
Ludois, Daniel C., "Capacitive Power Transfer for Rotor Field Current in Synchronous Machines," IEEE Transactions on Power Electronics, Institute of Electrical and Electronics Engineers, USA, vol. 27, No. 11, Nov. 1, 2012, pp. 4638-4645.
Lyon et al. "The Relationship Between Current Load and Temperature for Quasi-Steady State and Transient Conditions," SPIE—International Society for Optical Engineering. Proceedings, vol. 4020, (pp. 62-70), Mar. 30, 2000.
Makerbot, 10 Advantages of 3D Printing, 2020 (retrieved via the wayback machine), Makerbot.com (Year: 2020).
Matsuda, "Thermodynamics of Formation of Porous Polymeric Membrane from Solutions," Polymer Journal, vol. 23, No. 5, pp. 435-444 (1991).
Miyata et al., "Biomolecule-Sensitive Hydrogels," Advanced Drug Delivery Reviews, 54 (2002) pp. 79-98.
Molina, "Low Level Reader Protocol (LLRP)," Oct. 13, 2010, pp. 1-198.

(56) References Cited

OTHER PUBLICATIONS

Mouser Electronics, "LM317 3-Terminal Adjustable Regulator with Overcurrent/Overtemperature Self Protection", Sep. 30, 2016 (Sep. 30, 2016), XP0555246104, Retrieved from the Internet: URL: http://www.mouser.com/ds/2/405/lm317m-440423.pdf, pp. 1-9.
Mouser Electronics, "LM317M 3-Terminal Adjustable Regulator with Overcurrent/Overtemperature Self Protection", Mar. 31, 2014 (Mar. 31, 2014), XP0555246104, Retrieved from the Internet: URL: http://www.mouser.com/ds/2/405/lm317m-440423.pdf, pp. 1-8.
NF Monographs: Sodium Stearate, U.S. Pharmacopeia, http://www.pharmacopeia.cn/v29240/usp29nf24s0_m77360.html, accessed May 23, 2016.
Patrick J. Sweeney: "RFID for Dummies", Mar. 11, 2010, pp. 365-365, XP055150775, ISBN: 978-1-11-805447-5, Retrieved from the Internet: URL: books.google.de/books?isbn=1118054474 [retrieved on Nov. 4, 2014]—book not attached.
Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A ,2013:101A:502-517.
Peppas, "Physiologically Responsive Hydrogels," Journal of Bioactive and Compatible Polymers, vol. 6 (Jul. 1991) pp. 241-246.
Peppas, Editor "Hydrogels in Medicine and Pharmacy," vol. I, Fundamentals, CRC Press, 1986.
Pitt et al., "Attachment of Hyaluronan to Metallic Surfaces," J. Biomed. Mater. Res. 68A: pp. 95-106, 2004.
Pushing Pixels (GIF), published on dribble.com, 2013.
Qiu et al., "Environment-Sensitive Hydrogels for Drug Delivery," Advanced Drug Delivery Reviews, 53 (2001) pp. 321-339.
Qiu Li Loh et al.: "Three-Dimensional Scaffolds for Tissue Engineering Applications: Role of Porosity and Pore Size", Tissue Engineering Part B—Reviews, vol. 19, No. 6, Dec. 1, 2013, pp. 485-502.
Rotary Systems: Sealed Slip Ring Categories, Rotary Systems, May 22, 2017, retrieved from the internet: http://web.archive.org/we/20170522174710/http:/rotarysystems.com: 80/slip-rings/sealed/, retrieved on Aug. 12, 2020, pp. 1-2.
Sandvik, "Welding Handbook," https://www.meting.rs/wp-content/uploads/2018/05/welding-handbook.pdf, retrieved on Jun. 22, 2020. pp. 5-6.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Schroeter, John, "Demystifying UHF Gen 2 RFID, HF RFID," Online Article, Jun. 2, 2008, pp. 1-3, <https://www.edn.com/design/industrial-control/4019123/Demystifying-UHF-Gen-2-RFID-HF-RFID>.
Seils et al., Covidien Summary: Clinical Study "UCONN Biodynamics: Final Report on Results," (2 pages).
Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.
Slow Safety Sign, shutterstock.com [online], published on or before May 9, 2017, [retrieved on May 31, 2019], retrieved from the https://www.shutterstock.com/image-victor/slow-safety-sign-twodimensional-turtle-symbolizing- . . . see PDF in file for full URL] (Year: 2017).
Sodium stearate C18H35NaO2, Chemspider Search and Share Chemistry, Royal Society of Chemistry, pp. 1-3, 2015, http://www.chemspider.com/Chemical-Structure.12639.html, accessed May 23, 2016.
Solorio et al., "Gelatin Microspheres Crosslinked with Genipin for Local Delivery of Growth Factors," J. Tissue Eng. Regen. Med. (2010), 4(7): pp. 514-523.
Texas Instruments: "Current Recirculation and Decay Modes," Application Report SLVA321—Mar. 2009; Retrieved from the Internet: URL:http://www.ti.com/lit/an/slva321/slva321 [retrieved on Apr. 25, 2017], 7 pages.
The Sodem Aseptic Battery Transfer Kit, Sodem Systems, 2000, 3 pages.
Trendafilova et al., "Vibration-based Methods for Structural and Machinery Fault Diagnosis Based on Nonlinear Dynamics Tools," In: Fault Diagnosis in Robotic and Industrial Systems, IConcept Press LTD, 2012, pp. 1-29.
Tutorial overview of inductively coupled RFID Systems, UPM, May 2003, pp. 1-7, UPM Rafsec,<http://cdn.mobiusconsulting.com/papers/rfidsystems.pdf>.
U.S. Appl. No. 62/798,651, filed Jan. 30, 2019.
U.S. Appl. No. 62/840,602, filed Apr. 30, 2019.
V.K. Ahluwalia and Madhuri Goyal, A Textbook of Organic Chemistry, Section 19.11.3, p. 356, 2000.
Van Meer et al., "A Disposable Plastic Compact Wrist for Smart Minimally Invasive Surgical Tools," LAAS/CNRS (Aug. 2005).
Warning Sign Beveled Buttons, by Peter, flarestock.com [online], published on or before Jan. 1, 2017, [retrieved on Jun. 4, 2019], retrieved from the Internet [URL: https://www.flarestock.com/stock-images/warning-sign-beveled-buttons/70257] (Year: 2017).
Yan et al, Comparison of the effects of Mg—6Zn and Ti—3Al—2.5V alloys on TGF-β/TNF-α/VEGF/b-FGF in the healing of the intestinal track in vivo, Biomed. Mater. 9 (2014), 11 pages.
Yan et al., "Comparison of the effects of Mg—6Zn and titanium on intestinal tract in vivo," J Mater Sci: Mater Med (2013), 11 pages.
Yang et al.; "4D printing reconfigurable, deployable and mechanically tunable metamaterials," Material Horizions, vol. 6, pp. 1244-1250 (2019).
Young, "Microcellular foams via phase separation," Journal of Vacuum Science & Technology A 4(3), (May/Jun. 1986).
Youtube.com; video by Fibran (retrieved from URL https://www.youtube.com/watch?v=vN2Qjt51gFQ); (Year: 2018).

* cited by examiner

FIRED
RIGHT SIDE

SLOPE = $\frac{\Delta d}{\Delta t}$ = RATE OF CHANGE OF GAP

POWERED SURGICAL INSTRUMENT

CROSS-REFERENCE TO RELATED APPLICATIONS

This application is a continuation application claiming priority under 35 U.S.C. § 120 to U.S. patent application Ser. No. 17/217,636, entitled POWERED SURGICAL INSTRUMENT, filed Mar. 30, 2021, now U.S. Patent Application Publication No. 2021/0338233, which is a continuation application claiming priority under 35 U.S.C. § 120 to U.S. patent application Ser. No. 15/730,188, entitled POWERED SURGICAL INSTRUMENT, filed Oct. 11, 2017, now U.S. Patent Application Publication No. 2018/0085117, which is a continuation application claiming priority under 35 U.S.C. § 120 to U.S. patent application Ser. No. 14/640,746, entitled METHOD OF OPERATING A POWERED SURGICAL INSTRUMENT, filed Mar. 6, 2015, which issued on Nov. 7, 2017 as U.S. Pat. No. 9,808,246, the entire disclosures of which are hereby incorporated by reference herein.

BACKGROUND

The present disclosure relates to surgical instruments and, in various circumstances, to surgical stapling and cutting instruments and staple cartridges therefor that are designed to staple and cut tissue.

BRIEF DESCRIPTION OF THE DRAWINGS

The features and advantages of the present disclosure, and the manner of attaining them, will become more apparent and the present disclosure will be better understood by reference to the following description of the present disclosure taken in conjunction with the accompanying drawings, wherein:

FIG. 28, which is divided into

FIG. 108 illustrates a perspective cutaway view of the anvil and the magnet, FIG. 109 illustrates a side cutaway view of the anvil and the magnet, and FIG. 110 illustrates a top cutaway view of the anvil and the magnet;

FIG. 118 illustrates a cutaway view of the distal sensor plug and FIG. 119 further illustrates the magnetic field sensor and the processor operatively coupled to the flex board such that they are capable of communicating;

FIG. 120 illustrates an aspect of an end effector with a flex cable operable to provide power to sensors and electronics in the distal tip of the anvil portion;

Figure 123:
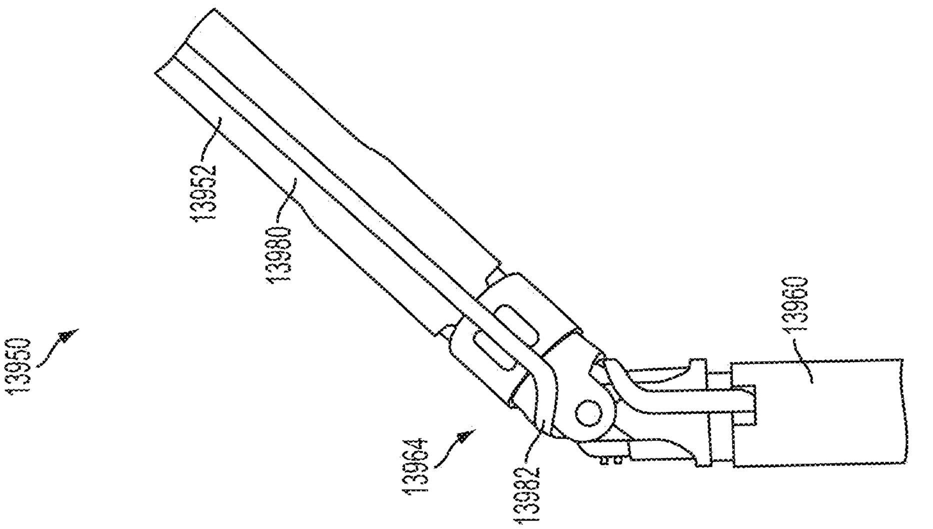
Figure 122:
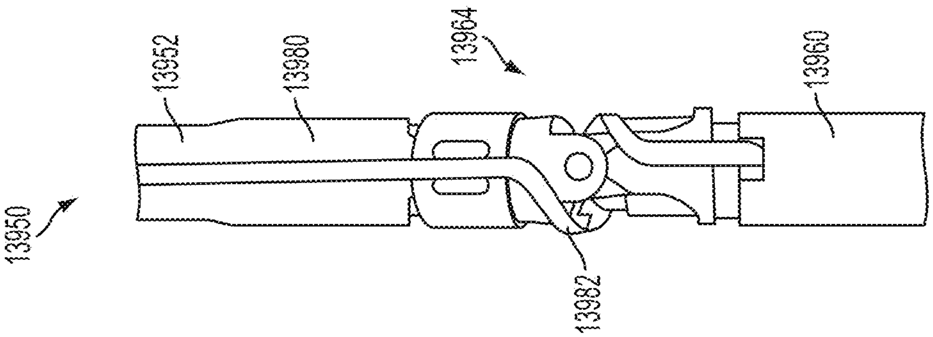
Figure 121:
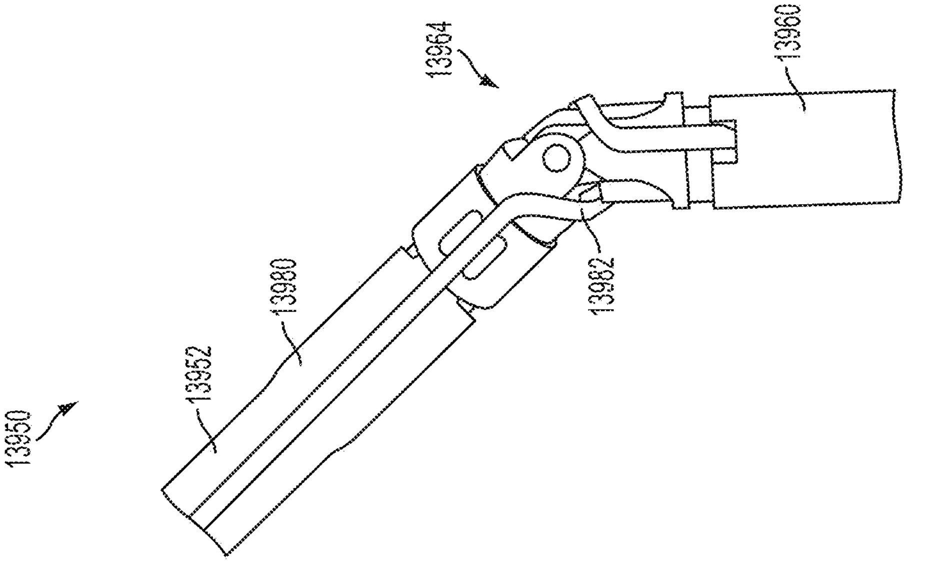
Figure 124:
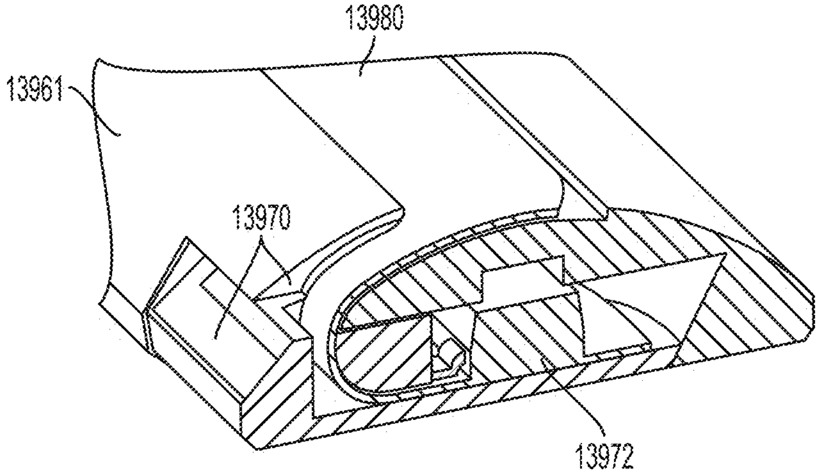
Figure 125:
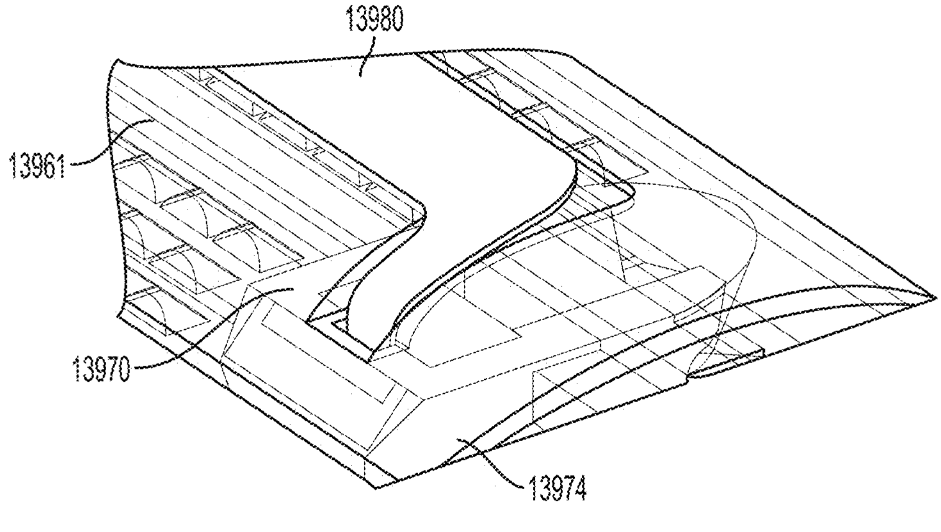

FIGS. 121-123 illustrate the operation of the articulation joint and flex cable of the end effector where FIG. 121 illustrates a top view of the end effector with the end effector pivoted −45 degrees with respect to the shaft assembly, FIG. 122 illustrates a top view of the end effector, and FIG. 123 illustrates a top view of the end effector with the end effector pivoted +45 degrees with respect to the shaft assembly;

FIG. 124 illustrates cross-sectional view of the distal tip of an aspect of an anvil with sensors and electronics; and FIG. 125 illustrates a cutaway view of the distal tip of the anvil.

Figure 126:
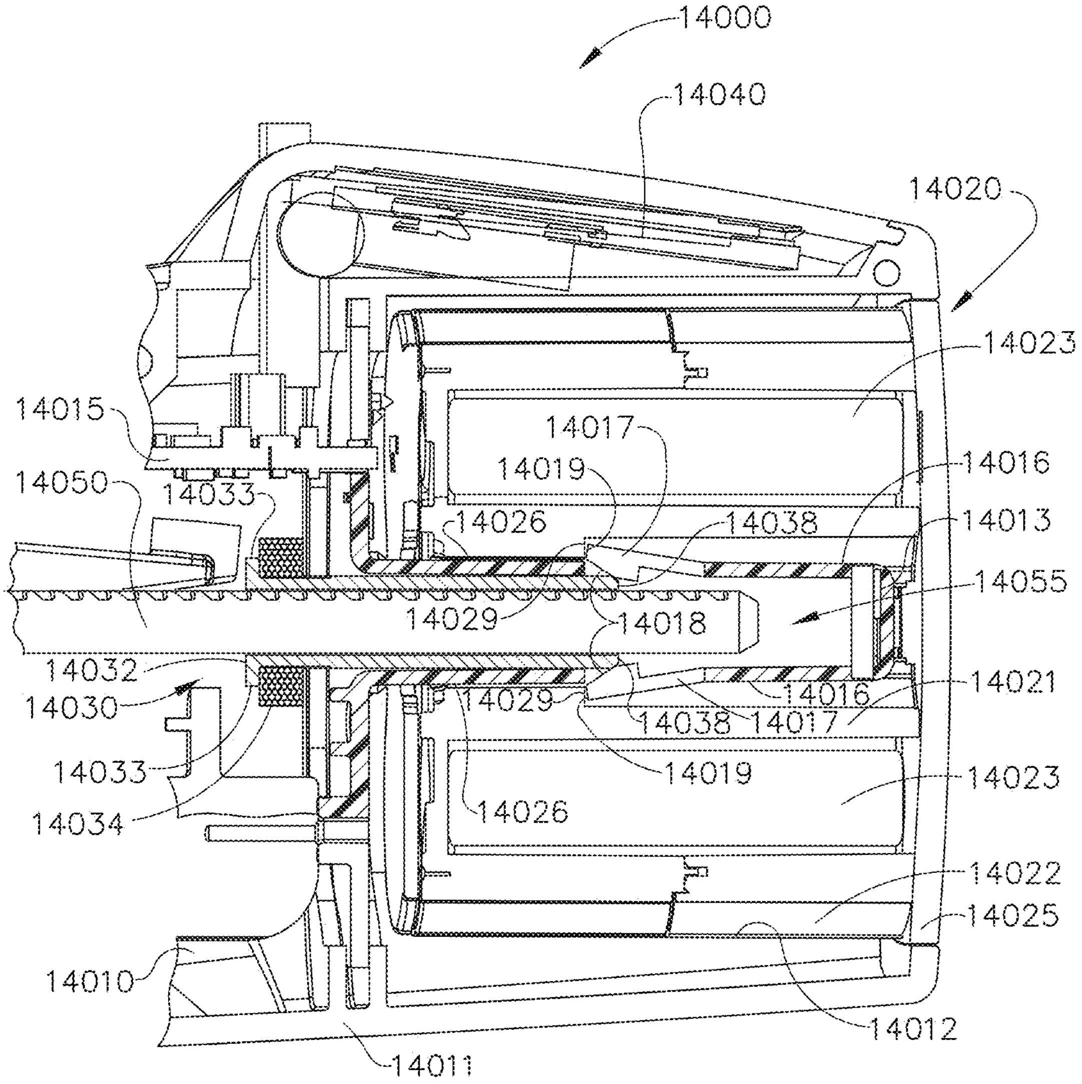
Figure 127:
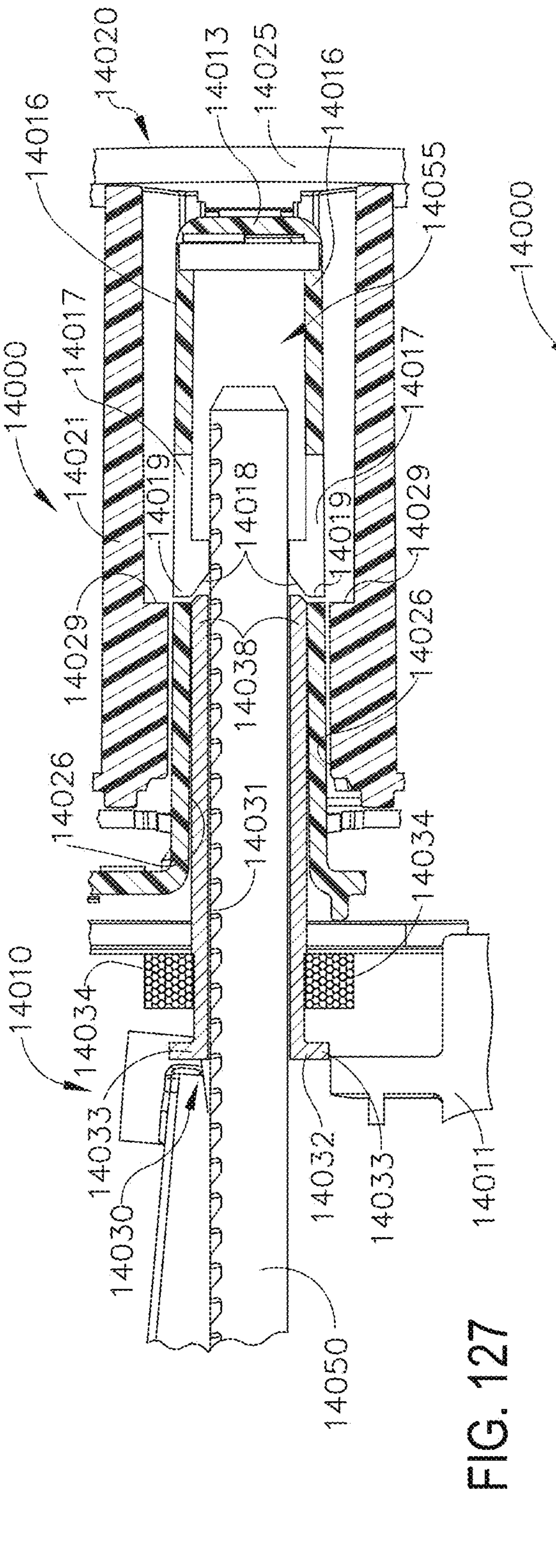
Figure 128:
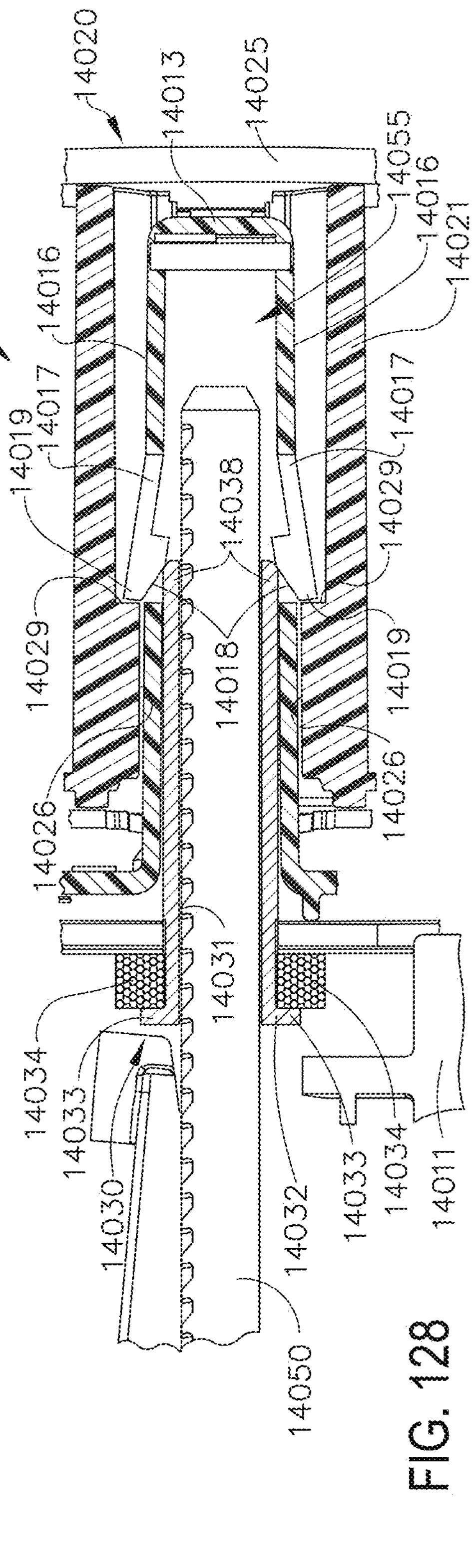
Figure 129:
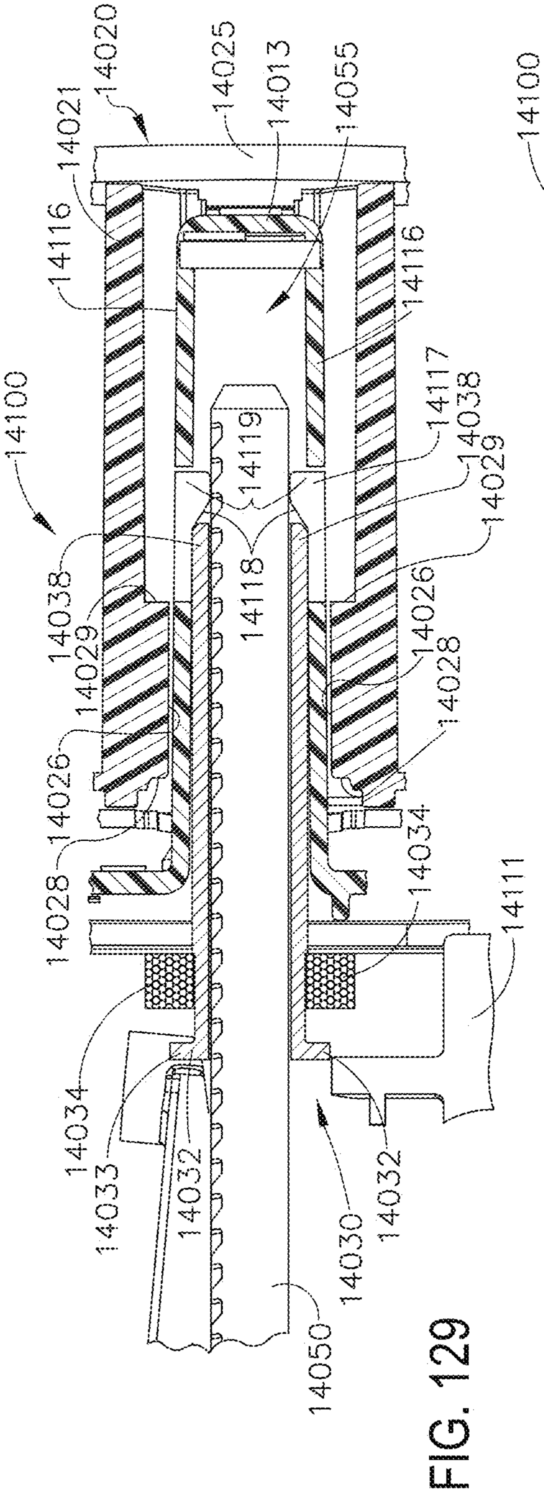
Figure 130:
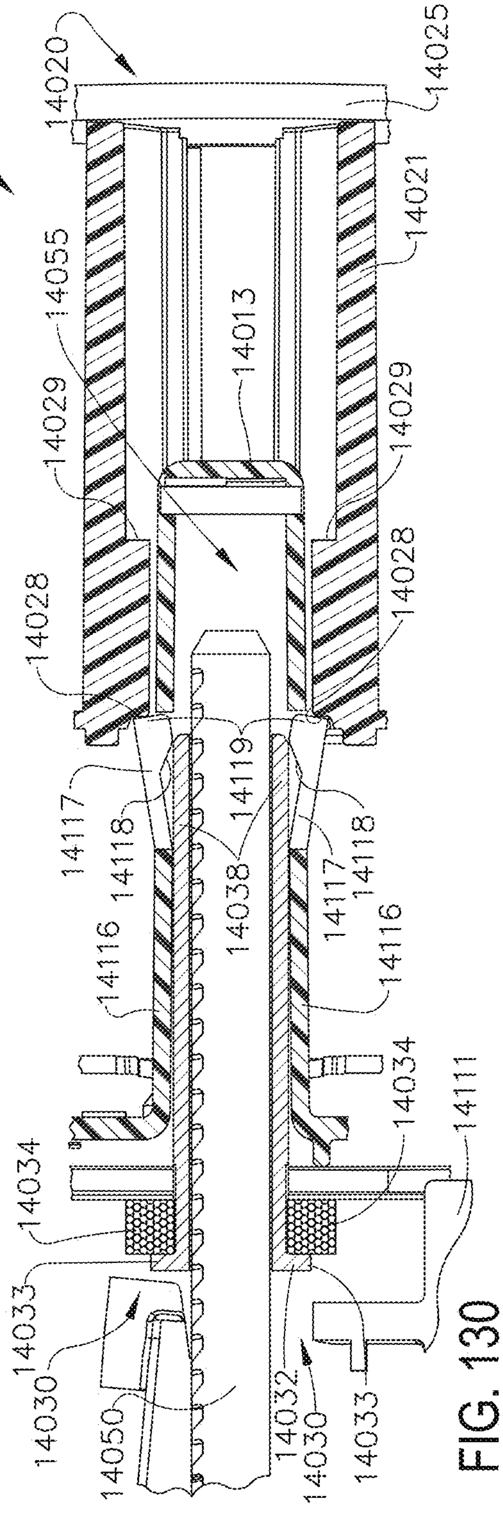
Figure 131:
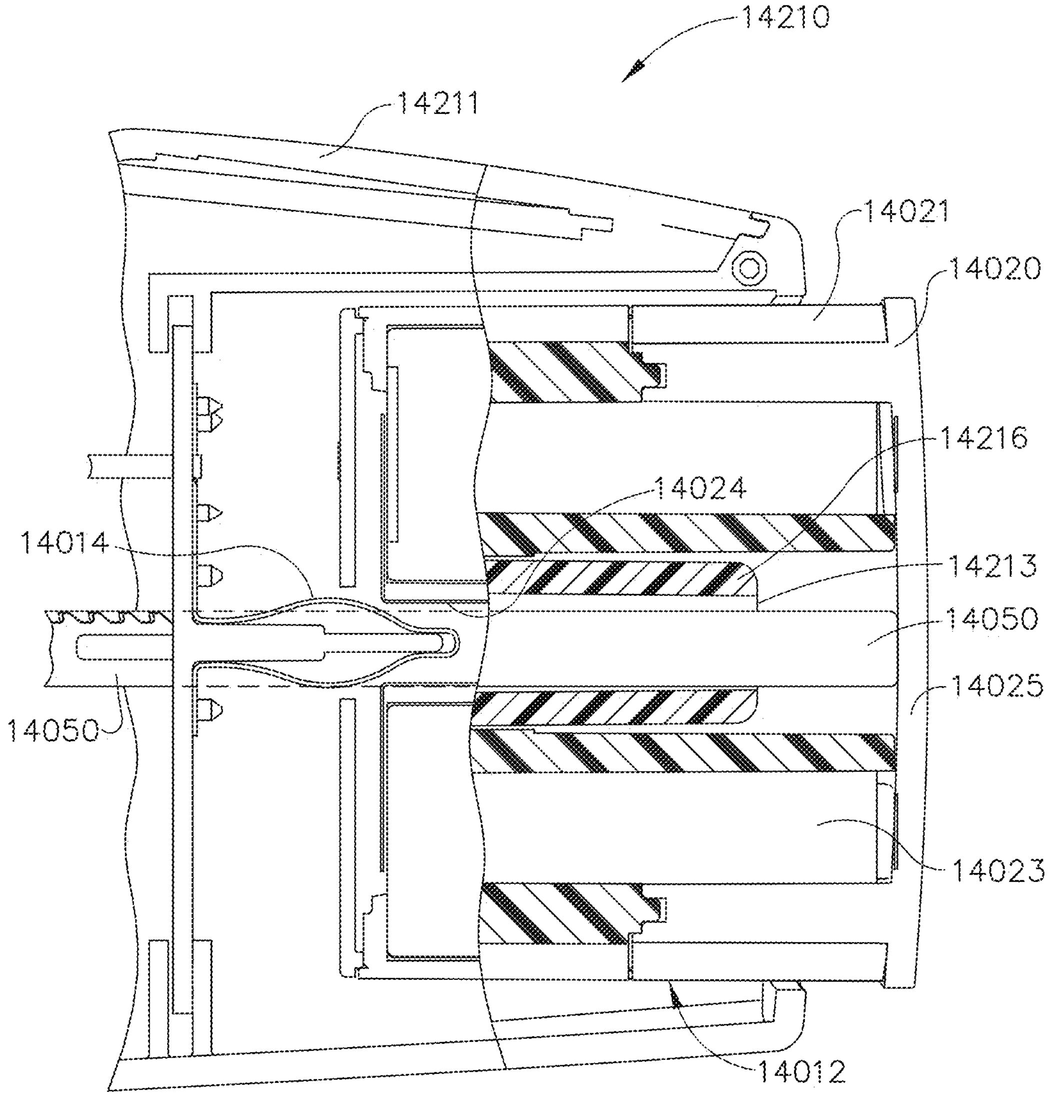
Figure 132:
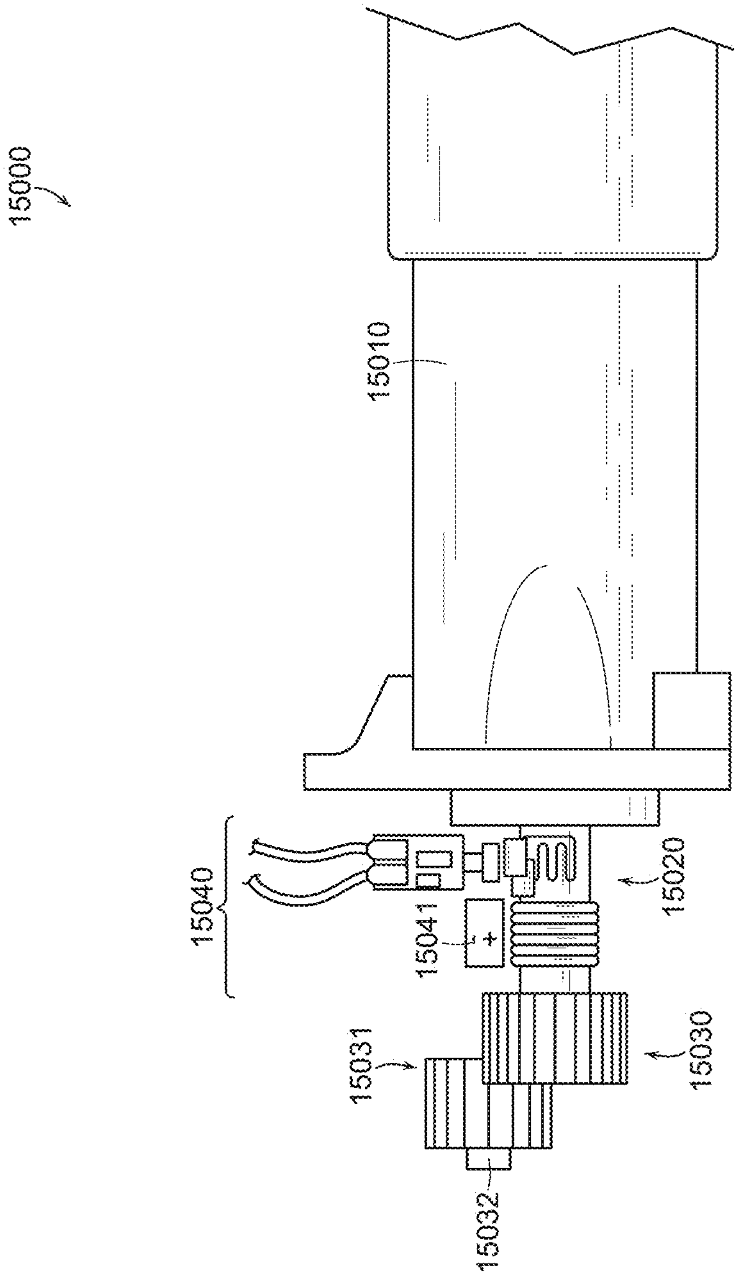
Figure 133:
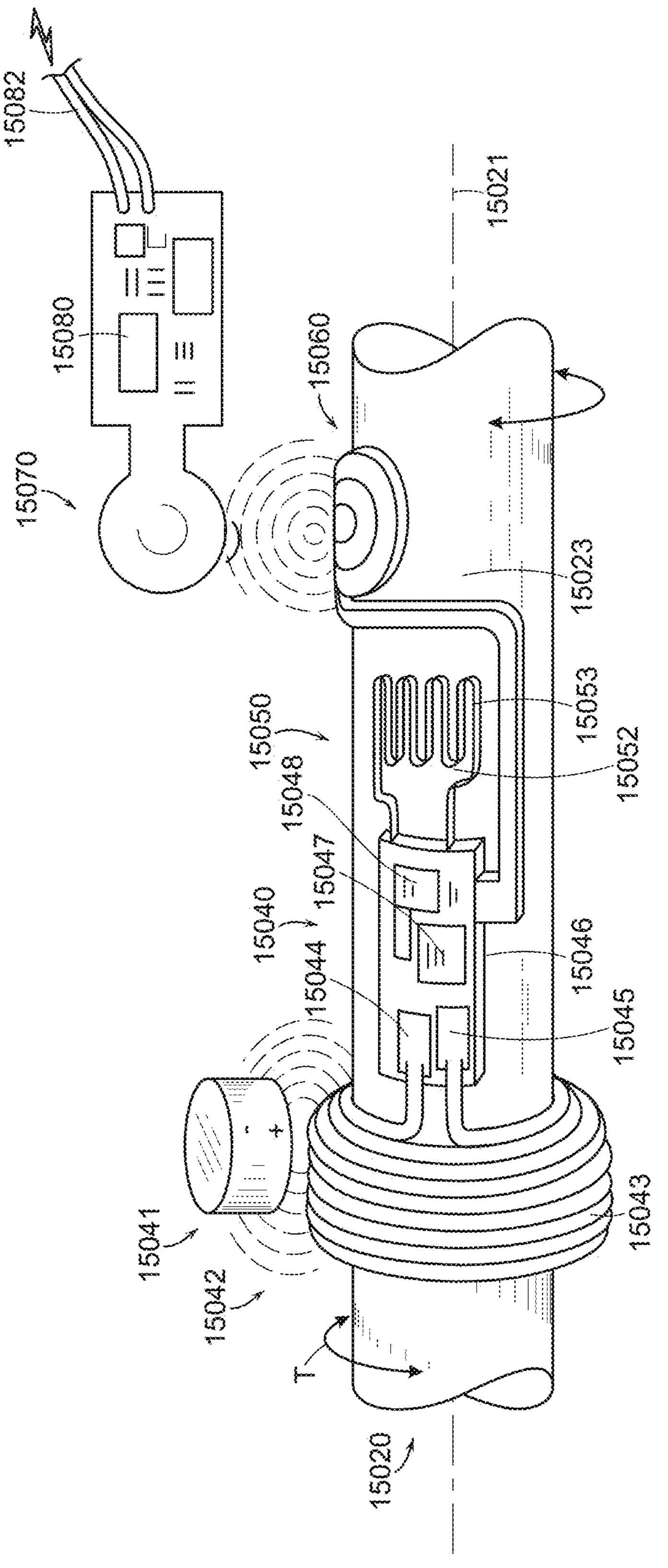
Figure 134:
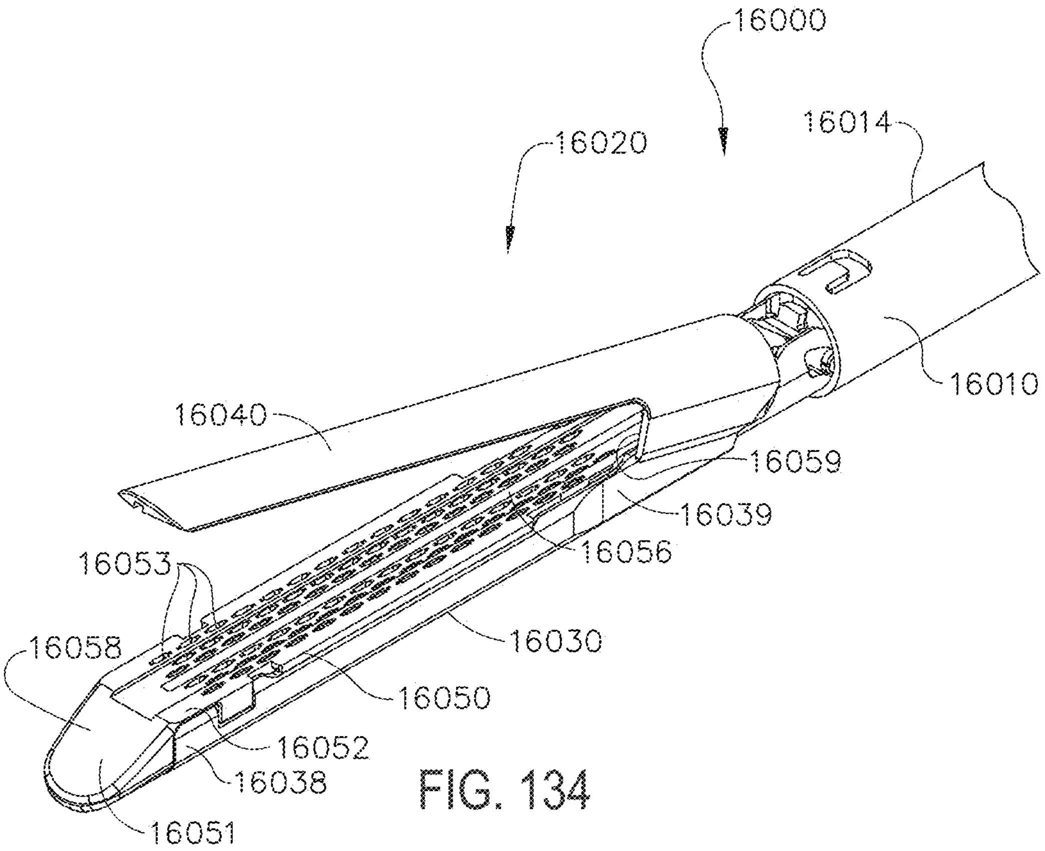
Figure 135:
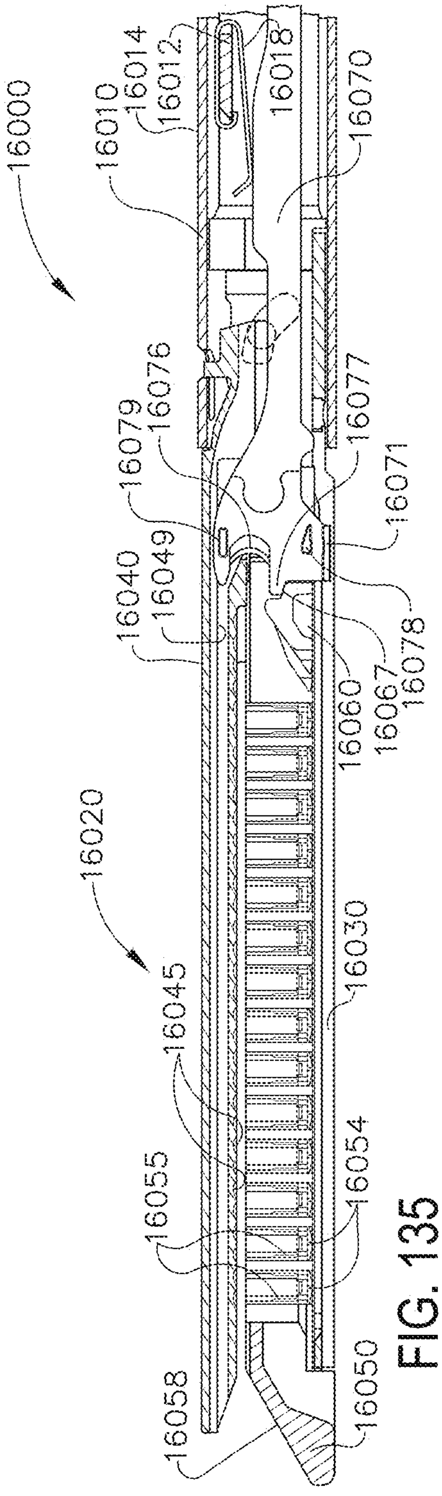
Figure 136:
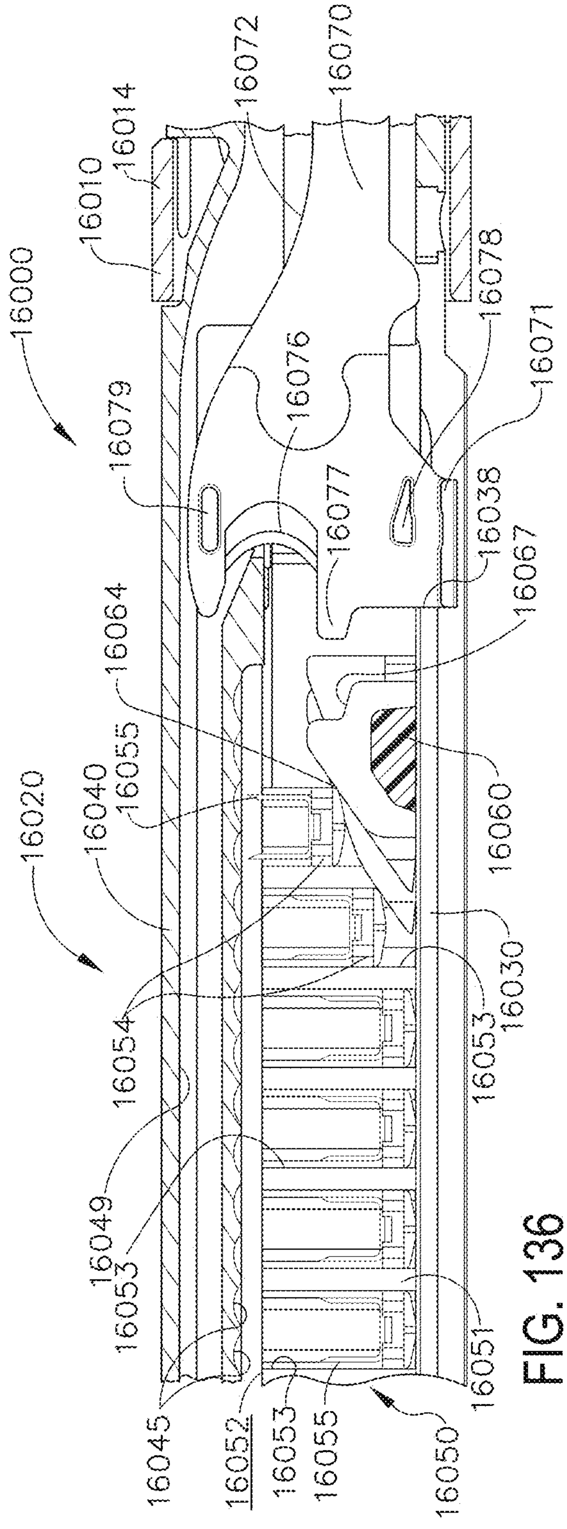
Figure 137:
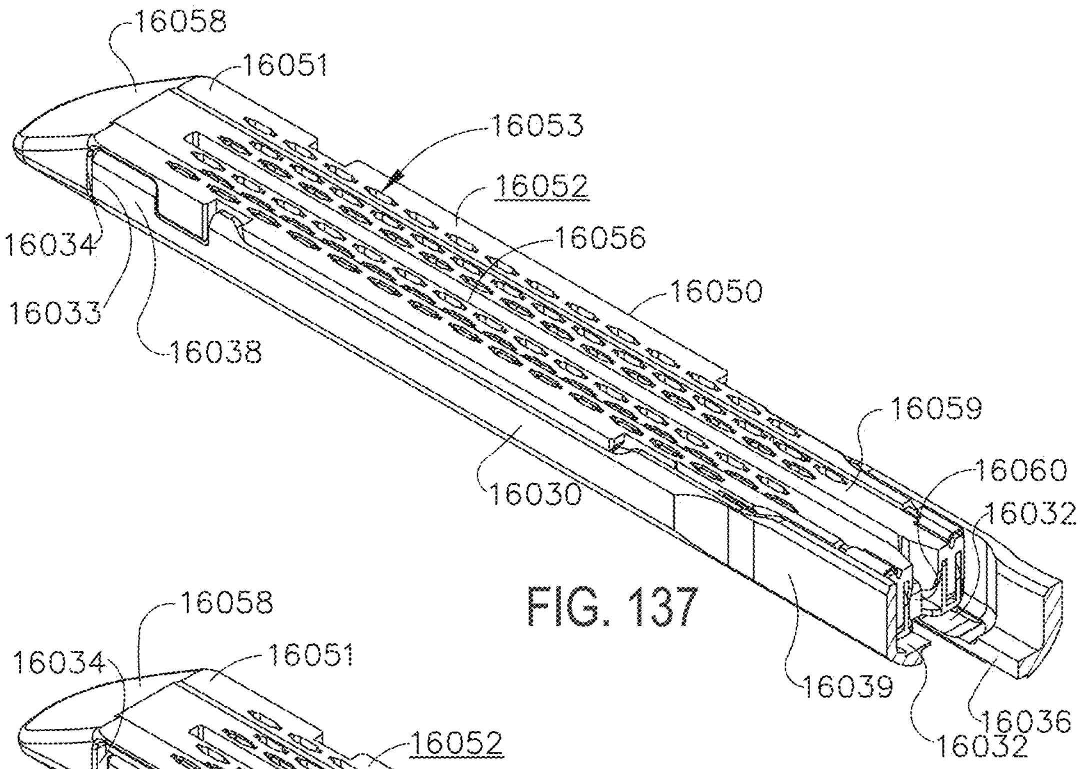
Figure 138:
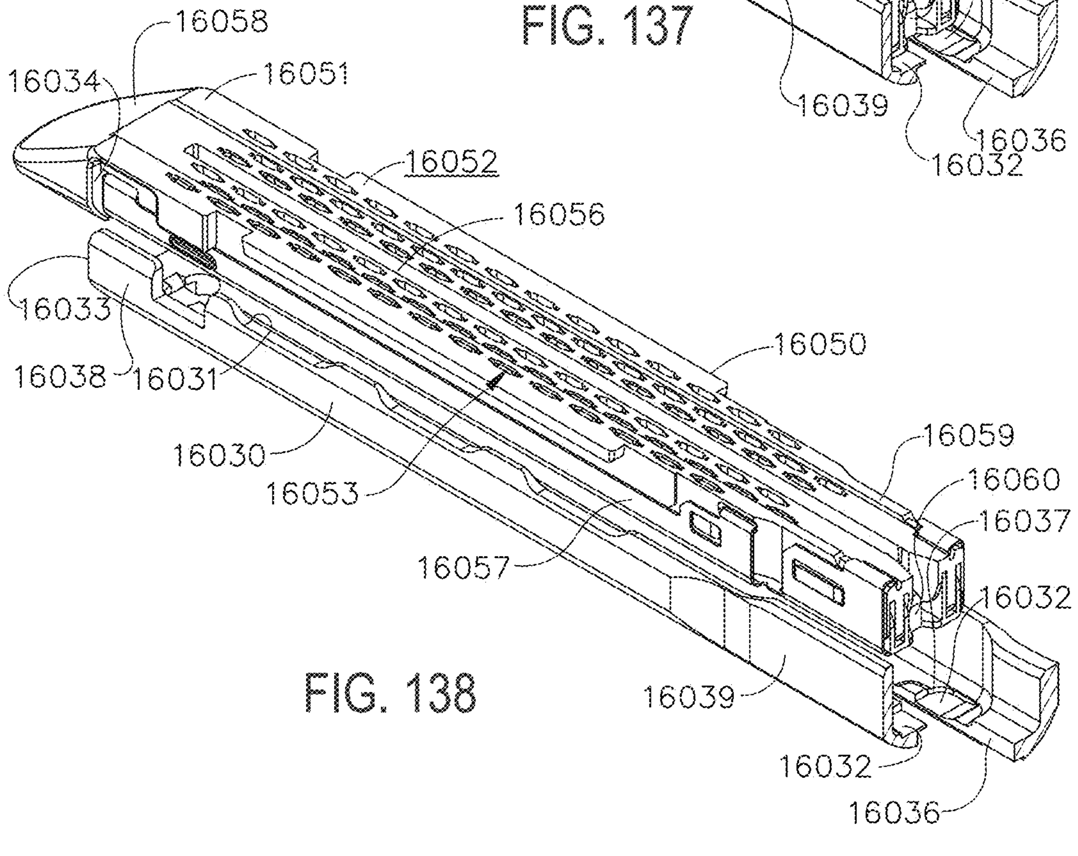
Figure 139:
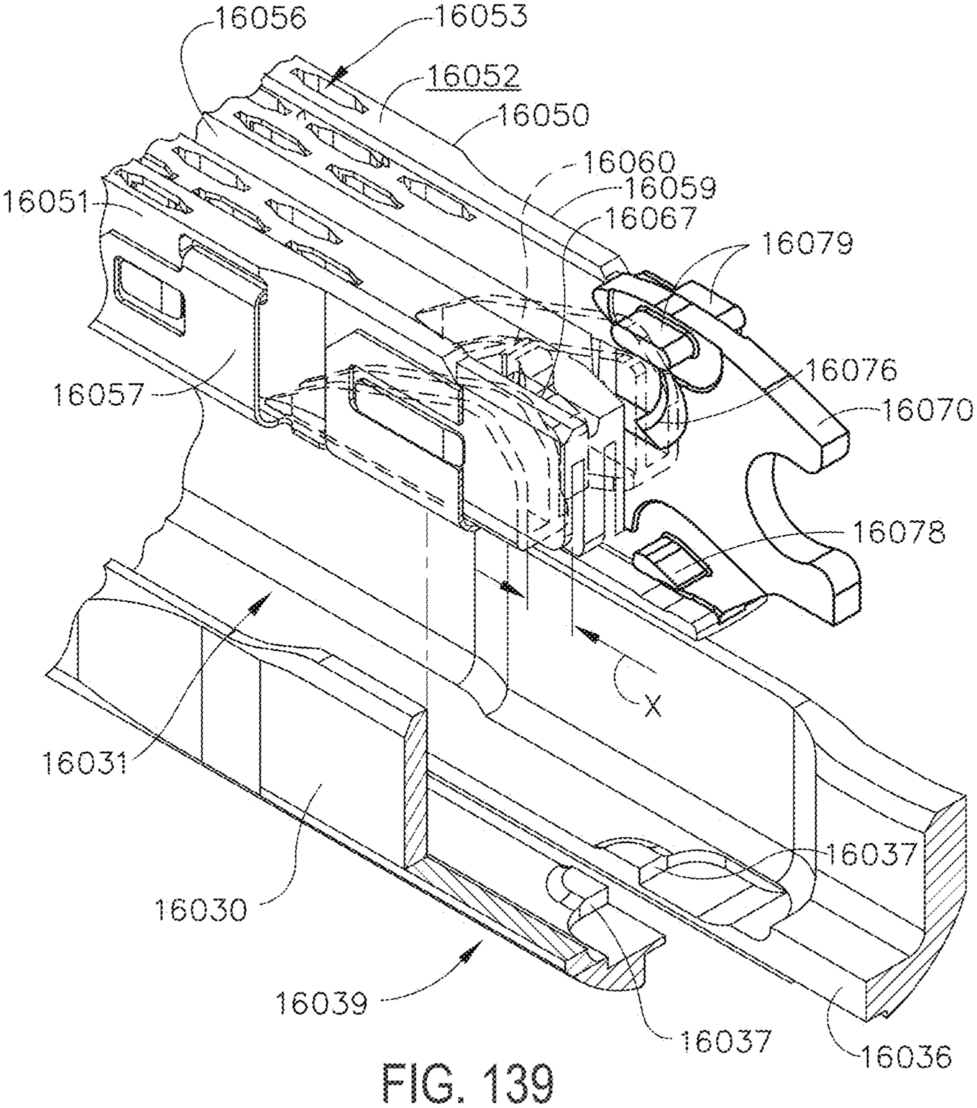
Figure 140:
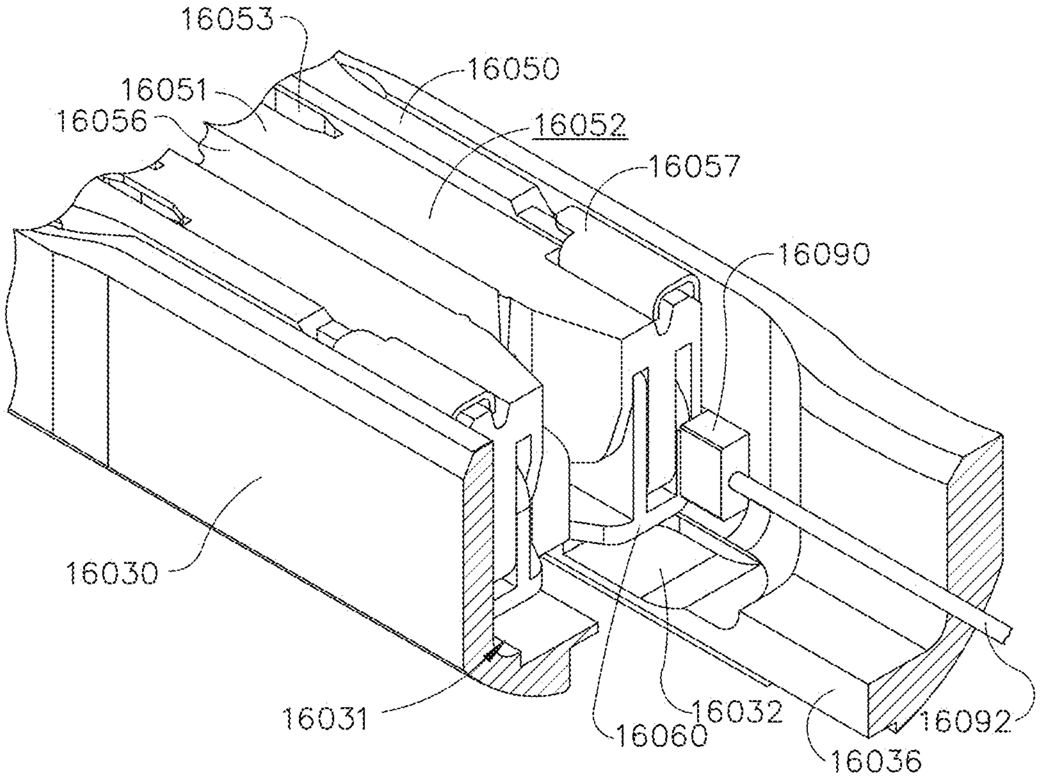
Figure 141:
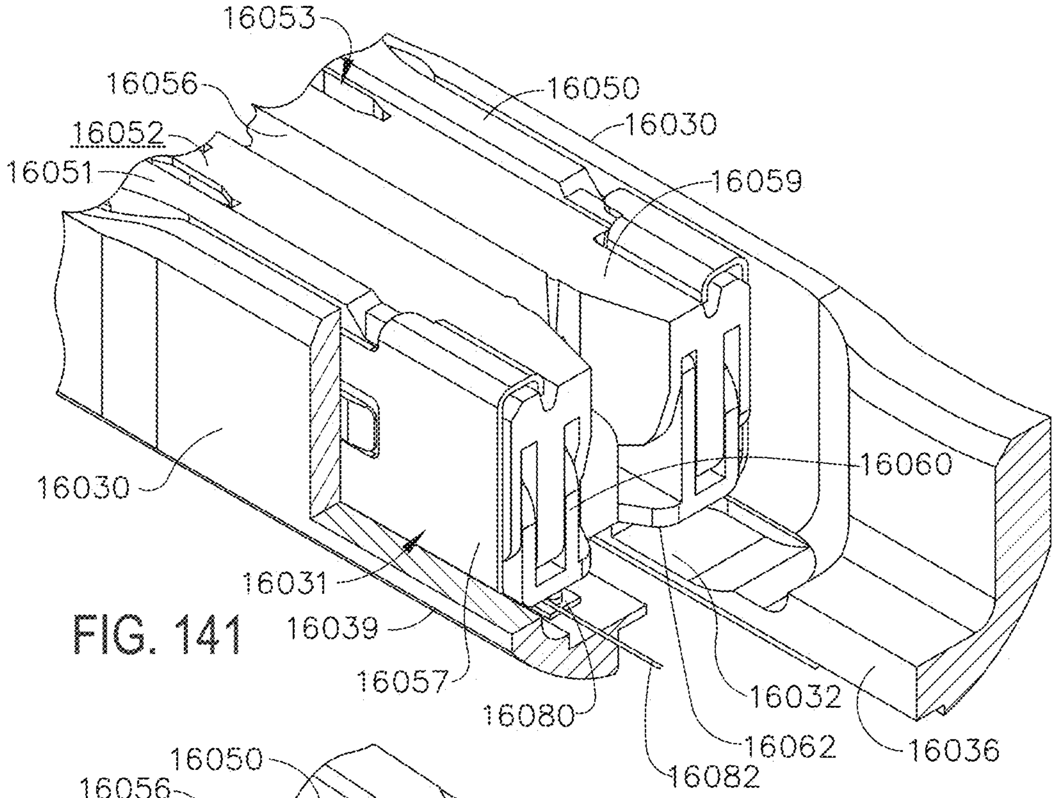
Figure 142:
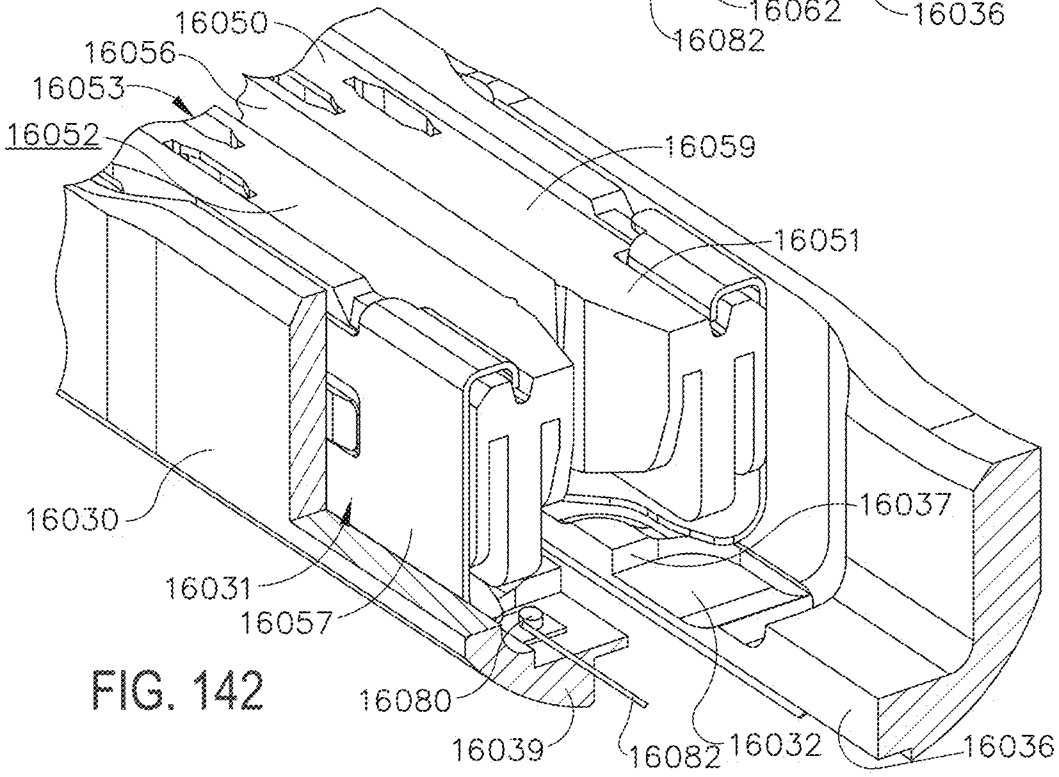
Figure 143:
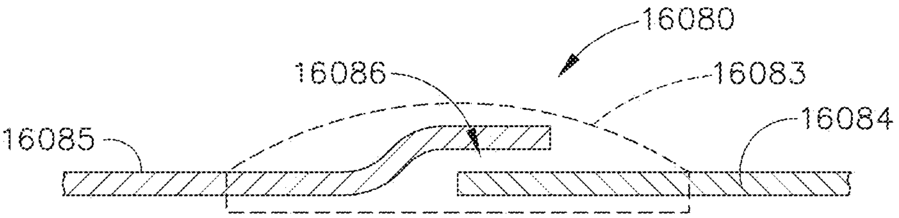
Figure 144:
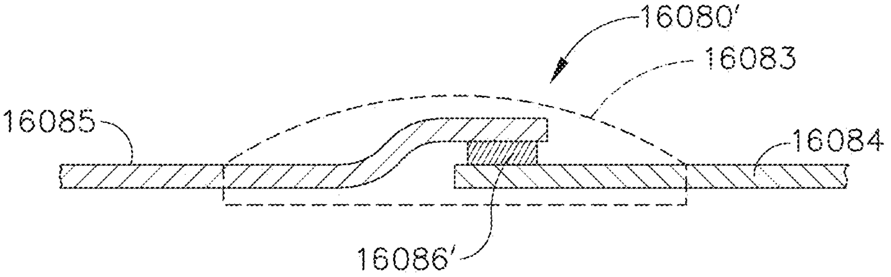

FIG. 126 is a partial cross-sectional view of a handle of a surgical instrument comprising a battery and a battery lock in accordance with at least one embodiment;

FIG. 127 is partial cross-sectional view of the handle of FIG. 126 illustrating the battery lock in an unlocked configuration;

FIG. 128 is a partial cross-sectional view of the handle of FIG. 126 illustrating the battery lock in a locked configuration;

FIG. 129 is a partial cross-sectional view of a handle of a surgical instrument comprising a battery lockout in accordance with at least one embodiment illustrated in an unlocked configuration;

FIG. 130 is a partial cross-sectional view of the handle of FIG. 129 illustrating the battery lockout in a locked-out configuration;

FIG. 131 is a partial cross-sectional view of a battery lockout in accordance with an alternative embodiment illustrated in a locked-out configuration;

FIG. 132 depicts a surgical instrument system comprising a motor including a shaft, a gear train, an output shaft operably coupled to the motor shaft, and power generation means mounted to the motor shaft in accordance with at least one embodiment;

FIG. 133 depicts the motor shaft of FIG. 132 which includes a strain gauge and means for transmitting information from the motor shaft, i.e., a rotating plane, to a stationary plane mounted to the motor shaft and, in addition, means for interpreting the information being transmitted from the motor shaft;

FIG. 134 is a perspective view of an end effector of a surgical stapling instrument including a cartridge channel, a staple cartridge positioned in the cartridge channel, and an anvil;

FIG. 135 is a cross-sectional elevational view of the surgical stapling instrument of FIG. 134 illustrating a sled and a firing member in an unfired position;

FIG. 136 is a detail view depicting the sled of FIG. 135 in a partially advanced position and the firing member in its unfired position;

FIG. 137 is a perspective view of the staple cartridge of FIG. 134 prior to being inserted into the cartridge channel of FIG. 134;

FIG. 138 is a perspective view of the staple cartridge of FIG. 134 fully seated in the cartridge channel of FIG. 134;

FIG. 139 is a schematic of the staple cartridge and cartridge channel of FIG. 134 and the sled and the firing member of FIG. 135 depicting a mis-insertion of the staple cartridge into the cartridge channel and the effect on the sled that such a mis-insertion can cause;

FIG. 140 is a partial perspective view of an end effector of a surgical stapling instrument in accordance with at least one embodiment including a sensor configured to sense whether a staple cartridge has been mis-inserted in the manner depicted in FIG. 139;

FIG. 141 is a partial perspective view of an end effector of a surgical stapling instrument in accordance with at least one embodiment including a sensor configured to detect whether the sled has been unintentionally advanced;

FIG. 142 is a partial perspective view of the end effector of FIG. 141 illustrating the sled in an unintentionally advanced position;

FIG. 143 is a cross-sectional view of the sensor of FIG. 141 in accordance with at least one embodiment; and FIG. 144 is a cross-sectional view of the sensor of FIG. 141 in accordance with at least one alternative embodiment.

DESCRIPTION

Applicant of the present application owns the following patent applications that were filed on Mar. 6, 2015 and which are each herein incorporated by reference in their respective entireties:

- U.S. patent application Ser. No. 14/640,795, entitled MULTIPLE LEVEL THRESHOLDS TO MODIFY OPERATION OF POWERED SURGICAL INSTRUMENTS; now U.S. Patent Application Publication No. 2016/0256185;
- U.S. patent application Ser. No. 14/640,832, entitled ADAPTIVE TISSUE COMPRESSION TECHNIQUES TO ADJUST CLOSURE RATES FOR MULTIPLE TISSUE TYPES; now U.S. Patent Application Publication No. 2016/0256154;
- U.S. patent application Ser. No. 14/640,935, entitled OVERLAID MULTI SENSOR RADIO FREQUENCY (RF) ELECTRODE SYSTEM TO MEASURE TISSUE COMPRESSION; now U.S. Patent Application Publication No. 2016/0256071;
- U.S. patent application Ser. No. 14/640,831, entitled MONITORING SPEED CONTROL AND PRECISION INCREMENTING OF MOTOR FOR POWERED SURGICAL INSTRUMENTS; now U.S. Patent Application Publication No. 2016/0256153;
- U.S. patent application Ser. No. 14/640,859, entitled TIME DEPENDENT EVALUATION OF SENSOR DATA TO DETERMINE STABILITY, CREEP, AND VISCOELASTIC ELEMENTS OF MEASURES; now U.S. Patent Application Publication No. 2016/0256187;
- U.S. patent application Ser. No. 14/640,817, entitled INTERACTIVE FEEDBACK SYSTEM FOR POWERED SURGICAL INSTRUMENTS; now U.S. Patent Application Publication No. 2016/0256186;
- U.S. patent application Ser. No. 14/640,844, entitled CONTROL TECHNIQUES AND SUB-PROCESSOR CONTAINED WITHIN MODULAR SHAFT WITH SELECT CONTROL PROCESSING FROM HANDLE; now U.S. Patent Application Publication No. 2016/0256155;
- U.S. patent application Ser. No. 14/640,837, entitled SMART SENSORS WITH LOCAL SIGNAL PROCESSING; now U.S. Patent Application Publication No. 2016/0256163;
- U.S. patent application Ser. No. 14/640,780, entitled SURGICAL INSTRUMENT COMPRISING A LOCKABLE BATTERY HOUSING; now U.S. Patent Application Publication No. 2016/0256161;
- U.S. patent application Ser. No. 14/640,765, entitled SYSTEM FOR DETECTING THE MIS-INSERTION OF A STAPLE CARTRIDGE INTO A SURGICAL STAPLER; now U.S. Patent Application Publication No. 2016/0256160; and
- U.S. patent application Ser. No. 14/640,799, entitled SIGNAL AND POWER COMMUNICATION SYSTEM POSITIONED ON A ROTATABLE SHAFT; now U.S. Patent Application Publication No. 2016/0256162.

Applicant of the present application owns the following patent applications that were filed on Feb. 27, 2015, and which are each herein incorporated by reference in their respective entireties:

U.S. patent application Ser. No. 14/633,576, entitled SURGICAL INSTRUMENT SYSTEM COMPRISING AN INSPECTION STATION; now U.S. Patent Application Publication No. 2016/0249919;

- U.S. patent application Ser. No. 14/633,546, entitled SURGICAL APPARATUS CONFIGURED TO ASSESS WHETHER A PERFORMANCE PARAMETER OF THE SURGICAL APPARATUS IS WITHIN AN ACCEPTABLE PERFORMANCE BAND; now U.S. Patent Application Publication No. 2016/0249915;
- U.S. patent application Ser. No. 14/633,576, entitled SURGICAL CHARGING SYSTEM THAT CHARGES AND/OR CONDITIONS ONE OR MORE BATTERIES; now U.S. Patent Application Publication No. 2016/0249919;
- U.S. patent application Ser. No. 14/633,566, entitled CHARGING SYSTEM THAT ENABLES EMERGENCY RESOLUTIONS FOR CHARGING A BATTERY; now U.S. Patent Application Publication No. 2016/0249918;
- U.S. patent application Ser. No. 14/633,555, entitled SYSTEM FOR MONITORING WHETHER A SUR- GICAL INSTRUMENT NEEDS TO BE SERVICED; now U.S. Patent Application Publication No. 2016/0249916;

U.S. patent application Ser. No. 14/633,542, entitled REINFORCED BATTERY FOR A SURGICAL INSTRUMENT; now U.S. Patent Application Publication No. 2016/0249908;

U.S. patent application Ser. No. 14/633,548, entitled POWER ADAPTER FOR A SURGICAL INSTRUMENT; now U.S. Patent Application Publication No. 2016/0249909;

U.S. patent application Ser. No. 14/633,526, entitled ADAPTABLE SURGICAL INSTRUMENT HANDLE; now U.S. Patent Application Publication No. 2016/0249945;

U.S. patent application Ser. No. 14/633,541, entitled MODULAR STAPLING ASSEMBLY; now U.S. Patent Application Publication No. 2016/0249927; and U.S. patent application Ser. No. 14/633,562, entitled SURGICAL APPARATUS CONFIGURED TO TRACK AN END-OF-LIFE PARAMETER; now U.S. Patent Application Publication No. 2016/0249917.

Applicant of the present application owns the following patent applications that were filed on Dec. 18, 2014 and which are each herein incorporated by reference in their respective entireties:

U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING MEMBER; now U.S. Patent Application Publication No. 2016/0174977;

U.S. patent application Ser. No. 14/574,483, entitled SURGICAL INSTRUMENT ASSEMBLY COMPRISING LOCKABLE SYSTEMS; now U.S. Patent Application Publication No. 2016/0174969;

U.S. patent application Ser. No. 14/575,139, entitled DRIVE ARRANGEMENTS FOR ARTICULATABLE SURGICAL INSTRUMENTS; now U.S. Patent Application Publication No. 2016/0174978;

U.S. patent application Ser. No. 14/575,148, entitled LOCKING ARRANGEMENTS FOR DETACHABLE SHAFT ASSEMBLIES WITH ARTICULATABLE SURGICAL END EFFECTORS; now U.S. Patent Application Publication No. 2016/0174976;

U.S. patent application Ser. No. 14/575,130, entitled SURGICAL INSTRUMENT WITH AN ANVIL THAT IS SELECTIVELY MOVABLE ABOUT A DISCRETE NON-MOVABLE AXIS RELATIVE TO A STAPLE CARTRIDGE; now U.S. Patent Application Publication No. 2016/0174972;

U.S. patent application Ser. No. 14/575,143, entitled SURGICAL INSTRUMENTS WITH IMPROVED CLOSURE ARRANGEMENTS; now U.S. Patent Application Publication No. 2016/0174983;

U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS; now U.S. Patent Application Publication No. 2016/0174975;

U.S. patent application Ser. No. 14/575,154, entitled SURGICAL INSTRUMENTS WITH ARTICULATABLE END EFFECTORS AND IMPROVED FIRING BEAM SUPPORT ARRANGEMENTS; now U.S. Patent Application Publication No. 2016/0174973;

U.S. patent application Ser. No. 14/574,493, entitled SURGICAL INSTRUMENT ASSEMBLY COMPRISING A FLEXIBLE ARTICULATION SYSTEM; now U.S. Patent Application Publication No. 2016/0174970; and U.S. patent application Ser. No. 14/574,500, entitled SURGICAL INSTRUMENT ASSEMBLY COMPRISING A LOCKABLE ARTICULATION SYSTEM; now U.S. Patent Application Publication No. 2016/0174971.

Applicant of the present application owns the following patent applications that were filed on Mar. 1, 2013 and which are each herein incorporated by reference in their respective entireties:

U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Pat. No. 9,700,309;

U.S. patent application Ser. No. 13/782,323, entitled ROTARY POWERED ARTICULATION JOINTS FOR SURGICAL INSTRUMENTS, now U.S. Pat. No. 9,782,169;

U.S. patent application Ser. No. 13/782,338, entitled THUMBWHEEL SWITCH ARRANGEMENTS FOR SURGICAL INSTRUMENTS, now U.S. Patent Application Publication No. 2014/0249557;

U.S. patent application Ser. No. 13/782,499, entitled ELECTROMECHANICAL SURGICAL DEVICE WITH SIGNAL RELAY ARRANGEMENT, now U.S. Pat. No. 9,358,003;

U.S. patent application Ser. No. 13/782,460, entitled MULTIPLE PROCESSOR MOTOR CONTROL FOR MODULAR SURGICAL INSTRUMENTS, now U.S. Pat. No. 9,554,794;

U.S. patent application Ser. No. 13/782,358, entitled JOYSTICK SWITCH ASSEMBLIES FOR SURGICAL INSTRUMENTS, now U.S. Pat. No. 9,326,767;

U.S. patent application Ser. No. 13/782,481, entitled SENSOR STRAIGHTENED END EFFECTOR DURING REMOVAL THROUGH TROCAR, now U.S. Pat. No. 9,468,438;

U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475;

U.S. patent application Ser. No. 13/782,375, entitled ROTARY POWERED SURGICAL INSTRUMENTS WITH MULTIPLE DEGREES OF FREEDOM, now U.S. Pat. No. 9,398,911; and U.S. patent application Ser. No. 13/782,536, entitled SURGICAL INSTRUMENT SOFT STOP, now U.S. Pat. No. 9,307,986.

Applicant of the present application also owns the following patent applications that were filed on Mar. 14, 2013 and which are each herein incorporated by reference in their respective entireties:

U.S. patent application Ser. No. 13/803,097, entitled ARTICULATABLE SURGICAL INSTRUMENT COMPRISING A FIRING DRIVE, now U.S. Pat. No. 9,687,230;

U.S. patent application Ser. No. 13/803,193, entitled CONTROL ARRANGEMENTS FOR A DRIVE MEMBER OF A SURGICAL INSTRUMENT, now U.S. Pat. No. 9,332,987;

U.S. patent application Ser. No. 13/803,053, entitled INTERCHANGEABLE SHAFT ASSEMBLIES FOR USE WITH A SURGICAL INSTRUMENT, now U.S. Patent Application Publication No. 2014/0263564;

U.S. patent application Ser. No. 13/803,086, entitled ARTICULATABLE SURGICAL INSTRUMENT COMPRISING AN ARTICULATION LOCK, now U.S. Patent Application Publication No. 2014/0263541;

U.S. patent application Ser. No. 13/803,210, entitled SENSOR ARRANGEMENTS FOR ABSOLUTE POSITIONING SYSTEM FOR SURGICAL INSTRUMENTS, now U.S. Patent Application Publication No. 2014/0263538;

U.S. patent application Ser. No. 13/803,148, entitled MULTI-FUNCTION MOTOR FOR A SURGICAL INSTRUMENT, now U.S. Patent Application Publication No. 2014/0263554;

U.S. patent application Ser. No. 13/803,066, entitled DRIVE SYSTEM LOCKOUT ARRANGEMENTS FOR MODULAR SURGICAL INSTRUMENTS, now U.S. Pat. No. 9,629,623;

U.S. patent application Ser. No. 13/803,117, entitled ARTICULATION CONTROL SYSTEM FOR ARTICULATABLE SURGICAL INSTRUMENTS, now U.S. Pat. No. 9,351,726;

U.S. patent application Ser. No. 13/803,130, entitled DRIVE TRAIN CONTROL ARRANGEMENTS FOR MODULAR SURGICAL INSTRUMENTS, now U.S. Pat. No. 9,351,727; and U.S. patent application Ser. No. 13/803,159, entitled METHOD AND SYSTEM FOR OPERATING A SURGICAL INSTRUMENT, now U.S. Patent Application Publication No. 2014/0277017.

Applicant of the present application also owns the following patent application that was filed on Mar. 7, 2014 and is herein incorporated by reference in its entirety:

U.S. patent application Ser. No. 14/200,111, entitled CONTROL SYSTEMS FOR SURGICAL INSTRUMENTS, now U.S. Pat. No. 9,629,629.

Applicant of the present application also owns the following patent applications that were filed on Mar. 26, 2014 and are each herein incorporated by reference in their respective entireties:

U.S. patent application Ser. No. 14/226,106, entitled POWER MANAGEMENT CONTROL SYSTEMS FOR SURGICAL INSTRUMENTS; now U.S. Patent Application Publication No. 2015/0272582;

U.S. patent application Ser. No. 14/226,099, entitled STERILIZATION VERIFICATION CIRCUIT; now U.S. Patent Application Publication No. 2015/0272581;

U.S. patent application Ser. No. 14/226,094, entitled VERIFICATION OF NUMBER OF BATTERY EXCHANGES/PROCEDURE COUNT; now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL; now U.S. Patent Application Publication No. 2015/0272574;

U.S. patent application Ser. No. 14/226,075, entitled MODULAR POWERED SURGICAL INSTRUMENT WITH DETACHABLE SHAFT ASSEMBLIES; now U.S. Pat. No. 9,743,929;

U.S. patent application Ser. No. 14/226,093, entitled FEEDBACK ALGORITHMS FOR MANUAL BAILOUT SYSTEMS FOR SURGICAL INSTRUMENTS; now U.S. Patent Application Publication No. 2015/0272569;

U.S. patent application Ser. No. 14/226,116, entitled SURGICAL INSTRUMENT UTILIZING SENSOR ADAPTATION; now U.S. Patent Application Publication No. 2015/0272571;

U.S. patent application Ser. No. 14/226,071, entitled SURGICAL INSTRUMENT CONTROL CIRCUIT HAVING A SAFETY PROCESSOR; now U.S. Pat. No. 9,690,362;

U.S. patent application Ser. No. 14/226,097, entitled SURGICAL INSTRUMENT COMPRISING INTERACTIVE SYSTEMS; now U.S. Patent Application Publication No. 2015/0272570;

U.S. patent application Ser. No. 14/226,126, entitled INTERFACE SYSTEMS FOR USE WITH SURGICAL INSTRUMENTS; now U.S. Patent Application Publication No. 2015/0272572;

U.S. patent application Ser. No. 14/226,133, entitled MODULAR SURGICAL INSTRUMENT SYSTEM; now U.S. Patent Application Publication No. 2015/0272557;

U.S. patent application Ser. No. 14/226,081, entitled SYSTEMS AND METHODS FOR CONTROLLING A SEGMENTED CIRCUIT; now U.S. Patent Application Publication No. 2015/0277471;

U.S. patent application Ser. No. 14/226,076, entitled POWER MANAGEMENT THROUGH SEGMENTED CIRCUIT AND VARIABLE VOLTAGE PROTECTION; now U.S. Pat. No. 9,733,663;

U.S. patent application Ser. No. 14/226,111, entitled SURGICAL STAPLING INSTRUMENT SYSTEM; now U.S. Pat. No. 9,750,499; and U.S. patent application Ser. No. 14/226,125, entitled SURGICAL INSTRUMENT COMPRISING A ROTATABLE SHAFT; now U.S. Patent Application Publication No. 2015/0280384.

Applicant of the present application also owns the following patent applications that were filed on Sep. 5, 2014 and which are each herein incorporated by reference in their respective entireties:

U.S. patent application Ser. No. 14/479,103, entitled CIRCUITRY AND SENSORS FOR POWERED MEDICAL DEVICE; now U.S. Patent Application Publication No. 2016/0066912;

U.S. patent application Ser. No. 14/479,119, entitled ADJUNCT WITH INTEGRATED SENSORS TO QUANTIFY TISSUE COMPRESSION; now U.S. Pat. No. 9,724,094;

U.S. patent application Ser. No. 14/478,908, entitled MONITORING DEVICE DEGRADATION BASED ON COMPONENT EVALUATION; now U.S. Pat. No. 9,737,301;

U.S. patent application Ser. No. 14/478,895, entitled MULTIPLE SENSORS WITH ONE SENSOR AFFECTING A SECOND SENSOR'S OUTPUT OR INTERPRETATION; now U.S. Pat. No. 9,757,128;

U.S. patent application Ser. No. 14/479,110, entitled USE OF POLARITY OF HALL MAGNET DETECTION TO DETECT MISLOADED CARTRIDGE; now U.S. Patent Application Publication No. 2016/0066915;

U.S. patent application Ser. No. 14/479,098, entitled SMART CARTRIDGE WAKE UP OPERATION AND DATA RETENTION; now U.S. Patent Application Publication No. 2016/0066911;

U.S. patent application Ser. No. 14/479,115, entitled MULTIPLE MOTOR CONTROL FOR POWERED MEDICAL DEVICE; now U.S. Patent Application Publication No. 2016/0066916; and U.S. patent application Ser. No. 14/479,108, entitled LOCAL DISPLAY OF TISSUE PARAMETER STABILIZATION; now U.S. Patent Application Publication No. 2016/0066913.

Applicant of the present application also owns the following patent applications that were filed on Apr. 9, 2014 and which are each herein incorporated by reference in their respective entireties:

- U.S. patent application Ser. No. 14/248,590, entitled MOTOR DRIVEN SURGICAL INSTRUMENTS WITH LOCKABLE DUAL DRIVE SHAFTS, now U.S. Patent Application Publication No. 2014/0305987;
- U.S. patent application Ser. No. 14/248,581, entitled SURGICAL INSTRUMENT COMPRISING A CLOSING DRIVE AND A FIRING DRIVE OPERATED FROM THE SAME ROTATABLE OUTPUT, now U.S. Pat. No. 9,649,110;
- U.S. patent application Ser. No. 14/248,595, entitled SURGICAL INSTRUMENT SHAFT INCLUDING SWITCHES FOR CONTROLLING THE OPERATION OF THE SURGICAL INSTRUMENT, now U.S. Patent Application Publication No. 2014/0305988;
- U.S. patent application Ser. No. 14/248,588, entitled POWERED LINEAR SURGICAL STAPLER, now U.S. Patent Application Publication No. 2014/0309666;
- U.S. patent application Ser. No. 14/248,591, entitled TRANSMISSION ARRANGEMENT FOR A SURGICAL INSTRUMENT, now U.S. Patent Application Publication No. 2014/0305991;
- U.S. patent application Ser. No. 14/248,584, entitled MODULAR MOTOR DRIVEN SURGICAL INSTRUMENTS WITH ALIGNMENT FEATURES FOR ALIGNING ROTARY DRIVE SHAFTS WITH SURGICAL END EFFECTOR SHAFTS, now U.S. Patent Application Publication No. 2014/0305994;
- U.S. patent application Ser. No. 14/248,587, entitled POWERED SURGICAL STAPLER, now U.S. Patent Application Publication No. 2014/0309665;
- U.S. patent application Ser. No. 14/248,586, entitled DRIVE SYSTEM DECOUPLING ARRANGEMENT FOR A SURGICAL INSTRUMENT, now U.S. Patent Application Publication No. 2014/0305990; and
- U.S. patent application Ser. No. 14/248,607, entitled MODULAR MOTOR DRIVEN SURGICAL INSTRUMENTS WITH STATUS INDICATION ARRANGEMENTS, now U.S. Patent Application Publication No. 2014/0305992.

Applicant of the present application also owns the following patent applications that were filed on Apr. 16, 2013 and which are each herein incorporated by reference in their respective entireties:

- U.S. Provisional Patent Application Ser. No. 61/812,365, entitled SURGICAL INSTRUMENT WITH MULTIPLE FUNCTIONS PERFORMED BY A SINGLE MOTOR;
- U.S. Provisional Patent Application Ser. No. 61/812,376, entitled LINEAR CUTTER WITH POWER;
- U.S. Provisional Patent Application Ser. No. 61/812,382, entitled LINEAR CUTTER WITH MOTOR AND PISTOL GRIP;
- U.S. Provisional Patent Application Ser. No. 61/812,385, entitled SURGICAL INSTRUMENT HANDLE WITH MULTIPLE ACTUATION MOTORS AND MOTOR CONTROL; and
- U.S. Provisional Patent Application Ser. No. 61/812,372, entitled SURGICAL INSTRUMENT WITH MULTIPLE FUNCTIONS PERFORMED BY A SINGLE MOTOR.

The present disclosure provides an overall understanding of the principles of the structure, function, manufacture, and use of the devices and methods disclosed herein. One or more examples of these aspects are illustrated in the accompanying drawings. Those of ordinary skill in the art will understand that the devices and methods specifically described herein and illustrated in the accompanying drawings are non-limiting examples. The features illustrated or described in connection with one example may be combined with the features of other examples. Such modifications and variations are intended to be included within the scope of the present disclosure.

Reference throughout the specification to "various aspects," "some aspects," "one aspect," or "an aspect", or the like, means that a particular feature, structure, or characteristic described in connection with the aspect is included in at least one aspect. Thus, appearances of the phrases "in various aspects," "in some aspects," "in one aspect", or "in an aspect", or the like, in places throughout the specification are not necessarily all referring to the same aspect. Furthermore, the particular features, structures, or characteristics may be combined in any suitable manner in one or more aspects. Thus, the particular features, structures, or characteristics illustrated or described in connection with one aspect may be combined, in whole or in part, with the features structures, or characteristics of one or more other aspects without limitation. Such modifications and variations are intended to be included within the scope of the present disclosure.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical," "horizontal," "up," and "down" may be used herein with respect to the drawings. However, surgical instruments are used in many orientations and positions, and these terms are not intended to be limiting and/or absolute.

Various example devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

FIGS. 1-6 depict a motor-driven surgical cutting and fastening instrument 10 that may or may not be reused. In the illustrated examples, the instrument 10 includes a housing 12 that comprises a handle assembly 14 that is configured to be grasped, manipulated and actuated by the clinician. The housing 12 is configured for operable attachment to an interchangeable shaft assembly 200 that has a surgical end effector 300 operably coupled thereto that is configured to perform one or more surgical tasks or procedures. As the present Detailed Description proceeds, it will be understood that the various unique and novel arrangements of the various forms of interchangeable shaft assemblies disclosed herein also may be effectively employed in connection with robotically-controlled surgical systems. Thus, the term "housing" also may encompass a housing or similar portion of a robotic system that houses or otherwise operably supports at least one drive system that is configured to generate and apply at least one control motion which could be used to actuate the interchangeable shaft assemblies disclosed herein and their respective equivalents. The term "frame" may refer to a portion of a handheld surgical instrument. The term "frame" also may represent a portion of a robotically controlled surgical instrument and/or a portion of the robotic system that may be used to operably control a surgical instrument. For example, the interchangeable shaft assemblies disclosed herein may be employed with various robotic systems, instruments, components and methods disclosed in U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, is incorporated by reference herein in its entirety.

Figure 1:
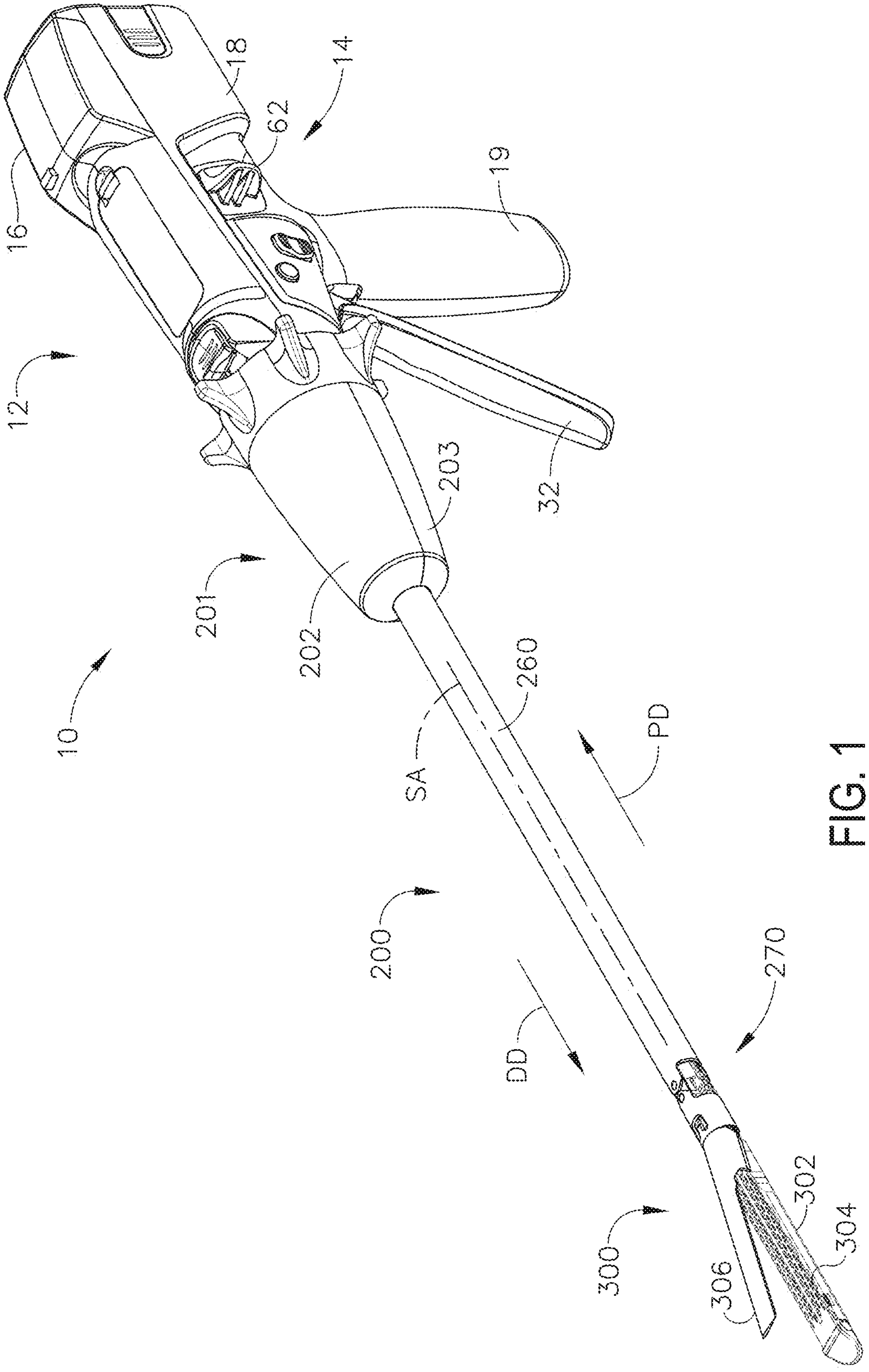
FIG. 1 is a perspective view of a surgical instrument that has an interchangeable shaft assembly operably coupled thereto.
Figure 2:
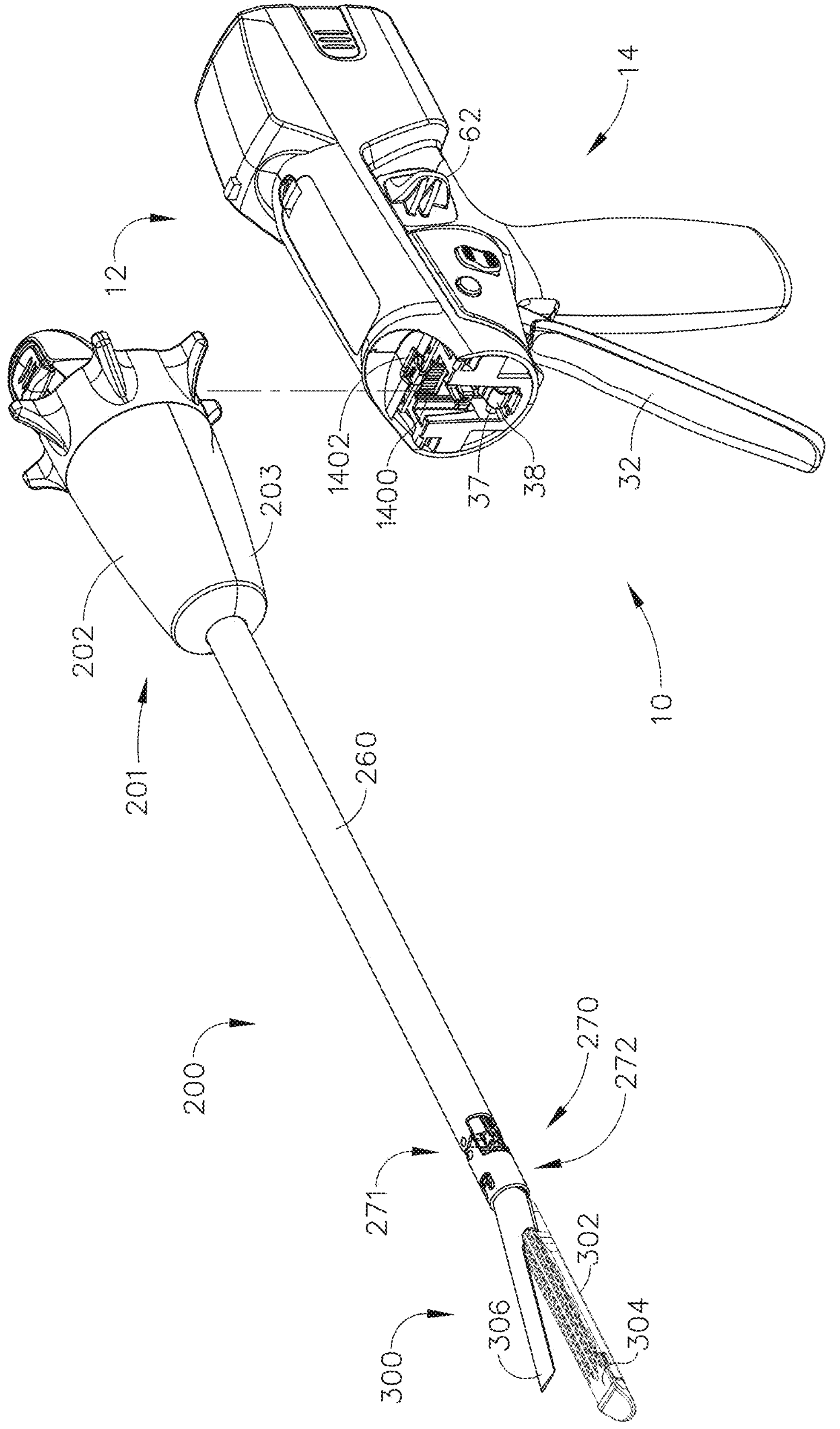
FIG. 2 is an exploded assembly view of the interchangeable shaft assembly and surgical instrument of FIG. 1.
Figure 3:
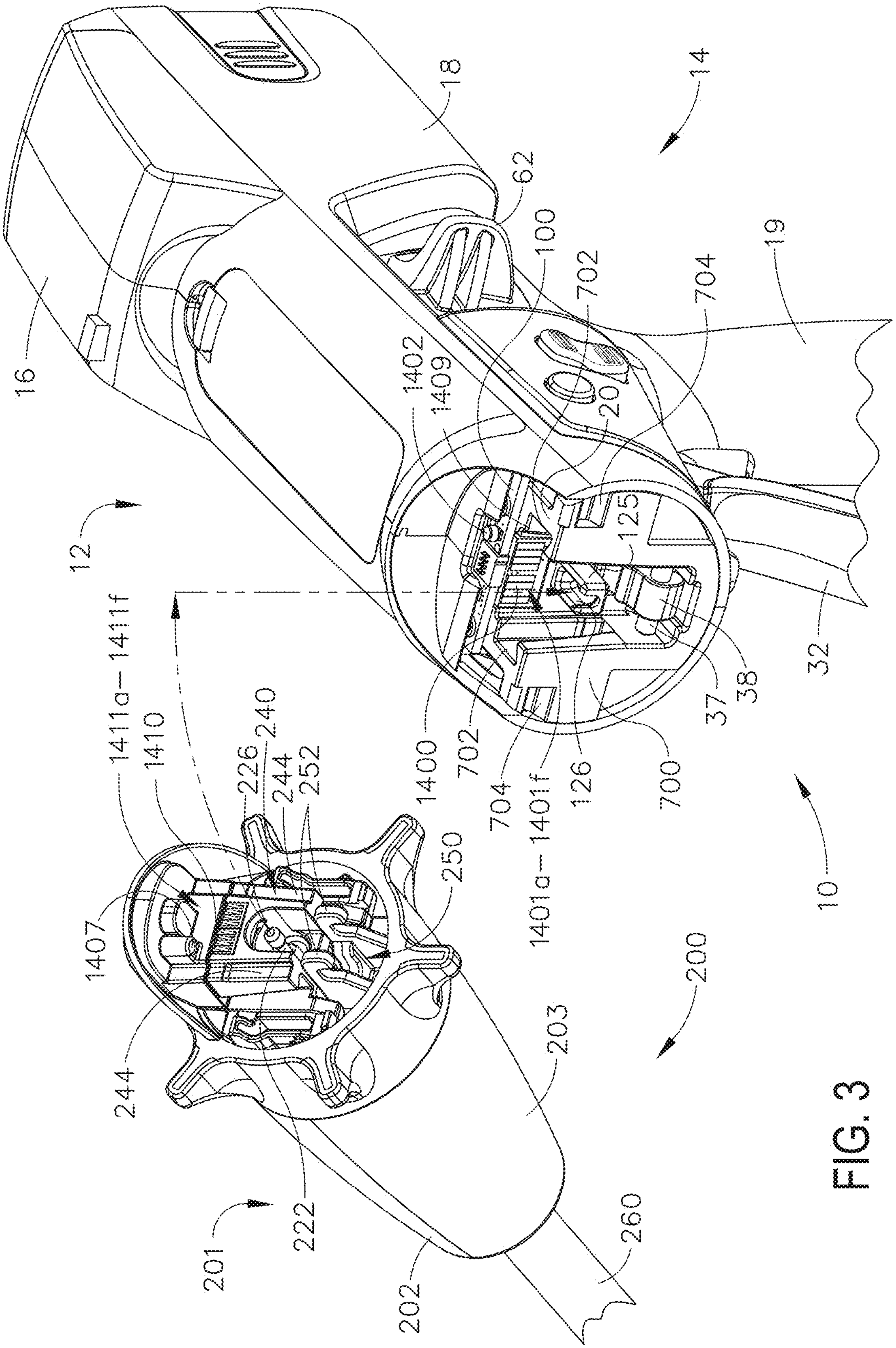
FIG. 3 is another exploded assembly view showing portions of the interchangeable shaft assembly and surgical instrument of FIGS. 1 and 2.

The housing 12 depicted in FIGS. 1-3 is shown in connection with an interchangeable shaft assembly 200 that includes an end effector 300 that comprises a surgical cutting and fastening device that is configured to operably support a surgical staple cartridge 304 therein. The housing 12 may be configured for use in connection with interchangeable shaft assemblies that include end effectors that are adapted to support different sizes and types of staple cartridges, have different shaft lengths, sizes, and types, etc. In addition, the housing 12 also may be effectively employed with a variety of other interchangeable shaft assemblies including those assemblies that are configured to apply other motions and forms of energy such as, for example, radio frequency (RF) energy, ultrasonic energy and/or motion to end effector arrangements adapted for use in connection with various surgical applications and procedures. Furthermore, the end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly.

Figure 4:
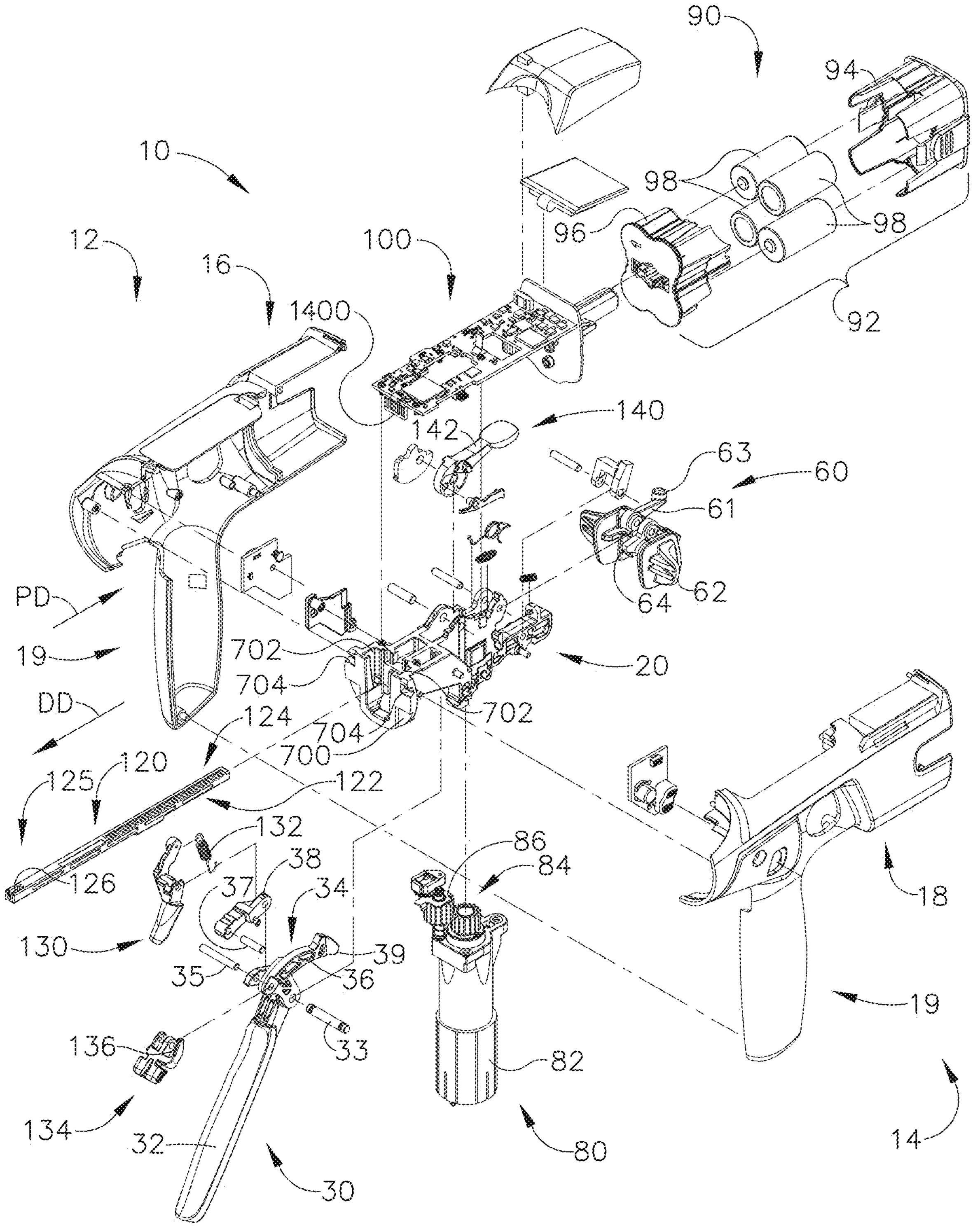
FIG. 4 is an exploded assembly view of a portion of the surgical instrument of FIGS. 1-3.
Figure 5:
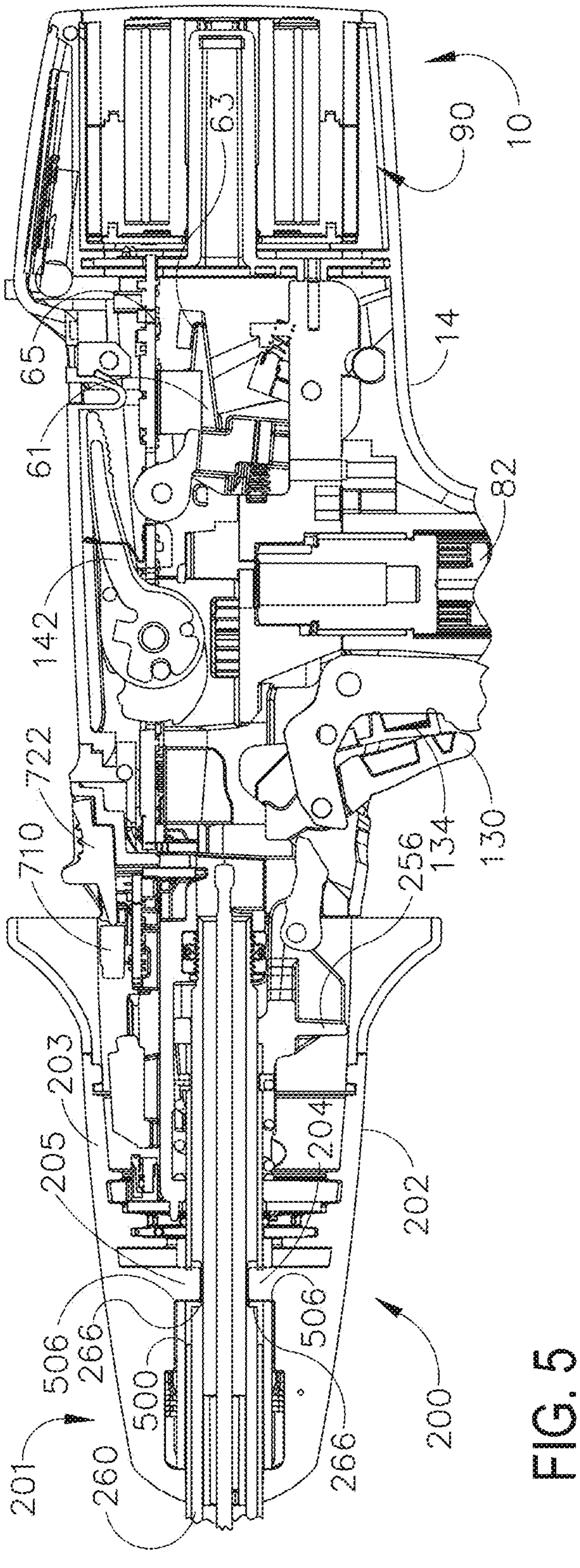
FIG. 5 is a cross-sectional side view of a portion of the surgical instrument of FIG. 4 with the firing trigger in a fully actuated position.

FIG. 1 illustrates the surgical instrument 10 with an interchangeable shaft assembly 200 operably coupled thereto. FIGS. 2 and 3 illustrate attachment of the interchangeable shaft assembly 200 to the housing 12 or handle assembly 14. As shown in FIG. 4, the handle assembly 14 may comprise a pair of interconnectable handle housing segments 16 and 18 that may be interconnected by screws, snap features, adhesive, etc. In the illustrated arrangement, the handle housing segments 16, 18 cooperate to form a pistol grip portion 19 that can be gripped and manipulated by the clinician. As will be discussed in further detail below, the handle assembly 14 operably supports a plurality of drive systems therein that are configured to generate and apply various control motions to corresponding portions of the interchangeable shaft assembly that is operably attached thereto.

Referring now to FIG. 4, the handle assembly 14 may further include a frame 20 that operably supports a plurality of drive systems. For example, the frame 20 can operably support a "first" or closure drive system, generally designated as 30, which may be employed to apply closing and opening motions to the interchangeable shaft assembly 200 that is operably attached or coupled thereto. In at least one form, the closure drive system 30 may include an actuator in the form of a closure trigger 32 that is pivotally supported by the frame 20. More specifically, as illustrated in FIG. 4, the closure trigger 32 is pivotally coupled to the housing 14 by a pin 33. Such arrangement enables the closure trigger 32 to be manipulated by a clinician such that when the clinician grips the pistol grip portion 19 of the handle assembly 14, the closure trigger 32 may be easily pivoted from a starting or "unactuated" position to an "actuated" position and more particularly to a fully compressed or fully actuated position. The closure trigger 32 may be biased into the unactuated position by spring or other biasing arrangement (not shown). In various forms, the closure drive system 30 further includes a closure linkage assembly 34 that is pivotally coupled to the closure trigger 32. As shown in FIG. 4, the closure linkage assembly 34 may include a first closure link 36 and a second closure link 38 that are pivotally coupled to the closure trigger 32 by a pin 35. The second closure link 38 also may be referred to herein as an "attachment member" and include a transverse attachment pin 37.

Still referring to FIG. 4, it can be observed that the first closure link 36 may have a locking wall or end 39 thereon that is configured to cooperate with a closure release assembly 60 that is pivotally coupled to the frame 20. In at least one form, the closure release assembly 60 may comprise a release button assembly 62 that has a distally protruding locking pawl 64 formed thereon. The release button assembly 62 may be pivoted in a counterclockwise direction by a release spring (not shown). As the clinician depresses the closure trigger 32 from its unactuated position towards the pistol grip portion 19 of the handle assembly 14, the first closure link 36 pivots upward to a point wherein the locking pawl 64 drops into retaining engagement with the locking wall 39 on the first closure link 36 thereby preventing the closure trigger 32 from returning to the unactuated position. See FIG. 18. Thus, the closure release assembly 60 serves to lock the closure trigger 32 in the fully actuated position. When the clinician desires to unlock the closure trigger 32 to permit it to be biased to the unactuated position, the clinician simply pivots the closure release button assembly 62 such that the locking pawl 64 is moved out of engagement with the locking wall 39 on the first closure link 36. When the locking pawl 64 has been moved out of engagement with the first closure link 36, the closure trigger 32 may pivot back to the unactuated position. Other closure trigger locking and release arrangements also may be employed.

Figure 13:
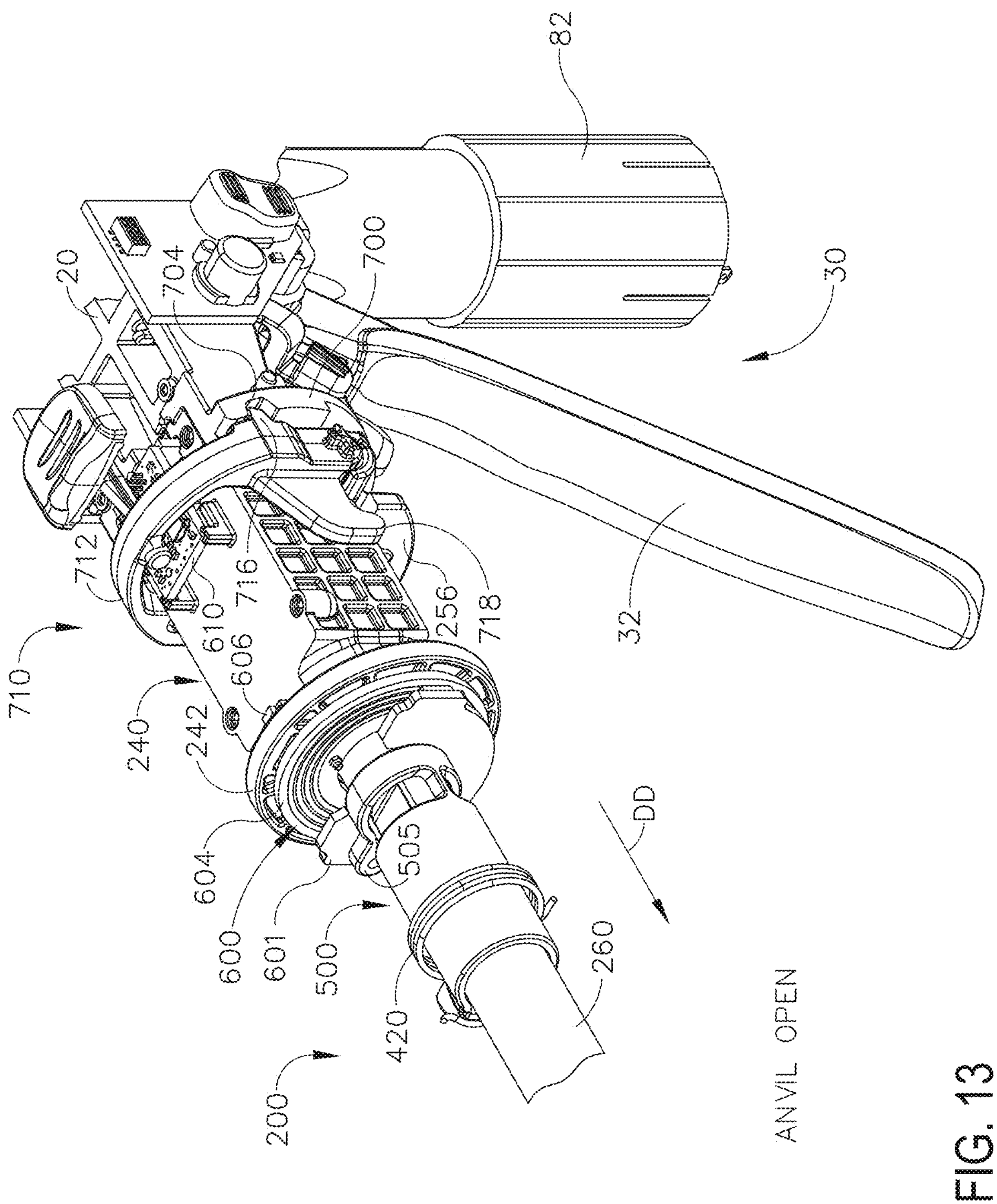
FIG. 13 is a perspective view of a portion of the interchangeable shaft assembly of FIG. 11 operably coupled to a portion of the surgical instrument of FIG. 1 illustrated with the closure trigger thereof in an unactuated position.
Figure 14:
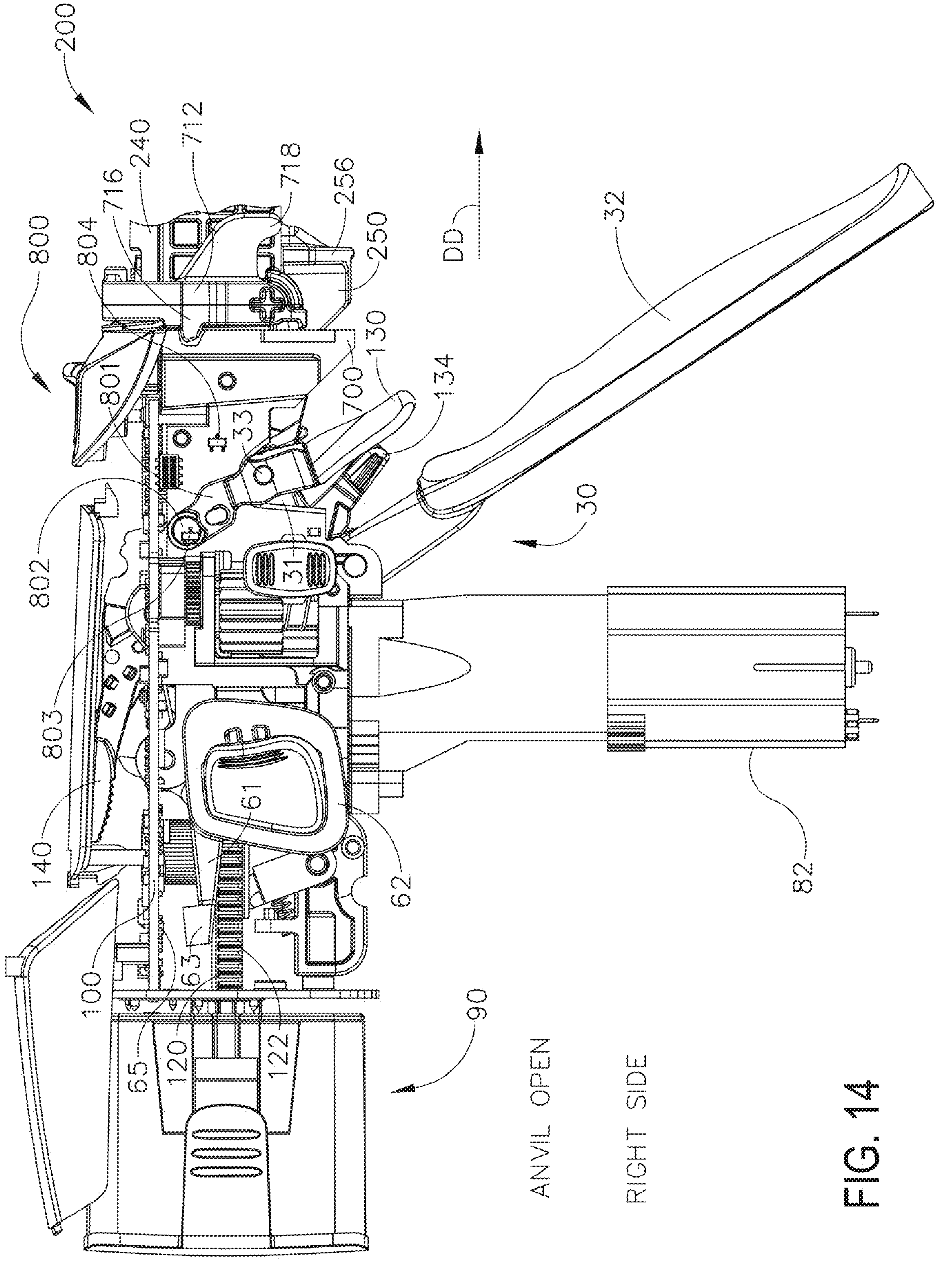
FIG. 14 is a right side elevational view of the interchangeable shaft assembly and surgical instrument of FIG. 13.
Figure 15:
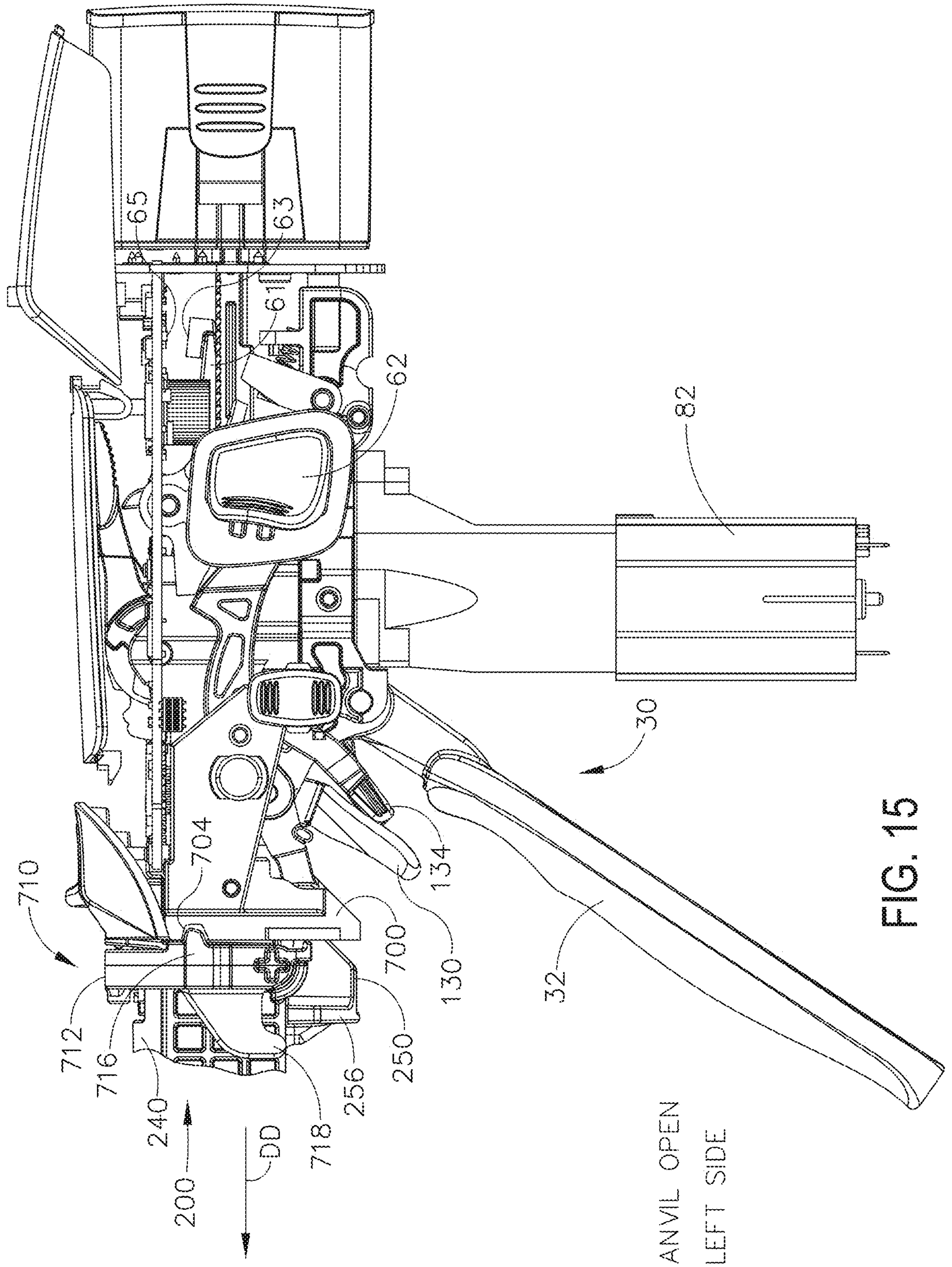
FIG. 15 is a left side elevational view of the interchangeable shaft assembly and surgical instrument of FIGS. 13 and 14.
Figure 16:
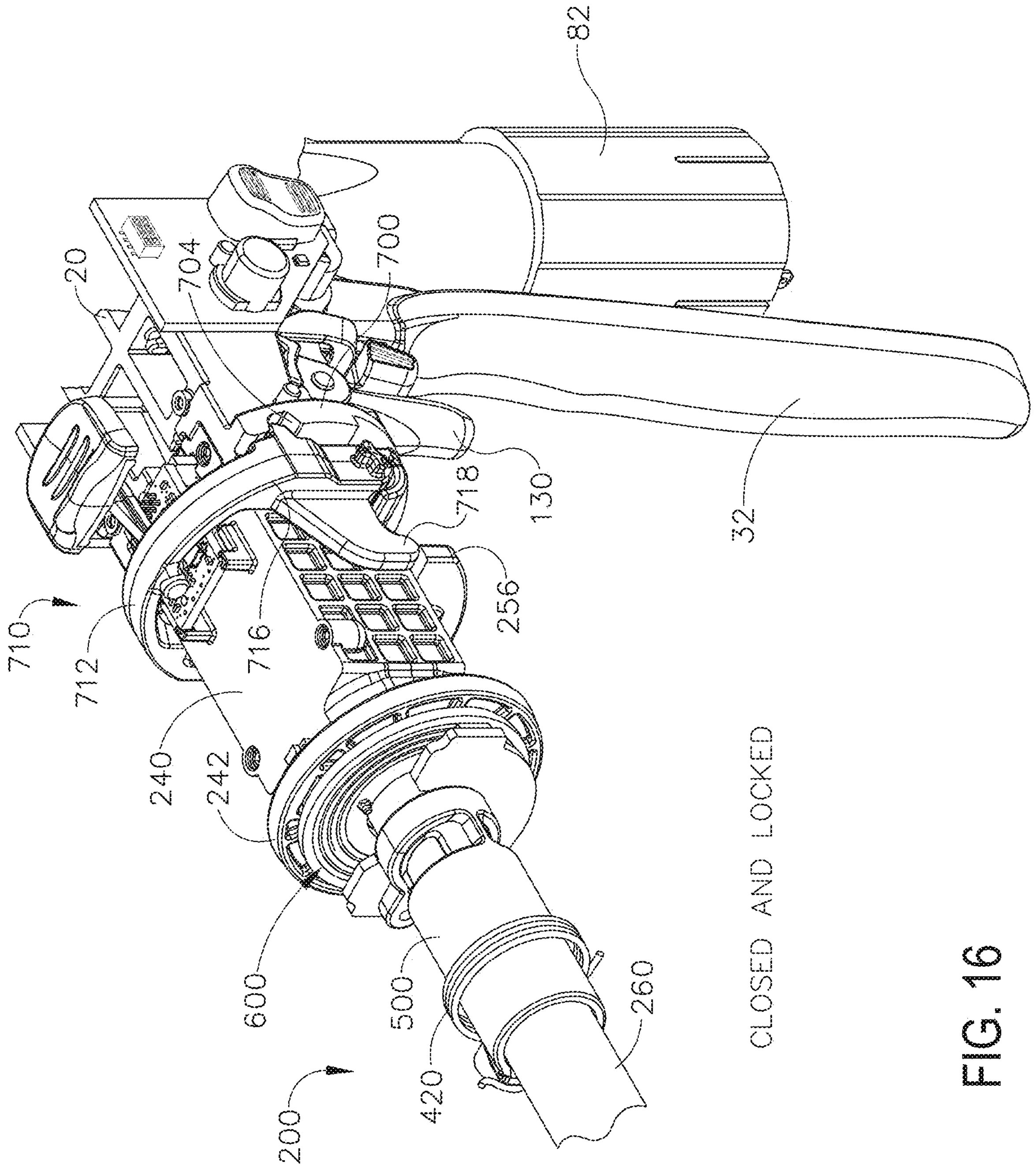
FIG. 16 is a perspective view of a portion of the interchangeable shaft assembly of FIG. 11 operably coupled to a portion of the surgical instrument of FIG. 1 illustrated with the closure trigger thereof in an actuated position and a firing trigger thereof in an unactuated position.
Figure 17:
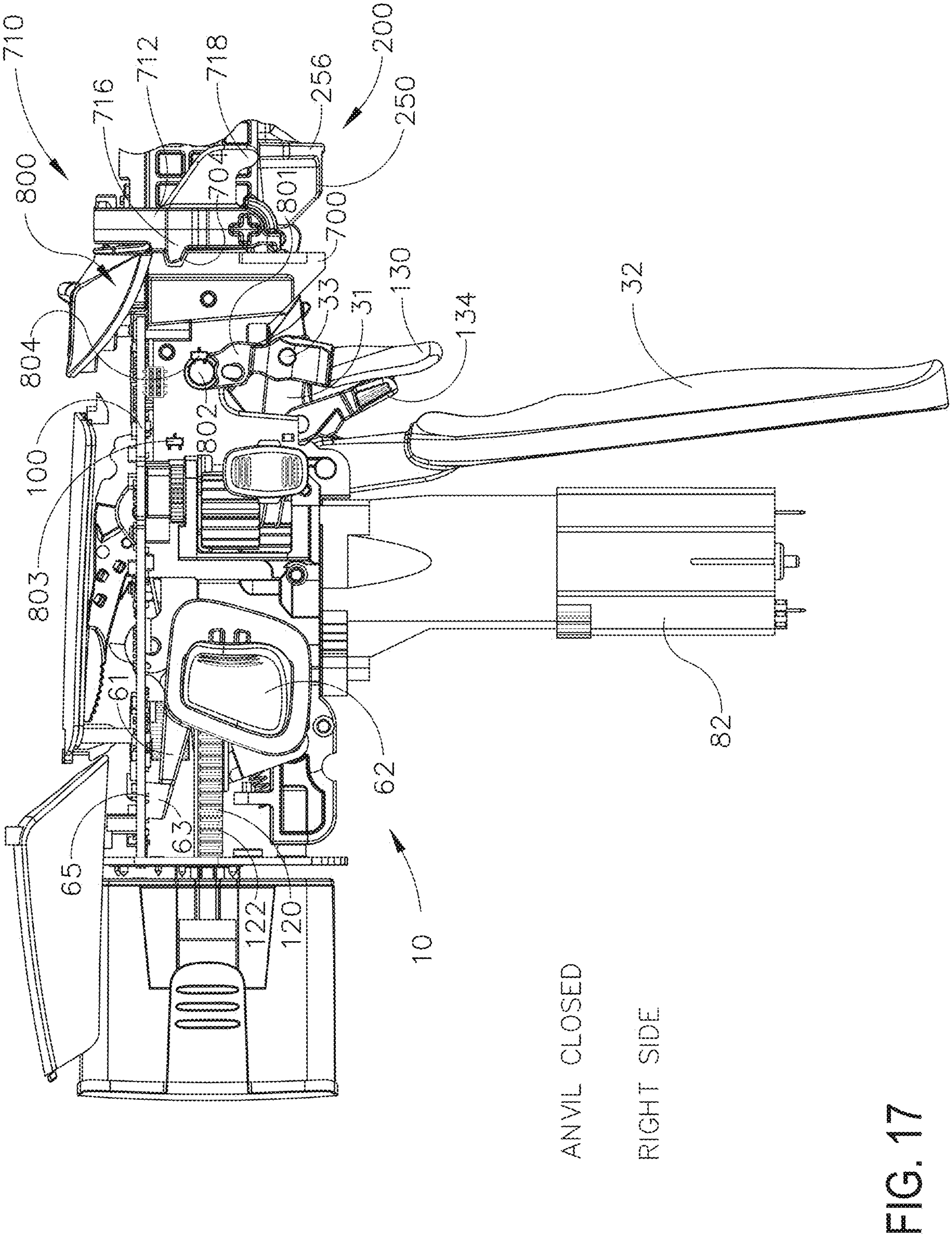
FIG. 17 is a right side elevational view of the interchangeable shaft assembly and surgical instrument of FIG. 16.
Figure 18:
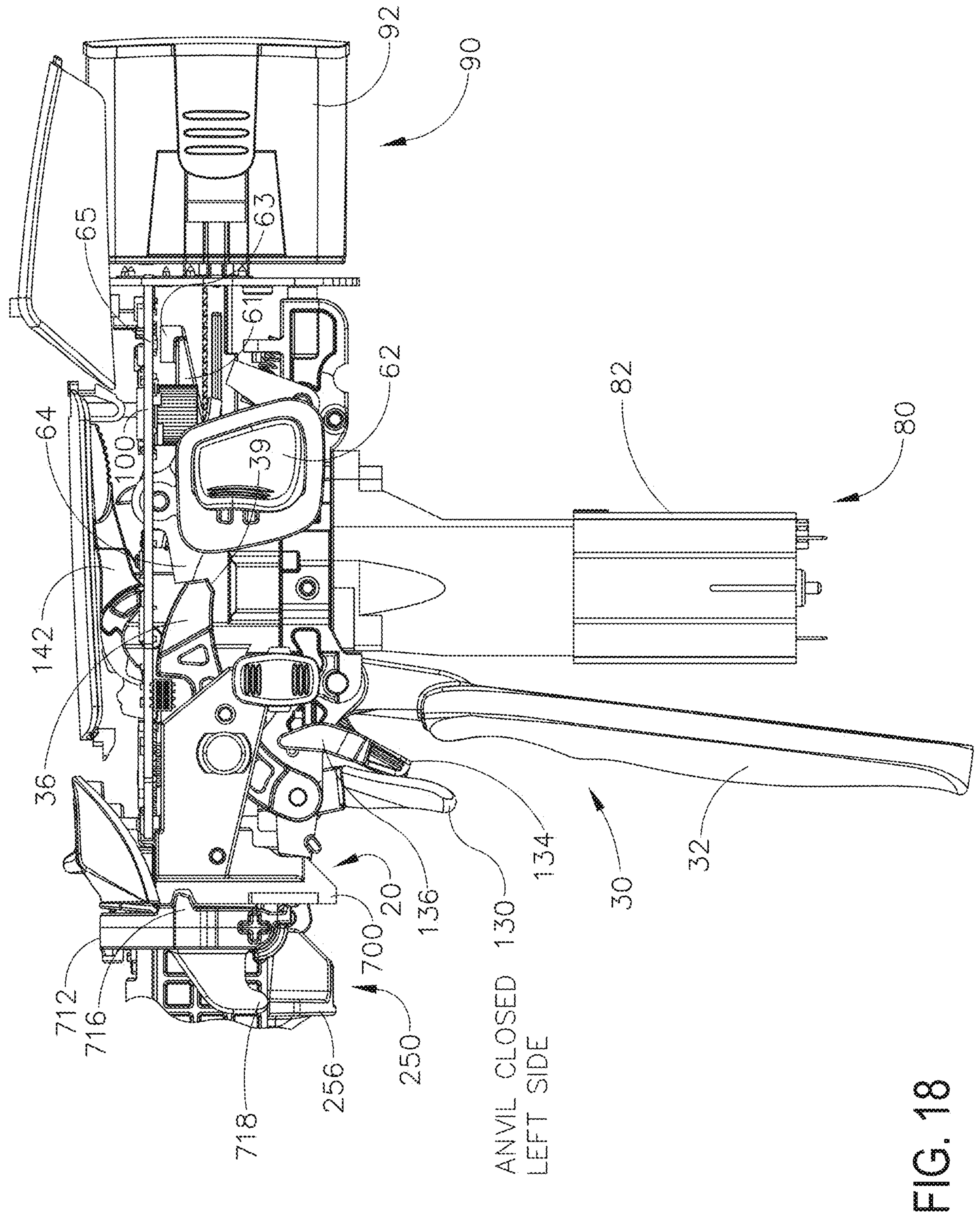
FIG. 18 is a left side elevational view of the interchangeable shaft assembly and surgical instrument of FIGS. 16 and 17.

Further to the above, FIGS. 13-15 illustrate the closure trigger 32 in its unactuated position which is associated with an open, or unclamped, configuration of the shaft assembly 200 in which tissue can be positioned between the jaws of the shaft assembly 200. FIGS. 16-18 illustrate the closure trigger 32 in its actuated position which is associated with a closed, or clamped, configuration of the shaft assembly 200 in which tissue is clamped between the jaws of the shaft assembly 200. Upon comparing FIGS. 14 and 17, the reader will appreciate that, when the closure trigger 32 is moved from its unactuated position (FIG. 14) to its actuated position (FIG. 17), the closure release button 62 is pivoted between a first position (FIG. 14) and a second position (FIG. 17). The rotation of the closure release button 62 can be referred to as being an upward rotation; however, at least a portion of the closure release button 62 is being rotated toward the circuit board 100. Referring to FIG. 4, the closure release button 62 can include an arm 61 extending therefrom and a magnetic element 63, such as a permanent magnet, for example, mounted to the arm 61. When the closure release button 62 is rotated from its first position to its second position, the magnetic element 63 can move toward the circuit board 100. The circuit board 100 can include at least one sensor configured to detect the movement of the magnetic element 63. In at least one aspect, a magnetic field sensor 65, for example, can be mounted to the bottom surface of the circuit board 100. The magnetic field sensor 65 can be configured to detect changes in a magnetic field surrounding the magnetic field sensor 65 caused by the movement of the magnetic element 63. The magnetic field sensor 65 can be in signal communication with a microcontroller 1500 (FIG. 19), for example, which can determine whether the closure release button 62 is in its first position, which is associated with the unactuated position of the closure trigger 32 and the open configuration of the end effector, its second position, which is associated with the actuated position of the closure trigger 32 and the closed configuration of the end effector, and/or any position between the first position and the second position.

As used throughout the present disclosure, a magnetic field sensor may be a Hall effect sensor, search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

In at least one form, the handle assembly 14 and the frame 20 may operably support another drive system referred to herein as a firing drive system 80 that is configured to apply firing motions to corresponding portions of the interchangeable shaft assembly attached thereto. The firing drive system may 80 also be referred to herein as a "second drive system". The firing drive system 80 may employ an electric motor 82, located in the pistol grip portion 19 of the handle assembly 14. In various forms, the motor 82 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor. The motor 82 may be powered by a power source 90 that in one form may comprise a removable power pack 92. As shown in FIG. 4, for example, the power pack 92 may comprise a proximal housing portion 94 that is configured for attachment to a distal housing portion 96. The proximal housing portion 94 and the distal housing portion 96 are configured to operably support a plurality of batteries 98 therein. Batteries 98 may each comprise, for example, a Lithium Ion ("LI") or other suitable battery. The distal housing portion 96 is configured for removable operable attachment to a control circuit board assembly 100 which is also operably coupled to the motor 82. A number of batteries 98 may be connected in series may be used as the power source for the surgical instrument 10. In addition, the power source 90 may be replaceable and/or rechargeable.

As outlined above with respect to other various forms, the electric motor 82 can include a rotatable shaft (not shown) that operably interfaces with a gear reducer assembly 84 that is mounted in meshing engagement with a with a set, or rack, of drive teeth 122 on a longitudinally-movable drive member 120. In use, a voltage polarity provided by the power source 90 can operate the electric motor 82 in a clockwise direction wherein the voltage polarity applied to the electric motor by the battery can be reversed in order to operate the electric motor 82 in a counter-clockwise direction. When the electric motor 82 is rotated in one direction, the drive member 120 will be axially driven in the distal direction "DD". When the motor 82 is driven in the opposite rotary direction, the drive member 120 will be axially driven in a proximal direction "PD". The handle assembly 14 can include a switch which can be configured to reverse the polarity applied to the electric motor 82 by the power source 90. As with the other forms described herein, the handle assembly 14 can also include a sensor that is configured to detect the position of the drive member 120 and/or the direction in which the drive member 120 is being moved.

Actuation of the motor 82 can be controlled by a firing trigger 130 that is pivotally supported on the handle assembly 14. The firing trigger 130 may be pivoted between an unactuated position and an actuated position. The firing trigger 130 may be biased into the unactuated position by a spring 132 or other biasing arrangement such that when the clinician releases the firing trigger 130, it may be pivoted or otherwise returned to the unactuated position by the spring 132 or biasing arrangement. In at least one form, the firing trigger 130 can be positioned "outboard" of the closure trigger 32 as was discussed above. In at least one form, a firing trigger safety button 134 may be pivotally mounted to the closure trigger 32 by pin 35. The safety button 134 may be positioned between the firing trigger 130 and the closure trigger 32 and have a pivot arm 136 protruding therefrom. See FIG. 4. When the closure trigger 32 is in the unactuated position, the safety button 134 is contained in the handle assembly 14 where the clinician cannot readily access it and move it between a safety position preventing actuation of the firing trigger 130 and a firing position wherein the firing trigger 130 may be fired. As the clinician depresses the closure trigger 32, the safety button 134 and the firing trigger 130 pivot down wherein they can then be manipulated by the clinician.

As discussed above, the handle assembly 14 can include a closure trigger 32 and a firing trigger 130. Referring to FIGS. 14-18A, the firing trigger 130 can be pivotably mounted to the closure trigger 32. The closure trigger 32 can include an arm 31 extending therefrom and the firing trigger 130 can be pivotably mounted to the arm 31 about a pivot pin 33. When the closure trigger 32 is moved from its unactuated position (FIG. 14) to its actuated position (FIG. 17), the firing trigger 130 can descend downwardly, as outlined above. After the safety button 134 has been moved to its firing position, referring primarily to FIG. 18A, the firing trigger 130 can be depressed to operate the motor of the surgical instrument firing system. In various instances, the handle assembly 14 can include a tracking system, such as system 800, for example, configured to determine the position of the closure trigger 32 and/or the position of the firing trigger 130. With primary reference to FIGS. 14, 17, and 18A, the tracking system 800 can include a magnetic element, such as permanent magnet 802, for example, which is mounted to an arm 801 extending from the firing trigger 130. The tracking system 800 can comprise one or more sensors, such as a first magnetic field sensor 803 and a second magnetic field sensor 804, for example, which can be configured to track the position of the magnet 802.

Upon comparing FIGS. 14 and 17, the reader will appreciate that, when the closure trigger 32 is moved from its unactuated position to its actuated position, the magnet 802 can move between a first position adjacent the first magnetic field sensor 803 and a second position adjacent the second magnetic field sensor 804.

Figure 18A:
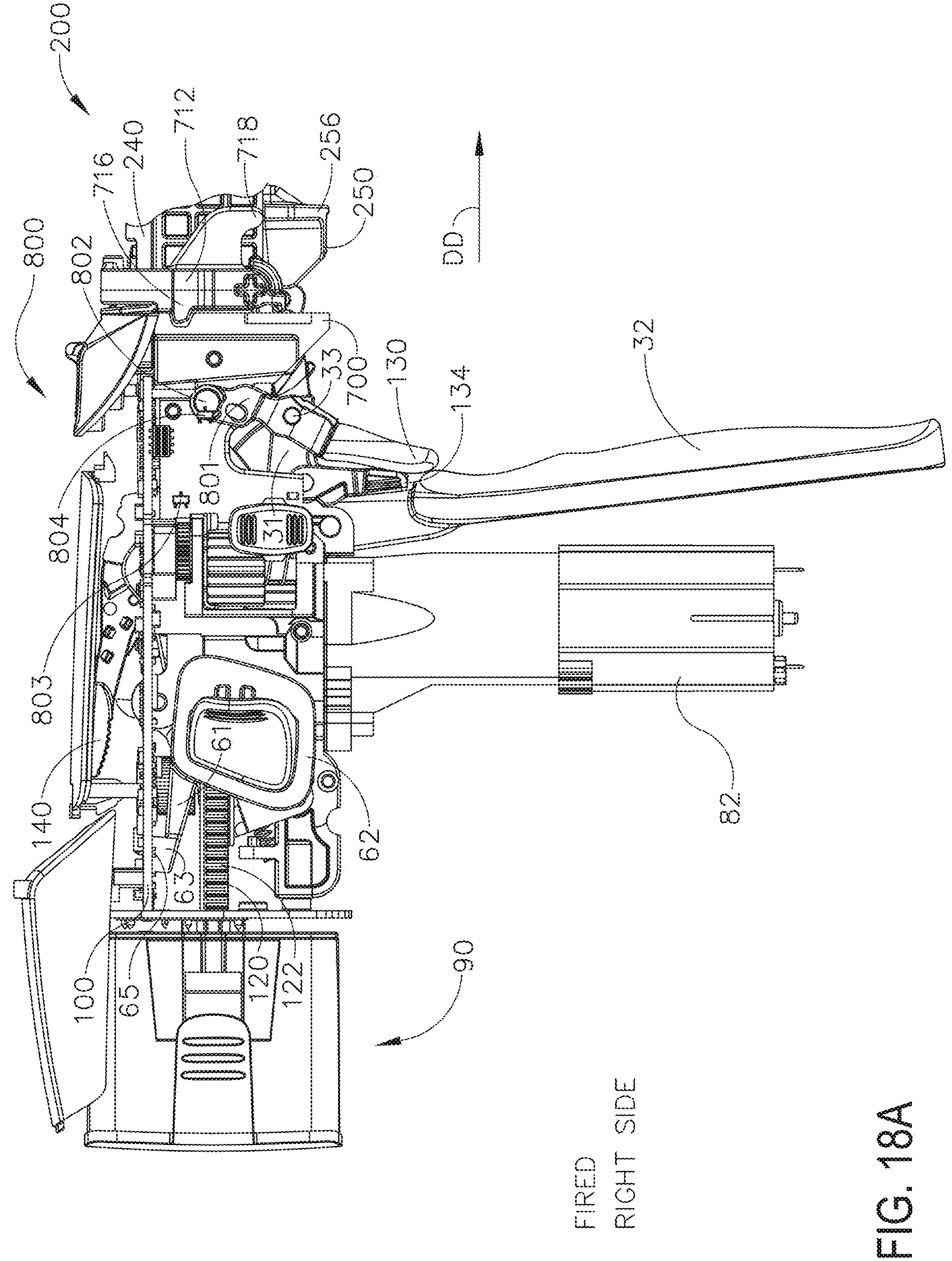
FIG. 18A is a right side elevational view of the interchangeable shaft assembly of FIG. 11 operably coupled to a portion of the surgical instrument of FIG. 1 illustrated with the closure trigger thereof in an actuated position and the firing trigger thereof in an actuated position.

Upon comparing FIGS. 17 and 18A, the reader will further appreciate that, when the firing trigger 130 is moved from an unfired position (FIG. 17) to a fired position (FIG. 18A), the magnet 802 can move relative to the second magnetic field sensor 804. The sensors 803 and 804 can track the movement of the magnet 802 and can be in signal communication with a microcontroller on the circuit board 100. With data from the first sensor 803 and/or the second sensor 804, the microcontroller can determine the position of the magnet 802 along a predefined path and, based on that position, the microcontroller can determine whether the closure trigger 32 is in its unactuated position, its actuated position, or a position therebetween. Similarly, with data from the first sensor 803 and/or the second sensor 804, the microcontroller can determine the position of the magnet 802 along a predefined path and, based on that position, the microcontroller can determine whether the firing trigger 130 is in its unfired position, its fully fired position, or a position therebetween.

As indicated above, in at least one form, the longitudinally movable drive member 120 has a rack of teeth 122 formed thereon for meshing engagement with a corresponding drive gear 86 of the gear reducer assembly 84. At least one form also includes a manually-actuatable "bailout" assembly 140 that is configured to enable the clinician to manually retract the longitudinally movable drive member 120 should the motor 82 become disabled. The bailout assembly 140 may include a lever or bailout handle assembly 14 that is configured to be manually pivoted into ratcheting engagement with teeth 124 also provided in the drive member 120. Thus, the clinician can manually retract the drive member 120 by using the bailout handle assembly 14 to ratchet the drive member 120 in the proximal direction "PD". U. S. Patent Application Publication No. 2010/0089970, now U.S. Pat. No. 8,608,045 discloses bailout arrangements and other components, arrangements and systems that also may be employed with the various instruments disclosed herein. U.S. patent application Ser. No. 12/249,117, entitled POWERED SURGICAL CUTTING AND STAPLING APPARATUS WITH MANUALLY RETRACTABLE FIRING SYSTEM, U.S. Patent Application Publication No. 2010/0089970, now U.S. Pat. No. 8,608,045, is hereby incorporated by reference in its entirety.

Figure 7:
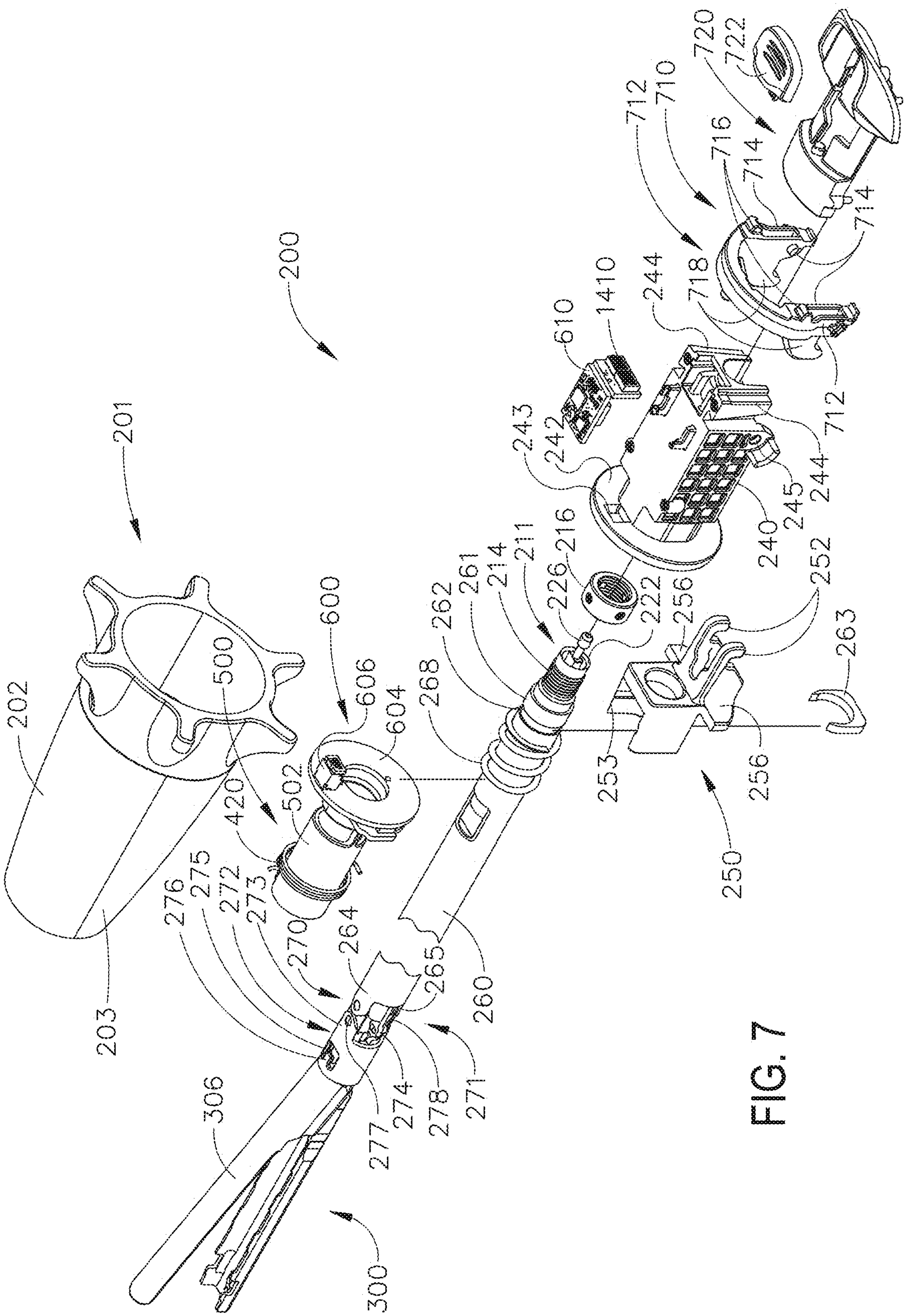
FIG. 7 is an exploded assembly view of one form of an interchangeable shaft assembly.
Figure 8:
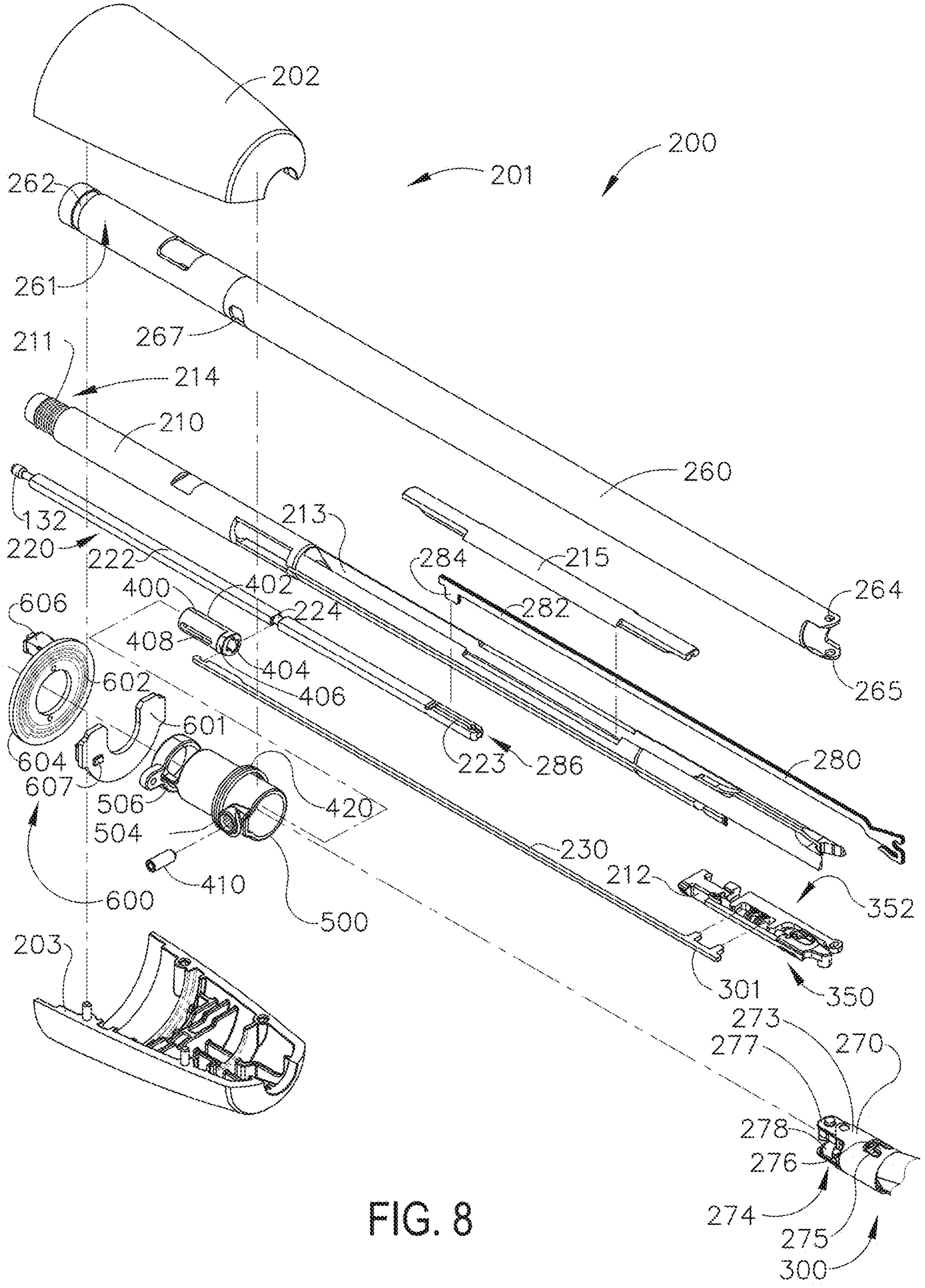
FIG. 8 is another exploded assembly view of portions of the interchangeable shaft assembly of FIG. 7.

Turning now to FIGS. 1 and 7, the interchangeable shaft assembly 200 includes a surgical end effector 300 that comprises an elongated channel 302 that is configured to operably support a staple cartridge 304 therein. The end effector 300 may further include an anvil 306 that is pivotally supported relative to the elongated channel 302. The interchangeable shaft assembly 200 may further include an articulation joint 270 and an articulation lock 350 (FIG. 8) which can be configured to releasably hold the end effector 300 in a desired position relative to a shaft axis SA-SA. Details regarding the construction and operation of the end effector 300, the articulation joint 270 and the articulation lock 350 are set forth in U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541. The entire disclosure of U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541, is hereby incorporated by reference herein. As shown in FIGS. 7 and 8, the interchangeable shaft assembly 200 can further include a proximal housing or nozzle 201 comprised of nozzle portions 202 and 203. The interchangeable shaft assembly 200 can further include a closure tube 260 which can be utilized to close and/or open the anvil 306 of the end effector 300. Primarily referring now to FIGS. 8 and 9, the shaft assembly 200 can include a spine 210 which can be configured to fixably support a shaft frame portion 212 of the articulation lock 350. See FIG. 8. The spine 210 can be configured to, one, slidably support a firing member 220 therein and, two, slidably support the closure tube 260 which extends around the spine 210. The spine 210 can also be configured to slidably support a proximal articulation driver 230. The articulation driver 230 has a distal end 231 that is configured to operably engage the articulation lock 350. The articulation lock 350 interfaces with an articulation frame 352 that is adapted to operably engage a drive pin (not shown) on the end effector frame (not shown). As indicated above, further details regarding the operation of the articulation lock 350 and the articulation frame may be found in U.S. patent application Ser. No. 13/803,086, now U.S. Patent Application Publication No. 2014/0263541. In various circumstances, the spine 210 can comprise a proximal end 211 which is rotatably supported in a chassis 240. In one arrangement, for example, the proximal end 211 of the spine 210 has a thread 214 formed thereon for threaded attachment to a spine bearing 216 configured to be supported within the chassis 240. See FIG. 7. Such an arrangement facilitates rotatable attachment of the spine 210 to the chassis 240 such that the spine 210 may be selectively rotated about a shaft axis SA-SA relative to the chassis 240.

Referring primarily to FIG. 7, the interchangeable shaft assembly 200 includes a closure shuttle 250 that is slidably supported within the chassis 240 such that it may be axially moved relative thereto. As shown in FIGS. 3 and 7, the closure shuttle 250 includes a pair of proximally-protruding hooks 252 that are configured for attachment to the attachment pin 37 that is attached to the second closure link 38 as will be discussed in further detail below. A proximal end 261 of the closure tube 260 is coupled to the closure shuttle 250 for relative rotation thereto. For example, a U shaped connector 263 is inserted into an annular slot 262 in the proximal end 261 of the closure tube 260 and is retained within vertical slots 253 in the closure shuttle 250. See FIG. 7. Such an arrangement serves to attach the closure tube 260 to the closure shuttle 250 for axial travel therewith while enabling the closure tube 260 to rotate relative to the closure shuttle 250 about the shaft axis SA-SA. A closure spring 268 is journaled on the closure tube 260 and serves to bias the closure tube 260 in the proximal direction "PD" which can serve to pivot the closure trigger into the unactuated position when the shaft assembly is operably coupled to the handle assembly 14.

In at least one form, the interchangeable shaft assembly 200 may further include an articulation joint 270. Other interchangeable shaft assemblies, however, may not be capable of articulation. As shown in FIG. 7, for example, the articulation joint 270 includes a double pivot closure sleeve assembly 271. According to various forms, the double pivot closure sleeve assembly 271 includes an end effector closure sleeve assembly 272 having upper and lower distally projecting tangs 273, 274. An end effector closure sleeve assembly 272 includes a horseshoe aperture 275 and a tab 276 for engaging an opening tab on the anvil 306 in the various manners described in U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541, which has been incorporated by reference herein. As described in further detail therein, the horseshoe aperture 275 and tab 276 engage a tab on the anvil when the anvil 306 is opened. An upper double pivot link 277 includes upwardly projecting distal and proximal pivot pins that engage respectively an upper distal pin hole in the upper proximally projecting tang 273 and an upper proximal pinhole in an upper distally projecting tang 264 on the closure tube 260. A lower double pivot link 278 includes upwardly projecting distal and proximal pivot pins that engage respectively a lower distal pin hole in the lower proximally projecting tang 274 and a lower proximal pin hole in the lower distally projecting tang 265. See also FIG. 8.

In use, the closure tube 260 is translated distally (direction "DD") to close the anvil 306, for example, in response to the actuation of the closure trigger 32. The anvil 306 is closed by distally translating the closure tube 260 and thus the shaft closure sleeve assembly 272, causing it to strike a proximal surface on the anvil 360 in the manner described in the aforementioned reference U.S. patent application Ser. No. 13/803,086, now U.S. Patent Application Publication No. 2014/0263541. As was also described in detail in that reference, the anvil 306 is opened by proximally translating the closure tube 260 and the shaft closure sleeve assembly 272, causing tab 276 and the horseshoe aperture 275 to contact and push against the anvil tab to lift the anvil 306. In the anvil-open position, the shaft closure tube 260 is moved to its proximal position.

As indicated above, the surgical instrument 10 may further include an articulation lock 350 of the types and construction described in further detail in U.S. patent application Ser. No. 13/803,086, now U.S. Patent Application Publication No. 2014/0263541, which can be configured and operated to selectively lock the end effector 300 in position. Such arrangement enables the end effector 300 to be rotated, or articulated, relative to the shaft closure tube 260 when the articulation lock 350 is in its unlocked state. In such an unlocked state, the end effector 300 can be positioned and pushed against soft tissue and/or bone, for example, surrounding the surgical site within the patient in order to cause the end effector 300 to articulate relative to the closure tube 260. The end effector 300 also may be articulated relative to the closure tube 260 by an articulation driver 230.

Figure 9:
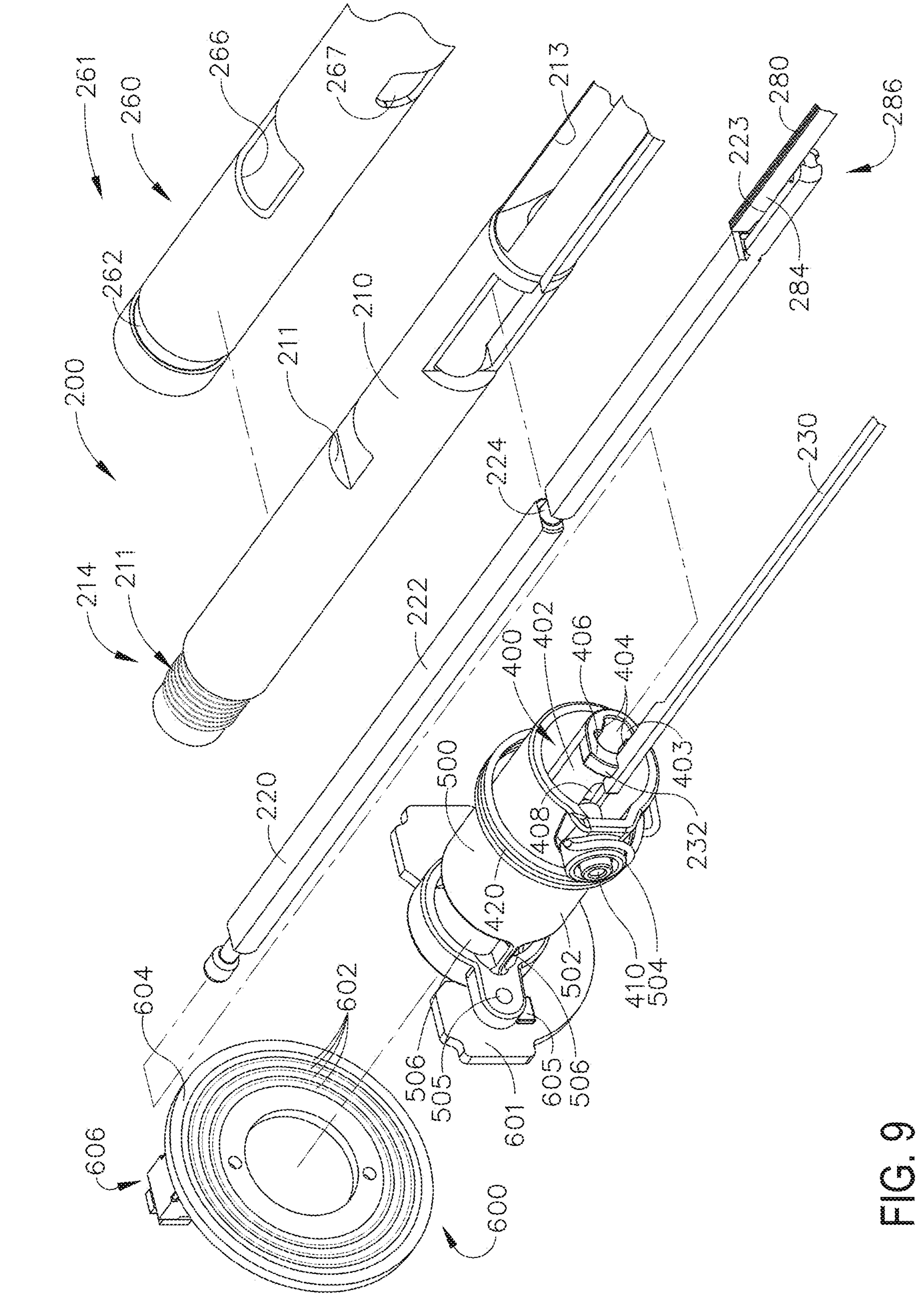
FIG. 9 is another exploded assembly view of portions of the interchangeable shaft assembly of FIGS. 7 and 8.

As was also indicated above, the interchangeable shaft assembly 200 further includes a firing member 220 that is supported for axial travel within the shaft spine 210. The firing member 220 includes an intermediate firing shaft portion 222 that is configured for attachment to a distal cutting portion or knife bar 280. The firing member 220 also may be referred to herein as a "second shaft" and/or a "second shaft assembly". As shown in FIGS. 8 and 9, the intermediate firing shaft portion 222 may include a longitudinal slot 223 in the distal end thereof which can be configured to receive a tab 284 on the proximal end 282 of the distal knife bar 280. The longitudinal slot 223 and the proximal end 282 can be sized and configured to permit relative movement therebetween and can comprise a slip joint 286. The slip joint 286 can permit the intermediate firing shaft portion 222 of the firing drive 220 to be moved to articulate the end effector 300 without moving, or at least substantially moving, the knife bar 280. Once the end effector 300 has been suitably oriented, the intermediate firing shaft portion 222 can be advanced distally until a proximal sidewall of the longitudinal slot 223 comes into contact with the tab 284 in order to advance the knife bar 280 and fire the staple cartridge positioned within the channel 302 As can be further seen in FIGS. 8 and 9, the shaft spine 210 has an elongate opening or window 213 therein to facilitate assembly and insertion of the intermediate firing shaft portion 222 into the shaft frame 210. Once the intermediate firing shaft portion 222 has been inserted therein, a top frame segment 215 may be engaged with the shaft frame 212 to enclose the intermediate firing shaft portion 222 and knife bar 280 therein. Further description of the operation of the firing member 220 may be found in U.S. patent application Ser. No. 13/803,086, now U.S. Patent Application Publication No. 2014/0263541.

Further to the above, the shaft assembly 200 can include a clutch assembly 400 which can be configured to selectively and releasably couple the articulation driver 230 to the firing member 220. In one form, the clutch assembly 400 includes a lock collar, or sleeve 402, positioned around the firing member 220 wherein the lock sleeve 402 can be rotated between an engaged position in which the lock sleeve 402 couples the articulation driver 360 to the firing member 220 and a disengaged position in which the articulation driver 360 is not operably coupled to the firing member 200. When lock sleeve 402 is in its engaged position, distal movement of the firing member 220 can move the articulation driver 360 distally and, correspondingly, proximal movement of the firing member 220 can move the articulation driver 230 proximally. When lock sleeve 402 is in its disengaged position, movement of the firing member 220 is not transmitted to the articulation driver 230 and, as a result, the firing member 220 can move independently of the articulation driver 230. In various circumstances, the articulation driver 230 can be held in position by the articulation lock 350 when the articulation driver 230 is not being moved in the proximal or distal directions by the firing member 220.

Referring primarily to FIG. 9, the lock sleeve 402 can comprise a cylindrical, or an at least substantially cylindrical, body including a longitudinal aperture 403 defined therein configured to receive the firing member 220. The lock sleeve 402 can comprise diametrically-opposed, inwardly-facing lock protrusions 404 and an outwardly-facing lock member 406. The lock protrusions 404 can be configured to be selectively engaged with the firing member 220. More particularly, when the lock sleeve 402 is in its engaged position, the lock protrusions 404 are positioned within a drive notch 224 defined in the firing member 220 such that a distal pushing force and/or a proximal pulling force can be transmitted from the firing member 220 to the lock sleeve 402. When the lock sleeve 402 is in its engaged position, the second lock member 406 is received within a drive notch 232 defined in the articulation driver 230 such that the distal pushing force and/or the proximal pulling force applied to the lock sleeve 402 can be transmitted to the articulation driver 230. In effect, the firing member 220, the lock sleeve 402, and the articulation driver 230 will move together when the lock sleeve 402 is in its engaged position. On the other hand, when the lock sleeve 402 is in its disengaged position, the lock protrusions 404 may not be positioned within the drive notch 224 of the firing member 220 and, as a result, a distal pushing force and/or a proximal pulling force may not be transmitted from the firing member 220 to the lock sleeve 402. Correspondingly, the distal pushing force and/or the proximal pulling force may not be transmitted to the articulation driver 230. In such circumstances, the firing member 220 can be slid proximally and/or distally relative to the lock sleeve 402 and the proximal articulation driver 230.

Figure 10:
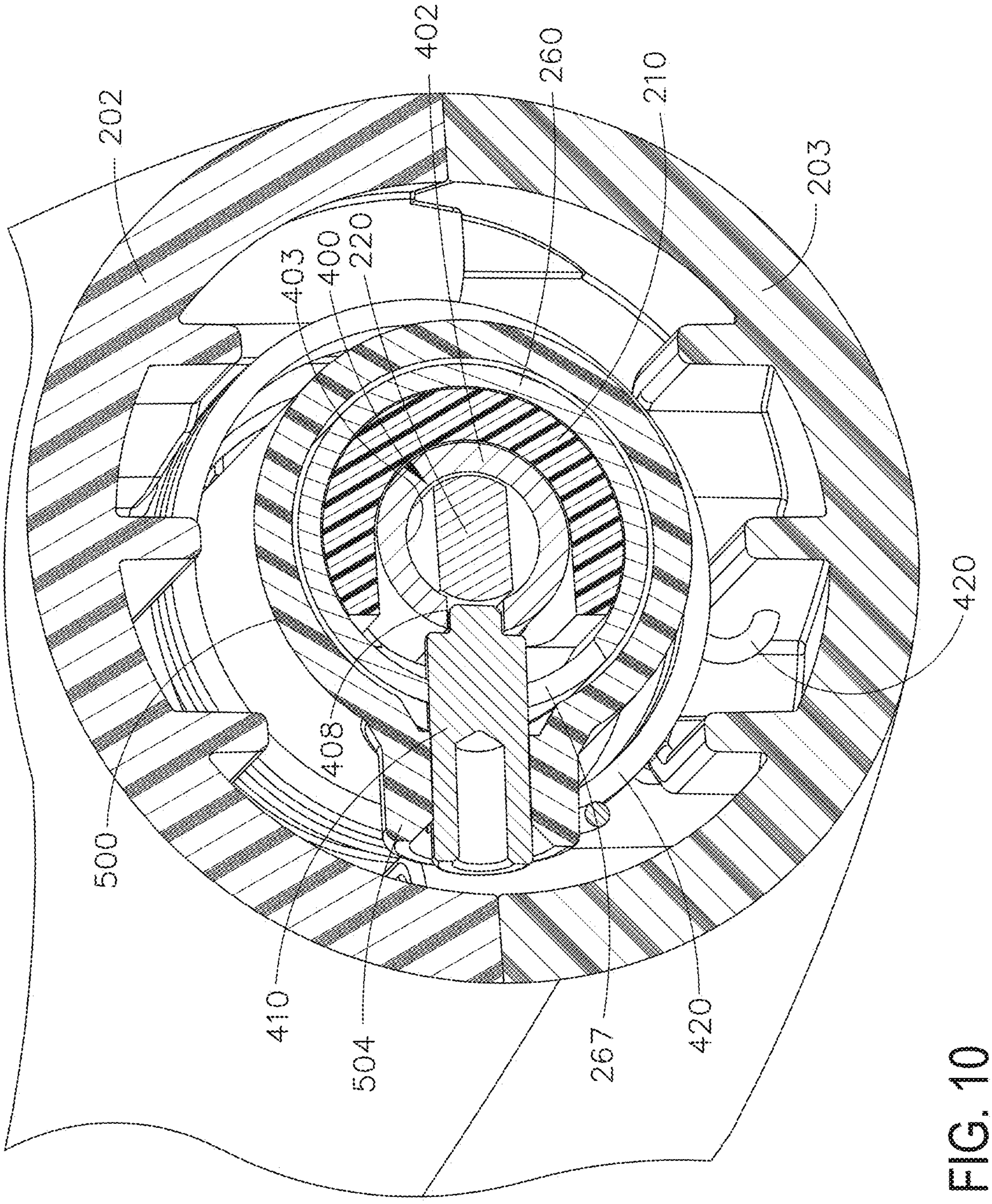
FIG. 10 is a cross-sectional view of a portion of the interchangeable shaft assembly of FIGS. 7-9.

As shown in FIGS. 8-12, the shaft assembly 200 further includes a switch drum 500 that is rotatably received on the closure tube 260. The switch drum 500 comprises a hollow shaft segment 502 that has a shaft boss 504 formed thereon for receive an outwardly protruding actuation pin 410 therein. In various circumstances, the actuation pin 410 extends through a slot 267 into a longitudinal slot 408 provided in the lock sleeve 402 to facilitate axial movement of the lock sleeve 402 when it is engaged with the articulation driver 230. A rotary torsion spring 420 is configured to engage the boss 504 on the switch drum 500 and a portion of the nozzle housing 203 as shown in FIG. 10 to apply a biasing force to the switch drum 500. The switch drum 500 can further comprise at least partially circumferential openings 506 defined therein which, referring to FIGS. 5 and 6, can be configured to receive circumferential mounts 204, 205 extending from the nozzle halves 202, 203 and permit relative rotation, but not translation, between the switch drum 500 and the proximal nozzle 201. As shown in those Figures, the mounts 204 and 205 also extend through openings 266 in the closure tube 260 to be seated in recesses 211 in the shaft spine 210. However, rotation of the nozzle 201 to a point where the mounts 204, 205 reach the end of their respective slots 506 in the switch drum 500 will result in rotation of the switch drum 500 about the shaft axis SA-SA. Rotation of the switch drum 500 will ultimately result in the rotation of eth actuation pin 410 and the lock sleeve 402 between its engaged and disengaged positions. Thus, in essence, the nozzle 201 may be employed to operably engage and disengage the articulation drive system with the firing drive system in the various manners described in further detail in U.S. patent application Ser. No. 13/803,086, now U.S. Patent Application Publication No. 2014/0263541.

As also illustrated in FIGS. 8-12, the shaft assembly 200 can comprise a slip ring assembly 600 which can be configured to conduct electrical power to and/or from the end effector 300 and/or communicate signals to and/or from the end effector 300, for example. The slip ring assembly 600 can comprise a proximal connector flange 604 mounted to a chassis flange 242 extending from the chassis 240 and a distal connector flange 601 positioned within a slot defined in the shaft housings 202, 203. The proximal connector flange 604 can comprise a first face and the distal connector flange 601 can comprise a second face which is positioned adjacent to and movable relative to the first face. The distal connector flange 601 can rotate relative to the proximal connector flange 604 about the shaft axis SA-SA. The proximal connector flange 604 can comprise a plurality of concentric, or at least substantially concentric, conductors 602 defined in the first face thereof. A connector 607 can be mounted on the proximal side of the connector flange 601 and may have a plurality of contacts (not shown) wherein each contact corresponds to and is in electrical contact with one of the conductors 602. Such an arrangement permits relative rotation between the proximal connector flange 604 and the distal connector flange 601 while maintaining electrical contact therebetween. The proximal connector flange 604 can include an electrical connector 606 which can place the conductors 602 in signal communication with a shaft circuit board 610 mounted to the shaft chassis 240, for example. In at least one instance, a wiring harness comprising a plurality of conductors can extend between the electrical connector 606 and the shaft circuit board 610. The electrical connector 606 may extend proximally through a connector opening 243 defined in the chassis mounting flange 242. See FIG. 7. U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552, is incorporated by reference in its entirety. U.S. patent application Ser. No. 13/800,025, entitled STAPLE CARTRIDGE TISSUE THICKNESS SENSOR SYSTEM, filed on Mar. 13, 2013, now U.S. Patent Application Publication No. 2014/0263551, is incorporated by reference in its entirety. Further details regarding slip ring assembly 600 may be found in U.S. patent application Ser. No. 13/803,086, now U.S. Patent Application Publication No. 2014/0263541.

Figure 11:
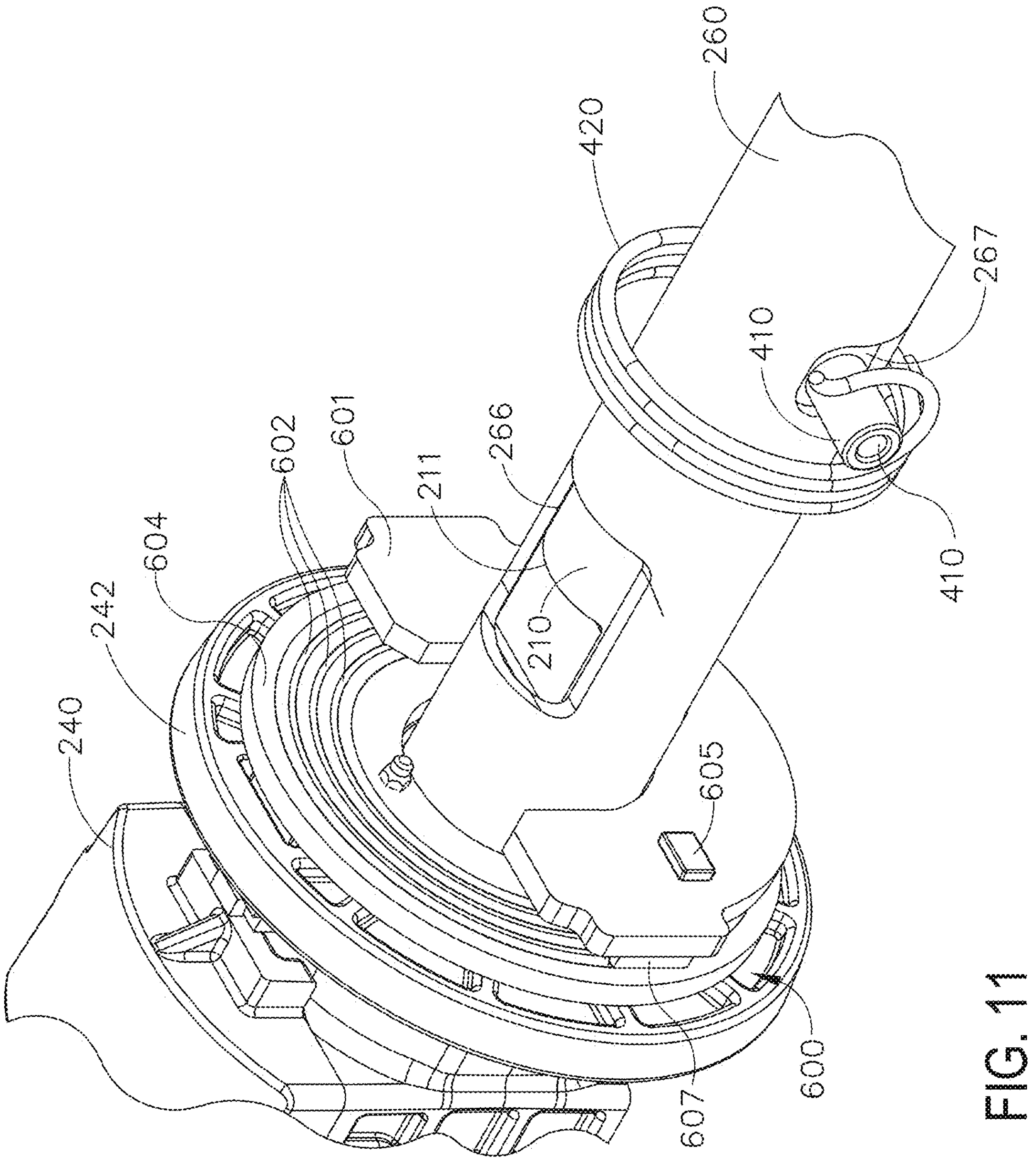
FIG. 11 is a perspective view of a portion of the shaft assembly of FIGS. 7-10 with the switch drum omitted for clarity.
Figure 12:
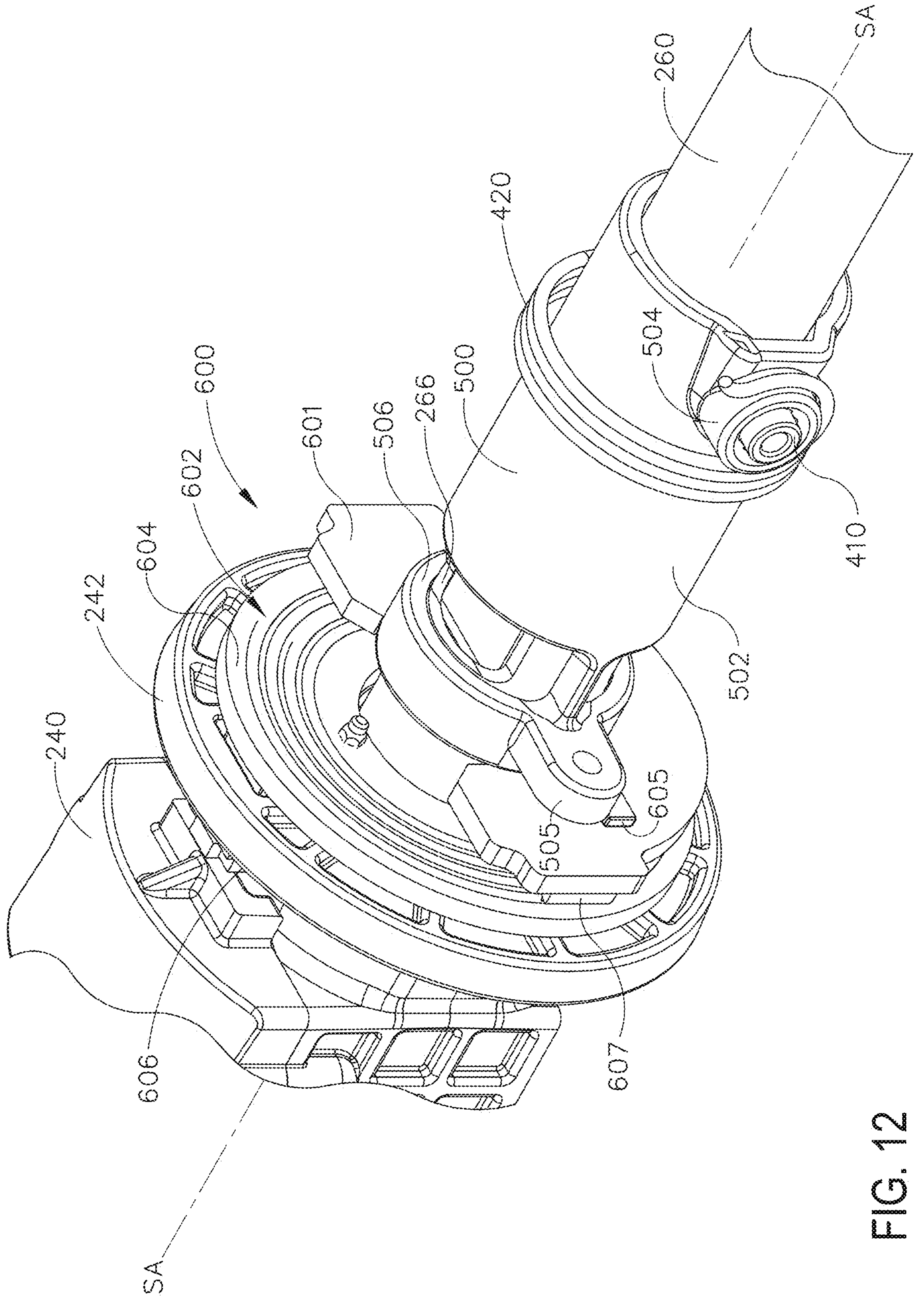
FIG. 12 is another perspective view of the portion of the interchangeable shaft assembly of FIG. 11 with the switch drum mounted thereon.

As discussed above, the shaft assembly 200 can include a proximal portion which is fixably mounted to the handle assembly 14 and a distal portion which is rotatable about a longitudinal axis. The rotatable distal shaft portion can be rotated relative to the proximal portion about the slip ring assembly 600, as discussed above. The distal connector flange 601 of the slip ring assembly 600 can be positioned within the rotatable distal shaft portion. Moreover, further to the above, the switch drum 500 can also be positioned within the rotatable distal shaft portion. When the rotatable distal shaft portion is rotated, the distal connector flange 601 and the switch drum 500 can be rotated synchronously with one another. In addition, the switch drum 500 can be rotated between a first position and a second position relative to the distal connector flange 601. When the switch drum 500 is in its first position, the articulation drive system may be operably disengaged from the firing drive system and, thus, the operation of the firing drive system may not articulate the end effector 300 of the shaft assembly 200. When the switch drum 500 is in its second position, the articulation drive system may be operably engaged with the firing drive system and, thus, the operation of the firing drive system may articulate the end effector 300 of the shaft assembly 200. When the switch drum 500 is moved between its first position and its second position, the switch drum 500 is moved relative to distal connector flange 601. In various instances, the shaft assembly 200 can comprise at least one sensor configured to detect the position of the switch drum 500. Turning now to FIGS. 11 and 12, the distal connector flange 601 can comprise a magnetic field sensor 605, for example, and the switch drum 500 can comprise a magnetic element, such as permanent magnet 505, for example. The magnetic field sensor 605 can be configured to detect the position of the permanent magnet 505. When the switch drum 500 is rotated between its first position and its second position, the permanent magnet 505 can move relative to the magnetic field sensor 605. In various instances, magnetic field sensor 605 can detect changes in a magnetic field created when the permanent magnet 505 is moved. The magnetic field sensor 605 can be in signal communication with the shaft circuit board 610 and/or the handle circuit board 100, for example. Based on the signal from the magnetic field sensor 605, a microcontroller on the shaft circuit board 610 and/or the handle circuit board 100 can determine whether the articulation drive system is engaged with or disengaged from the firing drive system.

Figure 6:
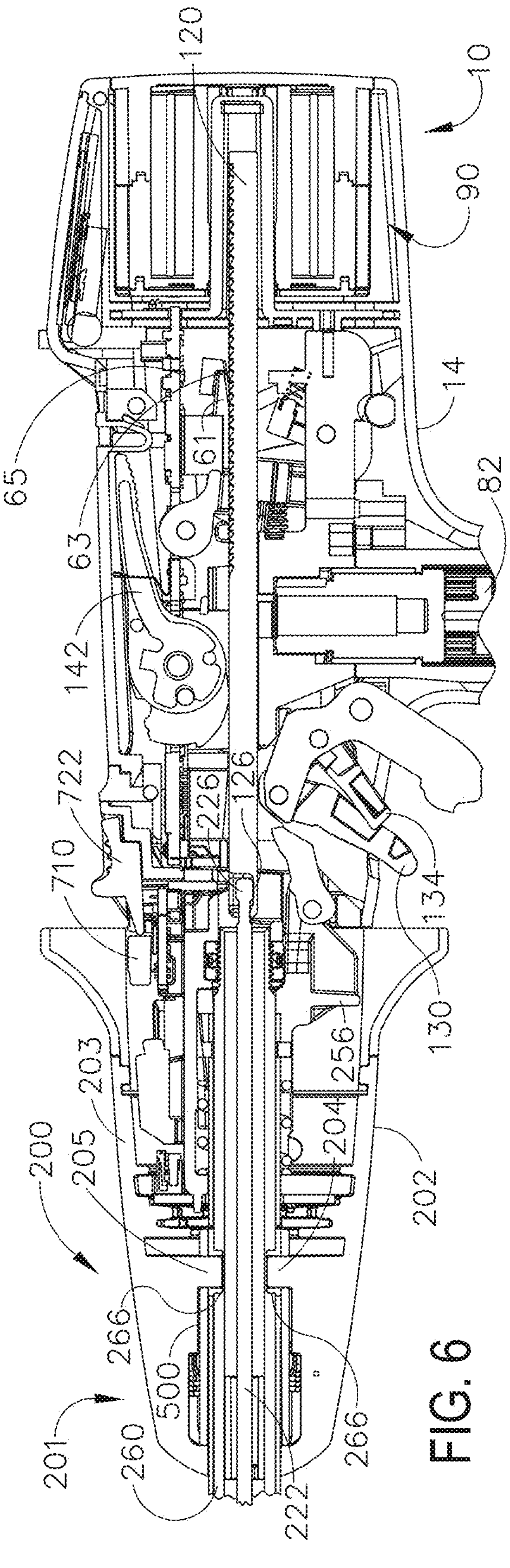
FIG. 6 is another cross-sectional view of a portion of the surgical instrument of FIG. 5 with the firing trigger in an unactuated position.

Referring again to FIGS. 3 and 7, the chassis 240 includes at least one, and preferably two, tapered attachment portions 244 formed thereon that are adapted to be received within corresponding dovetail slots 702 formed within a distal attachment flange portion 700 of the frame 20. Each dovetail slot 702 may be tapered or, stated another way, be somewhat V-shaped to seatingly receive the attachment portions 244 therein. As can be further seen in FIGS. 3 and 7, a shaft attachment lug 226 is formed on the proximal end of the intermediate firing shaft 222. As will be discussed in further detail below, when the interchangeable shaft assembly 200 is coupled to the handle assembly 14, the shaft attachment lug 226 is received in a firing shaft attachment cradle 126 formed in the distal end 125 of the longitudinal drive member 120 as shown in FIGS. 3 and 6, for example.

Various shaft assemblies employ a latch system 710 for removably coupling the shaft assembly 200 to the housing 12 and more specifically to the frame 20. As shown in FIG. 7, for example, in at least one form, the latch system 710 includes a lock member or lock yoke 712 that is movably coupled to the chassis 240. In the illustrated example, for example, the lock yoke 712 has a U-shape with two spaced downwardly extending legs 714. The legs 714 each have a pivot lug 716 formed thereon that are adapted to be received in corresponding holes 245 formed in the chassis 240. Such arrangement facilitates pivotal attachment of the lock yoke 712 to the chassis 240. The lock yoke 712 may include two proximally protruding lock lugs 714 that are configured for releasable engagement with corresponding lock detents or grooves 704 in the distal attachment flange 700 of the frame 20. See FIG. 3. In various forms, the lock yoke 712 is biased in the proximal direction by spring or biasing member (not shown). Actuation of the lock yoke 712 may be accomplished by a latch button 722 that is slidably mounted on a latch actuator assembly 720 that is mounted to the chassis 240. The latch button 722 may be biased in a proximal direction relative to the lock yoke 712. As will be discussed in further detail below, the lock yoke 712 may be moved to an unlocked position by biasing the latch button the in distal direction which also causes the lock yoke 712 to pivot out of retaining engagement with the distal attachment flange 700 of the frame 20. When the lock yoke 712 is in "retaining engagement" with the distal attachment flange 700 of the frame 20, the lock lugs 716 are retainingly seated within the corresponding lock detents or grooves 704 in the distal attachment flange 700.

When employing an interchangeable shaft assembly that includes an end effector of the type described herein that is adapted to cut and fasten tissue, as well as other types of end effectors, it may be desirable to prevent inadvertent detachment of the interchangeable shaft assembly from the housing during actuation of the end effector. For example, in use the clinician may actuate the closure trigger 32 to grasp and manipulate the target tissue into a desired position. Once the target tissue is positioned within the end effector 300 in a desired orientation, the clinician may then fully actuate the closure trigger 32 to close the anvil 306 and clamp the target tissue in position for cutting and stapling. In that instance, the first drive system 30 has been fully actuated. After the target tissue has been clamped in the end effector 300, it may be desirable to prevent the inadvertent detachment of the shaft assembly 200 from the housing 12. One form of the latch system 710 is configured to prevent such inadvertent detachment.

As can be most particularly seen in FIG. 7, the lock yoke 712 includes at least one and preferably two lock hooks 718 that are adapted to contact corresponding lock lug portions 256 that are formed on the closure shuttle 250. Referring to FIGS. 13-15, when the closure shuttle 250 is in an unactuated position (i.e., the first drive system 30 is unactuated and the anvil 306 is open), the lock yoke 712 may be pivoted in a distal direction to unlock the interchangeable shaft assembly 200 from the housing 12. When in that position, the lock hooks 718 do not contact the lock lug portions 256 on the closure shuttle 250. However, when the closure shuttle 250 is moved to an actuated position (i.e., the first drive system 30 is actuated and the anvil 306 is in the closed position), the lock yoke 712 is prevented from being pivoted to an unlocked position. See FIGS. 16-18. Stated another way, if the clinician were to attempt to pivot the lock yoke 712 to an unlocked position or, for example, the lock yoke 712 was in advertently bumped or contacted in a manner that might otherwise cause it to pivot distally, the lock hooks 718 on the lock yoke 712 will contact the lock lugs 256 on the closure shuttle 250 and prevent movement of the lock yoke 712 to an unlocked position.

Attachment of the interchangeable shaft assembly 200 to the handle assembly 14 will now be described with reference to FIG. 3. To commence the coupling process, the clinician may position the chassis 240 of the interchangeable shaft assembly 200 above or adjacent to the distal attachment flange 700 of the frame 20 such that the tapered attachment portions 244 formed on the chassis 240 are aligned with the dovetail slots 702 in the frame 20. The clinician may then move the shaft assembly 200 along an installation axis IA that is perpendicular to the shaft axis SA-SA to seat the attachment portions 244 in "operable engagement" with the corresponding dovetail receiving slots 702. In doing so, the shaft attachment lug 226 on the intermediate firing shaft 222 will also be seated in the cradle 126 in the longitudinally movable drive member 120 and the portions of pin 37 on the second closure link 38 will be seated in the corresponding hooks 252 in the closure yoke 250. As used herein, the term "operable engagement" in the context of two components means that the two components are sufficiently engaged with each other so that upon application of an actuation motion thereto, the components may carry out their intended action, function and/or procedure.

As discussed above, at least five systems of the interchangeable shaft assembly 200 can be operably coupled with at least five corresponding systems of the handle assembly 14. A first system can comprise a frame system which couples and/or aligns the frame or spine of the shaft assembly 200 with the frame 20 of the handle assembly 14. Another system can comprise a closure drive system 30 which can operably connect the closure trigger 32 of the handle assembly 14 and the closure tube 260 and the anvil 306 of the shaft assembly 200. As outlined above, the closure tube attachment yoke 250 of the shaft assembly 200 can be engaged with the pin 37 on the second closure link 38. Another system can comprise the firing drive system 80 which can operably connect the firing trigger 130 of the handle assembly 14 with the intermediate firing shaft 222 of the shaft assembly 200.

As outlined above, the shaft attachment lug 226 can be operably connected with the cradle 126 of the longitudinal drive member 120. Another system can comprise an electrical system which can signal to a controller in the handle assembly 14, such as microcontroller, for example, that a shaft assembly, such as shaft assembly 200, for example, has been operably engaged with the handle assembly 14 and/or, two, conduct power and/or communication signals between the shaft assembly 200 and the handle assembly 14. For instance, the shaft assembly 200 can include an electrical connector 1410 that is operably mounted to the shaft circuit board 610. The electrical connector 1410 is configured for mating engagement with a corresponding electrical connector 1400 on the handle control board 100. Further details regaining the circuitry and control systems may be found in U.S. patent application Ser. No. 13/803,086, the entire disclosure of which was previously incorporated by reference herein. The fifth system may consist of the latching system for releasably locking the shaft assembly 200 to the handle assembly 14.

Figure 19:
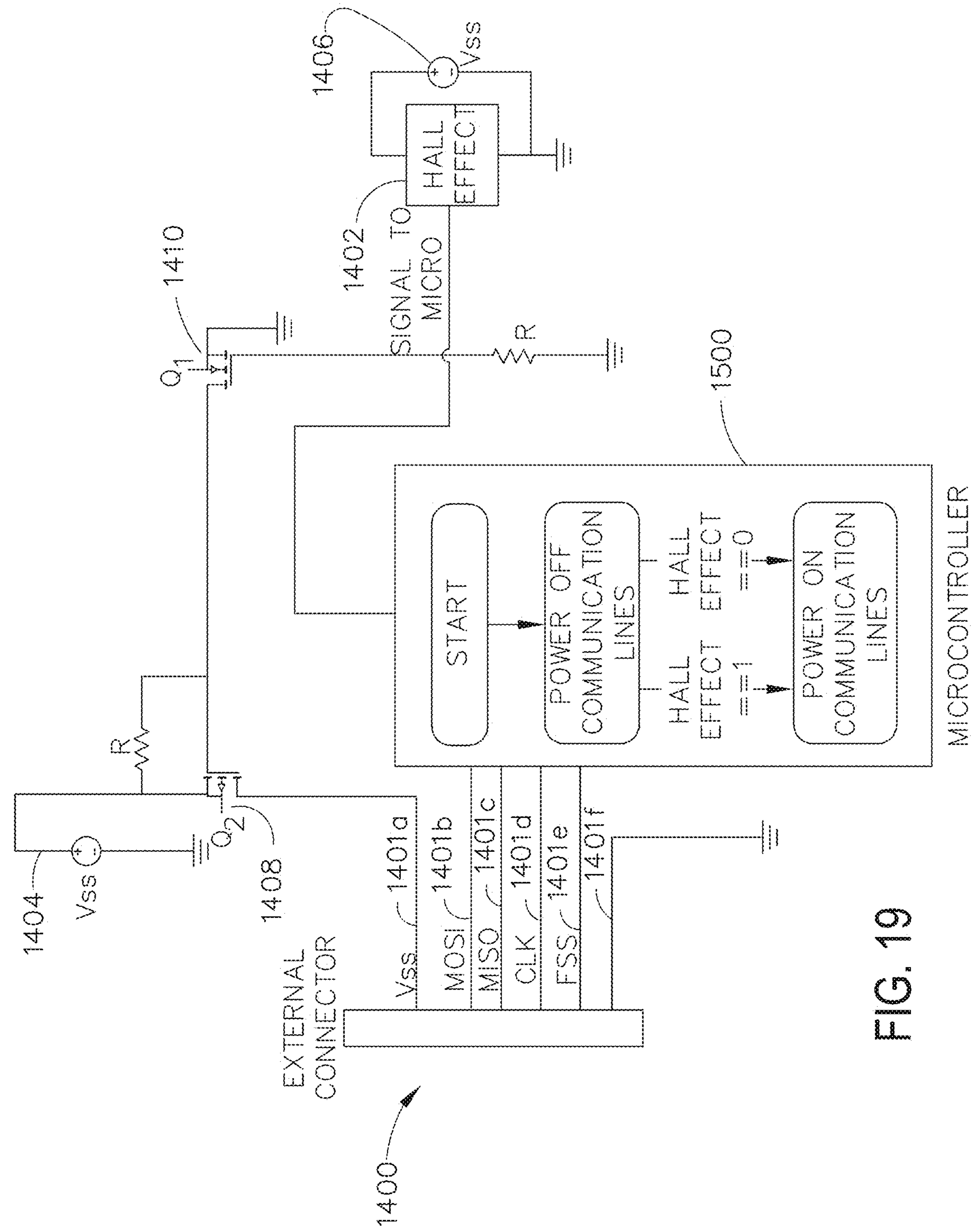
FIG. 19 is a schematic of a system for powering down an electrical connector of a surgical instrument handle when a shaft assembly is not coupled thereto.

Referring again to FIGS. 2 and 3, the handle assembly 14 can include an electrical connector 1400 comprising a plurality of electrical contacts. Turning now to FIG. 19, the electrical connector 1400 can comprise a first contact 1401*a*, a second contact 1401*b*, a third contact 1401*c*, a fourth contact 1401*d*, a fifth contact 1401*e*, and a sixth contact 1401*f*, for example. While the illustrated example utilizes six contacts, other examples are envisioned which may utilize more than six contacts or less than six contacts.

As illustrated in FIG. 19, the first contact 1401*a* can be in electrical communication with a transistor 1408, contacts 1401*b*-1401*e* can be in electrical communication with a microcontroller 1500, and the sixth contact 1401*f* can be in electrical communication with a ground. In certain circumstances, one or more of the electrical contacts 1401*b*-1401*e* may be in electrical communication with one or more output channels of the microcontroller 1500 and can be energized, or have a voltage potential applied thereto, when the handle 1042 is in a powered state. In some circumstances, one or more of the electrical contacts 1401*b*-1401*e* may be in electrical communication with one or more input channels of the microcontroller 1500 and, when the handle assembly 14 is in a powered state, the microcontroller 1500 can be configured to detect when a voltage potential is applied to such electrical contacts. When a shaft assembly, such as shaft assembly 200, for example, is assembled to the handle assembly 14, the electrical contacts 1401*a*-1401*f* may not communicate with each other. When a shaft assembly is not assembled to the handle assembly 14, however, the electrical contacts 1401*a*-1401*f* of the electrical connector 1400 may be exposed and, in some circumstances, one or more of the contacts 1401*a*-1401*f* may be accidentally placed in electrical communication with each other. Such circumstances can arise when one or more of the contacts 1401*a*-1401*f* come into contact with an electrically conductive material, for example. When this occurs, the microcontroller 1500 can receive an erroneous input and/or the shaft assembly 200 can receive an erroneous output, for example. To address this issue, in various circumstances, the handle assembly 14 may be unpowered when a shaft assembly, such as shaft assembly 200, for example, is not attached to the handle assembly 14.

In other circumstances, the handle 1042 can be powered when a shaft assembly, such as shaft assembly 200, for example, is not attached thereto. In such circumstances, the microcontroller 1500 can be configured to ignore inputs, or voltage potentials, applied to the contacts in electrical communication with the microcontroller 1500, i.e., contacts 1401*b*-1401*e*, for example, until a shaft assembly is attached to the handle assembly 14. Even though the microcontroller 1500 may be supplied with power to operate other functionalities of the handle assembly 14 in such circumstances, the handle assembly 14 may be in a powered-down state. In a way, the electrical connector 1400 may be in a powered-down state as voltage potentials applied to the electrical contacts 1401*b*-1401*e* may not affect the operation of the handle assembly 14. The reader will appreciate that, even though contacts 1401*b*-1401*e* may be in a powered-down state, the electrical contacts 1401*a* and 1401*f*, which are not in electrical communication with the microcontroller 1500, may or may not be in a powered-down state. For instance, sixth contact 1401*f* may remain in electrical communication with a ground regardless of whether the handle assembly 14 is in a powered-up or a powered-down state.

Furthermore, the transistor 1408, and/or any other suitable arrangement of transistors, such as transistor 1410, for example, and/or switches may be configured to control the supply of power from a power source 1404, such as a battery 90 within the handle assembly 14, for example, to the first electrical contact 1401*a* regardless of whether the handle assembly 14 is in a powered-up or a powered-down state. In various circumstances, the shaft assembly 200, for example, can be configured to change the state of the transistor 1408 when the shaft assembly 200 is engaged with the handle assembly 14. In certain circumstances, further to the below, a magnetic field sensor 1402 can be configured to switch the state of transistor 1410 which, as a result, can switch the state of transistor 1408 and ultimately supply power from power source 1404 to first contact 1401*a*. In this way, both the power circuits and the signal circuits to the connector 1400 can be powered down when a shaft assembly is not installed to the handle assembly 14 and powered up when a shaft assembly is installed to the handle assembly 14.

In various circumstances, referring again to FIG. 19, the handle assembly 14 can include the magnetic field sensor 1402, for example, which can be configured to detect a detectable element, such as a magnetic element 1407 (FIG. 3), for example, on a shaft assembly, such as shaft assembly 200, for example, when the shaft assembly is coupled to the handle assembly 14. The magnetic field sensor 1402 can be powered by a power source 1406, such as a battery, for example, which can, in effect, amplify the detection signal of the magnetic field sensor 1402 and communicate with an input channel of the microcontroller 1500 via the circuit illustrated in FIG. 19. Once the microcontroller 1500 has a received an input indicating that a shaft assembly has been at least partially coupled to the handle assembly 14, and that, as a result, the electrical contacts 1401*a*-1401*f* are no longer exposed, the microcontroller 1500 can enter into its normal, or powered-up, operating state. In such an operating state, the microcontroller 1500 will evaluate the signals transmitted to one or more of the contacts 1401*b*-1401*e* from the shaft assembly and/or transmit signals to the shaft assembly through one or more of the contacts 1401*b*-1401*e* in normal use thereof. In various circumstances, the shaft assembly 200 may have to be fully seated before the magnetic field sensor 1402 can detect the magnetic element 1407. While a magnetic field sensor 1402 can be utilized to detect the presence of the shaft assembly 200, any suitable system of sensors and/or switches can be utilized to detect whether a shaft assembly has been assembled to the handle assembly 14, for example. In this way, further to the above, both the power circuits and the signal circuits to the connector 1400 can be powered down when a shaft assembly is not installed to the handle assembly 14 and powered up when a shaft assembly is installed to the handle assembly 14.

In various examples, as may be used throughout the present disclosure, any suitable magnetic field sensor may be employed to detect whether a shaft assembly has been assembled to the handle assembly 14, for example. For example, the technologies used for magnetic field sensing include Hall effect sensor, search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

Referring to FIG. 19, the microcontroller 1500 may generally comprise a microprocessor ("processor") and one or more memory units operationally coupled to the processor. By executing instruction code stored in the memory, the processor may control various components of the surgical instrument, such as the motor, various drive systems, and/or a user display, for example. The microcontroller 1500 may be implemented using integrated and/or discrete hardware elements, software elements, and/or a combination of both. Examples of integrated hardware elements may include processors, microprocessors, microcontrollers, integrated circuits, application specific integrated circuits (ASIC), programmable logic devices (PLD), digital signal processors (DSP), field programmable gate arrays (FPGA), logic gates, registers, semiconductor devices, chips, microchips, chip sets, microcontrollers, system-on-chip (SoC), and/or system-in-package (SIP). Examples of discrete hardware elements may include circuits and/or circuit elements such as logic gates, field effect transistors, bipolar transistors, resistors, capacitors, inductors, and/or relays. In certain instances, the microcontroller 1500 may include a hybrid circuit comprising discrete and integrated circuit elements or components on one or more substrates, for example.

Referring to FIG. 19, the microcontroller 1500 may be an LM 4F230H5QR, available from Texas Instruments, for example. In certain instances, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available. Other microcontrollers may be readily substituted for use with the present disclosure. Accordingly, the present disclosure should not be limited in this context.

As discussed above, the handle assembly 14 and/or the shaft assembly 200 can include systems and configurations configured to prevent, or at least reduce the possibility of, the contacts of the handle electrical connector 1400 and/or the contacts of the shaft electrical connector 1410 from becoming shorted out when the shaft assembly 200 is not assembled, or completely assembled, to the handle assembly 14. Referring to FIG. 3, the handle electrical connector 1400 can be at least partially recessed within a cavity 1409 defined in the handle frame 20. The six contacts 1401*a*-1401*f* of the electrical connector 1400 can be completely recessed within the cavity 1409. Such arrangements can reduce the possibility of an object accidentally contacting one or more of the contacts 1401*a*-1401*f*. Similarly, the shaft electrical connector 1410 can be positioned within a recess defined in the shaft chassis 240 which can reduce the possibility of an object accidentally contacting one or more of the contacts 1411*a*-1411*f* of the shaft electrical connector 1410. With regard to the particular example depicted in FIG. 3, the shaft contacts 1411*a*-1411*f* can comprise male contacts. In at least one example, each shaft contact 1411*a*-1411*f* can comprise a flexible projection extending therefrom which can be configured to engage a corresponding handle contact 1401*a*-1401*f*, for example. The handle contacts 1401*a*-1401*f* can comprise female contacts. In at least one example, each handle contact 1401*a*-1401*f* can comprise a flat surface, for example, against which the male shaft contacts 1401*a*-1401*f* can wipe, or slide, against and maintain an electrically conductive interface therebetween. In various instances, the direction in which the shaft assembly 200 is assembled to the handle assembly 14 can be parallel to, or at least substantially parallel to, the handle contacts 1401*a*-1401*f* such that the shaft contacts 1411*a*-1411*f* slide against the handle contacts 1401*a*-1401*f* when the shaft assembly 200 is assembled to the handle assembly 14. In various alternative examples, the handle contacts 1401*a*-1401*f* can comprise male contacts and the shaft contacts 1411*a*-1411*f* can comprise female contacts. In certain alternative examples, the handle contacts 1401*a*-1401*f* and the shaft contacts 1411*a*-1411*f* can comprise any suitable arrangement of contacts.

In various instances, the handle assembly 14 can comprise a connector guard configured to at least partially cover the handle electrical connector 1400 and/or a connector guard configured to at least partially cover the shaft electrical connector 1410. A connector guard can prevent, or at least reduce the possibility of, an object accidentally touching the contacts of an electrical connector when the shaft assembly is not assembled to, or only partially assembled to, the handle. A connector guard can be movable. For instance, the connector guard can be moved between a guarded position in which it at least partially guards a connector and an unguarded position in which it does not guard, or at least guards less of, the connector. In at least one example, a connector guard can be displaced as the shaft assembly is being assembled to the handle. For instance, if the handle comprises a handle connector guard, the shaft assembly can contact and displace the handle connector guard as the shaft assembly is being assembled to the handle. Similarly, if the shaft assembly comprises a shaft connector guard, the handle can contact and displace the shaft connector guard as the shaft assembly is being assembled to the handle. In various instances, a connector guard can comprise a door, for example. In at least one instance, the door can comprise a beveled surface which, when contacted by the handle or shaft, can facilitate the displacement of the door in a certain direction. In various instances, the connector guard can be translated and/or rotated, for example. In certain instances, a connector guard can comprise at least one film which covers the contacts of an electrical connector. When the shaft assembly is assembled to the handle, the film can become ruptured. In at least one instance, the male contacts of a connector can penetrate the film before engaging the corresponding contacts positioned underneath the film.

As described above, the surgical instrument can include a system which can selectively power-up, or activate, the contacts of an electrical connector, such as the electrical connector 1400, for example. In various instances, the contacts can be transitioned between an unactivated condition and an activated condition. In certain instances, the contacts can be transitioned between a monitored condition, a deactivated condition, and an activated condition. For instance, the microcontroller 1500, for example, can monitor the contacts 1401*a*-1401*f* when a shaft assembly has not been assembled to the handle assembly 14 to determine whether one or more of the contacts 1401*a*-1401*f* may have been shorted. The microcontroller 1500 can be configured to apply a low voltage potential to each of the contacts 1401*a*-1401*f* and assess whether only a minimal resistance is present at each of the contacts. Such an operating state can comprise the monitored condition. In the event that the resistance detected at a contact is high, or above a threshold resistance, the microcontroller 1500 can deactivate that contact, more than one contact, or, alternatively, all of the contacts. Such an operating state can comprise the deactivated condition. If a shaft assembly is assembled to the handle assembly 14 and it is detected by the microcontroller 1500, as discussed above, the microcontroller 1500 can increase the voltage potential to the contacts 1401*a*-1401*f*. Such an operating state can comprise the activated condition.

The various shaft assemblies disclosed herein may employ sensors and various other components that require electrical communication with the controller in the housing. These shaft assemblies generally are configured to be able to rotate relative to the housing necessitating a connection that facilitates such electrical communication between two or more components that may rotate relative to each other. When employing end effectors of the types disclosed herein, the connector arrangements must be relatively robust in nature while also being somewhat compact to fit into the shaft assembly connector portion.

Figure 20:
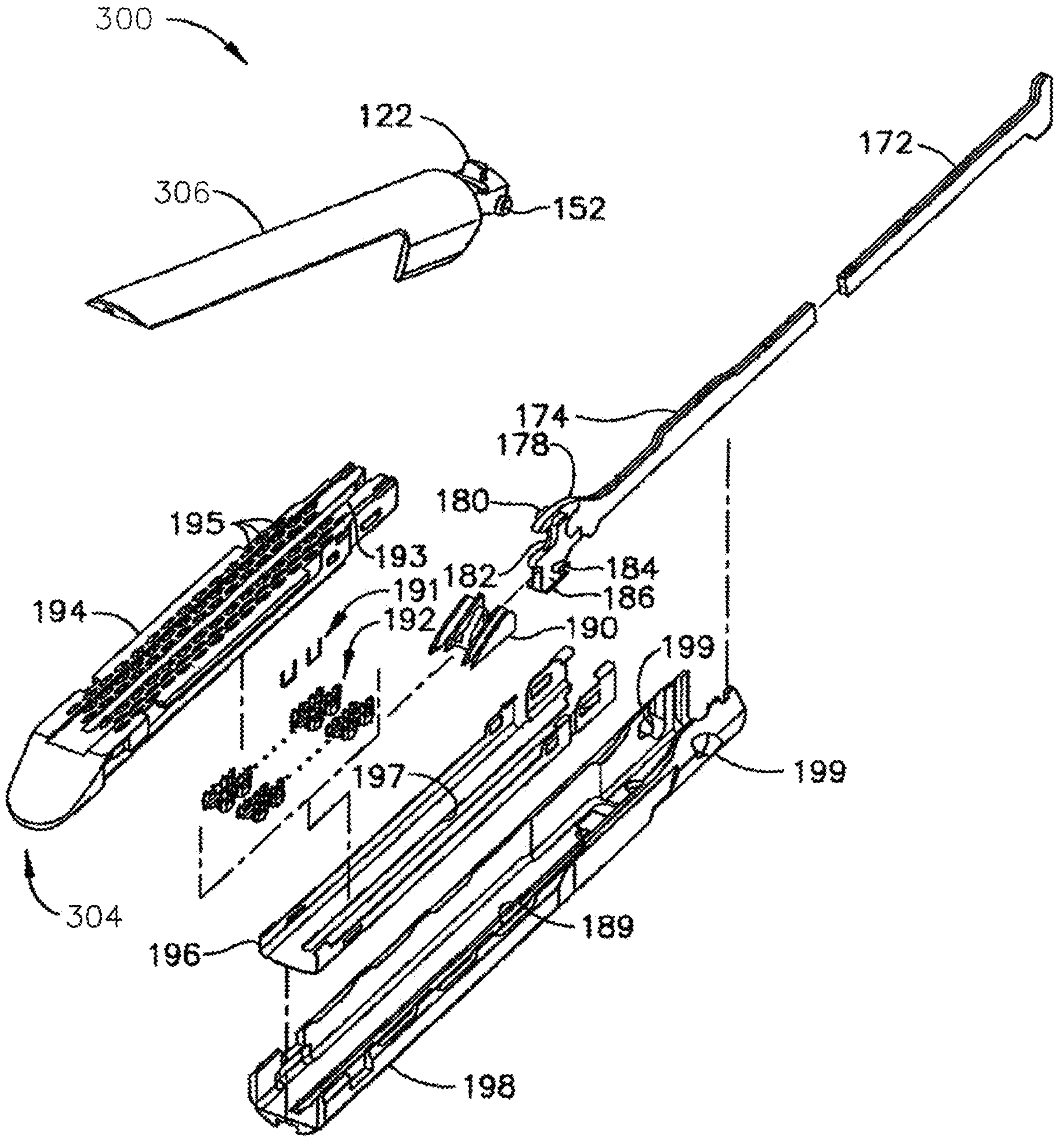
FIG. 20 is an exploded view of one aspect of an end effector of the surgical instrument of FIG. 1.

Referring to FIG. 20, a non-limiting form of the end effector 300 is illustrated. As described above, the end effector 300 may include the anvil 306 and the staple cartridge 304. In this non-limiting example, the anvil 306 is coupled to an elongate channel 198. For example, apertures 199 can be defined in the elongate channel 198 which can receive pins 152 extending from the anvil 306 and allow the anvil 306 to pivot from an open position to a closed position relative to the elongate channel 198 and staple cartridge 304. In addition, FIG. 20 shows a firing bar 172, configured to longitudinally translate into the end effector 300. The firing bar 172 may be constructed from one solid section, or in various examples, may include a laminate material comprising, for example, a stack of steel plates. A distally projecting end of the firing bar 172 can be attached to an E-beam 178 that can, among other things, assist in spacing the anvil 306 from a staple cartridge 304 positioned in the elongate channel 198 when the anvil 306 is in a closed position. The E-beam 178 can also include a sharpened cutting edge 182 which can be used to sever tissue as the E-beam 178 is advanced distally by the firing bar 172. In operation, the E-beam 178 can also actuate, or fire, the staple cartridge 304. The staple cartridge 304 can include a molded cartridge body 194 that holds a plurality of staples 191 resting upon staple drivers 192 within respective upwardly open staple cavities 195. A wedge sled 190 is driven distally by the E-beam 178, sliding upon a cartridge tray 196 that holds together the various components of the replaceable staple cartridge 304. The wedge sled 190 upwardly cams the staple drivers 192 to force out the staples 191 into deforming contact with the anvil 306 while a cutting surface 182 of the E-beam 178 severs clamped tissue.

Further to the above, the E-beam 178 can include upper pins 180 which engage the anvil 306 during firing. The E-beam 178 can further include middle pins 184 and a bottom foot 186 which can engage various portions of the cartridge body 194, cartridge tray 196 and elongate channel 198. When a staple cartridge 304 is positioned within the elongate channel 198, a slot 193 defined in the cartridge body 194 can be aligned with a slot 197 defined in the cartridge tray 196 and a slot 189 defined in the elongate channel 198. In use, the E-beam 178 can slide through the aligned slots 193, 197, and 189 wherein, as indicated in FIG. 20, the bottom foot 186 of the E-beam 178 can engage a groove running along the bottom surface of channel 198 along the length of slot 189, the middle pins 184 can engage the top surfaces of cartridge tray 196 along the length of longitudinal slot 197, and the upper pins 180 can engage the anvil 306. In such circumstances, the E-beam 178 can space, or limit the relative movement between, the anvil 306 and the staple cartridge 304 as the firing bar 172 is moved distally to fire the staples from the staple cartridge 304 and/or incise the tissue captured between the anvil 306 and the staple cartridge 304. Thereafter, the firing bar 172 and the E-beam 178 can be retracted proximally allowing the anvil 306 to be opened to release the two stapled and severed tissue portions (not shown).

Figure 21A:
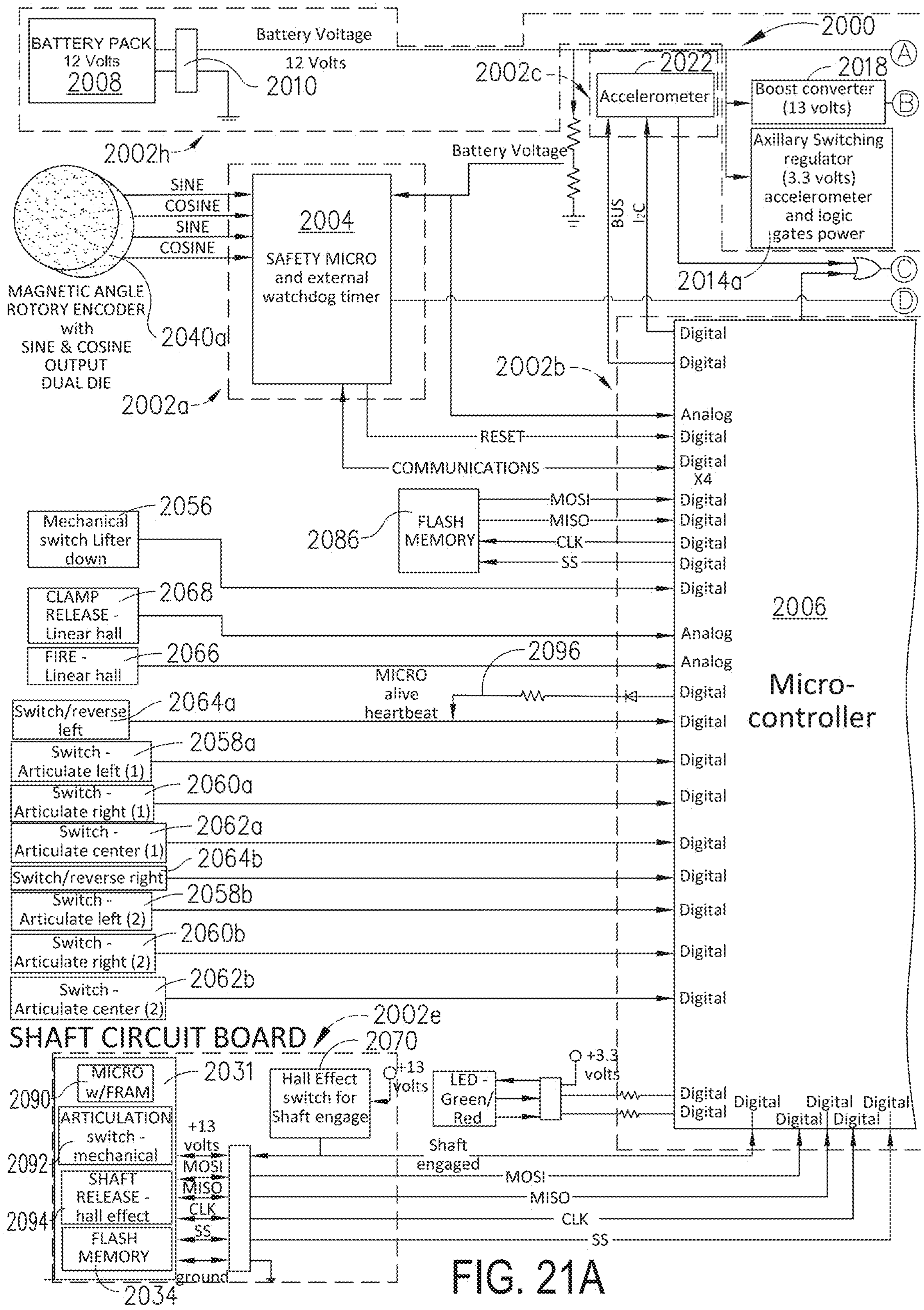
FIGS. 21A-21B is a circuit diagram of the surgical instrument of FIG. 1 spanning two drawings sheets.
Figure 21B:
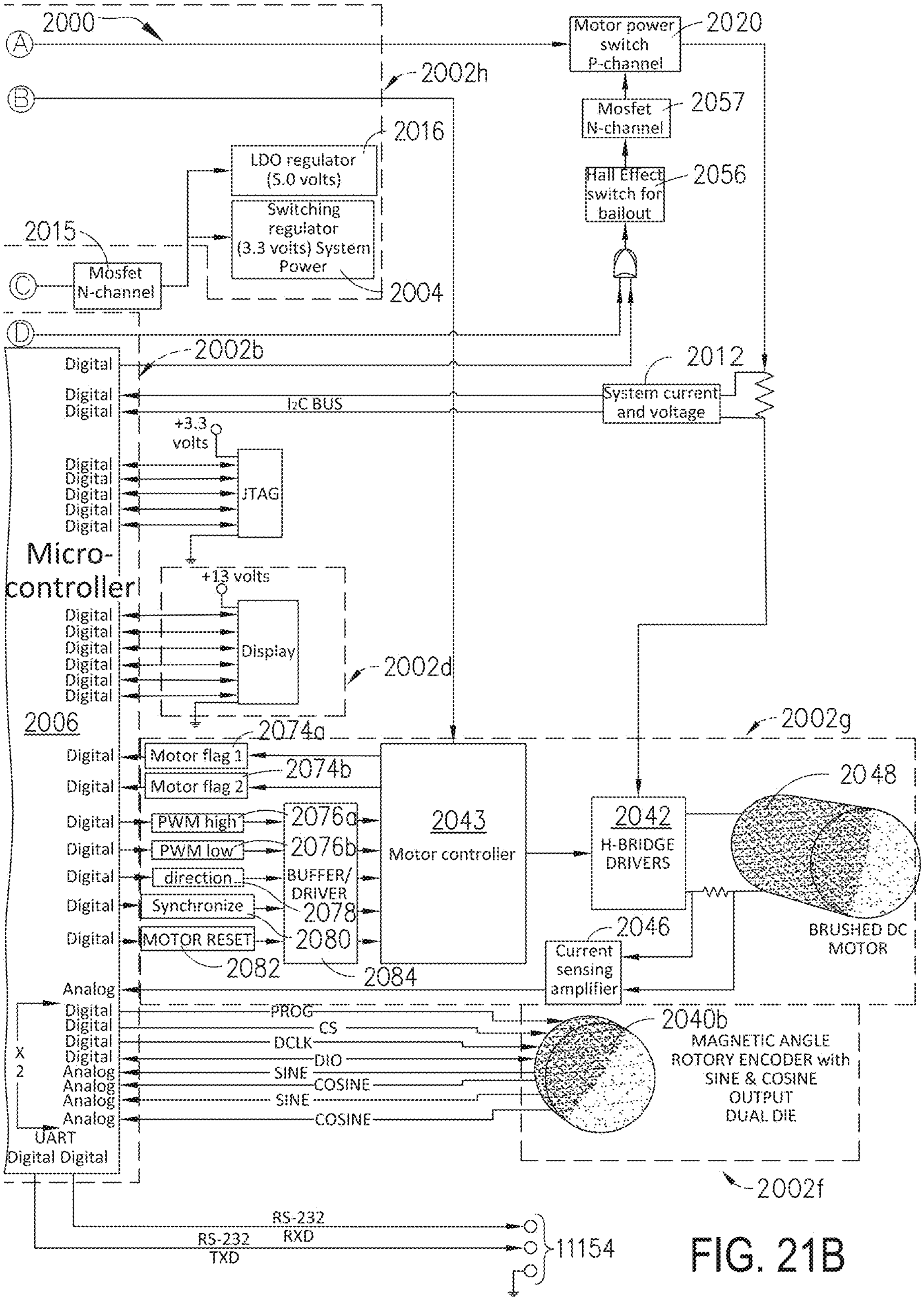

Having described a surgical instrument 10 (FIGS. 1-4) in general terms, the description now turns to a detailed description of various electrical/electronic components of the surgical instrument 10. Turning now to FIGS. 21A-21B, where one example of a segmented circuit 2000 comprising a plurality of circuit segments 2002*a*-2002*g* is illustrated. The segmented circuit 2000 comprising the plurality of circuit segments 2002*a*-2002*g* is configured to control a powered surgical instrument, such as, for example, the surgical instrument 10 illustrated in FIGS. 1-18A, without limitation. The plurality of circuit segments 2002*a*-2002*g* is configured to control one or more operations of the powered surgical instrument 10. A safety processor segment 2002*a* (Segment 1) comprises a safety processor 2004. A primary processor segment 2002*b* (Segment 2) comprises a primary processor 2006. The safety processor 2004 and/or the primary processor 2006 are configured to interact with one or more additional circuit segments 2002*c*-2002*g* to control operation of the powered surgical instrument 10. The primary processor 2006 comprises a plurality of inputs coupled to, for example, one or more circuit segments 2002*c*-2002*g*, a battery 2008, and/or a plurality of switches 2058*a*-2070. The segmented circuit 2000 may be implemented by any suitable circuit, such as, for example, a printed circuit board assembly (PCBA) within the powered surgical instrument 10. It should be understood that the term processor as used herein includes any microprocessor, microcontroller, or other basic computing device that incorporates the functions of a computer's central processing unit (CPU) on an integrated circuit or at most a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one aspect, the main processor 2006 may be any single core or multicore processor such as those known under the trade name ARM Cortex by Texas Instruments. In one example, the safety processor 2004 may be a safety microcontroller platform comprising two microcontroller-based families such as TMS570 and RM4x known under the trade name Hercules ARM Cortex R4, also by Texas Instruments. Nevertheless, other suitable substitutes for microcontrollers and safety processor may be employed, without limitation. In one example, the safety processor 2004 may be configured specifically for IEC 61508 and ISO 26262 safety critical applications, among others, to provide advanced integrated safety features while delivering scalable performance, connectivity, and memory options.

In certain instances, the main processor 2006 may be an LM 4F230H5QR, available from Texas Instruments, for example. In at least one example, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle SRAM, internal ROM loaded with StellarisWare® software, 2 KB EEPROM, one or more PWM modules, one or more QEI analog, one or more 12-bit ADC with 12 analog input channels, among other features that are readily available for the product datasheet. Other processors may be readily substituted and, accordingly, the present disclosure should not be limited in this context.

In one aspect, the segmented circuit 2000 comprises an acceleration segment 2002*c* (Segment 3). The acceleration segment 2002*c* comprises an acceleration sensor 2022. The acceleration sensor 2022 may comprise, for example, an accelerometer. The acceleration sensor 2022 is configured to detect movement or acceleration of the powered surgical instrument 10. In some examples, input from the acceleration sensor 2022 is used, for example, to transition to and from a sleep mode, identify an orientation of the powered surgical instrument, and/or identify when the surgical instrument has been dropped. In some examples, the acceleration segment 2002*c* is coupled to the safety processor 2004 and/or the primary processor 2006.

In one aspect, the segmented circuit 2000 comprises a display segment 2002*d* (Segment 4). The display segment 2002*d* comprises a display connector 2024 coupled to the primary processor 2006. The display connector 2024 couples the primary processor 2006 to a display 2028 through one or more display driver integrated circuits 2026. The display driver integrated circuits 2026 may be integrated with the display 2028 and/or may be located separately from the display 2028. The display 2028 may comprise any suitable display, such as, for example, an organic light-emitting diode (OLED) display, a liquid-crystal display (LCD), and/or any other suitable display. In some examples, the display segment 2002*d* is coupled to the safety processor 2004.

In some aspects, the segmented circuit 2000 comprises a shaft segment 2002*e* (Segment 5). The shaft segment 2002*e* comprises one or more controls for a shaft 2004 coupled to the surgical instrument 10 and/or one or more controls for an end effector 2006 coupled to the shaft 2004. The shaft segment 2002*e* comprises a shaft connector 2030 configured to couple the primary processor 2006 to a shaft PCBA 2031. The shaft PCBA 2031 comprises a first articulation switch 2036, a second articulation switch 2032, and a shaft PCBA EEPROM 2034. In some examples, the shaft PCBA EEPROM 2034 comprises one or more parameters, routines, and/or programs specific to the shaft 2004 and/or the shaft PCBA 2031. The shaft PCBA 2031 may be coupled to the shaft 2004 and/or integral with the surgical instrument 10. In some examples, the shaft segment 2002*e* comprises a second shaft EEPROM 2038. The second shaft EEPROM 2038 comprises a plurality of algorithms, routines, parameters, and/or other data corresponding to one or more shafts 2004 and/or end effectors 2006 which may be interfaced with the powered surgical instrument 10.

In some aspects, the segmented circuit 2000 comprises a position encoder segment 2002*f* (Segment 6). The position encoder segment 2002*f* comprises one or more magnetic rotary position encoders 2040*a*-2040*b*. The one or more magnetic rotary position encoders 2040*a*-2040*b* are configured to identify the rotational position of a motor 2048, a shaft 2004, and/or an end effector 2006 of the surgical instrument 10. In some examples, the magnetic rotary position encoders 2040*a*-2040*b* may be coupled to the safety processor 2004 and/or the primary processor 2006.

In some aspects, the segmented circuit 2000 comprises a motor segment 2002*g* (Segment 7). The motor segment 2002*g* comprises a motor 2048 configured to control one or more movements of the powered surgical instrument 10. The motor 2048 is coupled to the primary processor 2006 by an H-Bridge driver 2042 and one or more H-bridge field-effect transistors (FETs) 2044. The H-bridge FETs 2044 are coupled to the safety processor 2004. A motor current sensor 2046 is coupled in series with the motor 2048 to measure the current draw of the motor 2048. The motor current sensor 2046 is in signal communication with the primary processor 2006 and/or the safety processor 2004. In some examples, the motor 2048 is coupled to a motor electromagnetic interference (EMI) filter 2050.

In some aspects, the segmented circuit 2000 comprises a power segment 2002*h* (Segment 8). A battery 2008 is coupled to the safety processor 2004, the primary processor 2006, and one or more of the additional circuit segments 2002*c*-2002*g*. The battery 2008 is coupled to the segmented circuit 2000 by a battery connector 2010 and a current sensor 2012. The current sensor 2012 is configured to measure the total current draw of the segmented circuit 2000. In some examples, one or more voltage converters 2014*a*, 2014*b*, 2016 are configured to provide predetermined voltage values to one or more circuit segments 2002*a*-2002*g*. For example, in some examples, the segmented circuit 2000 may comprise 3.3V voltage converters 2014*a*-2014*b* and/or 5V voltage converters 2016. A boost converter 2018 is configured to provide a boost voltage up to a predetermined amount, such as, for example, up to 13V. The boost converter 2018 is configured to provide additional voltage and/or current during power intensive operations and prevent brownout or low-power conditions.

In some aspects, the safety segment 2002*a* comprises a motor power interrupt 2020. The motor power interrupt 2020 is coupled between the power segment 2002*h* and the motor segment 2002*g*. The safety segment 2002*a* is configured to interrupt power to the motor segment 2002*g* when an error or fault condition is detected by the safety processor 2004 and/or the primary processor 2006 as discussed in more detail herein. Although the circuit segments 2002*a*-2002*g* are illustrated with all components of the circuit segments 2002*a*-2002*h* located in physical proximity, one skilled in the art will recognize that a circuit segment 2002*a*-2002*h* may comprise components physically and/or electrically separate from other components of the same circuit segment 2002*a*-2002*g*. In some examples, one or more components may be shared between two or more circuit segments 2002*a*-2002*g*.

In some aspects, a plurality of switches 2056-2070 are coupled to the safety processor 2004 and/or the primary processor 2006. The plurality of switches 2056-2070 may be configured to control one or more operations of the surgical instrument 10, control one or more operations of the segmented circuit 2000, and/or indicate a status of the surgical instrument 10. For example, a bail-out door switch 2056 is configured to indicate the status of a bail-out door. A plurality of articulation switches, such as, for example, a left side articulation left switch 2058*a*, a left side articulation right switch 2060*a*, a left side articulation center switch 2062*a*, a right side articulation left switch 2058*b*, a right side articulation right switch 2060*b*, and a right side articulation center switch 2062*b* are configured to control articulation of a shaft 2004 and/or an end effector 2006. A left side reverse switch 2064*a* and a right side reverse switch 2064*b* are coupled to the primary processor 2006. In some examples, the left side switches comprising the left side articulation left switch 2058*a*, the left side articulation right switch 2060*a*, the left side articulation center switch 2062*a*, and the left side reverse switch 2064*a* are coupled to the primary processor 2006 by a left flex connector 2072*a*. The right side switches comprising the right side articulation left switch

2058*b*, the right side articulation right switch 2060*b*, the right side articulation center switch 2062*b*, and the right side reverse switch 2064*b* are coupled to the primary processor 2006 by a right flex connector 2072*b*. In some examples, a firing switch 2066, a clamp release switch 2068, and a shaft engaged switch 2070 are coupled to the primary processor 2006.

In some aspects, the plurality of switches 2056-2070 may comprise, for example, a plurality of handle controls mounted to a handle of the surgical instrument 10, a plurality of indicator switches, and/or any combination thereof. In various examples, the plurality of switches 2056-2070 allow a surgeon to manipulate the surgical instrument, provide feedback to the segmented circuit 2000 regarding the position and/or operation of the surgical instrument, and/or indicate unsafe operation of the surgical instrument 10. In some examples, additional or fewer switches may be coupled to the segmented circuit 2000, one or more of the switches 2056-2070 may be combined into a single switch, and/or expanded to multiple switches. For example, in one example, one or more of the left side and/or right side articulation switches 2058*a*-2064*b* may be combined into a single multi-position switch.

In one aspect, the safety processor 2004 is configured to implement a watchdog function, among other safety operations. The safety processor 2004 and the primary processor 2006 of the segmented circuit 2000 are in signal communication. A microprocessor alive heartbeat signal is provided at output 2096. The acceleration segment 2002*c* comprises an accelerometer 2022 configured to monitor movement of the surgical instrument 10. In various examples, the accelerometer 2022 may be a single, double, or triple axis accelerometer. The accelerometer 2022 may be employed to measures proper acceleration that is not necessarily the coordinate acceleration (rate of change of velocity). Instead, the accelerometer sees the acceleration associated with the phenomenon of weight experienced by a test mass at rest in the frame of reference of the accelerometer 2022. For example, the accelerometer 2022 at rest on the surface of the earth will measure an acceleration $g=9.8\ m/s^2$ (gravity) straight upwards, due to its weight. Another type of acceleration that accelerometer 2022 can measure is g-force acceleration. In various other examples, the accelerometer 2022 may comprise a single, double, or triple axis accelerometer. Further, the acceleration segment 2002*c* may comprise one or more inertial sensors to detect and measure acceleration, tilt, shock, vibration, rotation, and multiple degrees-of-freedom (DoF). A suitable inertial sensor may comprise an accelerometer (single, double, or triple axis), a magnetometer to measure a magnetic field in space such as the earth's magnetic field, and/or a gyroscope to measure angular velocity.

In one aspect, the safety processor 2004 is configured to implement a watchdog function with respect to one or more circuit segments 2002*c*-2002*h*, such as, for example, the motor segment 2002*g*. In this regards, the safety processor 2004 employs the watchdog function to detect and recover from malfunctions of the primary processor 2006. During normal operation, the safety processor 2004 monitors for hardware faults or program errors of the primary processor 2004 and to initiate corrective action or actions. The corrective actions may include placing the primary processor 2006 in a safe state and restoring normal system operation. In one example, the safety processor 2004 is coupled to at least a first sensor. The first sensor measures a first property of the surgical instrument 10 (FIGS. 1-4). In some examples, the safety processor 2004 is configured to compare the measured property of the surgical instrument 10 to a predetermined value. For example, in one example, a motor sensor 2040*a* is coupled to the safety processor 2004. The motor sensor 2040*a* provides motor speed and position information to the safety processor 2004. The safety processor 2004 monitors the motor sensor 2040*a* and compares the value to a maximum speed and/or position value and prevents operation of the motor 2048 above the predetermined values. In some examples, the predetermined values are calculated based on real-time speed and/or position of the motor 2048, calculated from values supplied by a second motor sensor 2040*b* in communication with the primary processor 2006, and/or provided to the safety processor 2004 from, for example, a memory module coupled to the safety processor 2004.

In some aspects, a second sensor is coupled to the primary processor 2006. The second sensor is configured to measure the first physical property. The safety processor 2004 and the primary processor 2006 are configured to provide a signal indicative of the value of the first sensor and the second sensor respectively. When either the safety processor 2004 or the primary processor 2006 indicates a value outside of an acceptable range, the segmented circuit 2000 prevents operation of at least one of the circuit segments 2002*c*-2002*h*, such as, for example, the motor segment 2002*g*. For example, in the example illustrated in FIGS. 21A-21B, the safety processor 2004 is coupled to a first motor position sensor 2040*a* and the primary processor 2006 is coupled to a second motor position sensor 2040*b*. The motor position sensors 2040*a*, 2040*b* may comprise any suitable motor position sensor, such as, for example, a magnetic angle rotary input comprising a sine and cosine output. The motor position sensors 2040*a*, 2040*b* provide respective signals to the safety processor 2004 and the primary processor 2006 indicative of the position of the motor 2048.

The safety processor 2004 and the primary processor 2006 generate an activation signal when the values of the first motor sensor 2040*a* and the second motor sensor 2040*b* are within a predetermined range. When either the primary processor 2006 or the safety processor 2004 to detect a value outside of the predetermined range, the activation signal is terminated and operation of at least one circuit segment 2002*c*-2002*h*, such as, for example, the motor segment 2002*g*, is interrupted and/or prevented. For example, in some examples, the activation signal from the primary processor 2006 and the activation signal from the safety processor 2004 are coupled to an AND gate. The AND gate is coupled to a motor power switch 2020. The AND gate maintains the motor power switch 2020 in a closed, or on, position when the activation signal from both the safety processor 2004 and the primary processor 2006 are high, indicating a value of the motor sensors 2040*a*, 2040*b* within the predetermined range. When either of the motor sensors 2040*a*, 2040*b* detect a value outside of the predetermined range, the activation signal from that motor sensor 2040*a*, 2040*b* is set low, and the output of the AND gate is set low, opening the motor power switch 2020. In some examples, the value of the first sensor 2040*a* and the second sensor 2040*b* is compared, for example, by the safety processor 2004 and/or the primary processor 2006. When the values of the first sensor and the second sensor are different, the safety processor 2004 and/or the primary processor 2006 may prevent operation of the motor segment 2002*g*.

In some aspects, the safety processor 2004 receives a signal indicative of the value of the second sensor 2040*b* and compares the second sensor value to the first sensor value. For example, in one aspect, the safety processor 2004 is coupled directly to a first motor sensor 2040*a*. A second motor sensor 2040*b* is coupled to a primary processor 2006, which provides the second motor sensor 2040*b* value to the safety processor 2004, and/or coupled directly to the safety processor 2004. The safety processor 2004 compares the value of the first motor sensor 2040 to the value of the second motor sensor 2040*b*. When the safety processor 2004 detects a mismatch between the first motor sensor 2040*a* and the second motor sensor 2040*b*, the safety processor 2004 may interrupt operation of the motor segment 2002*g*, for example, by cutting power to the motor segment 2002*g*.

In some aspects, the safety processor 2004 and/or the primary processor 2006 is coupled to a first sensor 2040*a* configured to measure a first property of a surgical instrument and a second sensor 2040*b* configured to measure a second property of the surgical instrument. The first property and the second property comprise a predetermined relationship when the surgical instrument is operating normally. The safety processor 2004 monitors the first property and the second property. When a value of the first property and/or the second property inconsistent with the predetermined relationship is detected, a fault occurs. When a fault occurs, the safety processor 2004 takes at least one action, such as, for example, preventing operation of at least one of the circuit segments, executing a predetermined operation, and/or resetting the primary processor 2006. For example, the safety processor 2004 may open the motor power switch 2020 to cut power to the motor circuit segment 2002*g* when a fault is detected.

In one aspect, the safety processor 2004 is configured to execute an independent control algorithm. In operation, the safety processor 2004 monitors the segmented circuit 2000 and is configured to control and/or override signals from other circuit components, such as, for example, the primary processor 2006, independently. The safety processor 2004 may execute a preprogrammed algorithm and/or may be updated or programmed on the fly during operation based on one or more actions and/or positions of the surgical instrument 10. For example, in one example, the safety processor 2004 is reprogrammed with new parameters and/or safety algorithms each time a new shaft and/or end effector is coupled to the surgical instrument 10. In some examples, one or more safety values stored by the safety processor 2004 are duplicated by the primary processor 2006. Two-way error detection is performed to ensure values and/or parameters stored by either of the processors 2004, 2006 are correct.

In some aspects, the safety processor 2004 and the primary processor 2006 implement a redundant safety check. The safety processor 2004 and the primary processor 2006 provide periodic signals indicating normal operation. For example, during operation, the safety processor 2004 may indicate to the primary processor 2006 that the safety processor 2004 is executing code and operating normally. The primary processor 2006 may, likewise, indicate to the safety processor 2004 that the primary processor 2006 is executing code and operating normally. In some examples, communication between the safety processor 2004 and the primary processor 2006 occurs at a predetermined interval. The predetermined interval may be constant or may be variable based on the circuit state and/or operation of the surgical instrument 10.

Figure 22:
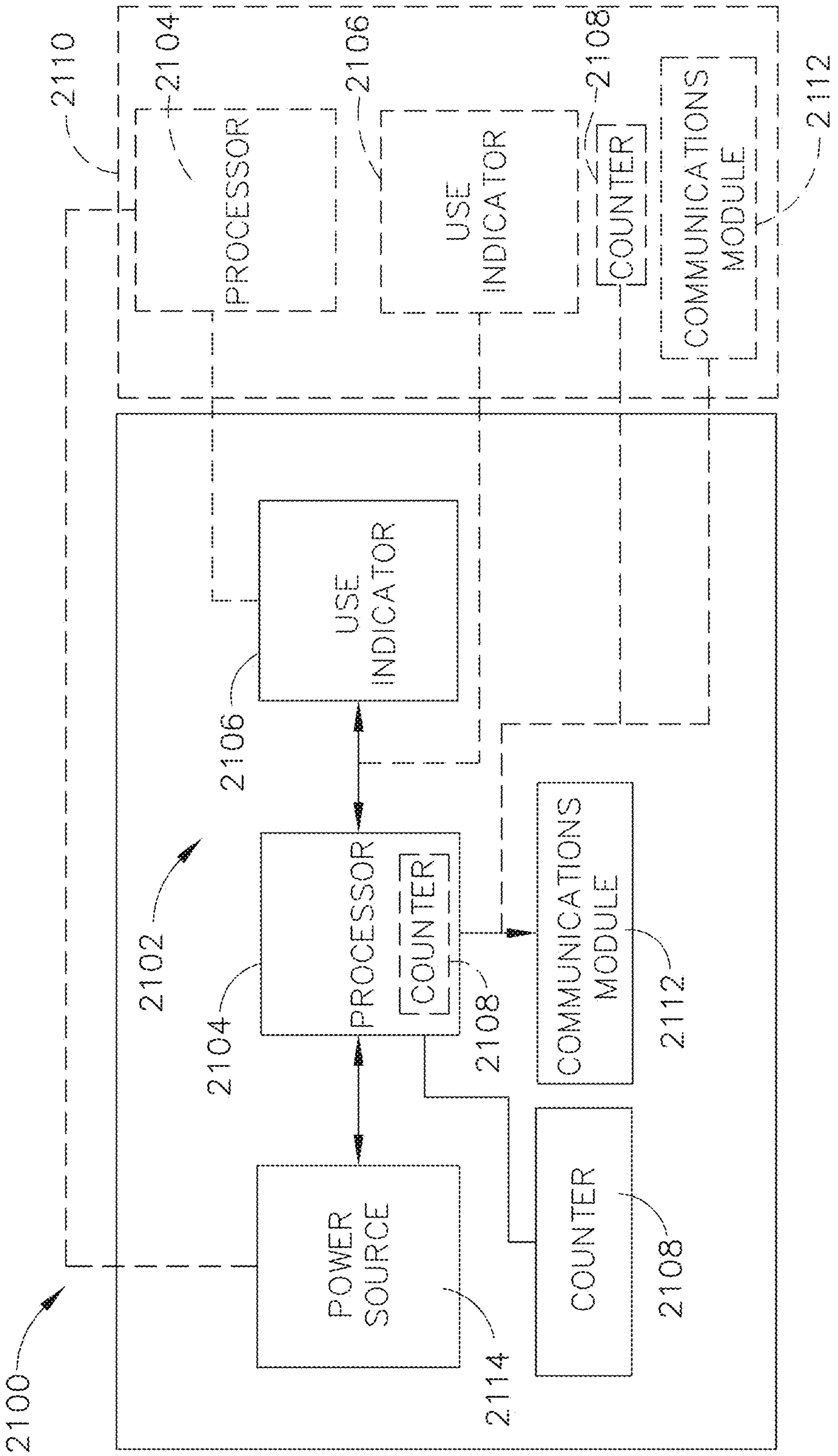
FIG. 22 illustrates one instance of a power assembly comprising a usage cycle circuit configured to generate a usage cycle count of the battery back.

FIG. 22 illustrates one example of a power assembly 2100 comprising a usage cycle circuit 2102 configured to monitor a usage cycle count of the power assembly 2100. The power assembly 2100 may be coupled to a surgical instrument 2110. The usage cycle circuit 2102 comprises a processor 2104 and a use indicator 2106. The use indicator 2106 is configured to provide a signal to the processor 2104 to indicate a use of the battery back 2100 and/or a surgical instrument 2110 coupled to the power assembly 2100. A "use" may comprise any suitable action, condition, and/or parameter such as, for example, changing a modular component of a surgical instrument 2110, deploying or firing a disposable component coupled to the surgical instrument 2110, delivering electrosurgical energy from the surgical instrument 2110, reconditioning the surgical instrument 2110 and/or the power assembly 2100, exchanging the power assembly 2100, recharging the power assembly 2100, and/or exceeding a safety limitation of the surgical instrument 2110 and/or the battery back 2100.

In some instances, a usage cycle, or use, is defined by one or more power assembly 2100 parameters. For example, in one instance, a usage cycle comprises using more than 5% of the total energy available from the power assembly 2100 when the power assembly 2100 is at a full charge level. In another instance, a usage cycle comprises a continuous energy drain from the power assembly 2100 exceeding a predetermined time limit. For example, a usage cycle may correspond to five minutes of continuous and/or total energy draw from the power assembly 2100. In some instances, the power assembly 2100 comprises a usage cycle circuit 2102 having a continuous power draw to maintain one or more components of the usage cycle circuit 2102, such as, for example, the use indicator 2106 and/or a counter 2108, in an active state.

The processor 2104 maintains a usage cycle count. The usage cycle count indicates the number of uses detected by the use indicator 2106 for the power assembly 2100 and/or the surgical instrument 2110. The processor 2104 may increment and/or decrement the usage cycle count based on input from the use indicator 2106. The usage cycle count is used to control one or more operations of the power assembly 2100 and/or the surgical instrument 2110. For example, in some instances, a power assembly 2100 is disabled when the usage cycle count exceeds a predetermined usage limit. Although the instances discussed herein are discussed with respect to incrementing the usage cycle count above a predetermined usage limit, those skilled in the art will recognize that the usage cycle count may start at a predetermined amount and may be decremented by the processor 2104. In this instance, the processor 2104 initiates and/or prevents one or more operations of the power assembly 2100 when the usage cycle count falls below a predetermined usage limit.

The usage cycle count is maintained by a counter 2108. The counter 2108 comprises any suitable circuit, such as, for example, a memory module, an analog counter, and/or any circuit configured to maintain a usage cycle count. In some instances, the counter 2108 is formed integrally with the processor 2104. In other instances, the counter 2108 comprises a separate component, such as, for example, a solid state memory module. In some instances, the usage cycle count is provided to a remote system, such as, for example, a central database. The usage cycle count is transmitted by a communications module 2112 to the remote system. The communications module 2112 is configured to use any suitable communications medium, such as, for example, wired and/or wireless communication. In some instances, the communications module 2112 is configured to receive one or more instructions from the remote system, such as, for example, a control signal when the usage cycle count exceeds the predetermined usage limit.

In some instances, the use indicator 2106 is configured to monitor the number of modular components used with a surgical instrument 2110 coupled to the power assembly 2100. A modular component may comprise, for example, a modular shaft, a modular end effector, and/or any other modular component. In some instances, the use indicator 2106 monitors the use of one or more disposable components, such as, for example, insertion and/or deployment of a staple cartridge within an end effector coupled to the surgical instrument 2110. The use indicator 2106 comprises one or more sensors for detecting the exchange of one or more modular and/or disposable components of the surgical instrument 2110.

In some instances, the use indicator 2106 is configured to monitor single patient surgical procedures performed while the power assembly 2100 is installed. For example, the use indicator 2106 may be configured to monitor firings of the surgical instrument 2110 while the power assembly 2100 is coupled to the surgical instrument 2110. A firing may correspond to deployment of a staple cartridge, application of electrosurgical energy, and/or any other suitable surgical event. The use indicator 2106 may comprise one or more circuits for measuring the number of firings while the power assembly 2100 is installed. The use indicator 2106 provides a signal to the processor 2104 when a single patient procedure is performed and the processor 2104 increments the usage cycle count.

In some instances, the use indicator 2106 comprises a circuit configured to monitor one or more parameters of the power source 2114, such as, for example, a current draw from the power source 2114. The one or more parameters of the power source 2114 correspond to one or more operations performable by the surgical instrument 2110, such as, for example, a cutting and sealing operation. The use indicator 2106 provides the one or more parameters to the processor 2104, which increments the usage cycle count when the one or more parameters indicate that a procedure has been performed.

In some instances, the use indicator 2106 comprises a timing circuit configured to increment a usage cycle count after a predetermined time period. The predetermined time period corresponds to a single patient procedure time, which is the time required for an operator to perform a procedure, such as, for example, a cutting and sealing procedure. When the power assembly 2100 is coupled to the surgical instrument 2110, the processor 2104 polls the use indicator 2106 to determine when the single patient procedure time has expired. When the predetermined time period has elapsed, the processor 2104 increments the usage cycle count. After incrementing the usage cycle count, the processor 2104 resets the timing circuit of the use indicator 2106.

In some instances, the use indicator 2106 comprises a time constant that approximates the single patient procedure time. In one example, the usage cycle circuit 2102 comprises a resistor-capacitor (RC) timing circuit 2506. The RC timing circuit comprises a time constant defined by a resistor-capacitor pair. The time constant is defined by the values of the resistor and the capacitor. In one example, the usage cycle circuit 2552 comprises a rechargeable battery and a clock. When the power assembly 2100 is installed in a surgical instrument, the rechargeable battery is charged by the power source. The rechargeable battery comprises enough power to run the clock for at least the single patient procedure time. The clock may comprise a real time clock, a processor configured to implement a time function, or any other suitable timing circuit.

Referring still to FIG. 22, in some instances, the use indicator 2106 comprises a sensor configured to monitor one or more environmental conditions experienced by the power assembly 2100. For example, the use indicator 2106 may comprise an accelerometer. The accelerometer is configured to monitor acceleration of the power assembly 2100. The power assembly 2100 comprises a maximum acceleration tolerance. Acceleration above a predetermined threshold indicates, for example, that the power assembly 2100 has been dropped. When the use indicator 2106 detects acceleration above the maximum acceleration tolerance, the processor 2104 increments a usage cycle count. In some instances, the use indicator 2106 comprises a moisture sensor. The moisture sensor is configured to indicate when the power assembly 2100 has been exposed to moisture. The moisture sensor may comprise, for example, an immersion sensor configured to indicate when the power assembly 2100 has been fully immersed in a cleaning fluid, a moisture sensor configured to indicate when moisture is in contact with the power assembly 2100 during use, and/or any other suitable moisture sensor.

In some instances, the use indicator 2106 comprises a chemical exposure sensor. The chemical exposure sensor is configured to indicate when the power assembly 2100 has come into contact with harmful and/or dangerous chemicals. For example, during a sterilization procedure, an inappropriate chemical may be used that leads to degradation of the power assembly 2100. The processor 2104 increments the usage cycle count when the use indicator 2106 detects an inappropriate chemical.

In some instances, the usage cycle circuit 2102 is configured to monitor the number of reconditioning cycles experienced by the power assembly 2100. A reconditioning cycle may comprise, for example, a cleaning cycle, a sterilization cycle, a charging cycle, routine and/or preventative maintenance, and/or any other suitable reconditioning cycle. The use indicator 2106 is configured to detect a reconditioning cycle. For example, the use indicator 2106 may comprise a moisture sensor to detect a cleaning and/or sterilization cycle. In some instances, the usage cycle circuit 2102 monitors the number of reconditioning cycles experienced by the power assembly 2100 and disables the power assembly 2100 after the number of reconditioning cycles exceeds a predetermined threshold.

The usage cycle circuit 2102 may be configured to monitor the number of power assembly 2100 exchanges. The usage cycle circuit 2102 increments the usage cycle count each time the power assembly 2100 is exchanged. When the maximum number of exchanges is exceeded the usage cycle circuit 2102 locks out the power assembly 2100 and/or the surgical instrument 2110. In some instances, when the power assembly 2100 is coupled the surgical instrument 2110, the usage cycle circuit 2102 identifies the serial number of the power assembly 2100 and locks the power assembly 2100 such that the power assembly 2100 is usable only with the surgical instrument 2110. In some instances, the usage cycle circuit 2102 increments the usage cycle each time the power assembly 2100 is removed from and/or coupled to the surgical instrument 2110.

In some instances, the usage cycle count corresponds to sterilization of the power assembly 2100. The use indicator 2106 comprises a sensor configured to detect one or more parameters of a sterilization cycle, such as, for example, a temperature parameter, a chemical parameter, a moisture parameter, and/or any other suitable parameter. The processor 2104 increments the usage cycle count when a sterilization parameter is detected. The usage cycle circuit 2102 disables the power assembly 2100 after a predetermined number of sterilizations. In some instances, the usage cycle circuit 2102 is reset during a sterilization cycle, a voltage sensor to detect a recharge cycle, and/or any suitable sensor. The processor 2104 increments the usage cycle count when a reconditioning cycle is detected. The usage cycle circuit 2102 is disabled when a sterilization cycle is detected. The usage cycle circuit 2102 is reactivated and/or reset when the power assembly 2100 is coupled to the surgical instrument 2110. In some instances, the use indicator comprises a zero power indicator. The zero power indicator changes state during a sterilization cycle and is checked by the processor 2104 when the power assembly 2100 is coupled to a surgical instrument 2110. When the zero power indicator indicates that a sterilization cycle has occurred, the processor 2104 increments the usage cycle count.

A counter 2108 maintains the usage cycle count. In some instances, the counter 2108 comprises a non-volatile memory module. The processor 2104 increments the usage cycle count stored in the non-volatile memory module each time a usage cycle is detected. The memory module may be accessed by the processor 2104 and/or a control circuit, such as, for example, the control circuit 200. When the usage cycle count exceeds a predetermined threshold, the processor 2104 disables the power assembly 2100. In some instances, the usage cycle count is maintained by a plurality of circuit components. For example, in one instance, the counter 2108 comprises a resistor (or fuse) pack. After each use of the power assembly 2100, a resistor (or fuse) is burned to an open position, changing the resistance of the resistor pack. The power assembly 2100 and/or the surgical instrument 2110 reads the remaining resistance. When the last resistor of the resistor pack is burned out, the resistor pack has a predetermined resistance, such as, for example, an infinite resistance corresponding to an open circuit, which indicates that the power assembly 2100 has reached its usage limit. In some instances, the resistance of the resistor pack is used to derive the number of uses remaining.

In some instances, the usage cycle circuit 2102 prevents further use of the power assembly 2100 and/or the surgical instrument 2110 when the usage cycle count exceeds a predetermined usage limit. In one instance, the usage cycle count associated with the power assembly 2100 is provided to an operator, for example, utilizing a screen formed integrally with the surgical instrument 2110. The surgical instrument 2110 provides an indication to the operator that the usage cycle count has exceeded a predetermined limit for the power assembly 2100, and prevents further operation of the surgical instrument 2110.

In some instances, the usage cycle circuit 2102 is configured to physically prevent operation when the predetermined usage limit is reached. For example, the power assembly 2100 may comprise a shield configured to deploy over contacts of the power assembly 2100 when the usage cycle count exceeds the predetermined usage limit. The shield prevents recharge and use of the power assembly 2100 by covering the electrical connections of the power assembly 2100.

In some instances, the usage cycle circuit 2102 is located at least partially within the surgical instrument 2110 and is configured to maintain a usage cycle count for the surgical instrument 2110. FIG. 22 illustrates one or more components of the usage cycle circuit 2102 within the surgical instrument 2110 in phantom, illustrating the alternative positioning of the usage cycle circuit 2102. When a predetermined usage limit of the surgical instrument 2110 is exceeded, the usage cycle circuit 2102 disables and/or prevents operation of the surgical instrument 2110. The usage cycle count is incremented by the usage cycle circuit 2102 when the use indicator 2106 detects a specific event and/or requirement, such as, for example, firing of the surgical instrument 2110, a predetermined time period corresponding to a single patient procedure time, based on one or more motor parameters of the surgical instrument 2110, in response to a system diagnostic indicating that one or more predetermined thresholds are met, and/or any other suitable requirement. As discussed above, in some instances, the use indicator 2106 comprises a timing circuit corresponding to a single patient procedure time. In other instances, the use indicator 2106 comprises one or more sensors configured to detect a specific event and/or condition of the surgical instrument 2110.

In some instances, the usage cycle circuit 2102 is configured to prevent operation of the surgical instrument 2110 after the predetermined usage limit is reached. In some instances, the surgical instrument 2110 comprises a visible indicator to indicate when the predetermined usage limit has been reached and/or exceeded. For example, a flag, such as a red flag, may pop-up from the surgical instrument 2110, such as from the handle, to provide a visual indication to the operator that the surgical instrument 2110 has exceeded the predetermined usage limit. As another example, the usage cycle circuit 2102 may be coupled to a display formed integrally with the surgical instrument 2110. The usage cycle circuit 2102 displays a message indicating that the predetermined usage limit has been exceeded. The surgical instrument 2110 may provide an audible indication to the operator that the predetermined usage limit has been exceeded. For example, in one instance, the surgical instrument 2110 emits an audible tone when the predetermined usage limit is exceeded and the power assembly 2100 is removed from the surgical instrument 2110. The audible tone indicates the last use of the surgical instrument 2110 and indicates that the surgical instrument 2110 should be disposed or reconditioned.

In some instances, the usage cycle circuit 2102 is configured to transmit the usage cycle count of the surgical instrument 2110 to a remote location, such as, for example, a central database. The usage cycle circuit 2102 comprises a communications module 2112 configured to transmit the usage cycle count to the remote location. The communications module 2112 may utilize any suitable communications system, such as, for example, wired or wireless communications system. The remote location may comprise a central database configured to maintain usage information. In some instances, when the power assembly 2100 is coupled to the surgical instrument 2110, the power assembly 2100 records a serial number of the surgical instrument 2110. The serial number is transmitted to the central database, for example, when the power assembly 2100 is coupled to a charger. In some instances, the central database maintains a count corresponding to each use of the surgical instrument 2110. For example, a bar code associated with the surgical instrument 2110 may be scanned each time the surgical instrument 2110 is used. When the use count exceeds a predetermined usage limit, the central database provides a signal to the surgical instrument 2110 indicating that the surgical instrument 2110 should be discarded.

The surgical instrument 2110 may be configured to lock and/or prevent operation of the surgical instrument 2110 when the usage cycle count exceeds a predetermined usage limit. In some instances, the surgical instrument 2110 comprises a disposable instrument and is discarded after the usage cycle count exceeds the predetermined usage limit. In other instances, the surgical instrument 2110 comprises a reusable surgical instrument which may be reconditioned after the usage cycle count exceeds the predetermined usage limit. The surgical instrument 2110 initiates a reversible lockout after the predetermined usage limit is met. A technician reconditions the surgical instrument 2110 and releases the lockout, for example, utilizing a specialized technician key configured to reset the usage cycle circuit 2102.

Figure 23:
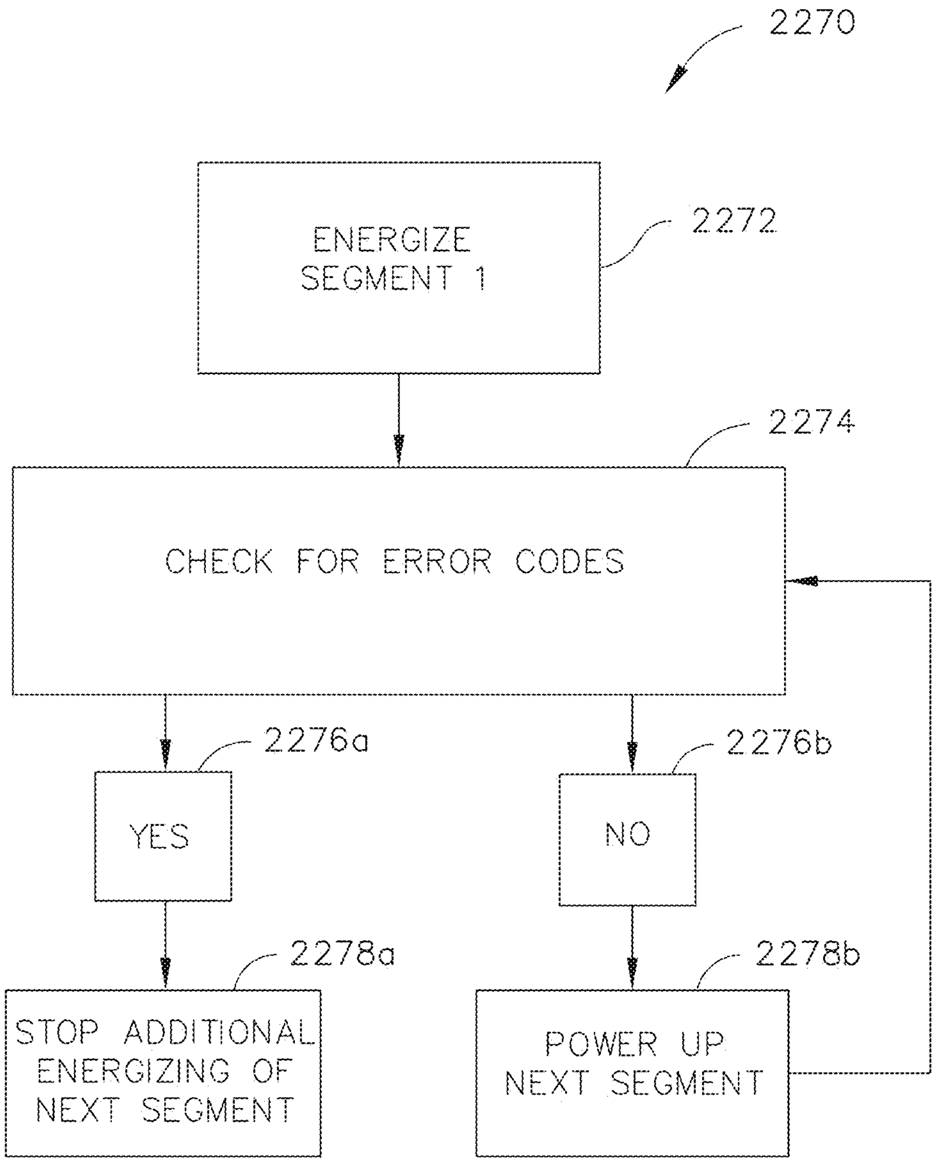
FIG. 23 illustrates one aspect of a process for sequentially energizing a segmented circuit.

In some aspects, the segmented circuit 2000 is configured for sequential start-up. An error check is performed by each circuit segment 2002*a*-2002*g* prior to energizing the next sequential circuit segment 2002*a*-2002*g*. FIG. 23 illustrates one example of a process for sequentially energizing a segmented circuit 2270, such as, for example, the segmented circuit 2000. When a battery 2008 is coupled to the segmented circuit 2000, the safety processor 2004 is energized 2272. The safety processor 2004 performs a self-error check 2274. When an error is detected 2276*a*, the safety processor stops energizing the segmented circuit 2000 and generates an error code 2278*a*. When no errors are detected 2276*b*, the safety processor 2004 initiates 2278*b* power-up of the primary processor 2006. The primary processor 2006 performs a self-error check. When no errors are detected, the primary processor 2006 begins sequential power-up of each of the remaining circuit segments 2278*b*. Each circuit segment is energized and error checked by the primary processor 2006. When no errors are detected, the next circuit segment is energized 2278*b*. When an error is detected, the safety processor 2004 and/or the primary process stops energizing the current segment and generates an error 2278*a*. The sequential start-up continues until all of the circuit segments 2002*a*-2002*g* have been energized. In some examples, the segmented circuit 2000 transitions from sleep mode following a similar sequential power-up process 11250.

Figure 24:
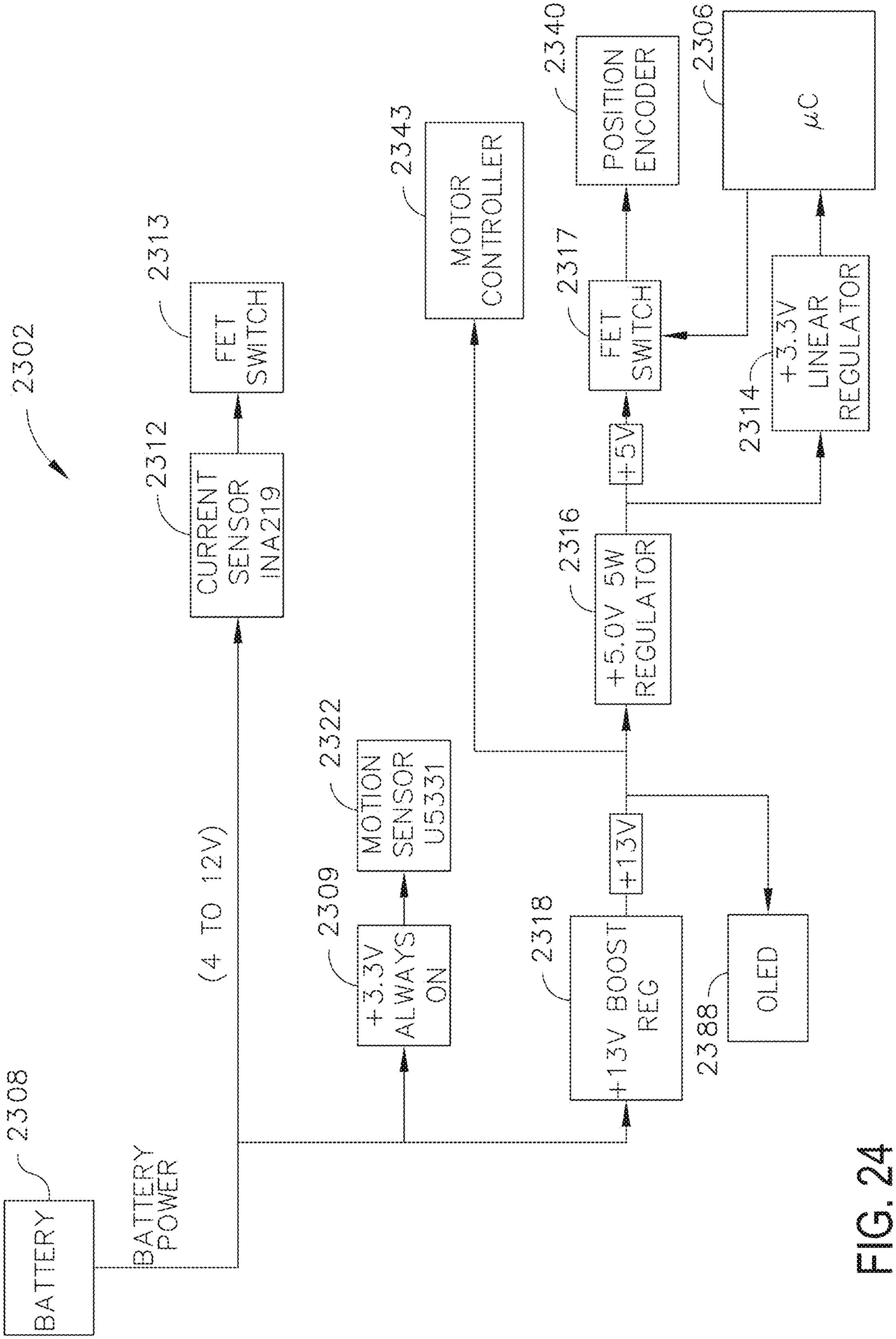
FIG. 24 illustrates one aspect of a power segment comprising a plurality of daisy chained power converters.

FIG. 24 illustrates one aspect of a power segment 2302 comprising a plurality of daisy chained power converters 2314, 2316, 2318. The power segment 2302 comprises a battery 2308. The battery 2308 is configured to provide a source voltage, such as, for example, 12V. A current sensor 2312 is coupled to the battery 2308 to monitor the current draw of a segmented circuit and/or one or more circuit segments. The current sensor 2312 is coupled to an FET switch 2313. The battery 2308 is coupled to one or more voltage converters 2309, 2314, 2316. An always on converter 2309 provides a constant voltage to one or more circuit components, such as, for example, a motion sensor 2322. The always on converter 2309 comprises, for example, a 3.3V converter. The always on converter 2309 may provide a constant voltage to additional circuit components, such as, for example, a safety processor (not shown). The battery 2308 is coupled to a boost converter 2318. The boost converter 2318 is configured to provide a boosted voltage above the voltage provided by the battery 2308. For example, in the illustrated example, the battery 2308 provides a voltage of 12V. The boost converter 2318 is configured to boost the voltage to 13V. The boost converter 2318 is configured to maintain a minimum voltage during operation of a surgical instrument, for example, the surgical instrument 10 (FIGS. 1-4). Operation of a motor can result in the power provided to the primary processor 2306 dropping below a minimum threshold and creating a brownout or reset condition in the primary processor 2306. The boost converter 2318 ensures that sufficient power is available to the primary processor 2306 and/or other circuit components, such as the motor controller 2343, during operation of the surgical instrument 10. In some examples, the boost converter 2318 is coupled directly one or more circuit components, such as, for example, an OLED display 2388.

The boost converter 2318 is coupled to one or more step-down converters to provide voltages below the boosted voltage level. A first voltage converter 2316 is coupled to the boost converter 2318 and provides a first stepped-down voltage to one or more circuit components. In the illustrated example, the first voltage converter 2316 provides a voltage of 5V. The first voltage converter 2316 is coupled to a rotary position encoder 2340. A FET switch 2317 is coupled between the first voltage converter 2316 and the rotary position encoder 2340. The FET switch 2317 is controlled by the processor 2306. The processor 2306 opens the FET switch 2317 to deactivate the position encoder 2340, for example, during power intensive operations. The first voltage converter 2316 is coupled to a second voltage converter 2314 configured to provide a second stepped-down voltage. The second stepped-down voltage comprises, for example, 3.3V. The second voltage converter 2314 is coupled to a processor 2306. In some examples, the boost converter 2318, the first voltage converter 2316, and the second voltage converter 2314 are coupled in a daisy chain configuration. The daisy chain configuration allows the use of smaller, more efficient converters for generating voltage levels below the boosted voltage level. The examples, however, are not limited to the particular voltage range(s) described in the context of this specification.

Figure 25:
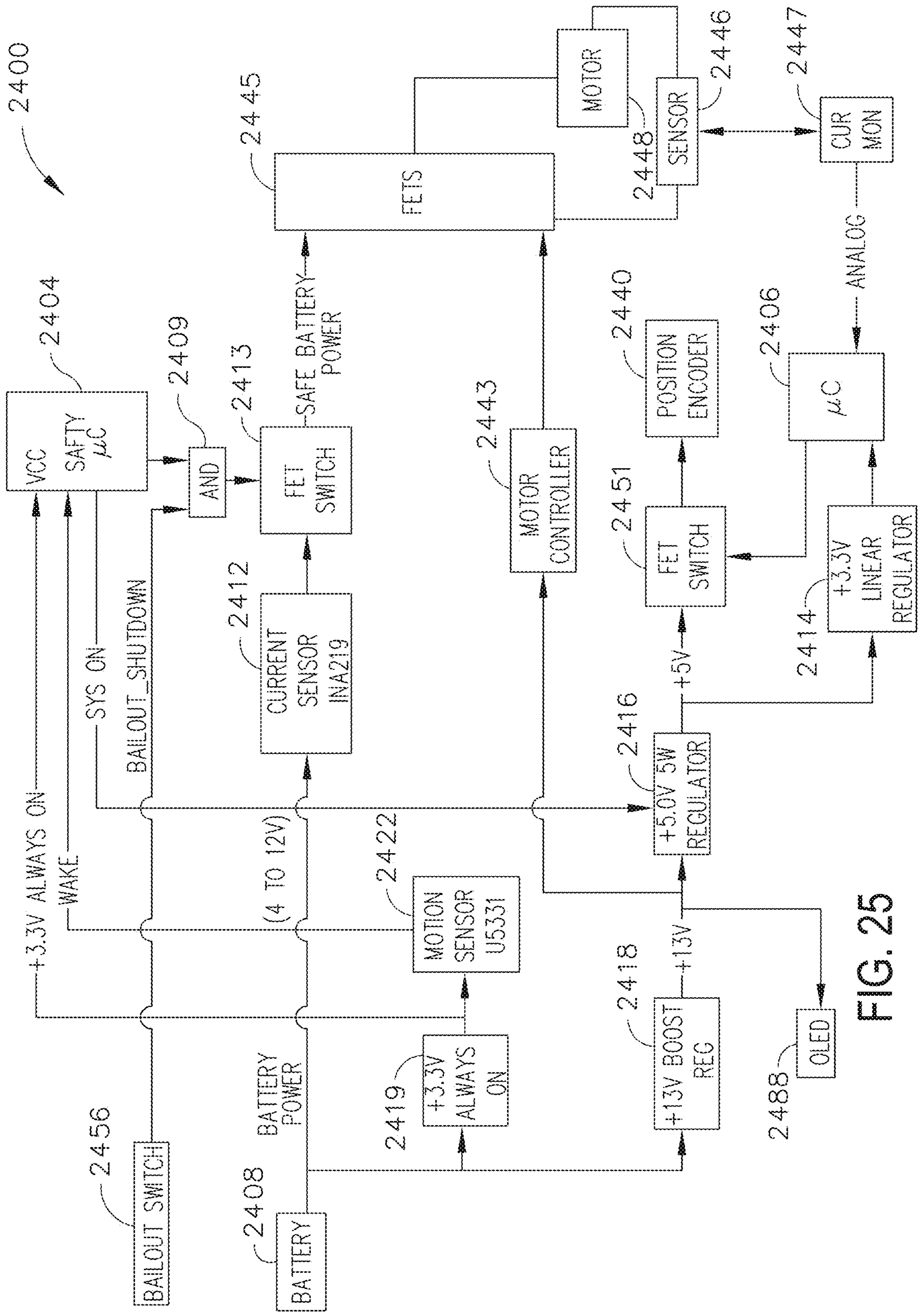
FIG. 25 illustrates one aspect of a segmented circuit configured to maximize power available for critical and/or power intense functions.

FIG. 25 illustrates one aspect of a segmented circuit 2400 configured to maximize power available for critical and/or power intense functions. The segmented circuit 2400 comprises a battery 2408. The battery 2408 is configured to provide a source voltage such as, for example, 12V. The source voltage is provided to a plurality of voltage converters 2409, 2418. An always-on voltage converter 2409 provides a constant voltage to one or more circuit components, for example, a motion sensor 2422 and a safety processor 2404. The always-on voltage converter 2409 is directly coupled to the battery 2408. The always-on converter 2409 provides a voltage of 3.3V, for example. The examples, however, are not limited to the particular voltage range(s) described in the context of this specification.

The segmented circuit 2400 comprises a boost converter 2418. The boost converter 2418 provides a boosted voltage above the source voltage provided by the battery 2408, such as, for example, 13V. The boost converter 2418 provides a boosted voltage directly to one or more circuit components, such as, for example, an OLED display 2488 and a motor controller 2443. By coupling the OLED display 2488 directly to the boost converter 2418, the segmented circuit 2400 eliminates the need for a power converter dedicated to the OLED display 2488. The boost converter 2418 provides a boosted voltage to the motor controller 2443 and the motor 2448 during one or more power intensive operations of the motor 2448, such as, for example, a cutting operation. The boost converter 2418 is coupled to a step-down converter 2416. The step-down converter 2416 is configured to provide a voltage below the boosted voltage to one or more circuit components, such as, for example, 5V. The step-down converter 2416 is coupled to, for example, a FET switch 2451 and a position encoder 2440. The FET switch 2451 is coupled to the primary processor 2406. The primary processor 2406 opens the FET switch 2451 when transitioning the segmented circuit 2400 to sleep mode and/or during power intensive functions requiring additional voltage delivered to the motor 2448. Opening the FET switch 2451 deactivates the position encoder 2440 and eliminates the power draw of the position encoder 2440. The examples, however, are not limited to the particular voltage range(s) described in the context of this specification.

The step-down converter 2416 is coupled to a linear converter 2414. The linear converter 2414 is configured to provide a voltage of, for example, 3.3V. The linear converter 2414 is coupled to the primary processor 2406. The linear converter 2414 provides an operating voltage to the primary processor 2406. The linear converter 2414 may be coupled to one or more additional circuit components. The examples, however, are not limited to the particular voltage range(s) described in the context of this specification.

The segmented circuit 2400 comprises a bailout switch 2456. The bailout switch 2456 is coupled to a bailout door on the surgical instrument 10. The bailout switch 2456 and the safety processor 2404 are coupled to an AND gate 2419. The AND gate 2419 provides an input to a FET switch 2413. When the bailout switch 2456 detects a bailout condition, the bailout switch 2456 provides a bailout shutdown signal to the AND gate 2419. When the safety processor 2404 detects an unsafe condition, such as, for example, due to a sensor mismatch, the safety processor 2404 provides a shutdown signal to the AND gate 2419. In some examples, both the bailout shutdown signal and the shutdown signal are high during normal operation and are low when a bailout condition or an unsafe condition is detected. When the output of the AND gate 2419 is low, the FET switch 2413 is opened and operation of the motor 2448 is prevented. In some examples, the safety processor 2404 utilizes the shutdown signal to transition the motor 2448 to an off state in sleep mode. A third input to the FET switch 2413 is provided by a current sensor 2412 coupled to the battery 2408. The current sensor 2412 monitors the current drawn by the circuit 2400 and opens the FET switch 2413 to shut-off power to the motor 2448 when an electrical current above a predetermined threshold is detected. The FET switch 2413 and the motor controller 2443 are coupled to a bank of FET switches 2445 configured to control operation of the motor 2448.

A motor current sensor 2446 is coupled in series with the motor 2448 to provide a motor current sensor reading to a current monitor 2447. The current monitor 2447 is coupled to the primary processor 2406. The current monitor 2447 provides a signal indicative of the current draw of the motor 2448. The primary processor 2406 may utilize the signal from the motor current 2447 to control operation of the motor, for example, to ensure the current draw of the motor 2448 is within an acceptable range, to compare the current draw of the motor 2448 to one or more other parameters of the circuit 2400 such as, for example, the position encoder 2440, and/or to determine one or more parameters of a treatment site. In some examples, the current monitor 2447 may be coupled to the safety processor 2404.

In some aspects, actuation of one or more handle controls, such as, for example, a firing trigger, causes the primary processor 2406 to decrease power to one or more components while the handle control is actuated. For example, in one example, a firing trigger controls a firing stroke of a cutting member. The cutting member is driven by the motor 2448. Actuation of the firing trigger results in forward operation of the motor 2448 and advancement of the cutting member. During firing, the primary processor 2406 closes the FET switch 2451 to remove power from the position encoder 2440. The deactivation of one or more circuit components allows higher power to be delivered to the motor 2448. When the firing trigger is released, full power is restored to the deactivated components, for example, by closing the FET switch 2451 and reactivating the position encoder 2440.

In some aspects, the safety processor 2404 controls operation of the segmented circuit 2400. For example, the safety processor 2404 may initiate a sequential power-up of the segmented circuit 2400, transition of the segmented circuit 2400 to and from sleep mode, and/or may override one or more control signals from the primary processor 2406. For example, in the illustrated example, the safety processor 2404 is coupled to the step-down converter 2416. The safety processor 2404 controls operation of the segmented circuit 2400 by activating or deactivating the step-down converter 2416 to provide power to the remainder of the segmented circuit 2400.

Figure 26:
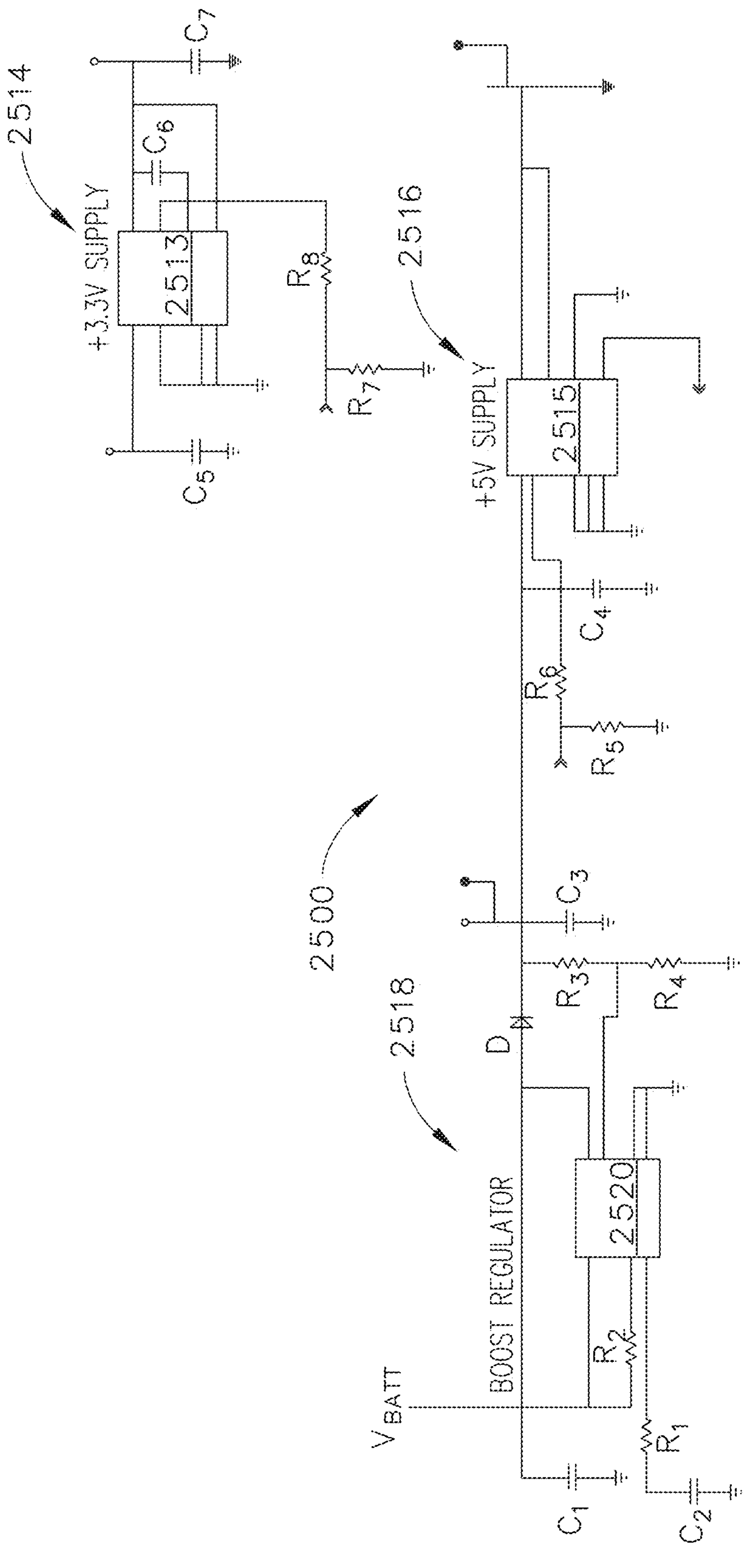
FIG. 26 illustrates one aspect of a power system comprising a plurality of daisy chained power converters configured to be sequentially energized.

FIG. 26 illustrates one aspect of a power system 2500 comprising a plurality of daisy chained power converters 2514, 2516, 2518 configured to be sequentially energized. The plurality of daisy chained power converters 2514, 2516, 2518 may be sequentially activated by, for example, a safety processor during initial power-up and/or transition from sleep mode. The safety processor may be powered by an independent power converter (not shown). For example, in one example, when a battery voltage $V_{BATT}$ is coupled to the power system 2500 and/or an accelerometer detects movement in sleep mode, the safety processor initiates a sequential start-up of the daisy chained power converters 2514, 2516, 2518. The safety processor activates the 13V boost section 2518. The boost section 2518 is energized and performs a self-check. In some examples, the boost section 2518 comprises an integrated circuit 2520 configured to boost the source voltage and to perform a self check. A diode D prevents power-up of a 5V supply section 2516 until the boost section 2518 has completed a self-check and provided a signal to the diode D indicating that the boost section 2518 did not identify any errors. In some examples, this signal is provided by the safety processor. The examples, however, are not limited to the particular voltage range(s) described in the context of this specification.

The 5V supply section 2516 is sequentially powered-up after the boost section 2518. The 5V supply section 2516 performs a self-check during power-up to identify any errors in the 5V supply section 2516. The 5V supply section 2516 comprises an integrated circuit 2515 configured to provide a step-down voltage from the boost voltage and to perform an error check. When no errors are detected, the 5V supply section 2516 completes sequential power-up and provides an activation signal to the 3.3V supply section 2514. In some examples, the safety processor provides an activation signal to the 3.3V supply section 2514. The 3.3V supply section comprises an integrated circuit 2513 configured to provide a step-down voltage from the 5V supply section 2516 and perform a self-error check during power-up. When no errors are detected during the self-check, the 3.3V supply section 2514 provides power to the primary processor. The primary processor is configured to sequentially energize each of the remaining circuit segments. By sequentially energizing the power system 2500 and/or the remainder of a segmented circuit, the power system 2500 reduces error risks, allows for stabilization of voltage levels before loads are applied, and prevents large current draws from all hardware being turned on simultaneously in an uncontrolled manner. The examples, however, are not limited to the particular voltage range(s) described in the context of this specification.

In one aspect, the power system 2500 comprises an over voltage identification and mitigation circuit. The over voltage identification and mitigation circuit is configured to detect a monopolar return current in the surgical instrument and interrupt power from the power segment when the monopolar return current is detected. The over voltage identification and mitigation circuit is configured to identify ground floatation of the power system. The over voltage identification and mitigation circuit comprises a metal oxide varistor. The over voltage identification and mitigation circuit comprises at least one transient voltage suppression diode.

Figure 27:
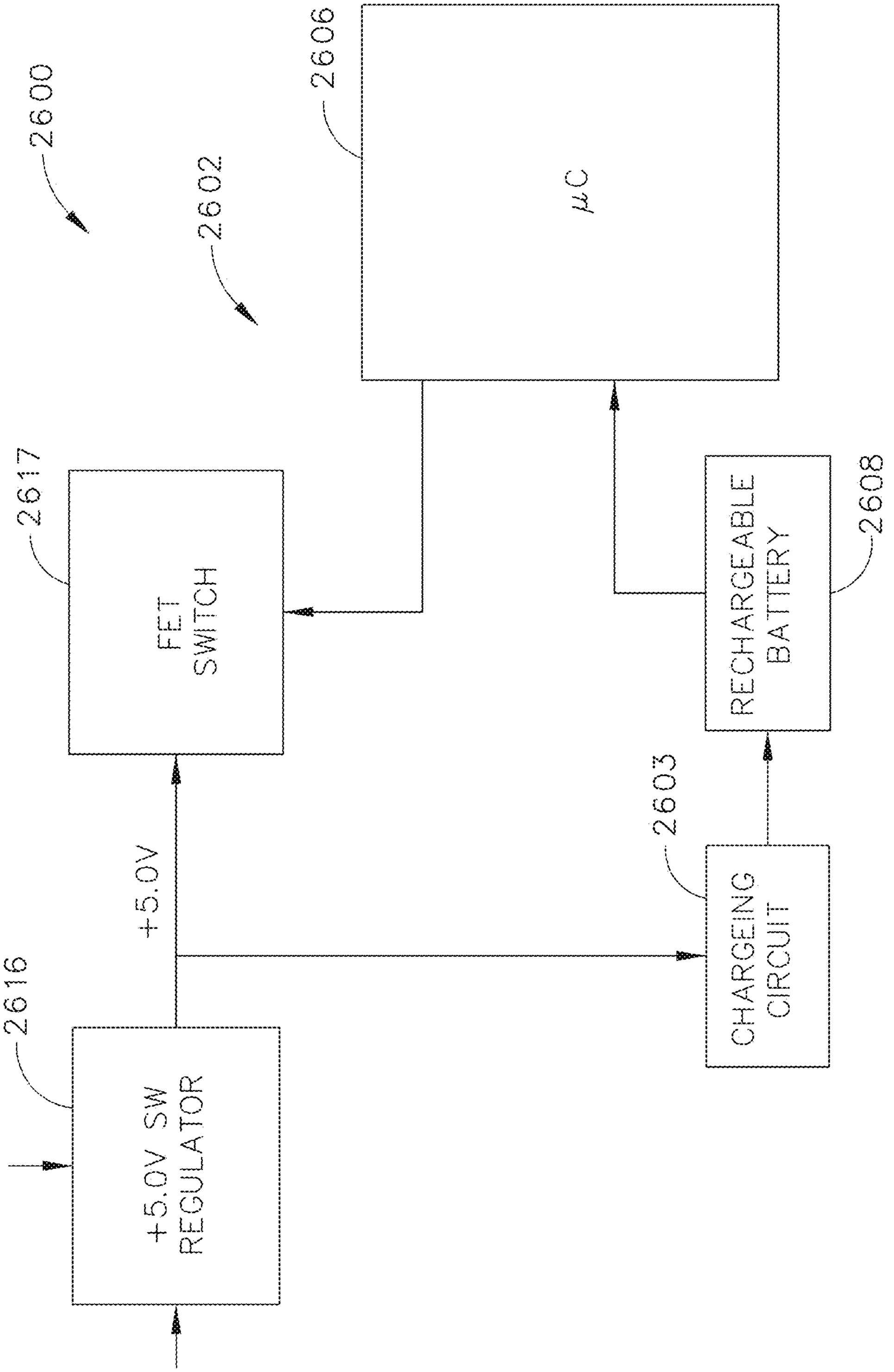
FIG. 27 illustrates one aspect of a segmented circuit comprising an isolated control section.

FIG. 27 illustrates one aspect of a segmented circuit 2600 comprising an isolated control section 2602. The isolated control section 2602 isolates control hardware of the segmented circuit 2600 from a power section (not shown) of the segmented circuit 2600. The control section 2602 comprises, for example, a primary processor 2606, a safety processor (not shown), and/or additional control hardware, for example, a FET Switch 2617. The power section comprises, for example, a motor, a motor driver, and/or a plurality of motor MOSFETS. The isolated control section 2602 comprises a charging circuit 2603 and a rechargeable battery 2608 coupled to a 5V power converter 2616. The charging circuit 2603 and the rechargeable battery 2608 isolate the primary processor 2606 from the power section. In some examples, the rechargeable battery 2608 is coupled to a safety processor and any additional support hardware. Isolating the control section 2602 from the power section allows the control section 2602, for example, the primary processor 2606, to remain active even when main power is removed, provides a filter, through the rechargeable battery 2608, to keep noise out of the control section 2602, isolates the control section 2602 from heavy swings in the battery voltage to ensure proper operation even during heavy motor loads, and/or allows for real-time operating system (RTOS) to be used by the segmented circuit 2600. In some examples, the rechargeable battery 2608 provides a stepped-down voltage to the primary processor, such as, for example, 3.3V. The examples, however, are not limited to the particular voltage range(s) described in the context of this specification.

Figure 28A:
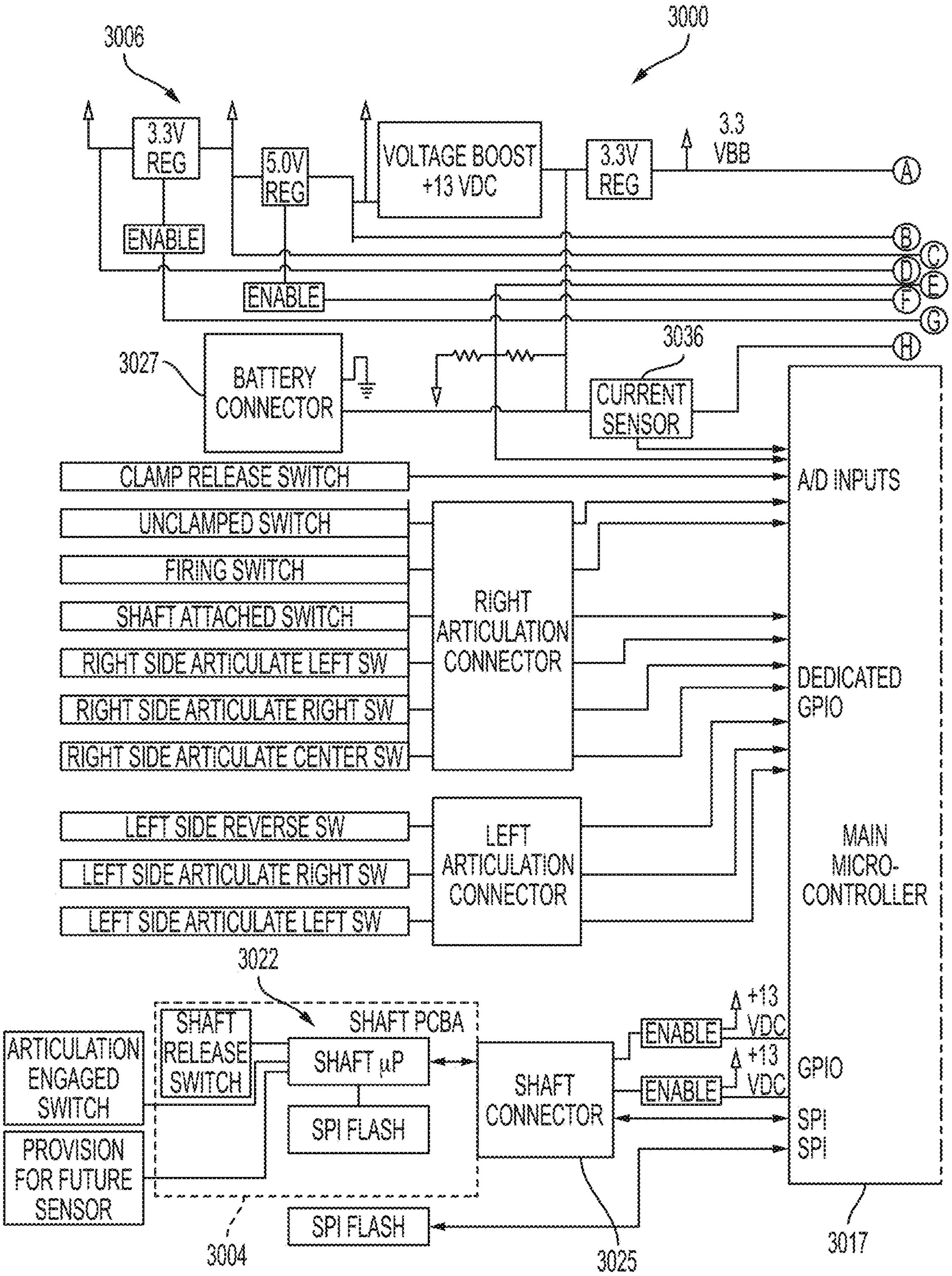
FIGS. 28A and 28B, is a circuit diagram of the surgical instrument of FIG. 1.
Figure 28B:
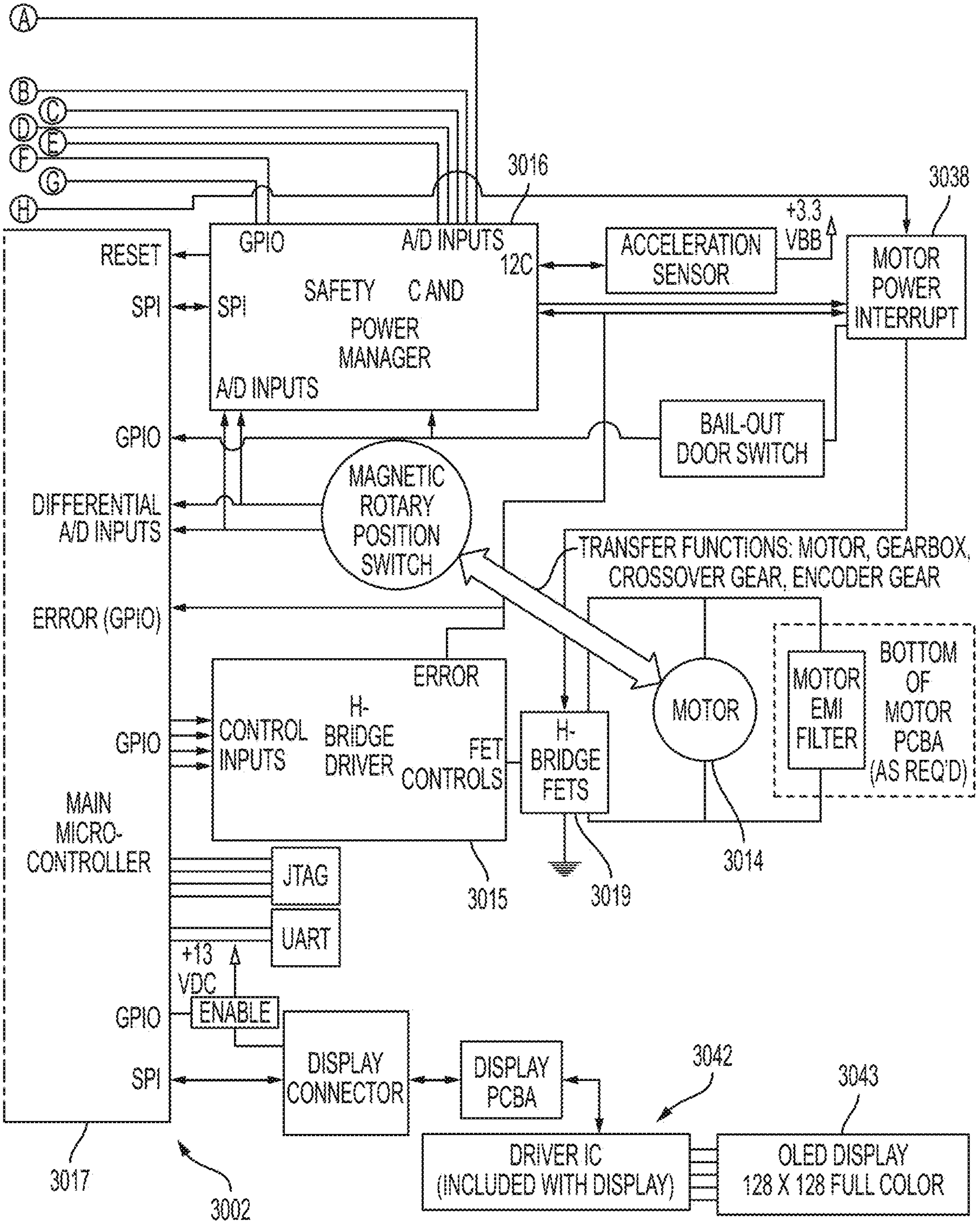

FIGS. 28A and 28B illustrate another aspect of a control circuit 3000 configured to control the powered surgical instrument 10, illustrated in FIGS. 1-18A. As shown in FIGS. 18A, 28B, the handle assembly 14 may include a motor 3014 which can be controlled by a motor driver 3015 and can be employed by the firing system of the surgical instrument 10. In various forms, the motor 3014 may be a DC brushed driving motor having a maximum rotation of, approximately, 25,000 RPM, for example. In other arrangements, the motor 3014 may include a brushless motor, a cordless motor, a synchronous motor, a stepper motor, or any other suitable electric motor. In certain circumstances, the motor driver 3015 may comprise an H-Bridge FETs 3019, as illustrated in FIGS. 28A and 28B, for example. The motor 3014 can be powered by a power assembly 3006, which can be releasably mounted to the handle assembly 14. The power assembly 3006 is configured to supply control power to the surgical instrument 10. The power assembly 3006 may comprise a battery which may include a number of battery cells connected in series that can be used as the power source to power the surgical instrument 10. In such configuration, the power assembly 3006 may be referred to as a battery pack. In certain circumstances, the battery cells of the power assembly 3006 may be replaceable and/or rechargeable. In at least one example, the battery cells can be Lithium-Ion batteries which can be separably couplable to the power assembly 3006.

Examples of drive systems and closure systems that are suitable for use with the surgical instrument 10 are disclosed in U.S. Provisional Patent Application Ser. No. 61/782,866, entitled CONTROL SYSTEM OF A SURGICAL INSTRUMENT, and filed Mar. 14, 2013, the entire disclosure of which is incorporated by reference herein in its entirety. For example, the electric motor 3014 can include a rotatable shaft (not shown) that may operably interface with a gear reducer assembly that can be mounted in meshing engagement with a set, or rack, of drive teeth on a longitudinally-movable drive member. In use, a voltage polarity provided by the battery can operate the electric motor 3014 to drive the longitudinally-movable drive member to effectuate the end effector 300. For example, the motor 3014 can be configured to drive the longitudinally-movable drive member to advance a firing mechanism to fire staples into tissue captured by the end effector 300 from a staple cartridge assembled with the end effector 300 and/or advance a cutting member to cut tissue captured by the end effector 300, for example.

As illustrated in FIGS. 28A and 28B and as described below in greater detail, the power assembly 3006 may include a power management controller which can be configured to modulate the power output of the power assembly 3006 to deliver a first power output to power the motor 3014 to advance the cutting member while the interchangeable shaft 200 is coupled to the handle assembly 14 (FIG. 1) and to deliver a second power output to power the motor 3014 to advance the cutting member while the interchangeable shaft assembly 200 is coupled to the handle assembly 14, for example. Such modulation can be beneficial in avoiding transmission of excessive power to the motor 3014 beyond the requirements of an interchangeable shaft assembly that is coupled to the handle assembly 14.

In certain circumstances, the interface 3024 can facilitate transmission of the one or more communication signals between the power management controller 3016 and the shaft assembly controller 3022 by routing such communication signals through a main controller 3017 residing in the handle assembly 14 (FIG. 1), for example. In other circumstances, the interface 3024 can facilitate a direct line of communication between the power management controller 3016 and the shaft assembly controller 3022 through the handle assembly 14 while the shaft assembly 200 (FIG. 1) and the power assembly 3006 are coupled to the handle assembly 14.

In one instance, the main microcontroller 3017 may be any single core or multicore processor such as those known under the trade name ARM Cortex by Texas Instruments. In one instance, the surgical instrument 10 (FIGS. 1-4) may comprise a power management controller 3016 such as, for example, a safety microcontroller platform comprising two microcontroller-based families such as TMS570 and RM4x known under the trade name Hercules ARM Cortex R4, also by Texas Instruments. Nevertheless, other suitable substitutes for microcontrollers and safety processor may be employed, without limitation. In one instance, the safety processor 2004 (FIG. 21A) may be configured specifically for IEC 61508 and ISO 26262 safety critical applications, among others, to provide advanced integrated safety features while delivering scalable performance, connectivity, and memory options.

In certain instances, the microcontroller 3017 may be an LM 4F230H5QR, available from Texas Instruments, for example. In at least one example, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available for the product datasheet. The present disclosure should not be limited in this context.

Figure 29:
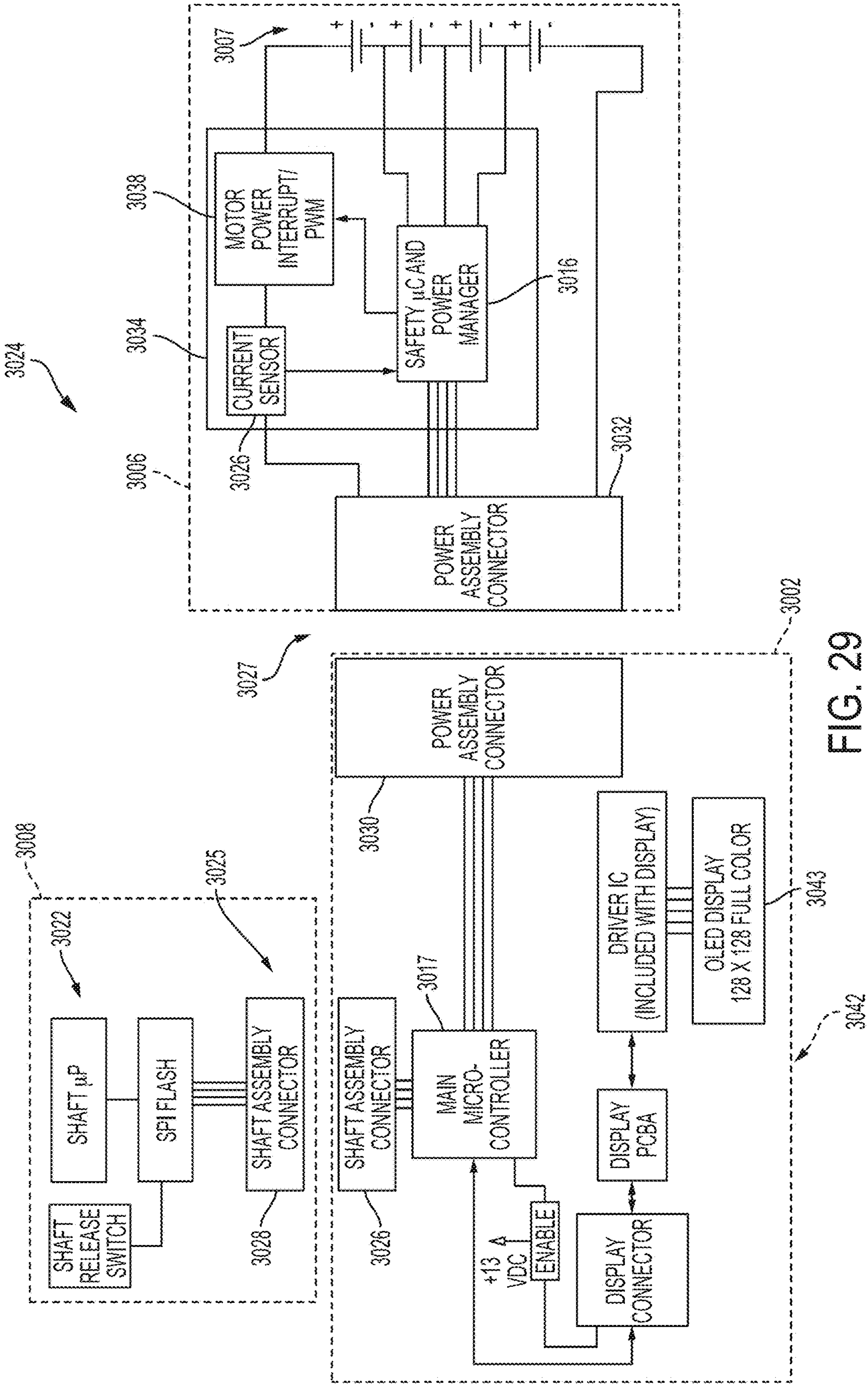
FIG. 29 is a block diagram the surgical instrument of FIG. 1 illustrating interfaces between the handle assembly 14 and the power assembly and between the handle assembly 14 and the interchangeable shaft assembly.

FIG. 29 is a block diagram the surgical instrument of FIG. 1 illustrating interfaces between the handle assembly 14 (FIG. 1) and the power assembly and between the handle assembly 14 and the interchangeable shaft assembly. As shown in FIG. 29, the power assembly 3006 may include a power management circuit 3034 which may comprise the power management controller 3016, a power modulator 3038, and a current sense circuit 3036. The power management circuit 3034 can be configured to modulate power output of the battery 3007 based on the power requirements of the shaft assembly 200 (FIG. 1) while the shaft assembly 200 and the power assembly 3006 are coupled to the handle assembly 14. For example, the power management controller 3016 can be programmed to control the power modulator 3038 of the power output of the power assembly 3006 and the current sense circuit 3036 can be employed to monitor power output of the power assembly 3006 to provide feedback to the power management controller 3016 about the power output of the battery 3007 so that the power management controller 3016 may adjust the power output of the power assembly 3006 to maintain a desired output.

It is noteworthy that the power management controller 3016 and/or the shaft assembly controller 3022 each may comprise one or more processors and/or memory units which may store a number of software modules. Although certain modules and/or blocks of the surgical instrument 14 (FIG. 1) may be described by way of example, it can be appreciated that a greater or lesser number of modules and/or blocks may be used. Further, although various instances may be described in terms of modules and/or blocks to facilitate description, such modules and/or blocks may be implemented by one or more hardware components, e.g., processors, Digital Signal Processors (DSPs), Programmable Logic Devices (PLDs), Application Specific Integrated Circuits (ASICs), circuits, registers and/or software components, e.g., programs, subroutines, logic and/or combinations of hardware and software components.

In certain instances, the surgical instrument 10 (FIGS. 1-4) may comprise an output device 3042 which may include one or more devices for providing a sensory feedback to a user. Such devices may comprise, for example, visual feedback devices (e.g., an LCD display screen, LED indicators), audio feedback devices (e.g., a speaker, a buzzer) or tactile feedback devices (e.g., haptic actuators). In certain circumstances, the output device 3042 may comprise a display 3043 which may be included in the handle assembly 14 (FIG. 1). The shaft assembly controller 3022 and/or the power management controller 3016 can provide feedback to a user of the surgical instrument 10 through the output device 3042. The interface 3024 can be configured to connect the shaft assembly controller 3022 and/or the power management controller 3016 to the output device 3042. The reader will appreciate that the output device 3042 can instead be integrated with the power assembly 3006. In such circumstances, communication between the output device 3042 and the shaft assembly controller 3022 may be accomplished through the interface 3024 while the shaft assembly 200 is coupled to the handle assembly 14.

Having described a surgical instrument 10 (FIGS. 1-4) and various control circuits 2000, 3000 for controlling the operation thereof, the disclosure now turns to various specific configurations of the surgical instrument 10 and control circuits 2000 (or 3000).

In various aspects the present disclosure provides techniques for data storage and usage. In one aspect, data storage and usage is based on multiple levels of action thresholds. Such thresholds include upper and lower ultimate threshold limits, ultimate threshold that shuts down motor or activates return is current, pressure, firing load, torque is exceeded, and alternatively, while running within the limits the device automatically compensates for loading of the motor.

In one aspect, the instrument 10 (described in connection with FIGS. 1-29) can be configured to monitor upper and lower ultimate threshold limits to maintain minimum and maximum closure clamp loads within acceptable limits. If a minimum is not achieved the instrument 10 cannot start or if it drops below minimum a user action is required. If the clamp load is at a suitable level but drops under minimum during firing, the instrument 10 can adjust the speed of the motor or warn the user. If the minimum limit is breached during operation the unit could give a warning that the firing may not be completely as anticipated. The instrument 10 also can be configured to monitor when the battery voltage drops below the lower ultimate limit the remaining battery power is only direct able towards returning the device to the I-beam parked state. The opening force on the anvil can be employed to sense jams in the end effector. Alternatively, the instrument 10 can be configured to monitor when the motor current goes up or the related speed goes down, then the motor control increases pulse width or frequency modulation to keep speed constant.

In another aspect, the instrument 10 can (FIG. 1) be configured to detect an ultimate threshold of current draw, pressure, firing load, torque such that when any of these thresholds are exceeded, the instrument 10 shuts down the motor or causes the motor to return the knife to a pre-fired position. A secondary threshold, which is less than the ultimate threshold, may be employed to alter the motor control program to accommodate changes in conditions by changing the motor control parameters. A marginal threshold can be configured as a step function or a ramp function based on a proportionate response to another counter or input. For example, in the case of sterilization, no changes between 0-200 sterilization cycles, slow motor 1% per use from 201-400 sterilization cycles, and prevent use over 400 sterilization cycles. The speed of the motor also can be varied based on tissue gap and current draw.

There are many parameters that could influence the ideal function of a powered reusable stapler device. Most of these parameters have an ultimate maximum and/or minimum threshold beyond which the device should not be operated. Nevertheless, there are also marginal limits that may influence the functional operation of the device. These multiple limits, from multiple parameters may provide an overlying and cumulative effect on the operations program of the device.

Accordingly, the present disclosure relates to surgical instruments and, in various circumstances, to surgical stapling and cutting instruments and staple cartridges therefor that are designed to staple and cut tissue.

Efficient performance of an electromechanical device depends on various factors. One is the operational envelope, i.e., range of parameters, conditions and events in which the device carries out its intended functions. For example, for a device powered by a motor driven by electrical current, there may be an operational region above a certain electrical current threshold where the device runs more inefficiently than desired. Put another way, there may be an upper "speed limit" above which there is decreasing efficiency. Such an upper threshold may have value in preventing substantial inefficiencies or even device degradation.

There may be thresholds within an operational envelope, however, that may form regions exploitable to enhance efficiency within operational states. In other words, there may be regions where the device can adjust and perform better within a defined operational envelope (or sub-envelope). Such a region can be one between a marginal threshold and an ultimate threshold. In addition, these regions may comprise "sweet spots" or a predetermined optional range or point. These regions also may comprise a large range within which performance is judged to be adequate.

An ultimate threshold can be defined, above which or below which an action or actions could be taken (or refrained from being taken) such as stopping the device. In addition, a marginal threshold or thresholds can be defined, above which or below which an action or actions could be taken (or refrained from being taken). By way of non-limiting example, a marginal threshold can be set to define where the current draw of the motor exceeds 75% of an ultimate threshold. Exceeding the marginal threshold can result, for example, in the device's beginning to slow motor speed at an increasing rate as it continues to climb toward the ultimate threshold.

Various mechanisms can be employed to carry out the adjustment(s) taken as a result of exceeding a threshold. For example, the adjustment can reflect a step function. It can also reflect a ramped function. Other functions can be utilized.

In various aspects, to enhance performance by additional mechanisms, an overlaying threshold can be defined. An overlaying threshold can comprise one or more thresholds defined by multiple parameters. An overlaying threshold can result in one or more thresholds being an input into the generation of another threshold or thresholds. An overlaying threshold can be predetermined or dynamically generated such as at runtime. The overlaying threshold may come into effect when you the threshold is defined by multiple inputs. For example, as the number of sterilization cycles exceeds 300 (the marginal threshold) but not 500 (the ultimate threshold) the device runs the motor slower. Then as the current draw exceeds its 75% marginal threshold it multiples the slow down going even slower.

Figure 30:
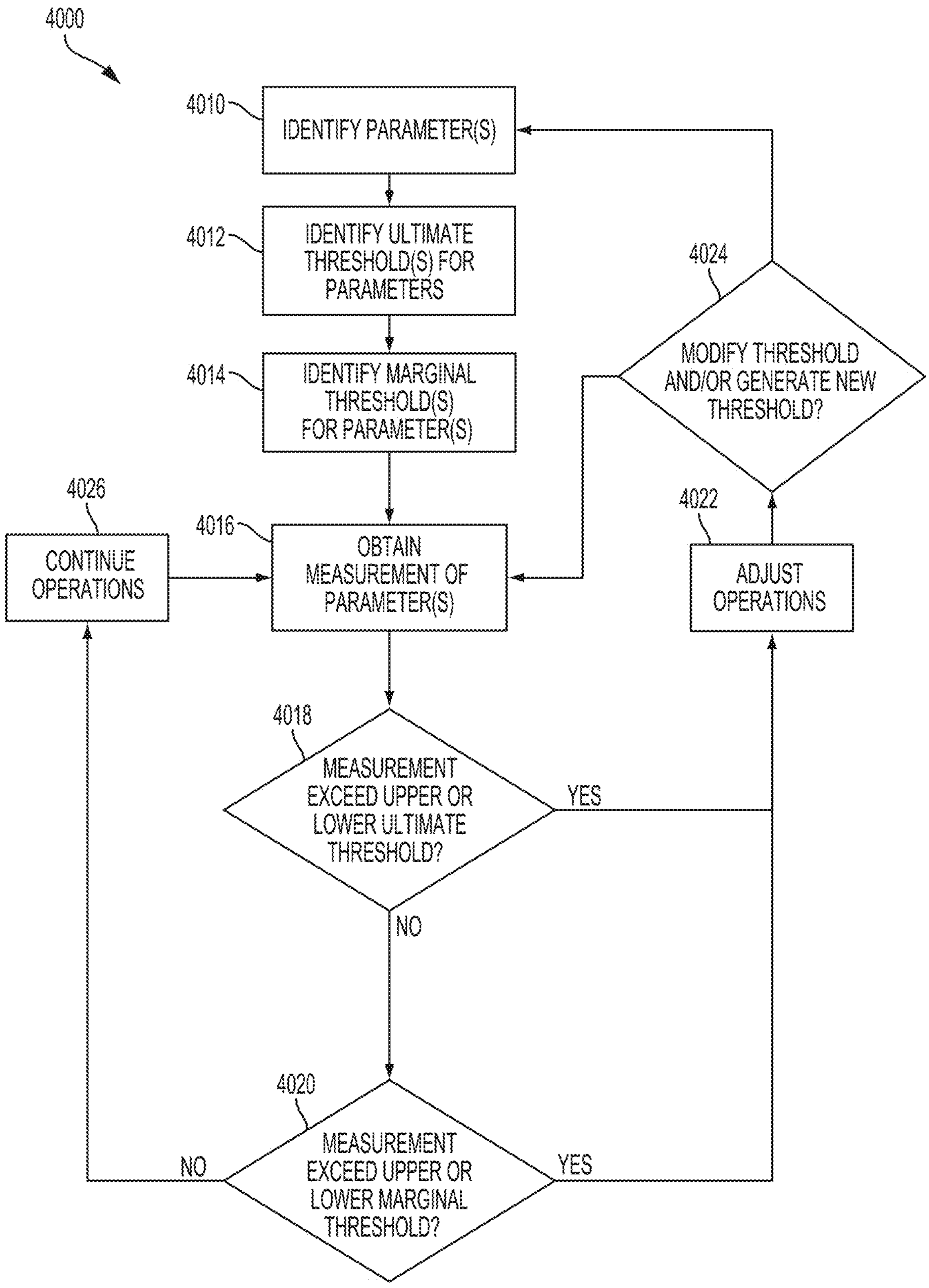
FIG. 30 illustrates one aspect of a process for utilizing thresholds to modify operations of a surgical instrument.

FIG. 30 is a logic diagram disclosing aspects of a multiple-level threshold system wherein a threshold rules framework 4000. Parameters can be identified 4010, such parameters representing quantities, amounts, states, events or more. For example, parameters identified can include one or more of current, voltage, tissue pressure, tissue thickness, jaw closure rate, tissue creep rate, firing load, knife thickness, torque, or battery usage. An ultimate threshold or thresholds for these parameters can be identified 4012. For instance, a predetermined current draw can be identified. As but one example, an ultimate electrical current draw threshold may be defined as 100% of a selected current magnitude. There can be an upper ultimate threshold, a lower ultimate threshold, multiple lower or upper ultimate thresholds depending on the circumstances, or a range defining an ultimate threshold. It will be appreciated that an "ultimate" threshold can be defined and/or calibrated in such a way as to remain essentially a unitary threshold but embody various action triggers. A marginal threshold or thresholds can be identified 4014. If the marginal threshold is exceeded, a motor control program can alter operations to accommodate change.

One or more thresholds can be monitored an acted on during a single surgical procedure, wherein the thresholds are independent of each other with no interaction. In addition, there can be an interactive association between thresholds of two or more parameters. For example, a marginal threshold for a parameter based on current draw can be 75% of the ultimate threshold. In addition, in connection with a parameter based on number of sterilization cycles, a marginal threshold may be set at 200 sterilization cycles, and an ultimate threshold at sterilization 400 cycles. Motor use can proceed normally from 0-199 cycles, and then slow by 1% from 200 cycles to 399. At cycle 400, motor use can be prevented. It will be appreciated, however, that there can be an interactive effect. In other words, because motor speed is reduced by 1% due to exceeding the sterilization cycle threshold, the current draw threshold can be correspondingly adjusted. This interactive effect can result in the motor running more slowly than it would if either input were considered independently.

Thus, the value of one threshold can be an input into the value of another threshold, or one threshold can be completely independent of another threshold. Where two or more thresholds are activated, it can be considered that there can be an overlaying threshold. As a result, multiple thresholds, defining multiple boundaries and limits, can have an overlaying or cumulative effect on operations of instrument 10 (FIGS. 1-4). And, one threshold in a multiple-threshold operation scenario can have a cause-and-effect with another threshold, or there may be no cause-and-effect and the thresholds may exist independent of each other.

In addition, a threshold can be dynamically set and/or reset depending on conditions experienced during surgery or other conditions. In other words, prior to a given surgical procedure, a module or modules can be preprogrammed into instrument 10 (FIGS. 1-4) or uploaded as needed. Also, a threshold can be dynamically determined, or uploaded, during a surgical procedure.

Turning briefly now to FIG. 1, numerous parameters can be assigned thresholds. Thus, in examples thresholds may be assigned based on tissue gap between the anvil 306 and staple cartridge 304, or anvil 306 and second jaw member 302, of an end effector 300, and motor speed varied thereby. In addition, in example thresholds based on current can vary motor speed control. Further, in various examples ultimate, marginal and overlaying thresholds can be established in connection with closure clamp loads in furtherance of an acceptable operating range. Plus, in various examples opening force on an anvil 306 can help to detect a jam. Further, in various examples if a minimum threshold is not achieved, the system may be prevented from starting or if it drops below a minimum then a user action can be required.

Still with reference to FIG. 1, in various aspects, it can be determined whether clamp load is acceptable and when clamp load drops under a minimum threshold during firing the speed of the motor can be adjusted and/or the clinician warned. In various examples, when a minimum threshold is exceeded during operation, instrument 10 can give a warning that the firing may not be completely as anticipated. Moreover, in various examples thresholds can be assigned wherein if battery charge falls below a threshold then remaining battery charge can be used to return the device to a parked state with respect to the I-beam.

However, thresholds can be referenced even during operations that do not exceed a threshold. Thus, for example, instrument 10 can, while running "within limits", compensate for the loading of the motor. For instance, if current goes up or related speed goes down, then motor control can increase pulse width or frequency modulation to help to maintain a constant speed. In other words, measures can be taken to improve and/or optimize operations of instrument 10 even while running "within limits."

In addition, dynamically during a surgical procedure, a threshold can be modified, or a new threshold generated. This can occur after several events including adjusting operations of the instrument 10.

Turning now back to FIG. 30, in various aspects a parameter or parameters are identified 4010. Further, an ultimate threshold or thresholds for a given parameter(s) are identified 4012. In addition, a marginal threshold or thresholds for a given parameter(s) are identified 4014. Measures 4010, 4012, and 4014 can be accomplished prior to the procedure, during the procedure, or both.

Measurements of a parameter(s) are obtained 4016. It can be determined whether the measurement of a given parameter exceeds an upper or lower ultimate threshold for the parameter 4018. When the answer is no, it can be determined whether the measurement of a given parameter exceeds an upper or lower marginal threshold for the parameter 4020. When the answer is no, operations can be continued 4026. And, measurements of a given parameter(s) can be again obtained.

When, however, the answer is yes to whether the measurement of a given parameter exceeds an upper or lower ultimate threshold for the parameter 4018, control can pass to where operations can be adjusted 4022. Many types of adjustments can be made. One example is to vary motor speed. It can be determined whether to modify a given threshold and/or generate a new threshold 4024. This can occur after operations have been adjusted 4022.

After operations are adjusted, it can be determined whether to modify a threshold or generate a new threshold. For example, a marginal threshold initially set at 75% can be set to a different value. In addition, a new threshold on the same parameter, or a new threshold on a new parameter, can be generated if desired.

Upon determining whether to modify a threshold or generate a new one, control can pass back to step 4016 where measurement of a parameter(s) is obtained. In addition, control can proceed to identify 4010 parameters.

When the answer to whether the measurement exceeds an upper or lower ultimate threshold is no, however, then it can be determined when the measurement exceeds an upper or lower marginal threshold. When the answer is yes, then operations can be adjusted 4022 and control proceed as above. When the answer is no, operations can be continued 4026 and control proceed to measuring a parameter(s).

It will be appreciated that the sequence of steps can be varied and is not limited to that specifically disclosed in FIG. 30. As just one example, after obtaining measurement of a parameter(s) 4016, it can then be determined whether a marginal threshold is exceeded 4020. In addition, an overlaying threshold can expressly be identified and considered in the course of the flow.

Figure 31:
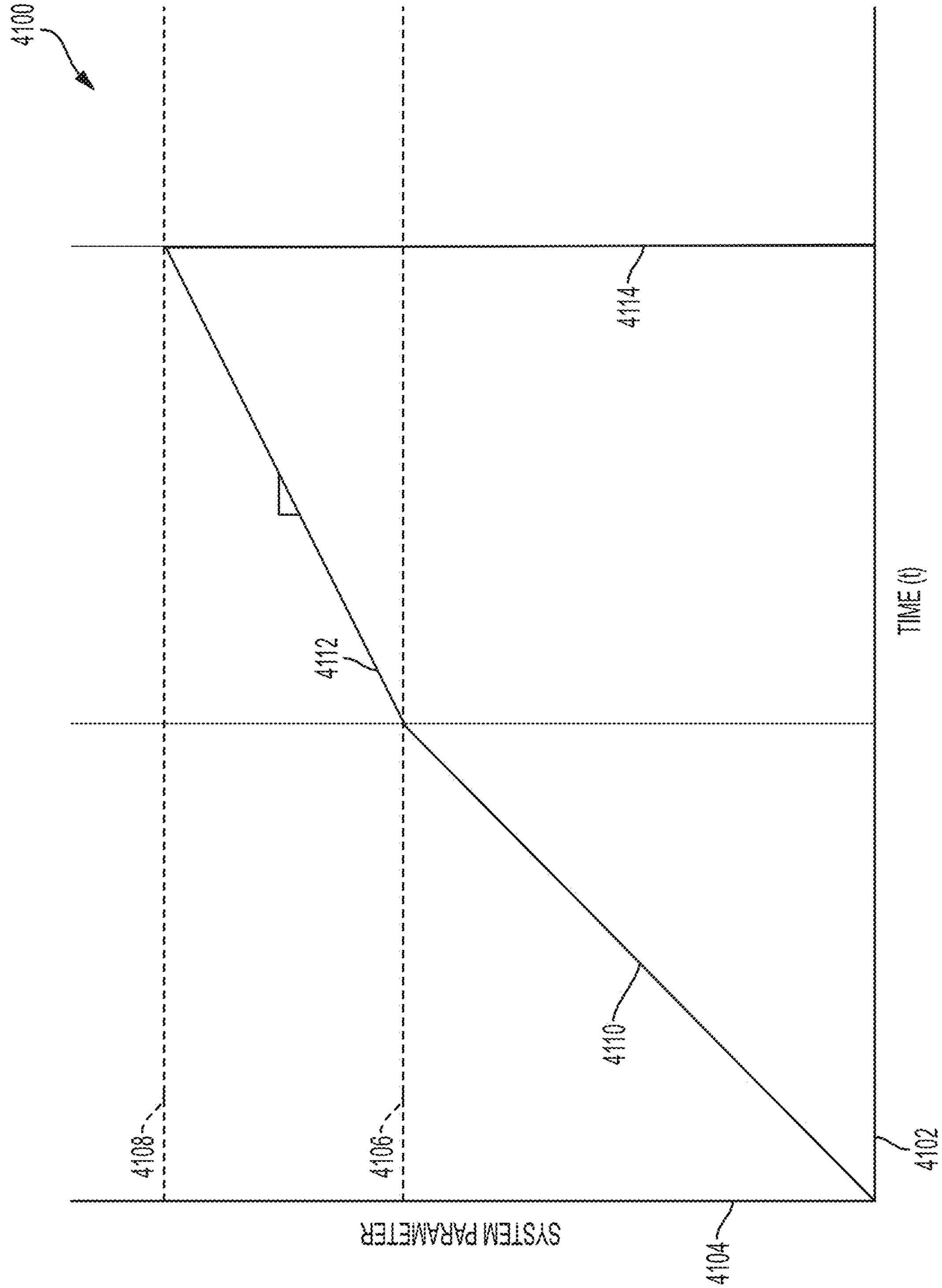
FIG. 31 illustrates an example graph showing modification of operations of a surgical instrument describing a linear function.

FIG. 31 is a graphical representation 4100 of instrument system parameters versus time depicting how, in one aspect, instrument system parameters can be adjusted in the event that a threshold is reached. Time (t) is shown along a horizontal (x) axis 4102 and the instrument System Parameter is shown along a vertical (y) axis 4104, marginal threshold 4104 and ultimate threshold 4106. In the graphical representation 4100 depicted in FIG. 34, the y-axis parameter 4102 is the one to which a threshold of instrument system parameter is assigned and the x-axis 4102 represents time. At a certain time during operation of instrument 10 (FIGS. 1-4), as evidenced by function 4110, a measurement can indicate that marginal threshold 4106 is reached. At this point, operations of the instrument 10 (FIGS. 1-4) can be adjusted. For example, when the y-axis 4104 parameter is electrical current draw by a motor, a function can be imposed on the subsequent electrical current draw and limit current in some fashion. In one example, the function can represent a linear progression 4112. At a certain time in the course of operation, an ultimate threshold 4108 can be reached. At this point, electrical current can be discontinued 4114. Accordingly, an adjustment mechanism can be accomplished via a linear function. An additional perspective with which to view the operational adjustment is that there can be a square-wave multiplier change.

Figure 32:
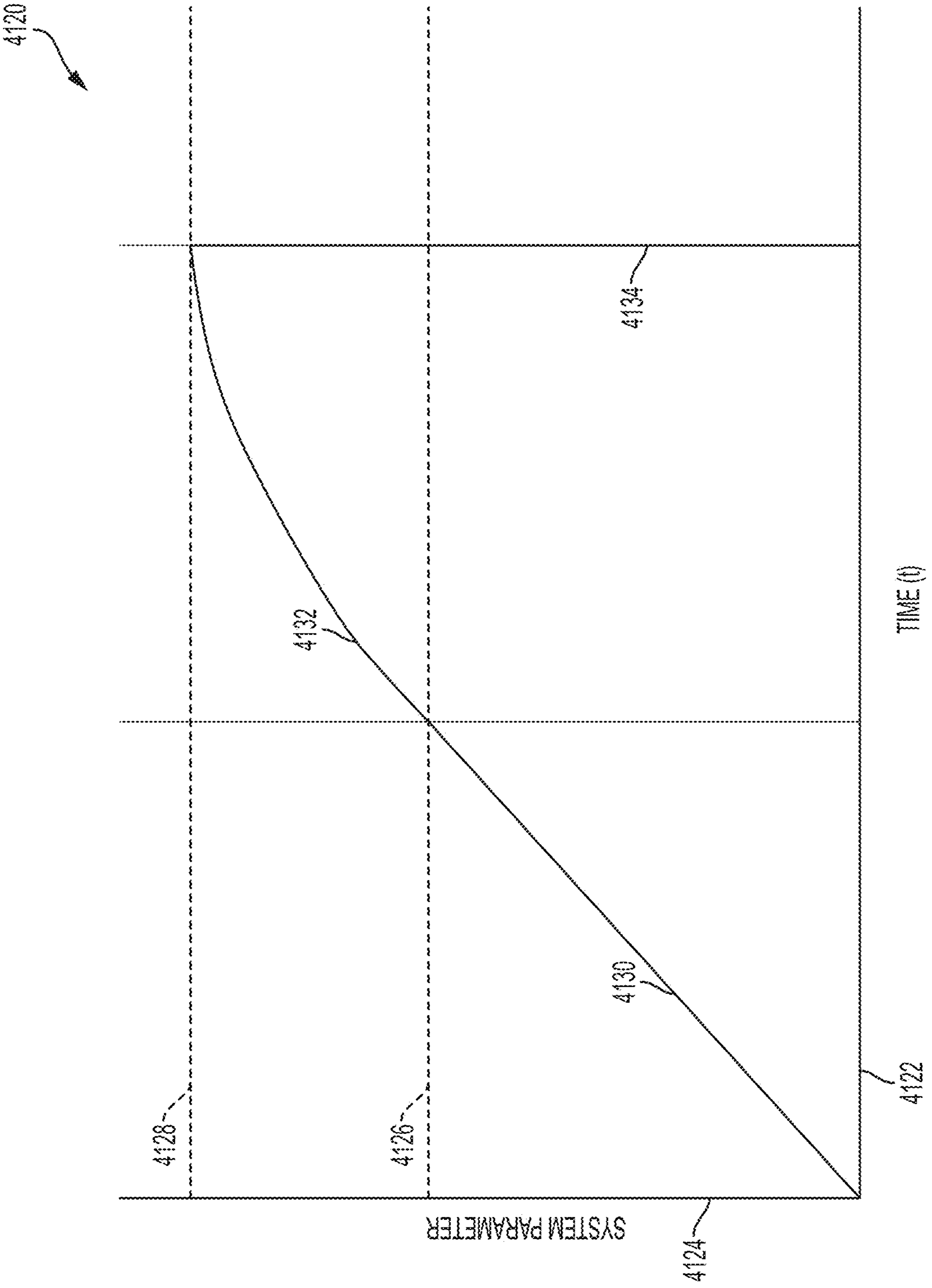
FIG. 32 illustrates an example graph showing modification of operations of a surgical instrument describing a non-linear function.

FIG. 32 is a graphical representation 4120 of instrument system parameter depicting how, in another aspect, a system parameter can be adjusted in the event that a threshold is reached. Time (t) is shown along a horizontal (x) axis 4122 and the number of Instrument Operations is shown along a vertical (y) axis 4124, marginal threshold 4126 and ultimate threshold 4128. Here the y-axis 4124 parameter is the one to which a threshold is assigned. At a certain time during operation of instrument 10 (FIGS. 1-4), a measurement can indicate that the marginal threshold 4126 is reached during the course of operation 4130. At this point, operations of the instrument 10 can be adjusted. For example, when the y-axis 4124 parameter is electrical current draw by a motor, a limit can be placed on the subsequent current draw representing a non-linear progression 4132. At a certain time after this, an ultimate threshold 4128 can be reached. At this point, current can be discontinued 4134. Accordingly, an adjustment mechanism can be accomplished via a non-linear function 4132, with a variable slope. An additional perspective with which to view the operational adjustment is that there is an exponential multiplier change; here, the closer the y-axis 4124 parameter comes to the ultimate threshold 4128, the rate at which current increases diminishes.

Figure 33:
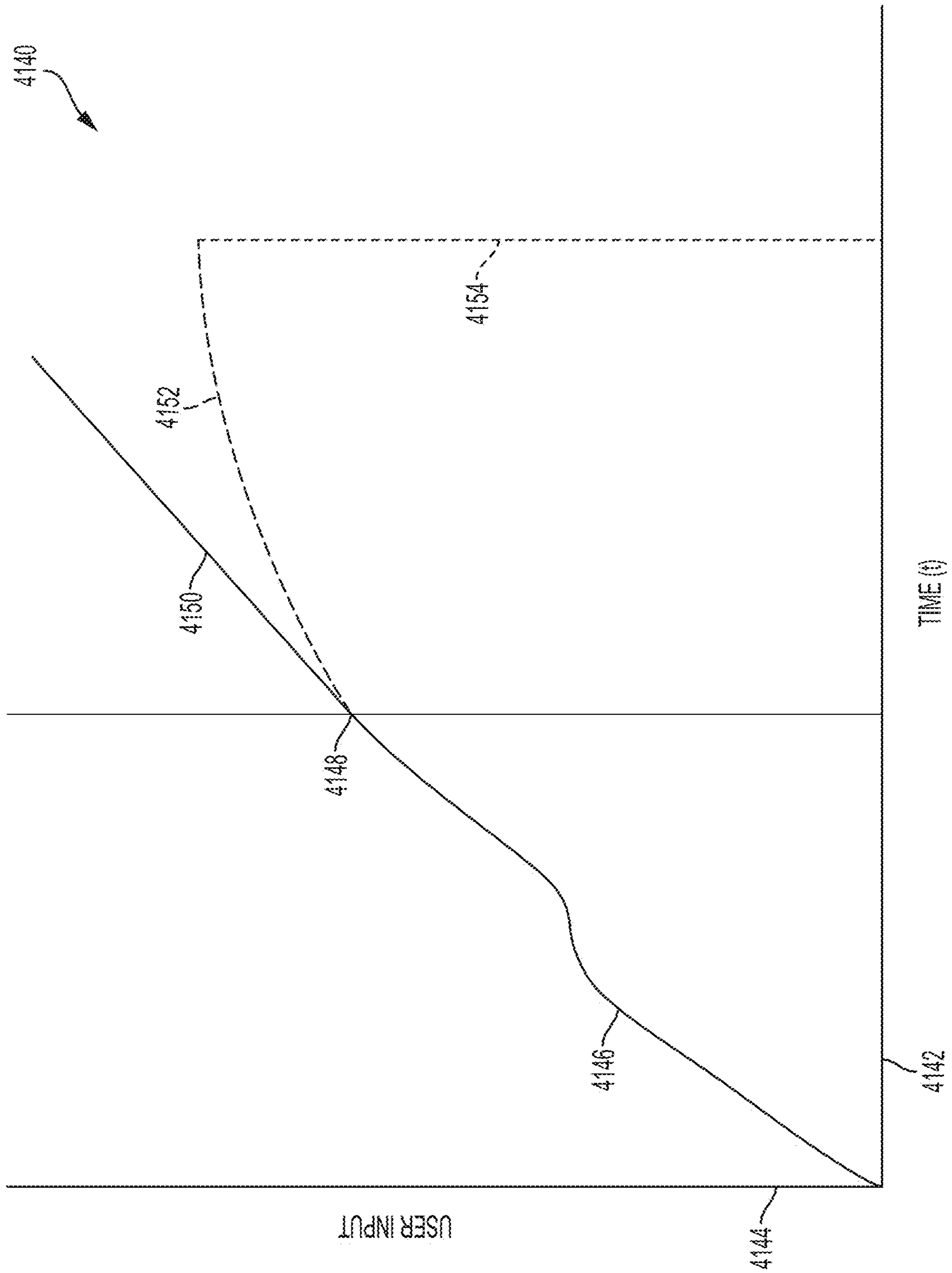
FIG. 33 illustrates an example graph showing modification of operations of a surgical instrument based on an expected user input parameter.

FIG. 33 is a graphical representation 4140 that represents one aspect wherein a response by instrument 10 (FIGS. 1-4) to clinician input (User Input) is detected and then a modification is made. Time (t) is shown along a horizontal (x) axis 4142 and User Input is represented along a vertical (y) axis 4144. In other words, a clinician, in performing a procedure, can actuate a response by instrument 10 such as depressing closure trigger 32 (FIG. 1) which may for example cause motor operation 4146. As motor speed increases there may or not be a threshold reached. At a certain point, however, here represented by the divergence point 4148 of curves 4150 and 4152, it can be determined that motor speed has reached an actual level, or a future level be predicted, that is or will be suboptimal or otherwise undesirable. At this point, rather than following the actual or expected speed curve 4150, instrument 10 can employ a control measure such as an algorithm to adapt or otherwise modify the output, thus regulating the motor. At a certain point, motor actuation can be discontinued 4154. In other words, instrument 10 can take an actual or expected y-axis parameter and, determining that such actual or expected measurement is excessive, employ an algorithm to modify such parameter. Put another way, measured clinician behavior can comprise a value for a threshold or thresholds.

Figure 34:
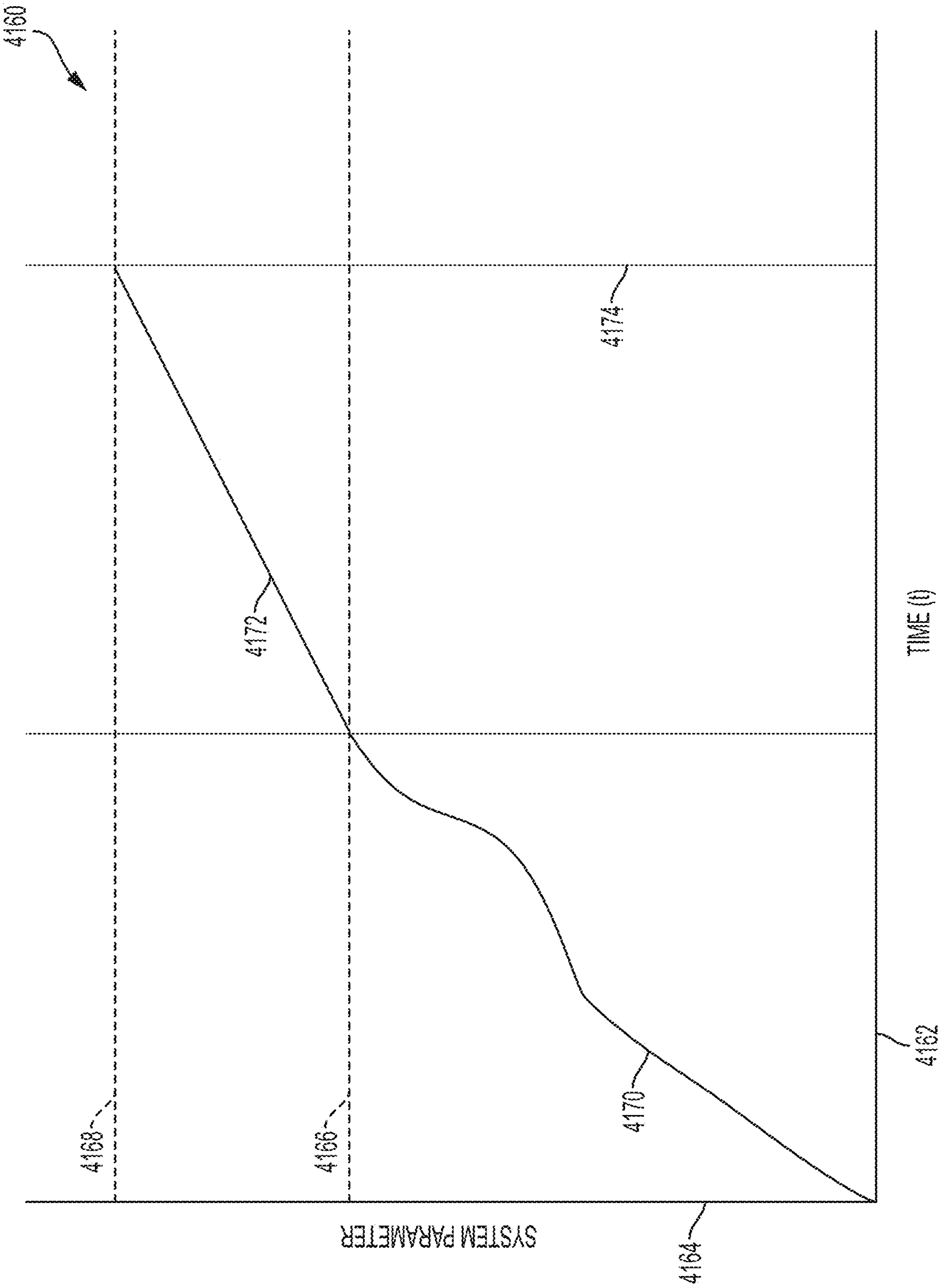
FIG. 34 illustrates an example graph showing modification of velocity of a drive based on detection of a threshold.

FIG. 34 is a graphical representation 4160 of instrument system parameters that represents one aspect wherein instrument 10 (FIGS. 1-4) detects whether a marginal threshold 4166 or ultimate threshold 4168 is reached, and responds accordingly. Time (t) is shown along the horizontal (x) axis 4162 and instrument System Parameters is shown along the vertical (y) axis 4164. For example, here the vertical (y) axis 4154 parameter can be the velocity of a drive, such as a closure drive system 30 (FIG. 1) or firing drive system 80 (FIG. 1). Instrument 10 can check whether during the course of operation 4170 a marginal threshold 4166 velocity is reached. When the marginal threshold 4166 is reached, a control measure such as an algorithm can be used to adapt or otherwise modify the velocity 4172. The modified velocity 4172 can be given by a linear or non-linear function. And, at an ultimate threshold, power to the motor can be discontinued 4174.

It will be appreciated that where FIG. 33 can represent a situation where an actual or predicted value is evaluated, whether or not an express threshold is provided, FIG. 34 is a graphical representation where thresholds are provided. It can be appreciated, however, that a threshold or thresholds can be implicitly given to FIG. 33 with equivalent results, insofar as a predetermined or dynamically determined value can serve as a functional equivalent of a threshold, or trigger actions associated with a threshold or thresholds. There may be two or more ceiling or floor values that can serve as such threshold functional equivalents.

Figure 35:
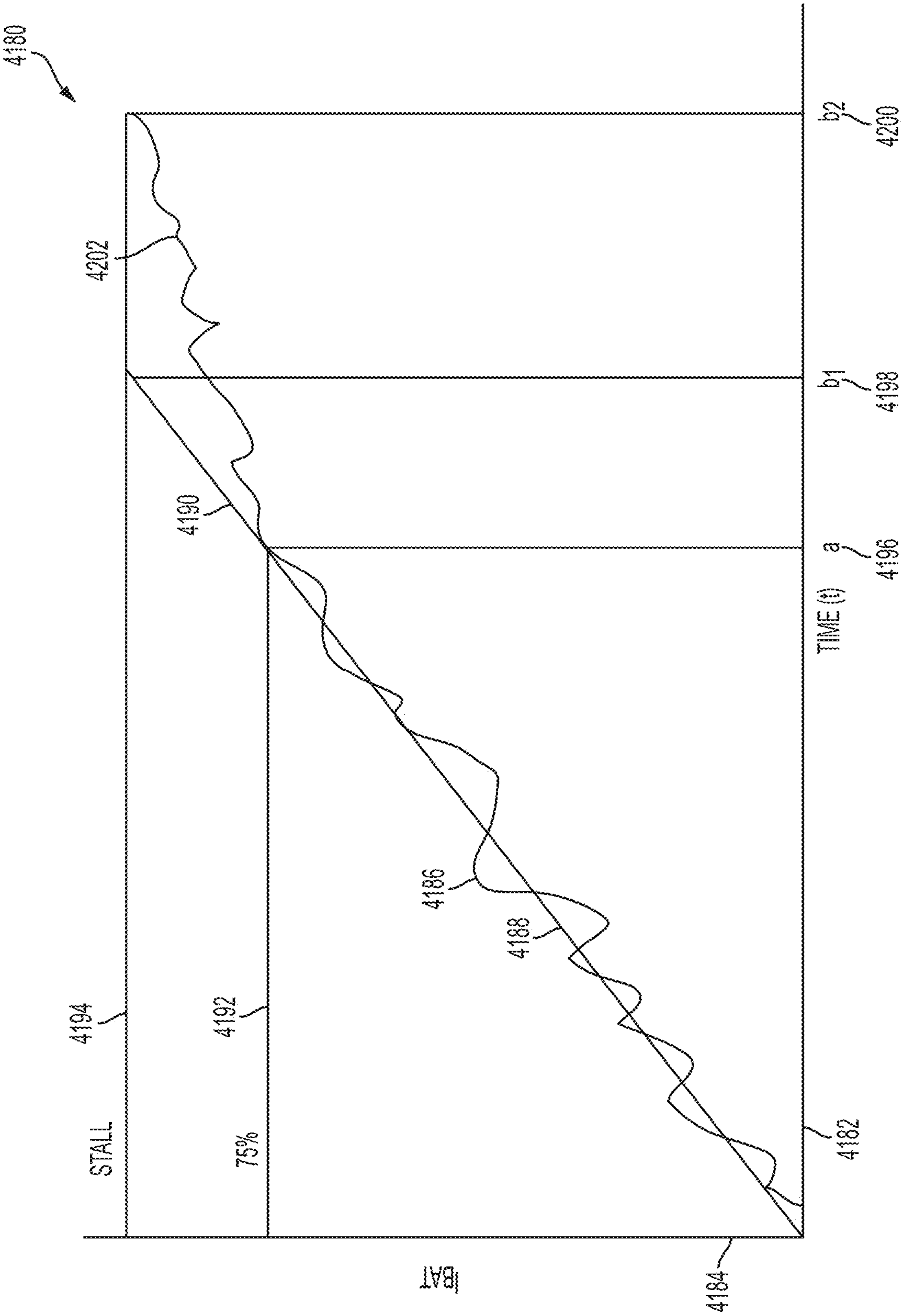
FIG. 35 illustrates an example graph showing modification in connection with operations based on battery current based on detection of a threshold.

Turning to another example using thresholds, FIG. 35 is a graphical representation 4180 of battery current versus time, where Time (t) is shown along the horizontal (x) axis 4182 and battery current $I_{BAT}$ is shown along the vertical (y) axis 4184. In one example battery current $I_{BAT}$ 4184 is monitored under varying operational conditions. As motor speed increases, current drawn 4186 from a battery 90 (FIG. 4) increases. Current drawn can increase in a non-linear manner depending on several factors; however, instrument 10 (FIGS. 1-4) can resolve the current drawn into a linear function 4188. The linear function can be based on (1) averaging overall current, (2) be based on a prediction of future current based on past and/or present current, both (1) and (2), or another function. Linear function 4188 can be extended out theoretically to linear function 4190, which is an extrapolated extension with the same slope as linear function 4188.

Once linear function 4188 reaches a marginal threshold 4192, instrument 10 (FIGS. 1-4) can take action to modify the response. Here the marginal threshold is given as 75% of an ultimate threshold 4194 wherein the ultimate threshold represents a motor stall; however, it will be appreciated that the selection of the marginal threshold or ultimate threshold can be made based on multiple factors. In other words, marginal threshold 4192 can be reached at time "a" 4196. If adjustments are not made, it is expected that motor stall would occur at time "b1" 4198. However, due to adjustments made by instrument 10, the actual motor stall will not occur until time "b2" 4200. It is possible that a stall might not occur at all, because the more graduated rise may help to prevent such an event. Function 4202, which is implemented via a control measure, can be based on slowing the motor, or another adjustment. It can manifest as a stepped, ramped or further function.

Employing the thresholds herein can give the clinician greater time to react and adapt, maintain a desired efficiency of the instrument, and prolong battery life. Thus, utilizing thresholds can provide multiple benefits in connection with ease of clinician use and protection of the instrument itself.

Figure 36:
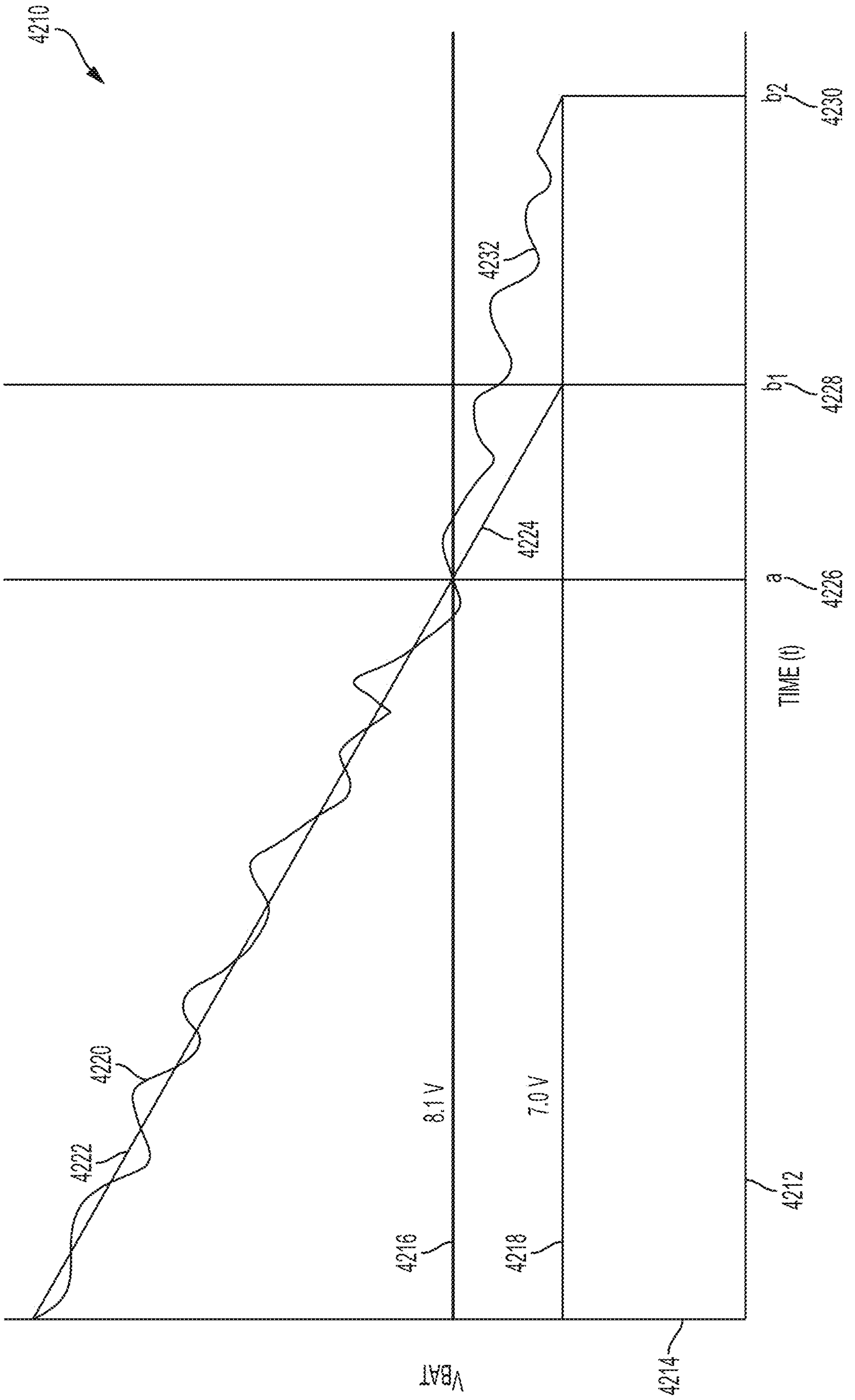
FIG. 36 illustrates an example graph showing modification in connection with operations based on battery voltage based on detection of a threshold.

Turning to another aspect, FIG. 36 is a graphical representation 4210 of battery voltage that shows Time (t) along the horizontal (x) axis 4212 and battery voltage VBAT along the vertical (y) axis 4214. In one example a threshold can be set in connection with battery voltage VBAT 4214. Here a marginal threshold 4216 can be set at 8.1V. Additionally, an ultimate threshold 4218 can be set at 7.0V. During the course of operation of instrument 10 (FIGS. 1-4), voltage can decrease over time. The curve described by measuring the voltage decrease 4220 is not necessarily linear. However, instrument 10 can resolve the voltage decrease into a linear function 4222. The linear function can be based on (1) averaging overall voltage, (2) be based on a prediction of future voltage based on past and/or present voltage, both (1) and (2), or another function. Linear function 4222 can be extrapolated out theoretically to linear function 4224, which has the same slope as linear function 4222.

Once linear function 4222 reaches a marginal threshold 4216, instrument 10 can take action to modify the response. Marginal threshold 4216 is reached at time "a" 4226. If adjustments are not made, it is expected that a depleted battery condition would occur at time "b1" 4228. However, due to adjustments made by instrument 10 (FIGS. 1-4), the actual depleted battery condition will not occur until time "b2" 4230. Again, it is possible that it may not occur at all. Function 4232, which can be implemented via a control measure, can be based on slowing the motor, or another adjustment. It can manifest as a stepped, ramped or further function.

Figure 37:
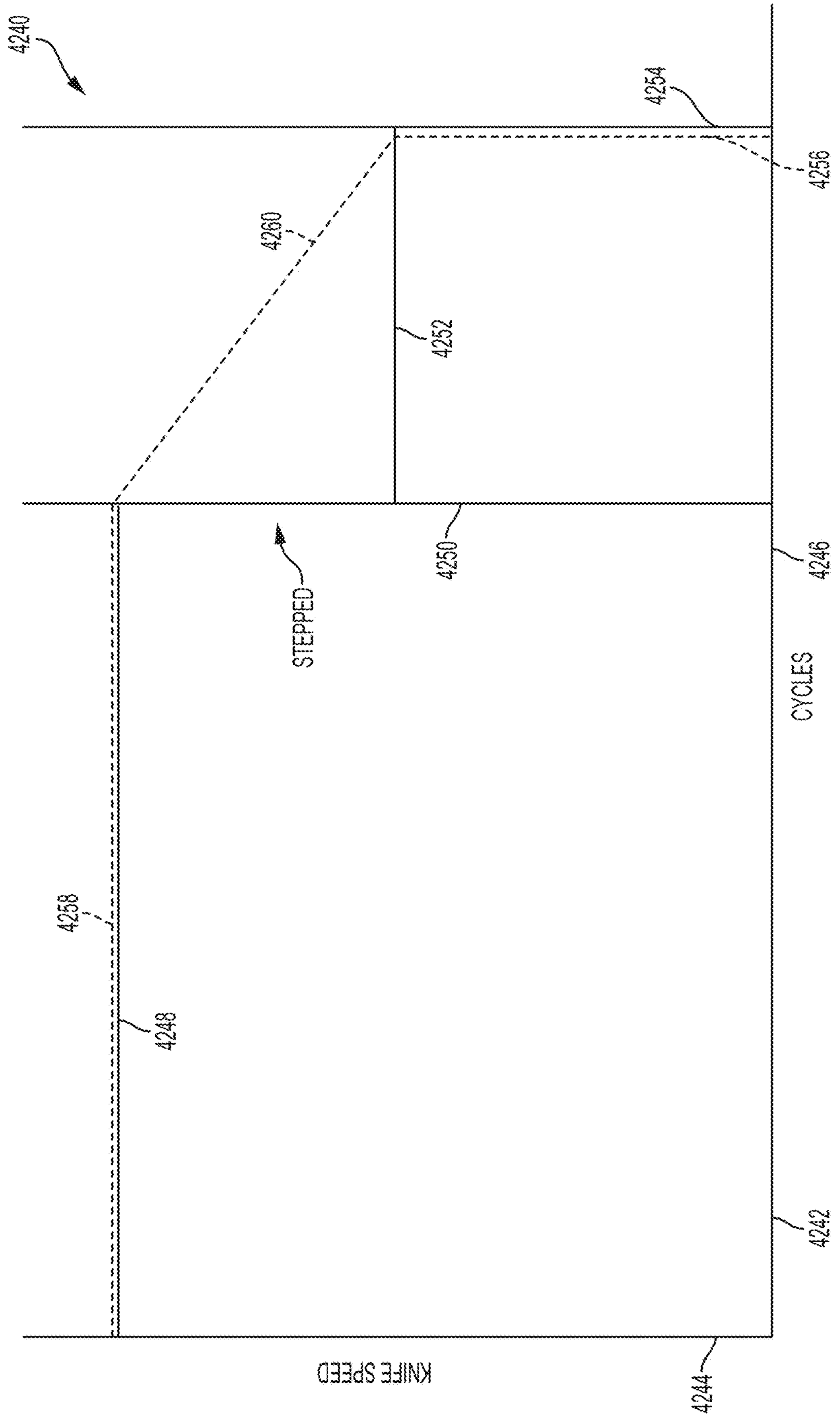
FIG. 37 illustrates an example graph showing modification of knife speed based on detection of a cycle threshold.

FIG. 37 is a graphical representation 4240 of knife speed versus number of cycles where and Cycles is shown along the horizontal (x) axis 4242 and Knife Speed is shown along the vertical (y) axis 4244. As shown in the example illustrated by FIG. 37, thresholds can be employed to adjust speed of a knife 280 (FIG. 8) based on the number of cycles. Relevant cycles can refer to an amount of firings performed by instrument 10 (FIGS. 1-4), sterilization cycles performed by instrument 10, or other measured events. An objective of managing instrument operation by this threshold mechanism is to maximize the likelihood that an incision will be effective, taking into account potential blunting of the knife 280 edge after multiple uses. In this example, firing of the knife can be initialized based on an expected speed. However, once a marginal threshold 4246 is reached based on number of cycles, speed can be reduced from speed 4248 to 4252, such as in a stepped manner 4250. Thus, once marginal threshold 4760 is exceeded, knife 280 will fire at a progressively lower speed. This will occur for a given number of cycles 4246 until ultimate threshold 4254 is reached. At this point, knife speed will be stepped down 4256 even more or of course instrument 10 can alert the clinician that it may be undesirable to incise with the knife, and can lock out firing. It will be understood that function 4248 shows employing a stepped function once a threshold 4246 is reached, and function 4258 shows employing a ramped function 4260 once a threshold 4246 is reached. Additional functions can be employed.

Further, it will be appreciated that the thresholds given in FIG. 37 have been defined on the x-axis 4711, whereas prior figures have shown thresholds on the y-axis 4712. It will also be appreciated that there can be an additional axis or axes taken into account, i.e., a z-axis or further axes, wherein the interrelationship of multiple variables can be considered. Further, thresholds from a first parameter can be considered along with thresholds from a second parameter, and one threshold can comprise an input into another threshold, and vice versa.

When a threshold is exceeded, the clinician can be notified. This can be based on a feedback system. In certain instances, the feedback system may comprise one or more visual feedback systems such as display screens, backlights, and/or LEDs, for example. In certain instances, the feedback system may comprise one or more audio feedback systems such as speakers and/or buzzers, for example. In certain instances, the feedback system may comprise one or more haptic feedback systems, for example. In certain instances, the feedback system may comprise combinations of visual, audio, and/or tactile feedback systems, for example. Such feedback can serve to alert or warn the clinician.

Figure 38:
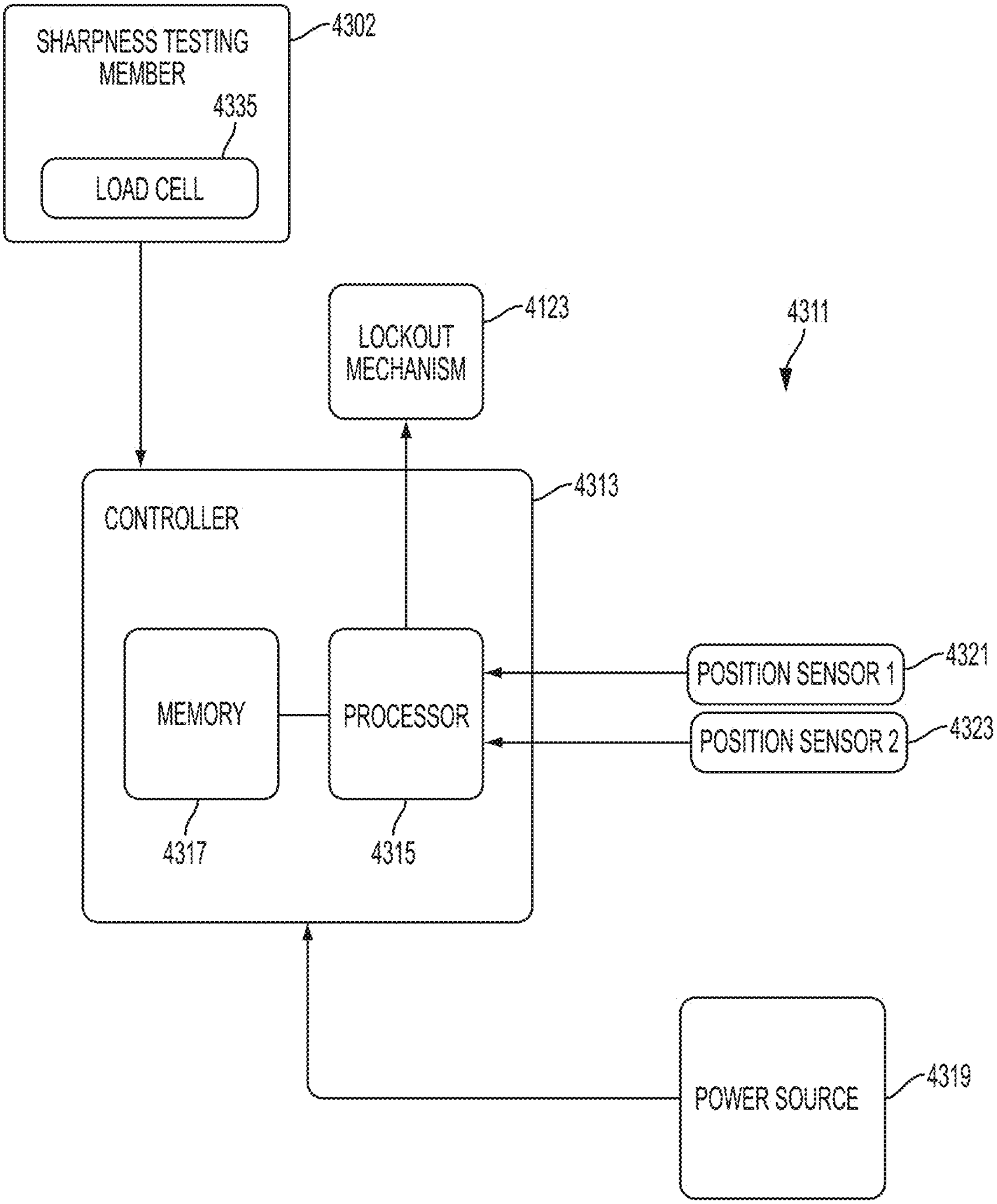
FIG. 38 illustrates a logic diagram of a system for evaluating sharpness of a cutting edge of a surgical instrument according to various aspects.

FIG. 38 illustrates a logic diagram of a system 4311 for evaluating sharpness of a cutting edge 182 (FIG. 20) of a surgical instrument 10 (FIGS. 1-4) according to various examples. FIG. 38 illustrates a sharpness testing system 4311 for evaluating sharpness of a cutting edge of a surgical instrument 10 according to various examples. In certain instances, the system 4311 can evaluate the sharpness of the cutting edge 182 by testing the ability of the cutting edge 182 to be advanced through a sharpness testing member 4302. For example, the system 4311 can be configured to observe the time period the cutting edge 182 takes to fully transect and/or completely pass through at least a predetermined portion of a sharpness testing member 4302. If the observed time period exceeds a predetermined threshold, the module 4310 may conclude that the sharpness of the cutting edge 182 has dropped below an acceptable level, for example.

In one aspect, the sharpness testing member 4302 can be employed to test the sharpness of the cutting edge 182 (FIG. 20). In certain instances, the sharpness testing member 4302 can be attached to and/or integrated with the cartridge body 194 (FIG. 20) of the staple cartridge 304 (FIGS. 1, 2, and 20), for example. In certain instances, the sharpness testing member 4302 can be disposed in the proximal portion of the staple cartridge 304, for example. In certain instances, the sharpness testing member 4302 can be disposed onto a cartridge deck or cartridge body 194 of the staple cartridge 304, for example.

In certain instances, a load cell 4335 can be configured to monitor the force (Fx) applied to the cutting edge 182 (FIG. 20) while the cutting edge 182 is engaged and/or in contact with the sharpness testing member 4302, for example. The reader will appreciate that the force (Fx) applied by the sharpness testing member 4302 to the cutting edge 182 while the cutting edge 182 is engaged and/or in contact with the sharpness testing member 4302 may depend, at least in part, on the sharpness of the cutting edge 182. In certain instances, a decrease in the sharpness of the cutting edge 182 can result in an increase in the force (Fx) required for the cutting edge 182 to cut or pass through the sharpness testing member 4302. The load cell 4335 of the sharpness testing member 4302 may be employed to measure the force (Fx) applied to the cutting edge 182 while the cutting edge 182 travels a predefined distance (D) through the sharpness testing member 4302 may be employed to determine the sharpness of the cutting edge 182.

In certain instances, the module 4311 may include a microcontroller 4313 ("controller") which may include a microprocessor 4315 ("processor") and one or more computer readable mediums or memory units 4317 ("memory"). In certain instances, the memory 4317 may store various program instructions, which when executed may cause the processor 4315 to perform a plurality of functions and/or calculations described herein. In certain instances, the memory 4317 may be coupled to the processor 4315, for example. A power source 4319 can be configured to supply power to the controller 4313, for example. In certain instances, the power source 4319 may comprise a battery (or "battery pack" or "power pack"), such as a Li ion battery, for example. In certain instances, the battery pack may be configured to be releasably mounted to the handle 14. A number of battery cells connected in series may be used as the power source 4319. In certain instances, the power source 4319 may be replaceable and/or rechargeable, for example.

In certain instances, the processor 4313 can be operably coupled to the feedback system and/or the lockout mechanism 4123, for example.

The module 4311 may comprise one or more position sensors. Example position sensors and positioning systems suitable for use with the present disclosure are described in U.S. patent application Ser. No. 13/803,210, entitled SENSOR ARRANGEMENTS FOR ABSOLUTE POSITIONING SYSTEM FOR SURGICAL INSTRUMENTS, and filed Mar. 14, 2013, now U.S. Patent Application Publication No. 2014/0263538, the disclosure of which is hereby incorporated by reference herein in its entirety. In certain instances, the module 4311 may include a first position sensor 4321 and a second position sensor 4323. In certain instances, the first position sensor 4321 can be employed to detect a first position of the cutting edge 182 (FIG. 20) at a proximal end of a sharpness testing member 4302, for example; and the second position sensor 4323 can be employed to detect a second position of the cutting edge 182 at a distal end of a sharpness testing member 4302, for example.

In certain instances, the position sensors 4321 and 4323 can be employed to provide first and second position signals, respectively, to the microcontroller 4313. It will be appreciated that the position signals may be analog signals or digital values based on the interface between the microcontroller 4313 and the position sensors 4321 and 4323. In one example, the interface between the microcontroller 4313 and the position sensors 4321 and 4323 can be a standard serial peripheral interface (SPI), and the position signals can be digital values representing the first and second positions of the cutting edge 182, as described above.

Further to the above, the processor 4315 may determine the time period between receiving the first position signal and receiving the second position signal. The determined time period may correspond to the time it takes the cutting edge 182 (FIG. 20) to advance through a sharpness testing member 4302 from the first position at a proximal end of the sharpness testing member 4302, for example, to a second position at a distal end of the sharpness testing member 4302, for example. In at least one example, the controller 4313 may include a time element which can be activated by the processor 4315 upon receipt of the first position signal, and deactivated upon receipt of the second position signal. The time period between the activation and deactivation of the time element may correspond to the time it takes the cutting edge 182 to advance from the first position to the second position, for example. The time element may comprise a real time clock, a processor configured to implement a time function, or any other suitable timing circuit.

In various instances, the controller 4313 can compare the time period it takes the cutting edge 182 (FIG. 20) to advance from the first position to the second position to a predefined threshold value to assess whether the sharpness of the cutting edge 182 has dropped below an acceptable level, for example. In certain instances, the controller 4313 may conclude that the sharpness of the cutting edge 182 has dropped below an acceptable level if the measured time period exceeds the predefined threshold value by 1%, 5%, 10%, 25%, 50%, 100% and/or more than 100%, for example.

Figure 39:
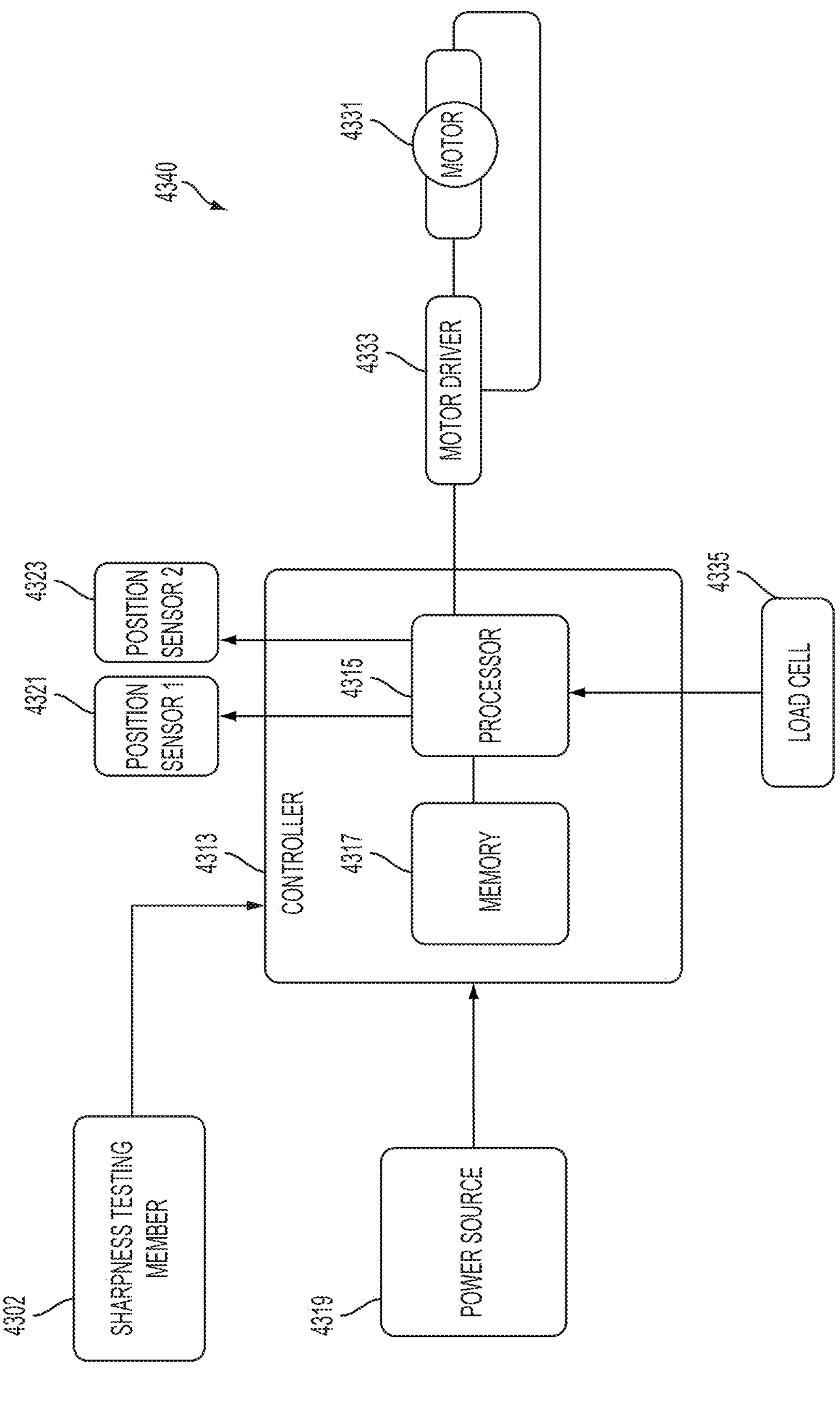
FIG. 39 illustrates a logic diagram of a system for determining the forces applied against a cutting edge of a surgical instrument by a sharpness testing member at various sharpness levels according to various aspects.

FIG. 39 illustrates a logic diagram of a system 4340 for determining the forces applied against a cutting edge of a surgical instrument 10 (FIGS. 1-4) by a sharpness testing member 4302 at various sharpness levels according to various aspects. Referring to FIG. 39, in various instances, an electric motor 4331 can drive the firing bar 172 (FIG. 20) to advance the cutting edge 182 (FIG. 20) during a firing stroke and/or to retract the cutting edge 182 during a return stroke, for example. A motor driver 4333 can control the electric motor 4331; and a microcontroller such as, for example, the microcontroller 4313 can be in signal communication with the motor driver 4333. As the electric motor 4331 advances the cutting edge 182, the microcontroller 4313 can determine the current drawn by the electric motor 4331, for example. In such instances, the force required to advance the cutting edge 182 can correspond to the current drawn by the electric motor 4331, for example. Referring still to FIG. 39, the microcontroller 4313 of the surgical instrument 10 can determine if the current drawn by the electric motor 4331 increases during advancement of the cutting edge 182 and, if so, can calculate the percentage increase of the current.

In certain instances, the current drawn by the electric motor 4331 may increase significantly while the cutting edge 182 (FIG. 20) is in contact with the sharpness testing member 4302 due to the resistance of the sharpness testing member 4302 to the cutting edge 182. For example, the current drawn by the electric motor 4331 may increase significantly as the cutting edge 182 engages, passes and/or cuts through the sharpness testing member 4302. The reader will appreciate that the resistance of the sharpness testing member 4302 to the cutting edge 182 depends, in part, on the sharpness of the cutting edge 182; and as the sharpness of the cutting edge 182 decreases from repetitive use, the resistance of the sharpness testing member 4302 to the cutting edge 182 will increase. Accordingly, the value of the percentage increase of the current drawn by the motor 4331 while the cutting edge is in contact with the sharpness testing member 4302 can increase as the sharpness of the cutting edge 182 decreases from repetitive use, for example.

In certain instances, the determined value of the percentage increase of the current drawn by the motor 4331 can be the maximum detected percentage increase of the current drawn by the motor 4331. In various instances, the microcontroller 4313 can compare the determined value of the percentage increase of the current drawn by the motor 4331 to a predefined threshold value of the percentage increase of the current drawn by the motor 4331. If the determined value exceeds the predefined threshold value, the microcontroller 4313 may conclude that the sharpness of the cutting edge 182 has dropped below an acceptable level, for example.

In certain instances, as illustrated in FIG. 39, the processor 4315 can be in communication with the feedback system and/or the lockout mechanism for example. In certain instances, the processor 4315 can employ the feedback system to alert a user if the determined value of the percentage increase of the current drawn by the motor 4331 exceeds the predefined threshold value, for example. In certain instances, the processor 4315 may employ the lockout mechanism to prevent advancement of the cutting edge 182 (FIG. 20) if the determined value of the percentage increase of the current drawn by the motor 4331 exceeds the predefined threshold value, for example. In certain instances, the system 4311 may include a first position sensor 4321 and a second position sensor 4323. The surgical instrument 10 (FIGS. 1-4) may include a load cell 4335.

In various instances, the microcontroller 4313 can utilize an algorithm to determine the change in current drawn by the electric motor 4331. For example, a current sensor can detect the current drawn by the electric motor 4331 during the firing stroke. The current sensor can continually detect the current drawn by the electric motor and/or can intermittently detect the current draw by the electric motor. In various instances, the algorithm can compare the most recent current reading to the immediately proceeding current reading, for example. Additionally or alternatively, the algorithm can compare a sample reading within a time period X to a previous current reading. For example, the algorithm can compare the sample reading to a previous sample reading within a previous time period X, such as the immediately proceeding time period X, for example. In other instances, the algorithm can calculate the trending average of current drawn by the motor. The algorithm can calculate the average current draw during a time period X that includes the most recent current reading, for example, and can compare that average current draw to the average current draw during an immediately proceeding time period time X, for example.

Figure 40:
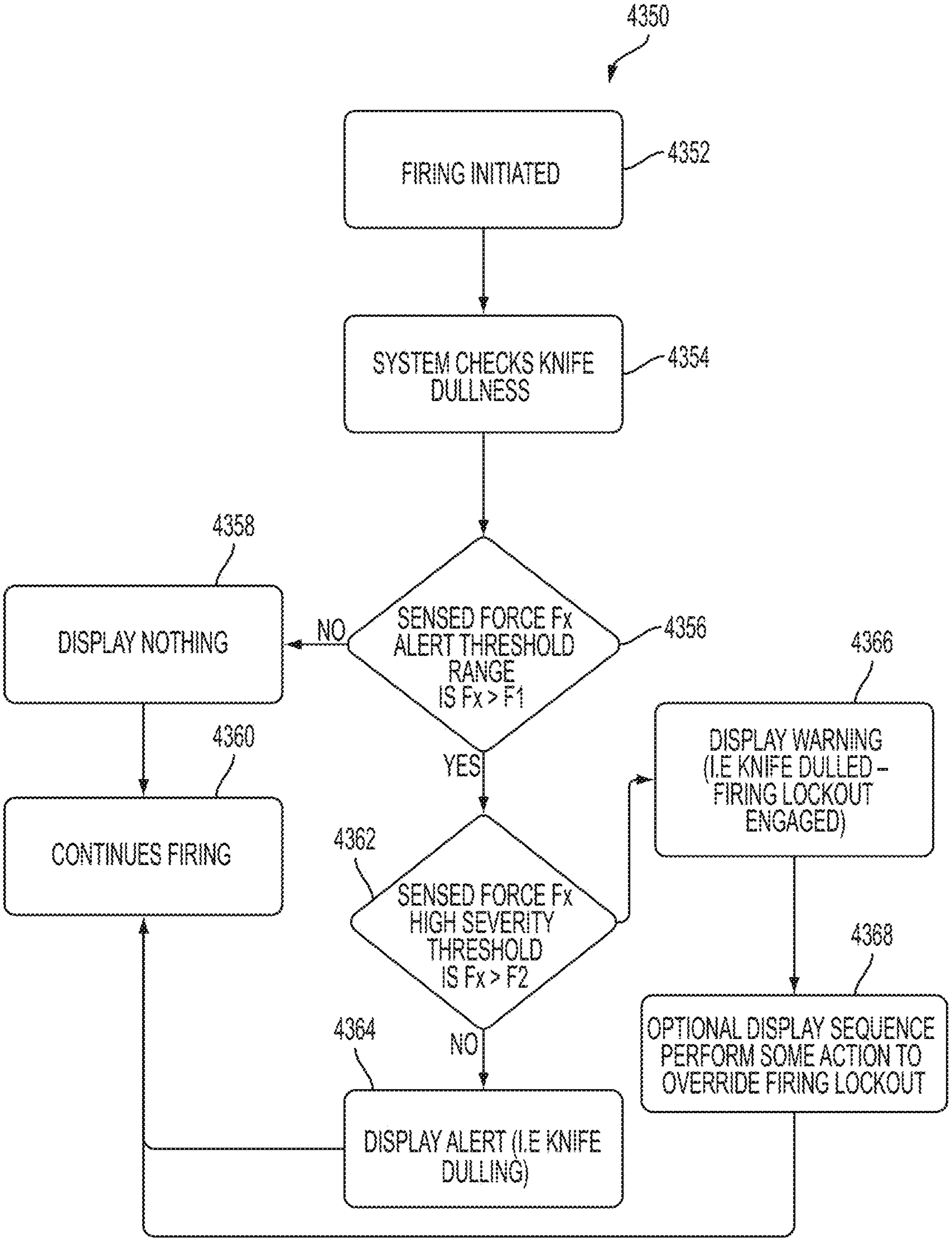
FIG. 40 illustrates a flow chart of a method for determining whether a cutting edge of a surgical instrument is sufficiently sharp to transect tissue captured by the surgical instrument according to various aspects.

FIG. 40 illustrates a logic diagram 4350 of a method for determining whether a cutting edge of a surgical instrument 10 (FIGS. 1-4) is sufficiently sharp to transect tissue captured by the surgical instrument 10 according to various aspects. Referring to FIG. 40, the logic diagram 4350 depicts a method for evaluating the sharpness of the cutting edge 182 (FIG. 20) of the surgical instrument 10; and various responses are outlined in the event the sharpness of the cutting edge 182 drops to and/or below an alert threshold and/or a high severity threshold, for example. In various instances, a microcontroller such as, for example, the microcontroller 4313 can be configured to implement the method 4350 depicted in FIG. 40. In certain instances, the surgical instrument 10 may include a load cell 4335, as illustrated in FIGS. 38 and 39, and the microcontroller 4313 may be in communication with the load cell 4335. In certain instances, the load cell 4335 may include a force sensor such as, for example, a strain gauge, which can be operably coupled to the firing bar 172, for example. In certain instances, the microcontroller 4313 may employ the load cell 4335 to monitor the force (Fx) applied to the cutting edge 182 as the cutting edge 182 is advanced during a firing stroke.

In various instances, the method 4350 begins by initiating 4352 firing of the surgical instrument 10 (FIGS. 1-4). Before, during, and/or after firing of the surgical instrument 10 is initiated 4352, a system checks 4354 the dullness of the cutting edge 182 by monitoring a force (Fx). The reader will appreciate that the force (Fx) is applied by the sharpness testing member 4302 to the cutting edge 182 while the cutting edge 182 is engaged and/or in contact with the sharpness testing member 4302, and, the force (Fx) may depend, at least in part, on the sharpness of the cutting edge 182. In certain instances, a decrease in the sharpness of the cutting edge 182 can result in an increase in the force (Fx) required for the cutting edge 182 to cut or pass through the sharpness testing member 4302.

The system senses 4356 the force (Fx) applied by the sharpness testing member 4302 to the cutting edge 182 (FIG. 20). When the force (Fx) sensed 4356 stays within an alert threshold range a display will display 4358 nothing and firing 4360 of the surgical instrument 10 (FIGS. 1-4) will proceed. When the force (Fx) sensed 4356 is outside the alert threshold range, the system 4354 will then determine if the force (Fx) is outside a high severity threshold range. The display will display 4364 an alert to the user of the surgical instrument 10 that the cutting edge 182 is dulling. At this stage, the user is aware that the cutting edge 182 is dulling and may need replaced. When the force (Fx) is sensed 4362 to be greater than the high severity threshold range, the display displays 4366 a warning indicating the force (Fx) applied to the cutting edge 182 is greater than the high severity threshold and that the cutting edge 182 is dull. If the cutting edge is determined to be dull, a firing lockout system may be engaged. The display may display 4368 an optional display sequence to allow the user of the surgical instrument 10 to override the firing lockout system and continue firing 4360 this surgical instrument 10.

In certain instances, the load cell 4335 (FIGS. 38, 39) can be configured to monitor the force (Fx) applied to the cutting edge 182 (FIG. 20) while the cutting edge 182 is engaged and/or in contact with the sharpness testing member 4302 (FIGS. 38, 39), for example. The reader will appreciate that the force (Fx) applied by the sharpness testing member 4302 to the cutting edge 182 while the cutting edge 182 is engaged and/or in contact with the sharpness testing member 4302 may depend, at least in part, on the sharpness of the cutting edge 182. In certain instances, a decrease in the sharpness of the cutting edge 182 can result in an increase in the force (Fx) required for the cutting edge 182 to cut or pass through the sharpness testing member 4302. For example, as illustrated graphically in FIG. 41, graphs 4336, 4338, and 4342 represent, respectively, the force (Fx) applied to the cutting edge 182 while the cutting edge 182 travels a predefined distance (D) through three identical, or at least substantially identical, sharpness testing members 4302. The graph 4336 corresponds to a first sharpness of the cutting edge 182; the graph 4338 corresponds to a second sharpness of the cutting edge 182; and the graph 4342 corresponds to a third sharpness of the cutting edge 182. The first sharpness is greater than the second sharpness, and the second sharpness is greater than the third sharpness.

Figure 41:
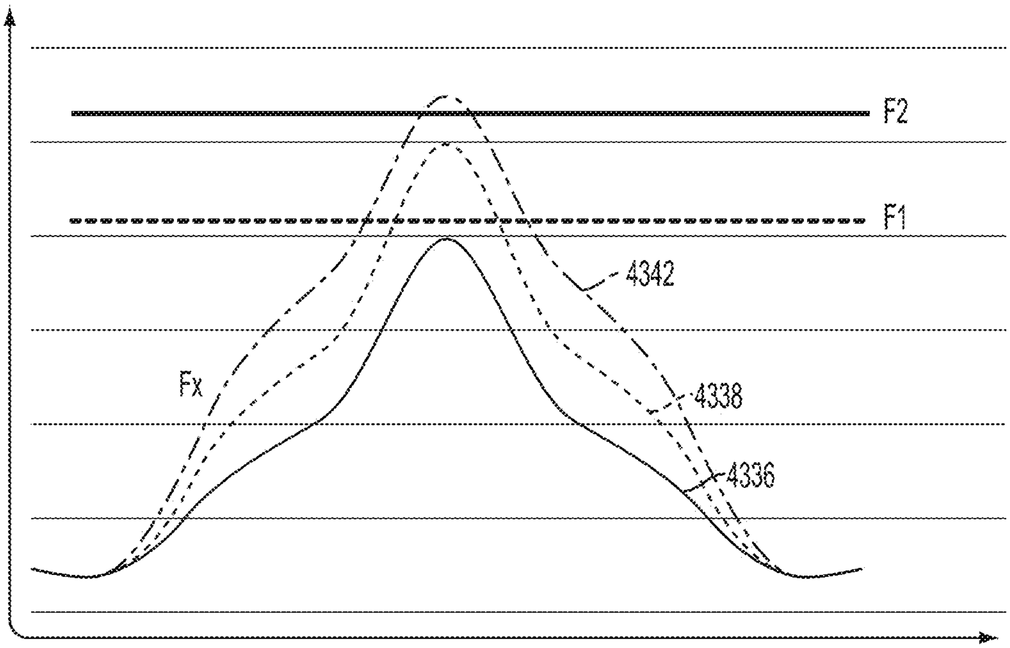
FIG. 41 illustrates a chart of the forces applied against a cutting edge of a surgical instrument by a sharpness testing member at various sharpness levels according to various embodiments.

In certain instances, the microcontroller 4313 (FIGS. 38, 39) may compare a maximum value of the monitored force (Fx) applied to the cutting edge 182 (FIG. 20) to one or more predefined threshold values. In certain instances, as illustrated in FIG. 41, the predefined threshold values may include an alert threshold (F1) and/or a high severity threshold (F2). In certain instances, as illustrated in the graph 4336 of FIG. 41, the monitored force (Fx) can be less than the alert threshold (F1), for example. In such instances, as illustrated in FIG. 41, the sharpness of the cutting edge 182 is at a good level and the microcontroller 4313 may take no action to alert a user as to the status of the cutting edge 182 or may inform the user that the sharpness of the cutting edge 182 is within an acceptable range.

In certain instances, as illustrated in the graph 4338 of FIG. 41, the monitored force (Fx) can be more than the alert threshold (F1) but less than the high severity threshold (F2), for example. In such instances, as illustrated in FIG. 40, the sharpness of the cutting edge 182 (FIG. 2) can be dulling but still within an acceptable level. The microcontroller 4313 may take no action to alert a user as to the status of the cutting edge 182. Alternatively, the microcontroller 4313 (FIGS. 38, 39) may inform the user that the sharpness of the cutting edge 182 is within an acceptable range. Alternatively or additionally, the microcontroller 4313 may determine or estimate the number of cutting cycles remaining in the lifecycle of the cutting edge 182 and may alert the user accordingly.

In certain instances, the memory 4317 (FIGS. 38, 39) may include a database or a table that correlates the number of cutting cycles remaining in the lifecycle of the cutting edge 182 (FIG. 20) to predetermined values of the monitored force (Fx). The processor 4315 (FIGS. 38, 39) may access the memory 4317 to determine the number of cutting cycles remaining in the lifecycle of the cutting edge 182 which correspond to a particular measured value of the monitored force (Fx) and may alert the user to the number of cutting cycles remaining in the lifecycle of the cutting edge 182, for example.

In certain instances, as illustrated in the graph 4342 of FIG. 41, the monitored force (Fx) can be more than the high severity threshold (F2), for example. In such instances, as illustrated in FIG. 40, the sharpness of the cutting edge 182 can be below an acceptable level. In response, the microcontroller 4313 may employ the feedback system to warn the user that the cutting edge 182 is too dull for safe use, for example. In certain instances, the microcontroller 4313 may employ the lockout mechanism to prevent advancement of the cutting edge 182 upon detection that the monitored force (Fx) exceeds the high severity threshold (F2), for example. In certain instances, the microcontroller 4313 may employ the feedback system to provide instructions to the user for overriding the lockout mechanism, for example.

Figure 42:
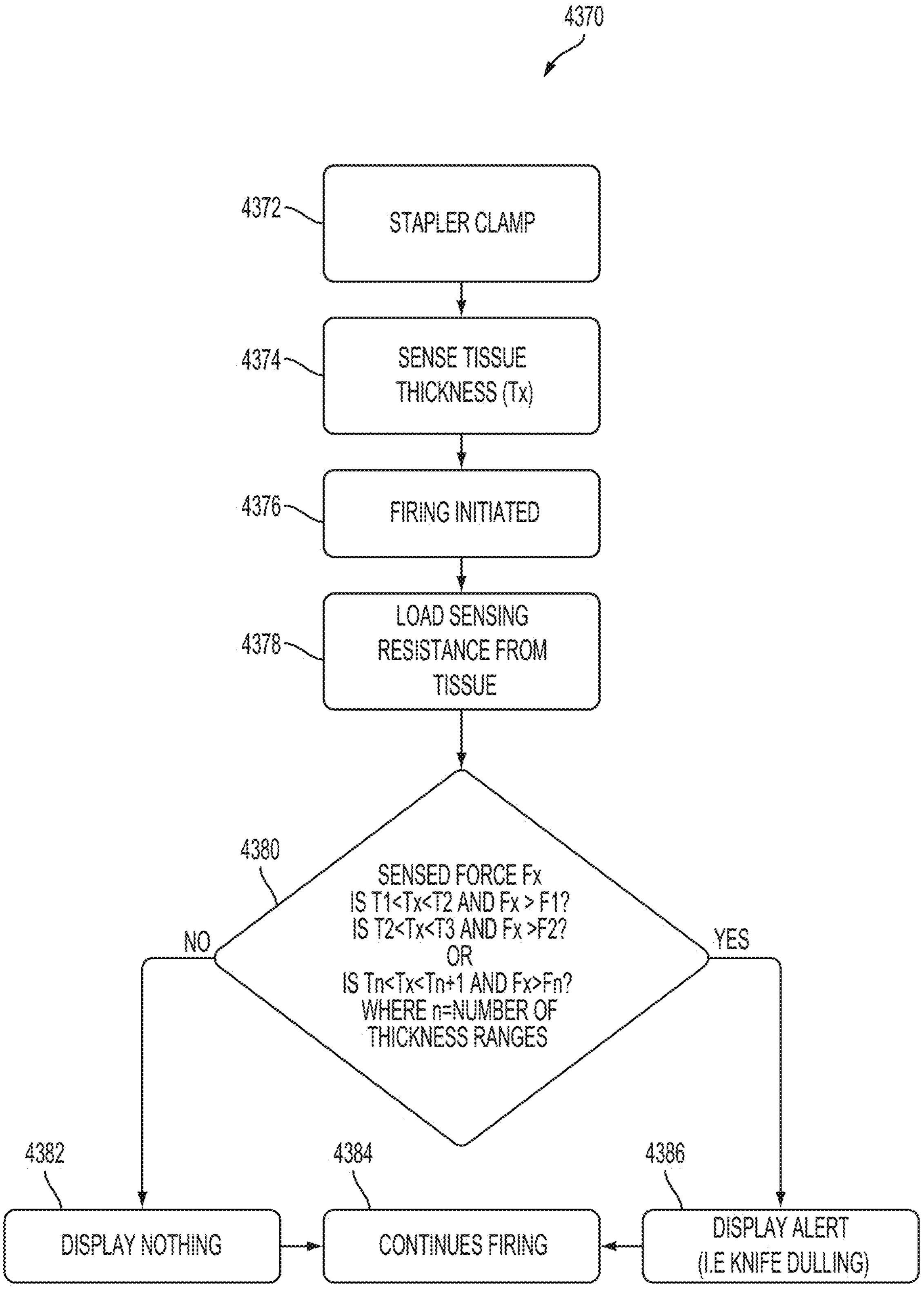
FIG. 42 illustrates a flow chart outlining a method for determining whether a cutting edge of a surgical instrument is sufficiently sharp to transect tissue captured by the surgical instrument according to various embodiments.

Referring now to FIG. 42, a method 4370 is depicted for determining whether a cutting edge such as, for example, the cutting edge 182 (FIG. 20) is sufficiently sharp to be employed in transecting a tissue of a particular tissue thickness that is captured by the end effector 300 (FIG. 1), for example. In certain instances, the microcontroller 4313 can be implemented to perform the method 4370 depicted in FIG. 42, for example. As described above, repetitive use of the cutting edge 182 may dull or reduce the sharpness of the cutting edge 182 which may increase the force required for the cutting edge 182 to transect the captured tissue. In other words, the sharpness level of the cutting edge 182 can be defined by the force required for the cutting edge 182 to transect the captured tissue, for example. The reader will appreciate that the force required for the cutting edge 182 to transect a captured tissue also may depend on the thickness of the captured tissue. In certain instances, the greater the thickness of the captured tissue, the greater the force required for the cutting edge 182 to transect the captured tissue at the same sharpness level, for example.

In certain instances, the cutting edge 182 (FIG. 20) may be sufficiently sharp for transecting a captured tissue comprising a first thickness but may not be sufficiently sharp for transecting a captured tissue comprising a second thickness greater than the first thickness, for example. In certain instances, a sharpness level of the cutting edge 182, as defined by the force required for the cutting edge 182 to transect a captured tissue, may be adequate for transecting the captured tissue if the captured tissue comprises a tissue thickness that is in a particular range of tissue thicknesses, for example. In certain instances, the memory 4317 (FIGS. 38, 39) can store one or more predefined ranges of tissue thicknesses of tissue captured by the end effector 300; and predefined threshold forces associated with the predefined ranges of tissue thicknesses. In certain instances, each predefined threshold force may represent a minimum sharpness level of the cutting edge 182 that is suitable for transecting a captured tissue comprising a tissue thickness (Tx) encompassed by the range of tissue thicknesses that is associated with the predefined threshold force. In certain instances, when the force (Fx) required for the cutting edge 182 to transect the captured tissue, comprising the tissue thickness (Tx), exceeds the predefined threshold force associated with the predefined range of tissue thicknesses that encompasses the tissue thickness (Tx), the cutting edge 182 may not be sufficiently sharp to transect the captured tissue, for example.

The method 4370 shown in FIG. 42 begins with clamping 4372 the tissue. Once the tissue to be transected is clamped, the thickness of the tissue is sensed 4374. After the tissue thickness is sensed 4374, firing of the surgical instrument can be initiated 4376 by the user. Once the surgical instrument begins firing, the force (Fx) applied to the cutting edge 182 (FIG. 20) is sensed 4378. The force (Fx) and the tissue thickness (Tx) is then compared 4380 to predetermined tissue thickness ranges and force ranges required to adequately transect the predetermined tissue thicknesses. For example, if the force (Fx) sensed is greater than a predetermined force range required to adequately transect tissue at the tissue thickness (Tx) that was sensed for the tissue clamped, a display will display 4386 an alert to the user that the cutting edge 182 is dulling. When the force (Fx) sensed is within the predetermined force range required to adequately transect tissue at the tissue thickness (Tx) that was sensed for the tissue clamped, the display may display 4382 nothing. In both instances, the surgical instrument continues 4384 firing to transect the tissue.

In various aspects, the present disclosure provides techniques for determining tissue compression and additional techniques to control the operation of the instrument 10 (described in connection with FIGS. 1-29) in response to the tissue compression. In one example, the cartridges may be configured to define variable compression algorithm which drives instrument 10 to close differently based on intended tissue type and thickness. In another example, the instrument 10 learns from surgeon use and original tissue compression profile to adapt closure based on load experienced during firing. When the instrument 10 experiences tissue compression loads that are dramatically different that those experienced for this cartridge type the instrument highlights this to the user.

Active adjustment of a motor control algorithm over time as the instrument become acclimated to the hospital's usage can improve the life expectancy of a rechargeable battery as well as adjust to tissue/procedure requirements of minimizing tissue flow, thus improving staple formation in the tissue seal.

Accordingly, the present disclosure relates to surgical instruments and, in various circumstances, to surgical stapling and cutting instruments and staple cartridges therefor that are designed to staple and cut tissue. For example, in various aspects the present disclosure provides an endosurgical instrument configured to sense the cartridge type or tissue gap to enable the handle to adjust the closure and firing algorithms to adjust for intended tissue properties. This adaptive algorithm adjustment can "learn" from the user's operations allowing the device to react and benefit two different systems. The first benefit provided by the disclosed adaptive algorithm includes tissue flow and staple formation. As the device learns the users' basic habits and step timings, the device can adjust the closure speed and firing speed to provide a more consistent and reliable output. The second benefit provided by the disclosed adaptive algorithm is related to the battery pack. As the device learns how many firings and what conditions the instrument was used, the device can adjust motor current needs/speed in a predefined manner to prolong battery life. There is a substantially small likelihood that a device used in a hospital that performs predominantly bariatric procedures would be operated in a manner similar to a device used in a hospital that performs mostly colorectal or thoracic procedures. Thus, when the device is used to perform substantially similar procedure, over time, the device is configured to learn and adjust its operational algorithm to maintain within the "ideal" discharge and tissue flow envelopes.

Safe and effective surgery requires due knowledge of, and respect for, the tissue involved. Clinicians are mindful that adjustments made during surgery may be beneficial. These adjustments include mechanisms to detect and promote desirable staple formation.

Endosurgical instruments can generate, monitor and process a substantial amount of data during their use in connection with a surgical procedure. Such data can be obtained from the surgical instrument itself, including battery usage. Additionally, data can be obtained from the properties of the tissue with which the surgical instrument interacts, including properties such as tissue compression. Further, data can be obtained from the clinician's interaction with the surgical instrument itself. The repository of data so obtained can be processed and, where desired, the surgical instrument can be designed to adapt to circumstances so as to promote a safe and effective outcome to the current surgical procedure, as well as lay the foundation for more generalized productive use by multiple clinicians. Such adaptive adjustments—both during a surgical procedure, and wherein the instrument "learns" based on usage patterns drawn from multiple surgical procedures—can provide numerous mechanisms to enhance the overall patient-care environment.

Figure 43:
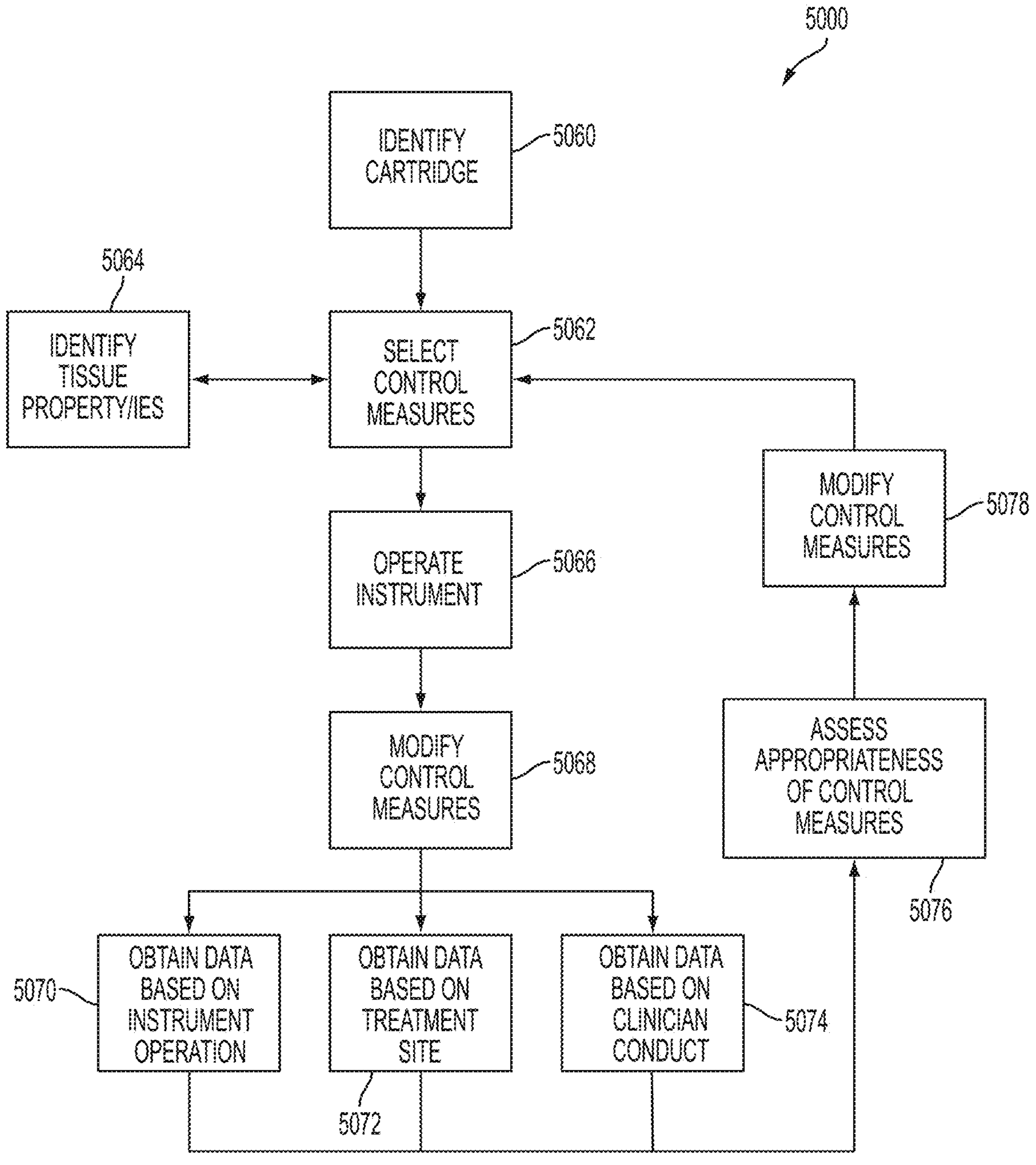
FIG. 43 illustrates one aspect of a process for adapting operations of a surgical instrument.

FIG. 43 illustrates one aspect of a process for adapting operations of a surgical instrument. As shown in FIG. 43, in various examples, an adaptive algorithm framework 5000 is provided. A staple cartridge can be identified 5060. Control measures, such as algorithms, can be selected 5062 based on the cartridge identified. These algorithms may include one or more variable compression algorithms that drives instrument 10 (FIGS. 1-4) to close in a different manner based on an expected tissue type and/or thickness. Tissue properties can be identified 5064 as an aid to selection of control measures. The clinician can operate 5066 instrument 10 to carry out a surgical procedure, including but not limited to stapling and/or incising tissue. Control measures can be modified 5068, with or without reference to data observed or generated during the course of a surgical procedure.

A surgical procedure can entail generating a significant amount of data on parameters. By way of non-limiting example, these parameters can include those associated with surgical instrument 10 (FIGS. 1-4) itself and its functionality, including but not limited to: speed of closure of the anvil 306 (FIG. 1) and staple cartridge 304 (FIG. 1), or speed of closure of anvil 306 and second jaw member 302 (FIG. 1); gap (e.g., distance) between anvil 306 and staple cartridge 304, or anvil 306 and second jaw member 302; voltage; current; motor(s') speed; power management, e.g., battery use; or sensor operation and accuracy.

Additional parameters that may be generated and observed in connection with a surgical procedure can also include those derived from the tissue being operated upon, including but not limited to: tissue compression; tissue thickness; tissue flow; tissue creep; tissue pressure; tissue stabilization; whether end effector 300 (FIG. 1) clamps a full or partial bite of tissue, and whether such partial bite is proximal or distal; speed of closure drive system 30 (FIG. 1); speed of firing drive system 80 (FIG. 4); staple performance; and/or determination if the tissue profile is consistent with healthy tissue or diseased tissue.

Further parameters that may be generated and observed in connection with a surgical procedure can also include those derived from the clinician, such as frequency of actuating closure trigger 32 (FIG. 1) by clinician; force applied on closure trigger 32 by clinician; frequency of actuating firing trigger 130 (FIG. 4) by clinician; force applied on firing trigger 130 by clinician; and/or step timing by clinician.

Even more, parameters can include to what extent the instrument 10: experiences tissue compression loads different from those expected for the cartridge type; experiences a wait period (such as for tissue creep) different from that expected; experiences a firing speed different from that expected; has undergone one or more sterilization cycles; and/or experiences different or similar patterns of use based on the clinical setting. For example, there may be meaningful differences among use of the instrument in a setting directed primarily to bariatric, colorectal, or thoracic procedures respectively.

On top of these, parameters can include accuracy and appropriateness of control measures themselves, such as algorithms, used in connection with operating the instrument. Feedback loops and/or logic paths can be developed that include one or more of algorithms, data based on instrument operation 5070, data based on the treatment site 5072, data based on clinician conduct 5074, and more. Added parameters can be considered and developed.

It will be apparent that there are numerous data resources that can be derived from a single surgical procedure. These data resources can be analyzed in various manners including as a single data point, a plurality of data points, a range or ranges, as a range or ranges, or based on added metrics such as rate of change of current, voltage, speed, or other parameter. Taking into account one, or many, of these data resources can enhance the safety and effectiveness of a single procedure.

In addition, these data resources can enhance the safety and effectiveness of future procedures by the same clinician to the extent that the surgical instrument can "learn" the basic habits and step timings of the clinician. In addition, data can be aggregated from multiple clinicians, further enabling the successful calibration of the surgical instrument in the context of the surgical procedure. It can be appreciated that the hospital or health center in which the data is compiled can develop a unique profile that can further enhance health outcomes. In addition, battery life can be prolonged, as it is learned how many firings and under what conditions the surgical instrument 10 is used. Thus, arrangements to adapt to numerous battery usage metrics are contemplated in examples.

Instrument 10 (FIGS. 1-4) can determine whether, based on data obtained 5070, 5072, 5074, a control measure is appropriate or not by various mechanisms. One mechanism is by identifying a predetermined value or values. Such value or values can comprise an acceptable, or expected, parameter. If data obtained 5070, 5072, 5074 leads to a determination that an acceptable range has been exceeded, then a new control measure(s) can be identified 5076 and control measures can be modified 5078 including setting forth a new acceptable value. Exceeding a range can be considered to mean going above a range, below or range, or otherwise going beyond a range. The second control measure can be a minor adaptation of the first control measure, or it can be an entirely new control measure. It will also be appreciated that the predetermined acceptable range can be a single data point, multiple data points, a function or other calculable equation, or any mechanism by which it can be determined that a measurement, property or other metric that can be resolvable into a calculable value differs from an actual, expected or predicted value. It is also understood that a control measure can be compared with another control measure, and the differential effectiveness of each determined, thus forming an input into another determination of whether and which control measures to adopt. Put another way, success of control measures can represent an input.

In addition, expected values for parameters can be embedded in control measures. In other words, an expected set of values for a tissue property can be embedded in a control measure that has been associated with instrument 10 (FIGS. 1-4). Thus, it will be evident that numerous expected values for numerous parameters can be populated into numerous control measures. These expected values can be referenced during operations of the instrument in order to determine control measures carried out by instrument 10. Further, observed values can be detected and analyzed by instrument 10 during operation. These observed values can be referenced and help determine the course of selection of current and future control measures of the instrument 10 during the procedure, and also programmed into instrument 10 to set new or modified benchmarks to help determine an acceptable range or ranges of control measures. Further predictions can be made during operation of the instrument 10. The predictions can inform the processing and analysis of measurements, can lead to modifying control measures, and generally adapting to operational circumstances.

Thus, data can be obtained from multiple sources. One source is data based on operation of the instrument (e.g., closure speed) 5070. Another source of data can be that derived from the treatment site 5072 (e.g., tissue thickness). A further source of data can be that based on clinician conduct 5074 (e.g., firing habits). Once this data 5070, 5072, 5074 is obtained, the appropriateness of control measures can be assessed 5076. For example, a certain tissue type may have been expected, and this tissue type was experienced during the procedure. However, it may be that the exudation resulting from clamping was heavier than anticipated. Also, it may be that the clinician has a habit of applying more pressure than may be desirable on the firing trigger 130 (FIG. 1). In short, there may be many data sources that can be consulted to analyze, improve on and potentially optimize efficacy of current and future uses of the instrument. As a result, control measures can be modified 5078 during and/or after a procedure for maximum success.

In one aspect, surgical instrument 10 (FIGS. 1-4) can comprise a plurality of modules, based on control mechanisms configurable from a controller and/or other processor, memory, and other systems therein for transmission, communication and processing of data. One of multiple possible modules can be based on a feedback system, as generalized and/or customized for a specific purpose or system. In addition, it will be apparent that there will be a processor 4315 (FIGS. 38, 39) and memory 4317 (FIGS. 38, 39) in operative communication with the surgical instrument 10 that can permit the functionality discussed herein.

Figure 44:
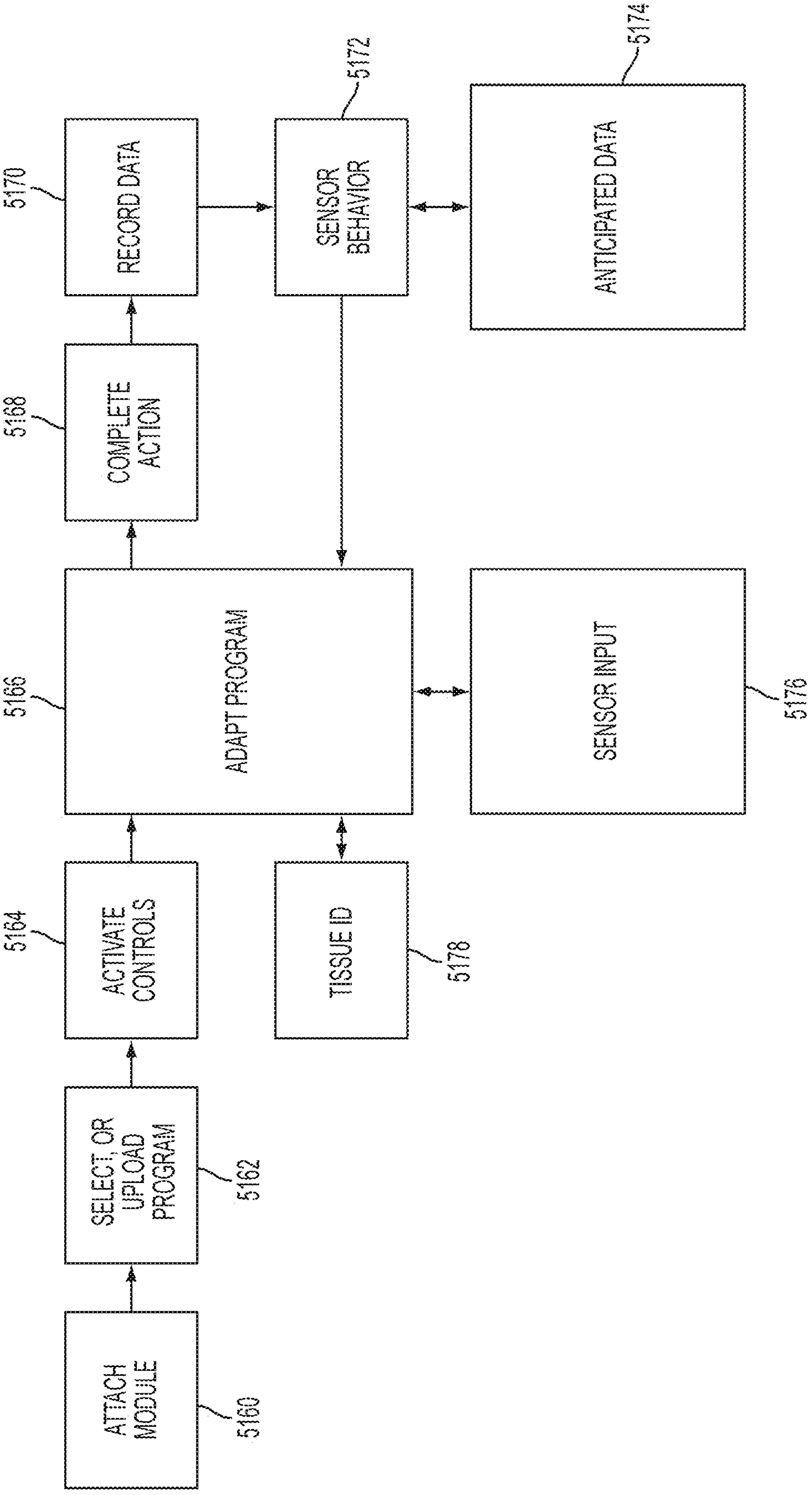
FIG. 44 illustrates one aspect of a process for adapting operations of a surgical instrument.

FIG. 44 illustrates one aspect of a process for adapting operations of a surgical instrument. As depicted in FIG. 44, a module can be attached 5160 or otherwise loaded to instrument 10 (FIGS. 1-4). The module can contain a program that is selected or uploaded 5162. Controls can be activated 5164 such that they can be ready to operate instrument 10. During or after usage of instrument 10, a program, including control measures, can be adapted 5166. For example, this can include adjusting the data rate within the instrument 10 or with respect to remote operation of the instrument 10. This can include adjusting speed, such as speed by which anvil 306 (FIG. 1) and cartridge 304 (FIG. 1) engage in a closure motion. This can also include a pulse from an emitter and sensor or to apply a pulse of electrical current to tissue, and the timing of such pulse. This can include adjusting a program to adapt to acceleration, such as acceleration of the instrument 10 if dropped, or transition from a sleep mode. A program can be adapted to handle an actual and/or expected load based on clamping force.

Instrument 10 (FIGS. 1-4) can be employed to complete an action 5168, for example to carry out a stapling procedure. Data can be recorded 5170 in appropriate memory locations of instrument 10. Sensor behavior 5172 can be assessed, such as to what extent a sensor accurately measured and/or measures a parameter. Anticipated data can be assessed 5174, including but not limited to tissue properties, wait period and firing speed. Foregoing mechanisms disclosed herein can provide an input to adapt a program 5166 further. In addition, a tissue identification 5178 can be performed, based on historical, actual or expected tissue properties, and this can provide an input to adapt a program 5166 further. In addition, tissue identification 5178 properties can be updated. Moreover, measured sensor input 5176 during a procedure can be used as an additional input to adapt a program 5166 further; such sensor measurements can include those of the gap between anvil 306 and cartridge 304, obtaining a derivative measurement including a derivative of a function, current, or torque.

Figure 45:
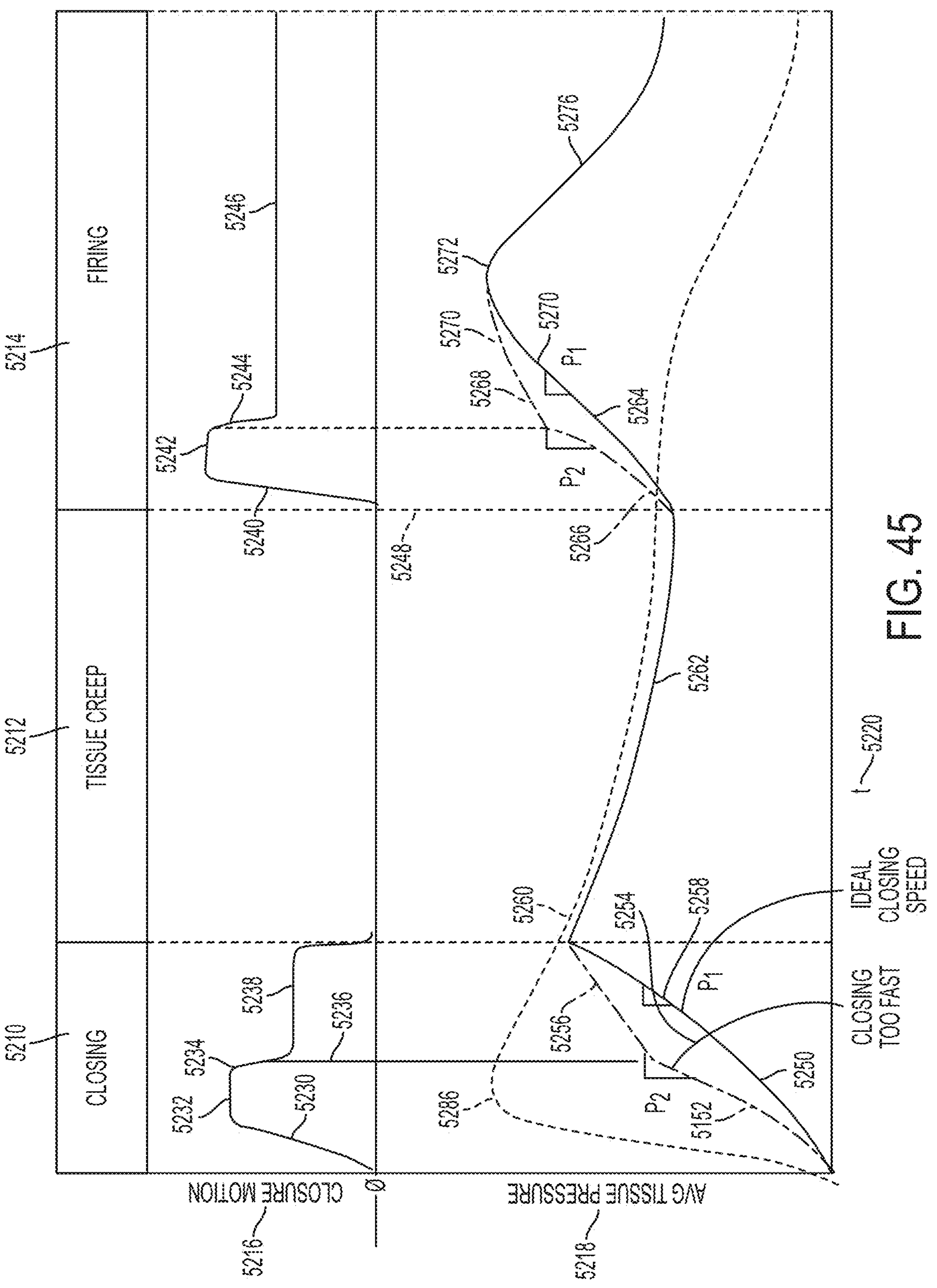
FIG. 45 illustrates one aspect of a mechanism for adapting operations of a surgical instrument in the context of closure motion and tissue pressure.

FIG. 45 illustrates one aspect of a mechanism for adapting operations of a surgical instrument in the context of closure motion and tissue pressure. In various aspects, closure motion 5216 can be adjusted based on a parameter. An example parameter can be average tissue pressure 5218. FIG. 45 is a diagram that illustrates three phases of carrying out a procedure with instrument 10 (FIGS. 1-4). Time (t) is shown along a bottom horizontal axis 5220, a bottom vertical axis represents average tissue pressure 5218 applied to tissue clamped between the jaw members of the end effector. A top vertical axis represents closure motion 5216 of the anvil 306 (FIG. 1) towards the cartridge 304 (FIG. 1) to engage tissue therebetween in a closure motion. A top horizontal axis represents closing 5210 of the anvil 306 (FIG. 1) of end effector to engage a cartridge 304 (FIG. 1) or second jaw member 302 (FIG. 1), tissue creep 5212 wherein material is allowed to exudate from the tissue section held within end effector 300 (FIG. 1), and firing 5214, which can comprise deploying a staple cartridge 304, applying electrosurgical energy, incising tissue, or other suitable surgical event. An anvil 306 can begin to close on a second jaw member 302, which is configured to receive a staple cartridge 304 therein. As anvil 306 closes toward cartridge 304 during a clamping operation, tissue pressure is determined by one or more mechanisms, such as by reference to one or more sensors. A plurality of sensors may comprise one or more identical sensors and/or different sensors. The plurality of sensors may comprise, for example, magnetic sensors, such as a magnetic field sensor, strain gauges, pressure sensors, inductive sensors, such as an eddy current sensor, resistive sensors, capacitive sensors, optical sensors, and/or any other suitable sensors or combination thereof.

During the closing phase 5210, the closure motion 5216 versus time of the jaw members is compared with average tissue pressure 5218 versus time. A first average tissue pressure versus time curve, represented by a dashed line includes three segments, includes a first segment 5286 during the closing phase 5210 of the anvil 306 (FIG. 1) towards the cartridge 304 (FIG. 1) to apply pressure against the tissue grasped therebetween. A second segment 5260 represents the tissue pressure during the tissue creep 5212 phase where the anvil 304 has stopped moving and the tissue is given an opportunity to creep. A third segment represents the tissue pressure during the firing phase during which the staples are deployed to seal the tissue ahead of advancement of the cutting member to cut the tissue.

A second average tissue pressure versus time curve, represented by a dashed-dot line, represents a typical curve observed when the anvil 306 (FIG. 1) is closing too fast 5254. This is represented by the first segment 5152 where the slope P2 of the average tissue pressure 5218 versus time is too steep during the closure motion curve segment 5230 during the acceleration of the closure motion and curve segment 5234 when the closure motion 5216 remains steady until a threshold 5236 average tissue slope 5218 is detected at which time the closure motion drops to a lower constant value shown by curve segment 5238 at which time the slope of the average tissue pressure 5216 curve segment 5256 decreases to reflect the slower closure motion 5216.

A third "ideal" tissue pressure versus time curve 5258 having an ideal slope is represented by a solid line curve segment 5250.

The tissue creep 5212 phase is entered after the tissue is grasped and the average tissue pressure reaches a predetermined threshold and the closure motion 5216 stops such that the jaw members, e.g., anvil 306 (FIG. 1) and cartridge 304 (FIG. 1), hold the tissue therebetween for a predetermined time before initiating the firing 5214 phase in which the staples and knife are deployed. During the tissue creep 5212 phase the average tissue pressure drops over the time period between closing 5210 and firing 5214 phases. The dashed-dot curve (adjusted closing too fast curve) and solid curve (ideal closing speed) segments 5262 overlap.

At a predetermined time 5248, the firing 5214 phase initiates. A typical firing 5214 cycle is represented by the dashed line average tissue pressure curve segment 5266. An ideal firing 5214 cycle is represented by the solid line average tissue pressure curve segment 5264 where the slope P1 increases 5270, reaches a peak 5272, and then gently decreases 5276. When the firing 5214 phase moves too rapidly as indicated by curve segment 5240, the slope P2 of the dashed-dot line average tissue pressure curve 5266 rises too steeply. When a predetermined slope threshold is detected, the firing speed is maintained constant as represented by firing curve speed segment 5242 and the slope 5270 of the dashed-dot line average tissue pressure curve 5266 decreases. After a predetermined time, the firing speed drops to a lower speed as represented by the firing speed curve segment 5246. After allowing for system response times, the dashed-dot line coincides with the solid line during the lower firing speed 5246.

Closure motion 5216, such as speed of closure, or another measured rate related to closure, can be determined. As the clamping operation progresses, and a parameter increases 5230, average tissue pressure is being measured. The parameter in question can be but is not limited to speed. Average tissue pressure can be plotted graphically. A curve 5252 described by such graph can be plotted. At a certain point closure motion 5216 can be steady 5232. However, a tissue pressure reading can suggest that the closure motion rate is too fast 5254 as indicated by, for example, the slope of curve 5252. It can also be the case that the closure motion rate was too fast, or is predicted to be too fast in the future. This can occur during a period where closure rate is steady 5232, or during a period where closure rate drops 5234 such as where thick, fluid-filled or unexpectedly dense tissue is encountered, among other reasons. Fluid in tissue could cause thickness to increase temporarily, causing undesirable staple deployment. To the extent that it is detected that the slope of average tissue pressure curve 5218 is growing too steep, adjustments can be made. It will also be appreciated that, independent of or in conjunction with slope, a secondary calculation can be made based on the observed parameters suggesting that the closure rate is too fast. An adjustment can be made, such as by decreasing the rate of change of closure motion 5216. For example, an ideal closing speed can be referenced based on stored control measures or dynamically obtained control measures, or both. An average tissue pressure curve reflecting such ideal closing speed 5258 can be referenced.

Accordingly, curve 5258 can influence closure motion 5216 such that the rate of closure is decreased 5238 or otherwise modified to adapt to circumstances encountered during a surgical procedure. It will be understood that an ideal closing speed can represent an optimal closing speed, or one within a range of adequate closing speeds.

Compression of clamped tissue can precede the firing 5214 phase. It may be desired that compression reach a certain average tissue pressure, and/or that the tissue is considered stabilized such that firing 5214 can be warranted. A measured tissue pressure can be reached at a point, for example, representing the intersection of curve 5252 and 5250. Upon reaching this point, the tissue can be allowed to stabilize and the exudate seep from the tissue. Tissue, in part because it is composed of solid and liquid material, tends to elongate when compressed; one way to account for this property is "tissue creep". When tissue is compressed, a certain amount of tissue creep 5212 can occur. Affording the compressed tissue an adequate amount of time under certain circumstances to accomplish tissue creep can therefore produce benefits. One benefit can be adequate staple formation. This can contribute to a consistent staple line. Accordingly, a certain time can be given to enable tissue creep 5212 prior to firing 5214.

Upon reaching a desirable point, firing 5214 can be commenced. Firing 5214 can comprise one or more actions or events, including deployment of an I-beam and/or other firing member towards and/or within end effector 300 (FIG. 1). An I-beam can comprise a cutting member deployable therein. The cutting member can comprise, for example, an I-Beam configured for simultaneously cutting of a tissue section located between an anvil 306 (FIG. 1) and a staple cartridge 304 (FIG. 1) and deploying staples from the staple cartridge 304.

During firing 5214, average tissue pressure can ascend along curve 5266, comparable with the rate of closure motion 5216. A slope can be calculated for average tissue pressure during firing 5214. The slope can be evaluated to be steeper than desired, perhaps due to an increasing rate of average tissue pressure change in combination with a stable firing rate 5242. If this condition or another condition provided for is detected, instrument 10 (FIGS. 1-4) can have the capability to adapt. Measures can be implemented to modify the firing curve 5268 such that a peak can be reached that would be similar to or identical to that obtainable from a more desirable tissue pressure curve 5274.

Accordingly, similar to adaptive mechanisms employed in connection with closing 5210, adaptive measures can be employed in connection with firing 5214.

Tissue-pressure curve 5286 can be referenced which can track a desired tissue-creep rate after reference to an ideal closing speed. Tissue-pressure curve 5286 can be programmed to operate in conjunction with, or be extrapolated from, the closing phase 5210 or firing phase 5214. Additionally, a given tissue type can be referenced that would give certain characteristics when surgical operations are carried out thereon, such characteristics embodying curve 5286. It will be appreciated that various purposes can be fulfilled by referencing tissue-pressure curve 5286, or another tissue-pressure curve, that might be considered an "ideal", desired, or otherwise "reference curve". Such a reference curve can assist in improving closing 5210, tissue creep 5212, and/or firing 5214. Such a reference curve or curves can be stored in instrument 10 (FIGS. 1-4) or be developed dynamically, or both, and can account for varying thickness of a tissue portion, and many other factors.

Figure 46:
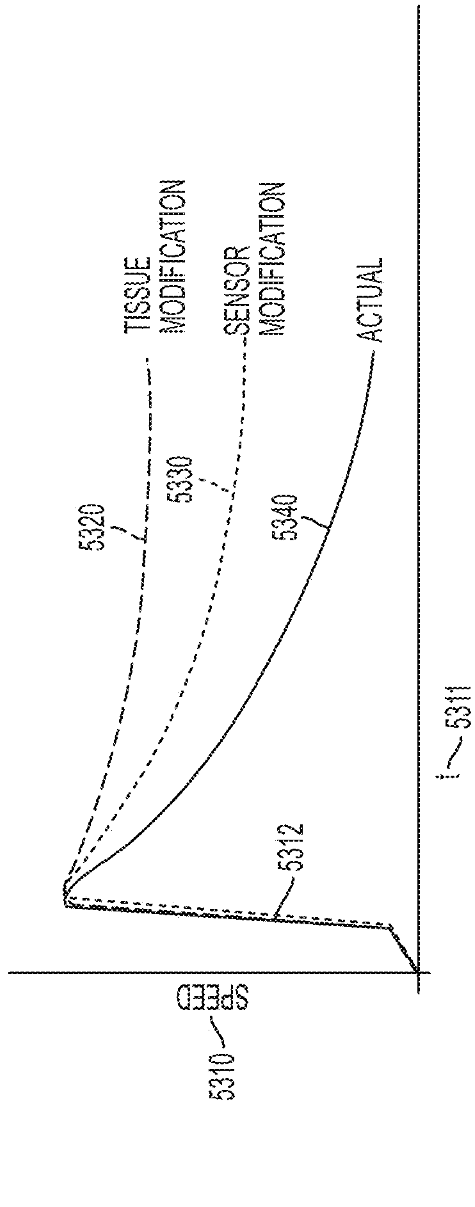
FIG. 46 illustrates one aspect of a mechanism for adapting speed associated with a parameter of a surgical instrument in the context of tissue modification and sensor modification.

In accordance with aspects, FIG. 46 illustrates adaptive mechanisms that can influence actual behavior of instrument 10 (FIGS. 1-4) in the process of carrying out a surgical procedure. Speed 5310 can be enumerated on the vertical (y) axis and time 5311 (*t*) is represented along the horizontal axis. Speed 5310 can represent speed of the motor, speed of closure of end effector 300 (FIG. 1), speed of firing rate, or another speed. As speed increases 5312, sensors can obtain measurements of various parameters. Based on control measures derived from stored algorithms, or dynamically generated algorithms, or both, one or more modifications can be made. One modification can be a tissue modification 5320 that will influence operation of instrument 10 such that speed is upwardly or downwardly adjusted in order to obtain a more desirable set of conditions. An additional modification can be a sensor modification 5330. Sensor modification 5330 can influence the characteristics or values of data transmitted to microcontroller 1500 (FIG. 19) and operatively associated memory units. Microcontroller 1500 can monitor and obtain data from sensors associated with for example end effector 300. Sensor modification can also influence parameter readings at one or more added sensor(s). For example, a primary sensor such as a magnetic field sensor located for example at a distal portion of anvil 306 (FIG. 1) can indicate a certain thickness of a bite of tissue; however, reference to a secondary sensor such as a strain gauge can be factored in such that the measured Hall effect voltage can be adjusted. As a result, inputs such as tissue modification 5320 and sensor modification 5330 can influence an actual speed 5340 that is adjusted to take into account one or both.

Figure 47:
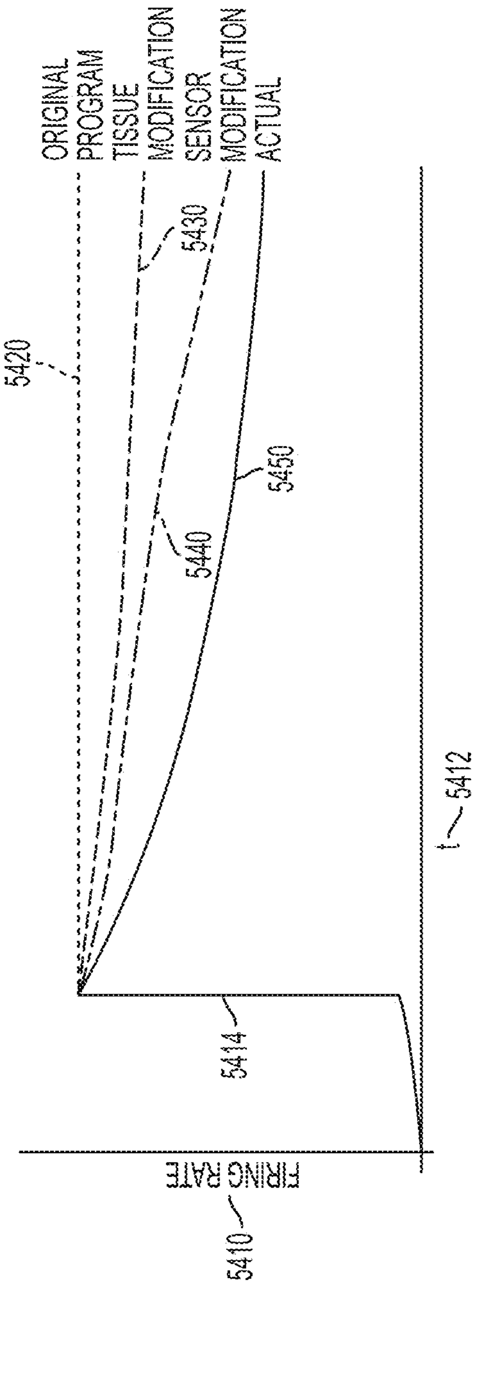
FIG. 47 illustrates one aspect of a mechanism for adapting firing rate associated with a parameter of a surgical instrument in the context of tissue modification and sensor modification.

Additionally, in accordance with aspects, FIG. 47 illustrates adaptive mechanisms that can influence actual behavior of a firing rate 5410 in the process of carrying out a surgical procedure. Firing rate 5410 can be enumerated on the vertical (y) axis and time 5412 (*t*) is represented along the horizontal (x) axis. Firing rate 5410 can represent a rate at which a firing member 220 (FIGS. 1 and 7) is longitudinally deployed, a rate at which tissue is incised, and/or a rate at which staples are deployed. In various examples, a firing rate 5410 value can ascend, upon actuation of a firing mechanism. Based on control measures derived from predetermined algorithms, or dynamically generated algorithms, or both, one or more modifications can be made to an original program in the memory that can define the firing rate (here, a steady firing rate 5420). One modification can be a tissue modification 5430 that can influence operation of instrument such that speed is upwardly or downwardly adjusted in order to obtain a more desirable set of conditions. An additional modification can be a sensor modification 5440. Sensor modification 5440 can influence the characteristics or values of data transmitted to microcontroller 1500 from sensors associated with for example end effector 300 (FIG. 1). Sensor modification 5440 can also influence parameter readings at one or more added sensor(s). For example, a primary sensor such as a magnetic field sensor on end effector 300 can indicate a certain thickness of a bite of tissue; however, reference to a secondary sensor such as a strain gauge can be factored in such that the measured Hall effect voltage can be adjusted. As a result, inputs such as tissue modification 5430 and sensor modification 5440 can influence an actual speed 5450 that is adjusted to take into account one or both.

Inputs can be given their actual weight, i.e., without selective weighting. However, in various aspects one or more inputs may not be weighted equally. Certain inputs may be given more weight than other inputs.

Figure 48:
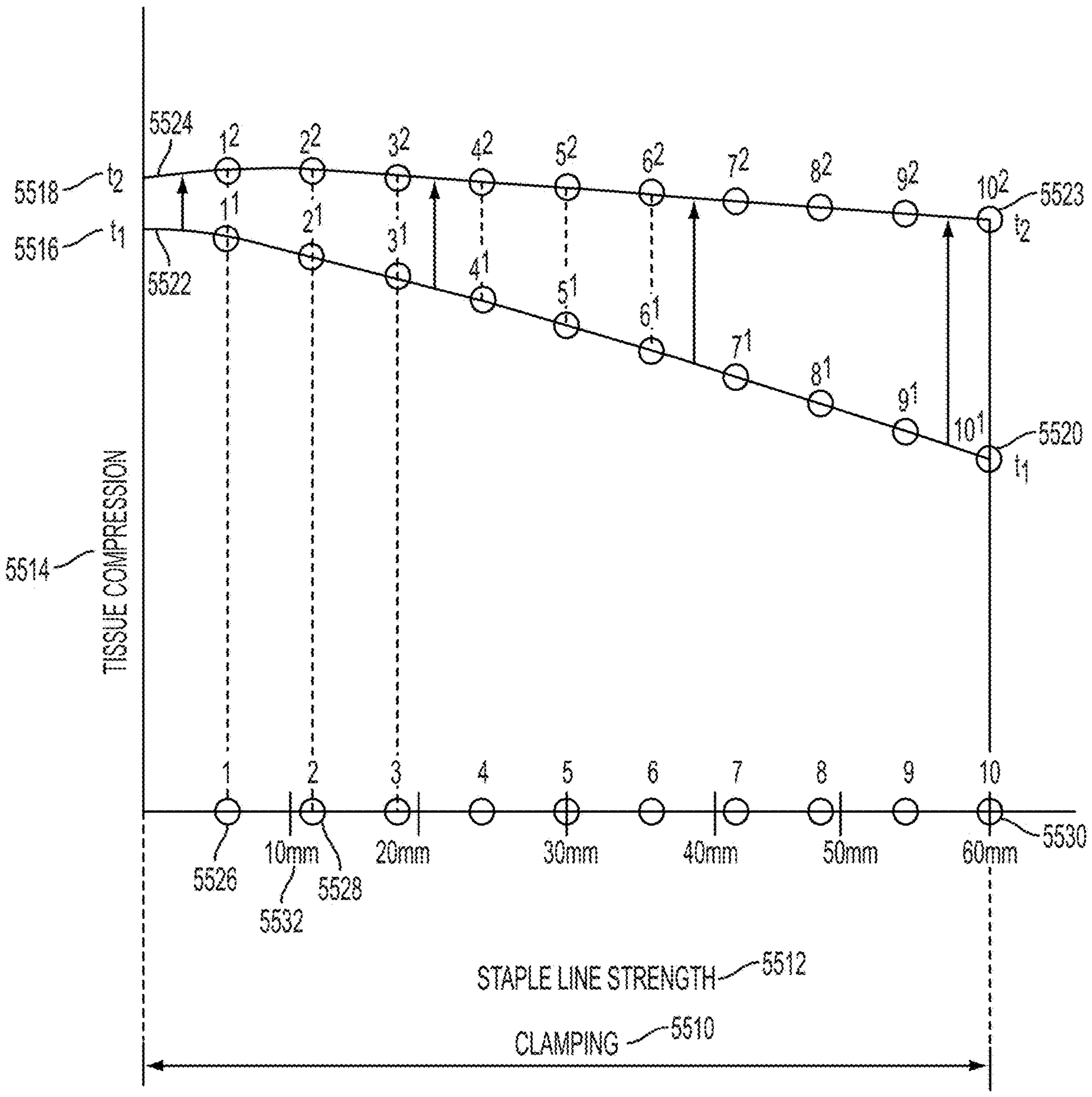
FIG. 48 illustrates one aspect of a mechanism for adapting operations associated with a surgical instrument in the context of tissue compression during a clamping phase.
Figure 49:
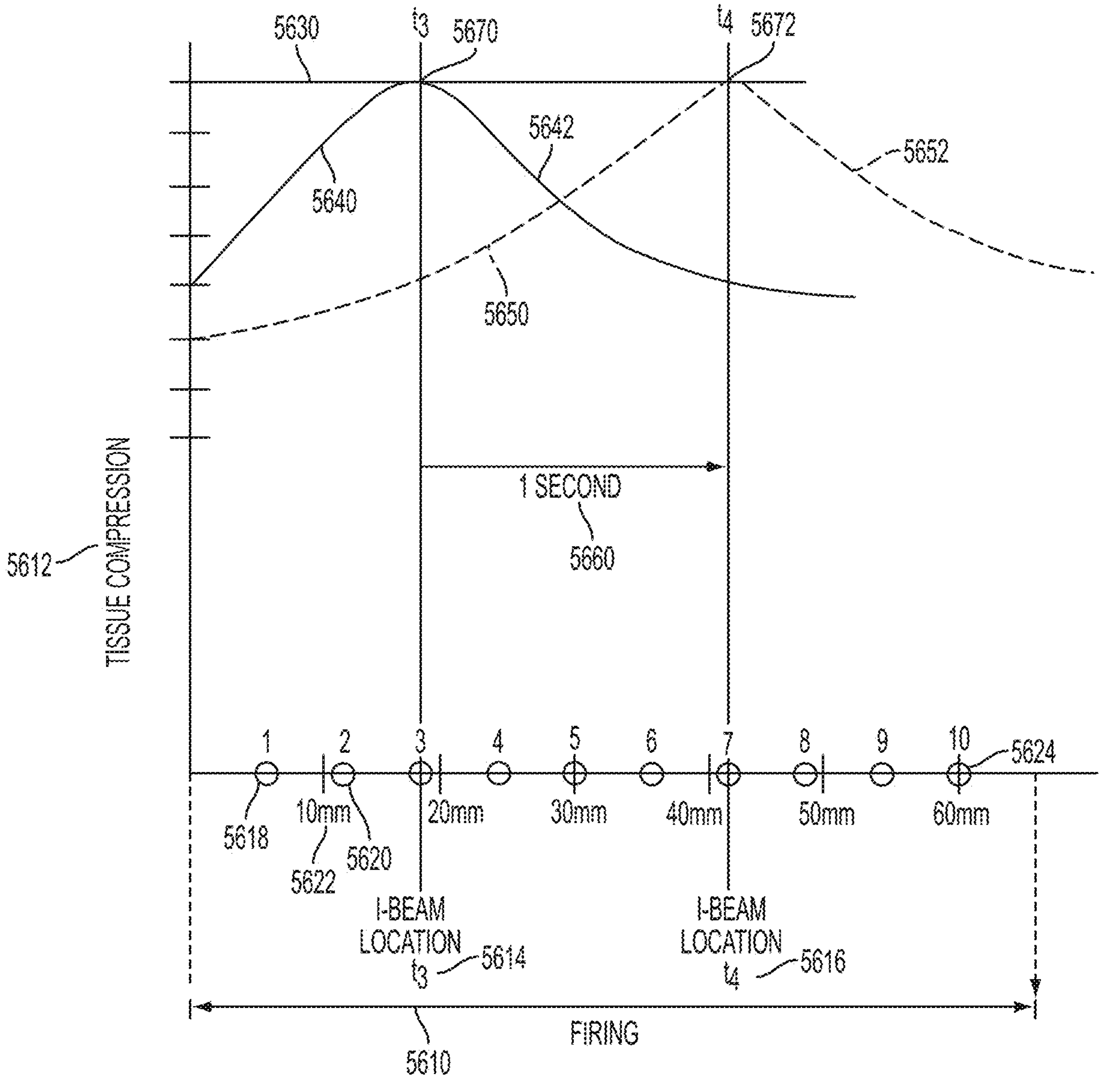
FIG. 49 illustrates one aspect of a mechanism for adapting operations associated with a surgical instrument in the context of tissue compression during a firing phase.

Adequate staple formation is a key consideration. Factors that influence staple formation include finding desirable operational envelopes based on tissue compression. FIGS. 48 and 49 illustrate example scenarios where a parameter such as differential tissue compression, as measured by impedance sensors, can result in adaptive firing procedures. FIG. 48 illustrates clamping 5510 operations where tissue compression 5514 is shown along the vertical (y) axis and staple cartridge size 5532 (*mm*) is shown along the horizontal (x) axis. Measurements from an end effector 300 (FIG. 1) can embrace a tissue portion of length up to 60 mm in this example, though it can be of a greater length in other examples. Tissue compression within the clamping end effector 300 can be measured by impedance sensors positioned, for example, every 6 mm, such as from 6 mm-60 mm. An impedance measurement can be taken at each sensor. During a surgical procedure, tissue can be compressed within end effector 300. Impedance measurements can be taken at times t1 5516 and t2 5518. At time t1 5516, a curve 5522 can be described toward 5520 by monitoring impedance measurements from one more of the impedance sensors (including impedance sensors 5526, 5528 and 5530). It will be appreciated that there may be ten impedance sensors as shown in the example, but there may be more or fewer. At a second time, t2 5518, a curve 5524 can be described toward 5523 by monitoring the same impedance measurements from one more of the impedance sensors (including impedance sensors 5526, 5528 and 5530). Impedance can be measured based on values from one or more of the impedance sensors, along a curve toward 5524. Comparing the impedance values for a given sensor from t1 and t2 can reveal a differential based on staple line length 5512. There may be multiple reasons. One reason can be that the clamped tissue exhibits different compression properties at different locations along staple line length 5512. An additional reason can be that there is a different tissue thickness; in other words, the tissue may exhibit pre-clamping thickness of a profile seen in FIG. 51. Further, tissue creep may have played a role. It is possible that all these reasons contribute to the observed properties, or there are other reasons. In any event, differential tissue compression over time can be observed.

FIG. 49 can illustrate a firing operation 5610, including but not limited to a firing operation based on FIG. 48. In FIG. 49, tissue compression 5612 is shown along a vertical (y) axis and staple cartridge size 5622 (*mm*) is shown along the horizontal (x) axis. As the I-beam traverses the tissue, tissue compression 5612 measurements are taken by monitoring impedance measurements from one more of the impedance sensors (including impedance sensors 5618, 5620 and 5624). During firing, tissue compression 5612 can rise to a threshold 5630 and then peak at time t3 5670 relative to I-beam location 5614. Subsequently, tissue compression falls between t3 5670 and t4 5672 (e.g., 1 second 5660) relative to I-beam location 5616. This operation can describe a rising curve 5640 and a falling curve 5642. It also may be observed that under certain circumstances a rising curve 5640 can exhibit a convex complexion, and a falling curve a concave complexion 5642. It may be predicted that an I-beam may take more time to traverse tissue with certain characteristics, e.g., thicker tissue, diseased tissue, etc. Accordingly, a different tissue compression profile may be prescribed such that tissue compression measurements observe a second curve 5650, 5652. In addition, second curve 5650, 5652 may result where there is a differential thickness of the pre-clamped tissue, such as that seen in FIG. 51. Portion 5810 is thinner than portion 5812. Traversing thicker tissue can act to slow the relative speed of the I-Beam, leading to different tissue compression measurements over time, and accordingly variable tissue profiles.

Accordingly, a differential in tissue compression measurements between t1 and t2 can lead to an adaptive response whereby control measures adjust a curve of tissue compression during a firing phase 5610. It will be appreciated, then, that the curve peaking at t4 can represent an adaptive curve based on tissue properties that can lead to improved results from the surgical procedure, battery usage, and other operations where an adaptive response can be used.

The shape of the curve can have significance. For example, a convex curve can reflect a rising tissue compression profile during a firing phase 5610. A concave curve can reflect a falling tissue compression profile during a firing phase 5610. A peak tissue compression measurement 5670, 5672 can fall between respective concave and convex curves. (For purposes of this disclosure, a perspective based on which concavity or convexity is found is based on viewing from a higher value on the y-axis than the peak of the curve.)

Figure 50:
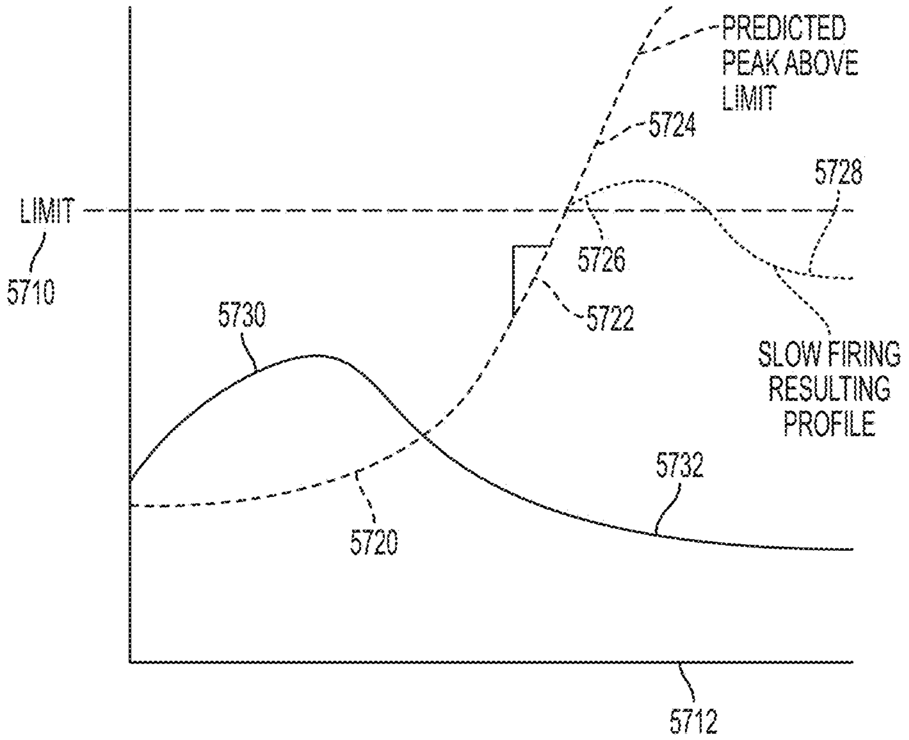
FIG. 50 illustrates one aspect of a mechanism for adapting operations associated with a surgical instrument in the context of slowing a firing event where a peak is predicted above a limit.

In conjunction with FIGS. 48 and 49, or as independent examples, control measures can wholly or partially adjust firing in order to prevent a parameter from rising above a certain limit. FIG. 50 shows an example scenario. A first curve 5730, 5732 can be a predicted firing profile stored by instrument 10 (FIGS. 1-4) for a given type of tissue. It will be seen that the vertical (y) axis parameter, such as tissue compression, over time (t) along the horizontal (x) axis 5172 can rise as in curve 5730, then fall as in curve 5732. However, it is possible that the values associated with the predicted firing profile diverge, during operation, from values actually observed during the surgical procedure. As a result, instrument 10 can take measures to adapt. For example, the observed measurements can fall along curve 5720, with a slower rate of rise but projected higher peak. Thus, the y-axis parameter can continue to rise. Under certain circumstances, it can be predicted that the curve for the y-axis parameter could breach predetermined, or dynamically determined, limit 5710 prior to reaching its peak. This prediction can be made based on a slope 5722 of the curve, in combination or not with input from the x-axis 5172 parameter (e.g., time). If it is determined that the peak is predicted to be above the limit 5726, or other portions of curve 5724 will breach the limit 5710, instrument 10 could adapt firing in order to provide for a slower firing rate. Doing so can result in the y-axis measurement falling along an adaptive curve 5728 based on slower firing. The adaptive curve can rise above the limit, or be constrained from doing by adapting operations accordingly.

Figure 51:
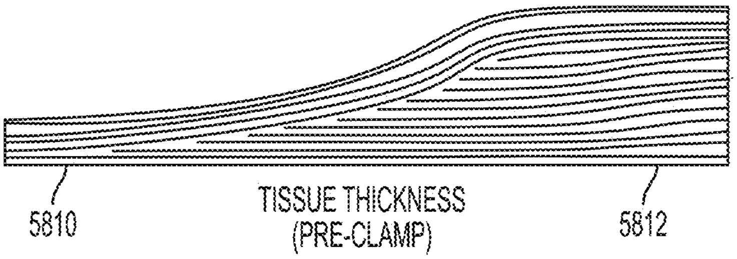
FIG. 51 illustrates a portion of tissue having a disparity in thickness.

FIG. 51 illustrates a portion of tissue prior to clamping. It can be seen that one end of the tissue 5810 is thinner than the other end 5812. In such circumstances, there can be differential forces and timings exerted by end effector 300

(FIG. 1) on the tissue, and by the tissue on end effector 300. The thickness disparity can be taken into account by instrument 10 (FIGS. 1-4) in adapting to such thickness. It may be the case that this tissue portion is similar to the one considered in connection with FIGS. 48-49. It also may be the case that another tissue portion is illustrated in connection with FIGS. 48-49, to show more general applicability. It may further be the case that FIG. 50 is a graphical representation of adaptive operations performed in connection with a tissue portion like that in FIG. 51; again, it also may be the case that FIG. 50 can show more generally adaptive operations in response to detecting measurement of certain parameters during the course of a surgical procedure and adjusting accordingly.

In various aspects, the present disclosure provides an instrument 10 (described in connection with FIGS. 1-29) configured to sense tissue compression when tissue is clamped between the jaw members of the end effector, such as, for example, between the anvil and the staple cartridge. In one example, the instrument 10 (FIGS. 1-4) can be configured to sense tissue contact in one of the jaw members such as the anvil and/or the staple cartridge. In another example, the instrument 10 can be configured to sense the pressure applied to the tissue by the jaw members. In yet another example, the instrument 10 can be configured to measure the electrical impedance (resistance) through the tissue between the jaw members. This may be achieved by embedding micro electrodes in at least one of the jaw members to drive a low amplitude, low energy, RF signal through the tissue to enable a nontherapeutic measurement of tissue impedance. The energy level is kept low enough to avoid therapeutic tissue effects such as coagulation, sealing, welding, or cautery. Further, the instrument 10 can include devices to produce two distinct measures from a single set of energized and return paths. In one example, multiple frequency signals can be overlaid to measure impedance in different places simultaneously. This can include a single active electrode with the channel and the anvil grounded through isolated paths with filters for different frequency RF signals. Otherwise, two isolated return paths with independent filters, which are part of the handle electronics system can be used. In another example, the sequential impedance measurements would be multiplexed at variable RF frequencies.

RF technology has been used in endocutters for some time. The challenge in employing the technology is in the delivery of high density RF energy and shorting between the jaw members of the end effector. Despite the shortcomings of using RF energy therapeutically, RF technology can be effectively employed sub-therapeutically to sense tissue compression rather than actually coagulating, sealing, or cauterizing tissue. In the sub-therapeutic sense, the endosurgical device can employ RF energy to sense internal tissue parameters and adjust the deployment of staples rather and being employed as an adjunct to the stapling operation to assist in sealing the tissue prior to cutting the tissue with a knife.

RF technology used in endosurgical medical devices, and for example, in RF endocutters, may introduce the challenges of handling high densities of energy and dealing with shorting. However, RF technology may be less challenging if used merely to sense tissue compression rather than, for example, cauterizing tissue. RF technology may be used as a way for medical devices, such as endocutters, to sense internal tissue parameters such as compression, and adjust stapling deployment in response. RF electrode and cautery devices may utilize the same electrodes for sensing tissue impedance as they do to melt tissue. These same electrodes may be implemented with significantly less electrical and power requirements as a tissue compression sensor system.

RF electrodes and cautery devices can utilize the same electrodes for sensing tissue impedance as they do to weld the tissue by applying energy thereto. Nevertheless, in the an endocutter instrument context, the RF electrodes can be employed to as a tissue compression sensor system with significantly less electronics and power needs relative to a fully equipped electrosurgical device. A single energized electrode on the cartridge, for example, or perhaps an isolated knife, can be used to make multiple tissue compression measurements simultaneously. If multiple RF signals are overlaid or multiplexed they can be transmitted down the single power conductor and then allowed to return on either the channel frame or the anvil of the device. If a filter is provided in the anvil and channel contacts before they join the common return path, the tissue impedance for both paths can be differentiated. This would provide a measure of through tissue versus lateral tissue compression. This filtered approach may be implemented proximal and distal as opposed to vertical and lateral depending on the placement of the filters and the location of the metallic electrically conductive return paths. The smaller frequency generator and signal processor may be implemented in a small package form factor on an existing circuit board or a sub circuit board without the need for extensive extra cost associated with an RF sealing/cauterization system.

Figure 52:
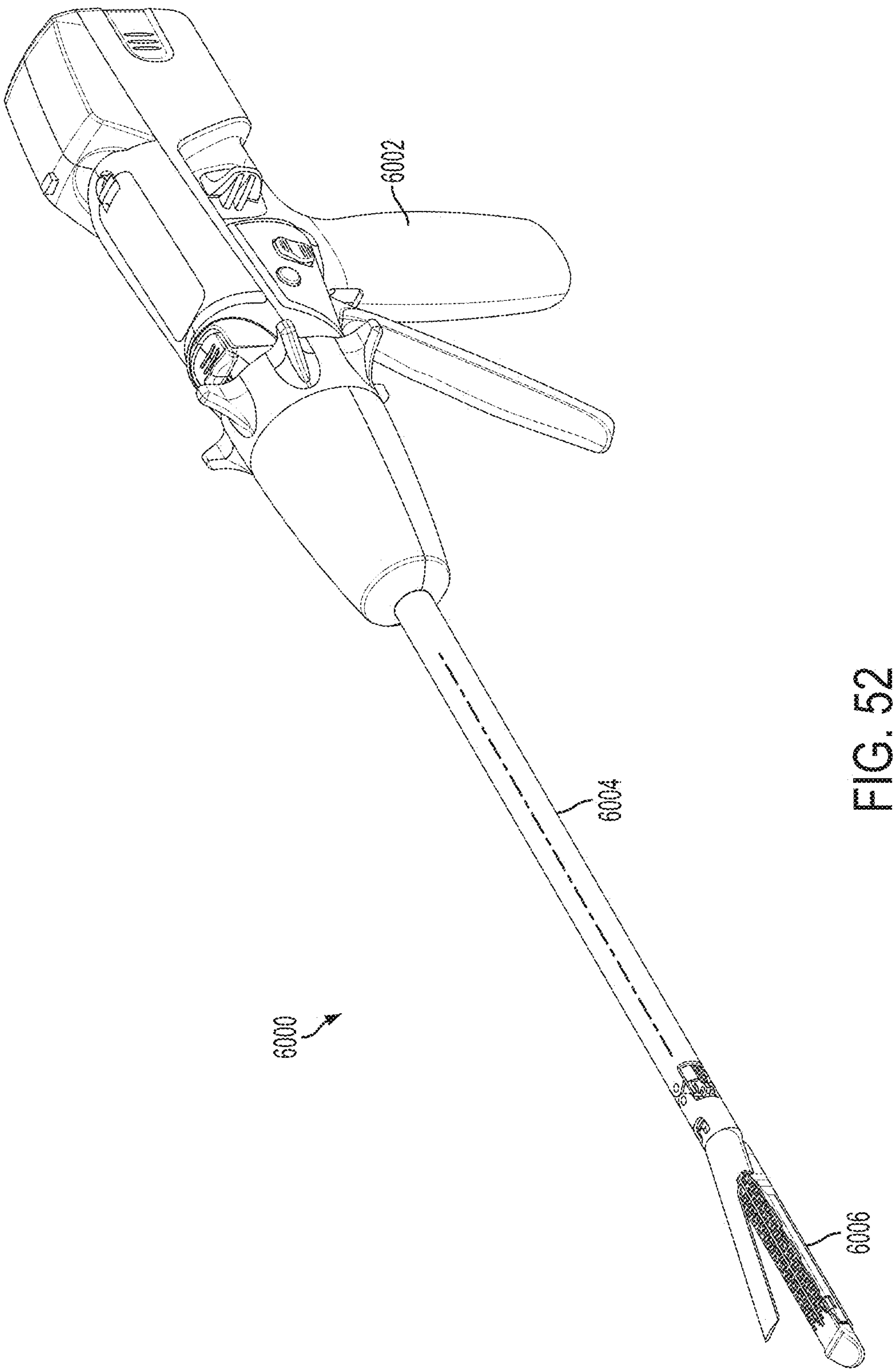
FIG. 52 depicts an example medical device that can include one or more aspects of the present disclosure.
Figure 53A:
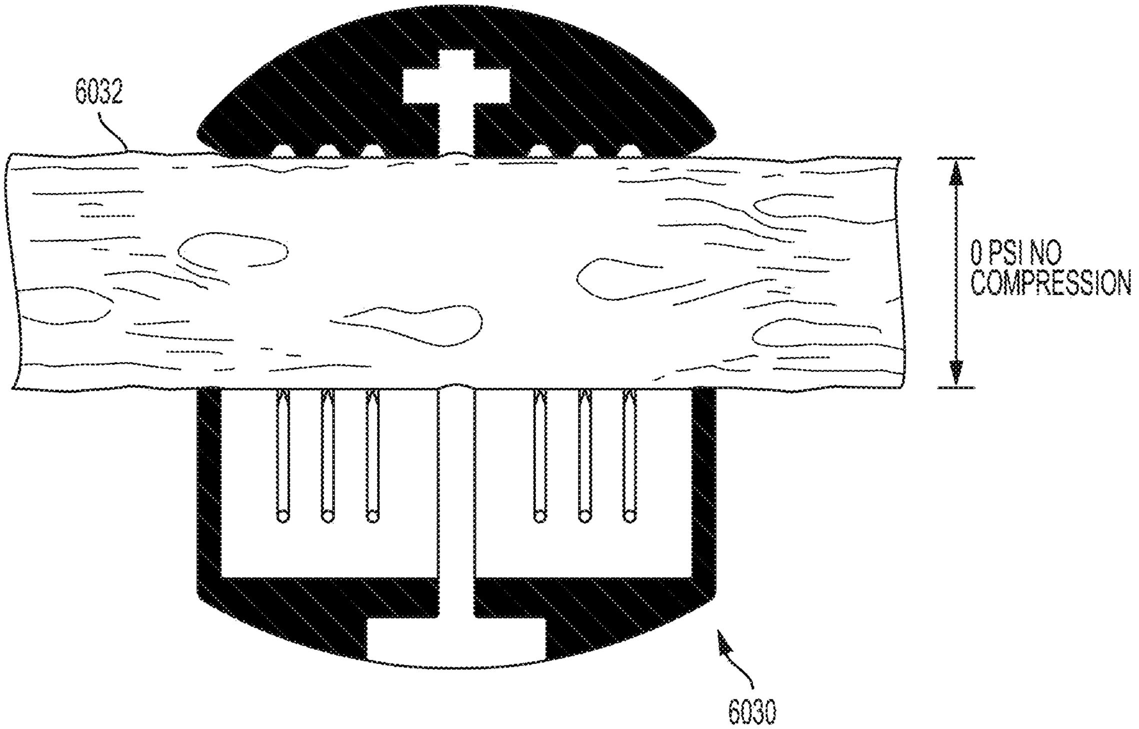
FIG. 53A depicts an example end-effector of a medical device surrounding tissue in accordance with one or more aspects of the present disclosure.
Figure 53B:
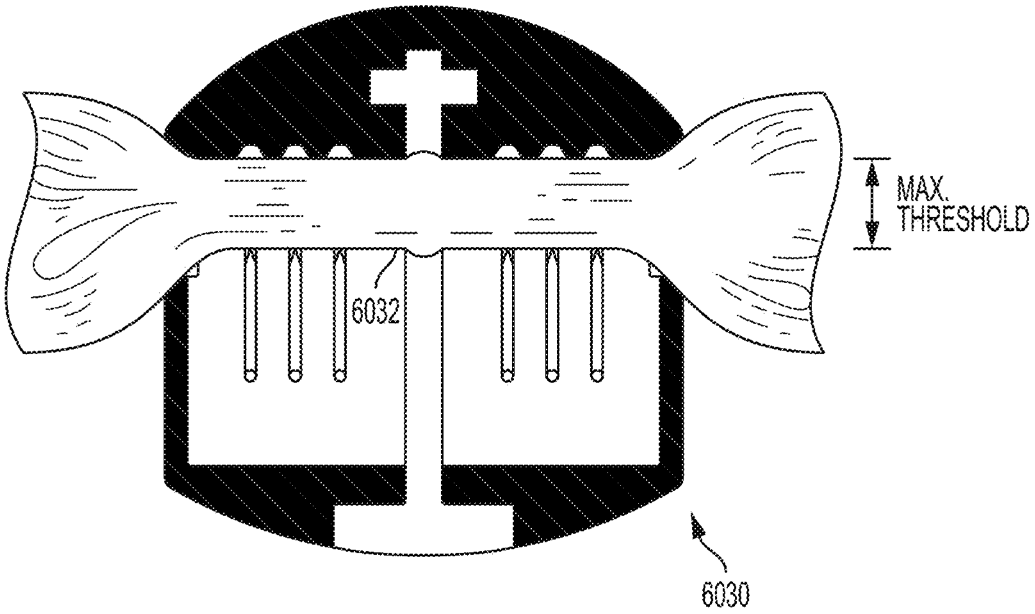
FIG. 53B depicts an example end-effector of a medical device compressing tissue in accordance with one or more aspects of the present disclosure.

Referring to FIG. 52, an endocutter 6000 may include a handle component 6002, a shaft component 6004, and an end-effector component 6006. The endocutter 6000 is similarly constructed and equipped as the motor-driven surgical cutting and fastening instrument 10 described in connection with FIGS. 1-29. Accordingly, for conciseness and clarity the details of operation and construction will not be repeated here. The end-effector 6006 may be used to compress, cut, or staple tissue. Referring now to FIG. 53A, an end-effector 6030 may be positioned by a physician to surround tissue 6032 prior to compression, cutting, or stapling. As shown in FIG. 53A, no compression may be applied to the tissue while preparing to use the end-effector. Referring now to FIG. 53B, by engaging the handle (e.g., handle 6002) of the endocutter, the physician may use the end-effector 6030 to compress the tissue 6032. In one aspect, the tissue 6032 may be compressed to its maximum threshold, as shown in FIG. 53B.

Figure 54A:
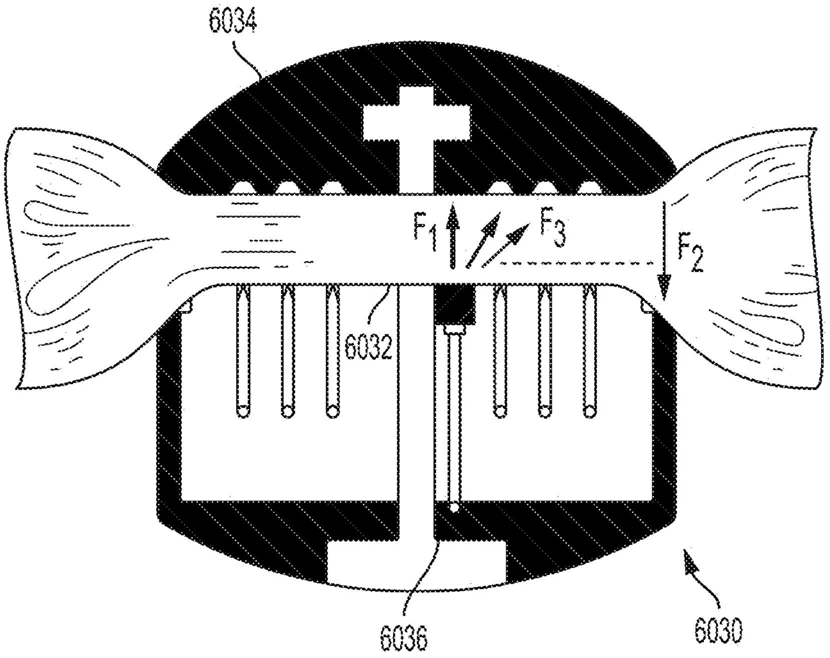
FIG. 54A depicts example forces exerted by an end-effector of a medical device compressing tissue in accordance with one or more aspects of the present disclosure.
Figure 54B:
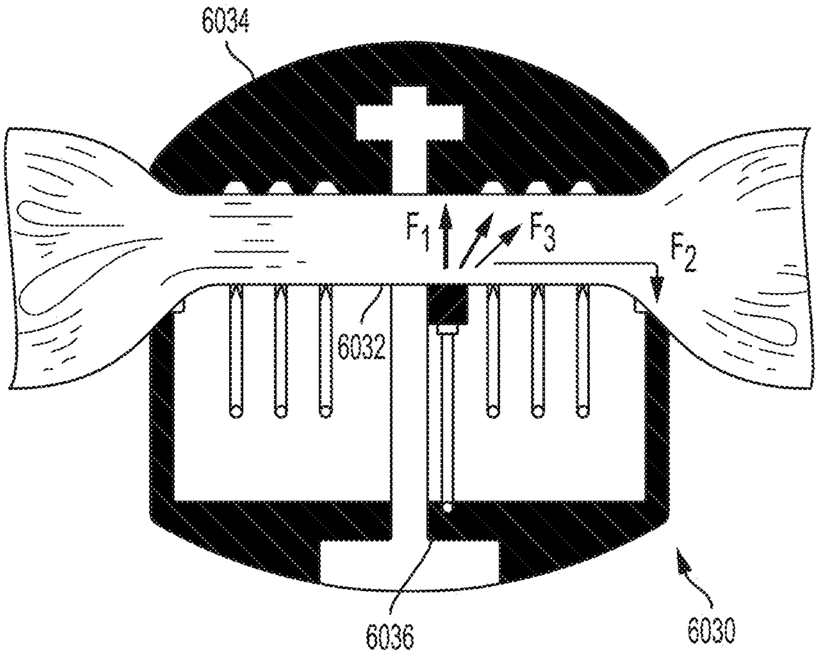
FIG. 54B also depicts example forces exerted by an end-effector of a medical device compressing tissue in accordance with one or more aspects of the present disclosure.

Referring to FIG. 54A, various forces may be applied to the tissue 6032 by the end-effector 6030. For example, vertical forces F1 and F2 may be applied by the anvil 6034 and the channel frame 6036 of the end-effector 6030 as tissue 6032 is compressed between the two. Referring now to FIG. 54B, various diagonal and/or lateral forces also may be applied to the tissue 6032 when compressed by the end-effector 6030. For example, force F3 may be applied. For the purposes of operating a medical device such as endocutter 6000, it may be desirable to sense or calculate the various forms of compression being applied to the tissue by the end-effector. For example, knowledge of vertical or lateral compression may allow the end-effector to more precisely or accurately apply a staple operation or may inform the operator of the endocutter such that the endocutter can be used more properly or safely.

The compression through tissue 6032 may be determined from an impedance of tissue 6032. At various levels of compression, the impedance Z of tissue 6032 may increase or decrease. By applying a voltage V and a current I to the tissue 6032, the impedance Z of the tissue 6032 may be determined at various levels of compression. For example, impedance Z may be calculated by dividing the applied voltage V by the current I.

Figure 55:
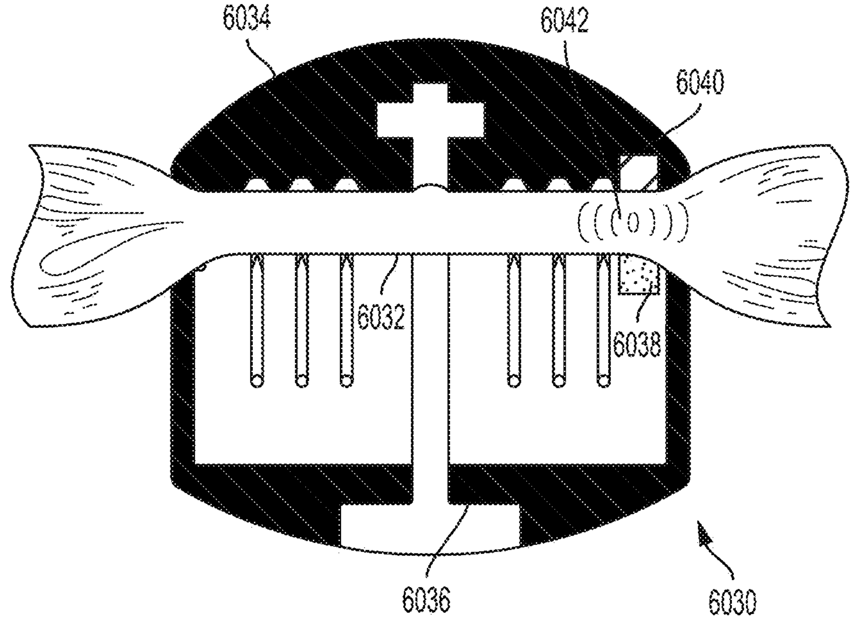
FIG. 55 depicts an example tissue compression sensor system in accordance with one or more aspects of the present disclosure.

Referring now to FIG. 55, in one aspect, an RF electrode 6038 may be positioned on the end-effector 6030 (e.g., on a staple cartridge, knife, or channel frame of the end-effector 6030). Further, an electrical contact 6040 may be positioned on the anvil 6034 of the end-effector 6030. In one aspect, the electrical contact may be positioned on the channel frame of the end-effector. As the tissue 6032 is compressed between the anvil 6034 and, for example, the channel frame 6036 of the end-effector 6030, an impedance Z of the tissue 6032 changes. The vertical tissue compression 6042 caused by the end-effector 6030 may be measured as a function of the impedance Z of the tissue 6032.

Figure 56:
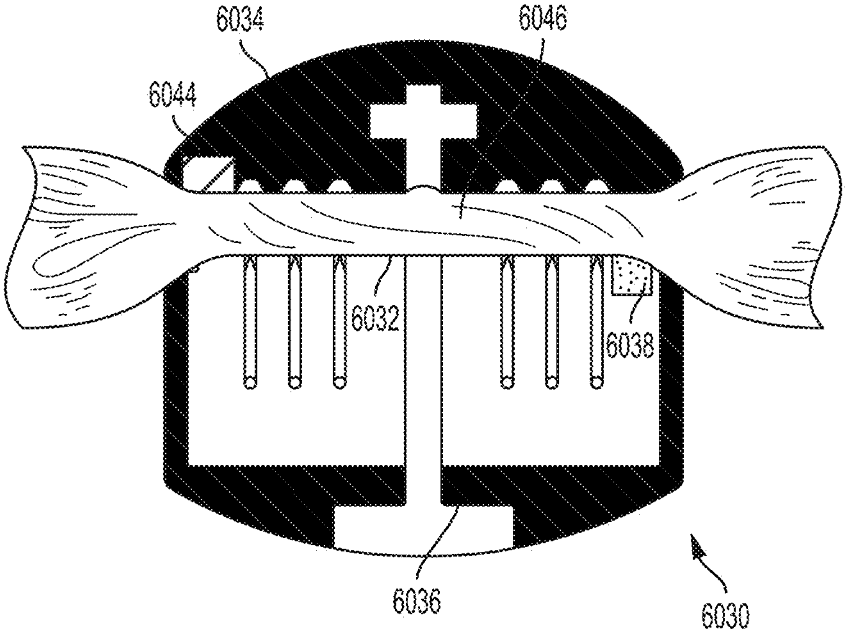
FIG. 56 also depicts an example tissue compression sensor system in accordance with one or more aspects of the present disclosure.

Referring now to FIG. 56, in one aspect, an electrical contact 6044 may be positioned on an opposite end of the anvil 6034 of the end-effector 6030 as the RF electrode 6038 is positioned. As the tissue 6032 is compressed between the anvil 6034 and, for example, the channel frame 6036 of the end-effector 6030, an impedance Z of the tissue 6032 changes. The lateral tissue compression 6046 caused by the end-effector 6030 may be measured as a function of the impedance Z of the tissue 6032.

Figure 57:
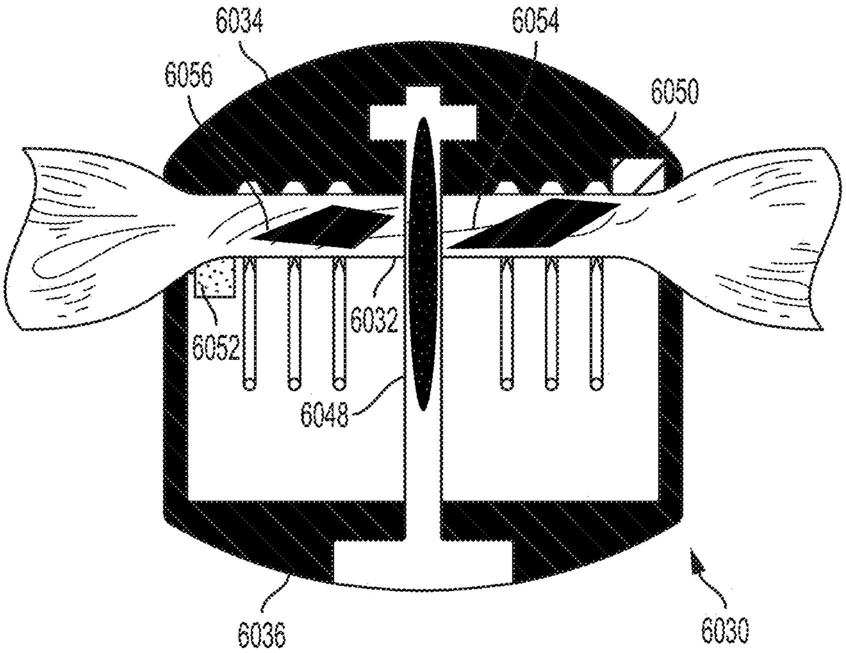
FIG. 57 also depicts an example tissue compression sensor system in accordance with one or more aspects of the present disclosure.

Referring now to FIG. 57, in one aspect, electrical contact 6050 may be positioned on the anvil 6034 and electrical contact 6052 may be positioned on an opposite end of the end-effector 6030 at channel frame 6036. RF electrode 6048 may be positioned laterally to the central to the end-effector 6030. As the tissue 6032 is compressed between the anvil 6034 and, for example, the channel frame 6036 of the end-effector 6030, an impedance Z of the tissue 6032 changes. The lateral compression or angular compressions 6054 and 6056 on either side of the RF electrode 6048 may be caused by the end-effector 6030 and may be measured as a function of different impedances Z of the tissue 6032, based on the relative positioning of the RF electrode 6048 and electrical contacts 6050 and 6052.

Figure 58:
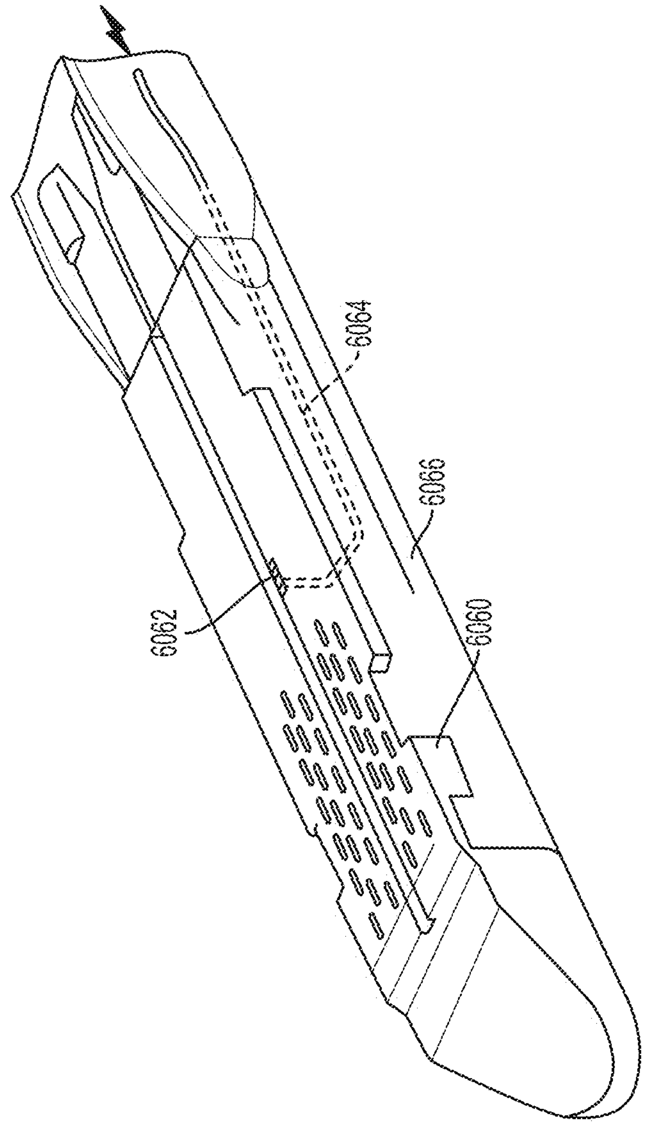
FIG. 58 depicts an example end-effector channel frame in accordance with one or more aspects of the present disclosure.

In accordance with one or more of the techniques and features described in the present disclosure, and as discussed above, an RF electrode may be used as an RF sensor. Referring now to FIG. 58, in one aspect, an RF sensor 6062 may be positioned on a staple cartridge 6060 inserted into a channel frame 6066 an end-effector. The RF electrode may run from a power line 6064 which may be powered by a power source in a handle (e.g., handle 6002) of an endocutter.

Figure 59:
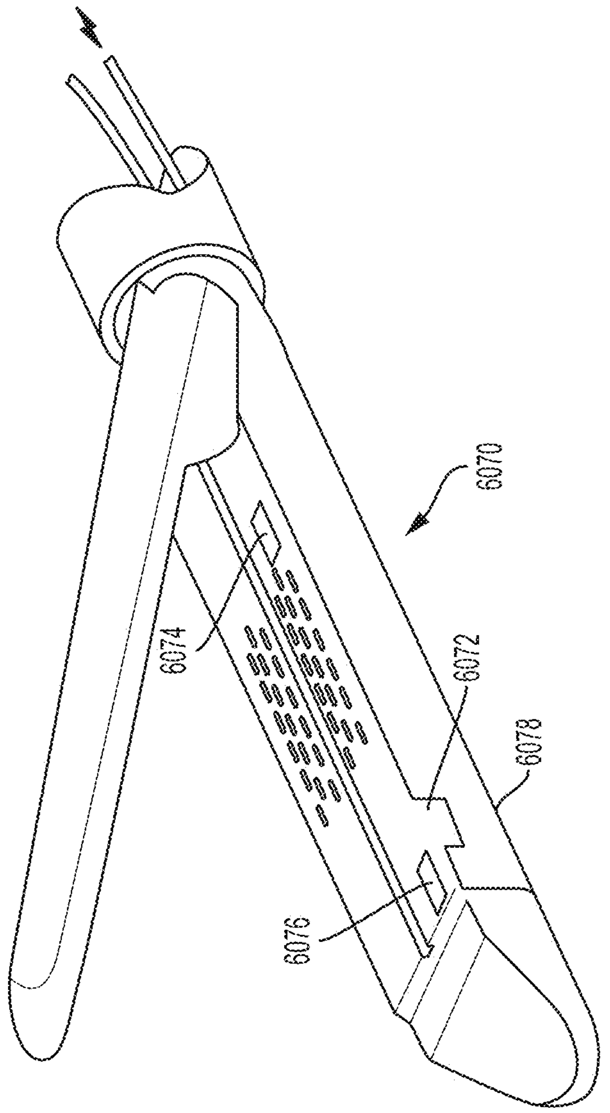
FIG. 59 depicts an example end-effector in accordance with one or more aspects of the present disclosure.

Referring now to FIG. 59, in one aspect, RF electrodes 6074 and 6076 may be positioned on a staple cartridge 6072 inserted into a channel frame 6078 of end-effector 6070. As shown, RF electrode 6074 may be placed in a proximal position of the end-effector relative to an endocutter handle. Further, RF electrode 6076 may be placed in a distal position of the end-effector relative to the endocutter handle. RF electrodes 6074 and 6076 may be utilized to measure vertical, lateral, proximal, or distal compression at different points in a tissue based on the position of one or more electrical contacts on the end-effector.

Figure 60:
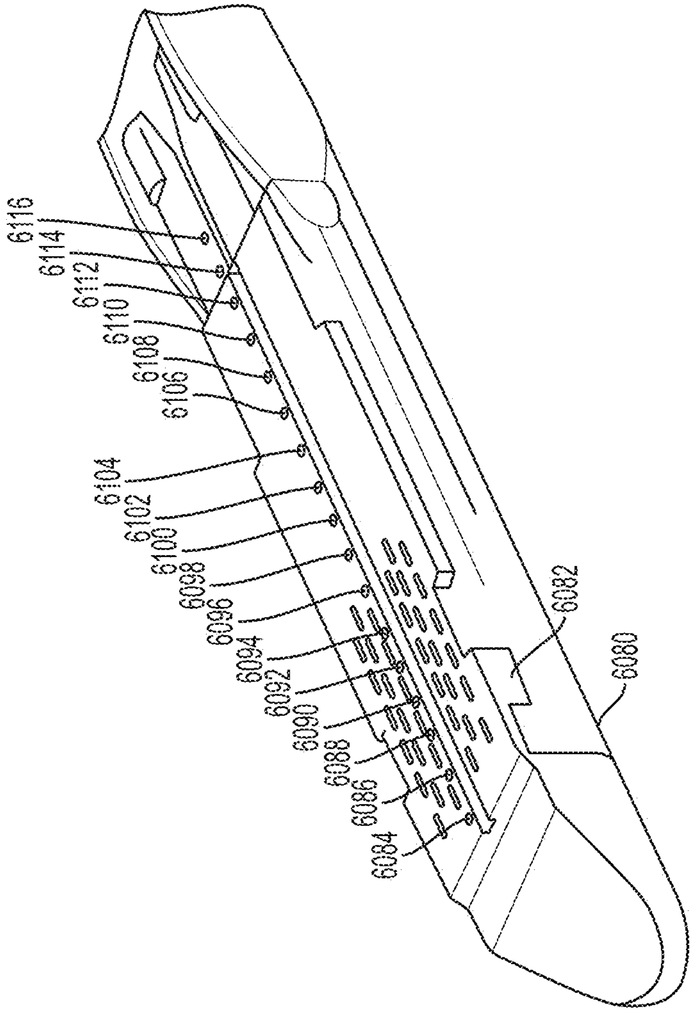
FIG. 60 also depicts an example end-effector channel frame in accordance with one or more aspects of the present disclosure.
Figure 61:
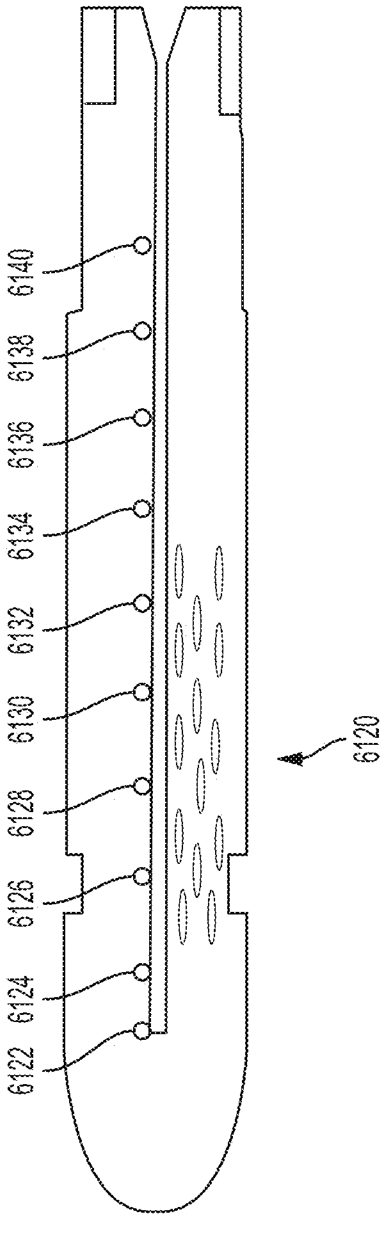
FIG. 61 also depicts an example end-effector channel frame in accordance with one or more aspects of the present disclosure.
Figure 62:
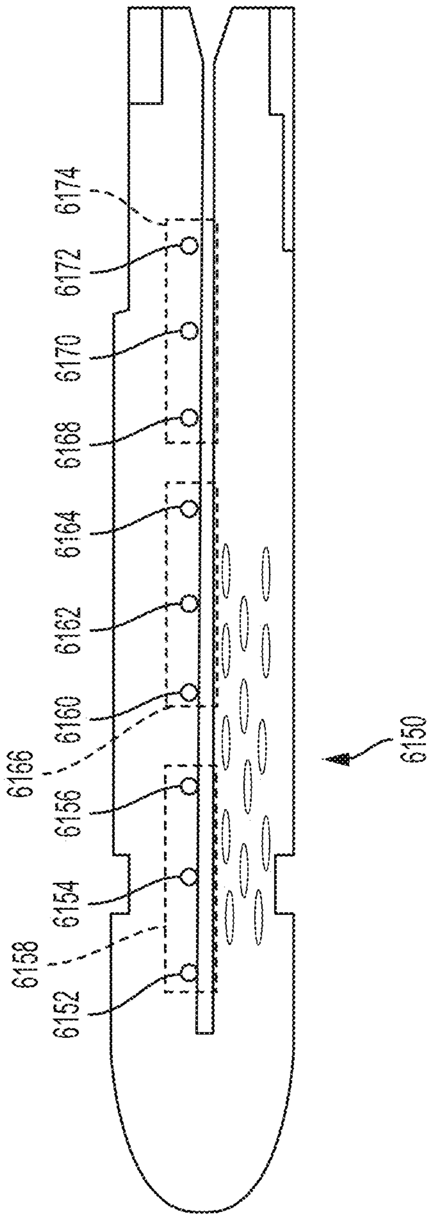
FIG. 62 also depicts an example end-effector channel frame in accordance with one or more aspects of the present disclosure.

Referring now to FIG. 60, in one aspect, RF electrodes 6084-6116 may be positioned on staple cartridge 6082 inserted into the channel frame 6080 (or other component of an end-effector) based on various points for which compression information is desired. Referring now to FIG. 61, in one aspect, RF electrodes 6122-6140 may be positioned on staple cartridge 6120 at discrete points for which compression information is desired. Referring now to FIG. 62, RF electrodes 6152-6172 may be positioned at different points in multiple zones of a staple cartridge based on how accurate or precise the compression measurements should be. For example, RF electrodes 6152-6156 may be positioned in zone 6158 of staple cartridge 6150 depending on how accurate or precise the compression measurements in zone 6158 should be. Further, RF electrodes 6160-6164 may be positioned in zone 6166 of staple cartridge 6150 depending on how accurate or precise the compression measurements in zone 6166 should be. Additionally, RF electrodes 6168-6172 may be positioned in zone 6174 of staple cartridge 6150 depending on how accurate or precise the compression measurements in zone 6174 should be.

Figure 63:
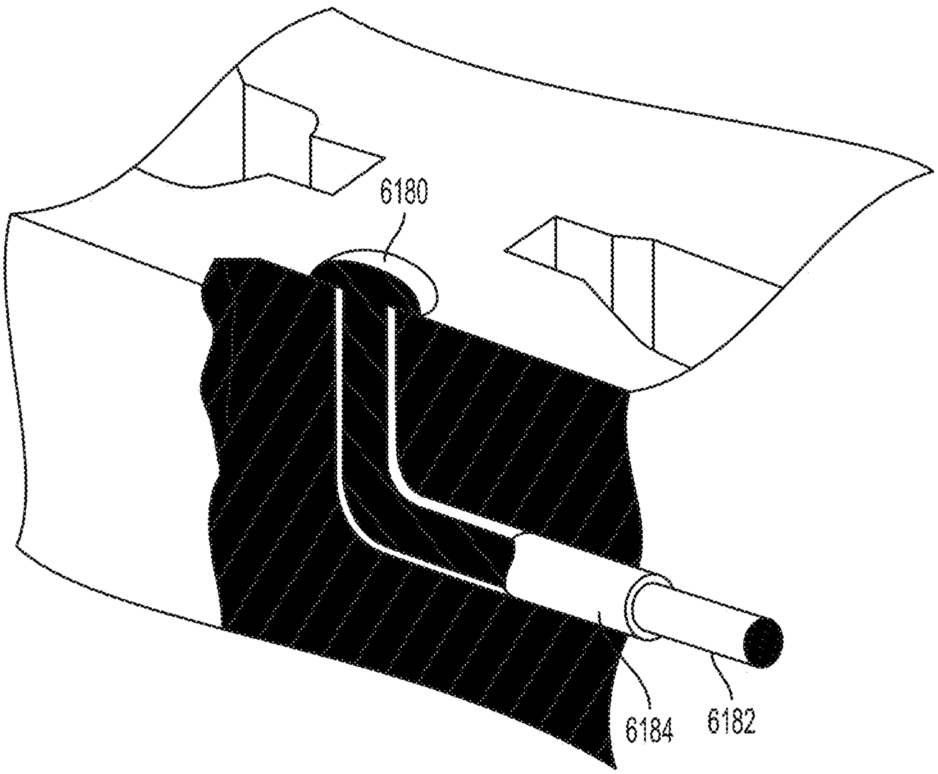
FIG. 63 depicts an example electrode in accordance with one or more aspects of the present disclosure.

The RF electrodes discussed herein may be wired through a staple cartridge inserted in the channel frame. Referring now to FIG. 63, in one aspect, an RF electrode may have a stamped "mushroom head" 6180 of about 1.0 mm in diameter. While the RF electrode may have the stamped "mushroom head" of about 1.0 mm in diameter, this is intended to be a non-limiting example and the RF electrode may be differently shaped and sized depending on each particular application or design. The RF electrode may be connected to, fastened to, or may form, a conductive wire 6182. The conductive wire 182 may be about 0.5 mm in diameter, or may have a larger or smaller diameter based on a particular application or design. Further, the conductive wire may have an insulative coating 6184. In one example, the RF electrode may protrude through a staple cartridge, channel frame, knife, or other component of an end-effector.

Figure 64:
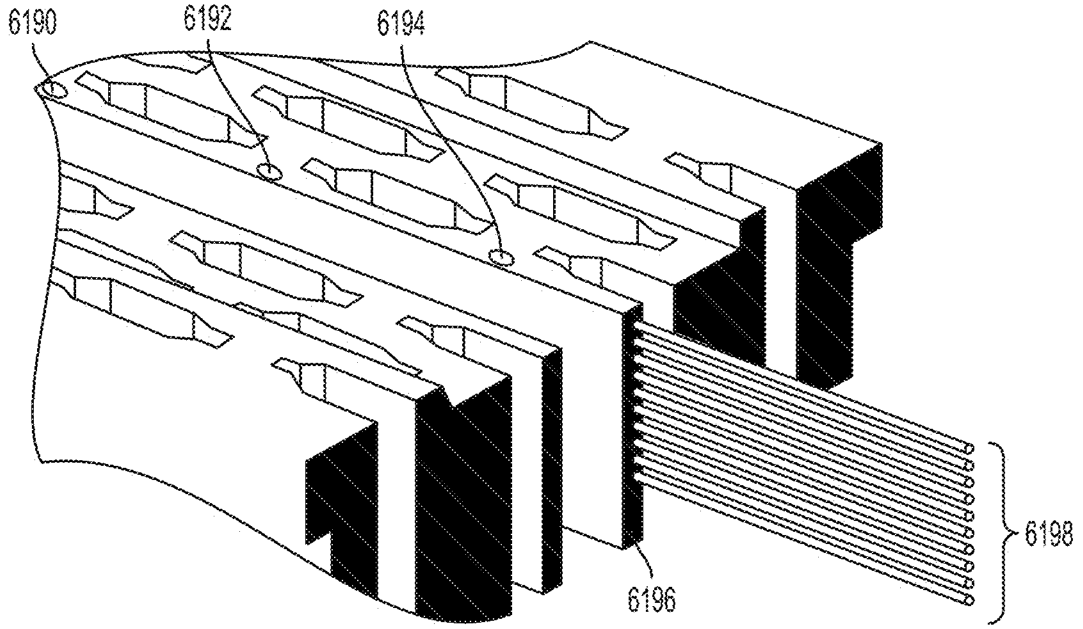
FIG. 64 depicts an example electrode wiring system in accordance with one or more aspects of the present disclosure.

Referring now to FIG. 64, the RF electrodes may be wired through a single wall or through multiple walls of a staple cartridge or channel frame of an end-effector. For example, RF electrodes 6190-6194 may be wired through wall 6196 of the staple cartridge or channel frame of an end-effector. One or more of wires 6198 may be connected to, fastened to, or be part of, RF electrodes 6190-6194 and may run through wall 6196 from a power source in, e.g., a handle of an endocutter.

Figure 65:
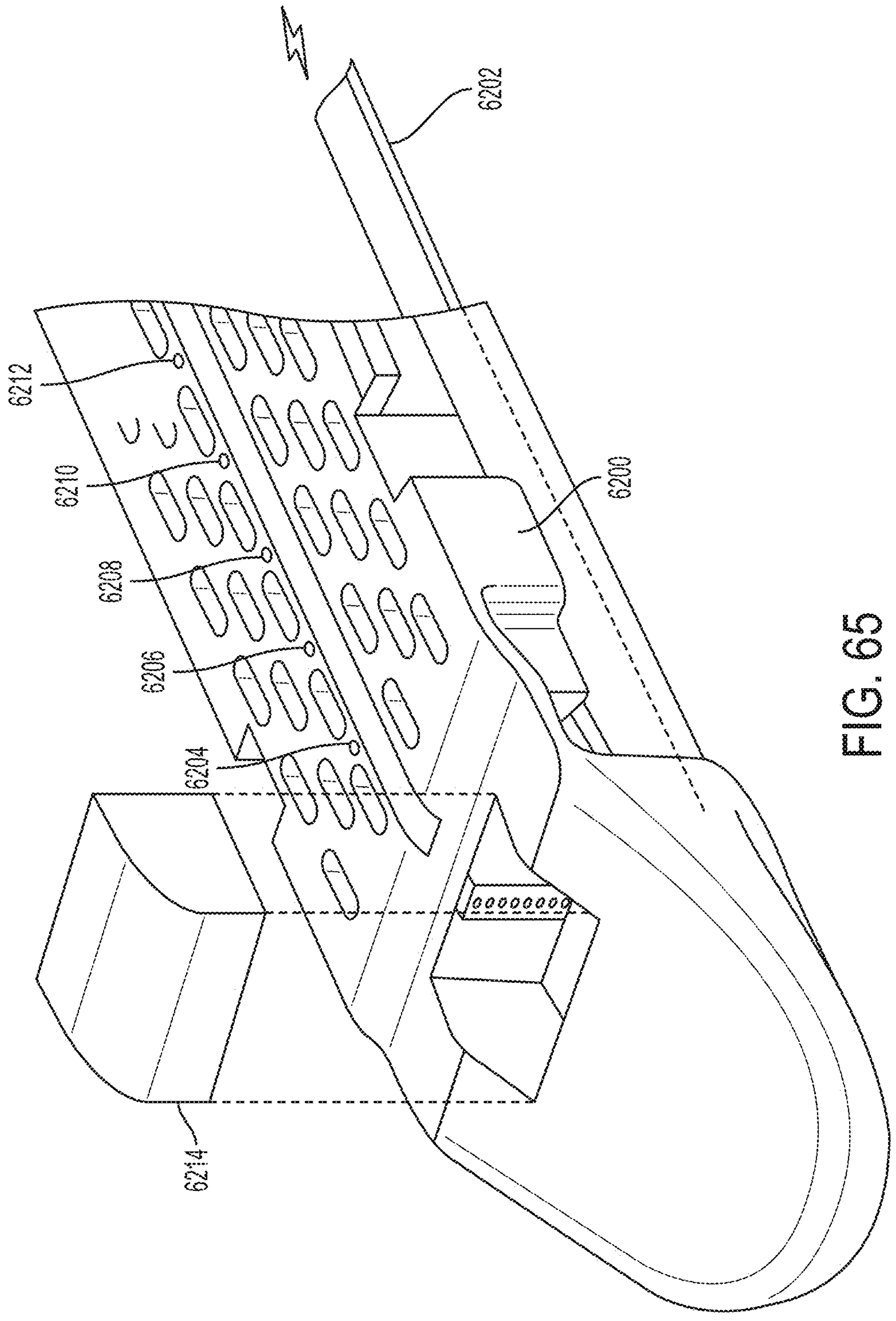
FIG. 65 also depicts an example end-effector channel frame in accordance with one or more aspects of the present disclosure.
Figure 66:
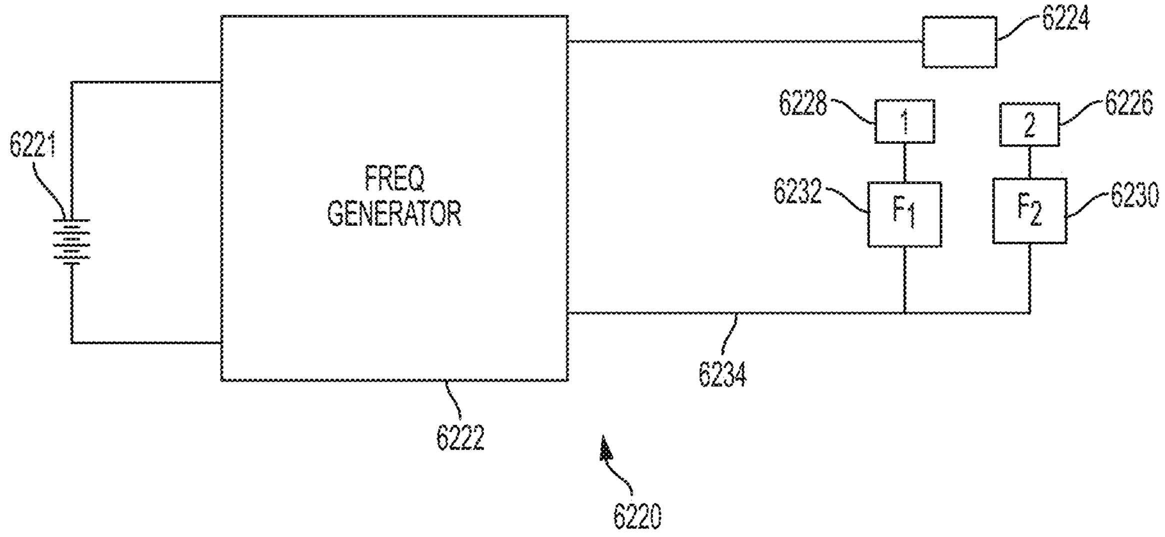
FIG. 66 is an example circuit diagram in accordance with one or more aspects of the present disclosure.

Referring now to FIG. 65, the power source may be in communication with the RF electrodes or may provide power to the RF electrodes through a wire or cable. The wire or cable may join each individual wire and lead to the power source. For example, RF electrodes 6204-6212 may receive power from a power source through wire or cable 6202, which may run through staple cartridge 6200 or a channel frame of an end-effector. In one example, each of RF electrodes 6204-6212 may have its own wire that runs to or through wire or cable 6202. The staple cartridge 6200 or channel frame also may include a controller 6214, such as the controller 2006 shown in connection with FIGS. 21A, 21B, or other controllers 2606 or 3017 shown in connection with FIGS. 27-29, for example. It will be appreciated that the controller 6214 should be suitably sized to fit in the staple cartridge 6200 or channel frame form factor. Also, the controller In various aspects, the tissue compression sensor system described herein for use with medical devices may include a frequency generator. The frequency generator may be located on a circuit board of the medical device, such as an endocutter. For example the frequency generator may be located on a circuit board in a shaft or handle of the endocutter. Referring now to FIG. 66, an example circuit diagram 6220 in accordance with one example of the present disclosure is shown. As shown, frequency generator 6222 may receive power or current from a power source 6221 and may supply one or more RF signals to one or more RF electrodes 6224. As discussed above, the one or more RF electrodes may be positioned at various locations or components on an end-effector or endocutter, such as a staple cartridge or channel frame. One or more electrical contacts, such as electrical contacts 6226 or 6228 may be positioned on a channel frame or an anvil of an end-effector. Further, one or more filters, such as filters 6230 or 6232 may be communicatively coupled to the electrical contacts 6226 or 6228 as shown in FIG. 66. The filters 6230 and 6232 may filter one or more RF signals supplied by the frequency generator 6222 before joining a single return path 6234. A voltage V and a current I associated with the one or more RF signals may be used to calculate an impedance Z associated with a tissue that may be compressed and/or communicatively coupled between the one or more RF electrodes 6224 and the electrical contacts 6226 or 6228.

Figure 67:
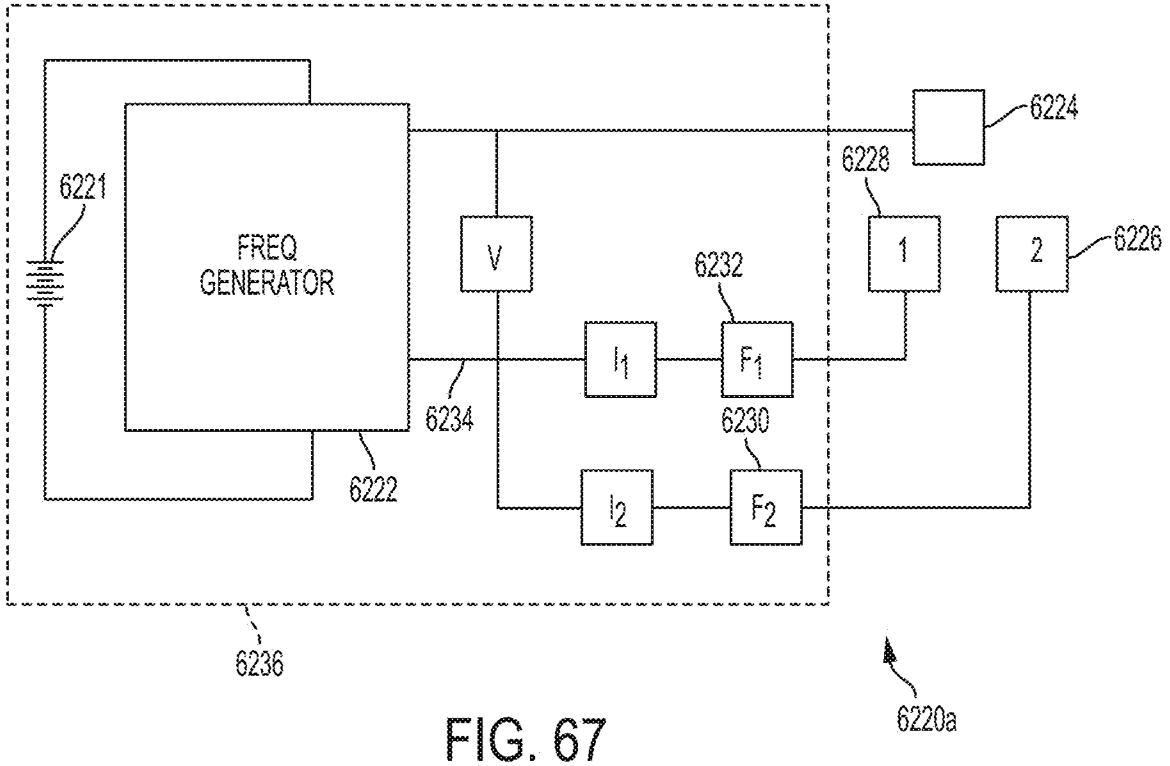
FIG. 67 is also an example circuit diagram in accordance with one or more aspects of the present disclosure.

Referring now to FIG. 67, various components of the tissue compression sensor system described herein may be located in a handle 6236 of an endocutter. For example, as shown in circuit diagram 6220*a*, frequency generator 6222 may be located in the handle 6236 and receives power from power source 6221. Also, current I1 and current I2 may be measured on a return path corresponding to electrical contacts 6228 and 6226. Using a voltage V applied between the supply and return paths, impedances Z1 and Z2 may be calculated. Z1 may correspond to an impedance of a tissue compressed and/or communicatively coupled between one or more of RF electrodes 6224 and electrical contact 6228. Further, Z2 may correspond to an impedance of a tissue compressed and/or communicatively coupled between one or more of RF electrodes 6224 and electrical contact 6226. Applying the formulas Z1=V/I1 and Z2=V/I2, impedances Z1 and Z2 corresponding to different compression levels of a tissue compressed by an end-effector may be calculated.

Figure 68:
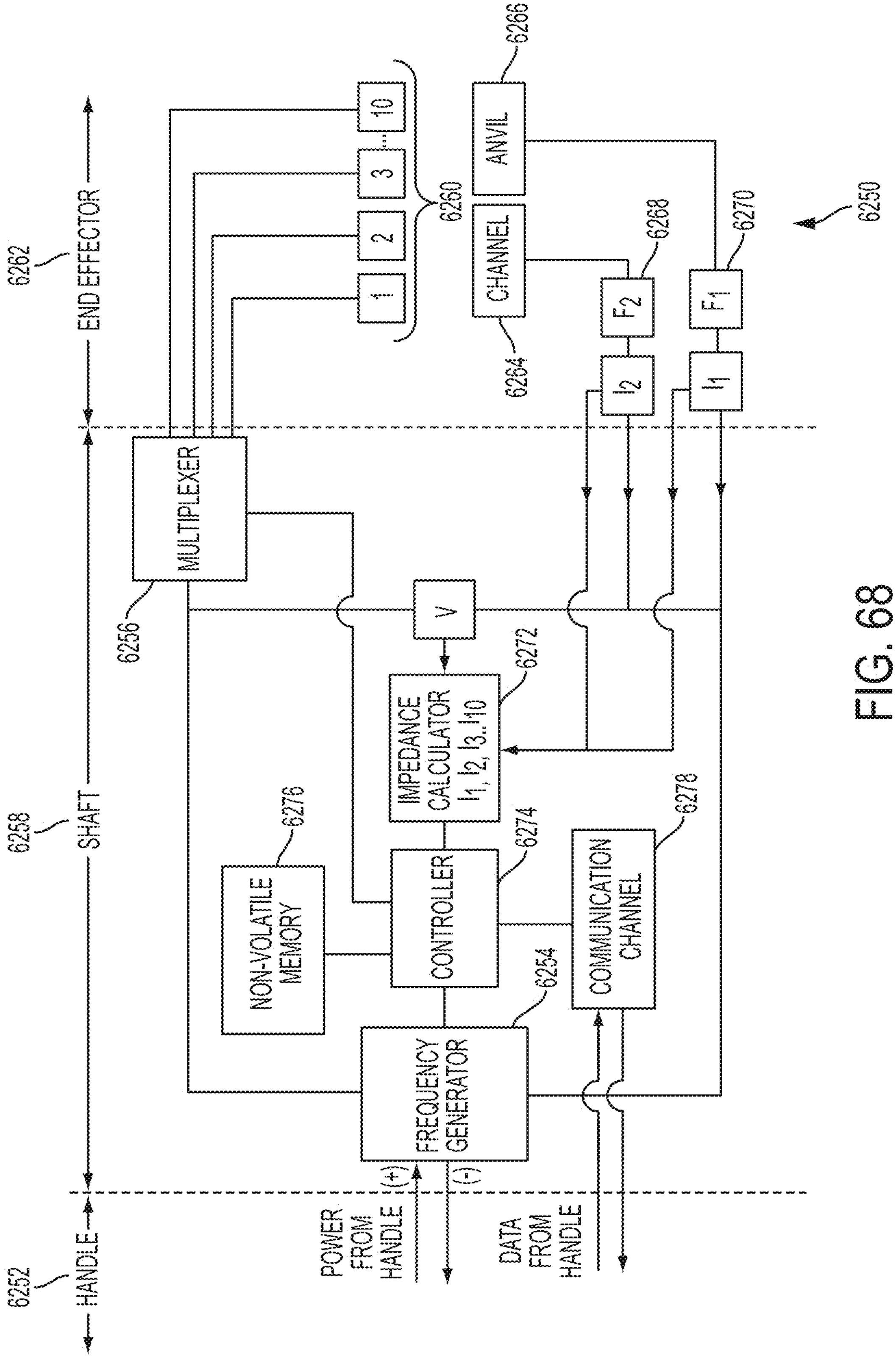
FIG. 68 is also an example circuit diagram in accordance with one or more aspects of the present disclosure.

Referring now to FIG. 68, one or more aspects of the present disclosure are described in circuit diagram 6250. In an implementation, a power source at a handle 6252 of an endocutter may provide power to a frequency generator 6254. The frequency generator 6254 may generate one or more RF signals. The one or more RF signals may be multiplexed or overlaid at a multiplexer 6256, which may be in a shaft 6258 of the endocutter. In this way, two or more RF signals may be overlaid (or, e.g., nested or modulated together) and transmitted to the end-effector. The one or more RF signals may energize one or more RF electrodes 6260 at an end-effector 6262 (e.g., positioned in a staple cartridge) of the endocutter. A tissue (not shown) may be compressed and/or communicatively coupled between the one or more of RF electrodes 6260 and one or more electrical contacts. For example, the tissue may be compressed and/or communicatively coupled between the one or more RF electrodes 6260 and the electrical contact 6264 positioned in a channel frame of the end-effector 6262 or the electrical contact 6266 positioned in an anvil of the end-effector 6262. A filter 6268 may be communicatively coupled to the electrical contact 6264 and a filter 6270 may be communicatively coupled to the electrical contact 6266.

A voltage V and a current I associated with the one or more RF signals may be used to calculate an impedance Z associated with a tissue that may be compressed between the staple cartridge (and communicatively coupled to one or more RF electrodes 6260) and the channel frame or anvil (and communicatively coupled to one or more of electrical contacts 6264 or 6266).

In one aspect, various components of the tissue compression sensor system described herein may be located in a shaft 6258 of the endocutter. For example, as shown in circuit diagram 6250 (and in addition to the frequency generator 6254), an impedance calculator 6272, a controller 6274, a non-volatile memory 6276, and a communication channel 6278 may be located in the shaft 6258. In one example, the frequency generator 6254, impedance calculator 6272, controller 6274, non-volatile memory 6276, and communication channel 6278 may be positioned on a circuit board in the shaft 6258.

The two or more RF signals may be returned on a common path via the electrical contacts. Further, the two or more RF signals may be filtered prior to the joining of the RF signals on the common path to differentiate separate tissue impedances represented by the two or more RF signals. Current I1 and current I2 may be measured on a return path corresponding to electrical contacts 6264 and 6266. Using a voltage V applied between the supply and return paths, impedances Z1 and Z2 may be calculated. Z1 may correspond to an impedance of a tissue compressed and/or communicatively coupled between one or more of RF electrodes 6260 and electrical contact 6264. Further, Z2 may correspond to an impedance of the tissue compressed and/or communicatively coupled between one or more of RF electrodes 6260 and electrical contact 6266. Applying the formulas Z1=V/I1 and Z2=V/I2, impedances Z1 and Z2 corresponding to different compressions of a tissue compressed by an end-effector 6262 may be calculated. In example, the impedances Z1 and Z2 may be calculated by the impedance calculator 6272. The impedances Z1 and Z2 may be used to calculate various compression levels of the tissue.

Figure 69:
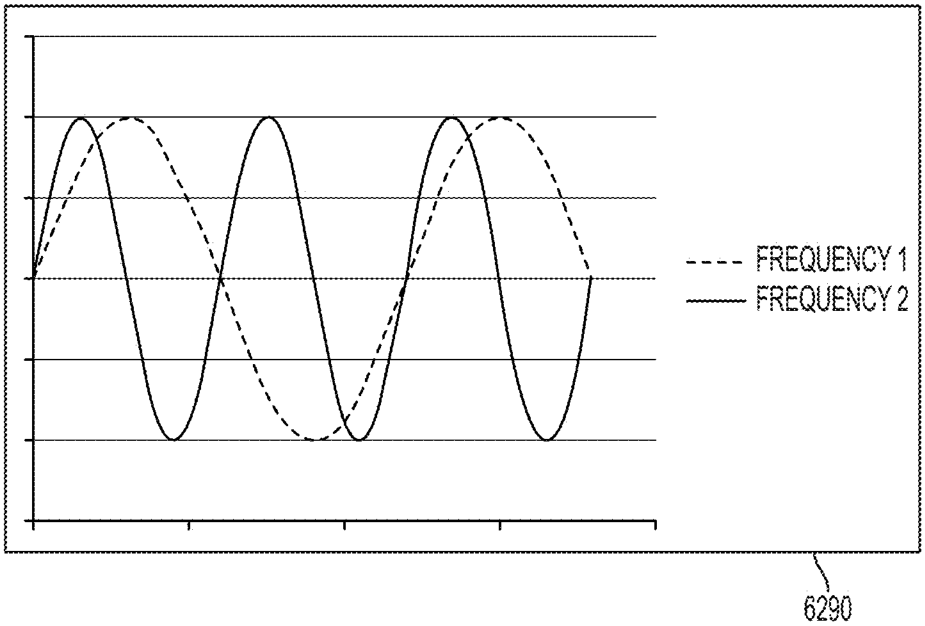
FIG. 69 is graph depicting an example frequency modulation in accordance with one or more aspects of the present disclosure.
Figure 70:
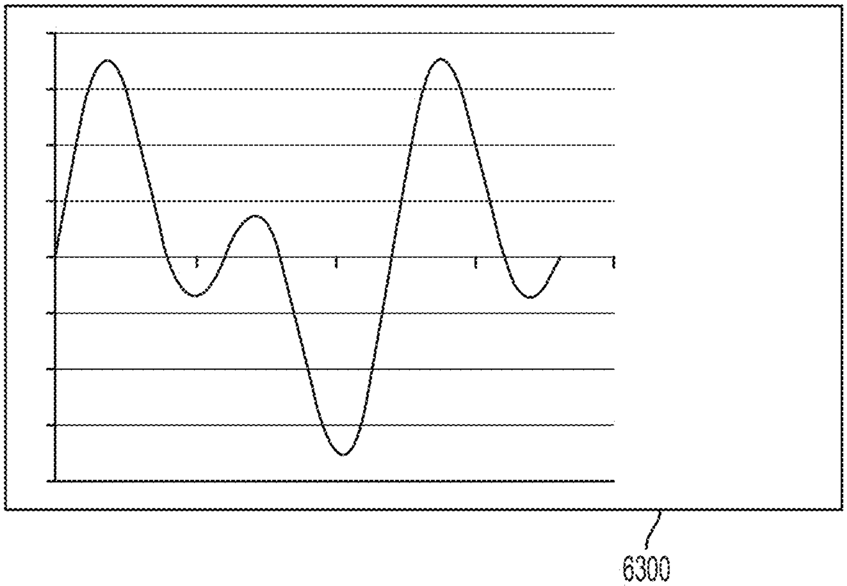
FIG. 70 is graph depicting a compound RF signal in accordance with one or more aspects of the present disclosure.
Figure 71:
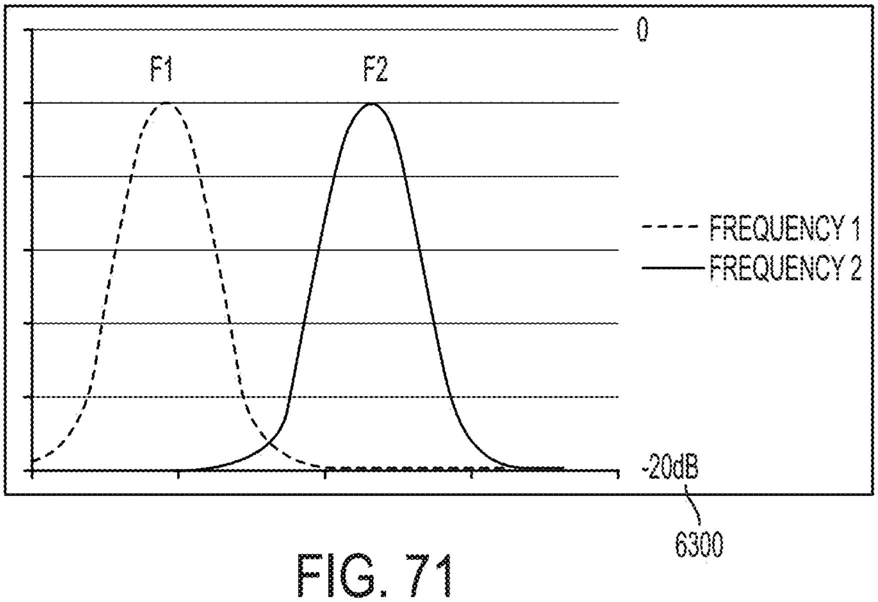
FIG. 71 is graph depicting filtered RF signals in accordance with one or more aspects of the present disclosure.

Referring now to FIG. 69, a frequency graph 6290 is shown. The frequency graph 6290 shows a frequency modulation to nest two RF signals. The two RF signals may be nested before reaching RF electrodes at an end-effector as described above. For example, an RF signal with Frequency 1 and an RF signal with Frequency 2 may be nested together. Referring now to FIG. 70, the resulting nested RF signal is shown in frequency graph 6300. The compound signal shown in frequency graph 6300 includes the two RF signals of frequency graph 6290 compounded. Referring now to FIG. 71, a frequency graph 6310 is shown. Frequency graph 6310 shows the RF signals with Frequencies 1 and 2 after being filtered (by, e.g., filters 6268 and 6270). The resulting RF signals can be used to make separate impedance calculations or measurements on a return path, as described above.

In one aspect, filters 6268 and 6270 may be High Q filters such that the filter range may be narrow (e.g., Q=10). Q may be defined by the Center frequency (Wo)/Bandwidth (BW) where Q=Wo/BW. In one example, Frequency 1 may be 150 kHz and Frequency 2 may be 300 kHz. A viable impedance measurement range may be 100 kHz-20 MHz. In various examples, other sophisticated techniques, such as correlation, quadrature detection, etc., may be used to separate the RF signals.

Using one or more of the techniques and features described herein, a single energized electrode on a staple cartridge or an isolated knife of an end-effector may be used to make multiple tissue compression measurements simultaneously. If two or more RF signals are overlaid or multiplexed (or nested or modulated), they may be transmitted down a single power side of the end-effector and may return on either the channel frame or the anvil of the end-effector. If a filter were built into the anvil and channel contacts before they join a common return path, the tissue impedance represented by both paths could be differentiated. This may provide a measure of vertical tissue vs lateral tissue compression. This approach also may provide proximal and distal tissue compression depending on placement of the filters and location of the metallic return paths. A frequency generator and signal processor may be located on one or more chips on a circuit board or a sub board (which may already exist in an endocutter).

In various aspects, the present disclosure provides techniques for monitoring the speed and precision incrementing of the drive motor in the instrument 10 (described in connection with FIGS. 1-29). In one example, a magnet can be placed on a planet frame of one of the stages of gear reduction with an inductance sensor on the gear housing. In another example, placing the magnet and magnetic field sensor on the last stage would provide the most precise incremental movement monitoring.

Conventional motor control systems employ encoders to detect the location and speed of the motor in hand held battery powered endosurgical instruments such as powered endocutter/stapler devices. Precision operation of endocutter/stapler devices relies in part on the ability to verify the motor operation under load. Simple sensor implementations may be employed to achieve verify the motor operation under load.

Accordingly, the present disclosure includes a magnetic body on one of the planetary carriers of a gear reduction system or employs brushless motor technology. Both approaches involve the placement of an inductance sensor on the outside housing of the motor or planetary gear system. In the case of a brushless motor, there are electromagnetic field coils (windings, inductors, etc.) arrayed radially around the center magnetic shaft of the motor. The coils are sequentially activated and deactivated to drive the central motor shaft. One or more inductance sensors can be placed outside of the motor and adjacent to at least some of the coils to sense the activation/deactivation cycles of the motor windings to determine the number times the shaft has been rotated. Alternatively, a permanent magnet can be placed on one of the planetary carriers and the inductance sensor can be placed adjacent to the radial path of the planetary carrier to measure the number of times that stage of the gear train is rotated. This implementation can be applied to any rotational components in the system with increasingly more resolution possible in regions with a relatively large number of rotations during function, or as the rotational components become closer (in terms of number of connections) to the end effector depending on the design. The gear train sensing method may be preferred since it actually measures rotation of one of the stages whereas the motor sensing method senses the number of times the motor has been commanded to energize, rather than the actual shaft rotation. For example, if the motor is stalled under high load, the motor sensing method would not be able to detect the lack of rotation because it senses only the energizing cycles not shaft rotation. Nevertheless, both techniques can be employed in a cost effective manner to sense motor rotation.

During stapling, for example, tissue is firmly clamped between opposing jaws before a staple is driven into the clamped tissue. Tissue compression during clamping can cause fluid to be displaced from the compressed tissue, and the rate or amount of displacement varies depending on tissue type, tissue thickness, the surgical operation (e.g., clamping pressure and clamping time). In various instances, fluid displacement between the opposing jaws of an end effector may contribute to malformation (e.g., bending) of staples between the opposing jaws. Accordingly, in various instances, it may be desirable to control the firing stroke, e.g., to control the firing speed, in relationship to the detected fluid flow, or lack thereof, intermediate opposing jaws of a surgical end effector.

Accordingly, also provided herein are methods, devices, and systems for monitoring speed and incremental movement of a surgical instrument drive train, which in turn provides information about the operational velocity of the device (e.g., jaw closure, stapling). In accordance with the present examples, the instrument 10 (FIGS. 1-4) does not include a motor encoder. Rather, the instrument 10 is equipped with a motor 7012 shown in FIG. 72, which illustrates a speed sensor assembly for a power train 7010 of the motor 7012, in accordance with an illustrative example. The speed sensor assembly can include a motor 7012 having an output shaft 7014 that is coupled directly or indirectly to a drive shaft. In some examples, the output shaft is connected to a gear reduction assembly, such as the planetary gear train 7020 shown in FIG. 72.

Figure 72:
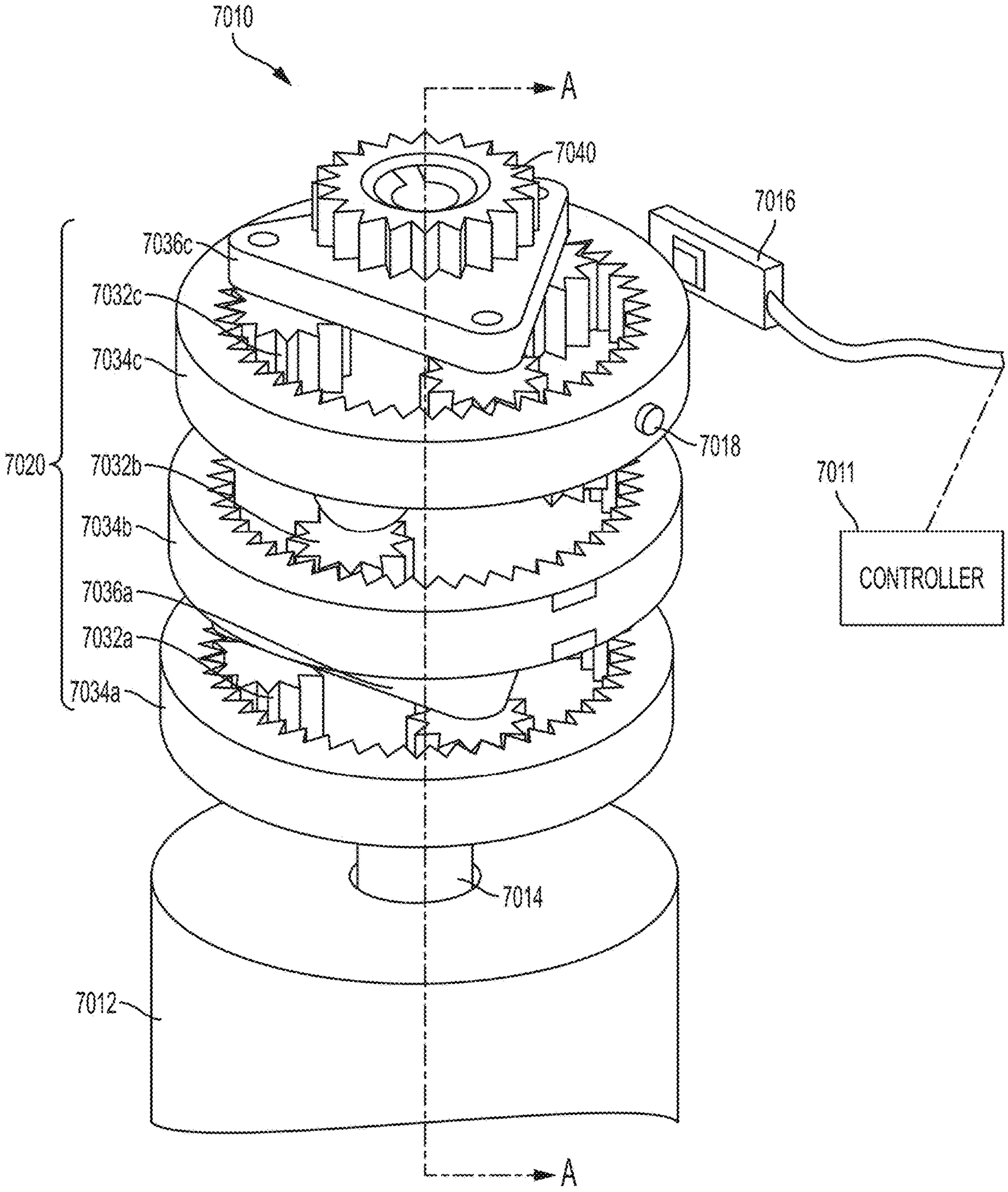
FIG. 72 is a plan view of a speed sensor assembly for a surgical instrument power train.

With continued reference to FIG. 72, the speed sensor assembly further includes at least one sensor 7016 that detects the rotational speed of any suitable component of the system. For example, the sensor may be a proximity sensor, such as an induction sensor, which detects movement of one or more detectable elements 7018 affixed to any rotating part of the gear reduction assembly. In FIG. 72, which is exemplary, the detectable element is affixed to the last stage annular gear 7034*c* and the sensor is positioned adjacent the radial path of the detectable element so as to detect movement of the detectable element. FIG. 72 is exemplary only—rotating components vary depending on design—and the sensor(s) can be affixed to any rotating component of the gear reduction assembly. For example, in another example, a detectable element is associated with the carrier gear of the final stage or even the drive gear. In some examples, a detectable element is located outside of the gear reduction assembly, such as on the driveshaft between gear reduction assembly and the end effector. In some example, a detectable element is located on a rotating component in the final gear reduction at the end effector.

With continued reference to FIG. 72, in one aspect motor 7012 is rotationally coupled to a gear reduction assembly, such as a planetary gear train 7020. However, any suitable gear reduction or transmission can be used and/or the motor can be coupled directly to a drive shaft (e.g., direct drive). The planetary gear train can include 1, 2, 3, 4, 5, or more stages. The planetary gear train illustrated in FIG. 72 has three stages. The planetary gear train is driven by a sun gear (7042 in FIG. 73) attached directly or indirectly to the motor output shaft 7014. The sun gear drives one or more first stage planet gears 7032*a*, which in turn engage a first stage annular gear 7034*a*. Any number of planet gears can be used such as, for example, 1, 2, 3, 4, 5 or more planet gears. First stage planet gears 7032*a* communicate with a first stage carrier 7036*a*, which includes or connects to a second stage sun gear (7038*a* in FIG. 73) that drives the second stage.

Similar to the first stage, the second stage includes one or more planet gears 7032*b*, an annular gear 7034*b*, and a carrier 7036*b* that includes or connects to a third stage sun gear (7038*b* in FIG. 73) that drives the third stage. Likewise, the third stage includes one or more planet gears 7032*c*, an annular gear 7034*c*, and a carrier 7036*c*. The final stage in the planetary gear train assembly is connected to a drive gear 7040, which can be the final effector in the gear reduction assembly, depending on design. The use of three planetary gear stages is exemplary only. Any suitable type of gear reduction assembly can be used in accordance with the present disclosure.

The sensor 7016 can be mounted in or near the gear reduction assembly in, near, or adjacent the radial path of detectable element 7018. The sensor can be any suitable sensor type capable of detecting rotational speed without an encoder. The sensor is used in conjunction with a detectable element capable of being detected by the sensor. For example, in some examples, the sensor is an inductance sensor and the detectable element is a metallic element. The inductance sensor can be configured to detect a change in inductance caused by a metallic object or magnet passing adjacent the inductive sensor. In some examples, the sensor is a magnetic field sensor, and the detectable element is a magnetic element. A magnetic field sensor can be configured to detect changes in a magnetic field surrounding the magnetic field sensor caused by the movement of the magnetic element.

Detectable elements can be affixed or integral with any rotating part or particular stage of the gear reduction assembly to measure the number of times that the part or stage rotates. For example, a single detectable element could be placed on drive gear 7040. Each complete rotation of the drive gear would cause the detectable element to pass the sensor one time, resulting in one detected rotation. In some examples, multiple detectable elements 7018 can be used within the same gear reduction assembly, by placing a plurality of detectable elements (e.g., 2, 3, 4, 5 or more) on the same component (e.g., a gear) and/or by placing one or more detectable elements on a plurality of different components (e.g., on two different gears). Placing multiple sensors equally spaced on a single component can provide refined information about incremental rotations. Similarly, resolution of speed monitoring can be increased by placing a detectable element(s) on a component that rotates more quickly relative to other components and/or by placing the detectable element closer (in terms of number of connections) to the end effector depending on the design. Using multiple detectable elements on different components provides a redundant, fail-safe system should one sensor or detectable element fail.

Sensors should be located close enough to detectable elements to ensure that each revolution of a detectable element is captured by its associated sensor. Multiple sensors can be placed in the same radial path of a detectable element. In addition, if detectable elements are placed on a plurality of different components (e.g., two different gears), a sensor can be placed adjacent the radial path of each detectable element. The sensor 7016 is in data communication with a controller 7011 such as the microcontroller 1500 (FIG. 19) or microcontroller 2006 (FIGS. 21A, 21B), processor 2104 (FIG. 22), or controller 2606 and 3017 shown in FIGS. 27-29, which is programmed to translate the number and/or rate of detection events into a speed reading useful to the user, such as using the speed indicator display shown in FIGS. 88-90.

Figure 73:
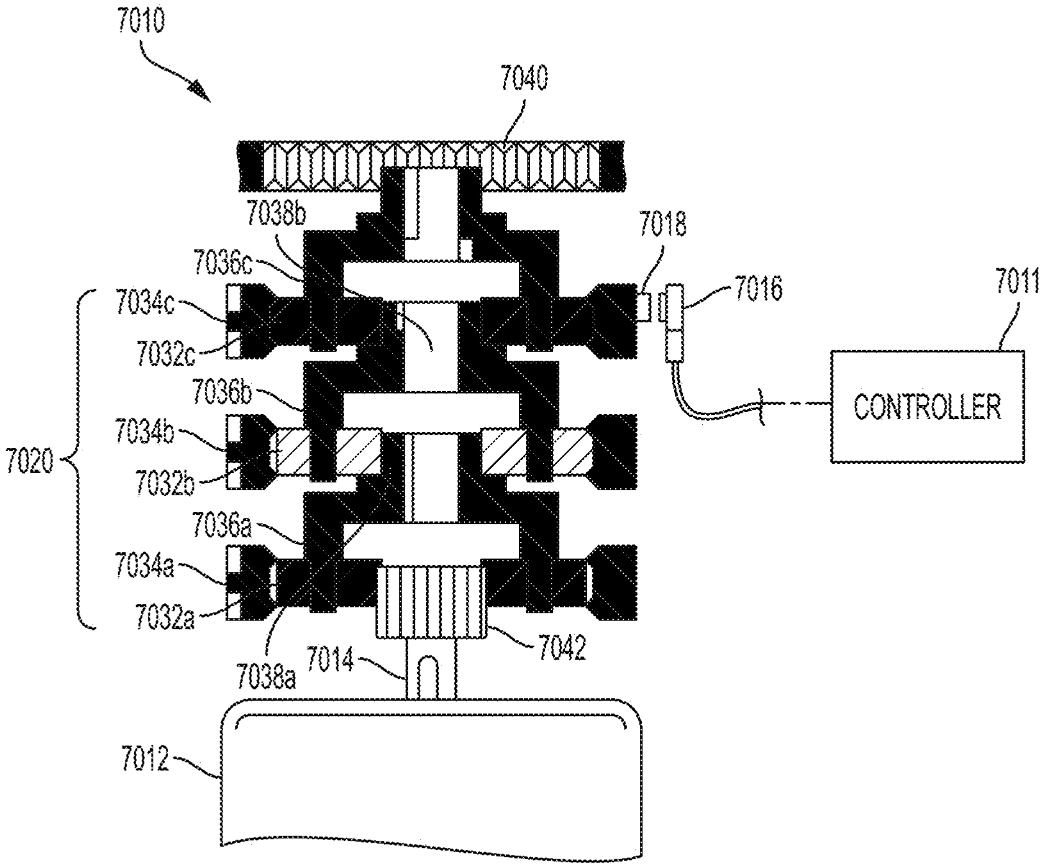
FIG. 73 is a longitudinal cross section through plane A of FIG. 71.

FIG. 73 shows a longitudinal cross section through plane A of FIG. 72. Clearly visible in FIG. 73 is sun gear 7042 coupled to output shaft 7014.

Figure 74:
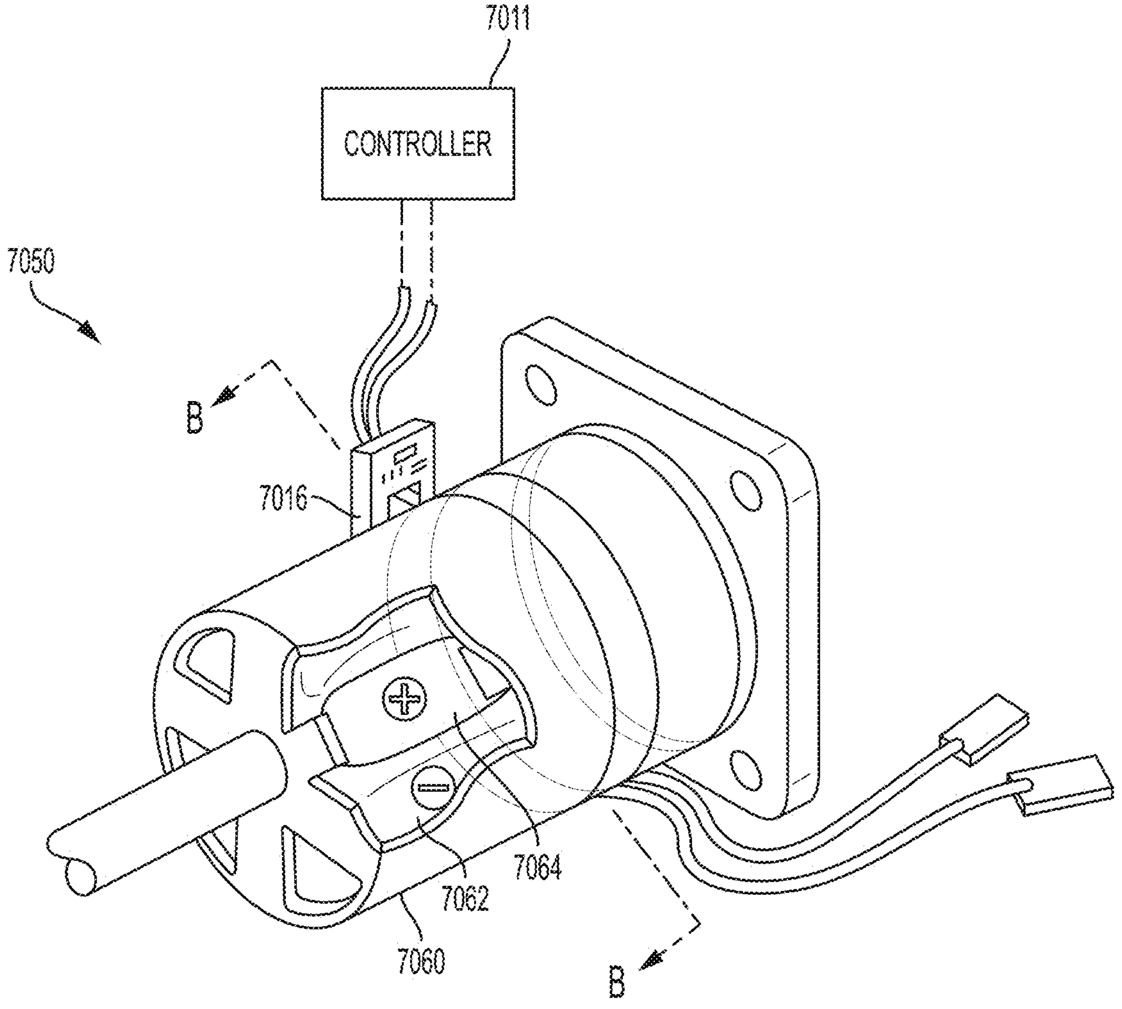
FIG. 74 is a perspective view of a speed sensor assembly for a brushless motor.

FIG. 74 illustrates a speed sensor assembly for 7050 for directly sensing the rotational speed of a brushless motor 7060, in accordance with an illustrative aspect. A brushless motor typically comprises electromagnetic field coils 7062, 7064 arrayed radially around a central magnetic shaft (7066 in FIG. 75). Negative 7062 and positive 7064 coils are alternately arranged around the central magnetic shaft, and these coils are sequentially activated and deactivated to drive the central magnetic shaft. One or more sensors 7016 can be placed adjacent these coils on the outside of the motor to monitor motor speed. The sensor induction field 7068 is affected each time an electromagnetic field coil passes the sensor. The sensor is in data communication with a controller 7011, such as the microcontroller 1500 (FIG. 19) or microcontroller 2006 (FIGS. 21A, 21B), processor 2104 (FIG. 22), or controller 2606 and 3017 shown in FIGS. 27-29, for example, which is programmed to translate the number and/or rate of detection events into a speed reading useful to the user, such as using a speed indicator display shown in FIGS. 88-90.

If the motor stalls, for example under high load, the sensor 7016 may still detect activation of the coils, which the sensor 7016 would interpret as motor rotation even though the motor is stalled. As a result, under certain operational circumstances, motor speed could be an inaccurate readout for operational tool speed. In one example, speed is measured using one or more sensors 7016 on the gear reduction assembly because this measures the actual speed of the gear assembly, or a stage of the gear assembly, rather than the speed of the motor. In addition, the closer the detectable element(s) and associated sensor(s) are to the end effector, the more likely the sensed speed accurately reflects operational tool speed. The ability to verify motor operation under load is important for precision operation of surgical instruments, such as staplers.

Figure 75:
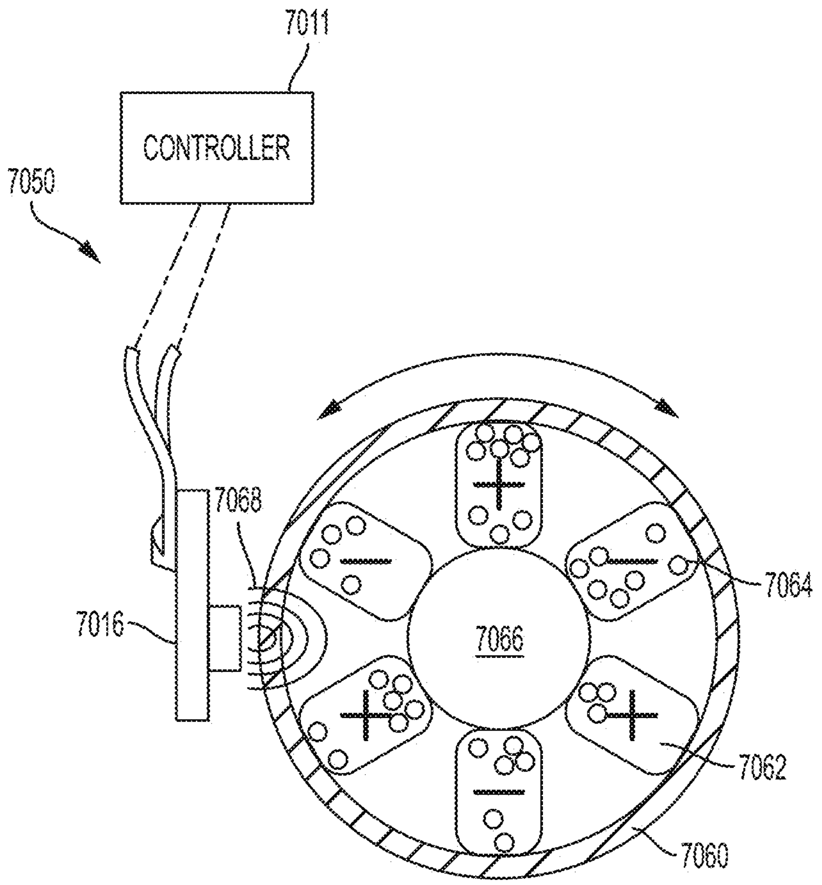
FIG. 75 is a transverse cross section through plane B of FIG. 73.

FIG. 75 illustrates a transverse cross section through plane B of the motor assembly shown in FIG. 74. The central magnetic shaft 7066 is visible in FIG. 75.

Sensor 7016 is in data communication with a controller 7011, such as the microcontroller 1500 (FIG. 19) or microcontroller 2006 (FIGS. 21A, 21B), processor 2104 (FIG. 22), or controller 2606 and 3017 shown in FIGS. 27-29, which is programmed to translate the number and/or rate of detection events into a speed reading useful to the user. The controller 7011 also can regulate motor speed to ensure safe operating parameters and/or to ensure that a constant speed and/or acceleration are maintained for particular surgical applications.

Various functions may be implemented utilizing the circuitry previously described, For example, the motor may be controlled with a motor controller 7011 similar those described in connection with FIGS. 21A, 21B, 24, 25, 28A, 28B, and 29, where the encoder is replaced with the monitoring speed control and precision incrementing of motor systems for powered surgical instruments described in connection with FIGS. 72-75. For example, the position encoder 2340 shown in FIG. 24 can be replaced with the sensor 7016 shown in FIGS. 72-75 coupled to the microcontroller 2306 in FIG. 24. Similarly, the position encoder 2440 shown in FIG. 25 can be replaced with the sensor 7016 shown in FIGS. 72-75 coupled to the microcontroller 2406 in FIG. 25.

In one aspect, the present disclosure provides an instrument 10 (described in connection with FIGS. 1-29) configured with various sensing systems. Accordingly, for conciseness and clarity the details of operation and construction will not be repeated here. In one aspect, the sensing system includes a viscoelasticity/rate of change sensing system to monitor knife acceleration, rate of change of impedance, and rate of change of tissue contact. In one example, the rate of change of knife acceleration can be used as a measure of for tissue type. In another example, the rate of change of impedance can be measures with a pulse sensor ad can be employed as a measure for compressibility. Finally, the rate of change of tissue contact can be measured with a sensor based on knife firing rate to measure tissue flow.

The rate of change of a sensed parameter or stated otherwise, how much time is necessary for a tissue parameter to reach an asymptotic steady state value, is a separate measurement in itself and may be more valuable than the sensed parameter it was derived from. To enhance measurement of tissue parameters such as waiting a predetermined amount of time before making a measurement, the present disclosure provides a novel technique for employing the derivate of the measure such as the rate of change of the tissue parameter.

The derivative technique or rate of change measure becomes most useful with the understanding that there is no single measurement that can be employed alone to dramatically improve staple formation. It is the combination of multiple measurements that make the measurements valid. In the case of tissue gap it is helpful to know how much of the jaw is covered with tissue to make the gap measure relevant. Rate of change measures of impedance may be combined with strain measurements in the anvil to relate force and compression applied to the tissue grasped between the jaw members of the end effector such as the anvil and the staple cartridge. The rate of change measure can be employed by the endosurgical device to determine the tissue type and not merely the tissue compression. Although stomach and lung tissue sometimes have similar thicknesses, and even similar compressive properties when the lung tissue is calcified, an instrument may be able to distinguish these tissue types by employing a combination of measurements such as gap, compression, force applied, tissue contact area, and rate of change of compression or rate of change of gap. If any of these measurements were used alone, the endosurgical it may be difficult for the endosurgical device to distinguish one tissue type form another. Rate of change of compression also may be helpful to enable the device to determine if the tissue is "normal" or if some abnormality exists. Measuring not only how much time has passed but the variation of the sensor signals and determining the derivative of the signal would provide another measurement to enable the endosurgical device to measure the signal. Rate of change information also may be employed in determining when a steady state has been achieved to signal the next step in a process. For example, after clamping the tissue between the jaw members of the end effector such as the anvil and the staple cartridge, when tissue compression reaches a steady state (e.g., about 15 seconds), an indicator or trigger to start firing the device can be enabled.

Also provided herein are methods, devices, and systems for time dependent evaluation of sensor data to determine stability, creep, and viscoelastic characteristics of tissue during surgical instrument operation. A surgical instrument 10, such as the stapler illustrated in FIG. 1, can include a variety of sensors for measuring operational parameters, such as jaw gap size or distance, firing current, tissue compression, the amount of the jaw that is covered by tissue, anvil strain, and trigger force, to name a few. These sensed measurements are important for automatic control of the surgical instrument and for providing feedback to the clinician.

The examples shown in connection with FIGS. 52-71 may be employed to measure the various derived parameters such as gap distance versus time, tissue compression versus time, and anvil strain versus time. Motor current may be monitored employing the current sensor 2312 in series with the battery 2308 as described in connection with FIG. 24, the current sensor 2412 in series with the battery 2408 shown in FIG. 25, or the current sensor 3026 in FIG. 29.

Figure 76:
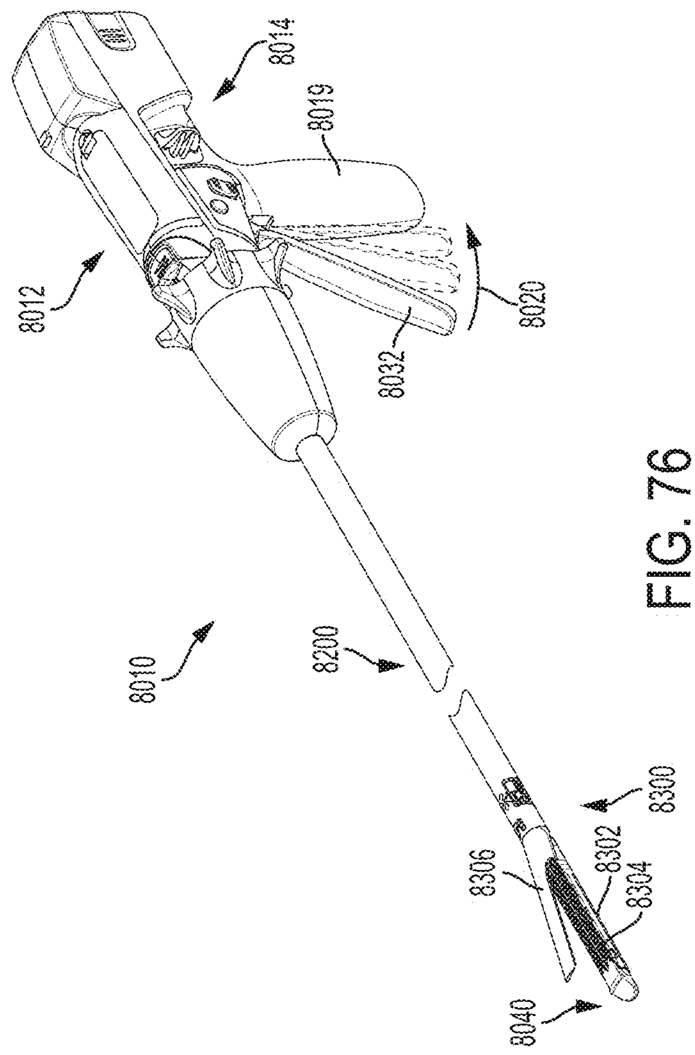
FIG. 76 is a perspective view of a surgical instrument with an articulable, interchangeable shaft.

Turning now to FIG. 76, a motor-driven surgical cutting and fastening instrument 8010 is depicted that may or may not be reused. The motor-driven surgical cutting and fastening instrument 8010 is similarly constructed and equipped as the motor-driven surgical cutting and fastening instrument 10 described in connection with FIGS. 1-29. In the example illustrated in FIG. 76, the instrument 8010 includes a housing 8012 that comprises a handle assembly 8014 that is configured to be grasped, manipulated and actuated by the clinician. The housing 8012 is configured for operable attachment to an interchangeable shaft assembly 8200 that has a surgical end effector 8300 operably coupled thereto that is configured to perform one or more surgical tasks or procedures. Since the motor-driven surgical cutting and fastening instrument 8010 is similarly constructed and equipped as the motor-driven surgical cutting and fastening instrument 10 described in connection with FIGS. 1-29, for conciseness and clarity the details of operation and construction will not be repeated here.

The housing 8012 depicted in FIG. 76 is shown in connection with an interchangeable shaft assembly 8200 that includes an end effector 8300 that comprises a surgical cutting and fastening device that is configured to operably support a surgical staple cartridge 8304 therein. The housing 8012 may be configured for use in connection with interchangeable shaft assemblies that include end effectors that are adapted to support different sizes and types of staple cartridges, have different shaft lengths, sizes, and types, etc. In addition, the housing 8012 also may be effectively employed with a variety of other interchangeable shaft assemblies including those assemblies that are configured to apply other motions and forms of energy such as, for example, radio frequency (RF) energy, ultrasonic energy and/or motion to end effector arrangements adapted for use in connection with various surgical applications and procedures. Furthermore, the end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly.

FIG. 76 illustrates the surgical instrument 8010 with an interchangeable shaft assembly 8200 operably coupled thereto. In the illustrated arrangement, the handle housing forms a pistol grip portion 8019 that can be gripped and manipulated by the clinician. The handle assembly 8014 operably supports a plurality of drive systems therein that are configured to generate and apply various control motions to corresponding portions of the interchangeable shaft assembly that is operably attached thereto. Trigger 8032 is operably associated with the pistol grip for controlling various of these control motions.

With continued reference to FIG. 76, the interchangeable shaft assembly 8200 includes a surgical end effector 8300 that comprises an elongated channel 8302 that is configured to operably support a staple cartridge 8304 therein. The end effector 8300 may further include an anvil 8306 that is pivotally supported relative to the elongated channel 8302.

The inventors have discovered that derived parameters can be even more useful for controlling a surgical instrument, such as the instrument illustrated in FIG. 76, than the sensed parameter(s) upon which the derived parameter is based. Non-limiting examples of derived parameters include the rate of change of a sensed parameter (e.g., jaw gap distance) and how much time elapses before a tissue parameter reaches an asymptotic steady state value (e.g., 15 seconds). Derived parameters, such as rate of change, are particularly useful because they dramatically improve measurement accuracy and also provide information not otherwise evident directly from sensed parameters. For example, impedance (i.e., tissue compression) rate of change can be combined with strain in the anvil to relate compression and force, which enables the microcontroller to determine the tissue type and not merely the amount of tissue compression. This example is illustrative only, and any derived parameters can be combined with one or more sensed parameters to provide more accurate information about tissue types (e.g., stomach vs. lung), tissue health (calcified vs. normal), and operational status of the surgical device (e.g., clamping complete). Different tissues have unique viscoelastic properties and unique rates of change, making these and other parameters discussed herein useful indicia for monitoring and automatically adjusting a surgical procedure.

Figure 77:
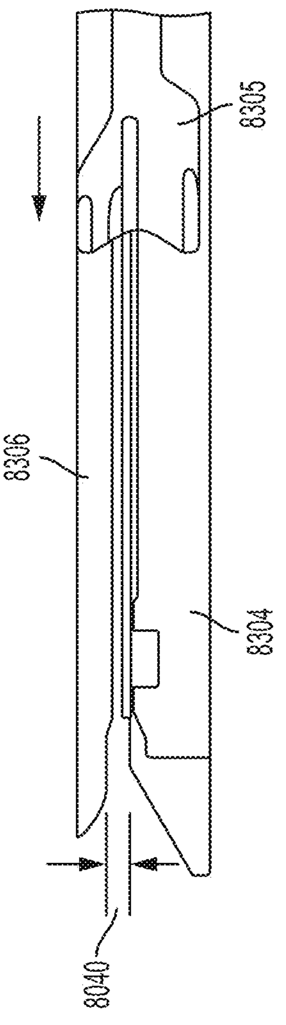
FIG. 77 is a side view of the tip of the surgical instrument shown in FIG. 76.
Figure 78A:
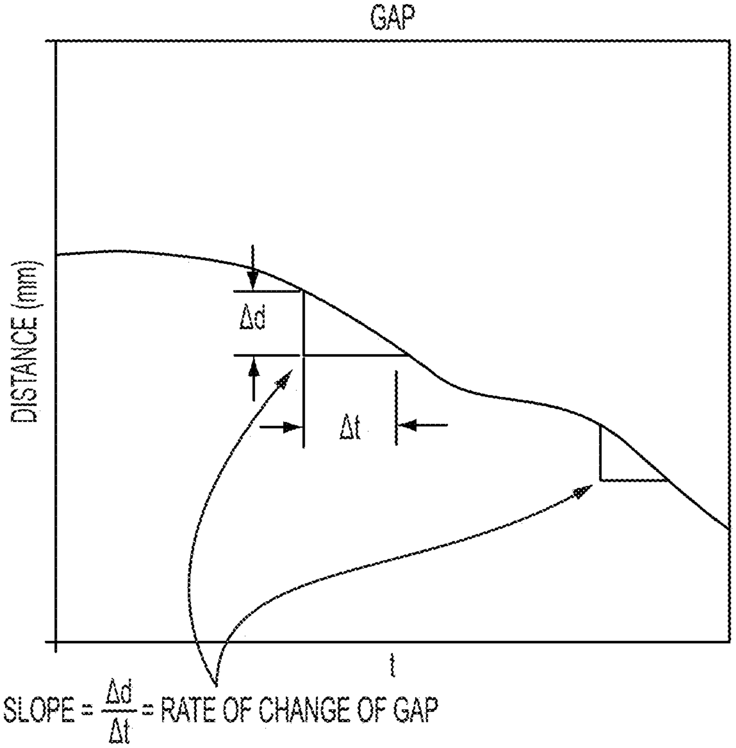
FIGS. 78A-78E are graphs plotting gap size over time (FIG. 78A), firing current over time (FIG. 78B), tissue compression over time (FIG. 78C), anvil strain over time (FIG. 78D), and trigger force over time (FIG. 78E)

FIGS. 78A-78E show exemplary sensed parameters as well as parameters derived therefrom. FIG. 78A is an illustrative graph showing gap distance over time, where the gap is the space between the jaws being occupied by clamped tissue. The vertical (y) axis is distance and the horizontal (x) axis is time. Specifically, referring to FIGS. 76 and 77, the gap distance 8040 is the distance between the anvil 8306 and the elongate channel 8302 of the end effector. In the open jaw position, at time zero, the gap 8040 between the anvil 8306 and the elongate member is at its maximum distance. The width of the gap 8040 decreases as the anvil 8306 closes, such as during tissue clamping. The gap distance rate of change can vary because tissue has non-uniform resiliency. For example, certain tissue types may initially show rapid compression, resulting in a faster rate of change. However, as tissue is continually compressed, the viscoelastic properties of the tissue can cause the rate of change to decrease until the tissue cannot be compressed further, at which point the gap distance will remain substantially constant. The gap decreases over time as the tissue is squeezed between the anvil 8306 and the staple cartridge 8304 of the end effector 8040. The one or more sensors described in connection with FIGS. 50-68 and FIG. 84 may be adapted and configured to measure the gap distance "d" between the anvil 8306 and the staple cartridge 8304 over time "t" as represented graphically in FIG. 78A. The rate of change of the gap distance "d" over time "t" is the Slope of the curve shown in FIG. 78A, where Slope=$\Delta d/\Delta t$.

Figure 78B:
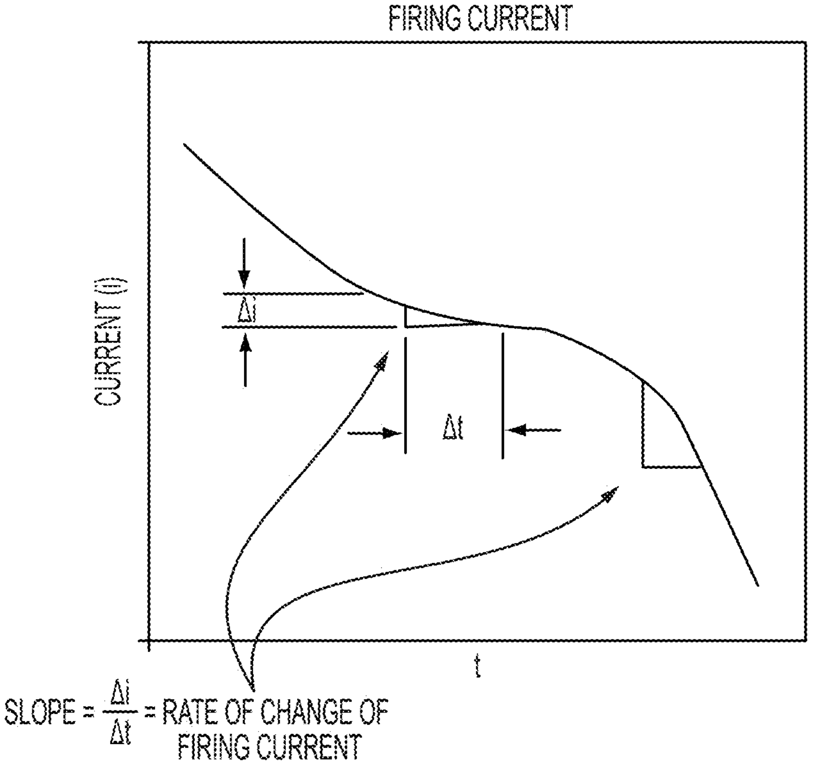

FIG. 78B is an illustrative graph showing firing current of the end effector jaws. The vertical (y) axis is current and the horizontal (x) axis is time. As discussed herein, the surgical instrument and/or the microcontroller, as shown in FIGS. 21-29, thereof can include a current sensor that detects the current utilized during various operations, such as clamping, cutting, and/or stapling tissue. For example, when tissue resistance increases, the instrument's electric motor can require more current to clamp, cut, and/or staple the tissue. Similarly, if resistance is lower, the electric motor can require less current to clamp, cut, and/or staple the tissue. As a result, firing current can be used as an approximation of tissue resistance. The sensed current can be used alone or more preferably in conjunction with other measurements to provide feedback about the target tissue. Referring still to FIG. 78B, during some operations, such as stapling, firing current initially is high at time zero but decreases over time. During other device operations, current may increase over time if the motor draws more current to overcome increasing mechanical load. In addition, the rate of change of firing current is can be used as an indicator that the tissue is transitioning from one state to another state. Accordingly, firing current and, in particular, the rate of change of firing current can be used to monitor device operation. The firing current decreases over time as the knife cuts through the tissue. The rate of change of firing current can vary if the tissue being cut provides more or less resistance due to tissue properties or sharpness of the knife 8305 (FIG. 77). As the cutting conditions vary, the work being done by the motor varies and hence will vary the firing current over time. A current sensor may be may be employed to measure the firing current over time while the knife 8305 is firing as represented graphically in FIG. 78B. For example, the motor current may be monitored employing the current sensor 2312 in series with the battery 2308 as described in connection with FIG. 24, the current sensor 2412 in series with the battery 2408 shown in FIG. 25, or the current sensor 3026 shown in FIG. 29. The current sensors 2312, 2314, 3026 may be adapted and configured to measure the motor firing current "i" over time "t" as represented graphically in FIG. 78B. The rate of change of the firing current "i" over time "t" is the Slope of the curve shown in FIG. 78B, where Slope=$\Delta i/\Delta t$.

Figure 78C:
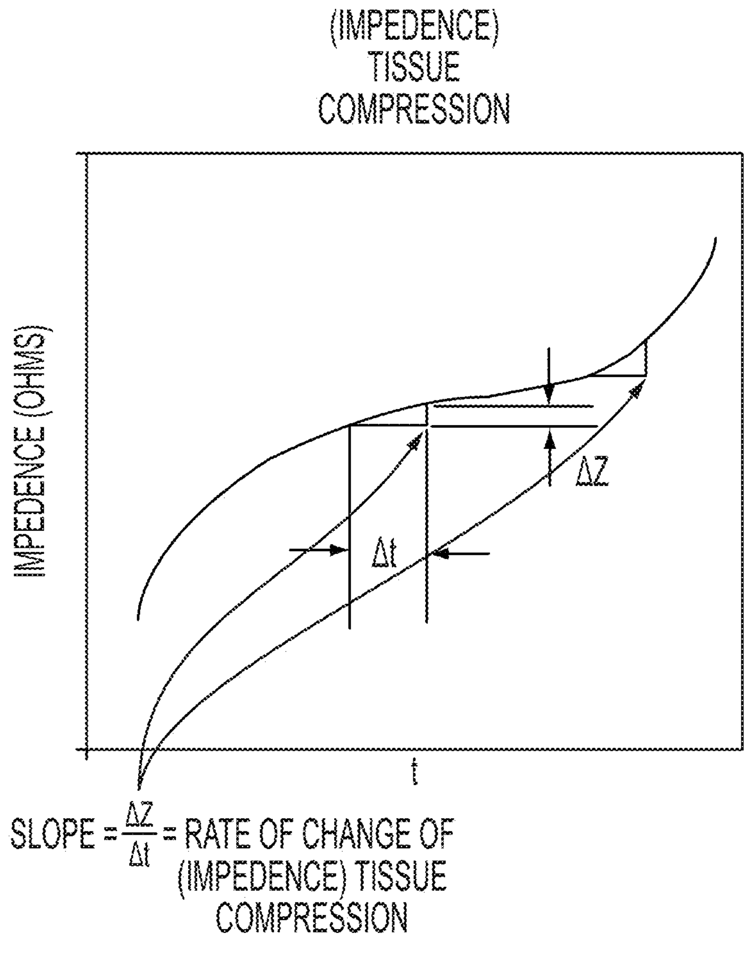

FIG. 78C is an illustrative graph of impedance over time. The vertical (y) axis is impedance and the horizontal (x) axis is time. At time zero, impedance is low but increases over time as tissue pressure increases under manipulation (e.g., clamping and stapling). The rate of change varies over time as because as the tissue between the anvil 8306 and the staple cartridge 8304 of the end effector 8040 is severed by the knife or is sealed using RF energy between electrodes located between the anvil 8306 and the staple cartridge 8304 of the end effector 8040. For example, as the tissue is cut the electrical impedance increases and reaches infinity when the tissue is completely severed by the knife. Also, if the end effector 8040 includes electrodes coupled to an RF energy source, the electrical impedance of the tissue increases as energy is delivered through the tissue between the anvil 8306 and the staple cartridge 8304 of the end effector 8040. The electrical impedance increase as the energy through the tissue dries out the tissue by vaporizing moistures in the tissue. Eventually, when a suitable amount of energy is delivered to the tissue, the impedance increases to a very high value or infinity when the tissue is severed. In addition, as illustrated in FIG. 78C, different tissues can have unique compression properties, such as rate of compression, that distinguish tissues. The tissue impedance can be measured by driving a sub-therapeutic RF current through the tissue grasped between the first and second jaw members 9014, 9016. One or more electrodes can be positioned on either or both the anvil 8306 and the staple cartridge 8304. The tissue compression/impedance of the tissue between the anvil 8306 and the staple cartridge 8304 can be measured over time as represented graphically in FIG. 78C. The sensors described in connection with FIGS. 50-68 and 84 may be adapted and configured to measure tissue compression/impedance. The sensors may be adapted and configured to measure tissue impedance "Z" over time "t" as represented graphically in FIG. 78C. The rate of change of the tissue impedance "Z" over time "t" is the Slope of the curve shown in FIG. 78C, where Slope=$\Delta Z/\Delta t$.

Figure 78D:
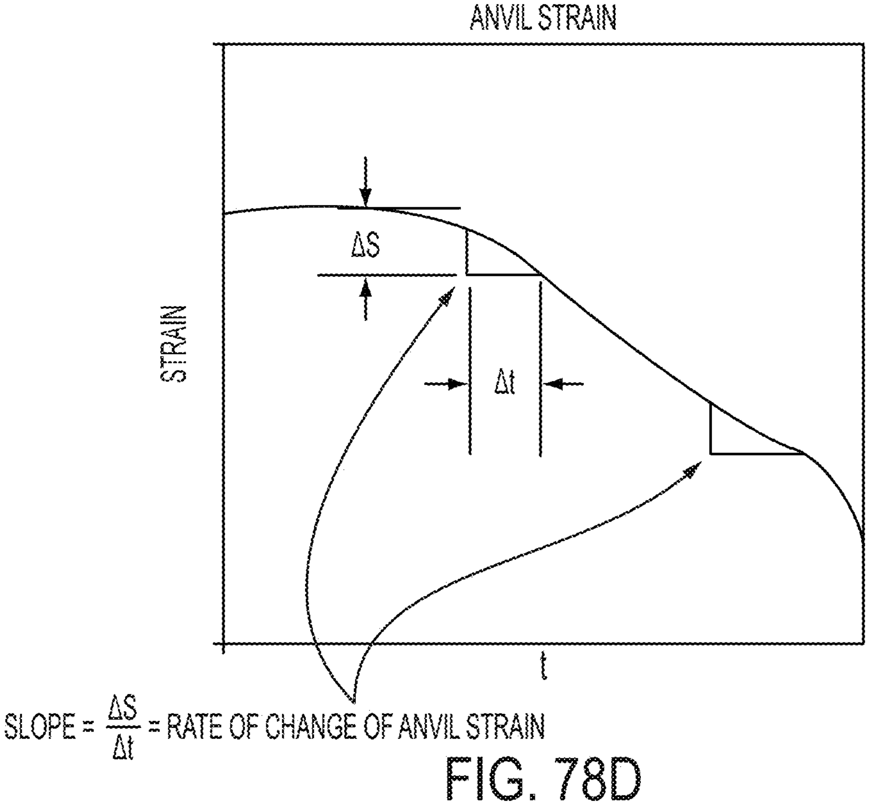

FIG. 78D is an illustrative graph of anvil 8306 (FIGS. 76, 77) strain over time. The vertical (y) axis is strain and the horizontal (x) axis is time. During stapling, for example, anvil 8306 strain initially is high but decreases as the tissue reaches a steady state and exerts less pressure on the anvil 8306. The rate of change of anvil 8306 strain can be measured by a pressure sensor or strain gauge positioned on either or both the anvil 8306 and the staple cartridge 8304 (FIGS. 76, 77) to measure the pressure or strain applied to the tissue grasped between the anvil 8306 and the staple cartridge 8304. The anvil 8306 strain can be measured over time as represented graphically in FIG. 78D. The rate of change of strain "S" over time "t" is the Slope of the curve shown in FIG. 78D, where Slope=ΔS/Δt.

Figure 78E:
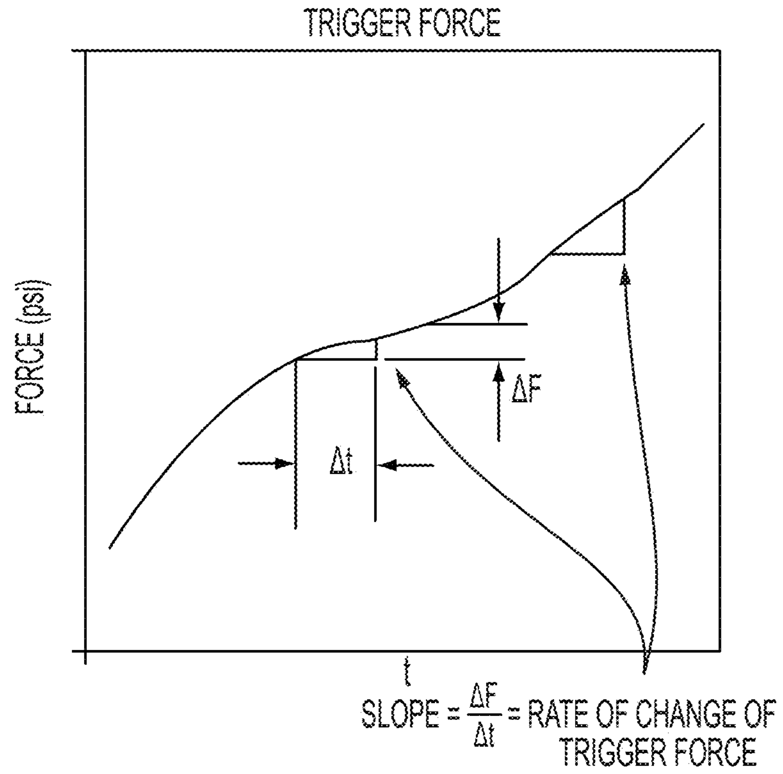

FIG. 78E is an illustrative graph of trigger force over time. The vertical (y) axis is trigger force and the horizontal (x) axis is time. In certain examples, trigger force is progressive, to provide the clinician tactile feedback. Thus, at time zero, trigger 8020 (FIG. 76) pressure may be at its lowest and trigger pressure may increase until completion of an operation (e.g., clamping, cutting, or stapling). The rate of change trigger force can be measured by a pressure sensor or strain gauge positioned on the trigger 8302 of the handle 8019 of the instrument 8010 (FIG. 76) to measure the force required to drive the knife 8305 (FIG. 77) through the tissue grasped between the anvil 8306 and the staple cartridge 8304. The trigger 8032 force can be measured over time as represented graphically in FIG. 78E. The rate of change of strain trigger force "F" over time "t" is the Slope of the curve shown in FIG. 78E, where Slope=ΔF/Δt.

Figure 79:
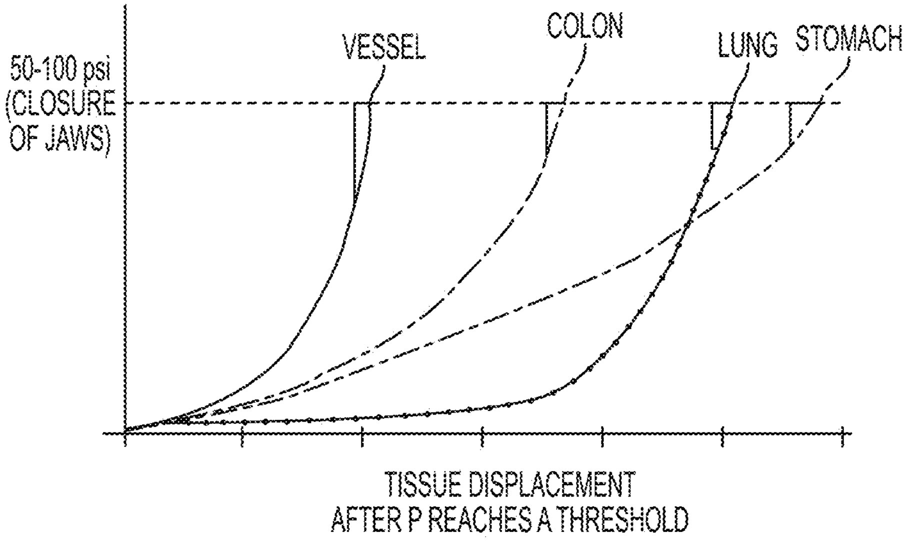
FIG. 79 is a graph plotting tissue displacement as a function of tissue compression for normal tissues.

For example, stomach and lung tissue can be differentiated even though these tissues can have similar thicknesses, and can have similar compressive properties if the lung tissue is calcified. Stomach and lung tissues can be distinguished by analyzing jaw gap distance, tissue compression, force applied, tissue contact area, compression rate of change, and jaw gap rate of change. For example, FIG. 79 shows a graph of tissue pressure "P" versus tissue displacement for various tissues. The vertical (y) axis is tissue pressure and the horizontal (x) axis is tissue displacement. When tissue pressure reaches a predetermined threshold, such as 50-100 pounds per square inch (psi), the amount of tissue displacement as well as the rate of tissue displacement before reaching the threshold can be used to differentiate tissues. For instance, blood vessel tissue reaches the predetermined pressure threshold with less tissue displacement and with a faster rate of change than colon, lung, or stomach tissue. In addition, the rate of change (tissue pressure over displacement) for blood vessel tissue is nearly asymptotic at a threshold of 50-100 psi, whereas the rate of change for colon, lung, and stomach is not asymptotic at a threshold of 50-100 psi. As will be appreciated, any pressure threshold can be used such as, for example, between 1 and 1000 psi, more preferably between 10 and 500 psi, and more preferably still between 50 and 100 psi. In addition, multiple thresholds or progressive thresholds can be used to provide further resolution of tissue types that have similar viscoelastic properties.

Figure 80:
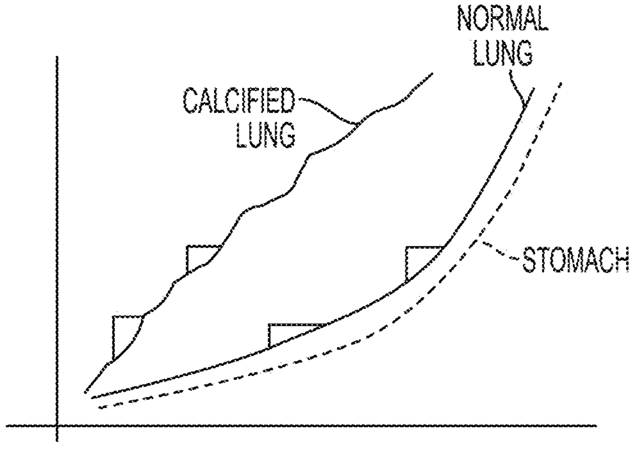
FIG. 80 is a graph plotting tissue displacement as a function of tissue compression to distinguish normal and diseased tissues.

Compression rate of change also can enable the microcontroller to determine if the tissue is "normal" or if some abnormality exists, such as calcification. For example, referring to FIG. 80, compression of calcified lung tissue follows a different curve than compression of normal lung tissue. Tissue displacement and rate of change of tissue displacement therefore can be used to diagnose and/or differentiate calcified lung tissue from normal lung tissue.

In addition, certain sensed measurements may benefit from additional sensory input. For example, in the case of jaw gap, knowing how much of the jaw is covered with tissue can make the gap measurement more useful and accurate. If a small portion of the jaw is covered in tissue, tissue compression may appear to be less than if the entire jaw is covered in tissue. Thus, the amount of jaw coverage can be taken into account by the microcontroller when analyzing tissue compression and other sensed parameters.

In certain circumstances, elapsed time also can be an important parameter. Measuring how much time has passed, together with sensed parameters, and derivative parameters (e.g., rate of change) provides further useful information. For example, if jaw gap rate of change remains constant after a set period of time (e.g., 5 seconds), then the parameter may have reached its asymptotic value.

Rate of change information also is useful in determining when a steady state has been achieved, thus signaling a next step in a process. For example, during clamping, when tissue compression reaches a steady state—e.g., no significant rate of change occurs after a set period of time—the microcontroller can send a signal to the display alerting the clinician to start the next step in the operation, such as staple firing. Alternatively, the microcontroller can be programmed to automatically start the next stage of operation (e.g., staple firing) once a steady state is reached.

Similarly, impedance rate of change can be combined with strain in the anvil to relate force and compression. The rate of change would allow the device to determine the tissue type rather than merely measure the compression value. For example, stomach and lung sometimes have similar thicknesses, and even similar compressive properties if the lung is calcified.

The combination of one or more sensed parameters with derived parameters provides more reliable and accurate assessment of tissue types and tissue health, and allows for better device monitoring, control, and clinician feedback.

Figure 84:
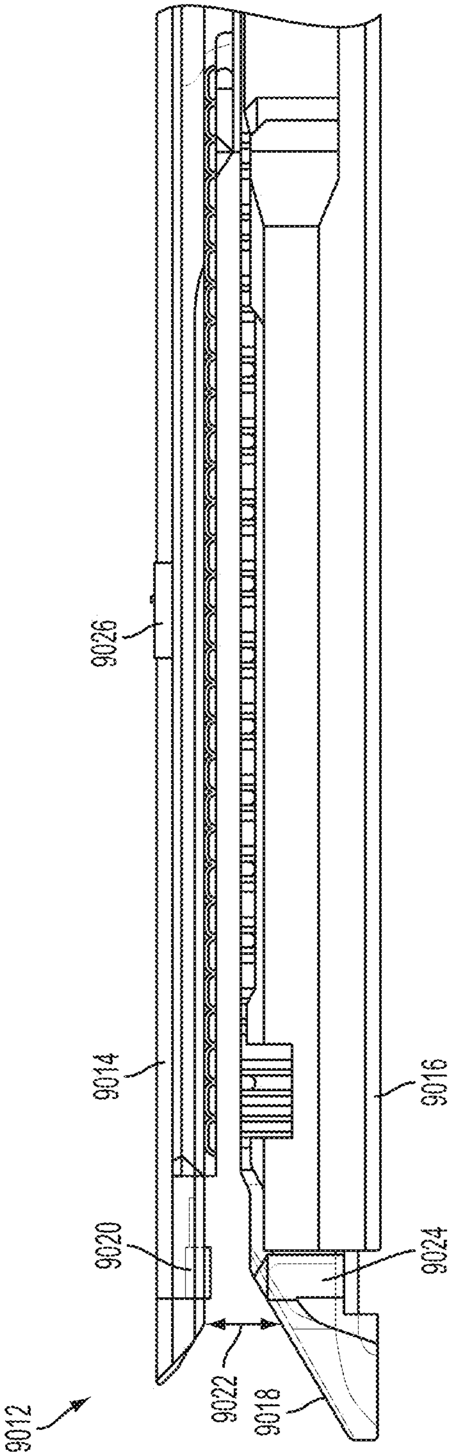
FIG. 84 illustrates a cross-sectional view of an end effector of the surgical instrument of FIG. 81 in accordance with one aspect.

Turning briefly to FIG. 84, the end effector 9012 is one aspect of the end effector 8300 (FIG. 76) that may be adapted to operate with surgical instrument 8010 (FIG. 76) to measure the various derived parameters such as gap distance versus time, tissue compression versus time, and anvil strain versus time. Accordingly, the end effector 9012 shown in FIG. 84 may include one or more sensors configured to measure one or more parameters or characteristics associated with the end effector 9012 and/or a tissue section captured by the end effector 9012. In the example illustrated in FIG. 84, the end effector 9012 comprises a first sensor 9020 and a second sensor 9026. In various examples, the first sensor 9020 and/or the second sensor 9026 may comprise, for example, a magnetic sensor such as, for example, a magnetic field sensor, a strain gauge, a pressure sensor, a force sensor, an inductive sensor such as, for example, an eddy current sensor, a resistive sensor, a capacitive sensor, an optical sensor, and/or any other suitable sensor for measuring one or more parameters of the end effector 9012.

In certain instances, the first sensor 9020 and/or the second sensor 9026 may comprise, for example, a magnetic field sensor embedded in the first jaw member 9014 and configured to detect a magnetic field generated by a magnet 9024 embedded in the second jaw member 9016 and/or the staple cartridge 9018. The strength of the detected magnetic field may correspond to, for example, the thickness and/or fullness of a bite of tissue located between the jaw members 9014, 9016. In certain instances, the first sensor 9020 and/or the second sensor 9026 may comprise a strain gauge, such as, for example, a micro-strain gauge, configured to measure the magnitude of the strain in the anvil 9014 during a clamped condition. The strain gauge provides an electrical signal whose amplitude varies with the magnitude of the strain.

In some aspects, one or more sensors of the end effector 9012 such as, for example, the first sensor 9020 and/or the second sensor 9026 may comprise a pressure sensor configured to detect a pressure generated by the presence of compressed tissue between the jaw members 9014, 9016. In some examples, one or more sensors of the end effector 9012 such as, for example, the first sensor 9020 and/or the second sensor 9026 are configured to detect the impedance of a tissue section located between the jaw members 9014, 9016. The detected impedance may be indicative of the thickness and/or fullness of tissue located between the jaw members 9014, 9016.

In one aspect, one or more of the sensors of the end effector 9012 such as, for example, the first sensor 9012 is configured to measure the gap 9022 between the anvil 9014 and the second jaw member 9016. In certain instances, the gap 9022 can be representative of the thickness and/or compressibility of a tissue section clamped between the jaw members 9014, 9016. In at least one example, the gap 9022 can be equal, or substantially equal, to the thickness of the tissue section clamped between the jaw members 9014, 9016. In one example, one or more of the sensors of the end effector 9012 such as, for example, the first sensor 9020 is configured to measure one or more forces exerted on the anvil 9014 by the second jaw member 9016 and/or tissue clamped between the anvil 9014 and the second jaw member 9016. The forces exerted on the anvil 9014 can be representative of the tissue compression experienced by the tissue section captured between the jaw members 9014, 9016. In one embodiment, the gap 9022 between the anvil 9014 and the second jaw member 9016 can be measured by positioning a magnetic field sensor on the anvil 9014 and positioning a magnet on the second jaw member 9016 such that the gap 9022 is proportional to the signal detected by the magnetic field sensor and the signal is proportional to the distance between the magnet and the magnetic field sensor. It will be appreciated that the location of the magnetic field sensor and the magnet may be swapped such that the magnetic field sensor is positioned on the second jaw member 9016 and the magnet is placed on the anvil 9014.

One or more of the sensors such as, for example, the first sensor 9020 and/or the second sensor 9026 may be measured in real-time during a clamping operation. Real-time measurement allows time based information to be analyzed, for example, by a processor, and used to select one or more algorithms and/or look-up tables for the purpose of assessing, in real-time, a manual input of an operator of the surgical instrument 9010. Furthermore, real-time feedback can be provided to the operator to assist the operator in calibrating the manual input to yield a desired output.

In various aspects, the present disclosure provides an instrument 10 (as described in connection with FIGS. 1-29) configured to provide rate and control feedback to the surgeon. In one example, the instrument 10 (FIGS. 1-4) comprises an energy device to provide rate/impedance feedback. In another example, the instrument 10 provides time dependency such as time between steps and/or rate of firing. In another example, the instrument 10 is configured with a display that the surgeon can monitor for error resolution. In one implementation, the display may be a flexible roll up display is contained within handle (no external display) in the event of failure user unrolls display to determine steps to release.

The present disclosure provides a novel feedback system for surgical instruments to enable the surgeon to balance the motor controlled speed of knife actuation with the thickness and stiffness of the tissue grasped between the jaw members of the end effector such as the anvil and the staple cartridge. The present technique for adjusting the knife actuation speed based on the thickness of the tissue and tissue flow can improve the consistency of staple formation to form a stapled seal.

Accordingly, the present disclosure provides the surgeon a feedback mechanism on the shaft or the handle of the endosurgical device. The feedback comprises a combination of the speed of the advancement of the knife, the tissue compression (impedance), the tissue gap (d), and force to advance (motor current draw). This combination can be displayed on an indicator comprising multiple zones, such as 5-9 zones, for example, with the mid zone indicating the most ideal speed for the force and tissue compression being handled. The more compression the slower the speed to keep the indicator balanced in the center. This would provide a surgeon a repeatable relative measure to judge thickness and tissue flow and the surgeon could then decide how far out of balance the endosurgical device can be operated within certain conditions in order to achieve overall good results. The present feedback mechanism also would provide the surgeon a good evaluation when the tissue and/or firing conditions are out of the ordinary to enable the surgeon to proceed cautiously with the operation during that particular firing. The feedback mechanism also can enable the surgeon to learn the best technique for firing the endosurgical device with limited to no in servicing.

Figure 81:
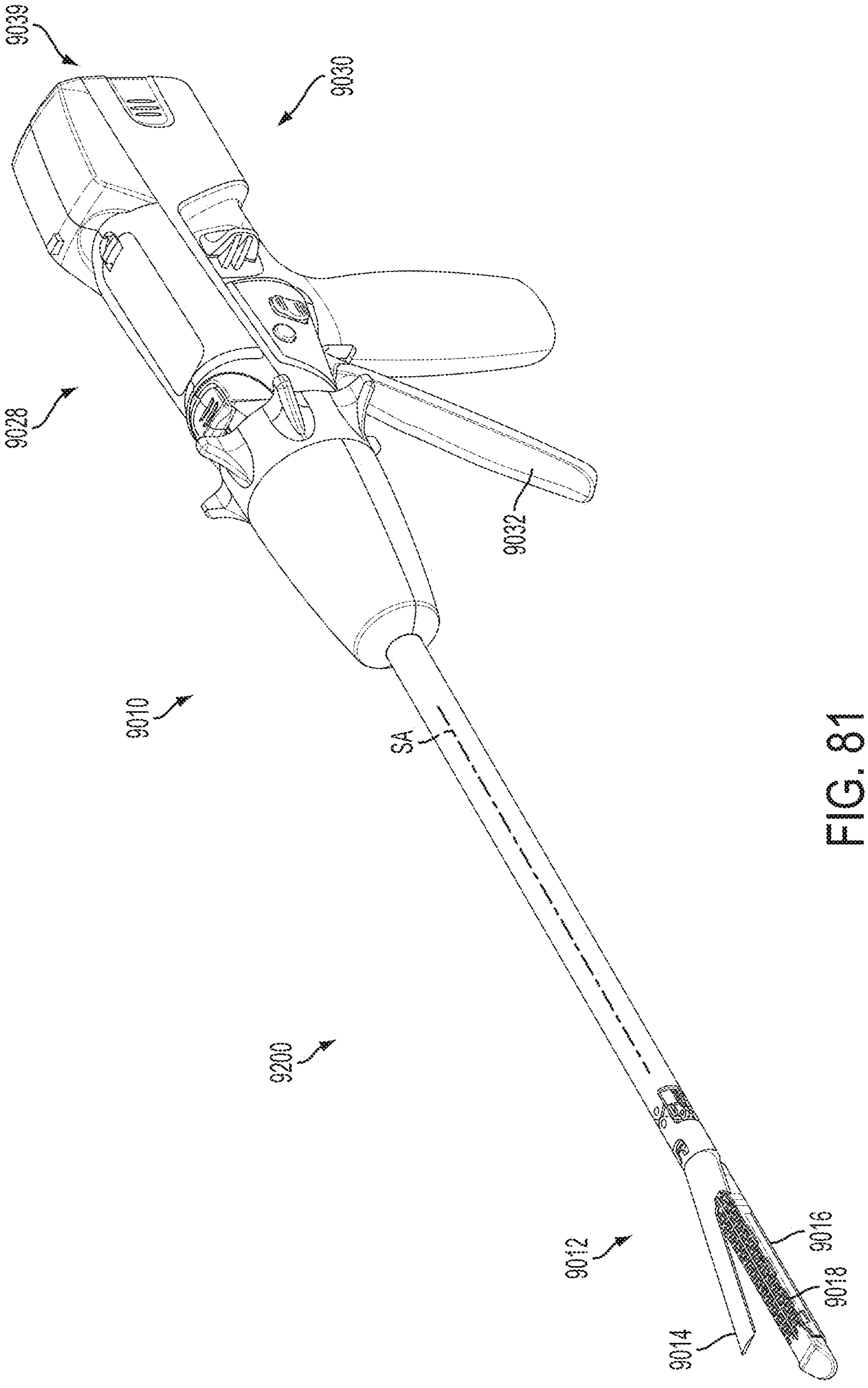
FIG. 81 illustrates a perspective view of a surgical instrument in accordance with one aspect.

Turning to the figures, FIG. 81 illustrates a surgical instrument 9010. The surgical instrument 9010 is similar in many respects to other surgical instruments described in the present disclosure. For example, the surgical instrument 9010 is similarly constructed and equipped as the motor-driven surgical cutting and fastening instrument 10 described in connection with FIGS. 1-29. Therefore, for conciseness and clarity the details of operation and construction will not be repeated here. Accordingly, the surgical instrument 9010, like other surgical instruments described in the present disclosure, comprises an end effector 9012. In the example illustrated in FIGS. 81-82, the end effector 9012 comprises a first jaw member, or anvil, 9014 pivotally coupled to a second jaw member 9016 to capture tissue between the first jaw member 9014 and the second jaw member 9016. The second jaw member 9016 is configured to receive a staple cartridge 9018 therein. The staple cartridge 9018 comprises a plurality of staples 9042. The plurality of staples 9402 is deployable from the staple cartridge 9018 during a surgical operation.

In alternative aspects, the end effector 9012 can be configured to seal tissue captured between the first jaw member 9014 and the second jaw member 9016. For example, the first jaw member 9014 and the second jaw member 9016 may each include an electrically conductive member. The electrically conductive members may cooperate to transmit energy through tissue captured therebetween to treat and/or seal the tissue. A power source such as, for example, a battery can be configured to provide the energy.

In certain instances, as illustrated in FIG. 81, the surgical instrument 9010 can be a motor-driven surgical cutting and fastening instrument that may or may not be reused. In the illustrated example, the instrument 9010 includes a housing 9028 that comprises a handle 9030 that is configured to be grasped, manipulated and actuated by the clinician. In the example illustrated in FIG. 81, the housing 9028 is operably coupled to a shaft assembly 9032 that has a surgical end effector 9012 configured to perform one or more surgical tasks or procedures.

The housing 9028 depicted in FIG. 81 is shown in connection with a shaft assembly 9032 that includes an end effector 9012 that comprises a surgical cutting and fastening device that is configured to operably support a surgical staple cartridge 9018 therein. The housing 9028 may be configured for use in connection with shaft assemblies that include end effectors that are adapted to support different sizes and types of staple cartridges, have different shaft lengths, sizes, and types, etc. In addition, the housing 9028 also may be effectively employed with a variety of other shaft assemblies including those assemblies that are configured to apply other motions and forms of energy such as, for example, radio frequency (RF) energy, ultrasonic energy and/or motion to end effector arrangements adapted for use in connection with various surgical applications and procedures.

Figure 82:
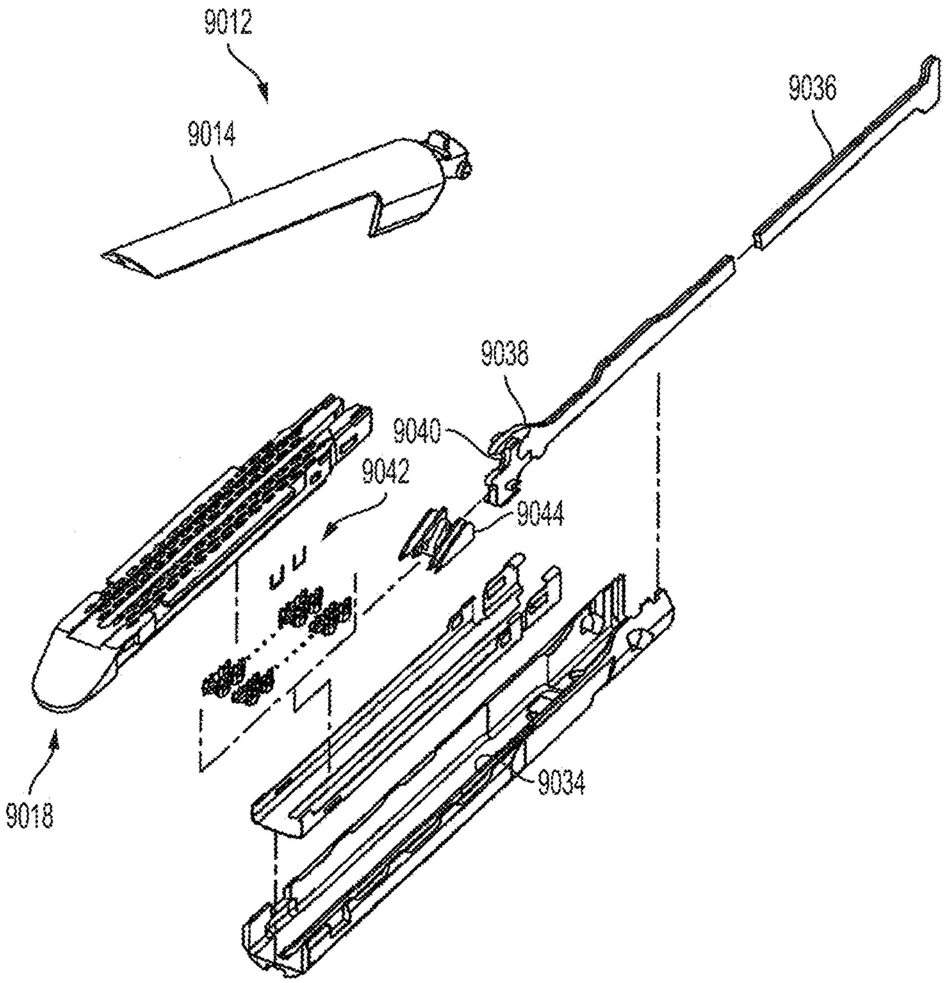
FIG. 82 illustrates an exploded view of the end effector of the surgical instrument of FIG. 81 in accordance with one aspect.

Referring to FIG. 82, a non-limiting form of the end effector 9012 is illustrated. As described above, the end effector 9012 may include the anvil 9014 and the staple cartridge 9018. In this non-limiting example, the anvil 9014 is coupled to an elongate channel 9034. In addition, FIG. 82 shows a firing bar 9036, configured to longitudinally translate into the end effector 9012. A distally projecting end of the firing bar 9036 can be attached to an E-beam 9038 that can, among other things, assist in spacing the anvil 9014 from a staple cartridge 9018 positioned in the elongate channel 9034 when the anvil 9014 is in a closed position. The E-beam 9038 can also include a sharpened cutting member 9040 which can be used to sever tissue as the E-beam 9038 is advanced distally by the firing bar 9036. In operation, the E-beam 9038 can also actuate, or fire, the staple cartridge 9018. The staple cartridge 9018 can include a plurality of staples 9042. A wedge sled 9044 is driven distally by the E-beam 9038 to force out the staples 9042 into deforming contact with the anvil 9012 while a cutting member 9040 of the E-beam 9038 severs clamped tissue.

Figure 83:
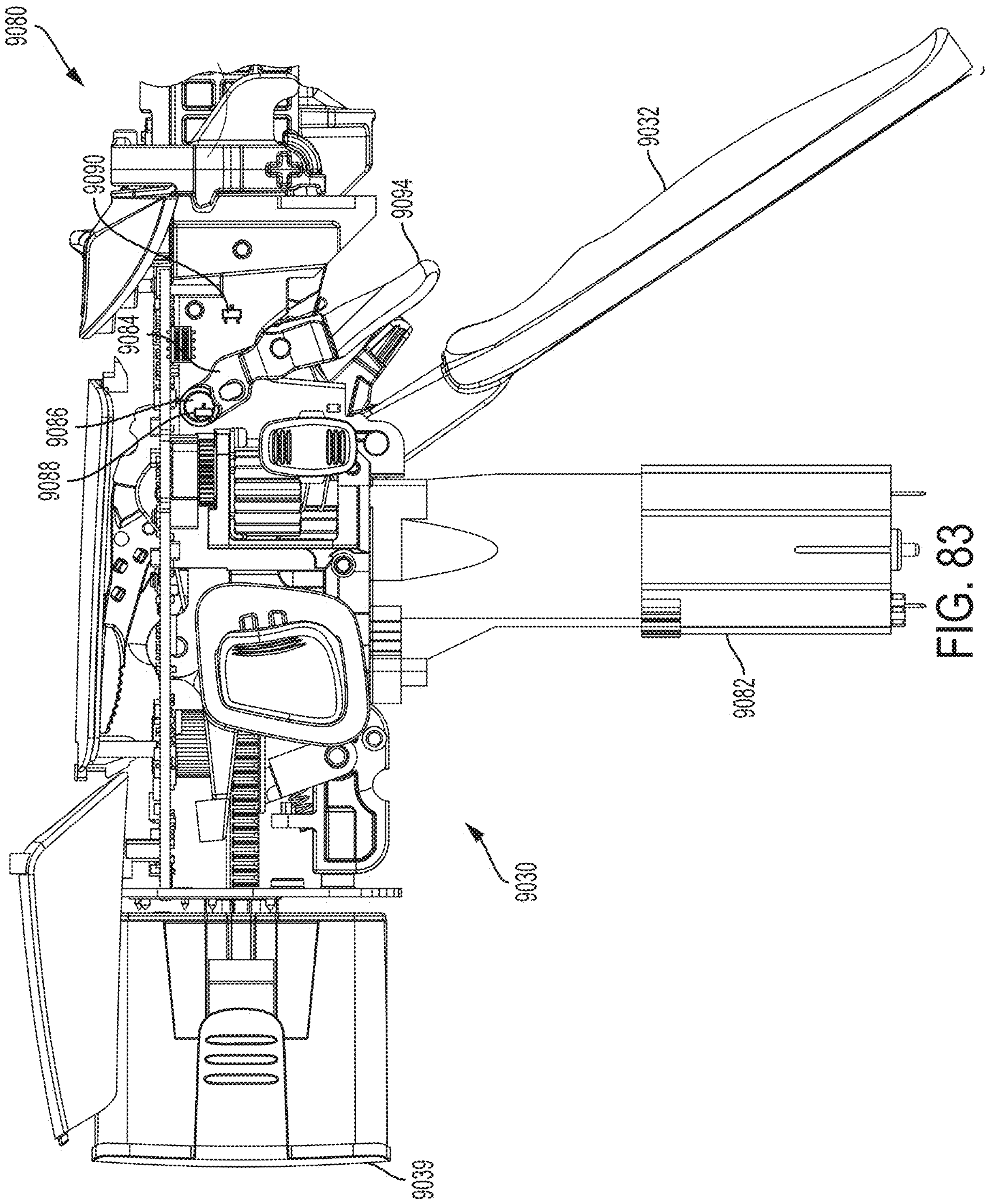
FIG. 83 illustrates a partial side view of a handle of the surgical instrument of FIG. 81 in accordance with one aspect.

In one aspect, as illustrated in FIGS. 81-83, a motor can be operably coupled to the firing bar 9036. The motor can be powered by a power source such as, for example, a battery 9039. The battery 9039 may supply power to the motor 9082 to motivate the firing bar 9036 to advance the E-beam 9038 to fire the staples 9042 into tissue captured between the anvil 9014 and the staple cartridge 9018 and/or advance the cutting member 9040 to sever the captured tissue. Actuation of the motor 9082 can be controlled by a firing trigger 9094 that is pivotally supported on the handle 9030. The firing trigger 9094 can be depressed by an operator of the surgical instrument 9010 to activate the motor 9082.

In one instance, the firing trigger 9094 can be depressed or actuated between a plurality of positions each yielding a different output value. For example, actuating the firing trigger 9094 to a first position may yield a first output value, and actuating the firing trigger 9094 to a second position after the first position may yield a second output value greater than the first output value. In certain instances, the greater the firing trigger 9094 is depressed or actuated, the greater the output value. In certain instances, the output is a characteristic of motion of the firing bar 9036 and/or the cutting member 9040. In one instance, the output can be the speed of the cutting member 9040 during advancement of the cutting member 9040 in a firing stroke. In such instance, actuating the firing trigger 9094 to a first position may cause the cutting member 9040 to travel at a first speed, and actuating the firing trigger 9094 to a second position may cause the cutting member 9040 to travel at a second speed different from the first speed. In certain instances, the greater the firing trigger 9094 is depressed or actuated, the greater the speed of travel of the cutting member 9040.

Figure 87:
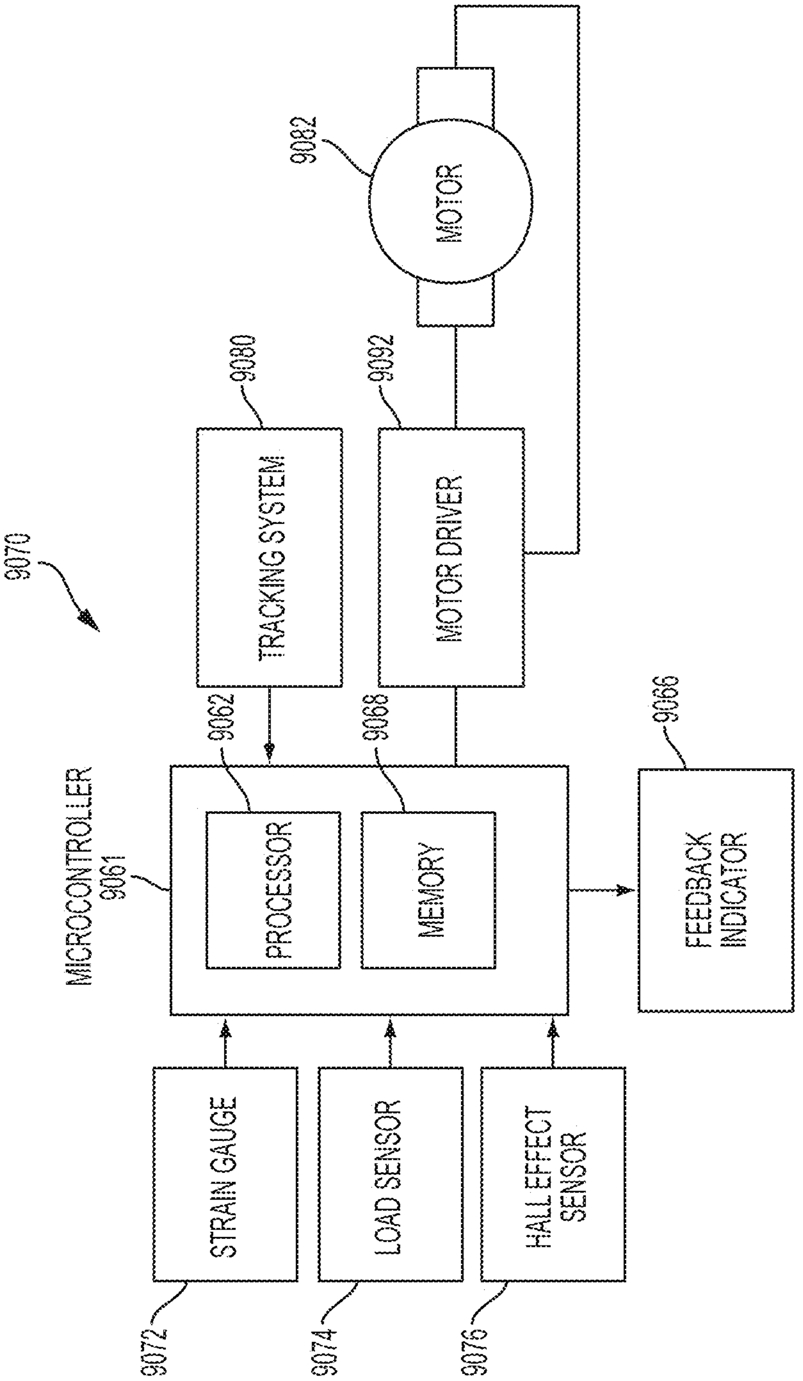
FIG. 87 illustrates a logic diagram of a feedback system in accordance with one aspect.

In the aspect illustrated in FIG. 83, a tracking system 9080 is configured to determine the position of the firing trigger 9094. The tracking system 9080 can include a magnetic element, such as permanent magnet 9086, for example, which is mounted to an arm 9084 extending from the firing trigger 9094. The tracking system 9080 can comprise one or more sensors, such as a first magnetic field sensor 9088 and a second magnetic field sensor 9090, for example, which can be configured to track the position of the magnet 9086. The sensors 9088 and 9090 can track the movement of the magnet 9086 and can be in signal communication with a microcontroller such as, for example, the microcontroller 9061 (FIG. 87). With data from the first sensor 9088 and/or the second sensor 9090, the microcontroller 9061 can determine the position of the magnet 9086 along a predefined path and, based on that position, the microcontroller 9061 can determine an output of the motor 9082. In certain instances, a motor driver 9092 can be in communication with the microcontroller 9061, and can be configured to drive the motor 9082 in accordance with an operator's manual input as detected by the tracking system 9080.

In certain instances, the magnetic field sensors can be configured to detect movement of the firing trigger 9094 through a firing stroke instead of, or in addition to, detecting discrete positions along the firing stroke. The strength of the magnetic field generated by the permanent magnet, as detected by the magnetic field sensors, changes as the permanent magnet 9086 is moved with the firing trigger 9094 through the firing stroke. The change in the strength of the magnetic field can be indicative of a characteristic of motion of the firing trigger 9094, which can detected by a microcontroller as a manual input.

The end effector 9012 may include one or more sensors configured to measure one or more parameters or characteristics associated with the end effector 9012 and/or a tissue section captured by the end effector 9012. In the example illustrated in FIG. 84, the end effector 9012 comprises a first sensor 9020 and a second sensor 9026. In various examples, the first sensor 9020 and/or the second sensor 9026 may comprise, for example, a magnetic sensor such as, for example, a magnetic field sensor, a strain gauge, a pressure sensor, a force sensor, an inductive sensor such as, for example, an eddy current sensor, a resistive sensor, a capacitive sensor, an optical sensor, and/or any other suitable sensor for measuring one or more parameters of the end effector 9012.

In certain instances, the first sensor 9020 and/or the second sensor 9026 may comprise, for example, a magnetic field sensor embedded in the first jaw member 9014 and configured to detect a magnetic field generated by a magnet 9024 embedded in the second jaw member 9016 and/or the staple cartridge 9018. The strength of the detected magnetic field may correspond to, for example, the thickness and/or fullness of a bite of tissue located between the jaw members 9014, 9016. In certain instances, the first sensor 9020 and/or the second sensor 9026 may comprise a strain gauge, such as, for example, a micro-strain gauge, configured to measure the magnitude of the strain in the anvil 9014 during a clamped condition. The strain gauge provides an electrical signal whose amplitude varies with the magnitude of the strain.

In some aspects, one or more sensors of the end effector 9012 such as, for example, the first sensor 9020 and/or the second sensor 9026 may comprise a pressure sensor configured to detect a pressure generated by the presence of compressed tissue between the jaw members 9014, 9016. In some examples, one or more sensors of the end effector 9012 such as, for example, the first sensor 9020 and/or the second sensor 9026 are configured to detect the impedance of a tissue section located between the jaw members 9014, 9016. The detected impedance may be indicative of the thickness and/or fullness of tissue located between the jaw members 9014, 9016.

In one aspect, one or more of the sensors of the end effector 9012 such as, for example, the first sensor 9012 is configured to measure the gap 9022 between the anvil 9014 and the second jaw member 9016. In certain instances, the gap 9022 can be representative of the thickness and/or compressibility of a tissue section clamped between the jaw members 9014, 9016. In at least one example, the gap 9022 can be equal, or substantially equal, to the thickness of the tissue section clamped between the jaw members 9014, 9016. In one example, one or more of the sensors of the end effector 9012 such as, for example, the first sensor 9020 is configured to measure one or more forces exerted on the anvil 9014 by the second jaw member 9016 and/or tissue clamped between the anvil 9014 and the second jaw member 9016. The forces exerted on the anvil 9014 can be representative of the tissue compression experienced by the tissue section captured between the jaw members 9014, 9016. In one embodiment, the gap 9022 between the anvil 9014 and the second jaw member 9016 can be measured by positioning a magnetic field sensor on the anvil 9014 and positioning a magnet on the second jaw member 9016 such that the gap 9022 is proportional to the signal detected by the magnetic field sensor and the signal is proportional to the distance between the magnet and the magnetic field sensor. It will be appreciated that the location of the magnetic field sensor and the magnet may be swapped such that the magnetic field sensor is positioned on the second jaw member 9016 and the magnet is placed on the anvil 9014.

One or more of the sensors such as, for example, the first sensor 9020 and/or the second sensor 9026 may be measured in real-time during a clamping operation. Real-time measurement allows time based information to be analyzed, for example, by a processor, and used to select one or more algorithms and/or look-up tables for the purpose of assessing, in real-time, a manual input of an operator of the surgical instrument 9010. Furthermore, real-time feedback can be provided to the operator to assist the operator in calibrating the manual input to yield a desired output.

Figure 85:
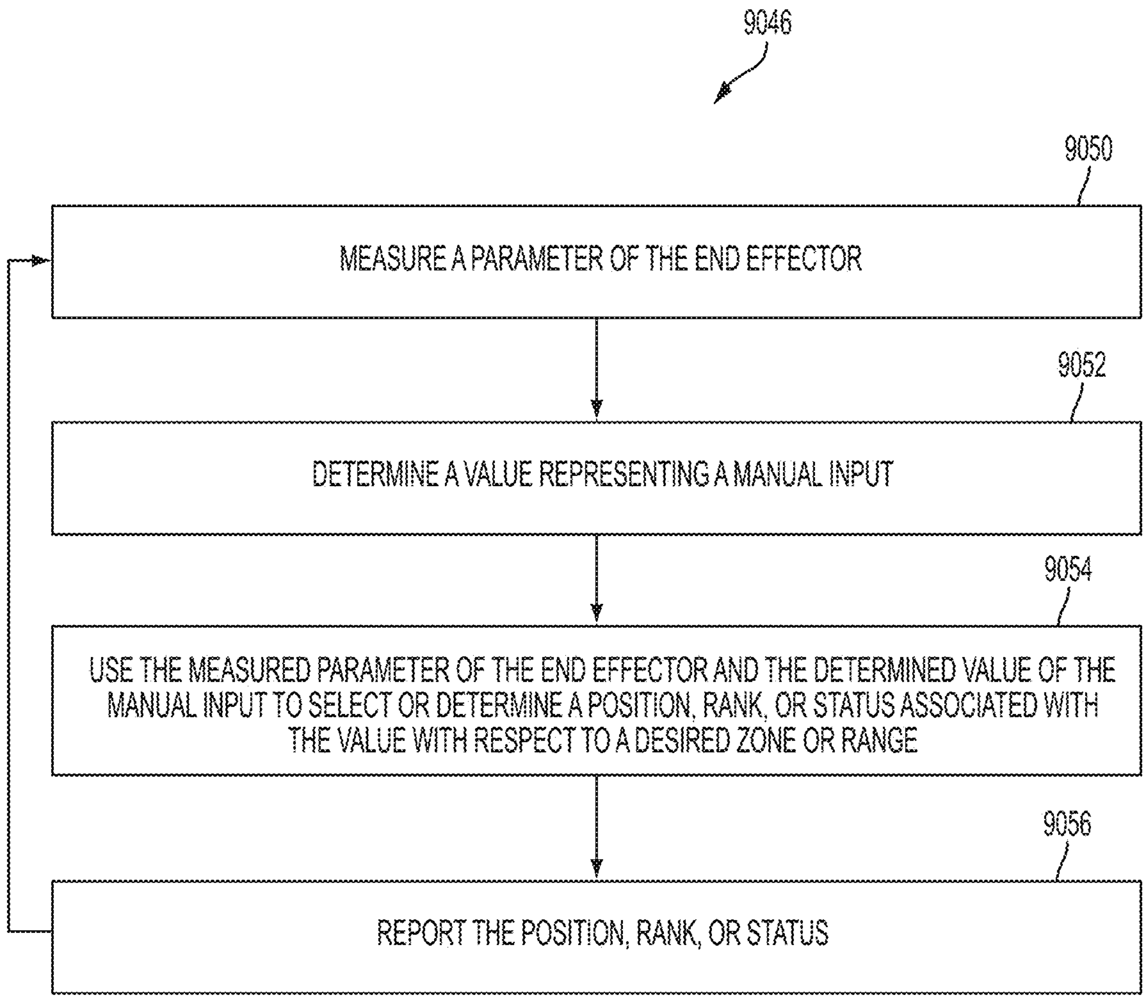
FIG. 85 illustrates a logic diagram of a process in accordance with one aspect.

FIG. 85 is a logic diagram illustrating one aspect of a process 9046 for assessing, in real-time, a manual input of an operator of the surgical instrument 9010 and providing real-time feedback to the operator as to the adequacy of the manual input. In the example illustrated in FIG. 85, the process starts at step or block 9050 where one or more parameters of the end effector 9012 are measured. Next at step 9052, a manual input of an operator of the surgical instrument 9010 is assessed. In one example, a value representative of the manual input is determined. Next at step 9054, the determined value is evaluated or assessed for a position, rank, and/or status with respect to a desired zone or range. The measurement of the parameters of the end effector 9012 and the determined value can be employed to select or determine the position, rank, and/or status associated with the determined value. In a following step 9056 of the process 9046, the position, rank, and/or status associated with the determined value is reported to the operator of the surgical instrument 9010. The real-time feedback allows the operator to adjust the manual input until a position, rank, and/or status within the desired zone or range is achieved. For example, the operator may change the manual input by increasing or decreasing the manual input while monitoring the real-time feedback until the position, rank, and/or status associated with a determined value that corresponds to a present manual input is within the desired zone or range.

Figure 86:
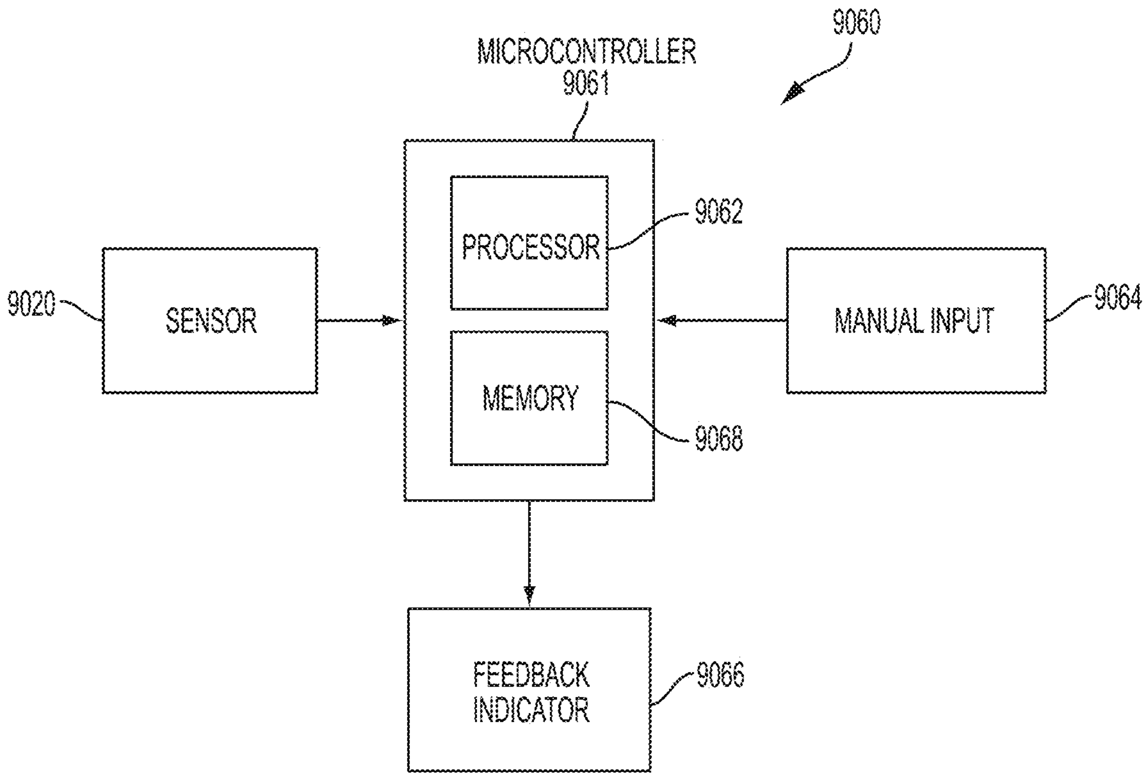
FIG. 86 illustrates a logic diagram of a feedback system in accordance with one aspect.

FIG. 86 is a logic diagram illustrating one aspect of a real-time feedback system 9060 for assessing, in real-time, a manual input 9064 of an operator of the surgical instrument 9010 and providing to the operator real-time feedback as to the adequacy of the manual input 9064. With reference to FIGS. 81-86, in the example illustrated in FIG. 86, the real-time feedback system 9060 is comprised of a circuit. The circuit includes a microcontroller 9061 comprising a processor 9062. A sensor such as, for example, the sensor 9020 is employed by the processor 9062 to measure a parameter of the end effector 9012. In addition, the processor 9062 can be configured to determine or receive a value representative of a manual input 9064 of an operator of the surgical instrument 9010. The manual input 9064 can be continuously assessed by the processor 9062 for as long as the manual input 9064 is being provided by the operator. The processor 9062 can be configured to monitor a value representative of the manual input 9064. Furthermore, the processor 9062 is configured to assign, select, or determine a position, rank, and/or status for the determined value with respect to a desired zone or range. The measurement of the parameter of the end effector 9012 and the determined value can be employed by the processor 9062 to select or determine the position, rank, and/or status associated with the determined value, as described in greater detail below. A change in the manual input 9064 yields a change in the determined value which, in turn, yields a change in the position, rank, and/or status assigned to the determined value with respect to the desired zone or range.

As illustrated in FIG. 86, the real-time feedback system 9060 may further include a feedback indicator 9066 which can be adjusted between a plurality of positions, ranks, and/or statuses inside and outside a desired zone or range. In one example, the processor 9062 may select a first position (P1), rank, and/or status that characterizes the manual input 9064 based on a measurement (M1) of a parameter of the end effector 9012 and a first determined value (V1) representing a first manual input (I1). In certain instances, the first position (P1), rank, and/or status may fall outside the desired zone or range. In such instances, the operator may change the manual input 9064 from the first manual input (I1) to a second manual input (I2) by increasing or decreasing the manual input 9064, for example. In response, the processor 9062 may adjust the feedback indicator 9066 from the first position (P1), rank, and/or status to a second position (P2), rank, and/or status, which characterizes the change to the manual input 9064. The processor 9062 may select the second position (P2), rank, and/or status based on the measurement (M1) of the parameter of the end effector 9012 and a second determined value (V2) representing a second manual input (12). In certain instances, the second position (P2), rank, and/or status may fall inside the desired zone or range. In such instances, the operator may maintain the second manual input (12) for a remainder of a treatment cycle or procedure, for example.

In the aspect illustrated in FIG. 86, the microcontroller 9061 includes a storage medium such as, for example, a memory unit 9068. The memory unit 9068 may be configured to store correlations between measurements of one or more parameters of the end effector 9012, values representing manual inputs, and corresponding positions, ranks, and/or statuses characterizing the manual input 9064 with respect to a desired zone or range. In one example, the memory unit 9068 may store the correlation between the measurement (M1), the first determined value (V1), and the first manual input (I1), and the correlation between the measurement (M1), the second determined value (V2), and the second manual input (12). In one example, the memory unit 9068 may store an algorism, an equation, or a look-up table for determining correlations between measurements of one or more parameters of the end effector 9012, values representing manual inputs, and corresponding positions, ranks, or statuses with respect to a desired zone or range. The processor 9062 may employ such algorism, equation, and/or look-up table to characterize a manual input 9064 provided by an operator of the surgical instrument 9010 and provide feedback to the operator as to the adequacy of the manual input 9064.

FIG. 87 is a logic diagram illustrating one aspect of a real-time feedback system 9070. The system 9070 is similar in many respects to the system 9060. For example, like the system 9060, the system 9070 is configured for assessing, in real-time, a manual input of an operator of the surgical instrument 9010 and providing to the operator real-time feedback as to the adequacy of the manual input. Furthermore, like the system 9060, the system 9070 is comprised of a circuit that may include the microcontroller 9061.

In the aspect illustrated in FIG. 87, a strain gauge 9072, such as, for example, a micro-strain gauge, is configured to measure one or more parameters of the end effector 9012, such as, for example, the amplitude of the strain exerted on the anvil 9014 during a clamping operation, which can be indicative of the tissue compression. The measured strain is converted to a digital signal and provided to the processor 9062. A load sensor 9074 can measure the force to advance the cutting member 9040 to cut tissue captured between the anvil 9014 and the staple cartridge 9018. Alternatively, a current sensor (not shown) can be employed to measure the current drawn by the motor 9082. The force required to advance the firing bar 9036 can correspond to the current drawn by the motor 9082, for example. The measured force is converted to a digital signal and provided to the processor 9062. A magnetic field sensor 9076 can be employed to measure the thickness of the captured tissue, as described above. The measurement of the magnetic field sensor 9076 is also converted to a digital signal and provided to the processor 9062.

In the aspect illustrated in FIG. 87, the system 9070 further includes the tracking system 9080 which can be configured to determine the position of the firing trigger 9094 (FIG. 83). As described above, the firing trigger 9094 can be depressed or actuated by moving the firing trigger 9094 between a plurality of positions, each corresponding to one of a plurality of values of a characteristic of motion of the firing bar 9036 and/or the cutting member 9040 during a firing stroke. As describe above, a characteristic of motion can be a speed of advancement of the firing bar 9036 and/or the cutting member 9040 during the firing stroke. In certain instances, a motor driver 9092 can be in communication with the microcontroller 9061, and can be configured to drive the motor 9082 in accordance with an operator's manual input as detected by the tracking system 9080.

Further to the above, the system 9070 may include a feedback indicator 9066. In one aspect, the feedback indicator 9066 can be disposed in the handle 9030. Alternatively, the feedback indicator can be disposed in the shaft assembly 9032, for example. In any event, the microcontroller 9061 may employ the feedback indicator 9066 to provide feedback to an operator of the surgical instrument 9010 with regard to the adequacy of a manual input such as, for example, a selected position of the firing trigger 9094. To do so, the microcontroller 9061 may assess the selected position of the firing trigger 9094 and/or the corresponding value of the speed of the firing bar 9036 and/or the cutting member 9040. The measurements of the tissue compression, the tissue thickness, and/or the force required to advance the firing bar 9036, as respectively measured by the sensors 9072, 9074, and 9076, can be used by the microcontroller 9061 to characterize the selected position of the firing trigger 9094 and/or the corresponding value of the speed of the firing bar 9036 and/or the cutting member 9040. In one instance, the memory 9068 may store an algorism, an equation, and/or a look-up table which can be employed by the microcontroller 9061 in the assessment. In one example, the measurements of the sensors 9072, 9074, and/or 9076 can be used to select or determine a position, rank, and/or a status that characterizes the selected position of the firing trigger 9094 and/or the corresponding value of the speed of the firing bar 9036 and/or the cutting member 9040. The determined position, rank, and/or status can be communicated to the operator via the feedback indicator 9066.

The reader will appreciate that an optimal speed of the firing bar 9036 and/or the cutting member 9040 during a firing stroke can depend on several parameters of the end effector 9012 such as, for example, the thickness of the tissue captured by the end effector 9012, the tissue compression, and/or the force required to advance the firing bar 9036 and, in turn, the cutting member 9040. As such, measurements of these parameters can be leveraged by the microcontroller 9061 in assessing whether a current speed of advancement of the cutting member 9040 through the captured tissue is within an optimal zone or range.

Figure 88:
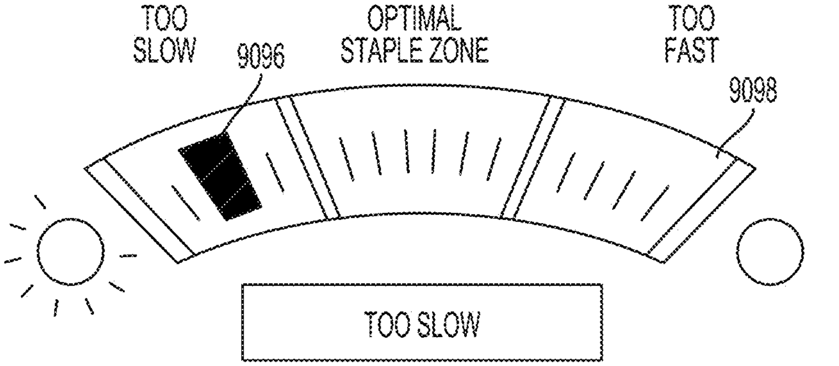
FIG. 88 illustrates a feedback indicator of a feedback system in accordance with one aspect.
Figure 89:
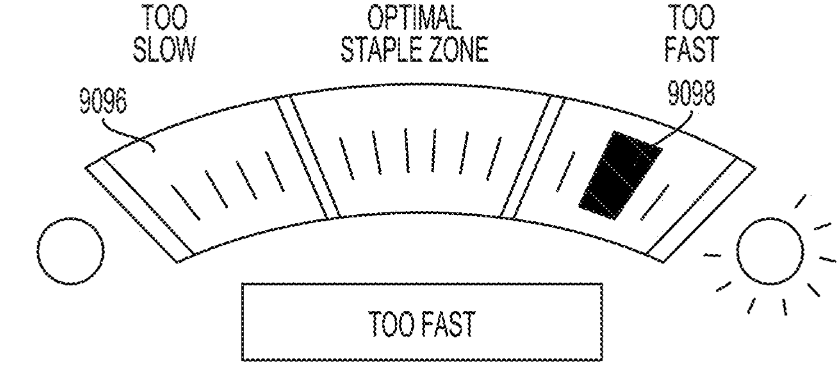
FIG. 89 illustrates a feedback indicator of a feedback system in accordance with one aspect.
Figure 90:
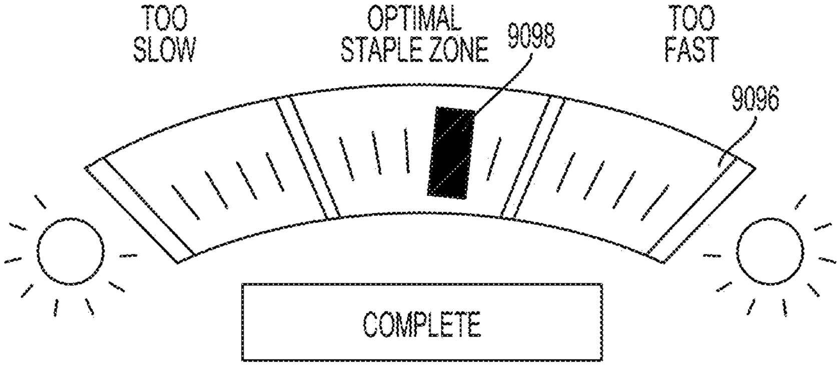
FIG. 90 illustrates a feedback indicator of a feedback system in accordance with one aspect.

In one aspect, as illustrated in FIGS. 88-90, the feedback indicator 9066 includes a dial 9096 and a pointer 9098 movable between a plurality positions relative to the dial 9096. The dial 9096 is divided to define an optimal zone, a so-called "TOO FAST" zone, and a so-called "TOO SLOW" zone. The pointer 9098 can be set to one of a plurality of positions within the three zones. In one example, as illustrated in FIG. 88, the pointer is set to a position in the "TOO SLOW" zone to alert the operator that a selected speed of advancement of the cutting member 9040 through the tissue captured by the end effector 9012 is below an optimal or a desired zone. As described above, such a characterization of the selected speed can be performed by the microcontroller 9061 based on one or more measurements of one or more parameters of the end effector 9012. In another example, perhaps after the operator increases the speed of the cutting member 9040 in response to the previous alert, the pointer is moved to a new position in the "TOO FAST" zone, as illustrated in FIG. 89, to alert the operator that a newly selected speed of the cutting member 9040 exceeds the optimal zone. The operator may continue to adjust the speed of the cutting member 9040 by adjusting the position of the firing trigger 9094 until the pointer lands in the optimal zone, as illustrated in FIG. 90. At such point, the operator may maintain the current position of the firing trigger 9094 for the remainder of the firing stroke.

Figure 91:
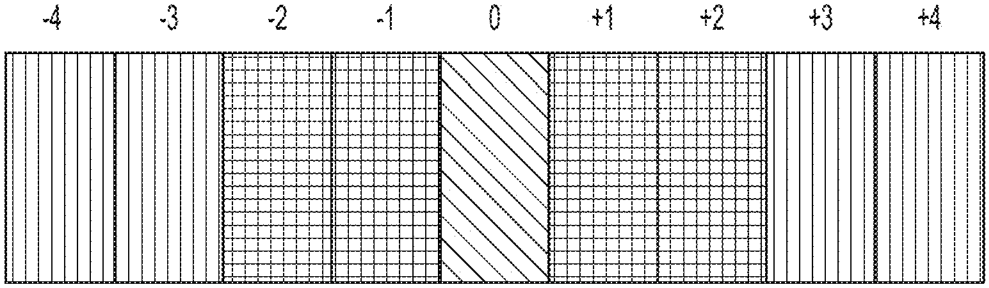
FIG. 91 illustrates a feedback indicator of a feedback system in accordance with one aspect.
Figure 92:
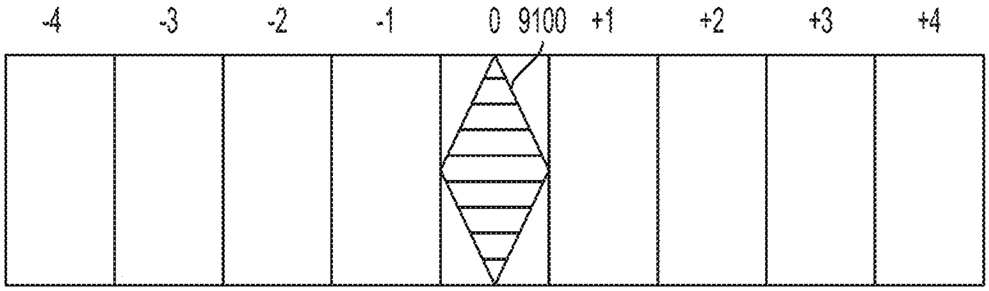
FIG. 92 illustrates a feedback indicator of a feedback system in accordance with one aspect.
Figure 93:
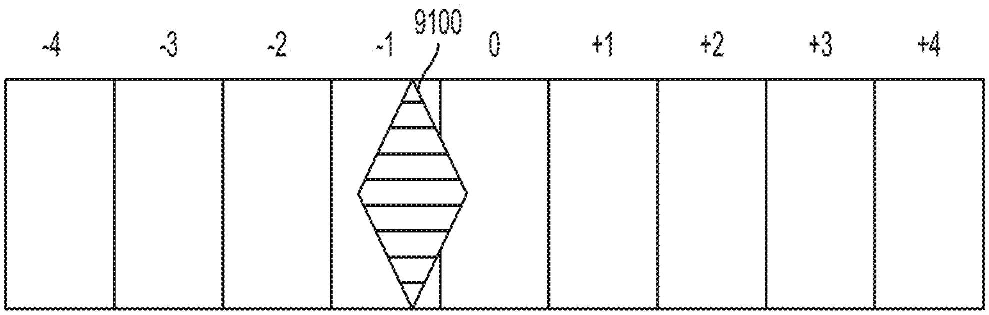
FIG. 93 illustrates a feedback indicator of a feedback system in accordance with one aspect.
Figure 94:
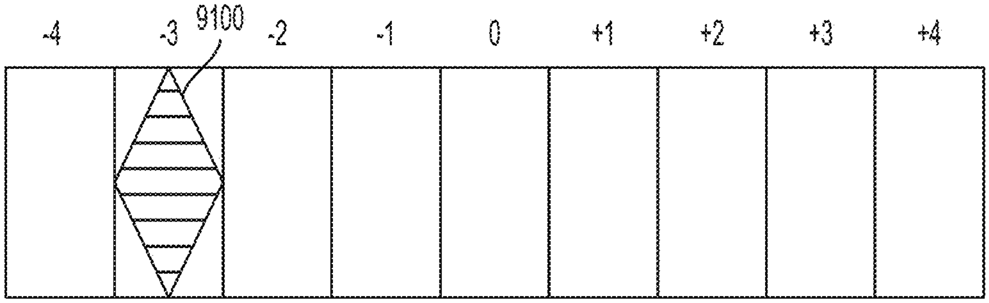
FIG. 94 illustrates a feedback indicator of a feedback system in accordance with one aspect.
Figure 95:
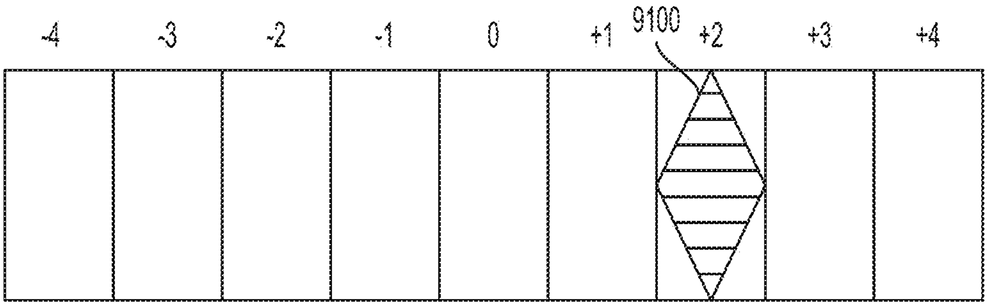
FIG. 95 illustrates a feedback indicator of a feedback system in accordance with one aspect.

In certain instances, the dial 9096 and the pointer 9098 can be replaced with a digital indicator. In one example, the digital indicator includes a screen that illustrates the above-identified three zones. A digital pointer can be transitioned between a plurality of positions on the screen to provide feedback to the operator in accordance with the present disclosure. In certain instances, as illustrated in FIGS. 91-93, the feedback indicator 9066 includes a plurality of zones with a middle zone indicating an optimal or ideal speed of the cutting member 9040. In the example illustrated in FIG. 91, nine zones are illustrated. However, in alternative examples, the feedback indicator 9066 may include five or seven zones, for example. As illustrated in FIG. 91, the plurality of zones can be color coded. For example, the middle zone can be in green. The first two zones to the right and the first two zones to the left of the middle zone can be in yellow. The remaining zones can be in red. In certain instances, as illustrated in FIG. 91, the nine zones can be numbered with the numbers −4, −3, −2, 0, +1, +2, +3, and +4, respectively from left to right. In at least one example, the plurality of zones can be numbered and color coded.

Figure 96:
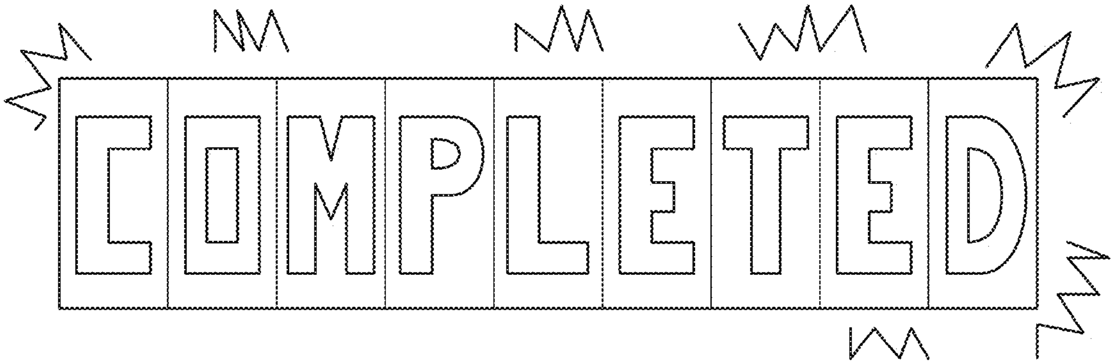
FIG. 96 illustrates a feedback indicator of a feedback system in accordance with one aspect.

In any event, as illustrated in FIGS. 92-95, a pointer 9100 is movable between a plurality of positions to point to one of the nine zones. An operator of the surgical instrument 9010 may squeeze the firing trigger 9094 while monitoring the position of the pointer 9100. Depending on the position taken by the pointer 9100, the operator may reduce or increase the pressure on the trigger 9094 until the pointer 9100 rests in the middle or optimal zone. At such point, the operator may maintain the current pressure on the firing trigger 9094 for the remainder of the firing stroke. In certain instances, as illustrated in FIG. 96, the feedback indicator 9066 may alert the operator that the firing stroke is completed.

In certain instances, as described above, the jaw members 9014, 9016 include electrically conductive layers configured to deliver energy to tissue captured between the jaw members 9014, 9016. An energy trigger or actuator can be moved or depressed between a plurality of positions or settings, in a similar manner to the firing trigger 9094, to deliver the energy to the tissue. The level or intensity of the energy delivered to the tissue may depend on the selected position. For example, depressing the energy trigger to a first position may yield a first energy level, and depressing the energy trigger to a second position, different from the first position, may yield a second energy level different from the first energy level. A tracking system, like the tracking system 9080, can track the position of the energy trigger and report such manual input to the microcontroller 9061. Alternatively, the resulting energy level can be monitored and reported to the microcontroller 9061. A current sensor or a voltage sensor, for example, can be employed to monitor the resulting energy level.

In any event, the microcontroller 9061 may be configured to characterize the selected position of the energy trigger and/or the resulting energy level in view of one or more measured parameters of the end effector 9012 and/or one or more characteristics of the captured tissue such as tissue thickness, tissue compression, and/or tissue impedance. One or more sensors can be employed to obtain measurements of one or parameters of the end effector and/or one or more characteristics of the captured tissue, which can be reported in real-time to the microcontroller 9061. In response, the microcontroller 9061 may characterize the selected position of the energy trigger and/or the resulting energy level by selecting or determining a position, rank, and/or status of the selected position of the energy trigger and/or the resulting energy level with respect to a desired zone or range. As described above, the memory unit 9068 can include an algorism, equation, and/or look-up table for determining the position, rank, and/or status of the selected position of the energy trigger and/or the resulting energy level. Furthermore, the position, rank, and/or status can be reported to the operator of the energy trigger in real-time via a feedback indicator, similar to the feedback indicator 9066, for example.

One of the advantages of the feedback methods and systems of the present disclosure is that they reduce the number of variables that an operator need to consider while providing a manual input such as, for example, actuating the firing trigger 9094. As such, the operator is relieved from having to manually consider each of the measured parameters of the end effector 9012 to estimate the adequacy of a manual input and/or an output value resulting from the manual input such as the speed of the cutting member 9040. Instead, a current manual input and/or an output value of the manual input can be automatically characterized by the microcontroller 9061 in view of all the measured parameters of the end effector 9012 to provide the operator with one consolidated real-time feedback through the feedback indicator 9066. The operator may then focus on such feedback and adjust the manual input to achieve an optimal result.

Further to the above, the feedback methods and systems of the present disclosure would give the operator a repeatable relative measure to judge the adequacy of a manual input. In addition, the operator could decide for themselves how far beyond an optimal zone, with respect to such relative measure, they are willing to reach comfortably to achieve a good outcome. Furthermore, the feedback methods and systems of the present disclosure would also give the operator a warning if the firing was out of the ordinary so that additional caution may be exercised. Furthermore, by focusing on the one consolidated real-time feedback, an operator can learn quicker the best way to fire a surgical instrument.

The present disclosure also provides novel techniques for modular reload to identify itself and define a program of operation of a motor controller to actuate the module.

One technique includes defining a table of programs and configuring a module to communicate to the handle which software programs (or other machine executable instructions) to select and execute. By way of contrast, other techniques are contemplated that do not include no operating programs in the handle portion of the endosurgical device and instead store the program in the module itself and uploads the program at the time of attachment for the handle to execute. In another technique, no programs would be executed in the handle. The handle would contain the motor controller, the actuation buttons, and even the power controller, but not the operating programs. The module would contain all the upper level logic and a sub-processor to execute the program such that each module includes a main processor and the program specific to that reload. When the shaft is attached to the handle, the processor becomes energized and it identifies the handle to which it is attached. Once identified the handle is slaved to the modular reload with the module giving and processing all commands. When a button is depressed, for example, the module responds and determines the next action and then communicates to the slaved motor controller how far and how fast to move and when to stop. With the inclusion of the master processor in the module there also should be a relatively high bandwidth communication bus between the module and the handle to enable the necessary communication traffic. This can be accomplished by holding the rotary shaft component of the modular attachment within a station frame attachment component such that the stationary part houses the processor and control program. Therefore, the communication bus does not have to also serve as a slip ring contact set.

As described herein, a surgical system can include modular components, which can be attached and/or combined together to form a surgical instrument. Such modular components can be configured to communicate and interact to affect surgical functions. Referring again to the surgical instrument 10 (FIGS. 1-4), the surgical instrument 10 includes a first modular component 14 (FIG. 1), e.g., a handle assembly 14, and a second modular component 200 (FIG. 1), e.g., an attachment assembly that includes an elongate shaft 260 (FIG. 1) and an end effector 300 (FIG. 1), which are described herein. The handle assembly 14 and the attachment assembly 200 can be assembled together to form the modular surgical instrument 10 or at least a portion thereof. Optionally, a different modular component may be coupled to the handle assembly 14, such as an attachment having different dimensions and/or features than those of the attachment assembly 200 (FIG. 1), for example. For example, alternative attachments can be interchangeable with the attachment assembly 200. In various instances, the surgical instrument 10 can include additional modular components, such as a modular battery 90 (FIG. 4), for example.

The modular surgical instrument 10 (FIGS. 1-4) can include a control system that is designed and configured to control various elements and/or functions of the surgical instrument 10. For example, the handle assembly 14 (FIG. 1) and the attachment assembly 200 (FIG. 1) can each comprise a circuit board 100 (FIG. 4), 610 (FIG. 7), respectively, having at least one control system. The control systems of the modular components 14, 200 can communicate and/or cooperate. In certain instances, a table of control modules can be accessible to the controller in the handle assembly 14 of the surgical system 10. The controller in the attachment assembly 200 can instruct the handle assembly 14 to select and implement at least one of the control module(s) from the table. In such instances, the controller in the handle assembly 14 can access and run the control module(s). In other instances, the controller in the attachment assembly 200 can include at least one control module. The appropriate control module(s) can be uploaded to the controller in the handle assembly 14, which can run the control module(s). In such instances, the controller in the handle assembly 14 can also access and run the control module(s). Additionally or alternatively, various control module(s) in the handle assembly 14 and/or the attachment assembly 200 can be updated. For example, the controller in the handle assembly 14 can be configured to download updated and/or modified control module(s) from the controller in the attachment assembly 200. U.S. patent application Ser. No. 14/226,133, entitled MODULAR SURGICAL INSTRUMENT SYSTEM, filed Mar. 26, 2014, now U.S. Patent Application Publication No. 2015/0272557, which describes various surgical systems and control systems thereof, is hereby incorporated by reference herein in its entirety.

In still other instances, a processor of the surgical instrument 10 (FIGS. 1-4) can comprise a master processor, and another processor of the surgical instrument 10 can comprise a slave processor. An operating system and/or a plurality of control modules can be accessible to the master processor. The operating system and/or the control modules can affect at least one surgical function with and/or by an element or subsystem of the surgical instrument 10, for example. A control module can comprise software, firmware, a program, a module, and/or a routine, for example, and/or can include multiple software, firmware, programs, control modules, and/or routines, for example. The control modules can affect a surgical function based on a pre-programmed routine, operator input, and/or system feedback, for example. In various instances, the master processor can be configured to direct information and/or commands to the slave processor. Moreover, the slave processor can be configured to receive information and/or commands from the master processor. The slave processor can act in response to the commands from the master processor. In various instances, the slave processor may not include a control module(s) and/or operating system, and the actions of the slave processor can be attributed to command(s) from the master processor and the control module(s) accessible to the master processor. As described herein, the control system in the attachment assembly 200 (FIG. 1) of the surgical instrument system 10 can include a master processor, and the control system in the handle assembly 14 (FIG. 1) of the surgical instrument system 10 can include at least one slave processor, for example.

Referring again to the surgical instrument 10 (FIGS. 1-4), the handle assembly 14 can be compatible with different attachments, which can be configured to affect different surgical functions. The various attachments can be interchangeable, and the different surgical functions can correspond to different tissue types and/or different surgical procedures, for example. Because different attachments can be configured to affect different surgical functions, control modules specific to the particular attachments can be stored on the respective attachments. For example, the attachment assembly 200 (FIG. 1) can store the specific control module(s) for operating the attachment assembly 200. Additionally, the attachment assembly 200 can include the upper level logic and sub-processor to run the control module(s). In such instances, the processor in the attachment assembly 200 can comprise a master control system and/or master processor that is configured to command a slave processor in the handle assembly 14 to implement the control module(s) stored on the attachment assembly 200.

Because each attachment includes the specific control module(s) for its operation and because the processor in the attachment comprises the master processor, the modular surgical instrument 10 is configured to run the most appropriate and up-to-date control module(s) for the particular attachment. Additionally, as updated and/or revised attachments and/or control module(s) therefor and designed and implemented, the updated and/or revised attachments are designed to properly work with handle assemblies that have less recent updates and/or revisions. In other words, updated and/or revised attachments can be retrofit to operate properly with existing and/or out-of-date handle assemblies.

As described herein, the handle assembly 14 (FIG. 1) includes a firing drive system 80 that includes a motor 82 (FIG. 4). The handle assembly 14 also includes a battery 90 (FIG. 90), a handle circuit board 100 (FIG. 4), and an electrical connector 1400 (FIG. 4). A motor controller, such as the motor controller 2043 (FIGS. 21A and 21B), for example, which is described herein, can be configured to control the operation of the motor 82. For example, the motor controller 2043 can initiate rotation of the motor 82 and/or can control the direction and/or speed of motor rotation.

As described herein, the attachment assembly 200 (FIG. 1) can include a shaft circuit board 610 and an electrical connector 1410 (FIG. 7). The electrical connector 1410 (FIG. 3) on the attachment assembly 200 can be configured to engage the electrical connector 1400 (FIG. 4) on the handle assembly 14 (FIG. 1) to provide a conduit and/or conductive pathway for transferring power and/or information between the handle assembly 14 and the attachment assembly 200. The electrical connectors 1400, 1410 can be mounted to stationary components of the surgical instrument 10 (FIGS. 1-4). Referring to FIG. 3, for example, the electrical connection 1410 in the attachment assembly 200 is mounted to the shaft chassis 244, which remains stationary relative to the intermediate firing shaft 222. Because the electrical connections 1400, 1410 are stationary relative to each other, the connections 1400, 1410 can provide a high bandwidth communication bus to enable traffic between the connections 1400, 1410.

In various instances, when the attachment assembly 200 (FIG. 1) is attached to the handle assembly 14 (FIG. 1), the electrical connectors 1400 (FIG. 3), 1410 (FIG. 3) can be engaged and the battery 90 (FIG. 4) in the handle assembly 14 can power the handle assembly 14 and the attachment assembly 200. For example, the battery 90 can provide power to the shaft circuit board 610 (FIG. 7) when the attachment assembly 200 is coupled to the handle assembly 14. In various instances, the battery 90 can automatically power the shaft circuit board 610 and/or components thereof when the attachment assembly 200 is connected to the handle assembly 14.

Figure 97:
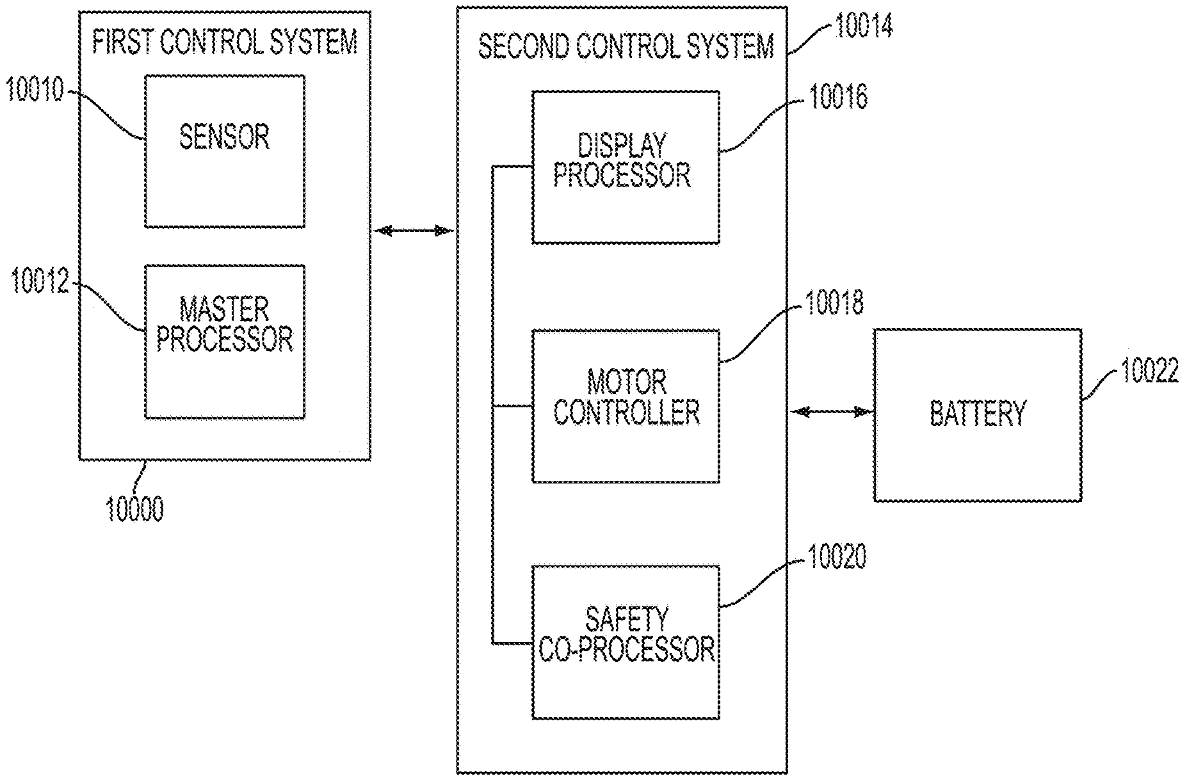
FIG. 97 is a schematic depicting control systems of the modular surgical instrument system of FIG. 1, according to various aspects of the present disclosure.

Referring now to FIG. 97, a schematic depicting the various control systems for a modular surgical instrument system, such as the surgical instrument 10 (FIGS. 1-4), for example, is depicted. A first control system 10000 can be positioned in a modular attachment, such as the attachment assembly 200 (FIG. 1), and a second control system 10014 can be positioned in a modular handle, such as the handle assembly 14 (FIG. 1). The attachment control system 10000 includes a master processor 10012, which is configured to issue commands to a slave processor. For example, the handle control system 10014 includes a slave processor 10018, which can be slaved to the master processor 10012 in the modular attachment 200. In various instances, the slave processor 10018 can correspond to a motor controller, such as the motor controller 2043 (FIGS. 21A and 21B), for example. In such instances, the motor controller 2043 in the handle assembly 14 of the surgical instrument 10 can be slaved to the master processor 10012 in the modular attachment 200. For example, the master processor 10012 can issue commands to the motor controller 2043, which can affect actuation of the motor 82 (FIG. 4), for example, and can control the direction and/or speed of motor rotation.

Referring still to FIG. 97, the control system 10000 in the modular attachment 200 can also include at least one sensor 10010, which can be in communication with the master processor 10012 in the modular attachment 200 (FIG. 1). Various exemplary sensors for detecting conditions within the shaft 260, within the end effector 300 (FIGS. 1 and 2), and/or at the surgical site are described herein. In certain instances, the master processor 10012 can select a control module and/or program to run based on feedback from the sensors 10010. For example, the thickness, density, and/or temperature of tissue detected by one of the sensors 10010 can be communicated to the master processor 10012 and the operating module(s) and/or program selected by the master processor 10012 can account for the detected condition(s) within the end effector 300.

The handle control system 10014 depicted in FIG. 97 also includes a display processor 10016, which can be similar to the display segment 2002*d* of segmented circuit 2000 (FIGS. 21A and 21B), for example. In certain instances, the display processor 10016 can be configured to control the information provided to and presented by a display. In various examples, the display can be integrally formed on the handle assembly 14 (FIG. 1) of the surgical instrument system 10 (FIG. 1). In still other instances, the display can be separate and/or remote from the handle assembly 14 and the attachment assembly 200 (FIG. 1). In at least one instance, the display processor 10016 is a slave to the master processor 10012 in the attachment assembly 200. For example, the master processor 10012 can send commands to the display processor 10016 and the display processor 10016 can implement the commands.

Referring still to FIG. 97, the control system 10014 in the handle assembly 14 (FIG. 1) can include a safety coprocessor 10020, which can be similar to the safety processor 2004 (FIGS. 21A and 21B), for example. In various instances, the safety coprocessor 10020 can be in signal communication with the master processor 10012 in the modular attachment 200 (FIG. 1). The master processor 10012 can issue commands to the safety coprocessor 10020, which can be specific to the modular attachment and/or the surgical functions performed by the particular modular attachment. For example, the master processor 10012 can initiate the safety operations of the safety coprocessor 10020. In various instances, after the safety operations of the safety coprocessor 10020 have been initiated, the safety coprocessor 10020 can run independently and can notify the master processor 10012 if a triggering event occurs.

The control system 10014 in the handle assembly 14 (FIG. 1) can be coupled to a battery 10022, which can be similar to the battery 90 (FIG. 4) positioned in the handle assembly 14 and the battery 2008 (FIGS. 21A and 21B) in the power segment 2002*h* (FIGS. 21A and 21B) of the segmented circuit 2000, which are described herein. The battery 10022 can power the control system 10014 in the handle assembly 14. Moreover, when the attachment assembly 200 is connected to the handle assembly 14, the battery 10022 can power the master control system 10000 in the attachment assembly 200 (FIG. 1). For example, the battery 10022 can power the master processor 10012 in the attachment assembly 200. In various instances, when the attachment assembly 200 is attached to the handle assembly 14, the battery 10022 can automatically power the master processor 10012. For example, current can flow to the master processor 10012 via the electrical connector 1400 (FIGS. 3 and 4) in the handle assembly 14 and the electrical connector 1410 (FIG. 7) in the attachment assembly 200.

In various instances, the master processor 10012 can include a plurality of control modules, which are specific to the surgical functions and/or components of the attachment assembly 200 (FIG. 1). The control modules can be accessible to and/or integral with the master processor 10012. In various circumstances, the master processor 10012 can include multiple tiers and/or levels of command and the control modules can be organized into multiple tiers. For example, the master processor 10012 can include a first tier of control modules, a second tier of control modules, and/or a third tier of control modules. Control modules of the first tier can be configured to issue commands to the control modules of the second tier, for example, and the control modules of the second tier can be configured to issue commands to the control modules of the third tier. In various instances, the master processor 10012 can include less than three tiers and/or more than three tiers, for example.

The control module(s) in the first tier can comprise high-level software, or a clinical algorithm. Such a clinical algorithm can control the high-level functions of the surgical instrument 10 (FIGS. 1-4), for example. In certain instances, the control module(s) in the second tier can comprise intermediate software, or framework module(s), which can control the intermediate-level functions of the surgical instrument 10, for example. In certain instances, the clinical algorithm of the first tier can issue abstract commands to the framework module(s) of the second tier to control the surgical instrument 10. Furthermore, the control modules in the third tier can comprise firmware modules, for example, which can be specific to a particular hardware component, or components, of the surgical instrument 10. For example, the firmware modules can correspond to a particular cutting element, firing bar, trigger, sensor, and/or motor of the surgical instrument 10, and/or can correspond to a particular subsystem of the surgical instrument 10, for example. In various instances, a framework module can issue commands to a firmware module to implement a surgical function with the corresponding hardware component. Accordingly, the various control modules of the surgical system 10 can communicate and/or cooperate during a surgical procedure.

The master processor 10012 can include and/or access the control modules of various tiers, which can affect different surgical functions. In certain instances, the motor controller 10018 may not include any control modules, and control modules may not be accessible to the motor controller 10018. For example, the motor controller 10018 may not include an operating system, framework module, and/or firmware module. In such instances, the motor controller 10018 can be slaved to the master processor 10012, and the motor controller 10018 can be configured to implement the commands issued by the master processor 10012.

As described herein, the master control system 1000 in the attachment assembly 200 can communicate with the control system 10014 in the handle assembly 14 (FIG. 1) to affect a surgical function. In use, referring primarily now to FIG. 98, modular components of a surgical instrument, such as the handle assembly 14 and the attachment assembly 200 (FIG. 1), can be attached 11000. Thereafter, at least one function can be initiated by a master processor, such as the master processor 10012 (FIG. 97), for example, which can include the control module(s) and/or operating program(s) specific to the attachment assembly 200 (FIG. 1) and the surgical function(s) to be performed by the attachment assembly 200.

Figure 98:
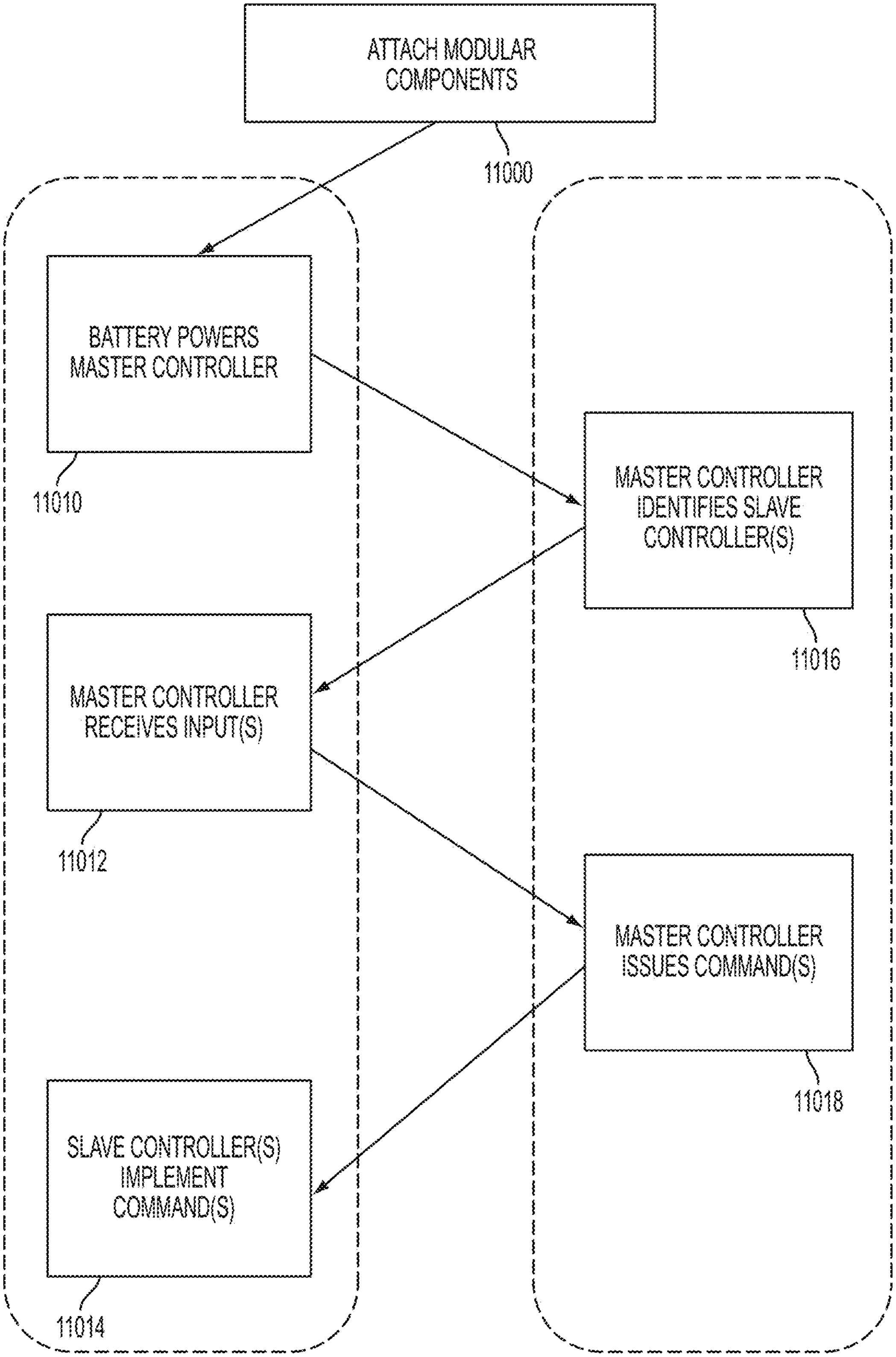
FIG. 98 is a logic diagram of a method for implementing a surgical function with the modular surgical instrument system of FIG. 1, according to various aspects of the present disclosure.

With reference primarily to both FIGS. 97 and 98, a battery, such as the battery 10022 can power 11010 the master processor 10012. As described herein, when the attachment assembly 200 (FIG. 1) is properly coupled to the handle assembly 14 (FIG. 1), the battery 10022 in the handle assembly 14 can power the master processor 10012. The powered master processor 10012 can identify 11016 at least one slave processor, such as the slave processors 10016 and 10018, for example. After the master processor 10012 identifies 11016 at least one of the slave processor(s) 10016, 10018, the master processor 10012 can issue commands to the slave processor(s) 10016, 10018. The commands can be based on a pre-programmed routine found in a control module accessible to the master processor 10012.

In various instances, the master processor 10012 can request information from other systems and/or controllers in the surgical instrument 10 (FIGS. 1-4). For example, the master processor 10012 can request information from a slaved processor. In certain instances, the master processor 10012 can request information from an input system, such as an actuation button and/or trigger on the handle assembly 14 (FIG. 1). Additionally or alternatively, the master processor 10012 can request information from a sensor and/or feedback system. For example, the master processor 10012 can communicate with at least one sensor 10010 to obtain information on at least one condition in the surgical instrument 10 and/or surgical site. The master processor 10012 can receive 11012 information and/or inputs.

The master processor 10012 can issue at least one command to at least one slave processor 10016, 10018 at step 11018. In certain instances, the command(s) can be based on the control module(s) accessible to the master processor 10012 and/or the feedback and/or input received at step 11012. For example, the master processor 10012 can command the slaved motor controller 10018 to operate the motor 82 (FIG. 4) in the handle assembly 14 at a particular power level, in a particular direction, and/or for a particular duration. The control sequence of the motor 82 can be determined and provided by a control module in the attachment assembly 200 (FIG. 1). As a result, the control sequence can correspond to the particular attachment assembly 200 and the surgical function to be performed by that attachment assembly 200.

At step 11014, the slaved processors 10016 and/or 10018 can implement the command(s) from the master processor 10012. In various instances, the master processor 10012 can request information from various slaved systems during and/or throughout implementation of the control sequence. In certain instances, based on the updated information, the master processor 10012 can issue a new and/revised command and/or commands. Additionally or alternatively, the master processor 10012 can issue additional commands to the slaved processor(s) throughout the operation of the surgical instrument 10 (FIGS. 1-4).

The present disclosure provides additional techniques to overcome challenges with conventional modular endosurgical devices. Two of these techniques, in the context of modular endocutters, include wire contacts to transmit power and receive signals from an end effector shaft configured to rotate, and the ability to upgrade the modular attachment with new tech and sensors while allowing the handle to readily accept the new tech.

The ability for the sensors in the end-effector to have the signal processing capability built into the sensor itself helps improve both of these issues. In one aspect, the sensor can be configured to supply the handle with processed information rather than supplying the handle with raw data to minimize the impact of newer sensors and the number of wires necessary to run them. In one aspect, a series of smart sensors can be placed in parallel along a single power line with the shaft of the device as the return path and using current draw "signal" the handle to stop, or start, or end etc. In accordance with this technique, the handle does not need to know what the sensor actually is or how to interpret the processed information being fed back to the controller. Likewise, the current draw can be monitored using a standard Morse Code like encoding technique on the power line to enable the handle to know what the issue is and which sensor identified the issue without any pairing or other couple communication requirement.

Figure 99:
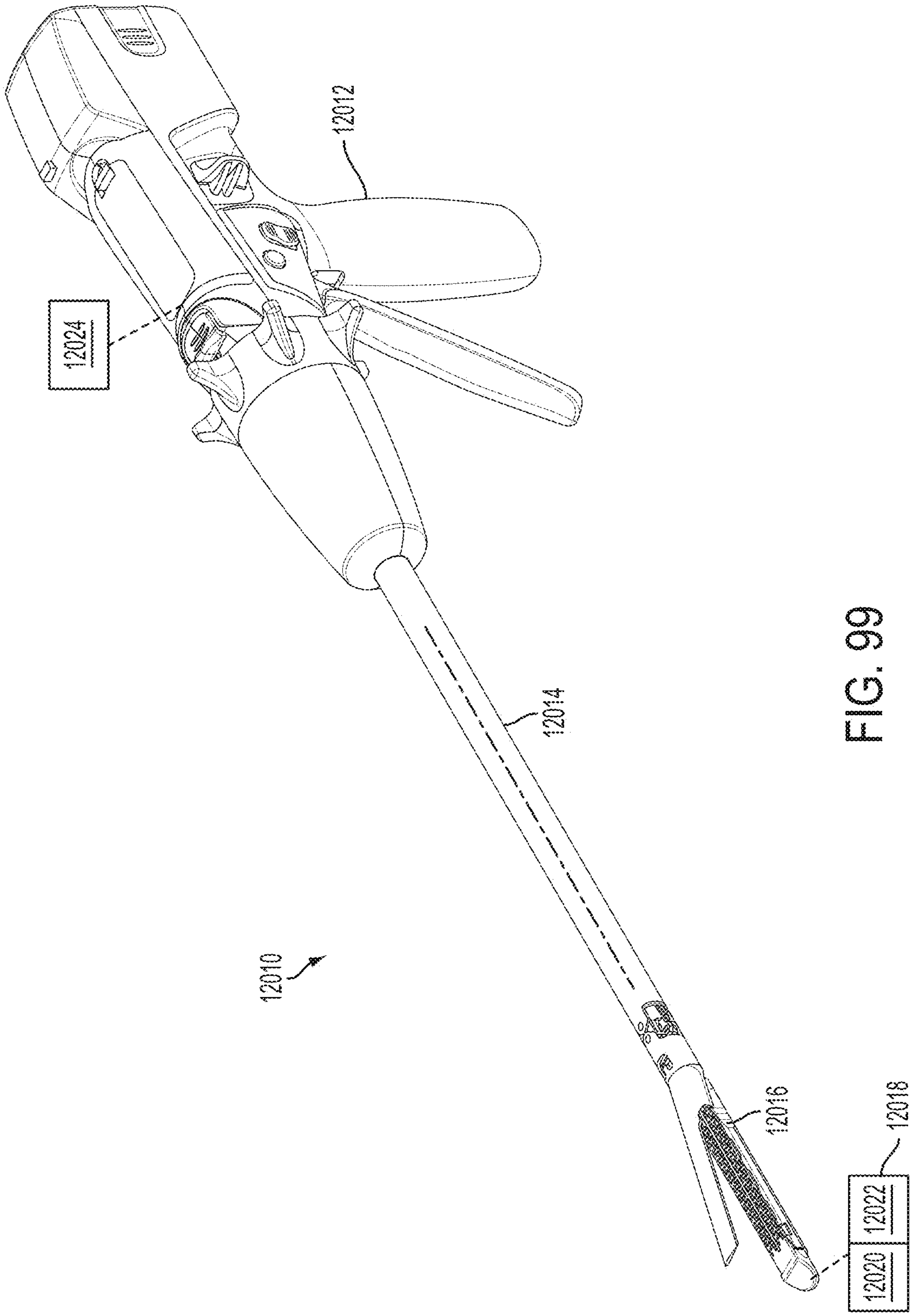
FIG. 99 depicts an example medical device that can include one or more aspects of the present disclosure.

Medical devices may be modular devices that include several separate components. For example, an endocutter such as endocutter 12010 as shown in FIG. 99 may include several large and small separate components. The endocutter 12010 is similarly constructed and equipped as the motor-driven surgical cutting and fastening instrument 10 described in connection with FIGS. 1-29. Accordingly, for conciseness and clarity the details of operation and construction will not be repeated here. Endocutter 12010 may include a handle component 12012, a shaft component 12014, and an end-effector component 12016. Each of the handle, the shaft, and the end-effector may include smaller but separate components such as sensors, transducers, motors, switches, controllers, processors etc., which may be programmable and interoperable with one another. In this way, endocutter 12010 may be a modular medical device.

In general, modular devices may have several challenges to overcome. For example, modular endocutter 12010 may require multiple wire contacts configured to transmit power and receive signals. A power source, such as a battery 90 (FIG. 4), may transfer power to one or more sensors, transducers, motors, switches, controllers, processors, or other modular components of the endocutter through various wires and wire contacts. One or more of these modular components may receive signals from one another in order to perform various calculations, processes, or actions to operate the endocutter. For example, a sensor in end-effector 12016 may be powered from a battery in handle 12012 through a wire in shaft 12014 and may send back signals or data to a microprocessor or microcontroller in handle 12012 through a different wire in shaft 12014. The shaft 12014 may be only a half inch in diameter and may have the ability to rotate, which may lead to challenges when swapping or upgrading modular components such as sensors.

In some systems, a sensor in the end-effector may send data to the handle. The data may require signal processing or other processing by one or more components in the handle in order to be used to operate the endocutter. Adding a new sensor or upgrading an existing sensor may require new wires to enable communication with the one or more components (e.g., a microprocessor) in the handle. Having to add new wires or wire contacts may negatively impact the ability to use new sensors or upgrade existing sensors and may be undesirable. The ability to upgrade the modular components (e.g., sensors) in, for example, the end-effector 12016, with new technology such as more advanced sensors, while allowing components in the handle 12012 (e.g., a microcontroller 12024) to readily accept output from the new sensors without adding new wires or new wire contacts may be desirable.

In one aspect of the present disclosure, one or more sensors in the end-effector (e.g., end-effector 12016) may have local or built-in signal processing capability. These sensors may be referred to as smart sensors. Rather than supplying the handle or one or more components therein with data that may require further processing, smart sensors with local signal processing may supply the handle with already processed data or information that can be used to operate the endocutter while minimizing or eliminating further processing.

For example, the end-effector 12016 may include a sensor 12020 and signal processing component 12022. The signal processing component 12022 may correspond to the sensor 12020 (i.e., may be configured to process data from sensor 12020). In one example, the signal processing component 12022 may be specially designed or configured to process signals or data received from the sensor 12020. Further, the signal processing component 12022 may generate processed information based on the signals or data received from sensor 12020. In this way, the signal processing component 12022 may process data received from the sensor 12020 of a surgical instrument (i.e., the endocutter 12010) locally to the sensor and into information usable by the surgical instrument.

The handle 12012 (or a component therein) may be configured to receive the processed information from the signal processing component 12022. For example, the signal processing component 12022 may transmit the processed information to handle 12012 via shaft 12014 (through, e.g., one or more wires). In this way, the processed information may be transmitted from the signal processing component 12022 to a controller 12024 (e.g., a microcontroller) of the surgical instrument (e.g., the endocutter 12010). Further, the surgical instrument (e.g., the endocutter 12010) may be controlled based on the processed information from the signal processing component 12022. For example, the end-effector 12016 may be stopped or started or a process of the endocutter 12010 may be ended based on the processed information. In one example, the controller 12024 may stop or start the end-effector based on the processed information.

The signal processing component 12022 and the sensor 12020 may be part of a single module 12018. The single module 12018 may be positioned in the end-effector 12016 and may be a modular component easily swapped into or out of the end-effector 12016. The sensor 12020 may be, for example, a magnetic field sensor, a magnetic sensor, an inductive sensor, a capacitive sensor, or another type of sensor used in medical devices or endocutters. The signal processing component 12022 may be the microcontroller 2006 (FIGS. 21A, 21B) or microcontroller 3017 (FIGS. 28A, 28B).

Figure 100:
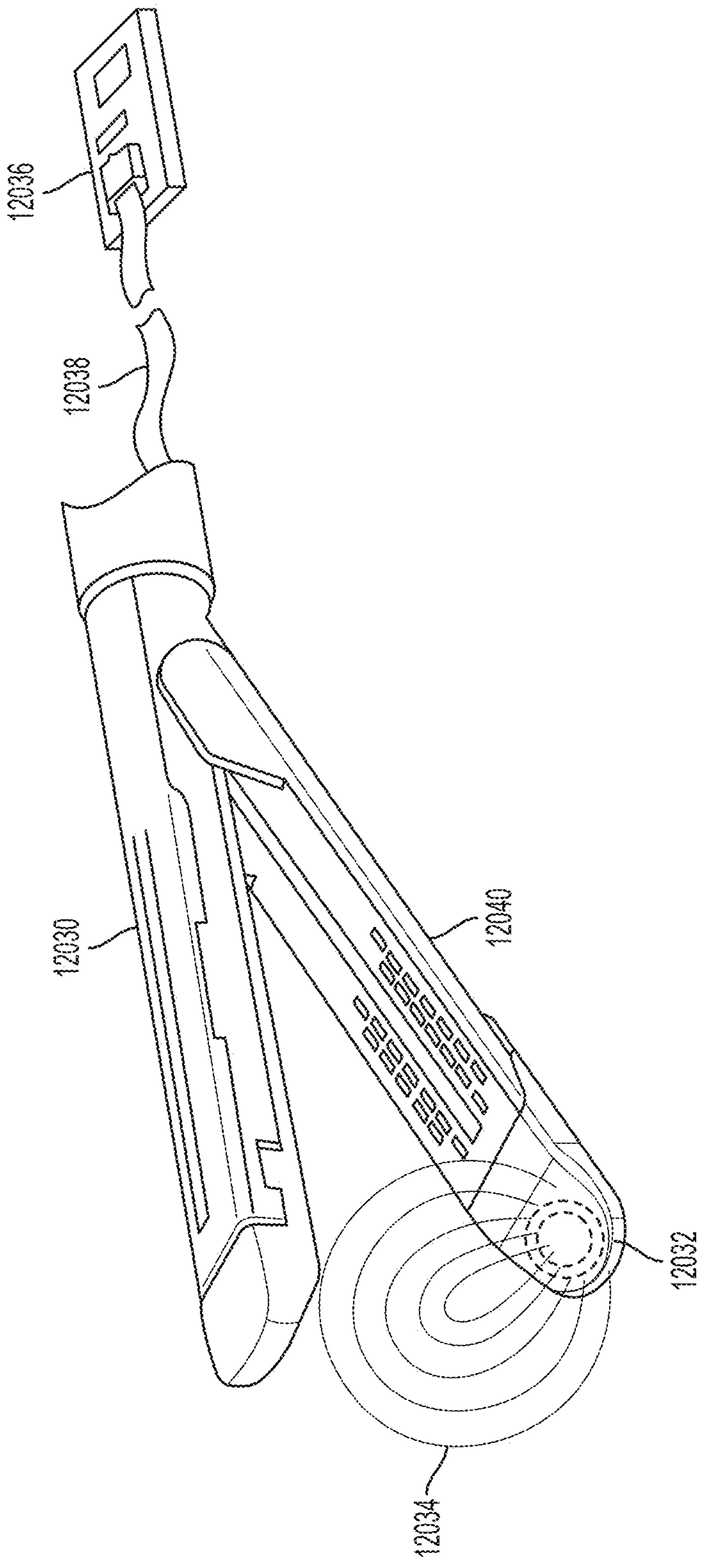
FIG. 100 depicts an example end-effector of a medical device that can include one or more aspects of the present disclosure.

In one aspect, the signal processing component may be a sensor circuit 12036 as shown in FIG. 100. The sensor circuit 12036 may be any suitable circuit configured to read signals from a sensor component such as an inductive coil 12032. The sensor circuit 12036 may be in communication with or be communicatively coupled to a sensor component in the end-effector 12030. For example, the sensor circuit 12036 may be communicatively coupled to an inductive coil 12032 via a wire or cable 12038. The inductive coil 12032 may produce a magnetic field 12034 and may be located at a distal end of an anvil 12040 of the end-effector 12030. The sensor circuit 12036 may receive data or signals from the sensor component (e.g., inductive coil 12032) and may process the data or signals to generate processed information which may be used to operate the end-effector 12030.

Figure 101:
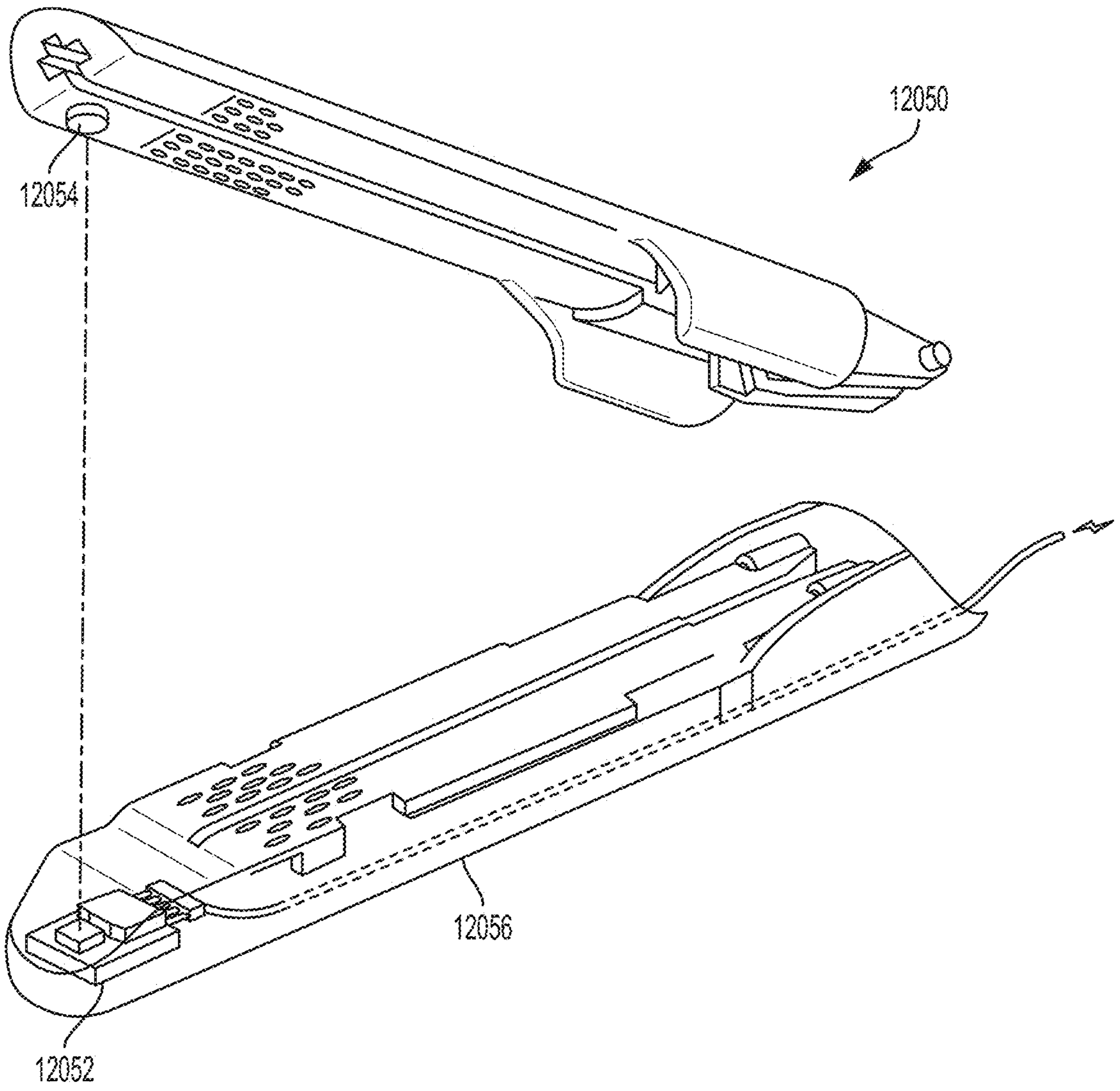
FIG. 101 also depicts an example end-effector of a medical device that can include one or more aspects of the present disclosure.
Figure 102:
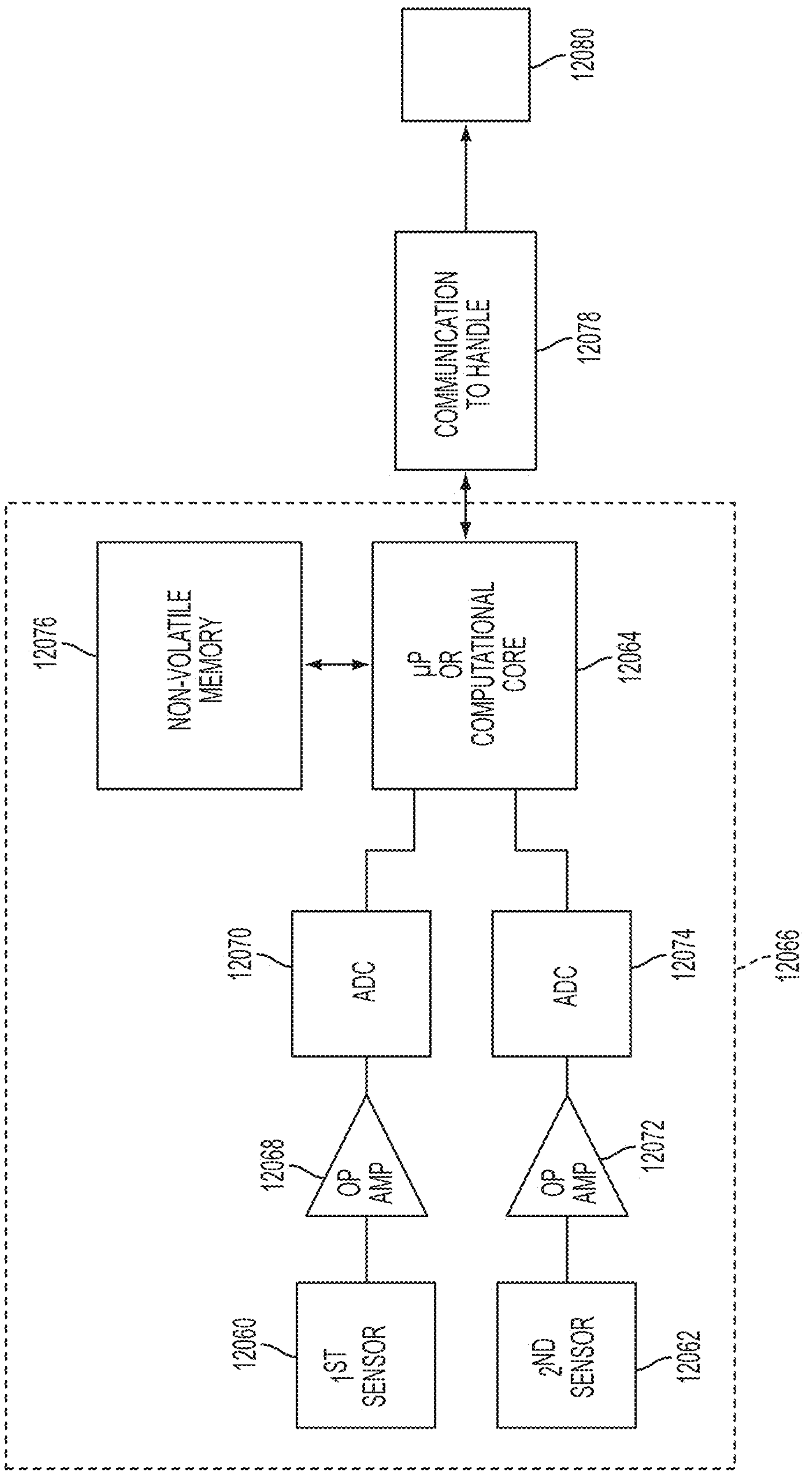
FIG. 102 is a diagram of a smart sensor component in accordance with an aspect the present disclosure.

While the sensor circuit 12036 is shown outside of the end-effector 12030 and the anvil 12040 in FIG. 100 for ease of disclosure, the sensor circuit 12036 may be local to the sensor component (e.g., inductive coil 12032) or may be part of a single module including the sensor component and the sensor circuit, such as single module 12018 of FIG. 99. For example, as shown in FIG. 101, a sensor circuit 12052 also may be positioned at a distal end of an anvil 12056 of an end-effector 12050. The sensor circuit 12052 may be local to, and in communication with, a sensing component such as magnet 12054.

Referring back to FIG. 99, the handle 12012 may include a controller 12024 which may be configured to control or otherwise operate the endocutter 12010. In one example, the controller 12012 may be a microcontroller and may be configured to receive the processed information from the signal processing component 12022 or the single module 12018. For example the shaft 12014 may be configured to communicatively couple the signal processing component 12022 of the end-effector 12016 and the handle 12012. The microcontroller 12024 in the handle 12012 may be in wired communication with the signal processing component 12022 via shaft 12014. In one example, the signal processing component 12022 may be in wireless communication with the microcontroller 12024 or with another component in handle 12012. While the controller 12024 may be configured to receive the processed information from the signal processing component 12022 or the single module 12018, this is not intended to be a limitation of the present disclosure as various other components (e.g., a microprocessor, display, interface, switch, etc.) in handle 12012 may be configured to receive the processed information from the signal processing component 12022 or the single module 12018.

In one aspect, a plurality of smart sensors may be positioned on a power line of an end-effector and may be communicatively coupled to a handle of an endocutter. The smart sensors may be positioned in series or parallel with respect to the power line. Referring now to FIG. 14, smart sensors 12060 and 12062 may be in communication with a signal processing component or a microprocessor 12064 which may be local to the smart sensors. Both the smart sensors 12060 and 12062 and the microprocessor 12064 may be located at the end-effector (represented by dashed-box 12066). For example, smart sensor 12060 may output signals or data to an operational amplifier 12068 and an ADC converter 12070, which may condition the signals or data for input into microprocessor 12064. Similarly, smart sensor 12062 may output signals or data to an operational amplifier 12072 and an ADC converter 12074, which may condition the signals or data for input into microprocessor 12064.

Smart sensors 12060 and/or 12062 may be different types of sensors or the same type of sensor, which may be, for example, magnetic field sensors, magnetic sensors, inductive sensors, capacitive sensors, or other types of sensors used in medical devices or endocutters. Component 12064, previously referred to as a microprocessor, also may be a computational core, FPGA (field programmable gate array), logic unit (e.g., logic processor or logic controller), signal processing unit, or other type of processor. The microprocessor 12064 may be in communication with a memory, such as non-volatile memory 12076, which may store calculation data, equipment information such as a type of cartridge inserted in the end-effector 12066, tabular data, or other reference data that may enable the microprocessor 12064 to process signals or data received from one or more of the smart sensors 12060 or 12062 for use in operating the end-effector 12066 or an endocutter.

Further, a shaft 12078 may include a return path through which at least one of the plurality of smart sensors (e.g., smart sensors 12060 or 12062) and the handle 12080 are communicatively coupled. The shaft may include one or more wires which may transfer information from the microprocessor 12064 to the handle 12080 for operation of the end-effector 12066 or endocutter. In one example, the information from the microprocessor 12064 may be communicated to the handle 12080 (by way of shaft 12078 or directly without use of shaft 12078) over one or more of: a wired-line, a single-wired line, a multi-wired line, a wireless communication protocol such as Bluetooth, an optical line, or an acoustic line.

In one aspect, at least one of a plurality of smart sensors positioned at an end-effector may include a signal processing component. For example, the signal processing component may be built into the smart sensor or may be locally coupled to the smart sensor as shown in single module 12018 of FIG. 99. The signal processing component may be configured to process data received from a sensor component (e.g., sensor component 12020) of at least one of the plurality of smart sensors. A controller 12024 (e.g., a microcontroller) at the handle may be communicatively coupled to at least one of the plurality of smart sensors.

In one aspect, a smart sensor may be configured for local signal processing in a medical device. The smart sensor may include at least one sensor component (e.g., sensor component 12020) and at least one processing component (e.g., processing component 12022). The processing component may be configured to receive data from the at least one sensor component and to process the data into information for use by the medical device. The medical device may be, for example, an endocutter, however this is not intended to be a limitation of the present disclosure. It should be understood that the techniques and features discussed herein for smart sensors with local signal processing may be used in any medical device where processing of sensor signals or data is used for operation of the medical device.

Further, a controller (e.g., controller 12024, microcontroller) in the medical device may be configured to receive the information (i.e., processed signals or data) from the at least one processing component (e.g., processing component 12022). As discussed above, the medical device may be a surgical instrument such as an endocutter and the smart sensor may be configured for local signal processing in the surgical instrument. Local signal processing may refer to, for example, processing signals or data from a sensor component at a processing component coupled to the sensor, where the resulting processed information may be used by a separate component. For example, the controller 12024 may be positioned in the handle 12012 of the surgical instrument (i.e., the endocutter 12010) and the smart sensor may be configured to be positioned in a separate component (i.e., the end-effector 12016) of the surgical instrument (i.e., the endocutter 12010), separate from the handle 12012. Thus, the controller 12024 may be positioned at the handle 12012 of the surgical instrument and the signal processing component 12022 and the sensor 12020 may be located in a component separate from the handle 12012 (e.g., end-effector 12016).

In this way, the handle or controller 12024 need not have information about the smart sensor, knowledge of what the smart sensor is doing, or capability to interpret data feed back from the smart sensor. This is because the processing component 12022 may transform or condition the data from the smart sensor and generate information from the data directly usable by the handle or controller 12024. The information generated by the processing component may be used directly, without the data from the smart sensor needing to be processed in another part of the medical device (e.g., near the handle 12012 or controller 12024). Thus, the surgical instrument may be controlled based on the (processed) information from the signal processing component local to the sensor.

In one aspect, a current draw on a power line communicatively coupled to the signal processing component 12022 (i.e., local to the sensor 12020) may be monitored. The current draw may be monitored by a microprocessor or other monitoring device at the shaft 12014 or the handle 12012, or at another microprocessor or other monitoring device separate from the signal processing component 12022. For example, the monitoring may be a standard Morse Code type monitoring of the current draw on the power line. An issue with the surgical instrument based on the current draw and a particular sensor may be determined by the separate microprocessor at, e.g., the handle 12012. In this way, the monitoring may allow the handle (or a processor or controller therein) to be informed of various issues related to signals or data received by one or more sensor and which particular sensor identified the issue, without a further communication requirement (e.g., pairing, or other coupled communication).

Figure 103:
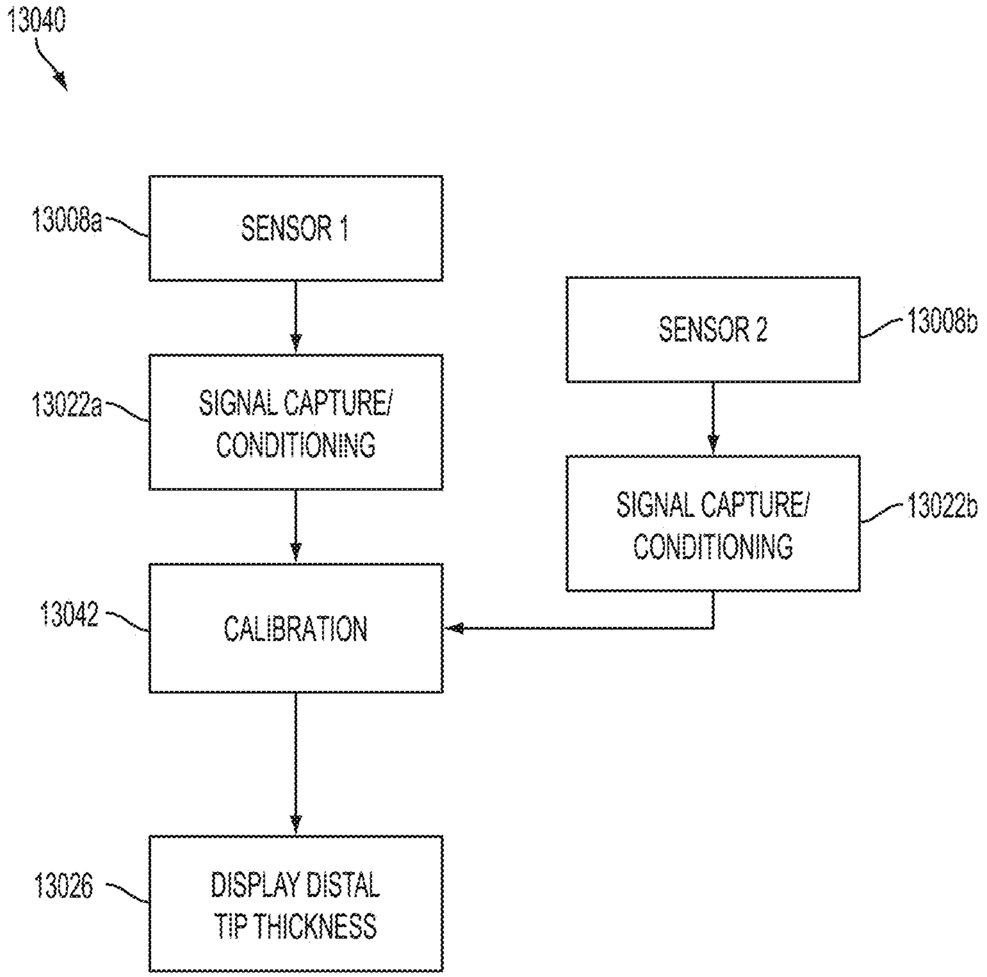
FIG. 103 is a logic diagram illustrating one aspect of a process for calibrating a first sensor in response to an input from a second sensor.

Turning now to FIG. 103, which is a logic diagram illustrating one aspect of a process 13040 for calibrating a first sensor 13008*a* in response to an input from a second sensor 13008*b*. The first sensor 13008*a* is configured to capture 13022*a* a signal indicative of one or more parameters of the end effector 13000. The first signal 13022*a* may be conditioned based on one or more predetermined parameters, such as, for example, a smoothing function, a look-up table, and/or any other suitable conditioning parameters. A second signal is captured 13022*b* by the second sensor 13008*b*. The second signal 13022*b* may be conditioned based on one or more predetermined conditioning parameters. The first signal 13022*a* and the second signal 13022*b* are provided to a processor, such as, for example, the primary processor 2006 (FIGS. 21A-21B). The primary processor 2006 calibrates 13042 the first signal 13022*a* in response to the second signal 13022*b*. The first signal 13022*a* is calibrated 13042 to reflect the fullness of the bite of tissue in the end effector 13000. The calibrated signal is displayed 13026 to an operator by, for example, a display 12026 embedded in the surgical instrument 10 (FIGS. 1-6).

Figure 104:
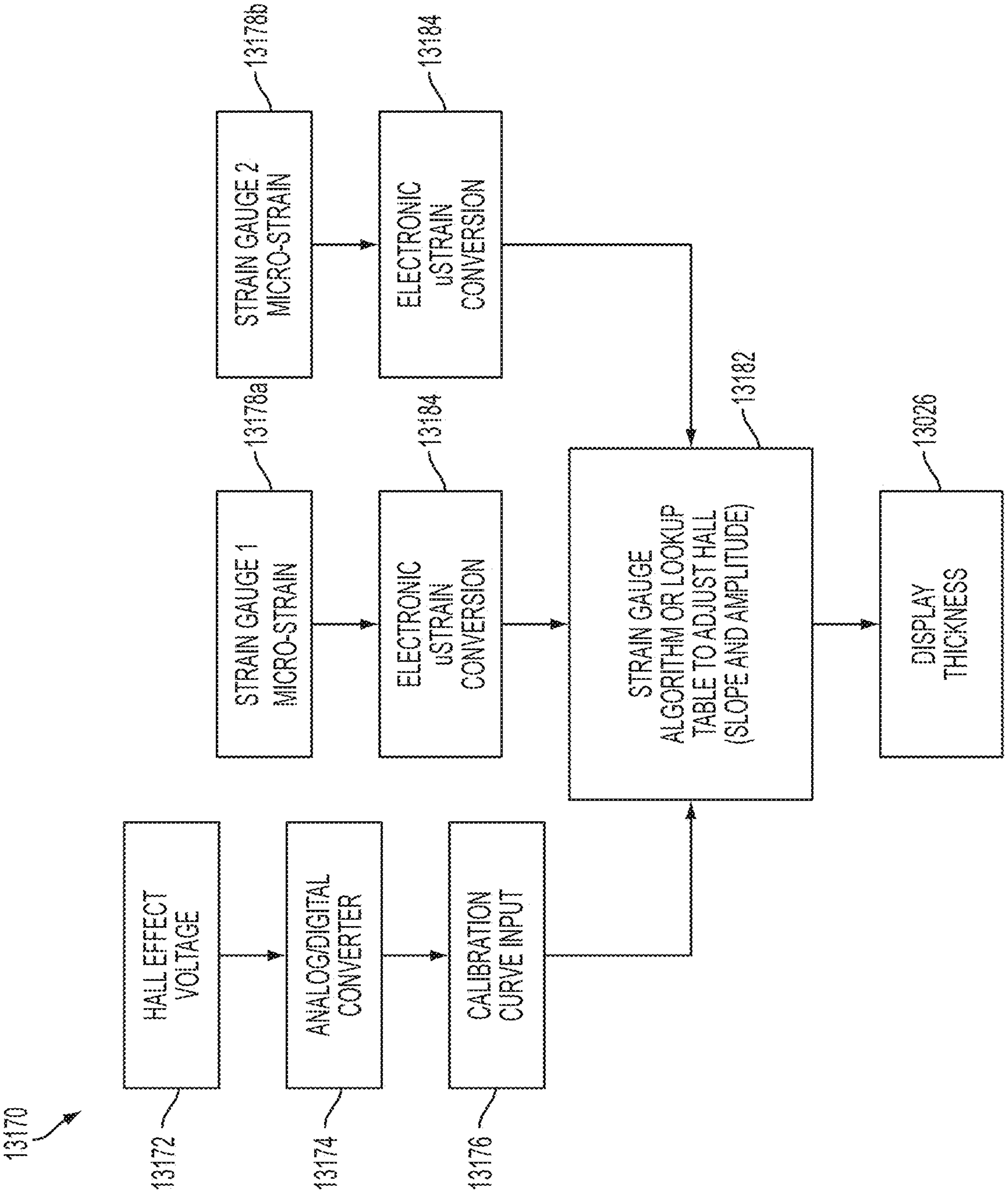
FIG. 104 is a logic diagram illustrating one aspect of a process for adjusting a measurement of a first sensor in response to a plurality of secondary sensors.

FIG. 104 is a logic diagram illustrating one aspect of a process 13170 for adjusting a measurement of a first sensor 13158 in response to a plurality of secondary sensors 13160*a*, 13160. In one example, a Hall effect voltage is obtained 13172, for example, by a magnetic field sensor. The Hall effect voltage is converted 13174 by an analog to digital convertor. The converted Hall effect voltage signal is calibrated 13176. The calibrated curve represents the thickness of a tissue section located between the anvil 13152 and the staple cartridge 13156. A plurality of secondary measurements is obtained 13178*a*, 13178*b* by a plurality of secondary sensors, such as, for example, a plurality of strain gauges. The input of the strain gauges is converted 13180*a*, 13180*b* into one or more digital signals, for example, by a plurality of electronic μStrain conversion circuits. The calibrated Hall effect voltage and the plurality of secondary measurements are provided to a processor, such as, for example, the primary processor 2006 (FIGS. 21A-21B). The primary processor utilizes the secondary measurements to adjust 13182 the Hall effect voltage, for example, by applying an algorithm and/or utilizing one or more look-up tables. The adjusted Hall effect voltage represents the true thickness and fullness of the bite of tissue clamped by the anvil 13152 and the staple cartridge 13156. The adjusted thickness is displayed 13026 to an operator by, for example, a display 12026 embedded in the surgical instrument 10 (FIGS. 1-6).

Figure 105:
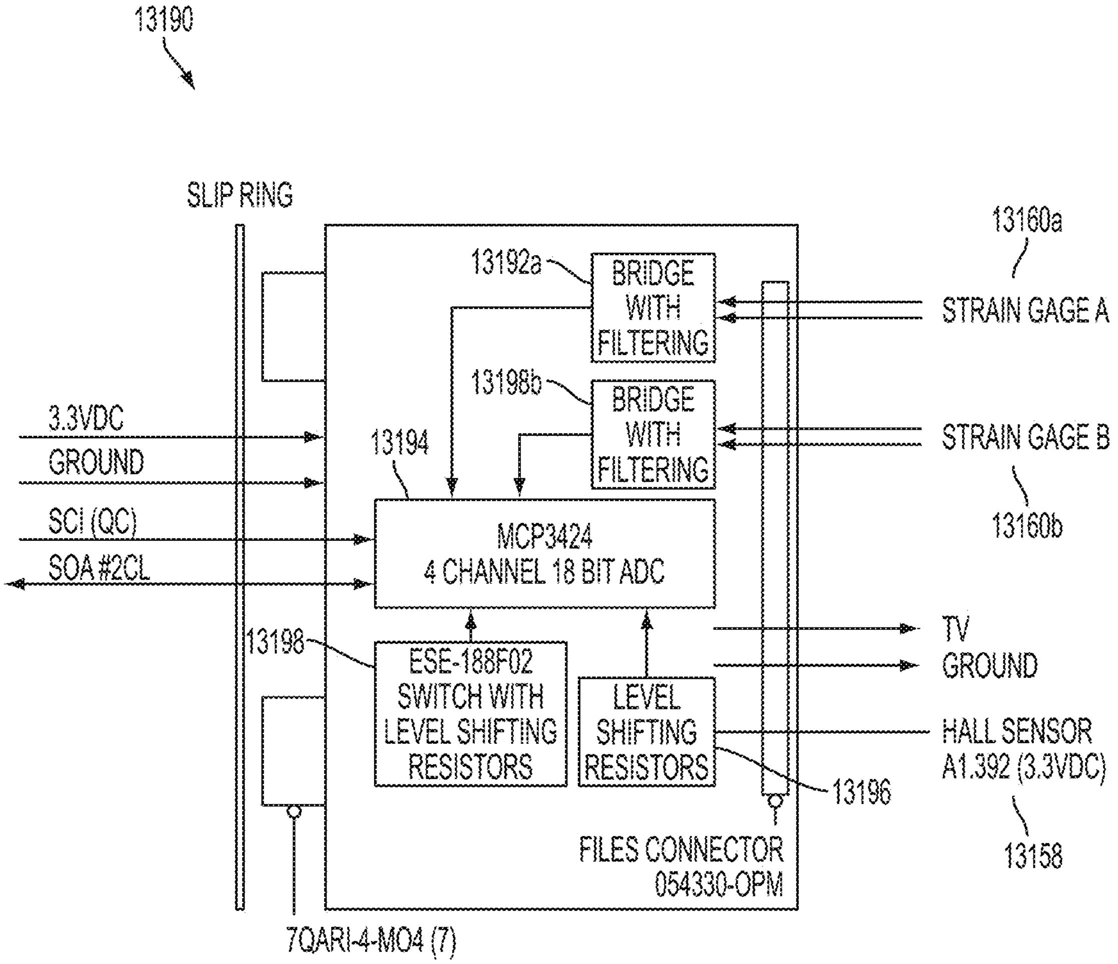
FIG. 105 illustrates one aspect of a circuit configured to convert signals from a first sensor and a plurality of secondary sensors into digital signals receivable by a processor.

FIG. 105 illustrates one aspect of a circuit 13190 configured to convert signals from the first sensor 13158 and the plurality of secondary sensors 13160*a*, 13160*b* into digital signals receivable by a processor, such as, for example, the primary processor 2006 (FIGS. 21A-21B). The circuit 13190 comprises an analog-to-digital convertor 13194. In some examples, the analog-to-digital convertor 13194 comprises a 4-channel, 18-bit analog to digital convertor. Those skilled in the art will recognize that the analog-to-digital convertor 13194 may comprise any suitable number of channels and/or bits to convert one or more inputs from analog to digital signals. The circuit 13190 comprises one or more level shifting resistors 13196 configured to receive an input from the first sensor 13158, such as, for example, a magnetic field sensor. The level shifting resistors 13196 adjust the input from the first sensor, shifting the value to a higher or lower voltage depending on the input. The level shifting resistors 13196 provide the level-shifted input from the first sensor 13158 to the analog-to-digital convertor.

In some aspects, a plurality of secondary sensors 13160*a*, 13160*b* are coupled to a plurality of bridges 13192*a*, 13192*b* within the circuit 13190. The plurality of bridges 13192*a*, 13192*b* may provide filtering of the input from the plurality of secondary sensors 13160*a*, 13160*b*. After filtering the input signals, the plurality of bridges 13192*a*, 13192*b* provide the inputs from the plurality of secondary sensors 13160*a*, 13160*b* to the analog-to-digital convertor 13194. In some examples, a switch 13198 coupled to one or more level shifting resistors may be coupled to the analog-to-digital convertor 13194. The switch 13198 is configured to calibrate one or more of the input signals, such as, for example, an input from a magnetic field sensor. The switch 13198 may be engaged to provide one or more level shifting signals to adjust the input of one or more of the sensors, such as, for example, to calibrate the input of a magnetic field sensor. In some examples, the adjustment is not necessary, and the switch 13198 is left in the open position to decouple the level shifting resistors. The switch 13198 is coupled to the analog-to-digital convertor 13194. The analog-to-digital convertor 13194 provides an output to one or more processors, such as, for example, the primary processor 2006 (FIGS. 21A-21B). The primary processor 2006 calculates one or more parameters of the end effector 13150 based on the input from the analog-to-digital convertor 13194. For example, in one example, the primary processor 2006 calculates a thickness of tissue located between the anvil 13152 and the staple cartridge 13156 based on input from one or more sensors 13158, 13160*a*, 13160*b*.

Figure 106:
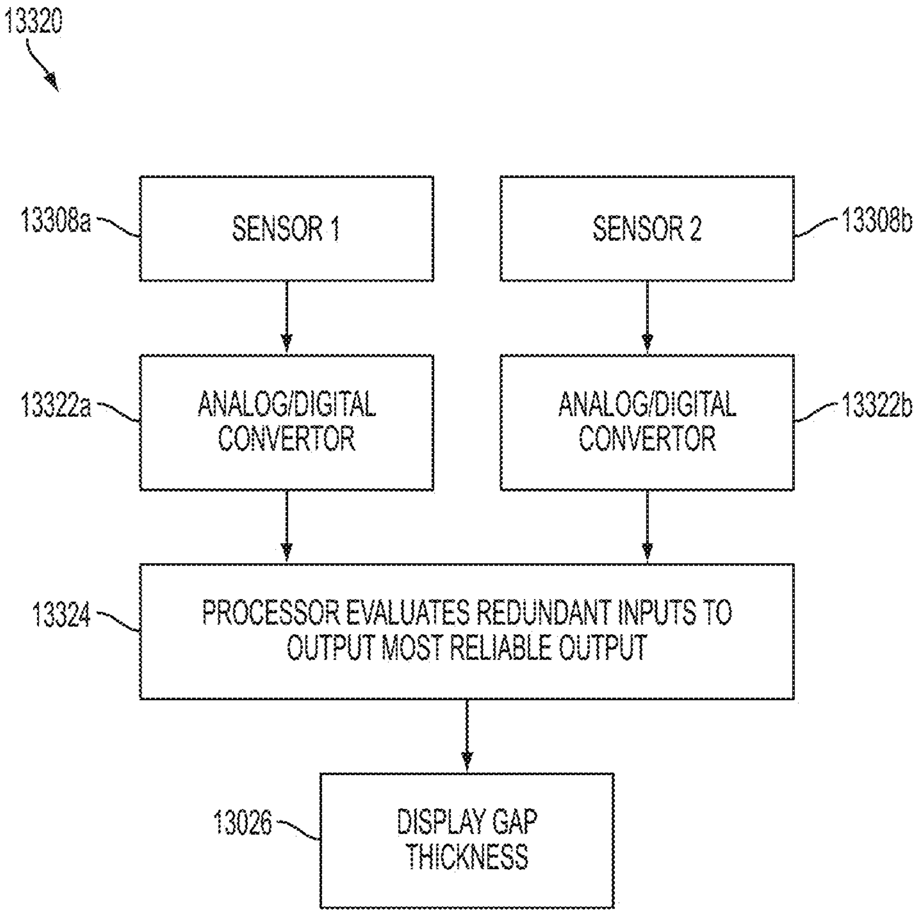
FIG. 106 is a logic diagram illustrating one aspect of a process for selecting the most reliable output from a plurality of redundant sensors.

FIG. 106 is a logic diagram illustrating one aspect of a process 13320 for selecting the most reliable output from a plurality of redundant sensors, such as, for example, the plurality of sensors 13308*a*, 13308*b*. In one example, a first signal is generated by a first sensor 13308*a*. The first signal is converted 13322*a* by an analog-to-digital convertor. One or more additional signals are generated by one or more redundant sensors 13308*b*. The one or more additional signals are converted 13322*b* by an analog-to-digital convertor. The converted signals are provided to a processor, such as, for example, the primary processor 2006 (FIGS. 21A-21B). The primary processor 2006 evaluates 13324 the redundant inputs to determine the most reliable output. The most reliable output may be selected based on one or more parameters, such as, for example, algorithms, look-up tables, input from additional sensors, and/or instrument conditions. After selecting the most reliable output, the processor may adjust the output based on one or more additional sensors to reflect, for example, the true thickness and bite of a tissue section located between the anvil 13302 and the staple cartridge 13306. The adjusted most reliable output is displayed 13026 to an operator by, for example, a display 2026 embedded in the surgical instrument 10 (FIGS. 1-6).

Figure 107:
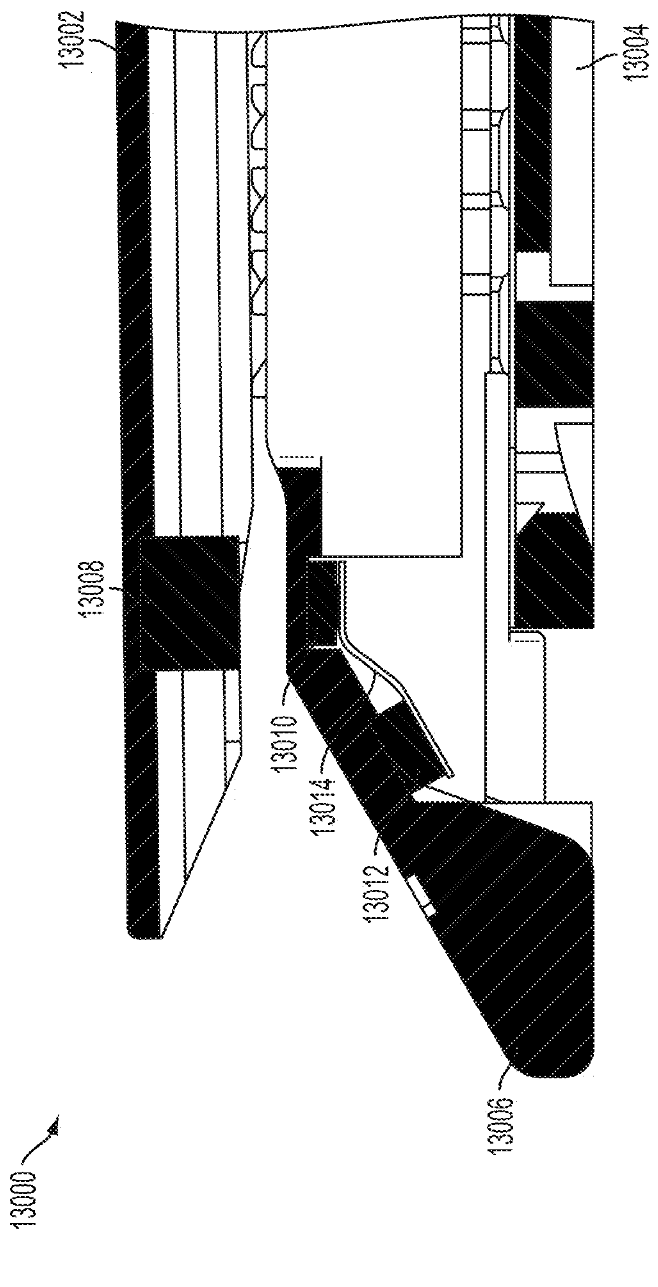
FIG. 107 illustrates a sideways cross-sectional view of one aspect of an end effector comprising a magnet and a magnetic field sensor in communication with processor.

FIG. 107 illustrates one aspect of an end effector 13000 comprising a magnet 13008 and a magnetic field sensor 13010 in communication with a processor 13012. The end effector 13000 is similar to the end effector 300 (FIG. 1) described above in connection with surgical instrument 10 (FIGS. 1-6). The end effector 13000 comprises a first jaw member, or anvil 13002, pivotally coupled to a second jaw member, or elongated channel 13004. The elongated channel 13004 is configured to operably support a staple cartridge 13006 therein. The staple cartridge 13006 is similar to the staple cartridge 304 (FIG. 1) described above in connection with surgical instrument 10 (FIGS. 1-6). The anvil 13008 comprises a magnet 13008. The staple cartridge comprises a magnetic field sensor 13010 and a processor 13012. The magnetic field sensor 13010 is operable to communicate with the processor 13012 through a conductive coupling 13014. The magnetic field sensor 13010 is positioned within the staple cartridge 13006 to operatively couple with the magnet 13008 when the anvil 13002 is in a closed position. The magnetic field sensor 13010 can be configured to detect changes in the magnetic field surrounding the magnetic field sensor 13010 caused by the movement of or location of magnet 13008.

Figure 109:
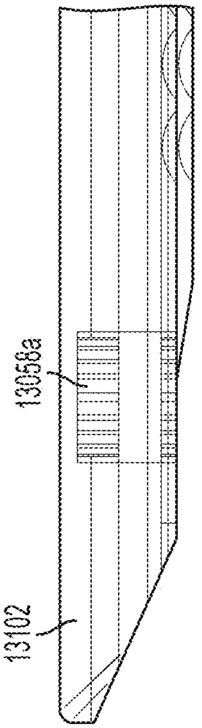
FIGS. 108-110 illustrate one aspect of an end effector that comprises a magnet where
Figure 110:
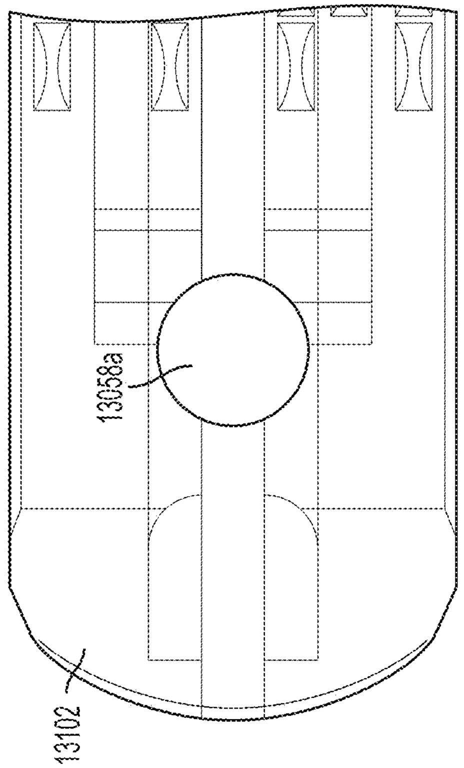
Figure 108:
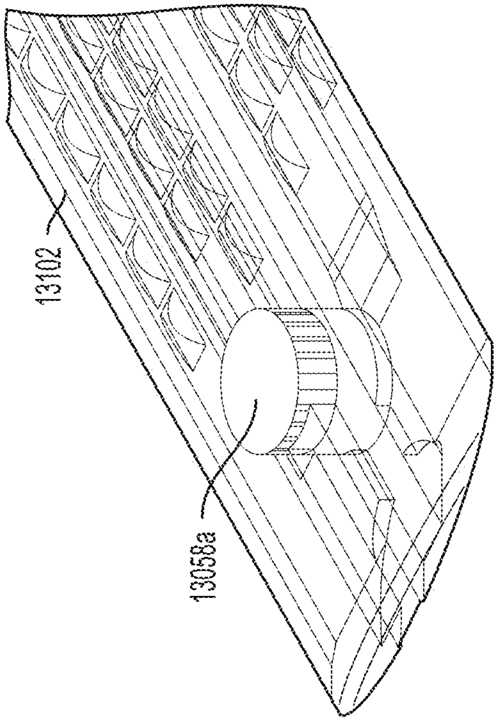

FIGS. 108-110 illustrate one aspect of an end effector that comprises a magnet where FIG. 108 illustrates a perspective cutaway view of the anvil 13102 and the magnet 13058*a*, in an optional location. FIG. 109 illustrates a side cutaway view of the anvil 13102 and the magnet 13058*a*, in an optional location. FIG. 110 illustrates a top cutaway view of the anvil 13102 and the magnet 13058*a*, in an optional location.

Figure 111:
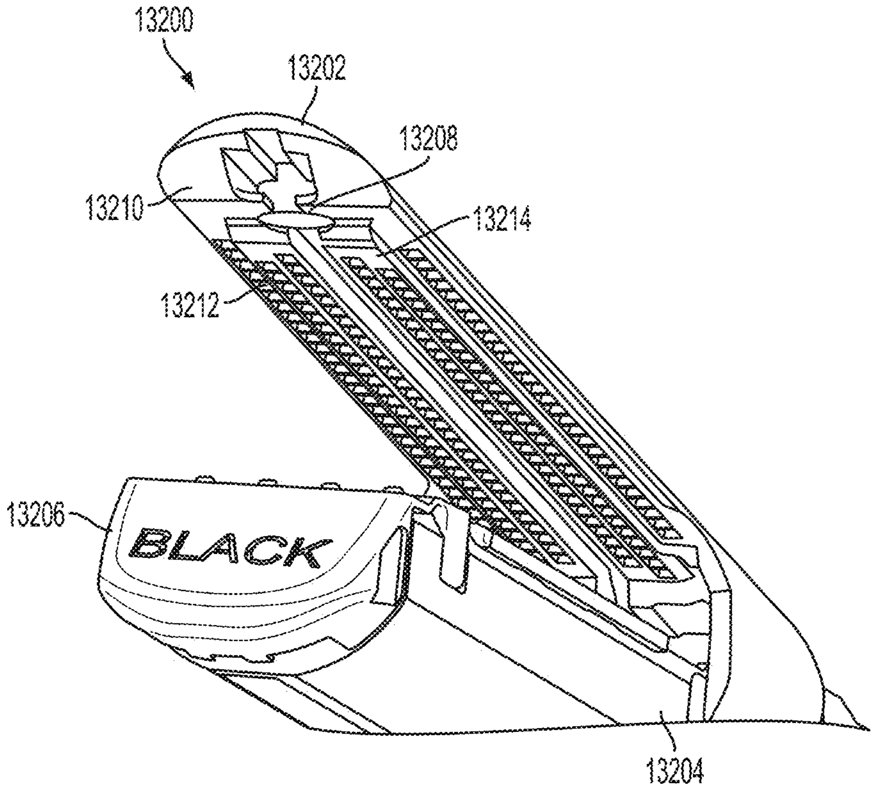
FIG. 111 illustrates one aspect of an end effector that is operable to use conductive surfaces at the distal contact point to create an electrical connection.

FIG. 111 illustrates one aspect of an end effector 13200 that is operable to use conductive surfaces at the distal contact point to create an electrical connection. The end effector 13200 is similar to the end effector 300 (FIG. 1) described above in connection with surgical instrument 10 (FIGS. 1-6). The end effector 13200 comprises an anvil 13202, an elongated channel 13204, and a staple cartridge 13206. The anvil 13202 further comprises a magnet 13208 and an inside surface 13210, which further comprises a number of staple-forming indents 13212. In some examples, the inside surface 13210 of the anvil 13202 further comprises a first conductive surface 13214 surrounding the staple-forming indents 13212. The first conductive surface 13214 can come into contact with second conductive surfaces 13222 on the staple cartridge 13206. The cartridge body comprises a number of staple cavities designed to hold staples (not pictured). In some examples the staple cavities further comprise staple cavity extensions that protrude above the surface of the cartridge body. The staple cavity extensions can be coated with the second conductive surfaces. Because the staple cavity extensions protrude above the surface of the cartridge body, the second conductive surfaces will come into contact with the first conductive surfaces 13214 when the anvil 13202 is in a closed position. In this manner the anvil 13202 can form an electrical contact with the staple cartridge 13206.

Figure 112:
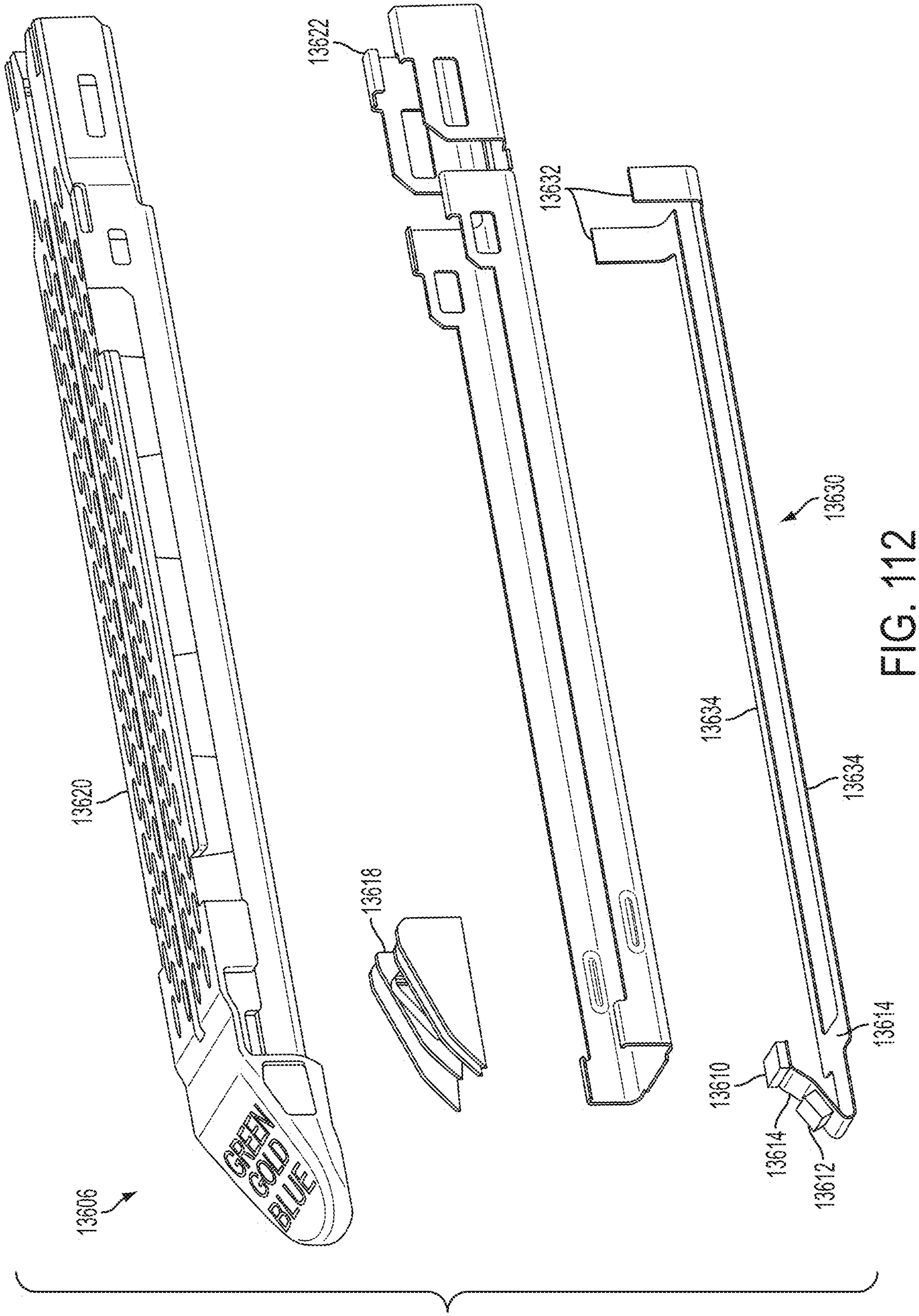
FIG. 112 illustrates one aspect of an exploded view of a staple cartridge that comprises a flex cable connected to a magnetic field sensor and processor.

FIG. 112 illustrates one aspect of a staple cartridge 13606 that comprises a flex cable 13630 connected to a magnetic field sensor 13610 and processor 13612. The staple cartridge 13606 is similar to the staple cartridge 13606 is similar to the staple cartridge 306 (FIG. 1) described above in connection with surgical instrument 10 (FIGS. 1-6). FIG. 112 is an exploded view of the staple cartridge 13606. The staple cartridge comprises 13606 a cartridge body 13620, a wedge sled 13618, a cartridge tray 13622, and a flex cable 13630. The flex cable 13630 further comprises electrical contacts 13632 at the proximal end of the staple cartridge 13606, placed to make an electrical connection when the staple cartridge 13606 is operatively coupled with an end effector, such as end effector 13800 described below. The electrical contacts 13632 are integrated with cable traces 13634, which extend along some of the length of the staple cartridge 13606. The cable traces 13634 connect 13636 near the distal end of the staple cartridge 13606 and this connection 13636 joins with a conductive coupling 13614. A magnetic field sensor 13610 and a processor 13612 are operatively coupled to the conductive coupling 13614 such that the magnetic field sensor 13610 and the processor 13612 are able to communicate.

Figure 113:
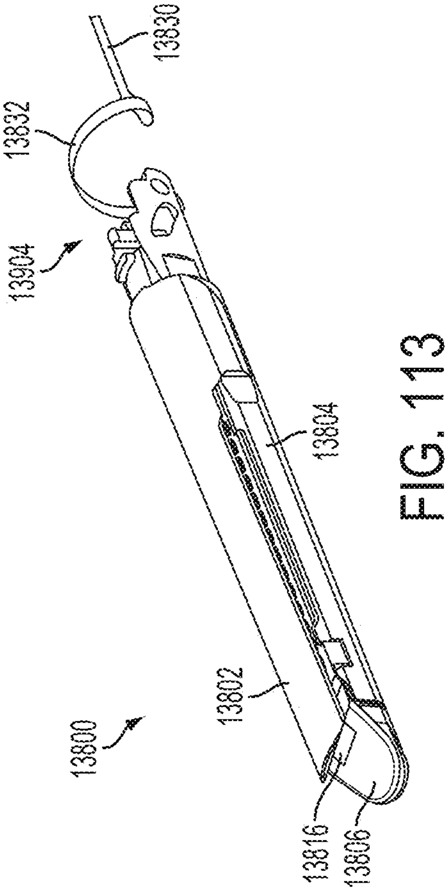
FIG. 113 illustrates the end effector shown in FIG. 112 with a flex cable and without the shaft assembly.

FIG. 113 illustrates one aspect of an end effector 13800 with a flex cable 13830 operable to provide power to a staple cartridge 13806 that comprises a distal sensor plug 13816. The end effector 13800 is similar to the end effector 300 (FIG. 1) described above in connection with surgical instrument 10 (FIGS. 1-6). The end effector 13800 comprises a first jaw member or anvil 13802, a second jaw member or elongated channel 13804, and a staple cartridge 13806 operatively coupled to the elongated channel 13804. The end effector 13800 is operatively coupled to a shaft assembly. The shaft assembly is similar to shaft assembly 200 (FIG. 1) described above in connection with surgical instrument 10 (FIGS. 1-6). The shaft assembly further comprises a closure tube that encloses the exterior of the shaft assembly. In some examples the shaft assembly further comprises an articulation joint 13904, which includes a double pivot closure sleeve assembly. The double pivot closure sleeve assembly includes an end effector closure sleeve assembly that is operable to couple with the end effector 13800.

Figure 114:
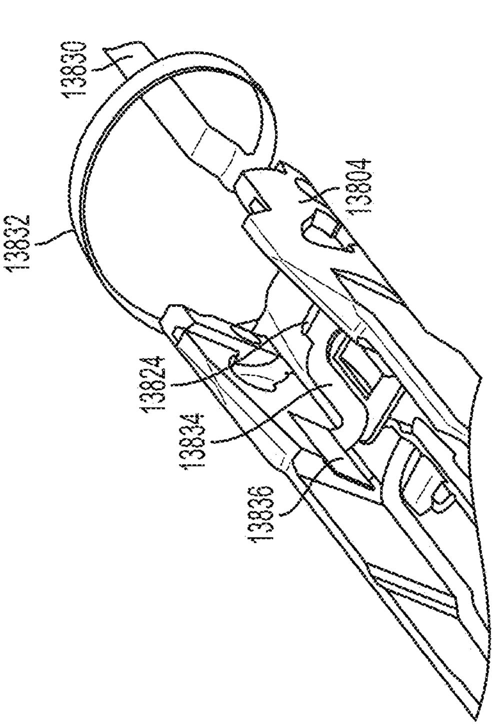
FIGS. 114 and 115 illustrate an elongated channel portion of an end effector without the anvil or the staple cartridge, to illustrate how the flex cable shown in FIG. 113 can be seated within the elongated channel.
Figure 115:
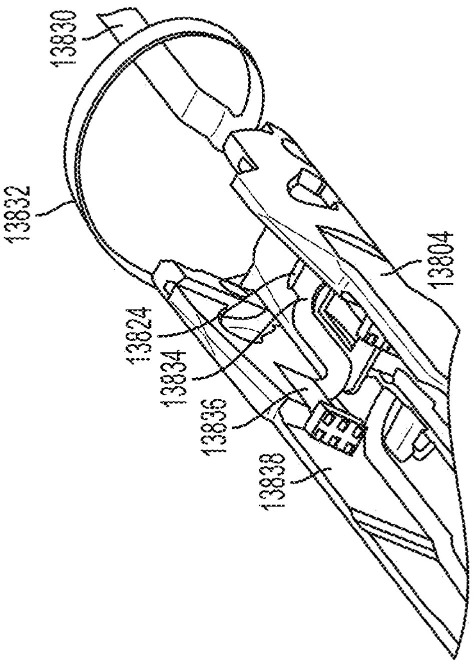

FIGS. 114 and 115 illustrate the elongated channel 13804 portion of the end effector 13800 without the anvil 13802 or the staple cartridge, to illustrate how the flex cable 13830 can be seated within the elongated channel 13804. In some examples, the elongated channel 13804 further comprises a third aperture 13824 for receiving the flex cable 13830. Within the body of the elongated channel 13804 the flex cable splits 13834 to form extensions 13836 on either side of the elongated channel 13804. FIG. 115 further illustrates that connectors 13838 can be operatively coupled to the flex cable extensions 13836.

Figure 116:
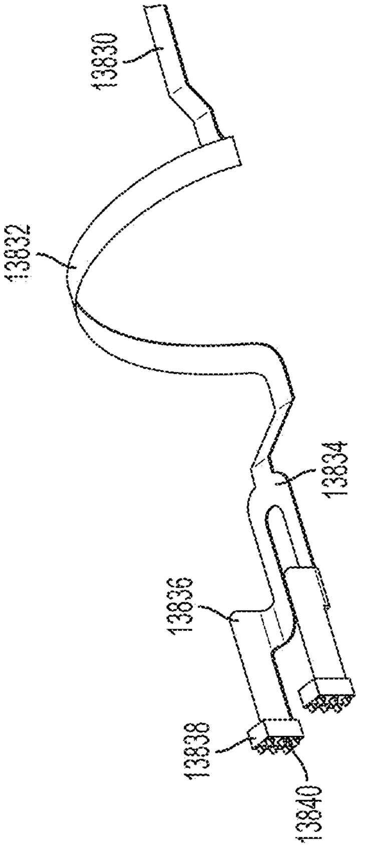
FIG. 116 illustrates a flex cable, shown in FIGS. 113-115, alone.

FIG. 116 illustrates the flex cable 13830 alone. As illustrated, the flex cable 13830 comprises a single coil 13832 operative to wrap around the articulation joint 13904 (FIG. 113), and a split 13834 that attaches to extensions 13836. The extensions can be coupled to connectors 13838 that have on their distal facing surfaces prongs 13840 for coupling to the staple cartridge 13806, as described below.

Figure 117:
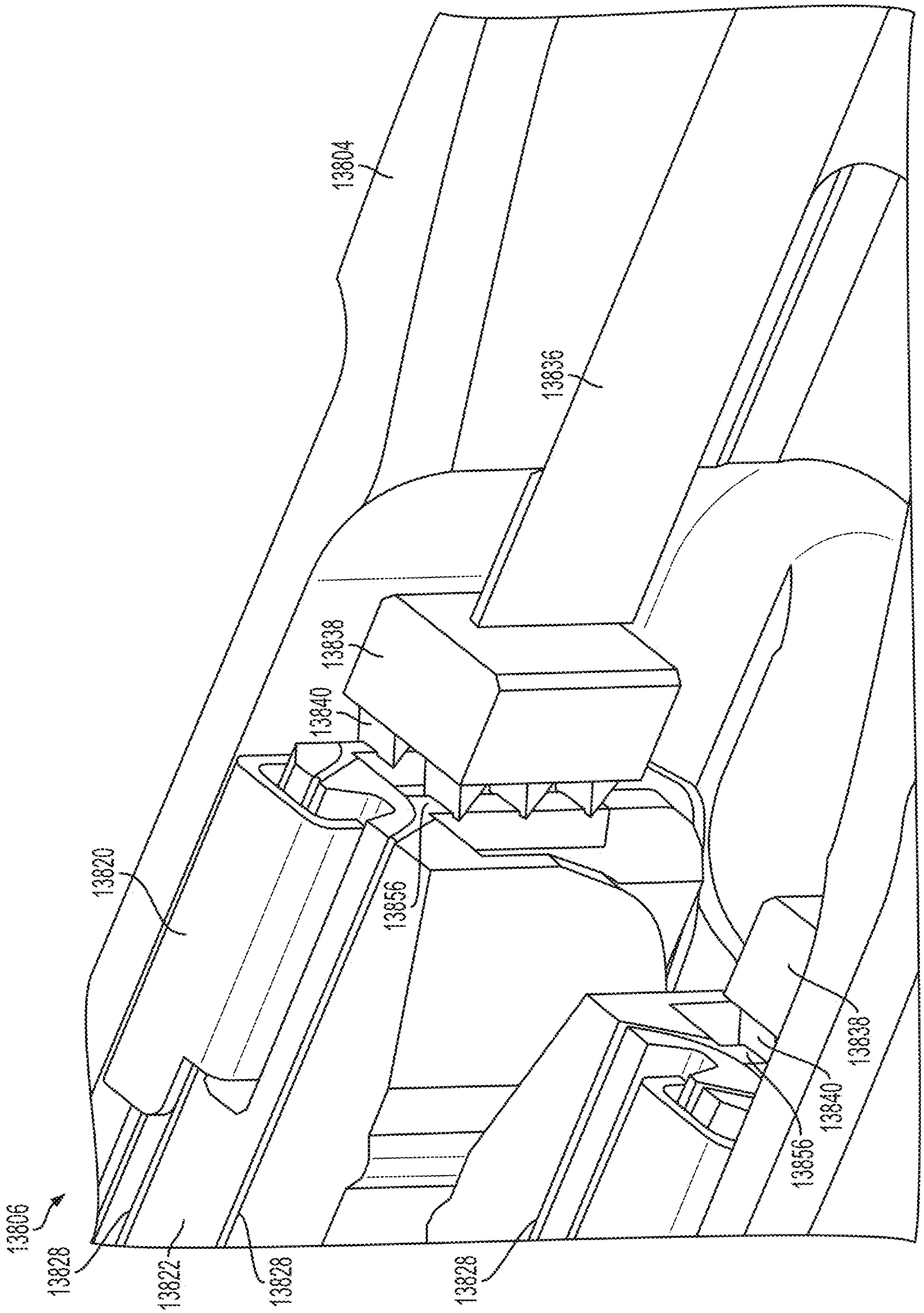
FIG. 117 illustrates a close up view of the elongated channel shown in FIGS. 114 and 115 with a staple cartridge coupled thereto.

FIG. 117 illustrates a close up view of the elongated channel 13804 shown in FIGS. 114 and 115 with a staple cartridge 13804 coupled thereto. The staple cartridge 13804 comprises a cartridge body 13822 and a cartridge tray 13820. In some examples the staple cartridge 13806 further comprises electrical traces 13828 that are coupled to proximal contacts 13856 at the proximal end of the staple cartridge 13806. The proximal contacts 13856 can be positioned to form a conductive connection with the prongs 13840 of the connectors 13838 that are coupled to the flex cable extensions 13836. Thus, when the staple cartridge 13806 is operatively coupled with the elongated channel 13804, the flex cable 13830, through the connectors 13838 and the connector prongs 13840, can provide power to the staple cartridge 13806.

Figure 118:
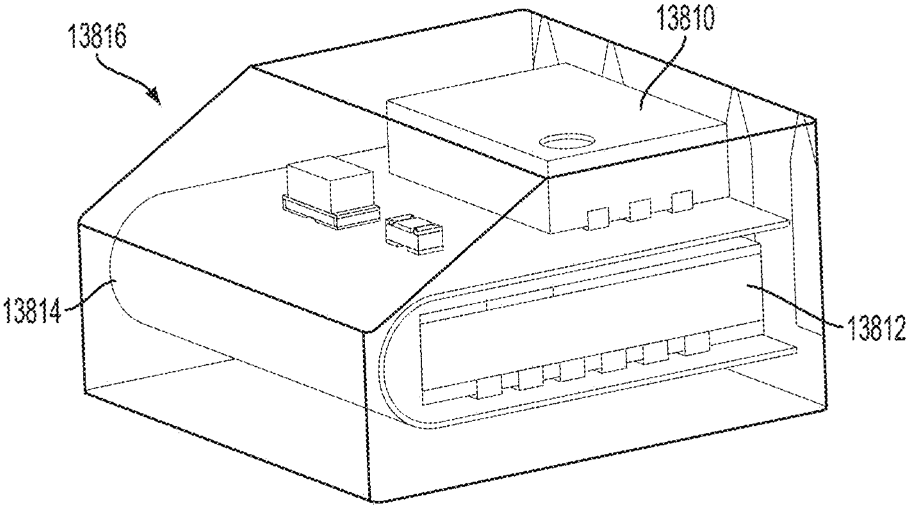
FIGS. 118 and 119 illustrate one aspect of a distal sensor plug where
Figure 119:
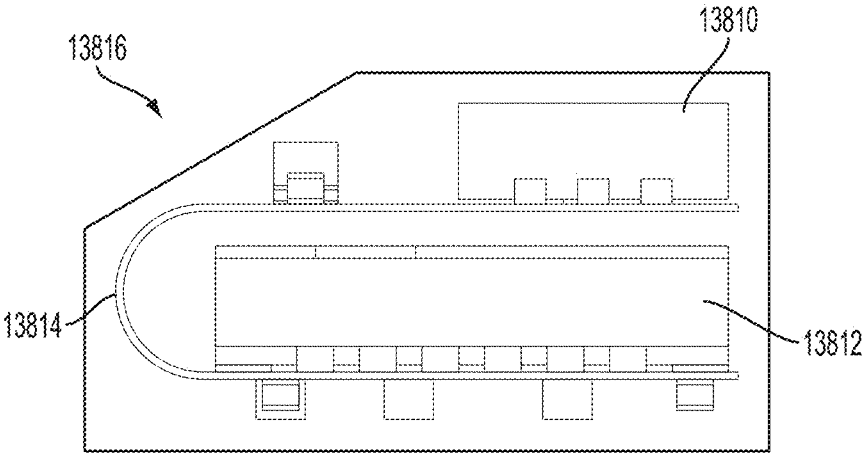

FIGS. 118 and 119 illustrate one aspect of a distal sensor plug 13816. FIG. 118 illustrates a cutaway view of the distal sensor plug 13816. As illustrated, the distal sensor plug 13816 comprises a magnetic field sensor 13810 and a processor 13812. The distal sensor plug 13816 further comprises a flex board 13814. As further illustrated in FIG. 119, the magnetic field sensor 13810 and the processor 13812 are operatively coupled to the flex board 13814 such that they are capable of communicating.

Figure 120:
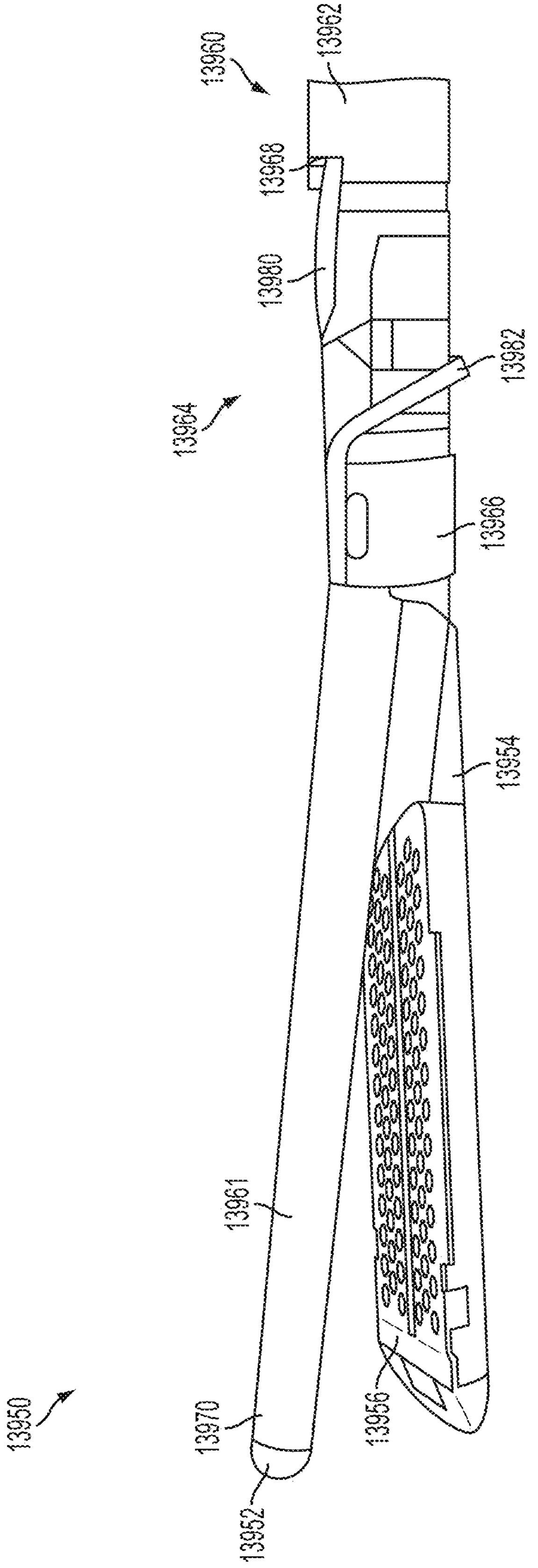

FIG. 120 illustrates one aspect of an end effector 13950 with a flex cable 13980 operable to provide power to sensors and electronics in the distal tip 13952 of the anvil 13961 portion. The end effector 13950 comprises a first jaw member or anvil 13961, a second jaw member or elongated channel 13954, and a staple cartridge 13956 operatively coupled to the elongated channel. The end effector 13950 is operatively coupled to a shaft assembly 13960. The shaft assembly 13960 further comprises a closure tube 13962 that encloses the shaft assembly 13960. In some examples the shaft assembly 13960 further comprises an articulation joint 13964, which includes a double pivot closure sleeve assembly 13966.

In various aspects, the end effector 13950 further comprises a flex cable 13980 that is configured to not interfere with the function of the articulation joint 13964. In some examples, the closure tube 13962 comprises a first aperture 13968 through which the flex cable 13980 can extend. In some examples, flex cable 13980 further comprises a loop or coil 13982 that wraps around the articulation joint 13964 such that the flex cable 13980 does not interfere with the operation of the articulation joint 13964, as further described below. In some examples, the flex cable 13980 extends along the length of the anvil 13961 to a second aperture 13970 in the distal tip of the anvil 13961.

FIGS. 121-123 illustrate the operation of the articulation joint 13964 and flex cable 13980 of the end effector 13950.

FIG. 121 illustrates a top view of the end effector 13952 with the end effector 13950 pivoted −45 degrees with respect to the shaft assembly 13960. As illustrated, the coil 13982 of the flex cable 13980 flexes with the articulation joint 13964 such that the flex cable 13980 does not interfere with the operation of the articulation joint 13964. FIG. 122 illustrates a top view of the end effector 13950. As illustrated, the coil 13982 wraps around the articulation joint 13964 once. FIG. 123 illustrates a top view of the end effector 13950 with the end effector 13950 pivoted +45 degrees with respect to the shaft assembly 13960. As illustrated, the coil 13982 of the flex cable 13980 flexes with the articulation joint 13964 such that the flex cable 13980 does not interfere with the operation of the articulation joint 13964.

FIG. 124 illustrates cross-sectional view of the distal tip of one aspect of an anvil 13961 with sensors and electronics 13972. The anvil 13961 comprises a flex cable 13980, as described with respect to FIGS. 121-123. As illustrated in FIG. 124, the anvil 13961 further comprises a second aperture 13970 through which the flex cable 13980 can pass such that the flex cable 13980 can enter a housing 13974 in the within the anvil 13961. Within the housing 13974 the flex cable 13980 can operably couple to sensors and electronics 13972 located within the housing 13974 and thereby provide power to the sensors and electronics 13972.

FIG. 125 illustrates a cutaway view of the distal tip of the anvil 13961. FIG. 125 illustrates one aspect of the housing 13974 that can contain sensors and electronics 13972 as illustrated by FIG. 124.

A surgical instrument can be powered by a battery. In at least one embodiment, the handle of the surgical instrument comprises a battery cavity and the battery can be inserted into and removed from the battery cavity. In certain embodiments, the surgical instrument can comprise a shaft assembly which includes a battery cavity and a battery removably positioned in the battery cavity. When the battery is seated in the battery cavity, the battery can supply power to the handle. The battery and/or the handle, for example, can comprise a releasable lock which releasably holds the battery in the battery cavity. In various instances, the releasable lock comprises a latch which can be depressed by the user of the surgical instrument to unlock the battery and permit the battery to be removed from the battery cavity. In various instances, the battery can be removed from the handle and replaced with another battery. U.S. Patent Application Publication No. 2012/0071711, entitled SURGICAL INSTRUMENTS AND BATTERIES FOR SURGICAL INSTRUMENTS, which was filed on Sep. 17, 2010, now U.S. Pat. Nos. 9,289,212, and 8,632,525, entitled POWER CONTROL ARRANGEMENTS FOR SURGICAL INSTRUMENTS AND BATTERIES, which was filed on Sep. 17, 2010, are incorporated by reference herein in their respective entireties.

Referring now to FIGS. 126-128, a surgical instrument 14000 comprises a handle 14010 including a housing 14011 and a battery cavity 14012 defined in the housing 14011. The surgical instrument 14000 further comprises an end effector configured to deploy staples from a staple cartridge; however, the surgical instrument 14000 can comprise any suitable end effector. The handle 14010 further comprises a firing member 14050 which is movable proximally and distally to articulate the end effector of the surgical instrument 14000 about an articulation joint. The firing member 14050 is also movable distally to fire staples from the staple cartridge and retractable proximally after the staples have been fired. FIGS. 126-128 depict the firing member 14050 in an unfired position. The firing member 14050 is movable proximally and distally by an electric motor and/or a hand crank, for example, and is translatable within a proximally-extending chamber 14016. The chamber 14016 comprises a proximal end 14013 which encloses the firing member 14050 and extends proximally into the battery cavity 14012. The chamber 14016 is sized and configured to provide a clearance gap 14055 for the firing member 14050 which, in at least one instance, permits the firing member 14050 to be retracted proximally from its unfired position in order to articulate the end effector. In other instances, as discussed in greater detail further below, the chamber 14016 comprises an open proximal end.

The surgical instrument 14000 further comprises a battery 14020 which is positionable in the battery cavity 14012 to supply power to the handle 14010. The battery 14020 comprises a battery housing 14021 having an outer surface 14022. The battery cavity 14012 and the outer surface 14022 of the battery 14020 are configured such that the battery 14020 is closely received in the battery cavity 14012. In at least one instance, the battery cavity 14012 and the outer surface 14022 are configured such that the battery 14020 can be inserted into the battery cavity 14012 in only one orientation, or in a limited number of orientations. The battery 14020 comprises a clearance aperture 14026 defined therein configured to receive the chamber 14016 when the battery 14020 is positioned in the battery cavity 14012. The handle 14010 further comprises one or more electrical contacts 14014 (FIG. 131) which are engaged by corresponding electrical contacts 14024 (FIG. 131) defined on the battery 14020 when the battery 14020 is fully seated in the battery cavity 14012. Moreover, a proximal end 14025 of the battery 14020 is flush, or at least substantially flush, with the handle housing 14011 when the battery 14020 is fully seated in the battery cavity 14012. When the battery 14020 is not fully seated in the battery cavity 14012, the battery contacts 14024 may not be engaged with the handle contacts 14014 and, in such a position, the battery 14020 cannot supply power to the handle 14010.

In various embodiments, the battery 14020 is the only power source available to the handle 14010. In other embodiments, more than one power source is available to the handle 14010. In at least one such embodiment, the battery 14020 is the primary power source for the handle 14010. Regardless of the embodiment utilized, the battery 14020 can provide a large portion of, if not all of, the power needed by the handle 14010. In the event that the battery 14020 were to be disconnected from the handle 14010 and/or removed from the battery cavity 14012 during a surgical procedure, the handle 14010 would become unpowered and/or underpowered. In some instances, removing the battery 14020 from the battery cavity 14012 may be preferred or required to replace a depleted battery 14020 with a fully-charged battery 14020, for instance. In other instances, removing the battery 14020 from the battery cavity 14012 during a critical point of the surgical procedure may not be preferred, such as when the firing member 14050 is being advanced distally to fire the staples from the staple cartridge, for example. In at least one such instance, a sudden loss of power may render a control circuit 14015 and/or display screen 14040 of the handle 14010 inoperable, for example. In light of the above, the handle 14010 includes a battery lock, or means which can prevent the battery 14020 from becoming electrically de-coupled from the handle 14010 and/or removed from the battery cavity 14012 at certain points during the operation of the handle 14010. There are other reasons for locking the battery 14020 in the handle 14010. For instance, the battery 14020 can be locked to the handle 14010 so that the handle 14010 and/or battery 14020 can be disposed of safely.

Referring again to FIGS. 126-128, the handle 14010 comprises one or more deployable locks 14017. Each lock 14017 is movable between an undeployed, or unlocked, position (FIG. 127) and a deployed, or locked, position (FIGS. 126 and 128). Each lock 14017 comprises a cantilever beam extending from a sidewall of the chamber 14016; however, any suitable configuration could be utilized. Each lock 14017 comprises a proximal end mounted to a sidewall of the chamber 14016 and a distal end which is movable relative to the proximal end. The proximal end of each lock 14017 can be pivotably attached to a sidewall of the chamber 14016. The locks 14017, and/or the sidewalls of the chamber 14016, can be comprised of a resilient material and can be configured to deflect when a biasing force is applied thereto. Each lock 14017 comprises a cam surface 14018 defined on the distal end thereof.

The handle 14010 further includes a lock actuator 14030 configured to move the locks 14017 between their undeployed position (FIG. 127) to their deployed position (FIG. 128). The lock actuator 14030 comprises a solenoid; however, the lock actuator 14030 could comprise any suitable actuator, such as an electric motor, for example. The lock actuator 14030 comprises a wire coil 14034 mounted in the handle housing 14011 and, in addition, an armature 14032 movable relative to the wire coil 14034. The armature 14032 comprises an elongate aperture 14031 defined therein which is sized and configured to permit the firing member 14050 to slide therein. In various instances, a clearance gap can be present between the firing member 14050 and the armature 14032.

The armature 14032 is comprised of a ferrous material, for example, and the wire coil 14034 is comprised of a conductive wire, such as copper wire, for example. When electrical current flows through the wire coil 14034 in a first direction, the field generated by the flowing current pushes the armature 14032 from a first, or distal, position (FIG. 127) to a second, or proximal, position (FIG. 128). The armature 14032 comprises a proximal end 14038 configured to engage the cam surfaces 14018 of the locks 14017 when the armature 14032 is moved proximally and deflect the locks 14017 outwardly, as illustrated in FIG. 128. When electrical current flows through the wire coil 14034 in a second, or opposite, direction, the field generated by the flowing current pushes the armature 14032 from its second, or proximal, position (FIG. 128) to its first, or distal, position (FIG. 127). When the armature 14032 is moved distally, the proximal end 14038 of the armature 14032 is disengaged from the cam surfaces 14018 of the locks 14017 and the locks 14017 can then resiliently deflect inwardly back to their undeployed positions. The locks 14017 can comprise any suitable configuration and, in at least one instance, the locks 14017 are integrally-molded with the chamber 14016 and can be attached to the chamber 14016 in a living-hinge arrangement, for example. In other instances, the locks 14017 can comprise separate components which are mounted to the chamber 14016, for example.

Further to the above, each lock 14017 comprises a lock shoulder 14019 which is displaced outwardly when the locks 14017 are displaced outwardly, as described above. When the locks 14017 are moved into their deployed positions, as illustrated in FIG. 128, the lock shoulders 14019 of the locks 14017 are moved behind lock shoulders 14029 defined in the battery housing 14021. When the lock shoulders 14019 are positioned behind the lock shoulders 14029 of the battery 14020 by the lock actuator 14030, the battery 14020 cannot be disengaged from the handle 14010. As a result, the battery contacts 14024 remain engaged with the handle contacts 14014 and the power supplied to the handle 14010 by the battery 14020 may not be interrupted. In the event that the user of the surgical instrument 14000 pulls on the battery 14020 when the battery lock 14030 has been actuated, the lock shoulders 14029 of the battery 14020 can abut the lock shoulders 14019 of the lock arms 14017. Moreover, the armature 14032 can buttress and support the lock arms 14017 in their deployed positions such that battery contacts 14024 do not break contact with the handle contacts 14014. It is envisioned that some relative movement between the battery 14020 and the handle 14010 may occur even though the battery lock 14030 has been actuated; however, such movement is insufficient to electrically decouple the battery 14020 from the handle 14010.

The armature 14032 comprises a stop 14033 defined on the distal end thereof which is configured to limit the proximal travel of the armature 14032. In at least one embodiment, the stop 14033 is configured to contact the wire coil 14034, as illustrated in FIG. 128. In various instances, the wire coil 14034 can remain energized to hold the armature 14032 in its proximal, or locked, position (FIG. 128). In certain instances, the armature 14032 can be held in place by friction forces between the armature 14032 and the walls of the chamber 14026, for example, even though the wire coil 14034 is not being energized. Similar to the above, the handle 14010 can include a distal stop configured to limit the distal movement of the armature 14032. As mentioned above, the wire coil 14034 of the lock actuator 14030 can be energized to actively move the armature 14032 proximally and distally; however, the lock actuator 14030 can include a biasing member, such as a spring, for example, which can be configured to bias the armature 14032 in either the proximal direction or the distal direction. For instance, in at least one embodiment, the wire coil 14034 is energized to move the armature 14032 proximally and a return spring is configured to move the armature 14032 distally after the wire coil 14034 is no longer energized. Alternatively, in at least one embodiment, the wire coil 14034 is energized to move the armature 14032 distally and a return spring is configured to move the armature 14032 proximally after the wire coil 14034 is no longer energized.

As discussed above, the lock actuator 14030 can be selectively actuated to deploy the locks 14017 and de-actuated to retract the locks 14017. The lock actuator 14030 is in signal communication with the control circuit 14015 which can control the actuation of the lock actuator 14030. The control circuit 14015 can include a microprocessor which can determine when to activate and de-activate the lock actuator 14030. The microprocessor can be configured to evaluate one or more operating parameters of the surgical instrument 14000 to determine whether to activate or de-activate the lock actuator 14030. For instance, the microprocessor can be configured to evaluate the voltage and/or current of the battery 14020 to determine whether the battery 14020 is sufficiently charged to operate the handle 14010 and, if the battery 14020 has a sufficient charge, activate the lock actuator 14030 to deploy the locks 14017, or, if the battery 14020 does not have a sufficient charge, de-activate the lock actuator 14030 to permit the battery 14020 to be removed from the handle 14010.

Alternatively, the control circuit 14015 can utilize the lock actuator 14030 to prevent the battery 14020 from being removed from the handle 14010 in the event that the control circuit 14015 determines that the handle 14010 has exceeded its useful life. The control circuit 14015 can determine that the handle 14010 has exceeded its useful life if the firing system of the handle 14010 has been operated a certain number of times and/or if the handle 14010 has been sterilized a certain number of times, for example. In certain instances, the lock actuator 14030 can prevent the battery 14020 from being moved relative to the handle 14010. In at least one such instance, the control circuit 14015 of the handle 14010 can utilize the display screen 14040 to indicate to the user that the battery 14020 has been locked in position and that the handle 14010 should be either disposed of or serviced. In certain instances, the battery 14020 can include indicia thereon and the lock actuator 14030 can be configured to permit the battery 14020 to be translated a limited distance to expose the indicia when a clinician pulls on the battery 14020. The indicia can be on the side of the battery housing 14021 and can visible above the handle housing 14011 after the battery 14020 has been displaced. The indicia can have a contrasting color to other portions of the battery housing 14021, for example, and/or written instructions to the user of the surgical instrument 14000 such as the word "dispose" and/or "service", for example. In certain instances, the battery housing 14021 can include detention features which can engage the handle housing 14011 and hold the battery 14020 in its displaced position.

In certain embodiments, further to the above, a battery housing can comprise a two-part housing—a first portion which includes the battery cells 14023 and the electrical contacts 14024 and a second portion which is separable from the first portion, for example. In ordinary use, the first portion and the second portion of the battery housing are connected together and are unmovable relative to one another. The first portion can include a gripping portion, such as the proximal end 14025, for example, which allows the user of the surgical instrument 14000 to grab the battery housing and remove both portions of the battery housing simultaneously. If the control circuit 14015 has determined that the handle 14010 has reached its end of life, the control circuit 14015 can actuate a lock actuator which engages and holds the second portion of the battery housing. When the user of the surgical instrument 14000 attempts to remove the battery 14020 from the battery cavity 14012 of the handle 14010 after the lock actuator has been actuated, the first portion of the battery housing can separate from the second portion thereby leaving the second portion behind in the battery cavity 14012. As a result of the second portion being locked within and unremovable from the battery cavity 14012, a new battery 14020 is not positionable in the battery cavity 14012. In various instances, the first portion and/or the second portion of such a battery housing can include indicia thereon explaining to the user of the surgical instrument 14000 that the handle 14010 is no longer usable. Such indicia may only be visible after the first housing portion has separated from the second housing portion. In certain instances, the first housing portion and the second housing portion can be connected by a ribbon which is exposed, or unfurled, when the first housing portion detaches from the second housing portion. The ribbon can include instructions thereon for handling, disposing, and/or refurbishing the handle 14010. When the handle 14010 is refurbished, the lock actuator can be reset and the second housing portion can be removed from the battery cavity 14012.

Further to the above, the handle and/or the battery can comprise an exposable portion which can be exposed by the control system when the control system determines that the handle and/or the battery is no longer suitable for use. The exposable portion can be displaced and/or otherwise exposed by an actuator operated by the control system. The exposable portion can include indicia, such as words and/or a contrasting color, for example, which only become visible when the control system has deactivated the handle and/or the battery in at least one way.

In various embodiments, the handle 14010 can include an override button in communication with the microprocessor which, when actuated, can instruct the microprocessor to deactivate the lock actuator and permit the battery to be removed. Other embodiments may not include such an override button.

In various instances, a surgical instrument may become unsuitable for use in a surgical procedure. A handle of a surgical instrument can become unsuitable for use when the handle has exceeded its intended number of uses, for example. A handle of a surgical instrument may also become unsuitable for use when it experiences excessive force loading and/or electrical faults, for example. Moreover, a handle of a surgical instrument may become unsuitable for use when another component of the surgical instrument is incorrectly attached to the handle and/or an incorrect component is attached to the handle. When the control system of the handle determines that the handle may be unsuitable for use, the control system may employ a battery lockout which can prevent a battery from being operably coupled to the handle, as described in greater detail further below.

A handle 14110 is depicted in FIGS. 129 and 130. The handle 14110 is similar to the handle 14010 in many respects. The handle 14110 comprises a handle housing 14111 which includes a battery cavity 14012 configured to receive a battery 14020, as described above. The handle housing 14111 further comprises a chamber 14116 configured to receive the firing member 14050 which, similar to the chamber 14016, extends into the battery cavity 14012. The handle 14110 further comprises one or more deployable lockout arms 14117. Each lockout 14117 is movable between an undeployed position (FIG. 129) and a deployed position (FIG. 130). Each lockout 14117 comprises a cantilever beam extending from a sidewall of the chamber 14116; however, any suitable configuration could be utilized. Each lockout 14117 comprises a distal end mounted to a sidewall of the chamber 14116 and a proximal end which is movable relative to the distal end. The distal end of each lockout 14117 can be pivotably attached to a sidewall of the chamber 14116. The lockouts 14117, and/or the sidewalls of the chamber 14116, can be comprised of a resilient material and can be configured to deflect when a biasing force is applied thereto. Each lockout 14117 comprises a cam surface 14118 defined on the proximal end thereof.

The handle 14110 further includes a lock actuator 14030 configured to move the lockouts 14117 from their undeployed position (FIG. 129) to their deployed position (FIG. 130). The lock actuator 14030 comprises a solenoid; however, the lock actuator 14030 could comprise any suitable actuator, such as a motor, for example. The lock actuator 14030 comprises a wire coil 14034 mounted in the handle housing 14111 and, in addition, an armature 14032 movable relative to the wire coil 14034. The armature 14032 comprises an elongate aperture 14031 defined therein which is sized and configured to permit the firing member 14050 to slide therein. In various instances, a clearance gap can be present between the firing member 14050 and the armature 14032.

The armature 14032 is comprised of a ferrous material, for example, and the wire coil 14034 is comprised of a conductive wire, such as copper wire, for example. When electrical current flows through the wire coil 14034 in a first direction, the field generated by the flowing current pushes the armature 14032 from a first, or distal, position (FIG. 129) to a second, or proximal, position (FIG. 130). The armature 14032 comprises a proximal end 14038 configured to engage the cam surfaces 14118 of the lockouts 14117 when the armature 14032 is moved proximally and deflect the lockouts 14117 outwardly, as illustrated in FIG. 130. When electrical current flows through the wire coil 14034 in a second, or opposite, direction, the field generated by the flowing current pushes the armature 14032 from its second, or proximal, position (FIG. 130) to its first, or distal, position (FIG. 129). When the armature 14032 is moved distally, the proximal end 14038 of the armature 14032 is disengaged from the cam surfaces 14118 of the lockouts 14117 and the lockouts 14117 can then resiliently deflect inwardly back to their undeployed positions.

Further to the above, each lockout 14117 comprises a lock shoulder 14119 which is displaced outwardly when the lockouts 14117 are displaced outwardly, as described above. When the lockouts 14117 are moved into their deployed positions, as illustrated in FIG. 130, the lock shoulders 14119 of the lockouts 14117 are moved in front of lock shoulders 14028 defined in the battery housing 14021. When the lock shoulders 14119 are positioned in front of the lock shoulders 14028 of the battery 14020 by the lock actuator 14030, the battery 14020 cannot be fully seated in the handle 14110. As a result, the battery contacts 14024 cannot engage the handle contacts 14014 and the battery 14020 cannot supply power to the handle 14110. In the event that the user of the handle 14100 pushes on the battery 14020 when the battery lockout 14130 has been actuated, the armature 14032 can buttress and support the lockouts 14117 in their deployed positions.

A handle 14210 is depicted in FIG. 131. The handle 14210 is similar to the handle 14010 and/or the handle 14110 in many respects. The handle 14210 comprises a handle housing 14211 including a battery cavity 14012 configured to receive a battery 14020. The handle housing 14211 further comprises a chamber 14216 configured to receive the firing member 14050 which, similar to the chamber 14016 and the chamber 14116, extends into the battery cavity 14012. The chamber 14216 of the handle 14210, however, comprises an open proximal end 14213. As illustrated in FIG. 131, the open proximal end 14213 is sized and configured to permit the firing member 14050 to extend therethrough. When the control system of the handle 14210 has determined that the handle 14210 is not suitable for use, further to the above, the control system can operate the electric motor which advances and retracts the firing member 14050 to position the firing member 14050 in a lockout position, i.e., a position in which the firing member 14050 prevents the electrical contacts 14024 of the battery 14020 from engaging the electrical contacts 14014 of the handle 14210. As illustrated in FIG. 131, the firing member 14050 can be retracted to a position in which the proximal end 14025 of the battery 14020, for example, contacts the firing member 14050 before the battery 14020 is sufficiently seated enough in the battery cavity 14012 to supply power to the handle 14210.

In at least one alternative embodiment, a handle of a surgical instrument system can include a battery cavity and at least one first electrical contact and at least one second electrical contact positioned in the battery cavity which are in communication with the control system of the handle. When the battery is fully seated in the battery cavity, the battery is electrically coupled with the first electrical contact and can fully power the handle. Similar to the above, the handle can include a battery lockout system which can be activated to prevent the battery from being fully seated in the battery cavity. Moreover, the battery lockout system can prevent the battery from being electrically coupled with the first electrical contact when the battery lockout system is activated. In contrast to the battery lockout systems described above, however, the battery lockout system of the current embodiment can permit the battery to be electrically coupled with the second electrical contact even though the battery lockout has been activated. In such instances, the control system of the handle can utilize the power supplied to the second electrical contact by the battery to operate the handle in a limited function mode.

In a limited function mode, further to the above, the control system may only be able to perform diagnostic functions to assess the condition of the handle and/or communicate the condition of the handle to the user. In at least one limited function mode, the control system may not be able to operate the electric motor to advance the firing member 14050 distally but it may be able to operate the electric motor to retract the firing member 14050 proximally, for example. The control system may also operate the display and/or permit the control buttons which interface with the display to be operated when the handle is being operated in a limited function mode, for example.

In at least one embodiment, further to the above, the first handle contact can be positioned deeper in the battery cavity than the second handle contact. In at least one such instance, the battery can include a battery contact which can engage the first handle contact or the second handle contact, depending on the depth in which the battery is inserted into the battery cavity. In at least one instance, the battery can comprise a first battery contact configured to engage the first handle contact when the battery is inserted to a first depth and a second battery contact configured to engage the second handle contact when the battery is inserted to a second depth which is different than the first depth.

In certain embodiments, further to the above, the firing member 14050 can be pushed proximally into the battery cavity 14012 to displace the battery 14020 proximally and electrically decouple the battery 14020 from the handle 14210. In such instances, the firing member 14050 can displace the battery 14020 proximally such that the battery contacts 14024 are no longer engaged with the handle contacts 14014. The control system of the handle can decouple the battery 14020 from the handle when the control system has determined that the handle is no longer suitable for use. In certain other embodiments, further to the above, the firing member 14050 can push a battery from a first position in which the battery is electrically coupled to a first electrical contact to a second position in which the battery is electrically decoupled from the first electrical contact and electrically coupled to a second electrical contact. Similar to the above, the control system of the handle may only use the power supplied to the second electrical contact to perform a limited number of functions. In such instances, the control system can switch itself between a fully-functional operating mode and a limited-function operating mode. In various instances, the handle housing can include a catch feature which can prevent the battery from being electrically decoupled from the second electrical contact and/or pushed entirely out of the battery cavity in the handle housing.

As discussed herein, the firing member 14050 can enter into a battery cavity to prevent a battery from being fully installed into a handle and/or contact a battery to at least partially displace the battery out of the battery cavity. In various other instances, the firing member 14050 itself may not block a battery cavity and/or push a battery proximally; rather, the proximal movement of the firing member 14050 out of its ordinary range of motion can trip a spring-loaded mechanism which can block a battery cavity and/or push a battery proximally, for example. In at least one instance, the spring-loaded mechanism can include at least one pre-stretched and/or at least one pre-compressed spring member that is released when tripped by the firing member 14050, for example. Such a spring-loaded mechanism can also deploy an indicator, for example, when it is tripped which can indicate to the user that the handle has entered into a different operating mode. In certain embodiments, the control system of a handle may actuate a spring-loaded mechanism directly without using the firing member 14050 to trip the spring-loaded mechanism. While a spring could be utilized to store energy and deliver that energy to a cocked actuator to perform the functions discussed herein, any suitable device capable of storing and releasing energy could be utilized. In various instances, the device can be pre-energized or pre-loaded when the handle is supplied to the user.

In addition to or in lieu of the above, the control system of a handle can move the firing member 14050, either proximally or distally, to an inoperative position to render the handle unusable if the control system detects a defect in the handle and/or otherwise determines that the handle should not be used. In at least one instance, the firing member 14050 can be moved, either proximally or distally, to a position in which the electric motor becomes mechanically decoupled from the firing member 16050 and the electric motor can no longer move the firing member 14050 proximally or distally, for example. In another instance, the firing member 14050 can be moved, either proximally or distally, to a position in which the firing member 14050 impedes the operability of another system of the handle, such as a closing system used to close an end effector of the surgical instrument. In certain instances, the firing member 14050 can be moved, either proximally or distally, to a position in which a modular shaft assembly cannot be operably coupled to the handle and/or the firing member 14050. In some instances, the firing member 14050 can be moved, either proximally or distally, to a position in which a modular shaft assembly cannot be operably de-coupled from the handle and/or the firing member 14050. In view of the above, the firing member 14050 of a handle can be moved out of a typical operating range of positions to render the handle inoperable in at least one capacity.

Further to the above, the firing member 14050 is movable within a firing operating range to fire staples from a staple cartridge and/or an articulation operating range to articulate the end effector of the surgical instrument. In certain embodiments, the firing member 14050 is movable within a clamping operating range to close an end effector and/or clamp tissue within the end effector. The firing operating range, the articulation operating range, and/or the clamping operating range can comprise the typical operating range of positions discussed above. As also discussed above, the firing member 14050 can be moved out of this typical operating range to change the operating state of the handle in some manner. In at least one embodiment, the firing member 14050 can be moved proximally out of its typical operating range to cycle or index a use counter after every time that the handle has been used. The use counter can be cycled mechanically and/or electronically. The use counter can be in communication with the processor of the handle which can utilize data from the use counter to determine whether the handle is still suitable for use. The control system of the handle, including the handle microprocessor, the use counter, and/or one or more sensors configured to monitor the electric motor which drives the firing member 14050, for example, can be part of a diagnostic system which determines whether the handle is suitable for use.

The exemplary embodiments illustrated in FIGS. 126-131 depict two lock arms or two lockout arms, as the case may be; however, one lock arm, or lockout arm, could be used. Moreover, more than two lock arms, or lockout arms, could be used. The lock arms, or lockout arms, of the exemplary embodiments are deployed simultaneously; however, other embodiments are envisioned in which they are deployed sequentially. Furthermore, the embodiment of FIGS. 126-128, which comprises a battery lock system, could be combined with the embodiment of FIGS. 129 and 130 and/or the embodiment of FIG. 131, which comprise battery lockout systems. In various embodiments, a single system can perform the battery lock and battery lockout functions described herein.

As discussed above, a surgical instrument can include a handle, a shaft assembly, and an end effector. The handle can include an electric motor having a rotatable output shaft which is operably coupled to a drive shaft in the shaft assembly. The output shaft can rotate the drive shaft or, alternatively, the rotary motion of the output shaft can be converted to translational motion before being transmitted to the drive shaft. In either event, a property of the output shaft can be measured while it is driving the drive shaft. Various embodiments can include one or more sensors, for example, positioned relative to the output shaft which can measure the motion of the drive shaft, for example. Such sensors are positioned off-board with respect to the shaft. Such embodiments can be useful; however, the off-board positioning of the sensors can limit the properties of the drive shaft which can be detected and/or the manner in which the properties of the drive shaft are detected. Various embodiments are discussed below which comprise one or more sensors which are positioned on the output shaft which can detect a property of the drive shaft. Such sensors are positioned on-board with respect to the shaft. Also discussed below are embodiments which can include a control circuit mounted to the shaft and/or means for transmitting power to the control circuit.

Referring now to FIGS. 132 and 133, a surgical instrument system 15000 comprises an electric motor 15010 including a rotatable shaft 15020. The electric motor 15010 can comprise any suitable electric motor, such as a direct current (DC) electric motor, for example. The electric motor 15010 is mounted in a handle of a surgical instrument; however, the electric motor 15010 can be mounted in any suitable portion of a surgical instrument, such as the shaft assembly extending from the handle, for example. In certain other embodiments, the electric motor 15010 can be part of a robotically-controlled assembly. In any event, the motor shaft 15020 is rotatably supported by any suitable number of bearings such that the shaft 15020 is rotatable by the electric motor 15010 about a longitudinal axis 15021.

Referring primarily to FIG. 132, the surgical instrument system 15000 further comprises a drive system 15030 operably coupled with the motor shaft 15020. The drive system 15030 is positioned in the handle of the surgical instrument; however, the drive system 15030 may be positioned in any suitable portion of the surgical instrument, such as the shaft assembly extending from the handle, for example. In certain other embodiments, the drive system 15030 can be part of a robotically-controlled assembly. In any event, the drive system 15030 comprises a transmission 15031 and an output shaft 15032. The transmission 15031 is configured to transmit rotary motion between the motor shaft 15020 to the output shaft 15032. The transmission 15031 comprises a plurality of intermeshed gears, for example. In various instances, the gears of the transmission 15031 are configured such that the rotational velocity of the output shaft 15032 is different than the rotational velocity of the motor shaft 15020. In at least one such instance, the rotational velocity of the output shaft 15032 is less than the rotational velocity of the motor shaft 15020. In various alternative embodiments, the gears of the transmission 15031 are configured such that the rotational velocity of the output shaft 15032 is the same as the rotational velocity of the motor shaft 15020.

Referring again to FIGS. 132 and 133, the surgical instrument system 15000 further comprises a sensor 15050 mounted to the output shaft 15020. The sensor 15050 comprises a strain gauge; however, any suitable sensor could be utilized. For instance, the sensor 15050 could comprise an accelerometer, for example. The strain gauge 15050 is mounted to the outside surface 15023 of the output shaft 15020. The strain gauge 15050 comprises a substrate, or backing, 15052 comprised of an insulative material which is flexible and conformable to the outside surface 15023 of the shaft 15020. The backing 15052 is attachable to the outside surface 15023 of the shaft 15020 by any suitable adhesive, such as cyanoacrylate, for example. The strain gauge 15050 further comprises a metallic wire 15053 mounted to the substrate 15052. When the shaft 15020 experiences a load and is elastically and/or plastically deformed by the load, the metallic wire 15053 is also deformed by the load and, as a result, the electrical resistance of the metallic wire 15053 changes. This change in resistance, usually measured using a Wheatstone bridge, is related to the strain, or deformation, being experienced by the shaft 15020 by a ratio known as a gauge factor.

When an electrical conductor, such as the metallic wire 15053, for example, is stretched within the limits of its elasticity such that it does not break or permanently deform, the electrical conductor will become narrower and longer which increases its electrical resistance from end-to-end. Conversely, when the electrical conductor is compressed such that it does not buckle, it will broaden and shorten which decreases its electrical resistance from end-to-end. The electrical conductor of a resistive strain gauge often comprises a long, thin conductive strip arranged in a continuous zig-zag pattern of parallel lines. These parallel lines of the conductive strip are usually spaced close together such that a large length of the conductive strip is positioned over a small area. Owing to the large length of the conductive strip, a small amount of stress in the direction of the orientation of the parallel lines results in a multiplicatively larger strain measurement over the effective length of the conductor—and hence a multiplicatively larger change in resistance—than would be observed with a single straight-line conductive wire. From the measured electrical resistance of the strain gauge 15050, the amount of stress being applied to the motor shaft 15020 may be inferred.

The surgical instrument system 15000 further comprises a control system 15040 which is positioned on the motor shaft 15020. The control system 15040 includes a circuit board 15046 mounted to the motor shaft 15020. The circuit board 15046 can be comprised of a printed circuit board and/or a flexible laminate, for example, and can be attached to the outside surface 15023 of the shaft 15020 utilizing one or more adhesives, for example. The control system 15040 can include a control circuit on the circuit board 15046. The control circuit comprises, among other things, a microprocessor 15047 and at least one memory chip 15048 in signal communication with the microprocessor 15047. The strain gauge 15050 is also in signal communication with the microprocessor 15047 which is configured to detect the resistance change in the metallic wire 15053 of the strain gauge 15050, as discussed above. When the shaft 15020 is rotated to operate the end effector articulation system, the tissue-clamping system, and/or the staple-firing system of a surgical instrument, for example, the shaft 15020 will experience forces and/or torques T that create strain within the shaft 15020 which is detected by the strain gauge 15050 and the microprocessor 15047, as discussed in greater detail further below. The microprocessor 15047 can include the Wheatstone bridge discussed above.

The strain gauge 15050, further to the above, can comprise any suitable strain gauge. For instance, the strain gauge 15050 can comprise a semiconductor strain gauge, a piezoresistor, a nano-particle based strain gauge, a fiber optic strain gauge, and/or a capacitive strain gauge, for example. Certain strain gauges are configured to measure strain along one axis while other strain gauges are configured to measure strain along more than one axis, such as two axes or three axes, for example. More than one strain gauge can be used to assess the strain of the shaft 5020. For example, a first strain gauge can be used to assess the strain of the shaft 5020 along a first axis and a second strain gauge can be used to assess the strain of the shaft 5020 along a second axis. In at least one such instance, a first strain gauge can be positioned and arranged to measure the strain along the longitudinal axis 5021 of the shaft 5020 and a second strain gauge can be positioned and arranged to measure the strain around the circumference of the shaft 5020. The strain measured along the circumferential axis of the shaft 5020 is orthogonal to the strain measured along the longitudinal axis; however, other embodiments are envisioned in which the first axis and the second axis are transverse, but not orthogonal to one another. In various instances, one or more strain gauges can be utilized to evaluate the total, or overall, strain being experienced by the shaft 15020 at a particular location on the shaft 15020. In certain instances, a plurality of strain gauges can be utilized to evaluate the strain of the shaft 15020 at a plurality of locations on the shaft 15020.

The strain gauge 15050 can be utilized to evaluate the strain, and the stress, being experienced by the shaft 15020. When the shaft 15020 is being utilized to drive an articulation system, a large increase in strain can indicate that the end effector of the surgical instrument may not be articulating properly. Similarly, a large increase in strain can indicate that the firing member of the surgical instrument may have become stuck when the shaft 15020 is being utilized to drive a firing system. The microprocessor 15047, and/or any other microprocessor of the surgical instrument, can be programmed to interpret the strain data and utilize the strain data to interpret whether the operation of the surgical instrument should be modified. For example, a strain reading supplied by the strain gauge 15050 to the microprocessor 15047 when the shaft 15020 is being utilized to articulate an end effector may exceed a maximum articulation strain threshold and, in such instances, the microprocessor 15047, for example, can be programmed to interrupt the operation of the motor 15010 driving the shaft 15020 when the strain reading exceeds the maximum articulation strain threshold. The same strain reading, if provided when the shaft 15020 is being utilized to fire staples from the end effector, may or may not exceed a maximum firing strain threshold. If the strain reading does not exceed the maximum firing strain threshold, then the microprocessor 15047 may not interrupt the operation of the electric motor 15010. If the strain reading exceeds the maximum firing strain threshold, then the microprocessor 15047 may interrupt the operation of the motor 15010. In certain instances, the maximum firing strain threshold is different than the maximum articulation strain threshold while, in other instances, they may be the same.

In some instances, further to the above, interrupting the motor 15010 may mean that the microprocessor 15047, and/or any other microprocessor of the surgical instrument, immediately pauses the motor 15010 until receiving an input from the user of the surgical instrument. Such an input can be a command to reverse the operation of the motor 15010 or a command to override the interruption of the motor 15010 and restart the motor 15010 to complete the articulation or firing process, as the case may be. In certain instances, interrupting the motor 15010 may mean slowing the motor 15010 down which can give the microprocessor 15047, for example, a longer period of time to evaluate the loading conditions being experienced by the shaft 15020. If the increase in strain represents a transient, or temporary, increase and the measured strain drops back below the relevant threshold, the microprocessor 15047 may not interrupt the motor 15010. If the microprocessor 15047 has slowed the motor 15010 in response to an elevated strain reading, the microprocessor 15047 may restore the original speed of the motor 15010 after the strain drops back below the relevant threshold. In other instances, the microprocessor 15047 may continue to operate the motor 15010 at the slower speed even though the strain has dropped back below the relevant threshold. If, however, the elevated strain reading above the relevant threshold persists, the microprocessor 15047 can operate the motor 15010 at the slower speed and/or pause the motor 15010 after a predetermined period of time has elapsed. In the event that the measured strain continues to increase over the threshold, the microprocessor 15047 can be programmed to stop the motor 15010.

As discussed above, the microprocessor 15047 is positioned on the shaft 5020. In order for the microprocessor 15047 to control the motor 15010 driving the shaft 15020, the microprocessor 15047 needs to be able to communicate with the motor 15010. In at least one instance, a slip ring system can be utilized to transmit one or more signals from the microprocessor 15047 to the motor 15010. The slip ring system can also be utilized to transmit and/or one or more signals from the motor 15010, and/or sensors monitoring the motor 15010, to the microprocessor 15047. In certain instances, a transmitter 15060 can be utilized to transmit data between the microprocessor 15047 and the motor 15010. The transmitter 15060 is mounted to the shaft 15020 and rotates with the shaft 15020. The transmitter 15060 is in signal communication with the microprocessor 15047 and, in at least one instance, can comprise a wireless frequency emitter configured to generate a wireless signal utilizing data provided by the microprocessor 15047. The frequency emitter can be in communication with the microprocessor 15047 via one or more power wires and/or one or more signal wires which are mounted to the shaft 15020. Alternatively, as described in greater detail further below, the transmitter 15060 can comprise an impendence field generator.

When the transmitter 15060 comprises a wireless frequency emitter, the surgical instrument can comprise a wireless frequency receiver 15070 configured to receive the signal emitted by the frequency emitter. The frequency receiver 15070 is positioned in the handle of the surgical instrument; however, the frequency receiver 15070 can be positioned in any suitable location in the surgical instrument. In various instances, the frequency receiver 15070 is in signal communication with the motor 15010 such that the data transmitted within the wireless signal and received by the frequency receiver 15070 can directly control the motor 15010. In other instances, the frequency receiver 15070 is in signal communication with a second microprocessor 15080 in the surgical instrument. The second microprocessor 15080 is positioned in the handle of the surgical instrument; however, the second microprocessor 15080 can be positioned in any suitable location in the surgical instrument. The second microprocessor 15080 can utilize the data transmitted from the microprocessor 15047, and/or any other data from one or more suitable inputs, to control the motor 15010. The second microprocessor 15080 is in signal communication with the motor 15010 via one or more signal and/or power wires 15082, for example. The second microprocessor 15080 can also be programmed to control the motor 15010 in the manner described above. In various instances, the microprocessors 15047 and 15080 can cooperate to control the motor 15010.

The control system 15040, the sensor 15050, and the transmitter 15060 comprise an on-board detection system configured to detect and evaluate one or more conditions of the shaft 15020. In the embodiment described above, the condition of the shaft 15020 is the operating load being experienced by the shaft 15020 and the sensor 15050 comprises a strain gauge configured to detect the operating load; however, any suitable condition of the shaft 15020 can be detected by one or more on-board sensors positioned on the shaft 15020. Moreover, the microprocessor 15047 can be configured to arrange the data provided to the microprocessor 15047 from a plurality of sensors into two or more signals and the wireless frequency emitter can be configured to emit those signals to the frequency receiver 15070. Such signals can then be provided to the microprocessor 15080 which can control the motor 15010 in response to the signals that it has received. One or more signal multiplexers and demultiplexers could be utilized.

While a wireless frequency emitter can be useful to communicate data between a rotating plane, i.e., the shaft 15020, and a fixed plane, i.e., the handle of the surgical instrument, for example, the transmitter 15060 can be configured to communicate data in any suitable manner. In at least one embodiment, as mentioned above, the transmitter 15060 can comprise an impedance field generator. In at least one instance, the impedance field generator can comprise an impedance coil mounted to the outside surface 15023 of the shaft 15020. The impedance field generator can be configured to generate a field which can be sensed by a field sensor 15070 positioned in the handle, for example. Similar to the above, the impedance field generator moves within a rotating plane and the field sensor is positioned within a fixed plane.

Further to the above, the magnitude of the field generated by the impedance field generator corresponds to the magnitude of the strain detected by the strain gauge 15050. For instance, higher emitted field intensities can be associated with larger strains while lower emitted field intensities can be associated with smaller strains. In at least one instance, the magnitude of the field emitted by the impedance field generator can be directly proportional to the magnitude of the strain detected by the strain gauge 15050. In such an embodiment, the field sensor can measure the intensity of the field created by the impedance field generator and communicate such information to the microprocessor 15080, for example. The microprocessor 15080 can comprise a calibration table which relates the data received from the field sensor to the load being experienced by the motor shaft 15020. The microprocessor 15080 can also be configured to adjust the speed of the electric motor 15010 in response to the data received from the strain gauge 15050 and the impedance field generator. For instance, the microprocessor 15080 can slow the electric motor 15010 when the measured strain is high. The microprocessor 15080 can also utilize any other suitable data to adjust the performance characteristics of the electric motor 15010. Such data could include the current draw of the motor 15010, the impedance of the tissue being stapled, the tissue gap between the anvil and the staple cartridge, and/or the strain that the anvil is experiencing, for example.

The impedance field generator described above transmits data between a moving shaft 15020 and the handle without the use of electrical contacts. As a result, it can be said that the impedance field generator communicates data from the shaft 15020 to the handle 'wirelessly'; however, it can also be stated that the impedance field generator is being used to affect a measurement that is being made adjacent to the moving shaft 15020 which is then turned into a data stream and interpreted.

As the reader will appreciate, the control system 15040, the sensor 15050, and the transmitter 15060 may require electrical power to operate. In at least one instance, one or more batteries can be mounted to shaft 15020 which can supply power to the control system 15040, the sensor 15050, and/or the transmitter 15060, for example. In addition to or in lieu of a battery, power can be supplied to the control system 15040, the sensor 15050, and/or the transmitter 15060, for example, via a slip ring system, such as the one described above, for example. In addition to or in lieu of the above, power can be transmitted wirelessly to the control system 15040, the sensor 15050, and/or the transmitter 15060, for example. In at least one such instance, the surgical instrument can include a magnet 15041 configured to generate a magnetic field 15042 which induces a current in a wire coil 15043 wound around the shaft 15020 when the shaft 15020 is rotated by the electric motor 15010. The wire coil 15043 is in electrical communication with the control system 15040 such that the current induced within the wire coil 15043 can supply power to the microprocessor 15047, the strain gauge sensor 15050, and/or the transmitter 15060, for example. In at least one such instance, the wire coil 15043 comprises a first end 15044 and a second end 15045 mounted to contacts on the board 15046.

The magnet 15041 comprises a permanent magnet; however, the magnet 15041 can comprise any suitable magnet, such as an electromagnet, for example. When the magnet 15041 comprises a permanent magnet, the magnet 15041 can continuously generate the magnetic field 15042. The permanent magnet 15041 is securely positioned in the surgical instrument such that the orientation and/or magnitude of the magnetic field 15042 does not change. The wire coil 15043 comprises a copper, or coper alloy, wire wrapped around the outside surface 15023 of the shaft 15020; however, the wire coil 15043 can be comprised of any suitable conductive material, such as aluminum, for example. The wire coil 15043 can be wrapped around the shaft 15020 any suitable number of times. Moreover, the wire coil 15043 can be positioned on the shaft 15020 at a location in which the intensity of the magnetic field 15042 is high, or at its highest. In at least one instance, the wire coil 15043 can be wrapped around the shaft 15020 such that the wire coil 15043 is aligned, or at least substantially aligned, with a polar axis of the magnetic field 15042. Generally, the current that is generated within the wire coil 15043 is directly proportional to the number of times that the wire coil 15043 is wound around the shaft 15020. Moreover, the current that is generated within the wire coil 15043 is directly proportional to the speed in which the shaft 15020 is rotated.

As discussed above, the magnet 15041 can comprise an electromagnet. The electromagnet 15041 can be powered by a battery of the surgical instrument, for example, to generate the magnetic field 15042. The electromagnet 15041 can be selectively activated, or energized, to selectively generate the magnetic field 15042. For instance, the electromagnet 15041 can be energized only when the shaft 15020 is being rotated by the motor 15010. In such instances, the electromagnet 15041 will not be energized when the shaft 15020 is not rotating. Such instances may be useful when prolonged pauses in the operation of the shaft 15020 are anticipated or are in the process of occurring. In at least one instance, the electromagnet 15041 may be energized prior to shaft 15020 being rotated by the motor 15010. In certain instances, the electromagnet 15041 may be de-energized after the shaft 15020 has stopped rotating. Such approaches can assure that the motion of the shaft 15020 can be fully utilized to induce current within the wire coil 15043. In various instances, the electromagnet 15041 may be energized whether or not the shaft 15020 is rotating. Such instances may be useful when only short pauses in the operation of the shaft 15020 are anticipated or are in the process of occurring.

When the shaft 15020 is not rotating, further to the above, the magnetic field 15042 does not induce a current within the wire coil 15043 and, as a result, the control system 15040, the sensor 15050, and the transmitter 15060 are not being powered by the magnetic field 15042. In at least one such instance, the microprocessor 15047 can enter into a sleep mode. When the motor 15010 begins to rotate the shaft 15020, the wire coil 15043 is rotated within the magnetic field 15042 and a current is generated within the wire coil 15043. The wire coil 15043 can be in electrical communication with an input gate in the microprocessor 15047 and can apply a voltage potential to the input gate which can, one, power the microprocessor 15047 and, two, cause the microprocessor 15047 to awaken from its sleep mode. In such an embodiment, as a result, the control system 15040 can be in a sleep mode when the shaft 15020 is not rotating and an active, or fully-powered, operating mode when the shaft 15020 is rotating.

In various instances, the control system 15040 can include and/or can have access to a power source when the shaft 15020 is not rotating. In such instances, the microprocessor 15047 can enter a low-power mode. In at least one instance, the control system 15040 can include one or more capacitive elements, such as supercapacitors, for example, that can be configured to store electrical power when the shaft 15020 is being rotated and current from the wire coil 15043 is being supplied to the control system 15040. When the shaft 15020 is no longer rotating and current from the wire coil 15043 is no longer being supplied to the control circuit 15040, the capacitive elements can supply electrical power to the microprocessor 15047, and/or any other portion of the control system 15040, and prevent the microprocessor 15047, and/or control system 15040, from entering into a completely unpowered state, at least for a period of time. Such capacitive elements could also release power to the microprocessor 15047, and/or any other portion of the control system 15040, the strain gauge 15050, and/or the transmitter 15060 when the shaft 15020 is rotating at a slow speed, i.e., a speed which is insufficient to generate the power necessary to operate such components in their fully-powered operating mode. In addition to or in lieu of the above, a battery mounted to the shaft 15020 can supply power to the microprocessor 15047, and/or any other portion of the control system 15040, the strain gauge 15050, and/or the wireless transmitter 15060 when the shaft 15020 is not rotating. Such a battery could also provide power to the microprocessor 15047, and/or any other portion of the control system 15040, the strain gauge 15050, and/or the transmitter 15060 when the shaft 15020 is rotating slowly and/or when such components are otherwise underpowered, for example.

Further to the above, the shaft 15020 may be stopped for a multitude of reasons. For instance, the user of the surgical instrument may choose to pause or stop the advancement of a firing member to assess whether the firing stroke of the firing member could or should be completed and, in such circumstances, the shaft 15020, which advances the firing member, may be paused or stopped. As discussed above, a current is not induced in the wire coil 15043 when the shaft 15020 is not rotating; however, it may be desirable to power the control system 15040, the sensor 15050, and/or the transmitter 15060 in order to collect, evaluate, and/or transmit data from the sensor 15050 while the shaft 15020 is not being rotated. A secondary power source described above is capable of facilitating such an operating state of the surgical instrument. In at least one alternative embodiment, a current can be induced in the wire coil 15043 even though the shaft 15020 is not rotating. For instance, a plurality of electromagnets 15041 can be positioned around the wire coil 15043 which can be selectively energized to create a rotating magnetic field 15042. In such an embodiment, the magnetic field 15042 can be rotated relative to the wire coil 15043 to induce a current in the wire coil 15043 and power the control system 15040, the sensor 15050, and/or the transmitter 15060 even though the shaft 15020 has been stopped.

In use, further to the above, a power source, such as a battery, for example, can be utilized to power the electric motor 15010 and rotate the shaft 15020. As described above, the rotation of the wire coil 15043 within a magnetic field 15042 generates a current within the wire coil 15043 which supplies power to the control circuit 15040, the sensor 15050, and/or the transmitter 15060 positioned on the shaft 15020. In such instances, this on-board shaft system recaptures a portion of the energy expended to rotate the shaft 15020 and utilizes that energy to sense, evaluate, and/or monitor the performance of the shaft 15020.

Various examples disclosed herein have been discussed in connection with the motor shaft 15020; however, such examples could be applied to any rotatable shaft and/or rotatable system, such as the shaft 15032, for example. Moreover, the examples disclosed herein could be applied to the rotatable shaft and/or rotatable system of any suitable surgical instrument. For instance, the examples disclosed herein could be applied to a robotic system, such as the DAVINCI robotic surgical system manufactured by Intuitive Surgical, Inc., for example. The entire disclosure of U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, is incorporated by reference herein. The examples disclosed herein could also be applied to non-surgical applications, such as the crankshaft and/or camshaft of a motor, for example.

A portion of a surgical stapling instrument 16000 is illustrated in FIGS. 134-139. The stapling instrument 16000 is usable with a manually-operated system and/or a robotically-controlled system, for example. The stapling instrument 16000 comprises a shaft 16010 and an end effector 16020 extending from the shaft 16010. The end effector 16020 comprises a cartridge channel 16030 and a staple cartridge 16050 positioned in the cartridge channel 16030. Referring primarily to FIGS. 137 and 138, the staple cartridge 16050 comprises a cartridge body 16051 and a retainer 16057 attached to the cartridge body 16051. The cartridge body 16051 is comprised of a plastic material, for example, and the retainer 16057 is comprised of metal, for example; however, the cartridge body 16051 and the retainer 16057 can be comprised of any suitable material. The cartridge body 16051 comprises a deck 16052 configured to support tissue, a longitudinal slot 16056, and a plurality of staple cavities 16053 defined in the deck 16052. Referring primarily to FIGS. 135 and 136, staples 16055 are removably positioned in the staple cavities 16053 and are supported by staple drivers 16054 which are also movably positioned in the staple cavities 16053. The retainer 16057 extends around the bottom of the cartridge body 16051 to keep the staple drivers 16054 and/or the staples 16055 from falling out of the bottom of the staple cavities 16053. The staple drivers 16054 and the staples 16055 are movable between an unfired position (FIG. 135) and a fired position by a sled 16060. The sled 16060 is movable between a proximal, unfired position (FIG. 135) toward a distal, fired position to eject the staples 16055 from the staple cartridge 16050, as illustrated in FIG. 136. The sled 16060 comprises one or more ramped surfaces 16064 which are configured to slide under the staple drivers 16054. The end effector 16020 further comprises an anvil 16040 configured to deform the staples 16055 when the staples 16055 are ejected from the staple cartridge 16050. In various instances, the anvil 16040 can comprise forming pockets 16045 defined therein which are configured to deform the staples 16055.

The shaft 16010 comprises a frame 16012 and an outer sleeve 16014 which is movable relative to the frame 16012. The cartridge channel 16030 is mounted to and extends from the shaft frame 16012. The outer sleeve 16014 is operably engaged with the anvil 16040 and is configured to move the anvil 16040 between an open position (FIG. 134) and a closed position (FIG. 135). In use, the anvil 16040 is movable toward a staple cartridge 16050 positioned in the cartridge channel 16030 to clamp tissue against the deck 16052 of the staple cartridge 16050. In various alternative embodiments, the cartridge channel 16030 and the staple cartridge 16050 are movable relative to the anvil 16040 to clamp tissue therebetween. In either event, the shaft 16010 further comprises a firing member 16070 configured to push the sled 16060 distally. The firing member 16070 comprises a knife edge 16076 which is movable within the longitudinal slot 16056 and is configured to incise the tissue positioned intermediate the anvil 16040 and the staple cartridge 16050 as the firing member 16070 is advanced distally to eject the staples 16055 from the staple cartridge 16050. The firing member 16070 further comprises a first cam 16071 configured to engage the cartridge channel 16030 and a second cam 16079 configured to engage the anvil 16040 and hold the anvil 16040 in position relative to the staple cartridge 16050. The first cam 16071 is configured to slide under the cartridge channel 16030 and the second cam 16079 is configured to slide within an elongate slot 16049 defined in the anvil 16040.

Further to the above, the staple cartridge 16050 is a replaceable staple cartridge. When a staple cartridge 16050 has been at least partially used, it can be removed from the cartridge channel 16030 and replaced with another staple cartridge 16050, or any other suitable staple cartridge. Each new staple cartridge 16050 comprises a cartridge body 16051, staple drivers 16054, staples 16055, and a sled 16060. The firing member 16070 is part of the shaft 16010.

When a staple cartridge 16050 is removed from the cartridge channel 16030, the firing member 16070 remains with the shaft 16010. That said, the shaft 16010 itself may be replaceable as well; however, such a replacement shaft 16010 could still be used in the manner described herein. In at least one such instance, the surgical instrument system 16000 could comprise a handle, a shaft 16010 replaceably attached to the handle, and a staple cartridge 16050 replaceably positioned in the cartridge channel 16030 extending from the shaft 16010, for example. FIG. 137 depicts a staple cartridge 16050 positioned over an opening 16031 defined in the cartridge channel 16030 and FIG. 138 depicts the staple cartridge 16050 fully seated in the cartridge channel 16030; however, it should be appreciated that several components of the end effector 16020, such as the anvil 16040, for example, and the firing member 16070 have been removed from FIGS. 137 and 138 to demonstrate the general premise of a staple cartridge 16050 being inserted into the cartridge channel 16030. It should be appreciated, however, that a staple cartridge 16050 is often inserted into the cartridge channel 16030 through the distal end 16038 of the channel 16030. In such instances, the proximal end 16059 of the staple cartridge 16050 is aligned with the distal end 16038 of the cartridge channel 16030 and the staple cartridge 16050 is then moved proximally to align the proximal end 16059 of the staple cartridge 16050 with the proximal end 16039 of the cartridge channel 16030 and, correspondingly, align the distal end 16058 of the staple cartridge 16050 with the distal end 16038 of the cartridge channel 16030. The cartridge channel 16030 comprises a datum 16033 configured to stop the proximal insertion of the staple cartridge 16050. More particularly, the cartridge body 16051 comprises a datum shoulder 16034 defined thereon configured to abut the datum 16033 when the staple cartridge 16050 has been inserted to the proper depth; however, it is possible for the staple cartridge 16050 to be inserted into the cartridge channel 16030 in a number of ways which can prevent the datum shoulder 16034 from contacting the datum 16033.

Regardless of the manner used to position a staple cartridge 16050 in the cartridge channel 16030, it is desired to position the sled 16060 of the staple cartridge 16050 directly in front of the firing member 16070 when the staple cartridge 16050 is positioned in the cartridge channel 16030. When the sled 16060 is positioned directly in front of the firing member 16070, the sled 16060 can keep the firing member 16070 from falling into a lockout when the firing member 16070 is advanced distally. More specifically, referring to FIG. 135, the sled 16060 includes a support shoulder 16067 which is configured to support a support tab 16077 extending distally from the firing member 16070 and hold a lock shoulder 16078 of the firing member 16070 above a lockout window 16037 (FIG. 137) defined in the cartridge channel 16030. If the sled 16060 has been advanced distally prior to the staple cartridge 16050 being fully seated in the cartridge channel 16030, as illustrated in FIG. 136, the support tab 16077 of the firing member 16070 will not be supported, or supportable, by the support shoulder 16067 of the sled 16060 and, as a result, the lock shoulder 16078 of the firing member 16070 will enter the lockout window 16037 when the firing member 16070 is advanced distally. In fact, the shaft 16010 includes a biasing spring 16018 resiliently engaged with a top surface 16072 of the firing member 16070 which biases the firing member 16070 toward the lockout window 16037. The entire disclosures of U.S. Pat. No. 7,143,923, entitled SURGICAL STAPLING INSTRUMENT HAVING A FIRING LOCKOUT FOR AN UNCLOSED ANVIL, which issued on Dec. 5, 2006; U.S. Pat. No. 7,044,352, SURGICAL STAPLING INSTRUMENT HAVING A SINGLE LOCKOUT MECHANISM FOR PREVENTION OF FIRING, which issued on May 16, 2006; U.S. Pat. No. 7,000,818, SURGICAL STAPLING INSTRUMENT HAVING SEPARATE DISTINCT CLOSING AND FIRING SYSTEMS, which issued on Feb. 21, 2006; U.S. Pat. No. 6,988,649, SURGICAL STAPLING INSTRUMENT HAVING A SPENT CARTRIDGE LOCKOUT, which issued on Jan. 24, 2006; and U.S. Pat. No. 6,978,921, SURGICAL STAPLING INSTRUMENT INCORPORATING AN E-BEAM FIRING MECHANISM, which issued on Dec. 27, 2005, are incorporated by reference herein. The above being said, it may be difficult for the clinician inserting the staple cartridge 16050 into the cartridge channel 16030 to determine whether the sled 16060 has been accidentally, or prematurely, pushed forward prior to inserting, and/or during the insertion of, the staple cartridge 16050 into the cartridge channel 16030. As described in detail further below, the surgical instrument system 16000 comprises means for assessing whether the sled 16060 has been prematurely advanced when the staple cartridge 16050 is positioned in the cartridge channel 16030.

When moving a staple cartridge 16050 proximally to insert the staple cartridge 16050 in the cartridge channel 16030, as described above, the sled 16060 can be accidentally or unintentionally bumped and pushed distally from its unfired position (FIG. 135) to a partially-fired position (FIG. 136). More particularly, referring now to FIG. 139, the sled 16060 in the staple cartridge 16050 can contact the firing member 16070 in the shaft 16010 in the event that the staple cartridge 16050 is mis-inserted into the cartridge channel 16030, i.e., inserted too far proximally into the cartridge channel 16030, which can move the sled 16060 distally a distance X. Even though the clinician may subsequently place the staple cartridge 16050 in its proper position in the cartridge channel 16030, the sled 16060 will have already been pushed out of its proper position in the staple cartridge 16050 and, as a result, the firing member 16070 will enter the lockout when the firing member 16070 is advanced distally. Accordingly, the surgical instrument system 16000 will be unable to fire the staple cartridge 16050. Turning now to FIG. 140, the surgical instrument system 16000 comprises a mis-insertion sensor 16090 configured to detect when a staple cartridge 16050 has been over-inserted, or moved too far proximally within the end effector 16020, at some point during the process of inserting the staple cartridge 16050 into the cartridge channel 16030.

Further to the above, the mis-insertion sensor 16090 is in signal communication with a control system of the surgical instrument system 16000. The control system can include a microprocessor and the mis-insertion sensor 16090 can be in signal communication with the microprocessor via at least one signal wire 16092 and/or a wireless signal transmitter and receiver system, for example. The mis-insertion sensor 16090 can comprise any suitable sensor. In at least one instance, the mis-insertion sensor 16090 can comprise a contact switch which is in an open condition when a staple cartridge 16050 is not in contact with the sensor 16090 and a closed condition when a staple cartridge 16050 is in contact with the sensor 16090. The mis-insertion sensor 16090 is positioned in the cartridge channel 16030 such that, if the staple cartridge 16050 is inserted properly in the cartridge channel 16030, the staple cartridge 16050 will not contact the mis-insertion sensor 16090. In various instances, the control system of the surgical instrument system 16000 can include an indicator which can indicate to the user of the surgical instrument system 16000 that the mis-insertion sensor 16090 and the microprocessor have not detected a mis-insertion of a staple cartridge 16050.

In the event that the staple cartridge 16050 is over-inserted into the cartridge channel 16030 and the staple cartridge 16050 contacts the mis-insertion sensor 16090, further to the above, the microprocessor can detect the closure of the sensor 16090 and take an appropriate action. Such an appropriate action may include warning the user of the surgical instrument system 16000 that the staple cartridge 16050 has been over-inserted and that the sled 16060 of the staple cartridge 16050 may have been moved distally pre-maturely. In at least one instance, the surgical instrument system 16000 can include an indicator which, when illuminated, can indicate to the user that the condition of the staple cartridge 16050 positioned in the cartridge channel 16030 is unreliable and that it should be removed and replaced with another staple cartridge 16050. In addition to or in lieu of the above, the surgical instrument system 16000 can include a display screen, for example, which could communicate this information to the user of the surgical instrument system 16000. In addition to or in lieu of the above, the microprocessor can deactivate the closure system of the surgical instrument system 16000 to prevent the anvil 16040 from being moved into a closed position when the microprocessor has determined that a staple cartridge 16050 has been over-inserted into the cartridge channel 16030 and/or that the condition of the staple cartridge 16050 positioned in the cartridge channel 16030 is unreliable. By preventing the anvil 16040 from closing, in the embodiments where the surgical instrument system 16000 comprises an endoscopic surgical stapler, for example, the end effector 16020 of the surgical instrument system 16000 cannot be inserted through a trocar into a patient and, thus, the surgical instrument system 16000 can require the user to replace the staple cartridge 16050 before the surgical instrument 16000 can be used.

When the mis-insertion sensor 16090 comprises a contact switch, further to the above, the sensor 16090 can be positioned in any suitable location in the cartridge channel 16030 in which a staple cartridge 16050 would make contact with the sensor 16090 if the staple cartridge 16050 is mis-inserted. As illustrated in FIG. 140, the mis-insertion sensor 16090 can be positioned on either side of a longitudinal slot 16036 extending through the cartridge channel 16030, for example. As discussed above, however, the mis-insertion sensor 16090 can comprise any suitable type of sensor and, as a result, the sensor 16090 can be positioned in any suitable position in the end effector 16020 and/or shaft 16010, depending on the type of sensor that is being used. For instance, the mis-insertion sensor 16090 can comprise a Hall Effect sensor, for example, which can emit a magnetic field and detect changes to that magnetic field when the staple cartridge 16050 is inserted into the cartridge channel 16030. In various instances, a large disturbance to the magnetic field can indicate that the staple cartridge 16050 is close to the sensor 16090. If the disturbance to the magnetic field exceeds a threshold level, then the microprocessor can determine that the staple cartridge 16050 was positioned too close to the sensor 16090 during the insertion of the staple cartridge 16050 into the cartridge channel 16030 and, as a result, the staple cartridge 16050 has been over-inserted into the cartridge channel 16030 at some point. In at least one instance, the cartridge body 16051, the retainer 16057, and/or the sled 16060 can include one or more magnetic elements which can be configured to disturb the magnetic field of the sensor 16090, for example.

In addition to or in lieu of the above, referring now to FIGS. 141 and 142, the surgical instrument system 16000 can comprise a sensor 16080 configured to directly detect whether the sled 16060 is in its correct, or unfired, position when the staple cartridge 16050 is positioned in the cartridge channel 16030. The sensor 16080 is positioned in a recess 16032 defined in the cartridge channel 16030; however, the sensor 16080 can be positioned in any suitable location. The sensor 16080 is aligned with the proximal end of the sled 16060 when the sled 16060 is in its unfired position, as illustrated in FIG. 141. In such instances, the sled 16060 is positioned over the sensor 16080 and is in contact with the sensor 16080. The sensor 16080 comprises a contact switch which is in a closed condition when the sled 16060 is engaged with the sensor 16080, for example. In various instances, the sensor 16080 can comprise a continuity sensor, for example. When the sled 16060 is advanced distally, the sled 16060 is no longer aligned with or in contact with the sensor 16080. In such instances, the contact switch of the sensor 16080 is in an open condition. The sensor 16080 is in signal communication with the microprocessor of the control system of the surgical instrument system 16000 via at least one signal wire 16082 and/or a wireless signal transmitter and receiver system, for example. When a staple cartridge 16050 is inserted into the channel, the sensor 16080 and the microprocessor can evaluate whether the sled 16060 is in its unfired position and, if it is not, take an appropriate action, such as the appropriate actions discussed above, for example.

Referring now to FIG. 143, the sensor 16080 comprises a first contact 16084 and a second contact 16085. The second contact 16085 comprises a free end positioned over the first contact 16084 which is movable between an open position in which a gap 16086 is present between the second contact 16085 and the first contact 16084 and a closed position in which the second contact 16085 is deflected into contact with the first contact 16084. The first contact 16084 and the second contact 16085 are comprised of an electrically conductive material, such as copper, for example, and, when the second contact 16085 is in contact with the first contact 16084, the sensor 16080 closes a circuit which permits current to flow therethrough. The sensor 16080 further comprises a flexible housing 16083 which surrounds the ends of the first contact 16084 and the second contact 16085. The housing 16083 comprises a sealed deformable membrane; however, any suitable configuration could be used. The housing 16083 is comprised of an electrically insulative material, such as plastic, for example. When the sled 16060 contacts the sensor 16080, as discussed above, the sled 16060 can push the housing 16083 downwardly and deflect the second contact 16085 toward the first contact 16084 to close the sensor 16080. If the sled 16060 has been advanced distally prior to the staple cartridge 16050 being fully seated in the cartridge channel 16030, the sled 16060 will not deflect the housing 16083 and the second contact 16085 downwardly. As a result of the above, the sensor 16080 can not only detect whether a staple cartridge 16050 is present in the cartridge channel 16030, but it can also detect whether the staple cartridge 16050 has been at least partially fired.

In addition to or in lieu of the above, the sensor 16080 can comprise any suitable sensor, such as a Hall Effect sensor, for example, which is configured to emit a magnetic field and detect changes to the magnetic field. The sled 16060 can include a magnetic element mounted thereto, such as on the bottom of the sled 16060, for example, and, when the staple cartridge 16050 is positioned in the cartridge channel 16030, the magnetic element can disrupt the magnetic field emitted by the sensor 16080. The sensor 16080 and the microprocessor of the surgical instrument control system can be configured to evaluate the magnitude in which the magnetic field has been disrupted and correlate the disruption of the magnetic field with the position of the sled 16060. Such an arrangement may be able to determine whether the sled 16060 is in an acceptable range of positions. For instance, the microprocessor may assess whether the disturbance of the magnetic field has exceeded a threshold and, if it has, the microprocessor can indicate to the user that the staple cartridge 16050 is suitable for use and, if the threshold has not been exceeded, the microprocessor can take a suitable action, as described above.

In addition to or in lieu of assessing whether a staple cartridge has been inserted to its proper depth in the cartridge channel 16030, the sensor 16080 can be configured to assess whether a staple cartridge 16050 has been fully seated in the cartridge channel 16030. For instance, referring again to FIG. 143, the sled 16060 may deflect the second contact 16085 enough to contact the first contact 16084 only when the staple cartridge 16050 is fully seated in the staple channel 16030. When the sensor 16080 comprises a Hall Effect sensor, for example, the threshold disturbance that the sled 16060 must create to indicate that the staple cartridge 16050 is suitable for use may not only require that the staple cartridge 16050 be inserted to its proper depth in the cartridge channel 16030 and that the sled 16060 be in its unfired position but it may also require that the staple cartridge 16050 be in its fully seated condition. Referring now to FIG. 144, an alternative sensor 16080' is depicted which comprises a pressure sensitive switch. The sensor 16080' comprises a variable resistive element 16086' positioned intermediate the first contact 16084 and the second contact 16085. In at least one instance, the variable resistive element 16086' can comprise a semi-conductive spacer, for example. The resistance of the variable resistive element 16086' is a function of the pressure, or force, being applied to it. For instance, if a low pressure is applied to the variable resistive element 16086' then the variable resistive element 16086' will have a low resistance and, correspondingly, if a high pressure is applied to the resistive element 16086' then the resistive element 16086' will have a high resistance. The microprocessor can be configured to correlate the resistance of the resistive element 16086' with the pressure being applied to the sensor 16080' and, ultimately, correlate the pressure being applied to the sensor 16080' with the height in which the staple cartridge 16050 is seated in the cartridge channel 16030. Once the resistance of the resistive element 16086' has exceeded a threshold resistance, the microprocessor can determine that the staple cartridge 16050 is ready to be fired. If, however, the resistance of the resistive element 16086' is below the threshold resistance, the microprocessor can determine that the staple cartridge 16050 has not been fully seated in the cartridge channel 16030 and take an appropriate action.

The present disclosure will now be described in connection with various examples and various combinations of such examples as described hereinbelow.

1. One example provides an electronic system for a surgical instrument, the electronic system comprising: an electric motor coupled to the end effector; a motor controller coupled to the motor; a parameter threshold detection module configured to monitor multiple parameter thresholds; a sensing module configured to sense tissue compression; a processor coupled to the parameter threshold detection module and the motor controller; and a memory coupled to the processor, the memory storing executable instructions that when executed by the processor cause the processor to monitor multiple levels of action thresholds and monitor speed of the motor and increment a drive unit of the motor, sense tissue compression, and provide rate and control feedback to the user of the surgical instrument.

2. Another example provides the electronic system of example 1, wherein the processor provides automatic compensation for motor load when thresholds detected by the parameter threshold detection module are within acceptable limits.

3. Another example provides the electronic system of example 1 or 2, wherein the parameter threshold detection module is configured to detect battery current and speed of the motor such that when the battery current increases or the speed of the motor decreases the motor controller increase a pulse width or frequency modulation to maintain the speed of the motor constant.

4. Another example provides the electronic system of any one of examples 1-3, wherein the parameter threshold detection module is configured to detect minimum and maximum threshold limits to control operation of the surgical instrument.

5. Another example provides the electronic system of example 4, wherein the parameter threshold detection module is configured to detect end effector closing force, end effector opening force, and speed of the motor.

6. Another example provides the electronic system of example 5, wherein when the end effector closing force decreases while a knife is translating through a knife channel in the end effector, the processor is configured to control the speed of the motor.

7. Another example provides the electronic system of example 5 or 6, wherein when the end effector closing force decreases while a knife is translating through a knife channel, the processor is configured to activate an alarm.

8. Another example provides the electronic system of any one of examples 4-7, wherein the processor is configured to activate the motor only after a minimum parameter threshold is detected.

9. Another example provides the electronic system of any one of examples 1-8, wherein the parameter threshold detection module is configured to detect an ultimate threshold associated with current draw, end effector pressure applied to tissue, firing load, or torque, wherein when the ultimate threshold is exceeded, the processor is configured to shut down the motor or cause the motor to retract the knife.

10. Another example provides the electronic system of example 9, wherein the parameter threshold detection module is configured to detect a secondary threshold which is less than the ultimate threshold, wherein control parameters are changed by the processor to accommodate the change in operation.

11. Another example provides the electronic system of example 9 or 10, wherein the parameter threshold detection module is configured to detect a marginal threshold in the form of either a step function or ramp function based on a proportional response to another input to the parameter threshold detection module.

12. Yet another example provides an electronic system for a surgical instrument, the electronic system comprising: an electric motor coupled to the end effector; a motor controller coupled to the motor; a sensing module configured to sense tissue compression; a processor coupled to the parameter threshold detection module and the motor controller; and a memory coupled to the processor, the memory storing executable instructions that when executed by the processor cause the processor to monitor the sensing module, wherein the sensing module is configured to sense multiple tissue parameters.

13. Another example provides the electronic system of example 12, wherein the sensing module is configured to sense tissue compression.

14. Another example provides the electronic system of example 12 or 13, wherein the sensing module is configured to sense tissue impedance.

15. Another example provides the electronic system of example 14, wherein the sensing module is coupled to electrodes to measure tissue impedance via sub-therapeutic RF energy.

16. Another example provides the electronic system of example 15, wherein the sensing module is configured to read overlaid multiple frequency signals to measure impedance in different locations simultaneously.

17. Another example provides the electronic system of example 15 or 16, wherein the sensing module comprises a multiplexor to measure impedance at variable RF frequencies sequentially.

18. Another example provides the electronic system of any one of examples 12-17, wherein the sensing module is configured to sense tissue pressure.

19. Another example provides the electronic system of any one of examples 12-18, wherein the sensing module is configured to sense tissue contact.

20. Another example provides the electronic system of any one of examples 12-19, wherein the sensing module is configured to sense viscoelasticity rate of change.

21. Yet another example provides an electronic system for a surgical instrument, the electronic system comprising: an electric motor coupled to the end effector; a motor controller coupled to the motor; a sensing module configured to sense tissue compression; a feedback module configured to provide rate and control feedback to a user of the surgical instrument; a processor coupled to the parameter threshold detection module and the motor controller; and a memory coupled to the processor, the memory storing executable instructions that when executed by the processor cause the processor to monitor the sensing module, wherein the sensing module is configured to sense multiple tissue parameters and provide feedback over the feedback module to a user of the instrument.

In accordance with various examples, the surgical instruments described herein may comprise one or more processors (e.g., microprocessor, microcontroller) coupled to various sensors. In addition, to the processor(s), a storage (having operating logic) and communication interface, are coupled to each other.

As described earlier, the sensors may be configured to detect and collect data associated with the surgical device. The processor processes the sensor data received from the sensor(s).

The processor may be configured to execute the operating logic. The processor may be any one of a number of single or multi-core processors known in the art. The storage may comprise volatile and non-volatile storage media configured to store persistent and temporal (working) copy of the operating logic.

In various aspects, the operating logic may be configured to perform the initial processing, and transmit the data to the computer hosting the application to determine and generate instructions. For these examples, the operating logic may be further configured to receive information from and provide feedback to a hosting computer. In alternate examples, the operating logic may be configured to assume a larger role in receiving information and determining the feedback. In either case, whether determined on its own or responsive to instructions from a hosting computer, the operating logic may be further configured to control and provide feedback to the user.

In various aspects, the operating logic may be implemented in instructions supported by the instruction set architecture (ISA) of the processor, or in higher level languages and compiled into the supported ISA. The operating logic may comprise one or more logic units or modules. The operating logic may be implemented in an object oriented manner. The operating logic may be configured to be executed in a multi-tasking and/or multi-thread manner. In other examples, the operating logic may be implemented in hardware such as a gate array.

In various aspects, the communication interface may be configured to facilitate communication between a peripheral device and the computing system. The communication may include transmission of the collected biometric data associated with position, posture, and/or movement data of the user's body part(s) to a hosting computer, and transmission of data associated with the tactile feedback from the host computer to the peripheral device. In various examples, the communication interface may be a wired or a wireless communication interface. An example of a wired communication interface may include, but is not limited to, a Universal Serial Bus (USB) interface. An example of a wireless communication interface may include, but is not limited to, a Bluetooth interface.

For various aspects, the processor may be packaged together with the operating logic. In various examples, the processor may be packaged together with the operating logic to form a SiP. In various examples, the processor may be integrated on the same die with the operating logic. In various examples, the processor may be packaged together with the operating logic to form a System on Chip (SoC).

Various aspects may be described herein in the general context of computer executable instructions, such as software, program modules, and/or engines being executed by a processor. Generally, software, program modules, and/or engines include any software element arranged to perform particular operations or implement particular abstract data types. Software, program modules, and/or engines can include routines, programs, objects, components, data structures and the like that perform particular tasks or implement particular abstract data types. An implementation of the software, program modules, and/or engines components and techniques may be stored on and/or transmitted across some form of computer-readable media. In this regard, computer-readable media can be any available medium or media useable to store information and accessible by a computing device. Some examples also may be practiced in distributed computing environments where operations are performed by one or more remote processing devices that are linked through a communications network. In a distributed computing environment, software, program modules, and/or engines may be located in both local and remote computer storage media including memory storage devices. A memory such as a random access memory (RAM) or other dynamic storage device may be employed for storing information and instructions to be executed by the processor. The memory also may be used for storing temporary variables or other intermediate information during execution of instructions to be executed by the processor.

Although some aspects may be illustrated and described as comprising functional components, software, engines, and/or modules performing various operations, it can be appreciated that such components or modules may be implemented by one or more hardware components, software components, and/or combination thereof. The functional components, software, engines, and/or modules may be implemented, for example, by logic (e.g., instructions, data, and/or code) to be executed by a logic device (e.g., processor). Such logic may be stored internally or externally to a logic device on one or more types of computer-readable storage media. In other examples, the functional components such as software, engines, and/or modules may be implemented by hardware elements that may include processors, microprocessors, circuits, circuit elements (e.g., transistors, resistors, capacitors, inductors, and so forth), integrated circuits, ASICs, PLDs, DSPs, FPGAs, logic gates, registers, semiconductor device, chips, microchips, chip sets, and so forth.

Examples of software, engines, and/or modules may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether one example is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more of the modules described herein may comprise one or more embedded applications implemented as firmware, software, hardware, or any combination thereof. One or more of the modules described herein may comprise various executable modules such as software, programs, data, drivers, application APIs, and so forth. The firmware may be stored in a memory of the controller and/or the controller which may comprise a nonvolatile memory (NVM), such as in bit-masked ROM or flash memory. In various implementations, storing the firmware in ROM may preserve flash memory. The NVM may comprise other types of memory including, for example, programmable ROM (PROM), erasable programmable ROM (EPROM), EEPROM, or battery backed RAM such as dynamic RAM (DRAM), Double-Data-Rate DRAM (DDRAM), and/or synchronous DRAM (SDRAM).

In some cases, various aspects may be implemented as an article of manufacture. The article of manufacture may include a computer readable storage medium arranged to store logic, instructions and/or data for performing various operations of one or more examples. In various examples, for example, the article of manufacture may comprise a magnetic disk, optical disk, flash memory or firmware containing computer program instructions suitable for execution by a general purpose processor or application specific processor. The examples, however, are not limited in this context.

The functions of the various functional elements, logical blocks, modules, and circuits elements described in connection with the examples disclosed herein may be implemented in the general context of computer executable instructions, such as software, control modules, logic, and/or logic modules executed by the processing unit. Generally, software, control modules, logic, and/or logic modules comprise any software element arranged to perform particular operations. Software, control modules, logic, and/or logic modules can comprise routines, programs, objects, components, data structures and the like that perform particular tasks or implement particular abstract data types. An implementation of the software, control modules, logic, and/or logic modules and techniques may be stored on and/or transmitted across some form of computer-readable media. In this regard, computer-readable media can be any available medium or media useable to store information and accessible by a computing device. Some examples also may be practiced in distributed computing environments where operations are performed by one or more remote processing devices that are linked through a communications network. In a distributed computing environment, software, control modules, logic, and/or logic modules may be located in both local and remote computer storage media including memory storage devices.

Additionally, it is to be appreciated that the aspects described herein illustrate example implementations, and that the functional elements, logical blocks, modules, and circuits elements may be implemented in various other ways which are consistent with the described examples. Furthermore, the operations performed by such functional elements, logical blocks, modules, and circuits elements may be combined and/or separated for a given implementation and may be performed by a greater number or fewer number of components or modules. As will be apparent to those of skill in the art upon reading the present disclosure, each of the individual examples described and illustrated herein has discrete components and features which may be readily separated from or combined with the features of any of the other several aspects without departing from the scope of the present disclosure. Any recited method can be carried out in the order of events recited or in any other order which is logically possible.

It is worthy to note that any reference to "one example" or "an example" means that a particular feature, structure, or characteristic described in connection with the example is comprised in at least one example. The appearances of the phrase "in one example" or "in one aspect" in the specification are not necessarily all referring to the same example.

Unless specifically stated otherwise, it may be appreciated that terms such as "processing," "computing," "calculating," "determining," or the like, refer to the action and/or processes of a computer or computing system, or similar electronic computing device, such as a general purpose processor, a DSP, ASIC, FPGA or other programmable logic device, discrete gate or transistor logic, discrete hardware components, or any combination thereof designed to perform the functions described herein that manipulates and/or transforms data represented as physical quantities (e.g., electronic) within registers and/or memories into other data similarly represented as physical quantities within the memories, registers or other such information storage, transmission or display devices.

It is worthy to note that some aspects may be described using the expression "coupled" and "connected" along with their derivatives. These terms are not intended as synonyms for each other. For example, some aspects may be described using the terms "connected" and/or "coupled" to indicate that two or more elements are in direct physical or electrical contact with each other. The term "coupled," however, also may mean that two or more elements are not in direct contact with each other, but yet still co-operate or interact with each other. With respect to software elements, for example, the term "coupled" may refer to interfaces, message interfaces, API, exchanging messages, and so forth.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The present disclosure applies to conventional endoscopic and open surgical instrumentation as well as application in robotic-assisted surgery.

Aspects of the devices disclosed herein can be designed to be disposed of after a single use, or they can be designed to be used multiple times. Examples may, in either or both cases, be reconditioned for reuse after at least one use. Reconditioning may include any combination of the steps of disassembly of the device, followed by cleaning or replacement of particular pieces, and subsequent reassembly. In particular, examples of the device may be disassembled, and any number of the particular pieces or parts of the device may be selectively replaced or removed in any combination. Upon cleaning and/or replacement of particular parts, examples of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, aspects described herein may be processed before surgery. First, a new or used instrument may be obtained and when necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device also may be sterilized using any other technique known in the art, including but not limited to beta or gamma radiation, ethylene oxide, plasma peroxide, or steam.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely examples and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically matable and/or physically interacting components, and/or wirelessly interactable, and/or wirelessly interacting components, and/or logically interacting, and/or logically interactable components.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that when a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even when a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

In summary, numerous benefits have been described which result from employing the concepts described herein. The foregoing disclosure has been presented for purposes of illustration and description. It is not intended to be exhaustive or limiting to the precise form disclosed. Modifications or variations are possible in light of the above teachings. The one or more examples were chosen and described in order to illustrate principles and practical application to thereby enable one of ordinary skill in the art to utilize the various examples and with various modifications as are suited to the particular use contemplated. It is intended that the claims submitted herewith define the overall scope.

What is claimed is:

1. A surgical instrument, comprising:

an electric motor;

an end effector to implement a tissue treatment; and a control circuit, comprising:

a primary processor configured to generate a first motor activation signal based on a first sensed parameter of the surgical instrument;

a safety processor in communication with the primary processor, wherein the safety processor is configured to generate a second motor activation signal based on a second parameter of the surgical instrument;

an AND gate to generate an output signal based on the first motor activation signal and the second motor activation signal; and a motor power switch coupled to the AND gate, the motor power switch comprising:

a closed state, wherein motor power is supplied to the electric motor; and an open state, wherein motor power is not supplied to the electric motor, wherein the motor power switch is transitionable from the open state to the closed state based on the output signal, wherein activation of the electric motor for the tissue treatment requires generation of the first motor activation signal by the primary processor and generation of the second activation signal by the safety processor.

2. The surgical instrument of claim 1, wherein the motor power switch is in the closed state based on the output signal being greater than or equal to a predetermined activation signal, and wherein the motor power switch is in the open state based on the output signal being less than the predetermined activation signal.

3. The surgical instrument of claim 2, further comprising:

a first sensor to measure the first parameter of the surgical instrument, wherein the first sensor is coupled to the primary processor; and a second sensor to measure the second parameter of the surgical instrument, wherein the second sensor is coupled to the safety processor.

4. The surgical instrument of claim 3, wherein the control circuit is to:

detect a value from the first sensor being outside a predetermined range; and determine, based on the value, that the output signal is less than the predetermined activation signal.

5. The surgical instrument of claim 3, wherein the control circuit is to:

detect a value from the second sensor being outside a predetermined range; and determine, based on the value, that the output signal is less than the predetermined activation signal.

6. The surgical instrument of claim 3 wherein the control circuit is to:

detect a first value from the first sensor being within a first predetermined range;

detect a second value from the second sensor being within a second predetermined range; and determine, based on the first value and the second value, that the output signal is greater than or equal to the predetermined activation signal.

7. The surgical instrument of claim 1, further comprising:

a firing beam operably responsive to the electric motor, wherein the firing beam is configured to move relative to said end effector during a firing stroke; and a bailout assembly configured to allow for manual retraction of the firing beam.

8. A surgical instrument, comprising:
an electric motor;
an end effector to implement a tissue treatment
a firing beam operably responsive to said electric motor, wherein said firing beam is configured to move relative to said end effector during a firing stroke;
a bailout assembly configured to allow for manual retraction of the firing beam; and
a control circuit comprising:
a current sensor to monitor a current draw associated with the control circuit;
a bailout switch coupled to the bailout assembly, wherein the bailout switch is configured to output a bailout shutdown signal;
a safety processor to configured output a safety signal indicative of an operational condition;
an AND gate to generate an output signal based on the bailout shutdown signal and the safety signal; and
a switch coupled to the AND gate, the switch comprising:
a closed state, wherein power is supplied to the electric motor; and
an open state, wherein power is not supplied to the electric motor, and wherein the switch is transitionable from the closed state to the open state when the current draw is above a current draw threshold, the bailout shutdown signal indicates a bailout condition, or the safety signal indicates an unsafe operational condition, or a combination thereof.

9. The surgical instrument of claim 8, wherein the switch is in the closed state based on the output signal being greater than or equal to a predetermined activation signal, and wherein the switch is in the open state based on the output signal being less than the predetermined activation signal.

10. The surgical instrument of claim 9, further comprising a sensor to measure a first parameter of the surgical instrument, wherein the sensor is coupled to the safety processor.

11. The surgical instrument of claim 10, wherein the control circuit is to determine the output signal is less than the predetermined activation signal, and wherein the bailout shutdown signal is indicative of at least one of the bailout condition being detected or the safety signal is indicative of the unsafe operational condition based on the first parameter of the surgical instrument being outside of a predetermined parameter range.

12. The surgical instrument of claim 10, wherein the control circuit is to determine the output signal is greater than or equal to the predetermined activation signal, and wherein the bailout shutdown signal is indicative of no bailout condition being detected and the safety signal is indicative of a safe operational condition based on the first parameter of the surgical instrument being within a predetermined parameter range.

13. The surgical instrument of claim 10, wherein the surgical instrument further comprises a primary processor to control an operation of the electric motor during the tissue treatment.

14. A surgical instrument, comprising:
an electric motor;
a firing drive operably responsive to said electric motor for a tissue treatment;
a bailout assembly configured to allow for manual retraction of the firing drive; and
a control circuit comprising:
a current sensor to monitor a current draw associated with the control circuit;
a primary processor to control an operation of the electric motor during the tissue treatment;
a bailout switch coupled to the bailout assembly, wherein the bailout switch is to output a bailout shutdown signal;
a safety processor to output a safety signal indicative of an operational condition;
an AND gate to generate an output signal based on the bailout shutdown signal and the safety signal; and
a switch comprising:
a closed state, wherein power is supplied to the electric motor; and
an open state, wherein power is not supplied to the electric motor, and wherein the switch is transitionable from the closed state to the open state when the current draw is above a current draw threshold, the bailout shutdown signal indicates a bailout condition, or the safety signal indicates an unsafe operational condition, or a combination thereof, wherein the control circuit is to:
determine the output signal is less than a predetermined activation signal based on at least one of the bailout shutdown signal or the safety signal indicating the unsafe operational condition; and
transition the switch from the open state to the closed state based on the output signal being less than the predetermined activation signal.

15. The surgical instrument of claim 14, wherein the control circuit is to determine the output signal is greater than or equal to a predetermined activation signal when the bailout shutdown signal is indicative of no bailout condition being detected and the safety signal is indicative of a safe operational condition.

* * * * *